United States Patent
Poulter et al.

(10) Patent No.: US 7,019,122 B1
(45) Date of Patent: Mar. 28, 2006

(54) **UNUSUAL RETROTRANSPOSON FROM THE YEAST *CANDIDA ALBICANS***

(75) Inventors: Russell Tony Masell Poulter, Dunedin (NZ); Walter Herman Maria Louis Luyten, Beerse (BE); Marianne Denise De Backer, Beerse (BE); Bart Jozef Maria Nelissen, Beerse (BE)

(73) Assignee: Janssen Pharmaceutica N.V., (BE)

( * ) Notice: Subject to any disclaimer, the term of this patent is extended or adjusted under 35 U.S.C. 154(b) by 0 days.

(21) Appl. No.: 09/430,590

(22) Filed: Oct. 29, 1999

Related U.S. Application Data

(60) Provisional application No. 60/106,342, filed on Oct. 30, 1998.

(51) Int. Cl.
*C07H 21/02* (2006.01)
*C07H 21/04* (2006.01)
*C12N 7/00* (2006.01)
*C12N 15/11* (2006.01)
*C12N 5/10* (2006.01)
*C12N 15/63* (2006.01)
*A61K 31/711* (2006.01)

(52) U.S. Cl. .................. 536/23.1; 536/23.4; 536/24.1; 435/235.1; 435/320.1; 435/325; 435/455; 514/44

(58) Field of Classification Search ............... 536/23.1, 536/24.1, 23.4; 435/235.1, 320.1, 69.1, 325, 435/455; 514/44
See application file for complete search history.

(56) References Cited

OTHER PUBLICATIONS

Mark L. Farman et al, MAGGY, a retrotransposon in the genome of the rice blast fungus *Magnaporthe grisea*, Mol Gen Genet 1996, 251:665-674, Springer-Verlag 1996.*

* cited by examiner

*Primary Examiner*—David Guzo
*Assistant Examiner*—Michael Burkhart
(74) *Attorney, Agent, or Firm*—Frommer Lawrence & Haug; Thomas J. Kowalski

(57) ABSTRACT

TCa2 is a Ty1/copia retrotransposon from the pathogenic yeast *Candida albicans*. In contrast to other retrotransposons it can appear as an abundant, extrachromosomal double-stranded DNA molecule, called pCal. The invention relates to the isolation and characterisation of TCa2 and pCal together with its uses for inducing random mutagenesis in a genome, as a component of a transposable element and of an expression vector.

14 Claims, 113 Drawing Sheets

FIG. 2C

```
3001 CTTATCCACTACACCTATGTCACACATTGTTCCTATGGCTGAAGGTATCCAGGGAAGGCAACTGGGCGCTCAGTACGAGGTACGCCGGAACATATGTGGAA
 869  L  S  T  T  P  M  S  H  I  V  P  M  A  E  G  I  Q  G  R  Q  S  G  A  Q  Y  E  V  R  G  T  Y  V  E

3101 AGTGAATATGACAATACAAATGACGTGATGCACATGCCCAAAGAGTCATATTCAGTTCAGCCAGCATGTTTACTTTAACTACGGGTAACAGTTCTAACCG
 902  S  E  Y  D  N  T  N  D  V  M  H  M  P  K  E  S  Y  S  V  Q  P  A  S  F  T  L  T  T  G  N  S  S  N  E

3201 AATATGTTATAAATGATGATCCAGTACAGATTACCCATTGAAGAATCCCGATGATTTTTCTAACCCTCTTCAACTAACTGAAGAATCACACGTATATGTATC
 936  Y  V  I  N  D  D  P  V  Q  I  T  I  E  N  P  D  D  F  S  N  P  L  Q  L  T  E  E  S  H  D  M  V  S

3301 CGAAGTAAAATCGATGAGAATCCTAAACCCAGTCTCCACGAGCTAACACCTGGGGATAATCCGGTCGTCAAACCTCCTCAACTTGGTACCGAGACTTCA
 969  E  V  K  S  D  E  N  P  K  P  S  L  H  E  L  T  P  G  D  N  P  V  S  K  P  P  Q  L  G  T  E  T  S
                                                                                                PPT2
3401 GTAATAGGGAAGTCTAAAGAGCCTATTACAAACCACACAAAGGAGCCCCCTTCCATCCAGGGGAGGGACCATAAACGCCTGGAATCTACTGCTCAGTTG
1002  V  I  G  K  S  K  E  P  I  T  N  H  T  K  D  A  P  S  I  Q  G  R  D  H  K  R  S  E  S  T  A  Q  V  G

3501 GACTATCACACCAACCCCAGACTGGTACTCCCGCTTCGGAGGAGTCAAAATGTCAGGAACAGATCATTTCGGTGTCGACGTTGTTAAAGAAACAGTCTC
1036  L  S  H  Q  P  Q  T  G  T  P  A  S  E  E  S  K  L  S  G  T  D  H  F  G  V  D  V  V  K  E  T  V  S

3601 AGAAGATTGGCATACTTCTGACTACCCAGAAACTAGTGCTGAAGATGAACAGCAAAATCCCTCGTTACTGGCTAATAAGAAATCGGTAACTGAAAAATA
1069  E  D  W  H  T  S  D  Y  P  E  T  S  A  E  D  E  Q  Q  N  P  S  L  S  A  N  K  N  R  V  T  E  K  I

3701 GATGAGGGAGAAAATATTTCATTTCCGGGGGTGATGATGATTCTGTCGTGATCAACTCAAATGTTGAGCAATCTAATGTTGAAACAGAGGATGCTGGTA
1102  D  E  G  E  N  I  S  F  P  G  G  D  D  D  S  V  V  I  N  S  N  V  E  Q  S  N  V  E  T  E  D  A  G  N

3801 ACAGTCCAATTCAAGACGAAGTTTCTCAAGAGGAAGAATACTTAATGAACAAACTGATATAGTTGATACTGTTGCTAAAGTTATTGAGAATGAAAAAT
1136  S  P  I  Q  D  E  V  S  Q  E  G  R  I  L  N  E  Q  T  D  I  V  D  T  V  A  K  V  I  E  N  E  K  I

3901 CTCTCCTATTAATTCATTAGATGATCATACTGAACTTGCTACAGACTCGGGAAATGATAGCAATTCAACAGAATCCGACATTCAATCGAAAAATGAAATA
1169  S  P  I  N  S  L  D  D  H  T  E  L  A  T  D  S  G  N  D  S  N  S  T  E  S  D  I  Q  S  K  N  E  I

4001 TCACCAGTGATTAATGAGAAAAATACTGAAATAATCCAAAACACATTGAAAGTATCCTTGCTGATAAGACATTGGATGAATTTGAAACGTATAATGTTG
1202  S  P  V  I  N  E  K  N  T  E  I  I  Q  K  H  I  E  S  I  L  A  D  K  R  L  D  E  F  E  T  Y  N  V  D

4101 ATGAAATTGAGAATGTGATTAATGACGATGACATTGCTGAAGCTAATCCACTACCAGATGAAATAATGATGTTCAGATGAATGAGAGTTTTGACAATAA
1236  E  I  E  N  V  I  N  D  D  D  I  A  E  A  N  P  L  P  D  E  N  N  D  V  Q  M  N  E  S  F  D  N  N

4201 TCATAGCATGTCACGAGCAAAGAAGAAATACACATTTGAGAAGAAGTTAACGAAAAAATTGCTGGTACTAAACATTCACTTGATCAACTGATCCAAGA
1269  H  S  M  S  R  A  K  K  K  Y  T  F  E  K  E  V  N  E  K  I  A  G  T  K  H  S  L  D  T  T  D  P  R

4301 GAAGCAATCAGATGTTAAATACTGGTGAAACCAAGAGAATCGAACCCAAGAAAGAGAGGTGCCTATCACTGTGAAATTAAACAAAGATCGCAATACA
1302  E  A  I  R  V  L  N  T  G  E  T  K  R  I  E  P  K  K  R  E  V  P  I  T  V  K  L  N  K  R  S  Q  Y  K

4401 AGTCACCATATGTTACAAGAAGTGGTAGAACGGTTATAAACCCGAGAGTCTATTTACATGCGGTCGTCAACAAAATCGACTATAATGATCCGGGATGGAT
1336  S  P  Y  V  T  R  S  G  R  T  V  I  N  P  K  R  Y  L  H  A  V  V  N  K  I  D  Y  N  D  P  G  W  I

4501 AAAGTCAATGAATGCTGAACTAGAGAAATTTAGATCAAAAGATGTTTACGAAGAAGTTCCAATTCCCACCGGGTGAAGCCTATATCTATGGGTTGGGTA
1369  K  S  H  N  A  E  L  E  K  F  R  S  K  D  V  Y  E  E  V  P  I  P  T  G  V  K  P  I  S  H  G  W  V

4601 CATACTGAGAAAATTGATTCTCTCAAAGGTGTTGTTCGGAAATCACGTTGTGTTGTCCATGGCAACAGACAAAAGAAAAATTGGATTATGACCCTTTA
1402  H  T  E  K  I  D  S  L  K  G  V  V  R  K  S  R  C  V  V  H  G  N  R  Q  K  E  K  L  D  Y  D  P  F  S

4701 GTGTTAGTTCACCTGTTATAGATCTTGTGACTATAAGATCTATTGACAATAATAGGTTGTGAATTAGGAATGACAATTCAACATTTACACTTCGAGTCGGC
1436  V  S  S  P  V  I  D  L  V  T  I  R  L  L  T  I  I  G  C  E  L  G  H  T  I  Q  H  L  D  V  E  S  A

4801 GTATCTAAATGCCTCTATTACTCATTCAAATCCAATTTATGTCTTTCCTCCTAAATCAGTACCTTTGAAGAAAAACCATTGTTGGTTATTGAAACGTTCT
1469  Y  L  N  A  S  I  T  H  S  N  P  I  Y  V  F  P  P  K  S  V  P  L  K  K  N  H  C  W  L  L  K  R  S

4901 GTCTATGGGTTAAAACAGTCGGGTTTGGAATGGTATCACACTATCAAAGAGTATTGGAAGACATTGTTTTACTCAAGTTTACACAATGATGGTTTAT
1502  V  Y  G  L  K  Q  S  G  L  E  W  Y  H  T  I  K  R  V  L  E  D  I  G  F  T  Q  V  L  H  N  D  G  L  F

5001 TTCACATTGAATATGAAGAGGGATCAGTAATATATTTAGGTTTATATGTTGATGATATTCTTATGGTTGGAAGTTCACAAAAGTTATTGATAATTTTGT
1536  H  I  E  Y  E  E  G  S  V  I  Y  L  G  L  Y  V  D  D  I  L  M  V  G  S  S  Q  K  V  I  D  N  F  V

5101 GGATCAATTTGAGAGATCATTTTGAAGTTAAAGTGTTTGGTGAAATATCAAATTATCTTGGTATTGAATTTCGTAAAACCGAATCTGGTTATATTTTATCT
1569  D  Q  L  R  D  H  F  E  V  K  V  F  G  E  I  S  N  Y  L  G  I  E  F  R  K  T  E  S  G  Y  I  L  S

5201 CAAGAAAAATTTCTCAAGAAATTACTTAAGGATTTCAAACTAGATGACTCATATGGGAAAAACATACCCTGGATTCCAAATGACAAATATGAAAAGTTG
1602  Q  E  K  F  L  K  K  L  L  K  D  F  K  L  D  D  S  Y  G  K  N  I  P  W  I  P  N  D  K  Y  E  K  V  A

5301 CAATAATTCGTGAAAACGTTAATCCAGAGAATGATTTTGAAAAGGTTCCGAATGAGACATTGCTTGACCCTGATGCTAAAAACTATACCAAAGTGGTGT
1636  I  I  R  E  N  V  N  P  E  N  D  F  E  K  V  P  N  E  T  L  L  D  P  D  A  K  K  L  Y  Q  S  G  V

5401 TGGCCTGCTTTTATGGGCTGCCACAAACACACGTCCAGATATATCGGTCGTAGTGAATTCGTTGGGTTCTAAATCTGCAAATCCAAATGTCCATGATTAT
1669  G  S  L  L  W  A  A  T  N  T  R  P  D  I  S  V  V  V  N  S  L  G  S  K  S  A  N  P  N  V  H  D  Y

5501 GAGAAATTGATTTATTGTCTTAGGTATATCCAAAAATAGCATGGGATATCACATTGAGTACAAAAGAAACAGATTGAATATACCACCAAAATCATTTGTTA
1702  E  K  L  I  Y  C  L  R  Y  I  K  N  S  M  G  Y  H  I  E  Y  K  R  N  R  L  N  I  P  P  K  S  F  V  I

5601 TCGAATGTTTCAGTCGATGCGTCATTTGCACCAGGATTGGATAGAAAATCTATTAGTGGAACTTTGATTTATGTGAATGGAAATTTGGTGCAATGGGCGAC
1736  E  C  F  S  D  A  S  F  A  P  G  L  D  R  K  S  I  S  G  T  L  I  Y  V  N  G  N  L  V  Q  W  A  T

5701 CAAAAAACAAACGGTCATAGCCAAAGCTCAGCAGCTTGTCAGCTTGTGAAATGTGGCTCTAAATTATACAATGTCAAAGCTATCGAAATAAAAAAACCATTTAATG
1769  K  K  Q  T  V  I  A  Q  S  S  A  A  C  E  M  L  A  L  N  Y  T  H  L  K  A  I  E  I  K  N  H  L  M

5801 GATTTGGGTTTTGAAGTAGGTAAGATACATTGTCATCAAGACAACCAAGCTGTGATTAAAGTTTTGAGAAATAACTATTGTCACCCACATCGACCAATAG
1802  D  L  G  F  E  V  G  K  I  H  C  H  Q  D  N  Q  A  V  I  K  V  L  R  N  N  Y  C  H  P  H  R  P  I  D

5901 ATATCTGCTATAAGTTTCTACGCCAATTGATCAATGATAAAGTATTTTCAATATCCTATGTGAAGACAAATGATAATTACGCCGATTGTATGACTAAGTG
1836  I  C  Y  K  F  L  R  Q  L  I  N  D  K  V  F  S  I  S  Y  V  K  T  N  D  N  Y  A  D  C  M  T  K  C

6001 TCTAAGTCGTGCTAAATTCAAAGCATTCGTTGAGGGTATGATAAAACGTTTAGACCCTAGAAGATAATAAACACTGATACAAATGCAATAACGGCAGAA
1869  L  S  R  A  K  F  K  A  F  V  E  G  M  I  K  R  L  D  L  E  D  N  Q  T  S  I  Q  N  A  I  T  A  E
                                                                                    PPT1
6101 TAAGTGGATTTATCATTACTATTATCGTAATGCTCAATCAGGCGAGTTTTGTTTGTGCACTATTTTGTGTCAGAAACTGATCAATGAAAATGATGGTTA
STOP  *                                                         TATA

6201 TTATGAGAATGCAAAATTTTTTCCATCACACATCAGGTGATGACAGAACTAAACTATATTGTCTAGTAAAATAGGGTATGAAATACCAACATCCCAGAA
                            TATA               POLY A
6301 TATCAACGAGATAGAAGGGAGCAGTTTCAATATATATCTTGTGAAAAATAACTTCGTTCTAATTCACTATACACAACTAGACGTGTACACGCTCAATCTC

6401 AGGTAAAGAAAGTTTATATTCCATCA 6426
```

FIG. 4

Protease
| | |
|---|---|
| 1731 (268) | TQWCLDSGATSHMC |
| copia (287) | CGFVLDSGASDHLI |
| Tnt1 (292) | SEWVVDTAASHHAT |
| Ty1 (456) | GHLLLDSGASRTLI |
| Ty4 (410) | KLVIIDTGSGVNIT |
| pCal (370) | KYLVYDTGATISVV |

Integrase (zinc finger)
| | | | |
|---|---|---|---|
| 1731 (397) | HKRNGH | -28- | CKTC |
| copia (419) | HERFGH | -30- | CEPC |
| Tnt1 (426) | HKRMGH | -25- | CDYC |
| Ty1 (599) | HRMLAH | -32- | CPDC |
| Ty4 (562) | HKRMGH | -29- | CQTC |
| pCal (568) | HLMSNH | -29- | CKVC |

Integrase (continued)
| | |
|---|---|
| 1731 (518) | KIKCIRSDNGGEFVNNVFDDYLKAHGIARQLTIPHTPQQNGVAERANRTLVEM |
| copia (543) | KVVYLYIDNGREYLSNEMRQFCVKKGISYHLTVPHTPQLNGVSERMIRTITEK |
| Tnt1 (543) | KLKRLRSDNGGEYTSREFEEYCSSHGIRHEKTVPGTPQHNGVAERMNRTIVEK |
| Ty1 (729) | SVLVIQMDRGSEYTNRTLHKFLEKNGITPCYTTTADSRAHGVAERLNRTLLDD |
| Ty4 (689) | KVREINSDRGTEFTNDQIEEYFISKGIHHILTSTQDHAANGRAERYIRTIITD |
| pCal (687) | KVAYFRSDNAPEFPQPSDLAEF...GIWRETIAAYSPELNGLAEVVNKLILQQ |

Reverse Transcriptase
| | | | |
|---|---|---|---|
| 1731 (880) | HHMDVCTAYLNSEL..KDTVYMKQPQGFTDAANPDQVLLLRKAIYGLKQSGREWN | -32- | ILVYVDDLIL |
| copia (999) | HQMDVKTAFLNGTL..KEEIYMRLPQGISCNS..DNVCKLNKAIYGLKQAARCWF | -34- | VLLYVDDVVI |
| Tnt1 (919) | EQLDVKTAFLHGDL..EEEIYMEQPEGFEVAGKKHMVCKLNKSLYGLKQAPRQWY | -33- | LLLYVDDMLI |
| Ty1 (1343) | TQLDISSAYLYADI..KEELYIRPPPHLGM...NDKLIRLKKSLYGLKQSGANWY | -29- | ICLFVDDMVL |
| Ty4 (1381) | KTLDINHAFLYAKL..EEEIYIPHPHD......RRCVVKLNKALYGLKQSPKEWN | -30- | IAVYVDDCVI |
| pCal (1461) | QHLDVESAYLNASITHSNPIYVFPPKSVPL..KKNHCWLLKRSVYGLKQSGLEWY | -33- | LGLYVDDILM |

RNase H
| | |
|---|---|
| 1731 (1129) | AFTGFVDADWGGDRLDRKSYTGYV |
| copia (1247) | KIIGYVDSDWAGSEIDRKSTTGYL |
| Tnt1 (1174) | ILKGYTDADMAGDIDNRKSSTGYL |
| Ty1 (1604) | KLVAISDASY.GNQPYYKSQIGNI |
| Ty4 (1639) | KVIAITDASV.GSEYDAQSRIGVI |
| pCal (1734) | VIECFSDASFAPG.LDRKSISGTL |

```
>retrotransposon_1 1309bp LTR kappa: 698-977
CTGGATAAAGAAATCAGAAAAGAGATAGCAGGAAAACCAGGAAAAGGTGACGATGATGACGACAGT
TGGGGATCTGT
GCCTGTTTCAATTCGAGTATTTGCTGAAGTTGAAAAGAAGTTGAAGCAAAAGAAAAGTTTGGCATCAAG
CTAGATATTTA
TATATGTATATGATTAGACCAACATAAAACTAGACGTCCAAATATTTATTTATTTATTTATTGATATAT
ATTCTTATTTA
TTACTGTTATGATCTTTTGATTCACACAGAGATTTAATCCAAATCAATACCTTTTGTTTTGTAGAAATC
TTTTGCTTCTT
CAATTTGTATTTTCAATTCTTTGTATTTATGTTCTTTGTCTTTGAATGTAACAATTCCCCAACCTAACG
TTGATAAGGCA
TAAGACCCAAATGTGACTAATCCCCACCATGGCAAGTATGGCAATATTTCATCGTGTATTTTAGCTGGA
GTTGGAATCAC
ACCTGTGATAAGAGCAAAATAAATAGCTGATAAGGCAAAAATTGTTAATCCTGTTTCAGTAGCTTTAGT
CATTCTTATAG
TTAGACTTGTTAAAGGGTAGTTGTGTTAATTGAAGATATGCTGGAAAACTATACTTTTCGTTGTTTTTT
TTTTTCAATCT
AGGTCGGGTGTGCTGTTATTTTTTTTCTCTCTTCTTGGTTCTTAGTATTGGATTATATGTTGGTTTATG
CGACGTTTGTG
TCAGGGAAATAACACCTTGATATAAGTCGTGCGTATTAGGTCAACATTGGTGAAAAATTTGCACTCATC
GAGAGCCAGGA
ATTAGTATAAAAAGAAGAGAAAAGAAAGATATTTAGGATATTTATTATATAGGGACCGAGTTTCAGGAG
ACACTTTTAGT
GGGCGTAAACTTCATTCACTCTGTTTTTGCTTATTACAAATTATCACCTATCGTGTACTAGGACTAAT
TCTCACGAATA
TTCCGTGTATACAAACACTTATTGCCAACTTATGGTGCGGAACTTTATTTGTCTGAACCAAAATCAAAG
TCACATCATTT
AAATGAACGTTGACATAAATAGATTCTTTATTCAATAGAAACAATTTCTTCCTTTNTCTTTTCTTTGTA
TTANTGGTTAG
ATTTCCATTCCATATACACACAAGATGTCAACGAAATCAGCAAATTCAACTGCTGTCAATTCATTTAAT
GCAAACCACTC
CAACTATGACGTTTTAGACCTTCATTCACCCCAGTTTTGGTCAATACATTCTTAGTACATCTTGGATT
AGCTACGAAAA
ACCCAGATGACACTTTCACTTTTGACATA
```

FIG. 18

```
>retrotransposon_2 1340bp LTR kappa: 770-1047
CCCNTTTGTNTGGTACATGTTAGACAGGCCCAAAAAATGGTATCATTTAGAACTGTATGGAGAACATTA
GTTTTGGTCCA
ACATTGCGTGATGATGGTATNTNTTTCGTATTATAGTACAATGATGGCTCAATGATTNATTTTAGGTTT
ATATGTGGATG
ATATCTTAATGGACAGAATCTCAGATGGAATCGTTATCAGATTTGTTGAACAAGAGAGAGTTTATTTCG
CGTNAAAATCA
ATTTAGGTCTCATGACAGAATATGTGAGATAAAATGTCCACGTAAGCAAAACTGGGTGATACTNTGAAT
TAAGAGATACT
CCTAAATAAGCAAACCAAGGATNTTAAACTACACAANTCGTATGGTAAAACGTGCTTTGAGTNCCAAAT
GATAGATGCGA
GATACCAACAAAATAGNACTGTCGCAAATGCTGAANACAATTTCACTGAGGTTCGAAATGNAAAATNAC
TTAANTCAATT
AAAAAATTTATACCAAAAGGTGGTCTGGAAGTGCTGATATGAACACGAAATTTAANGCATTCTGTGGAA
AATTCGTTTAA
GCTCACANTCGGAAAATACTACCATTCTACATTTGCAGAAAATTAAAATTGTGTTGTGAAATATCTACA
TCCTACAAAGT
TCAAGACATTTATTGATGGTATATTCAAAGGACTCGATGTTGAGAATGATAATAACCTGAACCAAGACG
CTACAAATGCT
AATTGAGTAATTCGTAATTGCTAAACAACGCCATTTCGAATCAGGGGAGTGTTGGTTTATGCGACGTTT
GTGTCAGGGAA
ATAACACCTTGATATAAGTCGTGCGTATTAGGTCAACATTGGTGAAAAATTTGCACTCATCGAGAGCCA
GGAATTAGTAT
AAAAAGAAGAGAAAAGAAAGATATTTAGGATATTTATTATATAGGGACCGAGTTTCAGGAGACACTTTT
AGTGGGCGTAA
ACTNCATTACTNTGTTTTTTGCTTATTGCAAATAATCCCTATCGTGTACTAGGACTAATTCTCACGAAT
ATTCCGTGTAT
ACAAACAAAATCAGACTTCTTGGTAAGCCCAGCCGAAACAGCCATACTTCTAGTGGATCTTTCTATACT
ACAACATTCAC
ACTGCTTGACCTACAACTACACATATTCCTTGTTATAAGGGCAATCTATCACACAAAAGATTTACTGTT
GACTCACAAGA
TATCAACTGTACTAATAAAGGAGTGCATTCTATGACCTTTGGAGAGGAACTATGTATAATATAAGAGAG
AAGGGACTAAA
GATCTATATATAATGAGCAGGATGGGTAACCCGGTGGGGTATTAGCACGCACACGACCTG
```

FIG. 19

>retrotransposon_3 556bp LTR kappa:1-216
CAACATTGGGTGAAAAAATTTGCACTCATCGAGAGCCAGGAATTAGTATAAAAAGAGGAGAAAGAAGGT
ATTTAGGATAT
TTATTATATAGGGACCGAGTTTCAGGAGACACTTTTAGTGGGCGTAAACTTCATTCACTCTGTTTTTTG
CTTATTACAAA
TTATCACCTATCGTGTACTAGGACTAATTCTCACGAATATTCCGTGTATACAAACATTATACGTGTCTG
TAACTACGCGA
AACTACTTCGTCTCAGTTTTTTGTTACAAACAACTTTCCGTATAGACCTGAGATTTTGTCAGCTTGATT
GAATGGAAGAG
TTTACTAAAGTACCAGAAAGGTGTTTTATAGATAACATGTAGATATATAAAAATGTTATATTACAAATG
ACTTCCAAAAG
AAACTGTACGAATTTTGCTGTTTATTAAAAACCAGTTCCTGAAAACTAGTATCTTAGCTTCAGTACATT
TAGCCCACCTA
AATTGGACCTATGACAAGTTCTACTTTCCCGACAATGCTAATATAGAGCAGTTTCTTCTTCTTCTTCTT
CCTCGTC

FIG. 20

```
>retrotransposon_4 2112bp Tca1-like LTR: 221-608
ATTTAATATGTTGGTATTGGCTACTGCCAACTTCTTAGCTGATGCAGATGCCATTGTTAATATTGTTAA
ATTGGGTAAAT
AGTATGAAGGAAGCTTTGGCAGGCGTTGTTATTTTTTTCACCAATTATTATCATCACCTGCGGAGGTTA
GTCAATTTGAG
ATTGTGCGAGGGAAAAAAAACGACCTCCATACACTACCTCAAGTATAAGTCCAGTCCAATTGTTCGCTA
TAGAGAGATTT
CCTAGCCGGAATGCACGACAATCCTGAGACGGAAGTCGATCGTCGATGCCCATGGTGCGTGGTGAAAAA
TTTTCTTAGAA
AATTTGTTCTTTCCTTCAACTGCTTTGAAGAGAGGGAGGTTCAAGTGGTTTAAGTACGACGGTCACAAA
GATTGCGGCTT
ATGAGGCCCGAACTGAGTTGAAATACAAAATCAAGATATAATTATATACCTTACTTGTCTATATTGTTT
TATAATACATT
CTTCAGATATTTAAATTTCTGTGTATCATCCTATAAAACAGAGATACATTCAGTGCATTTAGTATACTG
AGTGAACTGGT
ACCTGTGACATTCAAGATAACTGTTTCACGCACGCTGGCAGACGAACACCAATAGTATGATGAAGAACT
GACCATGGTGT
AAGAGGTTTGATGGAGTTTCTTTTTTTTTAGAAGAGGTTGATAAGCCAACAGATGAGGAGTAACAAGTAA
CTCGCAACATT
GTATAACATAAGTTTACATCAAATCAGAATTTACTAAGAAAATCAATCCATTCAAAAGGCACTCAATCA
TTGAAAAAACG
AGCTTAATGAGTAGACGGTCTGTTCATATGAAACAATTGAAAGGGTTGAATATTGTTTGGAAAATTATA
TAATTCATGTC
AAACTGGGAGGCTTAAATTATGGTCACTCCACAGATTATGAAACGTAGTTACACAATTCTTGGACCTGG
AAATCCCACAA
GAGAGCGTTAGTTAGTTTGCACTCTCCTCACCAGTTAAACTACCCATGATTCTCCAATGTGGCTTATTT
AAGTATCAGAC
AACAGATACATGGTTTCCAAGTGGTCTCATTTTTGGTTTACTGGAGTCTGCATTCCCCACAAAAGTACC
TTTCAAAACTA
ATTAATGTAGCTTCTATTTGATAGCCTCTGTTATGGAAATAGATTTGCTCTGCCCAGTGGGTGTAATTA
TTCCCAGCTGG
AACTATTCCGATAGATATGTTTTAATGTCAATTTAAATCTTGTAATAATAGTAAGGATGCGGTTTATCC
GCGATCTTCTT
AATACCTGTGGAGTTACTCCAGAACAGAGGTTCAATTTTTTCTTGGTTGGTAAATTATCCGAGTAACAC
GGGGTAGCTTG
GTTACTCCAGTTGAGAATGTAAACTATAGATGAAGATTTCAACACGCAATTATTACCCCACCTTGGCGA
ATTACTAATCG
ACTATTTGTTAATCCAGAAAAAATTATACACAAACACTGCCTTTTTTAAAAAAAGCGTTATTTTGATG
GAACGATAATT
AACGATGGTTCTGCACAAAAATGTGGTCCAAAGCCCCAGACTATTCTGAAGTATGATTTGTTACTTAAT
TTAGTGAATAA
TTAAACATAAAATCTGGAGAAAAATTTTTTTTTTGCTCTCATGACCAGTGGCAAATTCTTGGTAACGAG
GCTTAACATTA
ATCCGCAAATTACCTGGCAACAGAGAAAACACCCAGAAAGTTCTGTCGTATGAGAAAACCTACAGTTGT
TTCCGATTTCT
CCGAGCACTAAACATAAAGAGACCAGTAATGCTAAAAAAATTTTTATTTCTGCATTACTGTTTTAGCA
AATACACGTCT
AATTTATTGTATTTGTTAAACATTCTTTTCCTGAAATTTTAAGAAAATGTTTTGGTTTGTTGGAATTCC
ATTTAAACGGT
ACTTTGGGGTGCAGACAGCAATCCATTTGGAGAGTGGCAAGTCTACACGAATTTAGCTAAGGTTCACTA
TATCGTGTAAC
AAGAAATTTCTATACCAAATAAACAGCACTTGATTGAACTACAATATGTAAAAACTTGCTTTTATTACC
AGTCTTCATAC
ATACCCCGGTCTTCTCTTTTCAATATTCTGTA
```

FIG. 21

```
>retrotransposon_5 3742bp Tca1-like LTR: 2443-2830
TTAGAAAACAGGAAACAGCAATAGAGAGCAATAATTGAAAAATAGTGTTGTCAACAATAGAACAAATTG
GTCAAACTTTA
AATGCAAAACATGAAATTCCCAATTTCCAGAATAAATAATATCAGCATACATGGCCCCGAAAACTACTT
TACCGTGTCGC
TTTAACCCCCCCCTTCCTAAAACGAGACAATTAGACATACATTCCACAATTATCATAATCCCCTTTTTT
TTCCTTACAAA
ACACTTTATTTTTGTCGTTTTCGTTATTTGCTTCGACGACATTGTAAACTCTTTGGATTTGCAGTAGTA
GTGCTCCTGGT
GTAAGGTGGGTTTGGTTGTAGAGTAAAAGAAACGACAATTGATTACACCTCGATATGCATACGCATGGC
AAAGAGAATAC
CGAGTTAATAGTGAGTCTATTAGTGTTGCAGGAAAAGTTATACGAACAACATTTTGTTTAGTGTGGATA
TTCCAGATCAA
CAACAATATGACTAAAATCATAGCTCTAATTTTCAGTTTACCTTTGTTTATTACGATACTGCCACAGTC
GTGCTGTACCA
GGGTCAGTTTTAGAAAAACTATTCTAGAAATGATGAGTAGAAATGTACTATTATGAGCAATATTTCAAA
AAGTGAAATTA
TAATTGCTGCTGACAACACCAACAATACATACAAATTTGGAAACGAGCAAATCGAGAAAATTTCAATCC
GTTTAGCAAGT
TGTTCGTTGTCGTCATTGTCGATTAGTTTCAGTTTCTAGAGGTGAAATTTTCTATGGCACCAAAACCAA
AGCCTCAATTT
TAATTTACTCTGTGTGGTACAAAATACATTAGAGAGGATCCTCTCCAAACAGGATTGCAGGAAGTTTTA
CACGAGAATGA
TTTACTACACGACGTTGAATTAAAAAGCTCAACCAGTTTGTCAGCAATTTTGTTCTATCTGTTCAATTT
CTTGTATAAAA
TAAAGCAATATGAGAGAGCATCTAAATCAATAATGTCAACACAATATTAAACTTTGAGAAGGATTGTTC
AACAAAACAAT
CCGATGAATAGAAGAAGAATAATATCAAATTGTTCCTGATTGATTGTTGTTATTTATTTTTTATCTCCG
AATTCCTGCAC
AATGGCTCAACAACAGCCAACACGGATCACACATTAAATTTTTTTTCGTGCAGGACCCCGTGGTGGTG
GCTGTGGCTGT
GATTGTGATCATTGTAGTTTCTGCCTTGATGATGACAAAAAATGATAGAGTTCAGTATGAGGAAGAAAT
TAAGCGATATC
GGTTTATGATGTGTTTAGTTATTAATTGCTCTCAATGGTTTTCAACAACGTATACAAAACTGGTGGTGC
TTGAAACGAAT
GAGTAATACAGATCTAATTAAGCTGTGATTTTCTAAGTTTGCCTTGTCTCTACAGTTCAAAAAAAAAGA
ACAGAACACCT
CAGAGGCTGTTGTGATGCAATTTTTAGGAACCTCAACAACAACCACTGACTGATCTAAGCCAGCATCTG
TTTAATGGGTT
TTCAAAAAGAATGGGGCAAACGGGGAATTGAACCCCGGGCCTCCTCGAATTTTGTGTTTGGTGAACAAC
CCAAACGAGGA
ATCATACCACTAGACCATTCGCCCAATTCGATGACTTGGAATTATTCTAGTTATTTTTGACATACAAAG
CTCAGCTTTAT
TACAGATAGTCATGTTTGCATGGATGAATTAGTACTACTAATAATATAAGAAAACTAGTTAATTGGAGT
CAATGTCTTAT
ACATGTCTTCTGATGGGTTATGCATTGATTAATTATGAATTTCTTTTAAATACAATCTATTGCTATTAT
TTGTATGTAAA
ACTTTACCCAAAAACCAACAAAAAAGAGTGGTCTTGGATAAAGATTAAAGTAATTCCAAAAAGATTTGG
TAATTAGCTAT
ATTGTTTGACGTACATCTATAACTACAAATAGCCATTCAGTTTGATTATGTATATTGACATAGTTGGA
TTTGTAATTTC
TGTTAAAATGGAAAACCCTAATCAAATGTATATGTTGAATAGGTAGTTAAATTGTACAACCTACTACTT
GTTGTCAATTG
AATTCAGAGCCAATACTTATATCTCCTGGAAACTGATACACAAACGAATTGTTAAACTATAACACTCGA
CGTTCACATCT
AAGGATTCATCGTCGTTAAGATTTATACTCATTAGCAAACTCACTTGCCATATTAAACACTTCTCAATC
TATTTCCACA
ATCCAATTAATCAGCACGAAAACTAAGATACTATATATATCTGCCTATACCTGATATACACATGGCACA
TGGCGTATCCC
ACAAAAAACCGTCAAGACAACACCAATATGACAATGCCAATTATACAATTGCATATACCACGTGACTTC
ATTTTATGGTC
ATGAGAAATTAACTTATCATGGGGTTAGGCGAGAATATCAACTGTTCGCTATAGAGAGATTTCCTAGCC
GGAATGCACGA
CAATCCTGAGACGGAAGTCGATCGACGATGCCCATGGTGCGTGGTGAAAAATTTTCTTAGAAAATTTGT
TCTTTCCTTCA
ACTGCTTTGAAGAAAGGGAGGTTCAAGTGGTTTAAGTACGACGGTCACAAAGATTGCGGCTTATGAGGC
CCGAACTGAGT
TGAAATACAAAATCAAGATATAATTATATACCTTACTTGTCTATATTGTTTTATAATACATTCTTCAGA
TATTTAAATTT
CTGTGTATCATTCTATAAAACAGAGATACATTCAGTACATTTAGTATACTGAGTGAACTGGTACCTGTG
ACATTCAAGAT
AACTGTTTCGCGCACGCTGGCAGACGAACATCAACACTGATCATTTGTTTTTTTTTTATTTCTCCTTTT
TCTCCTTTTTC
TTTCTTTTTTCTTCTTTCTTCAGACGTTGTTGATTTATTTTATCGACAGCATCCTTTTCTTTGGCCACA
TATCCAAGCGA
TATACTGGCCAAAGCGAAGTCCTTTTATAAAGCAATGCTACCAAATGTAACAGTTCGAGGTCAGAAGAT
TAAGCGGGTAT
GTTCACACGGATATTTTATGGGGTATCACTTGTACCAAACACTTTGATACGATAAGAATATTTGTAATA
CTAACTTCAGT
GTCTTTCATAATCAGCTCATAACCTGTTGGAATTTAAATTCGTATGTTGTTCATTCAAAATTTTGATAA
ATGGGACGAGA
AATCATCGTTGCCTCCTAATTAGATTATGACTTAGTACTAACTAAACTGTTTATCATTTTTTAAAGCGT
TGGGCTCCATG
TTAGAATAGATTATTAGGGCGGTACGTATTTCATAATTTATATATAGGTACTTATTTTTACTAATTTAT
TGCACAGGAAA
AGATAAAGGTATCGATTATACCTATCAGCAAGGTTTAAGCAAAATGAAGTATTTTTACCATATTTTTC
CATTTTTATAT
AGATACATCAAGAGGTTTATTTTAAGTTCACCTGGATAAACCATTCAACTAACCCAATTGAATTGAATG
ACAATTTGATC
TCCAAAGAGGGATTCATTTCTATTCTGGAGAGATAAACGTCATTGTTTAGGAAAGAGCAAGAGATAAGA
AATCTTTTGTA
TATTGTATATATATTATTAATGTTATATTACACTATTGTTTGTTTGTTTGTTATAATTATATGTGAGAT
TTCATATGTAA
GATGTTGTTATCTCTTTCCATTATTTAGCTTTTTTGAAAAAGCTATCAATGGCTCCACGTTT
```

FIG. 22

```
>retrotransposon_6 1438bp Tca1-like LTR: 91-479
GTGTAGATGCAATAGGTGTATGAAATGTATCTAGATTATATCATGAAGCCCTTGCCAATAAAATCTAGC
CAAAAATTTGT
GTACTGCAATTGTTCGCTATAGAGAGATATCCTAGCCGGAATGCACGACAATCCTGAGACGGAAGTCGA
TCGTCGATGCC
CATGGTGCGTGGTGAAAAATTNTCTTAGAAAATTTGTTCTTTCCTTCAACTGCTTTTAAGAGAAGGGAG
GTTCAAGTGGT
TTAAGTACGACGGTCACAAAGATTGCGGCTTATGAGGCCCGAACTGAGTTGAAATACAAAATCAAGATA
TAATTATATAC
CTTACTTGTCTATATTGTTTTATAATACATTCTTCAGATATTTAAATTTCTGTGTATCATCCTATAAAA
CAGAGATACAT
TCAGTACATTTAGTATACTGAGTGAACTGGTACCTGTGACATTCAAGATAACTGTTTCGCGCACGCTGG
CAGACGAACAG
CAATTCTGTAATTGTCGTAGAGTAGCAACAAATCTTCCCGATGATTGGTACTTGTGTTAGTCTACACGA
CATGTGTTTTG
GTACACTTGAACTGTATGTCCAAGAATGGAAACATATGCGGGAAGGACGCGAAAGATGAGTTTGGTATA
GAAGGGATAAG
AACTGTAAAATATATTATGTAGTTATATATTTTAATTATGGGAAATTGAGTGTTTATTCTGTTCAACAA
GTTTCAACCGT
AGAGATTACATTTAAAGTCTGTGGTCGAAATCCACAAGATACAGCAAATTCATGAATTCACCTATTTAA
ATCAAGTTTAC
CAAGCACCATTGCCTAGAACTTGCCATATCATCAATTAAGTCAGACATTACTAATTTGAGCAAAGCTTT
TAGCTTAATGG
GCCAACTAATTTAAGTCGAATTGGTAATGCAATCTGTTCTTCATTTGAGTCGCTTGCTACGGCTCCATG
ACACATCCATT
TGATTGTTTTAATTCGAGCAATTATCCACCATAACTCTCAGTAATATCATTAACAGTTTTACGCTTAAT
AAGCATAGAAA
GTTGTATGAAGTTGTCTCCTAGGTATGCTAGAGAGATTTGTATATACGACCAGTAAAGAGTGTGATGAG
GTGTTTACTGT
AGGGTAAATTGCAATTGACTTGAGTTGATAGCGGTTATTACAAAAGTATAGATTCAACAAATTAAGACA
AGTACCAAACG
ATAGGCCGAATGTGACTTATACCGTTGAAGTTCAAGCGTTTTTAACAAATAGAAATGTGAGATTAATGA
GTTCGACAAAT
GTTTTACTAGATACTATTAATTTCGATGTACTATATAAGTTTAACCAGCTATAACCGGCAGAGCAGACT
TCCTGAAACTC
AAATTGGTTGTGTTTGGACTTGAGTTACACCACAAAGTTTGACAATCGTGAGGACATAGCAACCTATCA
AGCCACTCA
```

FIG. 23

```
>retrotransposon_7 1304bp Tca1-like LTR: 749-1133
TGAAGATCTGGCTTTGGCCAAAGTATCAGCTGCATTAGATACTGTCATTGGCATTGGCTTGAACCCACT
GGCTGTGGATG
TAACTGTGGAGCCAAAAGCTCGTAAAGCTTTGGCGTTCATGGAGAAAAATCTTTTAACAGACATTGTAT
AAACGTTGAAG
ATTAAAGAAAAAAAAAACAGAAAGATTACGAATAATTTGTTTTTAATTGGTGGGTATGAGGTGTTGCGC
AGTCGACTCAA
CAATTCTCTTTTGGTGCACAAAGTTGGTTTTATGGTCAACAATTACGGAGTACTGTCTGTAGTGATGTT
GAATCTAAGAC
GGAAATGCCTCCTTTACATTTGTTTCTATTCTCTTAAAATACATATTCAATTGTGTGTTTTAATTGAAA
ATTTGTTCATC
TTCATCTGATGATTGTGTAATCTTTGCGGGGGGGGGCGTGTCATGAACCAATCTCTTTGAGTCATAGG
ACGAGTCATCC
TATTGTGACTCATGGCTCATCTTACTCTCTTACTAATCTCTTACTTCATCTGTTTACTATAAATATGTC
TACTACTCCTC
TATTTTATTACCTCGTTTACTATTTTTATTCAATATATGATCTTATCTTTAAATTTCTTTTGACAAATA
CAATCAACTTA
CAAAACAAAAGAAAAAAGACTAATAAAATAGAATTAATGAAAAAAAAAAAAGACTAATAAAAGAAAAAG
AAAGAAGACTA
ACAAAAGAAAAAACAAACCGGAGAACCCTTCGCTGTAGAGGAATTTCCTAGCCGGATTGCACGACAATC
CTGAGACGGAA
TTCGATCGTTGATGACCGTGGTGCGAGGTGAAAAGTTTTCGTAGAAATTTTGTTCTCTCTTTCAAACTG
CTTTTAAGAAA
ATGAGGTTCAAGTGGTTTAAGTACGACGGTCACAAAGATTGCGACTTATGAGGACCGAACTAAGTTGAA
ATACAAAATCA
AGATATAATTATATACCTTACTTGTCTATATTGTTTTATAATACATTCTTCAGATATTTAAATTCCTGT
GTATCATCCTA
TAAAACAGACATACATTCAGTACATTTAATATACTGAGTGAGCTTGTATCTGTGACATTCAAGATATGT
TTCGCGCACGC
TGACAGACAAACATTTGGTTGTAAAAAAAAAAATATTGAAGAACCTCATCACCAAGATGTTTGAAAAAA
AAAAAAATCAA
ATACTTAATCGCAAGCTTTTCAATTTATTGATTGTTTGAATTAATTGAATATAAACAAAAAAAAAAAGA
ATTCAAATTCA
TTTGACATGTCAGTGGAAGTTAGA
```

FIG. 24A

```
>retrotransposon_8 3604bp POL protein: 591-3575
AGCCCCAAAATGGTTTTCCTAGNGGAGGATGGAATGGATGGGACCACCCACCAATTTGGTTCCCGGAAT
TTGGTTTAAAA
AAAAGTTTACGGGGATGATTTATTTCCAAACCCAGATGTTTCCTGCTGCTGAAAGAATTGGAAAAGCTC
TTTTCAGTNAC
AATCTAACTGAGAGAACTTGAAAGGGATCAGCATTTTTGTTATGTCAACATTTAATGACCAATGACCAC
CAGCACGATGA
TATTATTCTTAAATTTCTCGTTAGCGGTGTCTCACCATGGTACTTACATCTGCAAATTTACATGCTGTC
ATATAAACTTG
GATTCTCAAATTTGTTTTTAGAGATTTATGCTCAACATTATGAATTGTATAAAGCAGATCCCATTTACA
AATTGCCAGAT
AGTATGACATTGTTGAATGAAATAAGATCAAATAGAGATTATCCTAAAGTGGTAAATGCTGCAAAAAAT
ACAGTACAAGT
CAATAATGTTTCATCCAAGAACAATAAAAAGAAGGATGAATGACAACAATTAGCCAATAAAATTGAGGA
AGTAGGACGTT
ATAGCGAAATAAACGCAACATCTACATATCATGAAATTGGCGATACCAACAAAAACCAAAGGACAATTA
ATATTGAATTT
GAAAAATCATACAAAATTAAGTGAACAAAAGAAGAAAACAAACCTATTGGTATATGATCTGGGAGCCAC
AGTATCCGTGG
TGAATGATAAGACTTTACTTAACGACATTAAAGAATCAAATATCGAAATTGCAACTGCTGAAGGGGAGA
CATCTACGGCT
TATGCTTTAGGTACTCTAACCATATCTGTGAATGGATTGAATGCGAAATTAGATGGTGTTCTATACTTG
CCATCTATTCA
ATTAAACTTAATATCTATAAAACAATTTGAAGATTTATGCTACGCAATTTTGATTTCCGAAAATTTAAT
GTTTCTAGTTC
ACAGTGACCACGAACCTACGGTCATTGCGAAATATTCACCTAAAGATGACTTATACTCAGGCCCAAGAT
CGGGAAACTTT
CTTAAGAAGAATCATAATGAACAAAACCAAATTTTGCTTGACACTGCTAAAAAACTATTAGGATCAGAG
AACATATTTCT
GGAGAAATCACTGAAAAATCCAATGATTGATCAAGGAAAATTAGATCCGTTGAAAATGAACAATAAAGT
AGAAAGAGTTA
ACTATGTCAGCATACACAACATCAAACAAGAAGTGGCAGACAAATATATGATAAAAGATCTTTACTACT
ATCATTTATTA
ATTAATCACCTTTCACATGAAAAACTACAATTATTAGTAAAAAGGGGAGTGATTAAACCAGTCAAATCT
ACTTCGGCTGA
GTCGGCCATTTTAAATTGTCAGATATGTGTTGCAGCCCATGCAAAATTAGCTAGCCATAATCACACTCA
ACAACGGGAAT
TGGAGCGACCATTACAACGCCTCCATTTGGATACCGCCGGACCATTTACCTCAAATAAAACTAAGAGCT
ATCTTACAACC
GTGATTGATCAATTTTCCAGATATACTGAAGTTATTGTATCTGACACCAAAGCAGTCAAACAAAGCATA
TTGCATAGACT
TAGGGTCTGGAACAATAGATTTCAGTTTAAGATCGCGGAGATAAGATATGATAATGCATTGGAGTATCC
ATCGGCTGAGG
AGTTAGAGGAGTTAGGAATTTATAAACACCTTCTCCCAAACTACTCTCCTATGCTTAACGGTACAGCTG
AAGCAACCAAC
CGCCCCATTGTCCAAGGTATTTATAAGGTAGTGTTAAATTTTAGTTGTCAAGTATTAATACTTTTCCCA
TTTATAGTGGA
GTATGCGGTTCATATCCGGAATCATACACCTATAAAAGAATTTGATGGTGCTACTCCTTATGAACGTTA
CTATGGTTTAT
CTAAATACGTCATACCATTTTTTCAGTTTGGAACCGACGTTTTGATAAAATGTGCTAGTGTACAAGAAG
CTATTTCATTA
AAACTACCATCTTCAAGAGATAAAGCTTTTCCTACAGTGATGTTTGGTGCTTTTCTCGGTTACGGCTCA
GATTCCTTTAC
CTTCAGAGTTTTAGTTTCCACGAAAGGATATCCAGTTATTACAACATCAAACATCCGTCCAATAGCGAC
GATGCAAGTAC
TCAATGACTATTTGGCATACATATCGGAGAATAGCTCAATAAGCTATGACGATACATTCTTATCACCTT
```

FIG. 24B

```
TGAATCACCCA
ATGATTCGCACAAACCAACATGATAGACGTGGAGACAATATAAATGTCGAATATGAAAACCGTCCAAAT
GTACCATTTGA
ATATCATGCTGAACCTCCTCGTACAAATTCATCGACGGGAATTATCGATCGACCAGATATTAGACCTAG
AGCTGATCCCA
CCTGGCAACGTATGCCTGATGCCAACATACATCAGGAAACAACAACTGTACAGACTCCTGATCATGGGG
AGTTAGATACC
ATGATCAACAACGAACACCAACTACCACGATCTGGGGAGGGTAATTACCCCGGGCAACAGGTGCGCACC
GATATTATTGG
GCAATTCGAGATCGCGGGCCTACCACTCTAAACACTCCGATCGATCTAGGTGTACCCGATGAAACAGA
CGATATTAGTA
TGACATCAGAGAATCCAATTGATTCCCCAAATTCCGAGATGATCATATCCCCATCTTTACCCACAAATG
AATTGGAACAT
CAAATCGATATCAGTTCAGGGGAGATGTCGTTATTGCAAACGAATATGGAAGCAGATAACGAATTGAAA
ACAAATGAAAT
GGTATTATACAAATCAAAAAATGATGGTATTATCATTCAACAACAACAATTCACTGAAAATTTGTCAGA
TGAAAATGAAG
AAGATTCATCAACAGATGAGGAAACATTGGAAGACAAAAAACAACAGCGATTGGAATATAATATTTCAC
CAAACGATGAG
TGGATAAATAATGACGTTCAGAACGAAGATGACACACAAGTGCCACATGTTAAGGAACCAATCAATTAT
GAAACTCAAAG
TAGAAATGGAACAAACATGCCACGAATTGAAATGGGCATAATAGAAACTTAAGTGATGATGGAAAGAA
TACACCACGTG
AATTACGTATGGTCACCTACGATAATAATAAAAAAATTCAAAAGTACCAAAACAGTAATATCGAGATCC
TGGAACCCAGA
AACGAAAATAAAAACCACACATTCATTGAAAGCAACTTAGAATTACTTGACAATCAAGAAATGTTTCAA
GAAGATCCTCA
AGTTGAAGATATTCGATTGACAACTCCAAAAAAGGACAAATCGTTATCACCTGATTTCAATCAAACCCA
TAATGAAATAC
AACTATTCATGGCAGATATCAATGAAGATATGCTAGAAGAATATGATGAAAATATAAATATGAATGAAG
TGTTAGCTGAC
TCCACGGAGACGTTGGACAAAGAATTAGATTTAGATGAAGAAAGTGGAAGGATCGAATATATTGCTGAT
AGAGTTAGAAA
NAAGACAGAGGTACTGATGGTGCGCCACACGGGGAATTNTTTACAGAAAAATGGATAAAGATTTTTGGG
TCCATTAAAAA
GGCC
```

FIG. 25

>retrotransposon_8 POL protein 995aa
MKLAIPTKTKGQLILNLKNHTKLSEQKKKTNLLVYDSGATVSVVNDKTLLNDIKESNIEIATAEGETSTA
YALGTLTISVNGLNAKLDGVLYLPSIQLNLISIKQFEDLCYAILISENLMFLVHSDHEPTVIAKYSPKDD
LYSGPRSGNFLKKNHNEQNQILLDTAKKLLGSENIFSEKSSKNPMIDQGKLDPLKMNNKVERVNYVSIHN
IKQEVADKYMIKDLYYYHLLINHLSHEKLQLLVKRGVIKPVKSTSAESAILNCQICVAAHAKLASHNHTQ
QRELERPLQRLHLDTAGPFTSNKTKSYLTTVIDQFSRYTEVIVSDTKAVKQSILHRLRVWNNRFQFKIAE
IRYDNALEYPSAEELEELGIYKHLLPNYSPMLNGTAEATNRPIVQGIYKVVLNFSCQVLILFPFIVEYAV
HIRNHTPIKEFDGATPYERYYGLSKYVIPFFQFGTDVLIKCASVQEAISLKLPSSRDKAFPTVMFGAFLG
YGSDSFTFRVLVSTKGYPVITTSNIRPIATMQVLNDYLAYISENSSISYDDTFLSPLNHPMIRTNQHDRR
GDNINVEYENRPNVPFEYHAEPPRTNSSTGIIDRPDIRPRADPTWQRMPDANIHQETTTVQTPDHGELDT
MINNEHQLPRSGEGNYPGQQVRTDIIGQFRDRGPTTLNTPIDLGVPDETDDISMTSENPIDSPNSEMIIS
PSLPTNELEHQIDISSGEMSLLQTNMEADNELKTNEMVLYKSKNDGIIIQQQQFTENLSDENEEDSSTDE
ETLEDKKQQRLEYNISPNDEWINNDVQNEDDTQVPHVKEPINYETQSRNGTNMPRIEMGIIENLSDDGKN
TPRELRMVTYDNNKKIQKYQNSNIEISEPRNENKNHTFIESNLELLDNQEMFQEDPQVEDIRLTTPKKDK
SLSPDFNQTHNEIQLFMADINEDMLEEYDENINMNEVLADSTETLDKELDLDEESGRIEYIADRVRXKTE
VSMVRHTGNXLQKNG

FIG. 26

```
>retrotransposon_9 1249bp Tca2-like LTR: 541-820
TCTCTATGTAGGCTGACAGGTGAAAATTATGAATTAATTGCATTGGCCAATGACAAATGAATAGACAAA
ACAGCAAATAA
GGTTGCAAAAGTAGCCCAAACAAACTAGATTTCGGTTACGAATTTTCCATCTTTCAAAACAATGAATTT
GTTTAGAGCTC
TGTGCCATTTATTGCAACTAAAATGAATATGCAATTAAACAATCAGAGATGTATTGGATTATCCCCGTG
GTATACTTTTG
AGTTCACCATTTGTTTTTTTTTGGGGTTAAATTAGTGCTCCTACTAAAAATCGCATTTATCTTACACT
CACCATTTTGA
TAAGTTATCTCTGGTCAATCGCAAATACTATGCTTCTAATTAAGAGTTCTATGTAAATCCCATTTAATT
TTGATCAATCT
ATTGGTTTGAAGTAAGAGTTGATTTTCTGTAAAGATTTATTTGGCCAGTGTAGTTCGGTGTCAAAAATA
TATTATGATGT
ACACTAAAAAACACTAAATTTCAAGTCAATGGGGAACACAAAACTGAATTAATTACTATATGTTGGTTT
GTGCACTATTT
TGTGTCAGAAACTGATCAATGAAAATGATGGTTATTATGAGAATGGAAAATTTTCCATCACACATCAG
GTGATGACAGA
ACTAAACTATATTGTGTAGTATAAATAAGGGTATGAAATACCAACATCCCAGAATATCAACGAGATAGA
AGAGAGGAGTT
TCAATATATATCTTGTGAATAATAACTTCGTTCTAATTCACTATACACAACTAGACGTGTACACGCTCA
ATCTCAGGTAA
AGAAAGTTTATATTCCATCACTATATAACAACAATCAGGCTTTGCAAAAAAACATTTAAAACTAATACT
GGTAATATGGA
AATATAACGCCTCGTAGTTCTACGCACGTGGCATCCTTTATCTATTTATTCAATTTACCCCTAATTTAT
GAATTAGCTTA
ATAAGAGCAGTCAAATTAACACGGCTCAATTAATAGTACTTAATAATATGAAGCCGATCAATTAACCGA
TCCTTTGAATA
ATTTGAAAATAAAATAAAGTAATATAAATAGGTATGCATTTTCCCTACATTTATTTCCTCTTTCTATTT
TAATTTGTTTC
CTAAACAGCAACAACAACAATTGAAATTCAAAAATGGTTTCTGTTTCTAAATTATTGAACAATGGATTG
TTATTAGCTGG
TCAAAGTGTCTTCCAAGATGTTGCTACTCCACAGCAAGCTTCTGTGCAA
```

FIG. 27

```
>retrotransposon_10 5611bp Tca2-like LTR: 1136-1414
TCTCTATGTAGGCTGACAGGTGAAAATTATGAATTAATTGCATTGGCCAATGACAAATGAATAGACAAA
ACAGCAAATAA
GGTTGCAAAAGTAGCCCAAACAAACTAGATTTCGGTTACGAATTTTCCATCTTTCAAAACAATGAATTT
GTTTAGAGCTC
TGTGCCATTTATTGCAACTAAAATGAATATGCAATTAAACAATCAGAGATGTATTGGATTATCCCCGTG
GTATACTTTTG
AGTTCACCATTTGTTTTTTTTTTGGGGTTAAATTAGTGCTCCTACTAAAAATCGCATTTATCTTACACT
CACCATTTTGA
TAAGTTATCTCTGGTCAATCGCAAATACTATGCTTCTAATTAAGAGTTCTATGTAAATCCCATTTAATT
TTGATCAATCT
ATTGGTTTGAAGTAAGAGTTGATTTTCTGTAAAGATTTATTTGGCCAGTGTAGTTCGGTGTCAAAAATA
TATTATGATGT
ACACTAAAAAACACTAAATTTCAAGTCAATGGGGAACACAAAACTGAATTAATTACTATATGTTGGTTT
GTGCACTATTT
TGTGTCAGAAACTGATCAATGAAAATGATGGTTATTATGAGAATGGAAAATTTTCCATCACACATCAG
GTGATGACAGA
ACTAAACTATATTGTGTAGTATAAATAAGGGTATGAAATACCAACATCCCAGAATATCAACGAGATAGA
AGAGAGGAGTT
TCAATATATATCTTGTGAATAATAACTTCGTTCTAATTCACTATACACAACTAGACGTGTACACGCTCA
ATCTCAGGTAA
AGAAAGTTTATATTCCATCACTATATAACAACAATCAGGCTTTGCAAAAAAACATTTAAAACTAATACT
GGTAATATGGA
AATATAACGCCTCGTAGTTCTACGCACGTGGCATCCTTTATCTATTTATTCAATTTACCCCTAATTTAT
GAATTAGCTTA
ATAAGACAGTCAAATTAACACGGCTCAATTAATAGTACTTAATAATATGAAGCCGATCAATTAACCGA
TCCTTTGAATA
ATTTGAAAATAAAATAAAGTAATATAAATAGGTATGCATTTTCCCTACATTTATTTCCTCTTTCTATTT
TAATTTGTTTC
CTAAACAGCAACAACAACAATTGAAATTCAAAAATGGTTTCTGTTTCTAAATTATTGAACAATGGATTG
TTATTAGCTGG
TCAAAGTGTCTTCCAAGATGTTGCTACTCCACAGCAAGCTTCTGTGCAACAATATAACATCGTCAATTC
TCTTGGCGGTA
GTGCCCCTTATATTCAAAGAAACGGATATGGGATTTCTACTGATATCCCTGCTGGTTGTGAAATTGCTC
AAATTCAATTG
TATTCAAGACATGGTGAAAGATACCCAAGTAAAAGTAATGGTAAAAGTTTAGAAGCAATTTATGCTAAA
TTTGAAAACTA
CAAAGGTACTTTTAAAGGTGATTTGGCTTTCTTAAATGATTATACTTATTTTGTTACTGATAAAAACAA
TTACGAAAAGG
AAACTAGCCCAAAAAATTCTGAAGGAACCTATGCCGGTACAACCAATGCCTTGCGTCACGGTGCTGCGT
TTAGAGCCAAA
TATGGATCCTTATACAAGGAAAATTCAACATTACCAGTTTTCTCTTCCAATTCAGGTAGATGTTACCAA
ACTTCAAGATA
TTTTGCTAGAGGATTTTTAGGTGATGACTTTAAAGAAGGTAAAACTGTCAAGTTTAACATCATTTCTGA
AGATGCTGATG
TTGGTGCCAATAGTTTGACTCCAAGAAGTGCATGTTCCAAGAACAAAGAACGGAGCAGTAGTACTGCCA
AAAAATATAAC
ACAACATATTTAAATGCTATTGCTGAAAGATTAGTTAAACCAAACCCAGGTTTGAATTTGACTACAAGT
GATGTCAACAA
TTTATTCAGTTGGTGTGCTTATGAAATCAACGTCAGAGGAAGTTCACCATTCTGTGATTTATTCACCAA
TGAAGAATTCA
TTAAGAACTCTTATGGTAATGATCTTTCCAAATATTATTCTAATGGTGCTGGTAATAATTACACCAGAA
TCATTGGTTCA
GTGATTTTGAATTCATCCTTGGAACTTTTAAAAGACACCGAGAACTCTAATCAAGTATGGTTATCATTT
GCTCATGATAC
TGATTTAGAAATTTTCCATTCTGCTTTAGGATTATTGGAACCAGCTGAAGATTTACCAACATCTTACAT
CCCATTCCCTA
ACCCATACGTCCATTCTTCTATTGTTCCACAAGGTGCCAGAATATACACAGAAAAACTTCAATGTGGAA
ACGATGCTTAT
GTTAGATACATTATCAACGATGCTGTCGTGCCAATTCCAAAATGTGCTACTGGTCCAGGGTTCTCTTGT
AAACTTGATGA
TTTTGAAAATTTCGTTAAAGAAAGAATTGGAGATGTTGACTTTATTAAACAATGTGGTGTCAATAGTAC
CTACCCATCTG
AGCTTACTTTCTACTGGGATTATAAAAATGTCACTTACAATGCTCCTTTAGAATTGTAAGACATCATTA
GATCAATTTAG
ATATCCAAACATTTATTCGTTATTCTCTTCGTATATTATTTATATTCTTCCTTTTCTTGAAAAAAAAAA
TAGACAATTTA
TTTAGACTTTATAACTTTTACTTCGTGTTGCAACAAATTGAGCATTTTACACGAAACTTTAAATAATTG
AATCCTTCGAA
AACCAAAGTTTTATTGGTCGACGGGTTGGTTAACATGGAATATATCACTTTCTAATAACTATGTCACAC
CAACAAATATC
AATATGAGTGTTTCAGACAAATACCCAGAACTTGTTAGACAATTTTTCCTTCTTGATGAAGTGAAGGAA
ATTTTGCCGAA
CTATCCAAAATACAAAATTTTACTGCAAACTCCTGAAGTCGATCGTGAATACTACAAAAACATCACCAG
TCCTGAATTCA
TTAGACAATGGCAGCCAGAAGTCCTCAATCACTACCGAAATAACTGGACCGAAGTCACTCCTCTTTGTG
CTATTGTACAT
GATAGAACCATTGATGCCGGTTTGAGAATCCAAAAGTTTTTCCATCCATCCATCTTACCGAATGAACTT
CATGGCGATGT
TTGGATACTGGTAAAAGAGAACAAAGAAGAACTCGATGCCTTTATAGAAAATGTGCAATGTCTTCAAAA
TTATGTTAGAG
ATAGCTCCAACAGTAAATACACTTATTATCGTTGTGAGTATTGCAAAAAGAATAAAGGTGTTAAAAGTA
AAAAAACTGAT
TGCAAGCATAAAATTGCAGTACATGCTCTTGAAGGTGGAAAATACAAAATAGTCTGGCACTTTCAGCAT
AACCATGCTTT
```

FIG. 28

```
>retrotransposon_11 1308bp Tca2-like LTR: 136-416
TGGTGCCATTTTTAGAATTGATGTCTGAAATAGAATATGAGGTCCAGAGAAGTTTTATTTTTGTTATAC
ATCATTTTTTT
TTTTTGCTTTGTCTCACCGAATATTATTTGATTCCTAAAAAATTGTAATACCCTGTGTTGGTTTGTGCA
CTATTTTGTGT
CAGAAACTGATCTATGAAAATGATGGTTATTATGAGAATGGAAAATTTTTCCATCACACATCAGGTGAT
GACAGAACTAA
ATTATATTGTGTAGTATAATAAAGGGTATGAAATACCAACATCCCAGGATATCAATTATATAGAAGGGA
AGGAGTTTCAA
TATATATCTTGTGAATAATAACTTCGTTCTAATTCACTATTCACAACTAGGCGTGTACACGCTGAATCT
CAGGTAAAGAA
AGTTTATATTCCATCACTCTGAAGTCATACATTAATATTAAATAAACAATCTAACACTAGCATGCATTC
ATAACCTATAG
ATCATTCTAAACAAGCTGTTAACACAAATCCAATCAATTGAATTTATCATATAATGAAGTAACTTTTTT
CAAGCAACAT
CTATTCTTTTATTAATCTCGACGTCTGTTTGATTAAGTTGCTCTAACATTTTATTTAGATCCTTCTCTA
TATTTTCTGCA
ATATCAAACACCGATTGCTTTTTGTCTGAAGTTGCTGGTATATCACCACTTCCGCCAATTGTCGTATTT
CCACTGTCCTT
TGTTACTGACAGATTGGCACTGACATTACCTGAATTGTTCATGTTTGCTGTTGAAAGAGCAGGAACTGT
ACTTGGATAAG
CAGCCGATTCAAAAGAAGATGTGGACATGAGTGTCAAGAAAATGTGTAGAATCAGTACAAGACTGGAAA
ACAGAAGGAAC
AAAGTGAACTGGATATTGTAGTTTTGTTGATAGTACTCGCGAGCTTTAATTTTTTTTGTAACTGGCGG
AATCAGATCTT
ATGCAATACTCAAATCCAAAGAAACAGTCAATCCAGATGAAAGGCATGTAATCGCTAGTTTTCATAAAC
AGAATCATGTT
ACTAGTCATATTTTCTATAAAAATTCAATACTTCATTCTTTTTGTTCAATACTAACTATAAATGCTTAC
AAATAGATTCA
AATTTCAACCAGATCCACCACTTCATTAGGCTCAACCAATTCTTCATAAATAGAAACGTCTTCCTCAGC
CAAGCTTAATT
GATGGGAAACCCTAGCTTGCATTGAAGGAAAAATACATAATCCAAATAACAAACTGTCTTTCCNAATAT
TCTCAAAATTC
GACTTCACCGTCTTCCAACCAAGCAGGT
```

FIG. 29

```
>retrotransposon_12 1672bp Tca2-like LTR: 1346-1533
CCTATCAGGTACTTCCCCACTTGGATTGGCTTCTGCCTCTCTTCTTCTCCCAACCATCATCCCAATATC
ATTCCACCCAT
CGTCTTCATCGTTGTCGTCTTTTGTTGGTNTCTCTTCTTGTTTTTCTAGTTTACCACTATAAAAATCAA
TCAATTCAGTT
TGTTTTATGGCATCAGATTTATAAATTTTTTAATTTTATCAACATAATTATCAACAATCCAATCAAGA
TGTAATTTATT
CAATTTTTCTTGTAAAGAATCACCACCACCATTTCCTATTCCTTCCATTCTTGATAATATATTCCAATT
AGTTTCATGAC
ATAATTTCGTTAATTCATCTAAATCATTCAATTGTTGTTTATCATTAATAATTTGATTTATATTGATGG
AAATTTTATCA
ATTAAATTTTTAGAAATTTTAGAATTTAAATAATTTTTGATTATAGGATATTGTAATTCATTTATAAAT
CTAATTAAATT
AGTAATTGATTTAATAAAATTGTTGTCCTCGTTGTCTGATACAATTTCTAATTTAATAGTATCTTCCAA
TTCATCAACAA
TCAAACTAAGTTGTTTTGAAGGGGTGGGGGTGGAGTCCCCCAATATTGAATCCACTAATTTATCCCAAT
TTTCCTTATAT
TTATCGTATGCATTCATATTATTATGTCCATTTTTCAATAAAAACCGATTGAAATCTTGTAAAATTGCT
ATATTAGTAAT
AGTCAATGGATCAGGAATTAAAAGAATAGTTAAATATTCATTCAATTGATTAACAAAATTTTCATAAAG
TGAATCGACTC
GTTTCTTGATTTGTTTATATATAATATATTGAGAATTTGTATCAATGATGATTTGTTTAAATAAATTAT
TTAAATATTGT
AAATCTAATATACTTTGTAATGTTTTCGGTTTCCCCAAATACGTTTCAATTTCTTTTAATTTAGAATTG
ATCTCTTGTAA
TTCATTCAATTGTTGTAAATTGTCAGTAACGATTTCAAATTTATTATTCAATTCAGTAATTGTTAAATC
AGTTAAATTGT
TACTTTCAGTGGTATTTGAATCTTGAGGAATTTCTTCAAATTGTTTTCGGAAATCATTATCATTTTCAA
GGGTTGTTTTG
TTTATTTTGGATAATGTTTTATTTATGTTCTGTTCAATATCTTTTAAATATAATTCTTGATCTTCTAAT
TGTTGTTCAAT
CGATGGCATTATTGGTGTTGTATAAAAATGGAATTTTGTAAAGTTGAATGTGTTGGCAACACTTGTGTT
TGTATGGGCGT
ATATTTTTTGAGGAGATCAAAGCAAAAAATATTTTGAGACTTATACACGCAACATACAGAACAGTTGTT
GGTTTGTGCAC
TATTTTGTGTCAGAAACTGATCAATGAAAATGATGGTTATTATGAGAATGGAAAATTTTTCCATCACAC
ATCAGGTGATG
ACAGAACTAAACTATATTGTGTAGTATAAATAAGGGTATGAAATACCAACATCCCAGAATATCAACGAG
GATAGAANGGG
ANGGAGTTTCAATTANAATAATCCTGTNGAATAAATAAACTTCCGGNTCCTAAATTCNNCTAATACCNA
CCAAACCTTAG
NACCGTNGTAACANCGCCTCCAATCCTCCANGGGAAAAAGAAAANGTTTTAATAATTTCCCNATCCCGG
ATT
```

FIG. 30

```
>retrotransposon_13 690bp Tca2-like LTR: 464-690
TGATACGATTGAATGGTGGAGACAAAATATCCGATGTGTTGAAAGATAAAATTGTACTCGAATATCCCA
CAATATATGTT
GCTGCAAATGACGAGTGTTTACAAGATAGAATTATAGATAGCCTTCAATTGGCCGAGGAGGAAGAAGAT
GACACCACTGA
CTCAAGTGAGGATGATTCTAGTGACTCAGAGAGTGATGATGATGATAGTGATAGTGGTAGTGAAACCAG
TAGTATTGGAG
ACGGTTCAGGTGAAGATAACGATTCTGATTCGGCACCGGAAGAGACATCTCTGAAACTACCACCTTTTT
CACAGAAATTC
TTTGAAGCGTCAGCTGAGCCAAAACCAATAATAGAAGAGATAGGATCTAACAAGACTGTAGAAGAACCA
TAACGAATGAA
TATAAAATACTTGTATTATGTAGTGCCAATAAAAGTTGAAACGGTCGCACTACTTTTTAGTCCTGTTGG
TTTGTGCACTA
TTTTGTGTCAGAAACTGATCTATGAAAATGATGGTTATTATGAGAATGGAAAACTTTTCCATCACACAT
CAGGTGATGAC
AGAACTAAACTATATTGTATAGTATAAATAAGGGTATGAAATACCAACATCCCAGAATATTAATTATAT
AGAANGGAAGG
AGTTTAATATATATCCTGTGGAATAACAACTTCGGTCTAATTCACTATAC
```

FIG. 31

```
>retrotransposon_14 1912bp POL protein: 1169-1839
CTAGGTTTTAATTCACTATCATAAAGATCAATGGTTAGCCCAAAATTAAAATATGGAAGCCAAAACTTC
CGTGGTCAAAA
AATGAACTAAGAAGCTAAAGTCTTTTTGAAACAGTATGCCATTATGTTTTTCAGATGTTTTTACTTGGT
TGTTATATTAA
AATCCAAAGCTCTGGCTCTTATCAAGAATTTGTCAGTCAACTCATCATCAAATGAGTGGATATATTACT
TTCAAGAATCA
TCATTACCAAGTTGTCAAACGATTGCTAAGCAAATGTTGAAGAATACTGATTATTTCAGTTTTGAGAAA
CCTAACCCCAA
AGATAATTTAAGGAGAATCAAAATTTGAAAGAAAAGGATGAAAAGTTGGAGAAAGAAACCCTATTGAAA
ATTTAAGTACT
GATTGTTTCAGAAAATCATTGAATATGAAACAACAGAAAGGATATTTTACCAACTAATGAACATTTTCC
TCCCTTATACA
CCTTAAAATACATTAAATCCTTCTGGAATAGTTTTTTCTCACAAGACATTTTGGTGTATAACATTGGTA
CTATTGTTGCT
GTCATGACAAATAAGGAATGCTACAAAACGTCAAGGTAGAAGCTATCGATGTTTTTTCCAGCTAATGAC
AGGACAACGTT
AGAAACGAAGTGTGCAGACGATTTGGTTACAAAGATTGCAAGTGTATCAATTATGCTAGCATATACCTT
ATATTTTCGTT
GAGAGTATTTTTATCATCGTTGGTCTGCAAAACTTCAAAGAAGGGGTGCTATATGTGTTAAATGCTGAG
AATCGAACACT
GTATCTCATGGCGATAAAATTCAAAATATTGTCGTTAGTATGAGAAGATTTTGCTGATATTTACTTATA
TTTCACAATGT
TCAGTAAAGATCCTTATGACGGTGGTACAATATGGGACATGCTATCTGACACGTTGACAACCACTAAAA
TCAGCTGTTAC
CGATAGAGACCATACAGATTGACGCAACACATAAGTATACTCGAAAAGCTAACCCACCATATCAGGCAT
CAAGCCAAAAA
TCAATTTTGACTGAAAATGGACGTCATTAACTCTGAGTCGCTAAAATCAAGGTATGAAATATTTGCCAA
AGAGGAAATCG
ATCAGAGTCGCAATTTCTGTTCAATATTCAACCAAATACAATTTTCCAACCTATAAATCTCCACCATCT
GTGTTATGTGC
TGTCATTGAGTTTGCAACTGATATTTTTGCTATATCTTTACGTTGCAAAATATGCGGGGTGATGTTAAA
CTTACCCGAAT
TCTCCGTGTATCACATGTTATTATGCCAAATATGCATATCTAGGAAAACAGTCTCAACCATCTAACACA
CACATTTTCTC
ACCACTGAAGCTATGAAGATAGCCCATTCGGGAACGGTAAACGACGTAGCGGGAAAAATGTGCTTAAAA
GAATATGGGAA
AATAAACGGGTAGACGTCATTTCCCAGTACCATATTCTATTCAGTCGAACGTCTTCATTCTTATCAACG
GGGGACTGGTC
CAGAGACCTTTCTTATTTTATTGTGATTCAGTAGCGTCTACCATATACAATGATATTGTAACTTCCGAT
CAAGTGGAAAC
ACCGGGAGCTTCCAAAGTATGGTATCCGAATATAAAGCCACCCAAAATCCAATTCACCACGAGCTAACA
CCTGGGGAAAA
CGAGGTGTCTAAACCTCCTCAACTTGATTTCGAGACTTCGGTAGTAGGGAAGTTTAAAGGGCCTATTAC
AACCACAAAAG
TGGCACCACCACCCTCCATGGGAGGTCTATTAAGTACATGGAAACGCATGCTCTGGTTGATACATCACC
TCAATCAAAAA
AATTGGTGTTCCACATTCGAAGGAACTAAAACCGACGAGAACCTATCACACGGTGTCGACGATGATAAG
AAA
```

FIG. 32A

```
>retrotransposon_15 6140bp POL protein:   1555-4302; LTR regions: 979-
1292, 5212-5525
AGTAAAAAAAGAAGAAAAAAAAGCTAAAATTGGGACAATATGCTAAGTATATATAGGGGAAGACGTCGA
ACAGCAACCAC
GGAAAAATAATAGTGATTGTCTTTATCCGTTATTGGCTGGATGGCGACGCCACAACCTGAAATTGGTT
CCAACTGTTGA
GGATGATTTATGTTTGTGATTAGAACTAAAATCATTCGAGAAAAAAGGAATAGGAGAGAACCAACTTTA
GTCGTGTAAAA
AGTAACATCTGCCAATTATAAACTATACGTAGTCCAAATAATTTACGGTATATTTCTGTACCCCTTCTT
GGCAATATCAC
AAGAATATCATAATGTTCATGAACCCTCTTTGAACACGTAGACAAGTAAACCCAATGAGGGGGCAGTGT
TCTATTCTTGT
AAACTGCGCACCAAAAACGGGGCTTAAAAAATAAGTTATGAAAACTATAAATAACCATGAAAATCACCC
TACTCCCTTCC
TCCCTTCCTTCCTTCCTTCCTTCCTTTTCTCTTTTCCTCTACCCACACTACTCACAATGTTCGGTATTT
TTGAGGAAAAC
TACGATTCTGTTTACAAAGGCAACCACGAAGCCAAGTTCTCTCACGAAGCAGTTGCTGGTGCTGCTTCA
TTTGCTGCTGT
CAAGTTGTTTGAAGATAGACAAAGAAGAGAAGGGAAACCAGTTAGTCACGCCTTTGCTAAAGAAGCTTT
AGCTGCTATTG
CTGGTGGAGAAGTCGACAAATTATTTGAAACCAAAGGGTTGGACTATTTGGATAGAGAGAGACTTAGAG
ATCAAGCTATC
AACAACGCTCAAAGAGGTTACGACGACCATTACGGTCAACACGAAGAATGGTCTCCAGAACACAGACCA
CCTTTTGACTA
CCAAAGATATTAAGTAGAAACTGTGTAGTGAATTTACAATTTTTTTGACAAGAATTAACTTAAACCTCG
TTTTTAGGTTT
TGTGCGGCTTTTGTCAATTGACGATCCTGTATATTTCGTCATAATTCACACATTCTTAAAATTATGCAC
ACATCCTTGAA
ATGTGTTAATATTCCCAACATTATCAATTATATGTGTTCAGAATTGGTTGCAAAGTTATCAACTCAATT
CACGCTATATA
AACCTTACAAATTCTCTACATTTTTATATTTTTTATATTGGCTTTTCTTTTAGAATCAATCAATACTT
TTTTTATCATT
TAGATACATCTTTCATCTATTAATAGATTATCTTTCTATATATCAAAACACGACACAGTCACGTGCCAA
AAAGGATATAA
GAAGGAACTTCAGAAAATTAATTTTCTGATTATACTACTTACTAGATTTCATAAAGTCAATATCTGATT
GATACAACTTG
GTTCATTATTCATAAAACTTTACAACTAATTCNACAAGNAAACCCNACAAAAAAATCCNAATNAAATAA
```

FIG. 32B

```
TCNNNNNAATA
TTATAATTAATTAATTACAAAAAAAAACAAAAAAATACACACACACATACACACACACAAAATCTTGTT
GCAAAAAAAAA
AAAATAATAATAATATAATAAGAATTAATTAACAATGTCGTTTCCACGGACACATTCACCAAGACCATC
TGGTTCACGAG
AACAGGAAGATCTCACACTGATGATTAAAGCTTTTAGAGATTCAATGGAAGCTAAGCTTGACTTGCATT
CGCAGAAGCTT
ACTGCTTTGGTAGCAAACATTCCCAGAACGGACGAAGGGTTTGAAGATTTATCACAAAGGATCACTGTT
CTTAAAAATCA
TCAAAAAGCATTTTTGCCCAAACAAGAAAAAGAAATCGGAAGTCTTCTCCACAGACAAAGAGAGGAAGA
AGGTGATATTA
AGGATTTCAAAACAGTCGTTGGTGAAGAAAAAGAAGAATTGCACCAGGTTGAAGATTTCGTTTTAAAAG
ATCAAGAAGAA
TTACGAAACGTCGAAAAGAAAGTTTTGAAAGAAGAAGAAGAATTGCAAAAAGTGGAAGAGTCAATGGAA
AAGGAAAAACA
AGAGTTATACCAGGTTGAAGACTTTATTTTGCAAAGAGATGAGACGGTAAAGAAACTTGGAGAAAGCAA
TCAATCTCAAC
AGGAACCATATACACCTGCAACTTCTGGTTCGGATCAGAGATTCAGATCTCAACAACCTAACATTGGAA
ATACCTTAGCG
CAGGATCTAGCATTAATTCCAAAATTAGATCTGGAAATTTGCAAAATTGCAGTCAAATATCCAAAATTA
TTTGAAACAAA
ATTAAGACCACCACCACCCAGAGACTTTCAATATAAAATTCAACTCACAGACCACACTCAAATTTATTC
AAAACCATATA
AATGCAATCAAGAAGAACAAGCTCTCATCAAGGATTTCATCAATGAAAAATTAGAAGCAGGCGTTTTGG
TACCAGCTCCA
ATTGATGCTTGGTTACACCCAATATTTCCAATCAGAAAAACCAATGCCAACCAATCCTCCACCAAAATA
GCAGTTGATTT
AAGACGTCTCAATAAGGTCACAGTACGAATGTACACTTATCCAACAGACACAAAAGACCTCTTATCCTC
ACTAACAGATT
CCCACTATTTTAGCGCTTTAGACTTAAAGAATGCGTTCTATCAGGTAAGCATACACAAGGATAGTATAA
AATATTTGGG
ATTTCAACATCCGAGGGGAATTATTGCTTTACAACTTTACCGTTTGGAGCAATCAATTCCCCAACCATC
TTTACTAACTT
TGTGAGACAGATTTTAGAGGGGATCCCATGTATATTTATATACATGGATGATATCCTCATCCATACTAA
AACCTTACATG
ACCACATGTCATTACTCAGGAGAATCATGGAGAAACTAAATGAGCATCAGTTTCAAATGAATTATAACA
AGATGCAATTA
TTAACAACAAAAATCAATTTCTTAGGGTACAGCATTCAAGCGAACAAAATATCACCAGATATTTCCAAA
ATTCAAGCAAT
ACAAAATTGGGAATTGCCCACGACCACTACTCAAATCAGAGCATTTGTCAATTTCAGCAACCACTTTCG
CATCTTCATCC
CAGAAATAGCAAAATTTACTAATCCATTAAATGAATTATTGAAGAACAACAATGGTAAAAACATAAAGA
TTGAACACACC
CAAGCATCCATTGATGGTTACAAGGCATTAAAAGCCGCCATCATTGGATTGCCGACGCTTCAACTTTAC
AATCCAAAACT
ACCAACCATCATTTTCACAGATGCTAGCCACATGGTAGTAGGAGGATATTTATGTCAACCAACATTCAG
AAATGACAAAG
AAGTCCTTGTCCCAATTGCATTTTCATCACATAAATTAACAGAAACACAAAGCAGATATGCTGCTATGG
AAAAGGAACTT
TTGGCAATTATTGTGATATTGGAAAAATTTAGATATCACTGCAGCAATACGGTAGAGATCTATACAGAT
TATCAAAGTTT
GGCATCATATTTAGATAAGAAAACTACTCCACCACCGAGAATTGCTAGGTTTTTAGATCTAATTGGATC
ATTTTCCCCAA
AAGTGTACTATTTAAGTGGAAAGAAAAATTTCGTTGCTGATATCATTACAAGATATCAAACTCAAAATA
TTAAGGAATTG
GTAGATGAAGACAAGATACTAGGACAGACTTTTACAGTCAAGAGAAATTTGAAACAACAACTATTACCA
AGATTGGAAGC
AATTGAATTGGAAAATCTTAATGAATCACAGGTTCACAAAATCCAAACTTCATTAGAACAACAACAACA
ACATGATTTGG
AAGACAATGATGAAGAGTTACCTCTCCAACTGTTTAAATTAATGAATGATGAGTTATTTGTAATCATTA
ACAACCAACTT
TTAAAATACCTTCCAAGACTGGAATACAATGATATTTGTCAAACAATCCATGACAAACACCATCCATCA
ACTAGAGTAAC
AGACTACTTATGCACACTCGCATATTGGCATCCTGACCATCTATTAATTGCTACAAACATTACGAGAAA
GTGTCACTATT
GTCAACTAAACACGTCAATTCGTGAGGCCATTAGACCATACCGACCACTTGAACCACTCAAGGCATTTA
```

FIG. 32C

```
GCAGATGGGGA
ATGGACTACTCTGGACCATACTTTAACACAGTCCAACACAGGTACATATTAGTAGCCGTGGAATATGTC
ACTGGTTTAAC
TATTGCAGTACCAACATTGCACAAAGACGCAGATAACGCAATCAGTCTTTTACAATCAATCATTCTGAT
CATGTCAGCAC
CTACAGAATTAGTTACAGATCAAGGTAAAAAAATTTTCATCACAAGCTTTGGCTACCCTATGTGACCAG
AATAACATACA
AGACCATATTACCTCCGCCCACCACCCACGTGGGAATGGTCGGGTTGAGAAGGTGAACCACCTATTGAA
GAAAATATTGA
AAGCATTAACTAACGATACGATGCAAGACTGGGATTTAAAACTATATGACGCTTTAAGAATCTACAATG
CTACACCTACA
ATTTTTAACTACACTCCACTTTATCTTGCACTTGGAATTGAACCACACCATAATTTAAATCAATTACAA
AAAGATTTAAT
TGAAAATTTGCAAAAAGAATTGCCCCCAGAGGTCCAATCCACAGAAGAACACGAAGAAAACCCAAATGA
TGAACAACAAG
AAGAGGGCAGAGAACAACAAATTTCAAGAGAAGAACAACAGGACGGCAGAGATCTTGTACACTTAAGAA
TTTACGAATTG
GAAGCAATTAAGAAAGCTCGCAAGTTACACACAAATTTGAAAACACGAAGAAACGCAGTCCAAAATATG
TTAAAGGAACC
ATATGGCATTCCAGCACTTTTTACAAAGGGACAATGGGTATACAGAATTAGAGCTAAAGCACGAAAATA
TGAATCAAATT
TTGATGGTCCATATCAAGTTCAAGAAGTATTAGGTAAAGGTGCTTATAAATTGAGAGACATCACTGGAA
GAGAAAAGGA
ATCTACAATCAGGATCAGTTGAAGTTAGCATATTCAGCAGACAACGATCCAATACAGGTTTTTAGTTCT
TTTAATAAAGA
ATATGATCGAGTACAACAAAAATTGTTAGACAAAATTCAATCAGAAAGAGATCATCAATTAAATTGTTT
GTCAGTCCAAC
ATTTACACAGACAAAGAAGGTTACTCGATATATCCAGCTGTCTTGAGCAAATTCTGCAATAATTTCGCT
AATCATTGGAG
GAAAGGGTAGATGACGATCCTGCATATTTCGTCATAATTCACACATTCTTAAAATTATTCACACATCCT
TGAAATGTGTT
AATATTCCCAACATTATCAATTATATGTGTTCAGAATTGGTTGCAAAGTTATCAACTCAATTCACGCTA
TATAAACCTTA
CAATTTCTCTACATTTTTATATTTTTTATATTGGCTTTTCTTTTAGAATCAATCAATACTTTTTTTAT
CATTTAGATAC
ATCTTTCATCTATTAATAGATTATCTTTCTATATATCAAAACACGACACAGTCACGTGCCAAAAAGGAT
ATAAGAAGGAA
CTTCACTGAAATGCAATCACTTCGCATTATTCAAGATCTTTTTCTATTGTGGCTGGTTTTGGTGATTG
CTATGTTTGGT
TTTTTTTTTCTGGAACACAAGCAACCAAATTTTTCAACTGTTACGTCACACATTTACTGTCACACTCAC
TTACTGGCACA
CAAAGAACAAAGCAATCATCCGGCGTAAACTTTTGGTCTTTGAGATGCAAAAGTTGCAAAGCAATTGGC
ACTTCTACTAA
GATGGTTCCAGTAAAAATTGTGTTTTATAGTACATCAATAATCAAACAATACTTAATGATGTAACAATA
CCTTAAAAAGC
CCCCACTATATTTCTTTTTTTTTTAAGTTTGCTATATAATTTATTATGTGTTATTATTATTGACTTAAT
TGTTAGCATTT
TATTGCTTGAGATCGTTTGCTTGTCACTCCACCCTGAAGAAAATTTGAATAATTGCTATTAATTTATTT
ATTTCTTGGAC
ACACCCCGTATTGTCGTATGGGTATAAATTCCGTTTCATTTCTCCTCCCTATTTCATATTTCATAACTT
CTTAAATCAAT
ATTCAAACCAACTCCAAATTATAAACTATCAAACAAAGAAACAAAAAAACACACAACACA
```

FIG. 33

```
>retrotransposon_15 POL protein 916aa
MSFPRTHSPRPSGSREQEDLTSMIKAFRDSMEAKLDLHSQKLTALVANIPRTDEGFEDLSQRITVLKNHQ
KAFLPKQEKEIGSLLHRQREEEGDIKDFKTVVGEEKEELHQVEDFVLKDQEELRNVEKKVLKEEEELQKV
EESMEKEKQELYQVEDFILQRDETVKKLGESNQSQQEPYTPATSGSDQRFRSQQPNIGNTLAQDLALIPK
LDSEICKIAVKYPKLFETKLRPPPPRDFQYKIQLTDHTQIYSKPYKCNQEEQALIKDFINEKLEAGVLVP
APIDAWLHPIFPIRKTNANQSSTKIAVDLRRLNKVTVRMYTYPTDTKDLLSSLTDSHYFSALDLKNAFYQ
VSIHKDSIKYFGISTSEGNYCFTTLPFGAINSPTIFTNFVRQILEGIPCIFIYMDDILIHTKTLHDHMSL
LRRIMEKLNEHQFQMNYNKMQLLTTKINFLGYSIQANKISPDISKIQAIQNWELPTTTTQIRAFVNFSNH
FRIFIPEIAKFTNPLNELLKNNNGKNIKIEHTQASIDGYKALKAAIIGLPTLQLYNPKLPTIIFTDASHM
VVGGYLCQPTFRNDKEVLVPIAFSSHKLTETQSRYAAMEKELLAIIVILEKFRYHCSNTVEIYTDYQSLA
SYLDKKTTPPPRIARFLDLIGSFSPKVYYLSGKKNFVADIITRYQTQNIKELVDEDKILGQTFTVKRNLK
QQLLPRLEAIELENLNESQVHKIQTSLEQQQQHDLEDNDEELPLQSFKLMNDELFVIINNQLLKYLPRSE
YNDICQTIHDKHHPSTRVTDYLCTLAYWHPDHLLIATNITRKCHYCQLNTSIREAIRPYRPLEPLKAFSR
WGMDYSGPYFNTVQHRYILVAVEYVTGLTIAVPTLHKDADNAISLLQSIISIMSAPTELVTDQGKKIFIT
SFGYPM
```

FIG. 34A

```
>retrotransposon_16 3470bp POL protein: 309-2552
GTATATTTCAAGACGTTATTTCTTGTGACCCTTGGATGACTACTCAAAATACTTGACAGTTCAACCCAC
TATGCAACAAA
TCTGATGCTACTGCCGAAATTATCGAATTCATCAATCATTGGGAAAAGTTCTTTCTGGGAAATGGCAAT
TACCATACGAA
AATTCTCCGGTCGGATAATGGAGGGGAATTCTTAAACAAAACATTGACTACCTATCTTGATTCAAAATA
TATTACTCACC
AAACCTCCAATGCCTATGAACATCATGAGAATGGCGCTGCAGAACGAGCTATTAGATCGGTTAAAGACA
TGGCTCGAGTA
ATATTGCTTCAATCCAAATTACCAGTGCCGTTTTGGTCCCTAGCAACCCGATGTGCTGCGTTTGTTATG
AATCGTCTTCC
TCATAAACAATAAATGGTAAGATTCCTTATGAAGTATGGACTAAACAACTTGTCAATCTCAAAATGAT
GAAACCGTTTG
GCTCTCAAGTATATGTGAAAATTCCTATTGGAGTCAAAAGTTTTTCTGCACAAGCACTTTCTGGAATCA
TGGTGGGATAT
GCCACTAATAAGAAAGGCTACCTTGTATATGATCCCACACAAAATCGAATATTCACATCCTCACAAATA
ATATGTCATCC
GAGCATTTATCCAGCAGCCAACCTTACGTTTAACGAACCCTTAATTATCTCATCGAAAGTCACGGCTGC
TCATCTTCACC
CCCTTACCATTTCCAATTTAGTTATTCCACCTACCAATGCTGTATCTGAGACACCTCTTGCAAATTGTG
TGCTCTCCTCA
AATTCGTCAGTATGTCCCAAAGTTTGCCAATTACAAACTGTCTTGGAACATGGGGAGGATAAAATATAT
GCACTGATTAT
ACCAATATCGATCGGCAATATGAAACGCACAAGAACAAATGAAAACAAAATATGCCAGCTAGATGAATC
GAACAATACCA
CCATACCAGATAGTGTAATTTTATCGGCTAACAATGTGTTATTAAACTTAGAATCGAGATCTTCCATTC
CCAAAAGTTAT
AAGGAAGCTATAACATCTAATGAAAAATCCAAATGGGCTGATGCTATGGATAGCGAGTTTAATTCATTA
CAATCCAACAA
CACGTGGTCACTTGAACCACTACCGGAGGGACGCAAAGCTATTGGTGTCAAATGGGTTTATACAATCAA
GGACACCGGTC
GCTACAAGGCTCGCCTTGTGGCACTTGGTTATCGACAACAGGCTGGTGTGGACTTTCTCGAAACGTATG
CTCCCGTGATT
CGTGGAGAATCAATCAAACTAATCTTTGCACTCGCGTCAAAATCCAAACTAAGATTCATTCCATAGAT
GTTACCACAGC
TTTCCTCAACGGGGAAATACTGGAACTCATATTTGTGAAACAACCTCCGGGATATGAAGATAAGAAGCG
TCCTAATCATG
TTTGTAAGCTCAATCGCAGCTTATATGGGCTTAAGCAGCTGCCACTAATGTGGAACATTAAATTAAATG
ATGTACTTATA
AAGGAAGGTTTCCGTCGACTTGGTGGTGACTTAGGGATATACATTAGTAAGGACAAAAGAACAATAATG
GGAGTTTATGT
TGACGACATTCTCATTTGTGGACCTTCTGACAGTGAAATTGAACAAGTAAAGAACAACGTGAGAAAATA
```

FIG. 34B

```
CTTCTCAATAA
CTGATAATGGATTATGCCGAAAATTCCTTGGAATTAACGTCTATCAACAAGCAAATGAAATAAGATTAA
GTTTGAATGAT
TATATAAGGAGAATGATTGAGGAGTTAAAATTATCTGTCTCAGAAACAAACCCAGTATCTATACCATCT
GATGTCAATTA
TGAAATATTTAAAGTTAACGAAAATGATGATGAGAAACCATGTGATCAAACCAAATACCGAAGTTTGAT
AGGCAAGCTCT
TGTTTGCCAGTAATACTATAAGGTTTGACATCGCCTATTCTGTCAACTCCCTATCCAGGTTTATCAACG
ATCCCAAAGAA
AAACATTGGATTGCAGCTGTCAAGGTGGTAAAATATCTCAGTGGTACTCAACGGTATGGTATTTGTTAT
AACGGTAACGG
TGACTTGAATATTTACGCTGATAGTGATTGGGCTTCCACTCCATCTGATCGAAAGTCTATTACGGGGTA
CATTGTTACCT
ATGCTGGAGCGCCGATAAGTTGGCGTTCCAAGAAGCAGAACGTGATAGCCTTGAGTACGACAGAAGCGG
AGTTTATGGCT
CTCACAGAGTCCATAAAGGAAGCCCTTTGGCTAATATACATTTTTCGAGATATTAATGTGATATTGAAA
TTACCAATTGT
GATATATGAAGACAACCTACTGTGTCAGAAATTACTTGAAAATCCTCGATTCCATAATAGGACAAAACA
CATTGACTTGA
AATATAAATTTACCAAAGACCATATAGAAGCTGGTACAATCAAAGTGGAATCAACTAATTCAGCAGATA
ACTTAGCCGAC
ATGCTAACTAAACCTTTACCAAAAATTAAATTTAAACATTTAAGATGGCTAGCAGGATTAAGACCTTTA
GATTGATTAGA
TAATGATAAAATGAAATAAAGATTAATTTGGAGATGCAGGTTGATGGGGAGGATGTTGGAAAAATGAAA
TATGATCAATC
CTGCATCTAGAACCTGTGGCAGAATGAAACCTACGAGATTATGAATGACTTGTGAATACAAGTTGAATG
TTACAGAATGT
TACCAAGAAGGTTACACTTGAATATATGAATGACTAGAAAGTGAATTGAATGTTACAGAACCTGAATAA
CAATGTTACAC
GAATGTGTGAATGATATGAGTTTATCTATAGTAATGTGACATATACACAAAGGTGTGAATGACCGAGAA
AACAGATGTTA
CATTACGGGCACTGGAGAGTGCAAGTCTAAAGAATCTTGGAGTAGAAATAAGTAATATAAAAAGGACCA
AAGATTCTTTA
GAGAAAAGTAAATGAAACTATATTAGATTTTATATAACTAACTAACAAATAAATAAAAAATATAATATG
TCTACAATGCC
ACCAACTTCCAAACGTACTAGAAAGAGAACTAGAACCGATGATAATGCTGAACCAACTATTCAAGATCC
TTCACCGCCAC
TTGCTAATGTTGAACCCACAATTCAAGAGACTCCACCGCTGGTTGAAGTTAGTGATGAGACTAATTCAA
CTGAAATCAAT
GAGACAAATAGTAATACTCATGAAGAAACAAATGTATTAACTAATGTGCACTCCTCTCCAATCGAGACA
GTTACTGAGAG
GAACTTCAATTTTCAACAATAATAATATTGGTTGGATTTACACGTACGTTGTTGTTACAAAGACGTGAG
CAGAGTGAGAG
AGATCAACCTTCATATTCAATCTCATCTCAATCAACGCTCAATTTTTTTTTCTTCTCCCTCTCTTTGTT
GTTTAACTAAG
TTTGTTCCCTTCCATCCAAGCAAGTTAGAA
```

FIG. 35

>retrotransposon_16 POL protein 748aa
MARVILLQSKLPVPFWSLATRCAAFVMNRLPHKTINGKIPYEVWTKQLVNLKMMKPFGSQVYVKIPIGVK
SFSAQALSGIMVGYATNKKGYLVYDPTQNRIFTSSQIICHPSIYPAANLTFNEPLIISSKVTAAHLHPLT
ISNLVIPPTNAVSETPLANCVLSSNSSVCPKVCQLQTVLEHGEDKIYASIIPISIGNMKRTRTNENKICQ
LDESNNTTIPDSVILSANNVLLNLESRSSIPKSYKEAITSNEKSKWADAMDSEFNSLQSNNTWSLEPLPE
GRKAIGVKWVYTIKDTGRYKARLVALGYRQQAGVDFLETYAPVIRGESIKLIFALASKSKLKIHSIDVTT
AFLNGEISELIFVKQPPGYEDKKRPNHVCKLNRSLYGLKQSPLMWNIKLNDVLIKEGFRRLGGDLGIYIS
KDKRTIMGVYVDDILICGPSDSEIEQVKNNVRKYFSITDNGLCRKFLGINVYQQANEIRLSLNDYIRRMI
EELKLSVSETNPVSIPSDVNYEIFKVNENDDEKPCDQTKYRSLIGKLLFASNTIRFDIAYSVNSLSRFIN
DPKEKHWIAAVKVVKYLSGTQRYGICYNGNGDLNIYADSDWASTPSDRKSITGYIVTYAGAPISWRSKKQ
NVIALSTTEAEFMALTESIKEALWLIYIFRDINVILKLPIVIYEDNLSCQKLLENPRFHNRTKHIDLKYK
FTKDHIEAGTIKVESTNSADNLADMLTKPLPKIKFKHLRWLAGLRPLD

FIG. 36

```
>retrotransposon_17 1550bp LTR zeta: 887-1394
GTGTTGTGTTGGGTTTGAATTTCTGTATAACTCAATTTGGAGATTTTTTTTTTTTTTTTGAAATTT
TTATTAGTCGT
GTACATTGTTACAATTGTTTCTCGTTCCCCTTTTTTTTTCCTTTCTTTGTTTTGTTTTGTTTACCTTGT
GATAATTTTAT
ACGTGTTGAGAGGGCTCTCGTCGTGCCCGTGTCCGTTTCCGTTTCCGTGTCCTGTTGGGTCCCCTCCGC
CCATGCCGCAC
CGCACCGTACGGTAATGATATCTGATTGTTGTTGGAGCGTTCTTCGCTAACAGGTTCTTTCTTTTGTT
CAGGGGTTTCG
AAAGATAATGTAGAAACACCAGGGCTTATAACTGAGAGTTAGAGTAGTGGAGATTAGTAGTAGTAGTAC
AATCCTATAGC
CCAAACATTATTGGAGAGATCTTACCAAATAGCAATCATCATGATGTATTTACTACTACATAAATNATT
TAAGACGACAT
TTACCAGCAATAAACAACATGACCAACTAATTAACAAACATTTGAAAAACATAAAGTAATTAGAAAGTT
TAAAAAGTGTA
CAACCAGTGTGGAAAAAGAATGGAATTGGAATTGAACAAAGTTATTAATTACTGAAAAAGGAAATTTAA
TTTCTTGAAAG
GCAAATCTTTGTTTGTTTTTTTTTTTGGGTCTTTTCTTTCATTTAATAAGCGTGGGGTATTAATAGATA
ATGATATTGTT
GTTGTTATTGTGATATTGTTGTGAAATTTGACATATGATAAGATAAGTTTCTTTCTTTTCTTTCAACTA
GTATAATTGAA
CTAAAGACCACCACCACCACCACCACATAGTTAGCAACCTGATATGCTGTTCATGTAACAGTAAATTAT
CTTGGTACTAT
ACCACTTGTTGTAATATAGCTAATGCTAATTCTTGATTAGTGTGGAAAGCCTAATAAGGTTATATTGTG
CACAGGTTAAC
TACCTTAATATAGTTATTGTTAATACAGTTATTGCTGTTGACTACTATTGTTATTGTTAAATTAAAGTG
TTAGGTTGAGT
TAATTGATTAGTGAAAACCAACTAACTACCGTATTAAATTATTGTATTAAGATTGATTCCTATTAAGGA
TAAAACAGAGA
GTGTGTTAGAAAGAGAAAGGGTGGATTATAAATATGTGTAAAATCCCCTTTAGAGACTAACCACTAGAA
ATCTATTGATG
GTTTCATATATAGAGATTAACGATTATATTTATAATATAAGTTGGTAGTTGCTAGTATATNTGAAAGCA
CTACAGTATAG
TATGTCAGAATCAGATCATTTAAACTCTACTAATAATACAGGAAACACTTTCATTAGTCTAGATCAAGC
CAGTACAATAA
TGGCAGATCAAACTCAAGGAGCTAACCCACAACAATGATAATTCATCTTTTTGTCAAGACGATAGTTA
ATGTTACAAGC
ACTTTNATTGGGCTCGAAATAGTGGTAAATAGGGTCCATAGGATATGACCTGTTACAAGTTTATTTCGA
TGATCNAGCCG
GCCTCTGTGATTACGGCAATTATTTTTACC
```

FIG. 37

```
>retrotransposon_18 2132bp LTR zeta: 1418-1926
TTTTTAAAAGAATTAATTAAATATGATGGATGATAGAAATTAAAGGAAAAAGAAGAAGAACAAAACAAA
AGTTTAATTGA
AAAAAAAGGGAGAAATGAATATTGAATTATTCAGCTTTTATATTGCTGATAGATGTTGAAAAAAAAACG
GAAGAATGGGG
ATAGCAAAACTGTGGGTGAGATTAACTCATCTATGGCGCTAAAAGTCTTTTTTTTTTCTCTTTTATTAG
GGGCACATAA
ATTATTCTTTTCATTGATAATCCCGAGTCCGTTTTTTGTTCATTATTCGGAATATATTACCGTATTGGG
AACGATAATTA
TTATTAGTTCTCCCCGATGGTTCGATTTTGCTGGTGCAAAAATATAAATCCGATATAACTTTATTGGTG
CTTTGATAAAT
CCGTTTTATAAGTTGGTAGACATATACAGGATGATAATAATTTAACGGATTTATAAGTTGGAATCATTT
GGATGAATCCG
CTTGGGGAGGCGTTTTCCAATTTTAGAAGTTTAACTATCAATTTTATGTGACATCCGAGTATACACATT
TTGTGAATTTG
ATCTTGTAAACTCACTTGGTGTACCATGGCATTTATAACAACACTTTCTAGAATCGGCTGAGTTACATG
CATTTCCTCTA
TTTGTAGATTAATGGAAATTCATGAAATCGTTCACATTTTTTTCTATAATGAGTATCGTTCGGTTTCCA
TAAGTAGGGGA
CTAAAAATAATTGATATCTCTAATCAGTGACAGCTCTAGTCAACTTGACCGTAATGTTTGACGACCA
TTATATTTCTT
GTTTGAACTATTGATTTATGAGTGTTGTCGTAACAAAAGATCAATTCCCGTCAAAACGCATTTGGCACT
TAATCTTTGAT
TGAACCGATTTTGATCTCAAAACATAGTACCAAGGTCAATTATGTTCGCTAATGAAAGAAAGCTGTGAC
GAAAACCTCAA
ATTCATGAAGAAAGAATTACTGTTGTGGAAAATAAAAAAGTCTTTCTTCTGATACTTTACAAGTCCCTC
AACCACAAATA
CAAAAATGAAAGTTACCCATCGATCTTTTTCATTGGTTAAGAATTAATACGAGAATATCAAATTATCTT
AGAGAGGGTCT
CACAGAGCAACTTTCTGAGGCACACGGTCACCAACATGATTTGTTATAAAAAATTCAACCAAATTTTGG
AAAAAATGAAA
ACAAAACAAAACAAAATCTGAAACATCCCGAAAGTCACAAATGCTTGATTACTTAAAATTACTTATTTG
CTTCAAGACGC
TATTATTATTATTATGACATAATACTACTTGAATAACAGTGAACTGTAATTGTATTAAGAACAAATCAT
AACAAAGGAAG
ATGATGACGATGATGATGACCCCTTGAAATATCCCAGGGCACATGCATTGTGATGATTGTTGTAATATA
GCTAATGCTAA
TTCTTGATTAGTGTGGAAAGCCTAATAAGGTTATATTGTGCACAGGTTAACTACCTTAATATAGTTATT
GTTAATACAGT
TATTGCTGTTGACTACTATTGTTATTGTTAAATTAAAGTGTTAGGTTGAGTTAATTGATTAGTGAAAAC
CAACTAACTAC
CGTATTAAATTATTGTATTAAGATTGATTCCTATTAAGGATAAAACAGAGAGTGTGTTAGAAAGAGAAA
GGGTGGATTAT
AAATATGTGTAAAAATCCCCTTTAGAGACTAATCACTAGAAATCTATTGATGGTTTCATATATAGAGAT
TAACGATTATA
TTTATAATATAAGTTGGTAGTTGCTAGTATATTTGAAAGCACTACAGTATAGTATGTCAGAATCAGATC
ATTTAAACTCT
ACTAATAATACAGGAAACACTTTCATTAGTCTAGATCAAGCCAGTACAATAATGGCAGATCAAACTCAA
GGAGCTAACCC
ACAACAATTACCATATTATATGAAGAAGACTATAACAAAACTGTAGATAGTAGGGGATTGGGTATTTCC
GGGGGAGTAGA
AGTATTGGGGTTATCTAAGTCCATCTTTAACCACCCAACAATCCAACAACAACCCAACNACGTTTTTCC
CCAATTCTCNG
GAGATNACTTGATTAACTTNAAATTTTTCCNTGGCCAAAAAATTTCCTTTTC
```

FIG. 38

```
>retrotransposon_19 1734bp LTR zeta: 767-1274
AATAACCAACCAGCTGCTCATTTTTAGATGTATGTATTTTATAGGAAAATTGAATAACTTGTTATTACT
ATGGCCTGTTT
TCTAAAGCCAAGTTGTTTCTTCTTATATTTTTTTTTCTAAACACCGTTTGTTGAAGATGGCTTTATCC
GTATACTATTG
GGCGTCGATTTTCGCACAAAAGCTTTTATCCACGGAATATTTGCGATAATATAGTACAAAAGTGTTC
TAGTCTTGTAA
ATGTCCAATATTTTTAGTACAACGATGGAAACCCGTATAGCGCAGACACAGTTTGGATAGATTTACGTA
GGTGATGAGGA
GTTAAATTGAATATTCTTGTATAATTTCAAGAGCTGTGACTACTATTTAAATTTTTTCCACTTCACTTT
CTTTCTCTTCT
TTGACATTCAAGTTAGTCTTTCTGTATTTGAATAATACTACATTTATCATGTCTCACGTCTCAATTGTA
ACTGGTGCTTC
TAGAGGTACGTTTTAATGAACAAAATCTATGATGTTGAGACTTCCAATTTGAACTTTAGTACTAACTCA
AATAAAGGCAT
TGGTAAGGCTATCGCCGAAATTCTTTTAAAAACTCCATCTTCAAAAGTTGTGATTGTTGCTAGATCTCA
AGCTCCATTGG
AATCTTTCCAAAAGCAACACGGCTCGGACAGAGTAGCATTTGTTGCTGGTGATATTACAGATCCAGCAA
CGTCTAAGACT
GCTGTTGAAACTGCCATCTCCAAATTTGGTCAATTAAATGCTGTCATGTTGTAATATAGCTAATGCTAA
TTCTTGATTAG
TGTGGAAAGCCTAATAAGGTTATATTGTGCACAGGTTAACTACCTTAATATAGTTATTGTTAATACAGT
TATTGCTGTTG
ACTACTATTGTTATTGTTAAATTAAAGTGTTAGGTTGAGTTAATTGATTAGTGAAAACCAACTAACTAC
CGTATTAAATT
ATTGTATTAAGATTGATTCCTATTAAGGATAAAACAGAGAGTGTGTTAGAAAGAGAAAGGGTGGATTAT
AAATATGTGTA
AAATCCCCTTTAGAGACTAATCACTAGAAATCTATTGATGGTTTCATATATAGAGTTTAACGATTATAT
TTATAATATAA
GTTGGTAGTTGCTAGTATATTTGAAAGCACTACAGTATAGTATGTCAGAATCAGATCATTTAAACTCTA
CTAATAATACA
GGAAACACTTTCATTAGTCTAGATCAAGCCAGTACAATAATGGCAGATCAAACTCAAGGAGTTAACCCA
CAACATTTTGT
AGTCGTAAACTTGAAATTCAAAGAGAAGGGGGGGAATTAAATTGGGTGCAACGTGTTTGTCAAAAATTT
GGTGTGAAAAA
AATTAATTTAACACTCTGCATTGTACCATAGGGAATATAATACCCAGAAATAAGAGAAATTATCACGTG
AGACTAAAACT
AAATATAATAAATTAATATCACAATTGAGAAAGACACTGAAACTAACTTCTTGGTGTATTAATTTTCAA
CACTTGATCAC
AAGTGCGGGATTAATCATAATTGCAAAGAGTGTGTTAGAAAGAGCGAAGGTGGATTATGAATATTGGA
GAATCCTCTTT
AGAGACTATCCGCTAACAAAATAGATGAACTTGCTCAACAGAAACAACTAATCGACTAACTGACTAAAA
TTAATATACTA
AGTATAGATTAAGTTATCACGTTAATATTCTATACTATCCATCTCCATCACTTT
```

FIG. 39A

```
>retrotransposon_20 5734bp LTR zeta: 3344-3851
GAGATTGTAGTGAAGAATTCAGCTCATTATTACTGTTTTGTCGTTGCTGGAAGGAGGAGGGATAATTCA
ATGCGCCACAA
CAGTGTTACTATGCATGTGGTTCTGACTGACTGATATTGTTTAAAAATTAACCAGCTCTCAAATAACAA
AAGTTTAAATT
TTCAAGGTTTGTAAACATGGCAGCTAGTAGTAGGATGGTTCATAATATTAATTAATTATTAGTAATAAT
GGCTAAGTTTT
TGAAGCATTGTTTTAAATTTTCAAATTGAAATTCAATTTCATTACAAATGGATTACTAACGGAATTCCT
AAGCTCAACTG
AATACCGTGATTGAAACATTTGAATTTGTATCTTTTAGATTAGCTATTTTTACTTTTTTGTCATTGTA
GTTGGTTATGA
TAATTACAAGAAACTAAAGTTTAATATTTTAATATTCATTTTCTTTTTTGGCCAACTTGCAAATAACAC
ACAAACCCAAA
ATTAAATAATTAGATTTAATGCATGCATAATTACACAGAATGTTTAGCCTTAACAAGTATTCTAGAAAC
AAGAAAGAAAA
AATGTCGTCTTGGCGTTTATCTTAATTGTATTCTGTAAACTGGGTTAATTCTTATTTCCAACTTTTCAT
TTTTTTGGATC
TTGTATGGAATAAAAATTAAATATGGTATGTTTTAGGGTTGTATTAACAATACTTACAATTATCAATCA
TACAGCTTTAC
TATTTTTATTTATCAGCAAATAGGGGAATTCAAGTTGCATGTGTTATTCAGTGGCAGTGAATCATAAAA
CAGCCAACTTG
CAGCTTATTTCACTCCAGGAGCAATCATCACGGAATTCCGTTTCCCATCTCATTTTCATACTCTGTGGA
TTATGTATAGA
GGCTATTTACAATATCACCAAGCAGTAAAACATTCTCTCCTCAAAATAACAATAAGATTAGTCAAGATG
AACGACTTGAA
TCTATTCATATGCATTACACATTTAGTTTCTATTACAAATAGTGATGCAATGGTGCAAGATTACGTCTT
GTCTGCACTAA
CTATTTGTAACGATGATTATGTGATCAAGAATTGGAATTCTTATTATATTCAGTCGTGAGTGTAAGCTA
TTTCGTTAGGG
TTATCTTAACTCGAAGTTAAAGTTCCAAAACTATTCCATTTGGAGTTTCTGTTGTTGAGAAATACAAAA
TACTCTTCTTG
GTGGGGAGGAAATCCATTAATGATTATAAAATGAAACTCTTGGTAACCTAATTGAAACACCACATTCAG
TACATTTTCAA
CCGTCACTATTATTATTGTGGCAAATGGATTAAACAATAGACCTAACTTAATCTAATGGAAATTTTAAA
```

FIG. 39B

```
TCCATGAAAGG
GGTGAAAATTTGAAATCAAAATAACTATCTGAACTGAAATACCCCATGGATCTGATATCTTATACAATC
TATCAACTAAA
CAGGGAAGAGTACCTGGAATTCCAAATGACAATTCCTATTATAATTATTTAAACAGACTATGCCGTATT
GTTTGTGACAT
TCATTGTTTTCCACAACTCTAATGTCAAATTTTTGTTATTGTCATGTAATCCCGGTGTTTCTTTTTTCT
TTTCGGTGTTG
CGTTCCATGATATTTGTTATCTCTTGTTTAGATTGAGATAAAGAATTGGTTAGCAGTGTAGCCATTTA
TGAGTGGTTTG
TAAAAACAAGAATTACAAGGTTTGAATGAATTCCAGGCAGGCAGTATTATAAAACCTCGAAATAACTAA
TCAAACCATCA
GAAAAGAAAGCTTACTATGATGTACTGCTTAATCTCATATCTATCTTACAAACTTAATTCACTGATTGT
GGCTTGTCCGT
GAATAATTCGGAAACCTTGTCTTTTTCGGTCCAGTAGGGGGTGCCATAGTCTTGGGTGGTGACAAAAAA
AAAAAAAATTA
TAGTTGGGGTGGTGGGGTGTACGTCTGAGTAAGTCAGGGGAATGAACTCAAGACAAAAATAGAAGTTCT
AAACATGGTAC
GTTCTGCTAAGTAATATCATCGATCTATCTATTTTGCTCTAAATTTTCATAAGCAAATCCAGAACTTCC
TCGTCAGTTTC
AATTTCAAGCATACGAAGGGATAGTGATTAAATTATATTTTGAACCTTCTATTACTGATTAAGTGTTCC
TATTAGTCTAC
GGATTAGACGGTTAGAATGGGATTTNCAAAAGCACAAAGGTCAAGACTTATAGGAAATTCATAGAAAAA
ACACTCTGAAG
TACTCGATGGTTGGATATATAATAGTTTTGCTAATTTAAACTCTTGCTGTTCGGCTAAGCTATTGTACC
CAAATGCGGTA
CTCCGATAGTCTTATAAATAATACTTGGCAAAAGTTCAATAAATATATGTCAATGGTATTGCTTTCCAA
TTACCATTGAC
GAGGTTGTAAATTAATTCATACTTAGGTGACATCGATTAATTTAACAAATATGTCTGTTTCAACGCTTA
CATCATCAGTC
TTGCAGGAAAAATGTTATTGCCACGACACCTCAAATTAGCCCAACCCCTTCGTCTACCAAAACAATGTC
AAAAACCCACT
TAAAAGAAGTCGGACAAACCTGAACCCGGTATTTTATAAAGTAGTTTTGTGAATAATATCAGTACAACG
ATTACACTTTC
CGTCTCAAGACTGGAAGTTGCAAAGCCATGACAATTGCTCAACCAAATGTGAATTTTTAGGTTCCATAG
TCTTGATCGGG
TAATGTAAACACTTTAACTTTTAGTAAATGATACCACCAAGAAGAAAGCACTATTTTAAGCTTTATTTA
ACACTATACAT
TGGAAAATAAAAAAGTGGCTATGAGAATTAAACAAGATGACCGAGTAATTAAAATAGTGCTGTCGGTGT
TAAGCAATACC
GCTAGGGTTCAATCAATTAAGTGCTGCTTTTTTTTGTCGTTGTATTTCCATTCCTGCACTCCTTTCTTT
ACTCTTGCAAT
CTAACATATTTTTTTAAAAAGAAAACATATTGATACTTACATGTGGTAACTATTGTCTGATTCATCAA
TTCCGCTCTTC
AATCTCGGTGTTCGGATAATTTCGATGAAATTATAATTACCTGCCGCAATTCTAGAAATTCCTTTTTTT
TCTTTTCTTTT
TCTCGGAGTTGGTTCCAATACAAAGATTGAATTGAATTAGGTGAGAAGAAGAAGAGTCTTAACACCAGA
TGTATTACAGC
TTTAAACTTTGTTTCTAATTTGACCACAAAAAGTTGTCTGGACGCCTCAGTTTGAAATTAGTTTTGGGA
GATTTCTGTTT
TCTCATTGGCCTTACTCTATGGAAGTTTTTATACAAGAGCTTCCTTCTAAAATTAACTCTTTGTGTTGT
AATATAGCTAA
TGCTAATTCTTGATTAGTGTGGAAAGCCTAATAAGGTTATATTGTGCACAGGTTAACTACCTTAATATA
GTTATTGTTAA
TACAGTTATTGCTGTTGACTACTATTGTTATTGTTAAATTAAAGTGTTAGGTTGAGTTAATTGAATAGT
GAAAACCAACT
AACTACCGTATTAAATTATTGTATTAAGATTGATTCCTATTAAGGATAAAACAGAGAGTGTGTTAGAAA
GAGAAAGGGTG
GATTATAAATATGTGTAAAATCCCCTTTAGAGACTAACCACTAGAAATCTATTGATGGTTTCATATATA
GAGATTAACGA
TTATATTTATAATATAAGTTGGTAGTTGCTAGTATATTTGAAAGCACTACAGTTTAGTATGTCAGAATC
AGATCATTTAA
ACTCTACTAATAATACAGGAAACACTTTCATTAGTCTAGATCAAGCCAGTACAATAATGGCAGATCAAA
CTCAAGGAGCT
AACCCACAACACATTCTTCTTGTAAAATTAATTCTATTATAATTCAGGTCTTAGTCGACGCAAAATACC
ATGTTGCAATT
GTCCGTAAACAATTATACAACAATTTAACCAATGCAACATCAATTGAAATCAAGAATTCAACACTTGAA
```

FIG. 39C

```
CATTTTTCTTG
TTTTCAGATCTCGTCAAAACACCAGTCAATAAAGCTTGGAAAGTTTTAGCACAACCATCAAAGTAGAAA
GCCTAACTTAT
AGGTTCGAATTACGTGAATTTTGGTTTCACTAATCACGCCCCAAAAAAATTCANAAAAGCTTAGTATGT
AACATTTATTG
CAAATTTTTTATTGTTCGTCATAAATGATAATTAGTAAATGAGGTTACAGAATAGTTATGTTTTACTTC
ATAACCAATTC
TACTATTTTTTTTGTATTATAACCTCGGATAACACAAACAAAAAAAAGTACTACTACCAATTAATGT
TTAGTAGATTC
TACACAAACTTGATAATGCGGGAGTTATTTTTTTTGAAGCCACTTTATTTTCAGCCGACTTATCTAGC
TACGAGACAGA
ACAATACTTAGCACTAATTCTTAAAATTCCATACTATTTCTATCATTCAAAATGCATTTTAACAATCAA
TTGTCAAATGT
GAATGCAACAAAGTCCTGAATTTATAAAAAAAGTAGATCATTGATGCAAAAGTGAATTCTTTGGAAA
GCTTTACTTTG
AACCGAAAGGAGAAGGCAAGTCGTGCAACAAGTTATTATTTCGTGTACAGTATCCAATTTTGGTTTTTC
GACACTAGGTC
TAGACTCCAGAAACAAAGTCCTAATAAGAAAGGTGTTCAAAAACAATTTAATTTTAGTAAAAAACACA
ACCTGCATTTC
GCAATTTATGACCAAATTGAGTTAGCTAATTATAGGGCATCAACAATAATATCCAGCCTCACACAAATC
AGAAACAGTCA
TATAACAACTCGAATGCAAATATCAAGACTATGTTATGATAAGAGTAGTTGGGCCAATAAGATAAACA
GAAAAAGAAAA
TTTTATATTCTTTAAATCTTTGGGTGACAGATCAGCTCCAATTCTCTTGAAATTGGCACAAATACTTCG
TCTTTTTTCAT
TCATCAGTATATCACGTGTAGAATTGATGCTGATATTCAAAAATTACCCCTAAAGTTGCTTATCAACGC
AACTTAAGATT
TCATACAAGTCGATAACGAATCTGAATTTCAGCTTGCTCTTAGATTAAACAAAATGGTAGATTCAATCA
ATTAGATAACG
CCAAATAACATTTGATGTTTTGCGGCAATATTTGGATGGTGTCAACTAGGAGAAAATTGATTCCCCGCC
ATATCTCATAA
GCCTCTAGCTGTCCACTTTTCTAAATAATTGATATGGATCACCACATTGGGGTCTAAATGAAACAACGT
AACCCGAAAAC
GTGTCAAATTCGGAATTCGTATGTATAATTCAAACAATACAAGAAATATGGAGAAAGCAGATACACACA
TACACACTCAA
AGAGCTTGGTAGAATAACAATAACTTGATATAATACGTACTATTCATACACAATTACTTAATTGATTTG
CAATCATTCCT
AAAAAAATTCTCTTTTATTTTTTTTTAATTGGTAATATCGGTGGTATACAATGATTTACCTAGTTAAA
CAATTGAAAAC
AAGAAAGTATAAAATTTCTTCATTTATTTTGCTTACCCTCTACCTTGGTAATTACACCGATGTGAGTTT
GGAAATCTGAT
AATCCCAGAAATTGGATCTAATTGGNTCATATTTAGATTTCAACAAATCATAAACAGTTCTAGACTCCA
TGTATTTCTTT
TGGTGTGTGTATATTTTTGCCAATGTCTCCAAAGCAAATGGAACTCGTCACTTG
```

FIG. 40

```
>retrotransposon_21 1875bp LTR zeta: 812-1319
CCTCCGGCCGCTAATTACAAGGCTGCTTTATATTGTTATACCTTGGGGTAAATGCCCTCTGGCATTGAG
CTATTTCCAAT
TCCCACTTCGGTATTTTTTTTTACAGCCTCGTTAGACGAGTTCTTGATATTACTAAATTAGTTGTTTAC
TGAGTGGCCTG
ATGGTTCCTCGTCACTCTAGTTTTTGGTCTATATAAGGGTCAGAAATTTCCCTTCTCCTTAGGTCCATC
AAGTCAAGATA
TACATTAGTTGGTAGCATCGTATGGAATTTTCGTATGAACGGCATACCAAGTATTAATTTCCGATCGAA
ATTTTTTAGGA
CGTCTTGATAATCAGGACAAACATCATGAAAGGTCTATACGACGAAAGTTTACTTTACACAAGGGGAGA
CCATATGTCTT
CTTTATTAACAACTAGTTATATAGCGAACAAATAAGTTTATACAGAAATATATGTACACAAACAAAGTT
ATTGTTTATTA
ATTATTTAATTAGCTCGGAAGAATAACTCTGTGATACTGCATACATTCAAACAAAATCAATCTAGTTTC
CAACATCTTTT
TCACTTGGTAATGTAATTATTCTTGTTCTGGCACCGACAATGGGTATTGTTTTGTAGCTGGAGGACTAA
TATGGGTACC
ACCTCAATTTTTGGATCCCAGCTCCCACGCAGGGGTGGCTTCTGATCTAACTCACTTTCGAAAATATCC
TGATAGTTTCC
AATTAATTCAGCAAAATAGCTCTTGTTTGTACCCTTAACCAATGACATGATATCCTTTTTATTATCACC
GATACCACCTG
TGTCTTCGTCTTGTTGTAATATAGCTAATGCTAATTCTTGATTAGTGTGGAAAGCCTAATAAGGTTATA
TTGTGCACAGG
TTAACTACCTTAATATAGTTATTGTTAATACAGTTATTGCTGTTGACTACTATTGTTATTGTTAAATTA
AAGTGTTAGGT
TGAGTTAATTGATTAGTGAAAACCAACTAACTACCGTATTAAATTATTGTATTAAGATTGATTCCTATT
AAGGATAAAAC
AGAGAGTGTGTTAGAAAGAGAAAGGGTGGATTATAAATACGTGTAAAATCCCCTTTAGAGACTAACCAC
TAGAAATCTAT
TGATGGTTTCATAGATAGAGATTAACGATTATATTTATAATATAAGTTGGTAGTTGCTAGTATATTGA
AAGCACTACAG
TATAGTATGTCAGAATCAGATCATTTAAATTCTACTAATAATACAGGAAACACTTTCATTAGTCTAGAT
CAAGCCAGTAC
AATAATGGCAGATCAAACTCAAGGAGCTAACCCACAACACGTCTTCTTCAGTATTAGGGAACAACATAC
TAACTTGACCT
TTTCTAGCTTCAACCAAAAATTCCTCTATATCCATTAATGGAATTTCATCAAACTGAGCAGCCCCAAAA
AACGTTTTGCT
TCCAAAGTCTAAATGAGCATGGAATTTCCTTATGAAAGGTATACCAAGTATTAATTTCTTATGGAAGCT
GTCCACTACAG
CAAAATTCTCTTGGAATGTAATACCATTAAACTGGAACTTGAGGTTAATTATTTGGTTAAAGTTTCTGT
TGATTTTTGGT
CCAATAAAGTACCCAAACTACTAGAGCTCCAACAACATTTTCAGAAAATGGCCAATAATACAATAAGTG
GGTATATTTTA
TCAAAGAGTTTATATTATGGTTACTCGACGGGTATTATTCTCTGTTGGATTAAGGCATCTGGGCGACC
CAGTGGGACCA
AAATTCCAGAGTAGTGGTTTGGTTTAGGACTTTACCAAGGNCCATGATTAGGGAATATTNTAACCAAAA
AATTAAAATTA
CCATTTAATTCNAAAACCTAACCTAAATTCCCTAA
```

FIG. 41

```
>retrotransposon_22 1712bp LTR zeta: 672-1179
TAACCATGGAATTCCTNGAATTANTNATAATTAACCAAATTTTTTAGGGNTTATTAGGACCTAGGATTG
AATTCCATGTT
TATTTAATAATTAANCCCCAGTTTGGCCAACTATGAAATAGTATAATGGTTAAATGCAAAATAAATATA
GTATGAACAAT
ATGATAGTTTTAGTGTGAATTTTGAATAAGAAAAAGAAGGGATAAGGATATTTTTACTAGGAAACTCAA
TTATAATTACT
AATGATAAAAACTCCATCAGCTACTATTATTACTCAAATTTTAAATCATTTGTTTATCACCTACACAAA
CAGGGATTGTC
CAATATTGATTACTAAAATTAGAACAAATAAGAGAATATAATTGAAGTTAAATAATTCTTTTACTAAAT
CTATTGACCAA
GAACTACATCAAGGGAAAGTGTTGCATATACATCTAATGTTTATTCTTGGTTAGAGTATTGATACAAAA
TTATATCATCA
CCAACGAATCACATTAAGGGAAAGTGTTGTGCATATACCTGATGCTTAGTCTTGGTTAAAGTATTTGTG
TGAAAGGTTAT
CGTGACCAAAGATTATAGTAAGGGAAAGTATTATGAATAAATCCAATGTCTACTTTTACAGAAGTATTG
ACATGAGAGAT
TATAACTATCAAGAATTGCATTAAGGGAAAGTGTTGTAATATAGCTAATGCTAATTCTTGATTAGTGTG
GAAAGCCTAAT
AAGGTTATATTGTGCACAGGTTAACTACCTTAATATAGTTATTGTTAATACAGTTATTGCTGTTGACTA
CTATTGTTATT
GTTAAATTAAAGTGTTAGGTTGAGTTAATTGATTAGTGAAAACCAACTAACTACCGTATTAAATTATTG
TATTAAGATTG
ATTCCTATTAAGGATAAAACAGAGAGTGTGTTAGAAAGAGAAAGGGTGGATTATAAATATGTGTAAAAT
CCCCTTTAGAG
ACTAACCACTAGAAATCTATTGATGGTTTCATATATAGAGATTAACGATTATATTTATAATATAAGTTG
GTAGTTGCTAG
TATATTTGAAAGCACTACAGTATAGTATGTCAGAATCAGATCAATTAAACTCTACTAATAATACAGGAA
ACACTTTCATT
AGTCTAGATCAAGCCAGTACAATAATGGCAGATCAAACTCAAGGAGGTAACCCACTACAGGTTATGAGC
CTCGCCCGCTT
ATTGAATTTAGATAATATAGGGGCAATGAAAGCTTTTGAAAGTGTTGATTTTCCTGAATCATTAAAACT
AGAATCCAAGA
TTAATTTTCAAGTGTGGAGAAATGAAATCCTTAGATATGCACGTGGTATTGGTGCTGAGTTTGAAAACT
TTGTATTGAAT
GAAACTCCAGCTCACCTGTATGATCTTAGATTGGGAAATATGCTTCATCAATTATTGATTCGCACTGTG
AAAGAAAAAGT
TAGAATGCCTAGGCAAGAACTTGGAAAATCAGGAAAAGAACTTTATCTTGATCTTATTAAATCATTCGG
TACTCAATACC
CATACGATAAATTTGAGATAGTTAAATACTATTGGGATCAGTTAACAAACCCTTTAATTAATGTGAAGA
GACGTTTTGAA
ATTGAAGAAGTATGGGTTCAATACATTAATGCTCAAACTGCAACAGAGAGAAGTTCTTAATTCATTT
GTTTGGTTACA
TTTGTCAAAATCTATATTACCACAAGAGTACC
```

FIG. 42

```
>retrotransposon_23 1540bp LTR zeta: 467-974
TGTGGAATTAAGATGACTTTGTGATTAAATTGTTGACTTCTTTAAGCCTTTTAATGTGGAGGAAAAAGA
AAAATCTATAA
TTAAAAAAAAAAAGATAAAGCAGATAATTCTTTGATCTTTATATACTTGGTCTATATGTAGTAGGGGA
AAGTCGGAGTC
GGAATTTGAAAAAAAAAGAGAAAAAAGAACGAATATTTAGACTGTAAAATTCAAACCCCTGCTGATTAG
TATATAAAAAA
AATGAGTTCATTTTTCCTTTCTTTTTTTTTTTTCGCGCGGATAGCAACGGTCATTAAGTTAACGAGAT
AAAAAGAAAC
AACCAGATAATTATGAAAAGTTGTGATGGTGTCACGTGCGAACATGAGAGTCATGAATTTTGACGAAAA
CGTCAAGCTTC
AGTTTACAAAAGACCTCTTTATTAAAATCGAATTGCTTATAGGGTCGTCGATGATGAGAAGGTGTATGT
TGTAATATAGC
TAATGCTAATTCTTGATTAGTGTGGAAAGCCTAATAAGGTTATATTGTGCACAGGTTAACTACCTTAAT
ATAGTTATTGT
TAATACAGTTATTGCTGTTGACTACTATTGTTATTGTTAAATTAAAGTGTTAGGTTGAGTTAATTGATT
AGTGAAAACCA
ACTAACTACCGTATTAAATTATTGTATTAAGATTGATTCCTATTAAGGATAAAACAGAGAGTGTGTTAG
AAAGAGAAAGG
GTGGATTATAAATATGTGTAAAATCCCCTTTAGAGACTAACCACTAGAAATCTATTGATGGTTTCATAT
ATAGAGATTAA
AGATTATATTCATAATATAAGTTGGTAGTTGCTAGTATATTTGAAAGCACTACAGTATAGTATGTCAGA
ATCAGATCAAT
TAAACTCTACTAATAATACAGGAAACACTTTCATTAGTCTAGATCAAGCCAGTACAATAATAGCAGATC
AAACTCAAGGA
GGTAACCCACAACATAGAATACGTTTTCAACTACTTAAGTATCCACTAACCTAAATTTTTTTTTAATA
AAATTTCATTG
TATTAGTCTTTCTTACTGCTTTTAATCAACTATAAGTATAGGTTTCCGTTTTTTTTGCAGTAAAATTTA
TCGTTCAGGAG
AAATAACAAAATGTACACGACTTATTCGCAGCATTTTTTTTTTGTTTTGGGTTTTTGTATCAAATTGT
TACAACAACAA
CAACAACCTCAATTCTTAACCAAATCTACCCCTCCTATTTTTTTTNCNCATACACACAATACATCTTAC
ACTATCTTTTG
ATAGGCTTTATNGAAGANGTATTTANGGNGTGTAATGACAATCTGCTTAACNCATATATNTATNTANNG
NNNGTNGTCAA
CAATAGCTTTATCTACTTTTTTTTTTTGGNNACNCCNGNAACTTCAGGNCCACNNNTTTGCCNATTTTG
GGGCCCCNATT
NGGAAAACATGGGNATTGGGANNACAGCTTTTTTTAGGNNNAAANGGGTNTTNCCNTTTNTGGTGGGCT
TGGAAAGNAAC
AGCNTNTAAANNAATGGGCT
```

FIG. 43

```
>retrotransposon_24 2025bp LTR zeta: 787-1294

TGGGGAGCAAATGTGAAATTAAAGAGTGTGGTGATATGTAATTTTTTTCAAAAAAGATTGGATTGACG
AAGCATTATAT
ATTCGTCTAAAAACCATTTTTGCTGGTTCCGCAATAAATCTCGGAGATTATTTCTCGATTACCAATTTA
TGTTGTTTTGT
GACATTTCTTATATTTTGTTCTATTTTACACGACTATTTATTGTTAATAAATATGTCACCTAAAGAATA
TTTCTATTTAG
TTTTACATATGTTTTTTGACGACAATCAACTATTACAAATTAACCTACATTTTTTAATTTGAATATATA
CAATTTATATT
GAATTAACATTACCATTTAGTTTTTGATAAGAATAGATTGCGCTATTTCAAACATTTGTTAAATTATTT
ATTGTGAAACA
ACTATGTAGAATAAAAGTATGAACAAATTCTACGTTCATCATGTGGGGTGTGCCTTCATATATATCTTT
GGATGAGAATG
CCAAGAAAAATGATGGCGTGACAATTCAATACGGCAAAACAAACTAATCCCCTCTAAGATTTTACTAGT
GTGTTTCCCTA
TCGTCTGAGGAAAAGGTAACAAAACATCGTTTAACCAATTGGTGTTTGTTACGATGGTGACGTTGAGTA
CTGCATATAGT
TGCAACGGCAAATTGCATCCAGCGAGTTAACAGCGAATGGCAAAGTGAAGCCTCCGACTTGTGTTCATT
GACTACTGGGA
TTGGACTGGGAATAACGACTTAACTAATTAATGTTCTCGTGGACTCGTTTAGCTAGAACTAACATTTGT
TATAATATAGC
TAATGCTAATTCTTGATTAGTGTGGAAAGCCTAATAAGGTTATATTGCGCACAGGTTAACTCCCTTAAT
ATAGTTATTGT
TAANNCAGTTATTGTTGTTGACTACTATTGTTATTGTTAAATTAAAGTGTTAGGGTTAGTTAATTGATT
AGTGAAAACCA
ACTAACTACCGTATTAAATTATTGTATTAAGATTGATTCCTATTAAGGATAAAACAGAGAGTGTGTTAG
AAAGAGAAAGG
GTGGATTATAAATATGTGTAAAATCCCCTTTAGAGACTAACCACTAGAAATCTATTGATGGTTTCATAT
ATAGAGATTAA
CGATTATATTTATAATATAAGTTGGTAGTTGCTAGTATATTTGAAAGCACTACAGTATAGTATGTCAGA
ATCAGATTATT
TAAACTCTACTAATAATACAGGAAACACTTTCATTAGTCTAGATCAAGCCAGTACAATAATGGCAGATC
AAACTCAAGGA
GCTAACCCACAACAGCATTGATTATATAATCATCTATGTAGCCAATATACACTACCGTCCAAACTCCCA
CTACACACTTG
TAACAGTGTTTTACAAATCTATGAACGAATAACCGATTCAAATGACACAATAAAGAACATTTCACCGAT
TTGAATTGCTA
ATCGGTACTATAATATTGATGGAAGGTTAAGAGTTTAATGCTACCCTAGGTTTACCGGAGATCAACAGT
TGCATATACAA
AACGTGTTATCTGTCTACGAATGGCTTTCTATGTGTATAAAATGTTTCATCAATTGATAATTAATTATT
AATCTGCTTAC
TGAGGTAAACCCCTTTTAATGCAATAGCAAATATGAGGTATTTTTTTGCTATTGACATGCGTATATGAA
TCCATTTGTAT
CAAATTGCCGATATAATGAAATGGAATTAAGGGAAAAAAAAAAGTTTATATCCAAATTCATGCGATTA
ACAGGTTCTTG
TGATTATAATTGGTAACCCCCTCCCCCCTAAAACTCATATCTGCCAAAAGAGGAGGATATTTGAATATG
CTATTATGAAC
CCCATTGATTTTGACTACAATTGGATTTGTCGGGTATTGAAACCCAAACATATTATAATTTGCTATGCG
TTTAAATCAAC
CGTTTACTGGTAGATCCTATACTATAAATACAGCCAACAATCCCCAATTGTTCAGATAAAGTAACACTC
AATATCATTTG
ATCAATCAATCAAGAGGATTACAAA
```

FIG. 44A

```
>retrotransposon_25 3583bp
AAAANNTTCCCCATNGCCTATTCCTAGGNCCCAAAACCAGTTGTCCGAAACTCCATGGATGCCAGAAGT
GGTGGTCCTCC
GCCGTTATGGTTGGAAAAGAAAAAGAAACTTGACGAATTGAAAGTCAAAGAAGAGCGGCAAGAAAGAAG
GAAGAAGGGGC
AAAGAAAAAGGAAGAAGAGGCAAAGAAAAAGGCAGAGGAAGCGAAGAAGTGTTTTATTTTACTTTTCTG
TCAAATTTGCA
CTACTTTTAATTTGTGTGCAAATATTCTATTTTACTTGATTTTTATATACTTTTATTTTACAATACTTT
TTTATAGGACT
TTTTATATCTTTTCTTTATCAACTGTTCGCTATAGGGTAGGTCTTCCAAGCTAATTTTACCCGACACAA
GATGAAATATT
TTCTGTTGAGCACTCGTTGTCGACAGTGAAAAATTTTCACTCAAGAAAATATTTTATCATCACTTTTTC
TAGAAGGGAGG
TTCAAGTGTTGGAGAATAGACAGCGAACACCTGATATTCCCAAGGTCGAATTAGATTGAAAGATAAATA
ATAGTCATATT
TATTTTGTATTTAGTCAATAAATTATCTTTTTATATTTAAATTCTTAGTATTGTCATACCACGTAGATT
GATACGGACAT
ACTTAGCACATTTAACATATATTAAGCACCGATTACCTGTGACATTCCGGAGTTTACTGTTTCGCGCAC
GCTGGCAGACG
AACATCAACTCATCTTTTATACAATATATTCTTACGATTATAACTTTCAATTAAGAAATACAACTTCTT
ATTAGCATTCT
CCTACAAGTTCTTAAGTTCCTAGGAATTTCTTCGAAACTATAATTAAAGACGGAAAAGTGTAAAACAAA
CAGAAAGCAGA
GGAGGCCAAGAAGAAAGCAGAGGAGGCCGCCCCACAAAAGTTTGACAACTTTGACGACTTTATTGGCTT
TGACATCAACG
ACAATACCAACGACGAAGACATGTTGTCCAACATGGACTACGAGGACCTAAAATTGGACGACAAAGTAC
CTGCCACCACA
GACAACAACTTGGACATGAACAACATACTTGAAAACGACGAGCTGATACTAGACGGGTTGAACATGACA
TTGCTCGACAA
TGGCGACCACGTAAACGAAGAGTTTGATGTAGACAGCTTTTTAAACCAGTTTGGTAATTAGGGGCTCTG
TTCTACAAGAC
ATATACAGATAGTGCAGGAATAAGAAAAGAAATATTTTATATAGCTATATATTTCAAGTGTTTATTCTG
TTCAACAAGTT
CTAACCGTAGATACACCAAATCACCAAGTCAGACATTACTGAGCTAGCTTAACGGTCCAACTACTTTAA
ATTGCAATCCG
TTCTTTACTTGAGTCAGTCGACTCTACAACAACTATCCTGAGGTGATTATTTTTTGGTGGAAATTTTGA
CCAAATTCTTA
AGCAAAAATCTAGTTTCTACTGATAAATAAATACACATTGCTCTACTTCTGTACTCCACACTCTGCTAT
TGCTTGATAGC
CATCCTTAAATCAACAGAATCCACTAATTCTGCTACTTCCAGAACCATGACTACTCTACATTTTTAACC
ATCTCAATTAA
TTACCATCTTTTTCTCTCATTATTTGGCACTATGGCCGAGTTGGTCTAAGGCGGTAGACTCAAGAATTA
TTCTTCTCCTG
CGATCCAGGGGTTTCTACTATCGTAAGATGCAGGAGTTCGAATCTCCTTGGTGTCATTATTTTTTTTTT
TCCAAGAACCT
CTCATTTTTTTTTTTCAAAAATTATTTCTACAATTTCCTCTATTCTTAAAAATCTTTGGTATTAAACTA
AAAATGTACCT
AACTAAACTACTAGGCTGGAAAATAATAAATCTAACGTTAACGAAATAAGCAAAAGTAATTTTTTTTTT
TCAAGACAATT
CCATGTTTGGGGATGAAAACTGCCTGCAATTATATATCCTGTAACAATCCCCTTATATCAACAACAACC
CGAGAACAACA
AAAAGTCCACTGGCAGAAACCTTACCACCAATATTCTCAATTTGTGTCACTGATTGGGCAGTTTGTGTC
GATATCCATGA
TGTGGTCAAACTGGCAGCAGTGGTAGATGGATAAACACTTTCAGCAGCAACAGTAACCGAGTTGACAAC
TTCCTTAGCAG
CTTGTGTATCACACTCTTCATCATCATCCCAGCTATCATCCTCATCGTCACACTCTGGTTCAGGAGTTT
GATCATCTTCA
TCATCGTAGCCATCTTCACCAGGGCAAACATAATCGTTACCAGATCCACCCCACCAGCTTCCAGACGAT
CCACCAGTAAC
TGAAGAAGAACCGGAATCACCTGAACTAACACCAGAACTGGATCCAGAAGTAGTACCACCACTTGATCC
AGCACCAGAAC
CCCACCAAGAGCCTGTGCCAGATCCAGAACTTGATCCACCTGTTGGCACACATTCGCCATCATCTTCTT
CATACCATTCC
CATTCACCATCATCAGAGGAGCCACTGGCAGAACCACCGGCATTGTCTTCCCCTTCATAGCCATCATCT
TCCCAGTCATC
TGGATAGACAGTGTGTGTGGTAATAACAGTCACAGTCGTGGTATATAGCTGTCCACCTGGAGCAACAGT
TGTCAGTGGAC
ATGTGGTTGTGATTGTCAACGTAACAGTTTCATCACAGATTTCACCAGATTGTGTGAGATAAGTGGTAA
ATGTCTGACCA
CCACCAGTATATGTGATAGAAACAACTTCCGTTTCAGTATGTTGATTAGTGGTTGGAGGTAATTTTGTG
GTGAGTGTTTG
AGTTGTTGGCACCCCATCGGAAGTAAATGTTCTAGTGGTTGACACAGTTGGATGGATAGTAGGAATTTC
AGTTTCACAAT
CAGTCTCGTCATCGTCGTCATCAGAAGTGGTTGACTTTGTTGGGAGAACAGTAATAGATCCTGACCCAG
TTGGAATAATA
GTTGGAAGAACAGACGTTGTTGGAAGAACTGACCCACTTGGAATGATGGTTGGAACGTCTGTCTCACAA
```

FIG. 44B

```
TCAGTCTCAAT
TATCTTCTGTAGTGGCTTTTTGAAACAACTGACGAGACACTTGTCTTACTTTGACTGGTGATTGGAAGG
GTTGGAATTGT
AGGACCAAAATTTGGGGCTTCCATTGGATCTTTACACTCTCCACCACTGCACAACTTTAATTTGGAACC
ACAACTGGAAC
TAGTTTCTGTTTCAAGGCTTTACCAGTTGACCTGATCGTAATAAGCCACGGGGTTACCAACTTGTTGCA
TCTTCACTGAT
CAGCCATCAATCTTTGATAAGCCCTGATTTCTCTCATCTATGCAACAATCTTCTATTGTGAATCATTTG
TTTTGCTAAAC
TTGTAGTTGGTGTCCAAAAAAAAAAGTGATGTAAAATTTAAATTTTTCTGAACTTGTCGTGTAAAAAAG
TCTCCAGAAAA
AGGGACAACACACACACCAATTTTTCACCATACCACACAATTCACCAATAAGCTCTCTCATATCCATCN
AATAATTACAG
TACAGCCTCCTATTCNCAATTTTTGGNATTTAAACCAGTTCCCTTGGCAGGTCACCAGTTCAT
```

FIG. 45

```
>retrotransposon_26 770bp POL protein: 2-322, LTR san: 390-377
TGATTTGAGAAATACCATTGAAGATCTAGAGTTAAAAATAAGGAATTTGCATGTACATGAGGATAATCA
AGCGGTCATTA
CAATCTTAAAGAATGATAATTTCCACCCACATAGACCGATTGATATATGTTACAAATTTCTCAGACAAA
AATTGAAAGAT
GGATTTTTTTCAATATCATATGTTGAATCTGGAGATAATTTAGCTGACTCATTCACGAAAGCTTTAGGA
AGAAATAAATT
GATTGAACATACCAAAAGGATTAGAGAAAGAAAGGATTATGATAATAATGCTACACTGATAGTGGACGT
TAGGACGCTCG
AAGAGATTAAGATAAACAAGAAATTGGTACATCATTAATTAATTTAGCTGTTTACCTGAATCAGGGGAG
TGTTCGCTATA
GGGTAGGTCTTCCAAGCTAATTTTACCCGACACAAGATGAAATATTTCTGTTGAGCACTCGTTGTCGA
CAGTGAAAAAT
TTTCACTCAAGAAAATATTTTATCATCACTTTTTCTAGAATGGAGGTTCAAGTGTTGGAGAATAGACAG
CGAACACCTGA
TATTCCCAAGGTCGAATTAGATTGAAAGATAAATAATAGTCATATTTATTTTGTATTTAGTCAATAAAT
TATCTTTTTAT
ATTTAAATTCTTAGTATTGTCATACCACGTAGATTGATACGGACATACTTAGCACATTTAACATATATT
AAGCACCGATT
ACCTGTGACATTCCGGAGTTTACTGTTTCGCGCACGCTGGCAGACGAACA
```

FIG. 46

>retrotransposon_26 POL protein 106aa
DLRNTIEDLELKIRNLEVHEDNQAVITILKNDNFHPHRPIDICYKFLRQKLKDGFFSISYVESGDNLAD
S
FTKALGRNKLIEHTKRIRERKDYDNNATSIVDVRTL

FIG. 47

```
>retrotransposon_27 598bp LTR san: 143-523
CTTCAATGCTTCACTTGTACTAGTACCCATGATTGTATAGTGGTGTGGTTGATCGACTTCAATATAACA
AGAGAGAGATG
AGATGAGATGCTTTTATCGCGTATATATTTTTTTTTCCATTGACAATTCTGATTTCACAAATTGTTCGC
TATAGGGTAGG
TCTTCCAAGCTAATTTTACCCGACACAAGATGAAATATTTTCTGTTGAGCACTCGTTGTCGACAGTGAA
AAATTTTCACT
CAAGAAAATATTTTATCATCACTTTTTCTAGAATGGAGGTTCAAGTGTTGGAGAATAGACAGCGAACAC
CTGATATTCCC
AAGGTCGAATTAGATTGAAAGATAAATAATAGTCATATTTATTTTGTATTTAGTCAATAAATTATCTTT
TTATATTTAAA
TTCTTAGTATTGTCATACCACGTAGATTGATACGGACATACTTAGCACATTTAACATATATTAAGCACC
GATTACCTGTG
ACATTCCGGAGTTTACTGTTTCGCGCACGCTGGCAGACGAACAGATTAGAAGCTTGGTAAATCTTTGGT
TATTCATCACG
TCTTGAGAATAATACAAAGTTTAATATAGTATTTTCAA
```

FIG. 48

```
>retrotransposon_28 1082bp LTR san: 558-939
ATAACCACAATAATCGGCCTCGTAAACGTCGTCAGTGGCTCAAACACATTGCTGCACCTTGAGCTCTAG
AACAACCCCAC
ACTCACTAGCCATCGCCACACCAACAACCAAATTGCTGATCCAGAAAAAATACCACCCCCGTAGTCCGG
CTTGTATGGAA
TAATTGCTTGGCCAGGTACGTCCCCACCTCATCGTGTCTTTTCTGGTTGAAATATGTCATCTCCCGGGC
TAACAGTACCG
TATCTCTGTGGCTGGGGCATCTATACTCTTTCATTCTCGGCTTACAAATCTATCTTGTTCACACATTTC
ATATATCTGGG
ACTTGTCGAACTCTCTGCACTCTATCATAAACTGGAACTCGCTTGCATTCTGGGACACACACTGGAGCT
GGAATCCATGG
TCAGGAAATGTGAAAATTTTCTTCTCGGGAAATATTTGTGACAATTAGTCCTAGTACACGATAGTTTCA
TTACGCCCACT
AAAAGTGTCTACTGAAACTCGGTCTCTATATCGTCAATATCTTTCATTTCTCTTCCTGGCTTTTCACTG
CGACTTATTGT
TCGCTATAGGGTAGGTCTTCCAAGCTAATTTTACCCGACACAAGATGAAATATTTTCTGTTGAGCACTC
GTTGTCGACAG
TGAAAAATTTTCACTCAAGAAAATATTTTCATCATCACTTTTTCTAGAAAGGAGGTTCAAGTGTTGGAG
AATAGACAGCG
AACACCTGATATTCCCAAGGTCGAATTAGATTGAAAGATAAATAATAGTCATATTTATTTTGTATTTAG
TCAATAAATTA
TCTTTTTATATTTAAATTCTTAGTATTGTCATACCACGTAGATTGATACGGACATACTTAGCACATTTA
ACATATATTAA
GCACCGATTACCTGTGACATTCCGAAGTTTACTGTTTCGCGCACGCTGGCAGACGAACACTTATCAAGG
TGCTACTCCCG
CGCATCAGTTTCCTCTGGGTTCTCTTTTTGATCTTGGTGAACTACCTTTTTTTCCCACTCGCGTGAGAA
GTTCAACACTT
TTTTTTACCCATCCACCAAACTTTATTCTTTTCCCCACCATG
```

FIG. 52

Table 1    Transformed colonies per μg DNA

|  | S. cerevisiae | C. maltosa | C. albicans |
|---|---|---|---|
| pRPU3 | 5000 | 8600 | 6500 |
| pRC2312 | 1600 | 6500 | 400 |

H963RU INSERTION SITE DATA

URA3+ DERIVATIVES OF H963R

| STRAIN | Insertion contig | Insertion site |
|---|---|---|
| H963RU3 | contig4-2991 | 19819(map) |
| H963RU6 | contig4-2780 | 9287(map) |
| H963RU8 | contig4-2777 | 6779(map) |
| H963RU10 | contig4-2296 | 5331(map) |
| H963RU18 | contig4-3108 | 80597(map) |
| H963RU30 | contig4-2882 | 6932(map) |
| H963RU43 | contig4-2025 | 3046(map) |
| H963RU46 | contig4-2386 | 5829(map) |
| H963RU50 | contig4-2668 | 8204(map) |
| H963RU52 | contig4-3105 | 58586(map) |
| H963RU53 | contig4-2396 | 2867(map) |
| H963RU59 | contig4-2854 | 2175(map) |
| H963RU63 | contig4-3072 | 24619(map) |
| H963RU65 | contig4-2294 | 1556(map) |

FIG. 61A
Integration of pRU1A into hOG1051
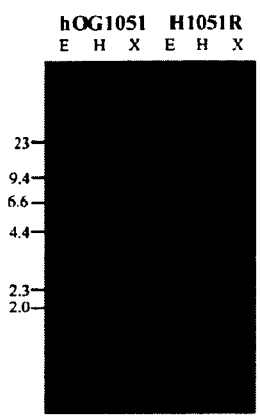
Integration of pRU1A into hOG963
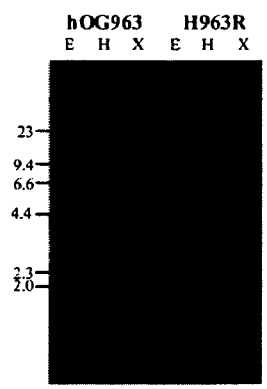
FIG. 61B
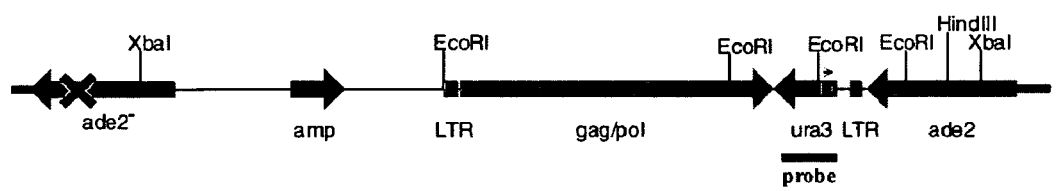

FIG. 65A
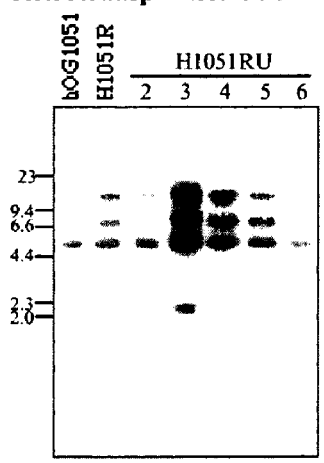
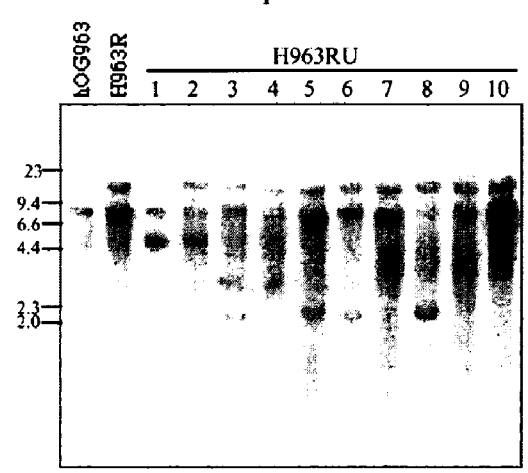
FIG. 65B
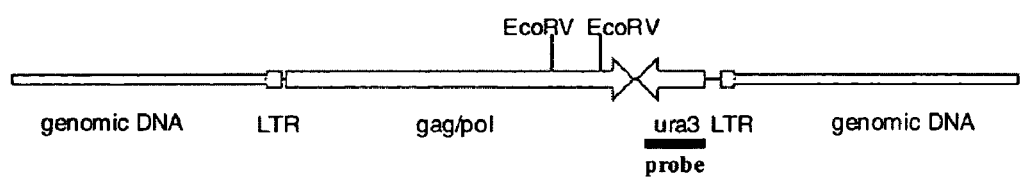

FIG. 69

```
                              insertion site
                                    ⇓
contig4-2991     TATATATGTT  AATATACACT
contig4-2780     GAGTCTGTAA  GAAATCACCA
contig4-2777     GCCACTTTGG  AGTACATTCG
contig4-2296     TATTCGGTTT  TAAATAAATT
contig4-3108c    AAAAAATAGA  GAACGCGCTG
contig4-2882c    TCTTTCTTTT  TCTTGACACT
contig4-2025c    TTCTATTTTT  GGTTTTCTTG
contig4-2386     GTATAACAAC  ATTTGTAACA
contig4-2668     GCCTCCTTTG  GATTTCTATA
contig4-3105c    ATTGTTCATT  AATTTCTTAA
contig4-2396c    CTGGAGCTAA  AAATAATACA
contig4-2824     ATACTAAATT  ATAATATAAA
contig4-3072     AATAGAGAAG  AAAAAAAATA
contig4-2294     TTGTGTATCG  TATACCATCG
```

FIG. 71A

```
>retrotransposon_01 994bp Incyte: 1..994; kappa LTR: 548..827
TAGATATTTATATATGTATATGATTAGACCAACATAAAACTAGACGTCCAAATATTTATTTATTTATTTA
TTGATATATATTCTTATTTATTACTGTTATGATCTTTTGATTCACACAGAGATTAATCCAAATCAATAC
CTTTTGTTTTGTAGAAATCTTTTGCTTCTTCAATTTGTATTTTCAATTGTTTGTATTTATGTTCTTTGTC
TTTGAATGTAACAATTCCCCAACCTAACGTTGATAAGGCATAAGACCCAAATGTGACTAATCCCCACCAT
GGCAAGTATGGCAATATTTCATCGTGTATTTTAGCTGGAGTTGGAATCACACCTGTGATAAGAGCAAAAT
AAATAGCTGATAAGGCAAAAATTGTTAATCCTGTTTCAGTAGCTTTAGTCATTCTTATAGTTAGACTTGT
TAAAGGGTAGTTGTGTTAATTGAAGATATGCTGGAAAACTATACTTTTCGTTGTTTTTTTTTTCAATCT
AGGTCGGGTGTGCTGTTATTTTTTTTCTCTCTTCTTGGTTCTTAGTATTGGATTATATGTTGGTTTATGC
GACGTTTGTGTCAGGGAAATAACACCTTGATATAAGTCGTGCGTATTAGGTCAACATTGGTGAAAAATTT
GCACTCATCGAGAGCCAGGAATTAGTATAAAAAGAAGAGAAAAGAAAGATATTTAGGATATTTATTATAT
AGGGACCGAGTTTCAGGAGACACTTTTAGTGGGCGTAAACTTCATTCACTCTGTTTTTTGCTTATTACAA
ATTATCACCTATCGTGTACTAGGACTAATTCTCACGAATATTCCGTGTATACAAACACTTATTGCCAACT
TATGGTGCGGAACTTTATTTGTCTGAACCAAAATCAAAGTCACATCATTTAAATGAACGTTGACATAAAT
AGATTCTTTATTCAATAGAAACAATTTCTTCCTTTTTCTTTTCTTTGTATTATTGGTTAGATTTCCATTC
CATATACACACAAG
>retrotransposon_02 1348bp Incyte: 1..1348; kappa LTR: 764..1043, POL
(contains stop codons): <136..714
TGTATGGTACATGTACGACAGCCCAAAAAATGGTATCATTTAGAACTGTATTGGAGAACATTAGTTTTGG
TCCAACATTGCGTGATGATGGTATGTTTTTCGTATTATAGTACAATGATGGCTCAATGATTTATTTTAGG
TTTATATGTGGATATCTTAATGGACAGAATCTCAGATGGAATCGTTATCAGATTTGTTGAACAAGAG
AGAGTTTATTTCGCGTCAAAATCAATTTAGGTCTCATGACAGAATATGTGAGATAAAATGTCCACGTAAG
CAAAACTGGGTGATACTTTGAATTAAGAGATACTCCTAAATAAGCAAACCAAGGATTTAAACTACACAA
TTCGTATGGTAAAACGTGCTTTGAGTTCCAAATGATAGATGCGAGATACCAACAAAATAGAACTGTCGCA
AATGCTGAAGACAATTTCACTGAGGTTCGAAATGAAAAATTACTTAATTCAATTAAAAAATTTATACCAA
AAGGTGGTCTGGAAGTGCTGATATGAACACGAAATTTAATGCATTCTGTGGAAAATTCGTTTAAGCTCAC
AATCGGAAAATACTACCATTCTACATTTGCAGAAAATTAAAATTGTGTTGTGAAATATCTACATCCTACA
AAGTTCAAGACATTTATTGATGGTATATTCAAAGGACTCGATGTTGAGAATGATAATAACCTGAACCAAG
ACGCTACAAATGCTAATTGAGTAATTCGTAATTGCTAAACAACGCCATTTCGAATCAGGGGAGTGTTGGT
TTATGCGACGTTTGTGTCAGGGAAATAACACCTTGATATAAGTCGTGCGTATTAGGTCAACATTGGTGAA
AAATTTGCACTCATCGAGAGCCAGGAATTAGTATAAAAAGAAGAGAAAAGAAAGATATTTAGGATATTTA
TTATATAGGGACCGAGTTTCAGGAGACACTTTTAGTGGGCGTAAACTTCATTCACTCTGTTTTTTGCTTA
TTACAAATTATCACCTATCGTGTACTAGGACTAATTCTCACGAATATTCCGTGTATACAAACATTATACG
TGTCTGTAACTACGCGAAACTACTTCGTCTCAGTTTTTTGTTACAAACAACTTTCCGTATAGACCTGAGA
TTTTGTCAGCTTGATTGAATGGAAGAGTTTACTAAAGTACCAGAAAGGTGTTTTATAGATAACATGTAGA
TATATAAAAATGTTATATTACAAATGACTTCCAAAAGAAACTGTACGAATTTTGCTGTTTATTAAAAACC
AGTTCCTGAAAACTAGTATCTTAGCTTCAGTACATTTAGCCCACCTAAATTGGACCTATGACAAGTTCTA
CTTTCCCGACAATGCTAA
>retrotransposon_03 3034bp public: 1..85/2131..3034, Incyte: 86..2130; kappa
LTR: 75..354
TGGTTGGTCTTATCAGTAGAGGAGTGAGTATCAGTTGCTGTGGTTTTTTTTTTTTTTGTCGTCTTCAA
ATTTTGTTGGTTTATGCGACGTTTGTGTCAGGGAAATATCACCTTGATATAAGTCGTGCGTATTAGGTCA
ACATTGGTGAAAAATTTGCACTCATCGAGAGCCAGGAATTAGTATAAAAGAAGAGAAAAGAAAGATATT
TAGGATATTTATTATATAGAGACCGAGTTTCAATAGACACTTTTAGTGGGCGTAAACTTCATTTACTCTG
TTTTTTGCTTATTACAAATTATCACCTATCGTGTACTAGGACTAATTCTCACGAATATTCCGTGTATACA
AACAAAATTTTCGAAACTAGTCAATCACAACAAATTTGTTTGAGTTCAACTGAAACGATAACAACCATCA
TAATTCGATTGAATACTTTGTGTCGTCTCTTTCTTTCTATGCATTCTACTACTTGTCGACTACATATATC
CAGCCATGTCTTGCATATATCCTAGCAACTCCTCCCTCCCCGCTATTGTTGTTGTTTTTTTAATAATAT
TTAGTATATGTATCAATGGTAAAACTATTTTTTGTATTTTTTTTGGTTTGTAAATTTTGATAGTTTTT
TTATTGAAAACTTCAAATCTCAAAAATTTCTAATAACAACAACGACAACAATTATTAAATGATACTCTAC
TCAAAAGAAATTTGATGAAATGCCAAGAACAATATAATTTAGTCAGTACATTAATACTCAATTACAAC
AACAACAACAACAACAACAACAACTGTTCAATGCAATAATAAGAGAGAAACCAATAGAACTAATTTA
GTTTTTCAAATAGCCAACCTTCAAAAAAAAATAAATTATGTGAATGCATAAAATATGTATTATTAGTAGT
AGTTTGTAGTTGTTGTAACCAGAATTCTCAATACATACTTTTTCATATCGATCCTTTTCTTCTTCCTCC
TCGATTTTTGGATTATATTAACTAAATTTTGCATTTACGTTTATAATGATTTTCAATACAAAAAAAAAG
CATTATAAACTATATATTATCTTGAATAGTAAAAATAAATTAGTATTGATAGAAAGTTTTTTACATCTGA
```

FIG. 71B

```
CATTATTTACTAATTTAAGGAAGAATGGGACTTAAAAAAATATCTAAAAACCCATGTGTTCTAGTTTTTC
ATTTGTTATTAGCTTATTATACTTTACATTATTATTTTTGCTATAATCTAGAAAAAAAAAAGTAGACTTT
AGATCTAATGTATAATTGGTATATTGATAGTTTTTAATGTTTTTTTTATTAAATCATTTCATTTATTTG
GTCTTCTTTGTTTTGGTATTGTCTATGTGGGGTGGCGGAGTTGGGTGCAACGCAAACAAAAATATTTTT
AGCAATTAAGTTTTTGCCGTACTGTATGGAAATTAGTTCCATTATGATAGCATTTTGCATCTTTGATTAA
TTTTTATCATTCCATAGCAACAATTACTTCTTTCTCCTCCGGTGTCAATCAATCCCATATAGGTCTTGCA
TTGTTTTGTCAAACGTTTCAAATTGGGAATTGTTTAGTTTGAAAAACTATAGATTTCCTTATCTTGATTC
AGATCTCTCTCAGCCATGCTTATGTAACTTAGCTATTGTTTCTGTTATTGTTATTGTTGTTTGGTGAT
TATCGACATTTGGGTTCATTTTATAAAAGCAAACGAGAGATCGATAGCAATTATAAAAACCATTACACAC
ACCCAAAAAATCAAAGTAATATGTTATCTAATAGGACAACTGATGTATCCTTTAATTTAAATATTTTGG
AATAAAAGTACACCCCTTTCCATCATATTCATGTGCAATTTAAAAGGAATCAATTATCAAAAACCCAACT
AACCAACAAGTTTCTGGTATATAGCCTTTCTGTCCAATTTTTTTTTTTTTTGAAATCTAAACTACTGG
CCTCTTTAAACTAAAATCAAAGATCACTTCTTAATTAGTTTTGTAGATCCAGAATCGTTACCAATACTGT
TAATAAATGATTGAATGATGTAATTTCAAATAGCAATCGTTGAGTATATTATAATCAATGAATAGCTAGA
TTAGAGACAATTATAATAATAACGAATCATCACAAAAAAAAAAGTGGTGTACAGAAACGTATGTATGT
AAACTAGATACAATGGAAAGGGCTGGGAGCGGAGGGGGGGGGGGGGTTTAATTCTGATTAAGAAAAAA
AGGGGAAGGACATGGAATTTATCCACATGAGAGAAAGGGTTCCTAAAAGATGTCCTTTACGGTGGGCCCG
GGGAACCCCAATTTTCAGAAATTTCACCTGTTTGGGGCGCATAATGTTCACAACCCAGGGTTGCCTTAAT
GACGTATTCTTTACAATTTCATCAAACCAGTTGTTGTTGTTTAAATAAAAGTTGATAGTTGTATTGCTCA
AATTCAAGGGGGGAGGGGGTGGTGAATTCATATTTCTCATATATCACACTCATATTTGCGAATACTTGAA
TTACTCTACATTTATGCTTTTCACATGGATCAATTTAATATAAGTACATCAATCCAATATGAACATGAAT
GTACCAACTAAAATTAGGTGTTAGTCTGAATTCTTGTTCACCATTGTTTAGTTTTGTTTGTGATGAATCT
CAAGATACAGATTGGTTTTACAATAATACGTTTGTTGTTGCTGTATGAACAGGCAGTCACCCTTCCTCCC
CCACAAAAACATATTCTGTATAATCTATGTAATATTATAAGATCCAATCAAAACATCACCACCAAATAAT
ACTGTAGTAATGCCTAATCTAATTACTAAATAGAAATATAGAATGGGGTATGGTTGAGATTTTTGGGTAA
GGTCCAATTTGCCAAAAAAAAAAAAATATGCAACCTTTTTCCCTCCTCCACCTCCTTCCTATTTCGTGAA
ATTCGGTAGAATCCGAAAGACTAATGAAGAAAAAATCAAGAAAAAAGGTTAAGGTCATTGATCAATTGAT
GGCAAATATGTAAGTAAGTTCGAT
>retrotransposon_04 3504bp public: 1..466/2581..3504, Incyte: 467..2580;
Tca1-like LTR: 688..1075
TTTTCTCTTCTAGCTTGCAATTTTTGTTGACGTTTACTAGTAGCAGAATTGGTTTGTTTAGTTTCTGCTT
GTTGTTCCTCTGGTGTAGAGCCATTTGATTTATTCTTTTTAATGAATGGTAAAATAAAATTACTCAATTT
GTAAATAGCAAATCCAGGAATTATCAAGTACCCATACCATACTTTATTACTTCCAAAAATAATCATCAAA
ATATCGAACCCCCAAGTCAAATAGATAACATCAAAATAATATTCATATAAACTCCCCAGTAATCTAATGT
CTTCACCACTTGAAACTAAAGAGTTACCATTGGTATATTTGGGACGACCAAATTTTTCCAAAGAATATTG
TAAAAATATACTTGGGATGGAGAAAATTATCCACGGTTTATAGGAAGATGGACGATGGAAAATGGAGATA
ATTAAAAACACAATAATGTTAATTGATGCGGAAATGATTAATAATTGATTTAATATGTTGGTATTGGCTA
CTGCCAACTTCTTAGCTGATGCAGATGCCATTGTTAATATTGTTAAATTGGGTAAATAGTATGAAGGAAG
CTTTGGCAGGCGTTGTTATTTTTTTCACCAATTATTATCATCACCTGCGGAGGTTAGTCAATTTGAGATT
GTGCGAGGGAAAAAAAACGACCTCCATACACTACCTCAAGTATAAGTCCAGTCCAATTGTTCGCTATAGA
GAGATTTCCTAGCCGGAATGCACGACAATCCTGAGACGGAAGTCGATCGTCGATGCCCATGGTGCGTGGT
GAAAAATTTTCTTAGAAAATTTGTTCTTTCCTTCAACTGCTTTGAAGAGAGGGAGGTTCAAGTGGTTTAA
GTACGACGGTCACAAAGATTGCGGCTTATGAGGCCCGAACTGAGTTGAAATACAAAATCAAGATATAATT
ATATACCTTACTTGTCTATATTGTTTTATAATACATTCTTCAGATATTTAAATTTCTGTGTATCATCCTA
TAAAACAGAGATACATTCAGTGCATTTAGTATACTGAGTGAACTGGTACCTGTGACATTCAAGATAACTG
TTTCACGCACGCTGGCAGACGAACACCAATAGTATGATGAAGAACTGACCATGGTGTAAGAGGTTTGATG
GAGTTTCTTTTTTAGAAGAGGTTGATAAGCCAACAGATGAGGAGTAACAAGTAACTCGCAACATTGTA
TAACATAAGTTTACATCAAATCAGAATTTACTAAGAAAATCAATCCATTCAAAAGGCACTCAATCATTGA
AAAAACGAGCTTAATGAGTAGACGGTCTGTTCATATGAAACAATTGAAAGGGTTGAATATTGTTTGGAAA
ATTATATAATTCATGTCAAACTGGGAGGCTTAAATTATGGTCACTCCACAGATTATGAAACGTAGTTACA
CAATTCTTGGACCTGGAAATCCCACAAGAGAGCGTTAGTTAGTTTGCACTCTCCTCACCAGTTAAACTAC
CCATGATTCTCCAATGTGGCTTATTTAAGTATCAGACAACAGATACATGGTTTCCAAGTGGTCTCATTTT
TGGTTTACTGGAGTCTGCATTCCCCACAAAAGTACCTTTCAAAACTAATTAATGTAGCTTCTATTTGATA
GCCTCTGTTATGGAAATAGATTTGCTCTGCCCAGTGGGTGTAATTATTCCCAGCTGGAACTATTCCGATA
GATATGTTTAATGTCAATTTAAATCTTGTAATAATAGTAAGGATGCGGTTTATCCGCGATCTTCTTAAT
ACCTGTGGAGTTACTCCAGAACGAGGTTCAATTTTTTCTTGGTTGGTAAATTATCCGAGTAACACGGGG
TAGCTTGGTTACTCCAGTTGAGAATGTAAACTATAGATGAAGATTTCAACACGCAATTATTACCCCACCT
TGGCGAATTACTAATCGACTATTTGTTAATCCAGAAAAAATTATACACAAACACTGCCTTTTTTAAAAA
```

FIG. 71C

```
AAGCGTTATTTTGATGGAACGATAATTAACGATGGTTCTGCACAAAAATGTGGTCCAAAGCCCCAGACTA
TTCTGAAGTATGATTTGTTACTTAATTTAGTGAATAATTAAACATAAAATCTGGAGAAAAATTTTTTTT
TGCTCTCATGACCAGTGGCAAATTCTTGGTAACGAGGCTTAACATTAATCCGCAAATTACCTGGCAACAG
AGAAAACACCCAGAAAGTTCTGTCGTATGAGAAAACCTACAGTTGTTTCCGATTTCTCCGAGCACTAAAC
ATAAAGAGACCAGTAATGCTAAAAAAATTTTTATTTCTGCATTACTGTTTTTAGCAAATACACGTCTAAT
TTATTGTATTTGTTAAACATTCTTTTCCTGAAATTTTAAGAAAATGTTTTGGTTTGTTGGAATTCCATTT
AAACGGTACTTTGGGGTGCAGACAGCAATCCATTTGGAGAGTGGCAAGTCTACACGAATTTAGCTAAGGT
TCACTATATCGTGTAACAAGAAATTTCTATACCAAATAAACAGCACTTGATTGAACTACAATATGTAAAA
ACTTGCTTTTATTACCAGTCTTCATACATACCCCGGTCTTCTCTTTTCAATATTCTGTATATGTCTTTAC
AACTCTTAACACTCCGTAAATGTGCCTTTCGAATACTTTTGCAGCTGGATATTTTCCGGTGCACCTTTT
CAGTTATCTTTGCAACTTTTCGCGAGCAATGACAAAAGTTTGGGGCGTGAGGCAACAAAATGCATGGCA
TTACCAGTACAGTATCGCCACAAGTGGTTTTCCTTGGCATTTCTTGATTGTTTAGTAGAACAATTCAATA
AGACTTTTTTGATCATGAATTTTTTTGCCATGAAGGTGCTTTCATTGTTCAAGGTTGAAGGGAATTGA
AAAATTTGTAGAGTCACAATCAAATGACTTGATAATTTGATAGAAAAAAAAAGAAACCTTAAAAAATAT
TCATACCAATGTATGCATAACCATAAAGAACTTACTAATTATGCACCTGCAATCAGAAAGTCATTTCTTA
CGATGATTTGCCAAATGACCGTAAAACGACTAGCAAAAACAGTGACATTTTTTTTGAAAAGGTGGAGATG
AAAACCATTCTGGTTTGTTTCGTCATTTACACAAATATTCGACACAAAAACTATTAATTCAATACAAACA
AAAAAATGTGCAGGAAGTCTTGGAACCGATACAAAAATTTTTACAAACCACGTACACTATTGTTTTGGGG
AAGAATTAGTCGGGGAAGAAGGCCCAGAAACTTGAGTAAAGAGTGGATTCAACACTTTATAATAGTATCA
TTTTGTAACACAAAAATGAAATACACCCAATAAAAACTGTTGAAACATTTATCCGTCAAGCTTATTCGAT
GGAGTACAACACTTTACATTTCTTCCGAAACAATAACTATATAAACCCATGTAAGTCTCCCCTCTTTTGT
TTCAAACGTCTTATCAATTTTTCTCTTCACTACTTTTCCAACTTAACAATCTTCACTTATAATCTAACG
AATC
>retrotransposon_05 3955bp Incyte: 1..3955; Tca1-like LTR: 2656..3043
TGTTAATTGATACTAAGTGTAATTGATTGGAATACTAGAAAAAAAAGAAGAAGAAGAAAAGAAAGAAGA
AAAAACTCAACTTTCTTTCGAAAATCAAGGATCAATGTTGGTATTTATATACTTTTTTTTTTAGTCAAAC
TCTACGAAATGAAATTCAAAGAGAATAATCCACAGAAGAGGAGAGAGGGCAAAAGTGGGGGGACCAAAGG
GGGTTAGAAAACAGGAAACAGCAATAGAGAGCAATAATTGAAAAATAGTGTTGTCAACAATAGAACAAAT
TGGTCAAACTTTAAATGCAAAACATGAAATTCCCAATTTCCAGAATAAATAATATCAGCATACATGGCCC
CGAAAACTACTTTACCGTGTCGCTTTAACCCCCCCCTTCCTAAAACGAGACAATTAGACATACATTCCAC
AATTATCATAATCCCCTTTTTTTTCCTTACAAAACACTTTATTTTTGTCGTTTTCGTTATTTGCTTCGAC
GACATTGTAAACTCTTTGGATTTGCAGTAGTAGTGCTCCTGGTGTAAGGTGGGTTTGGTTGTAGAGTAAA
AGAAACGACAATTGATTACACCTCGATATGCATACGCATGGCAAAGAGAATACCGAGTTAATAGTGAGTC
TATTAGTGTTGCAGGAAAAGTTATACGAACAACATTTTGTTTAGTGTGGATATTCCAGATCAACAACAAT
ATGACTAAAATCATAGCTCTAATTTTCAGTTTACCTTTGTTTATTACGATACTGCCACAGTCGTGCTGTA
CCAGGGTCAGTTTTAGAAAAACTATTCTAGAAATGATGAGTAGAAATGTACTATTATGAGCAATATTTCA
AAAAGTGAAATTATAATTGCTGCTGACAACACCAACAATACATACAAATTTGGAAACGAGCAAATCGAGA
AAATTTCAATCCGTTTAGCAAGTTGTTCGTTGTCGTCATTGTCGATTAGTTTCAGTTTCTAGAGGTGAAA
TTTTCTATGGCACCAAAACCAAAGCCTCAATTTTAATTTACTCTGTGTGGTACAAAATACATTAGAGAGG
ATCCTCTCCAAACAGGATTGCAGGAAGTTTTACACGAGAATGATTTACTACACGACGTTGAATTAAAAAG
CTCAACCAGTTTGTCAGCAATTTTGTTCTATCTGTTCAATTTCTTGTATAAAATAAAGCAATATGAGAGA
GCATCTAAATCAATAATGTCAACACAATATTAAACTTTGAGAAGGATTGTTCAACAAAACAATCCGATGA
ATAGAAGAAGAATAATATCAAATTGTTCCTGATTGATTGTTGTTATTTATTTTTTATCTCCGAATTCCTG
CACAATGGCTCAACAACAGCCAACACGGATCACACATTAAATTTTTTTTCGTGCAGGACCCCGTGGTGG
TGGCTGTGGCTGTGATTGTGATCATTGTAGTTTCTGCCTTGATGATGACAAAAAATGATAGAGTTCAGTA
TGAGGAAGAAATTAAGCGATATCGGTTTATGATGTGTTTAGTTATTAATTGCTCTCAATGGTTTTCAACA
ACGTATACAAAACTGGTGGTGCTTGAAACGAATGAGTAATACAGATCTAATTAAGCTGTGATTTTCTAAG
TTTGCCTTGTCTCTACAGTTCAAAAAAAAAGAACAGAACACCTCAGAGGCTGTTGTGATGCAATTTTAG
GAACCTCAACAACAACCACTGACTGATCTAAGCCAGCATCTGTTTAATGGGTTTTCAAAAAGAATGGGC
AAACGGGGAATTGAACCCGGGCCTCCTCGAATTTTGTGTTTGGTGAACAACCCAAACGAGGAATCATAC
CACTAGACCATTCGCCCAATTCGATGACTTGGAATTATTCTAGTTATTTTTGACATACAAAGCTCAGCTT
TATTACAGATAGTCATGTTTGCATGGATGAATTAGTACTACTAATAATATAAGAAAACTAGTTAATTGGA
GTCAATGTCTTATACATGTCTTCTGATGGGTTATGCATTGATTAATTATGAATTTCTTTTAAATACAATC
TATTGCTATTATTTGTATGTAAAACTTTACCCAAAAACCAACAAAAAGAGTGGTCTTGGATAAAGATTA
AAGTAATTCCAAAAAGATTTGGTAATTAGCTATATTGTTTTGACGTACATCTATAACTACAAATAGCCAT
TCAGTTTGATTATGTATATTGACATAGTTGGATTTGTAATTTCTGTTAAAATGGAAAACCCTAATCAAAT
GTATATGTTGAATAGGTAGTTAAATTGTACAACCTACTACTTGTTGTCAATTGAATTCAGAGCCAATACT
TATATCTCCTGGAAACTGATACACAAACGAATTGTTAAACTATAACACTCGACGTTCACATCTAAGGATT
```

FIG. 71D

```
CATCGTCGTTAAGATTTATACTCATTAGCAAACTCACTTGCCATATTAAACACTTCTCAATCTATTTCCC
ACAATCCAATTAATCAGCACGAAAACTAAGATACTATATATATCTGCCTATACCTGATATACACATGGCA
CATGGCGTATCCCACAAAAAACCGTCAAGACAACACCAATATGACAATGCCAATTATACAATTGCATATA
CCACGTGACTTCATTTTATGGTCATGAGAAATTAACTTATCATGGGGTTAGGCGAGAATATCAACTGTTC
GCTATAGAGAGATTTCCTAGCCGGAATGCACGACAATCCTGAGACGGAAGTCGATCGACGATGCCCATGG
TGCGTGGTGAAAAATTTTCTTAGAAAATTTGTTCTTTCCTTCAACTGCTTTGAAGAAAGGGAGGTTCAAG
TGGTTTAAGTACGACGGTCACAAAGATTGCGGCTTATGAGGCCCGAACTGAGTTGAAATACAAAATCAAG
ATATAATTATATACCTTACTTGTCTATATTGTTTTATAATACATTCTTCAGATATTTAAATTTCTGTGTA
TCATTCTATAAAACAGAGATACATTCAGTACATTTAGTATACTGAGTGAACTGGTACCTGTGACATTCAA
GATAACTGTTTCGCGCACGCTGGCAGACGAACATCAACACTGATCATTTGTTTTTTTTTATTTCTCCTT
TTTCTCCTTTTTCTTTCTTTTTCTTCTTTCTTCAGACGTTGTTGATTTATTTTATCGACAGCATCCTTT
TCTTTGGCCACATATCCAAGCGATATACTGGCCAAAGCGAAGTCCTTTTATAAAGCAATGCTACCAAATG
TAACAGTTCGAGGTCAGAAGATTAAGCGGGTATGTTCACACGGATATTTTATGGGGTATCACTTGTACCA
AACACTTTGATACGATAAGAATATTTGTAATACTAACTTCAGTGTCTTTCATAATCAGCTCATAACCTGT
TGGAATTTAAATTCGTATGTTGTTCATTCAAAATTTTGATAAATGGGACGAGAAATCATCGTTGCCTCCT
AATTAGATTATGACTTAGTACTAACTAAACTGTTTATCATTTTTAAAGCGTTGGGCTCCATGTTAGAAT
AGATTATTAGGGCGGTACGTATTTCATAATTTATATATAGGTACTTATTTTTACTAATTTATTGCACAGG
AAAAGATAAAAGGTATCGATTATACCTATCAGCAAGGTTTAAGCAAAATGAAGTATTTTTACCATATTTT
TCCATTTTTATATAGATACATCAAGAGGTTTATTTTAAGTTCACCTGGATAAACCATTCAACTAACCCAA
TTGAATTGAATGACAATTTGATCTCCAAAGAGGGATTCATTTCTATTCTGGAGAGATAAACGTCATTGTT
TAGGAAAGAGCAAGAGATAAGAAATCTTTTGTATATTGTATATATATTATTAATGTTATATTACACTATT
GTTTGTTTGTTTGTTATAATTATATGTGAGATTTCATATGTAAGATGTTGTTATCTCTTTCCATTATTTA
GCTTTTTTGAAAAAGCTATCAATGGCTCCACGTTT
>retrotransposon_06 1434bp public: 1..1434; Tca1-like LTR: 87..475
TAGATGCAATAGGTGTATGAAATGTATCTAGATTATATCATGAAGCCCTTGCAATAAAATCTAGCCAAAA
ATTTGTGTACTGCAATTGTTCGCTATAGAGAGATATCCTAGCCGGAATGCACGACAATCCTGAGACGGAA
GTCGATCGTCGATGCCCATGGTGCGTGGTGAAAAATTTTCTTAGAAAATTTGTTCTTTCCTTCAACTGCT
TTTAAGAGAAGGGAGGTTCAAGTGGTTTAAGTACGACGGTCACAAAGATTGCGGCTTATGAGGCCCGAAC
TGAGTTGAAATACAAAATCAAGATATAATTATATACCTTACTTGTCTATATTGTTTTATAATACATTCTT
CAGATATTTAAATTTCTGTGTATCATCCTATAAAACAGAGATACATTCAGTACATTTAGTATACTGAGTG
AACTGGTACCTGTGACATTCAAGATAACTGTTTCGCGCACGCTGGCAGACGAACAGCAATTCTGTAATTG
TCGTAGAGTAGCAACAAATCTTCCCGATGATTGGTACTTGTGTTAGTCTACACGACATGTGTTTGGTAC
ACTTGAACTGTATGTCCAAGAATGGAAACATATGCGGGAAGGACGCGAAAGATGAGTTTGGTATAGAAGG
GATAAGAACTGTAAAATATATTATGTAGTTATATATTTTAATTATGGGAAATTGAGTGTTTATTCTGTTC
AACAAGTTTCAACCGTAGAGATTACATTTAAAGTCTGTGGTCGAAATCCACAAGATACAGCAAATTCATG
AATTCACCTATTTAAATCAAGTTTACCAAGCACCATTGCCTAGACTTGCCATATCATCAATTAAGTCAG
ACATTACTAAATTTGAGCAAAGCTTTTAGCTTAATGGGCCAACTAATTTAAGTCGAATTGGTAATGCAATC
TGTTCTTCATTTGAGTCGCTTGCTACGGCTCCATGACACATCCATTTGATTGTTTTAATTCGAGCAATTA
TCCACCATAACTCTCAGTAATATCATTAACAGTTTTACGCTTAATAAGCATAGAAAGTTGTATGAAGTTG
TCTCCTAGGTATGCTAGAGAGATTTGTATATACGACCAGTAAAGAGTGTGATGAGGTGTTTACTGTAGGG
TAAATTGCAATTGACTTGAGTTGATAGCGGTTATTACAAAAGTATAGATTCAACAAATTAAGACAAGTAC
CAAACGATAGGCCGAATGTGACTTATACCGTTGAAGTTCAAGCGTTTTAACAAATAGAAATGTGAGATT
AATGAGTTCGACAAATGTTTTACTAGATACTATTAATTTCGATGTACTATATAAGTTTAACCAGCTATAA
CCGGCAGAGCAGACTTCCTGAAACTCAAATTGGTTGTGTTTGGACTTGAGTTACACCACAAAGTTTGACA
ATCGTGAGGACATAGCAACCTATCAAGCCACTCA
>retrotransposon_07 1608bp Incyte: 1..1030, public: 1031..1608; Tca1-like
LTR: 1048..1435
TGCTAGTATGTATTTTGGCTCTTTGATCCTGAATGCGACAATGCAATACAAATAGTAGAAATAATGATGG
TGATACTACTAGTATTAATAATAATCCGAGAAACGATATCACAAAATAAATCAGTGCCCAATGAGGTTGA
TGCACAAATATTAGTGGTGTGTAAAACTAAAGAGAATATCTCGCTATGATTTCTATTGATAAGAAAAGAT
GAGAGATTAAGGAAATATCTTCTGTAAAGTTGTATCGCCACCTTTTTTTTTGTAGTAGTAGTATCGGTT
TTGGTTTTGGTTTTCTCATTAGTTAAGATTCTTGCGATAAGGCACGACCTTGATCATTTGCATGTTTCTC
GTTTAATTGTTTTTATTTCTTTTTTTTTTTATGGTGTGTGGTAGTAGTTACAGATATCGACGGTTGCAAGT
GCACGAGTGCTGCGACTGACCGGATCGTCATGCTAAAAGATTCAGGGGTGTGTAAGAGCGTGCCAAGTCG
AGGAGGAACCAACATTTCACAACTGCTTCAGGATAGGGCATTCTTTTTCTTCTTTCTATTTGATCTAGCC
TTGCGTCTATTCGTGTTGTTGGTTGGTACAAGCGAATATCCCAATAAGGTTTTTGTTGCCTATGTGCATC
GTGTTGTAGCATAGTAACGAGAGATACGATTCTTCTTCTTCTCCTTCCCCTTTTCTTTGGATTGCTTTAT
ATTTATATATATATATTGTCATCATCGTCACGAAATTCACTATCATTATCAATTATTTTGTTTTTTCTCT
```

FIG. 71E

```
ATCTTTGTCCTCCTCGTTTAATCCTTATCACAGTTTTGGGTTGTTGCAATTTCTTTTCATTCTCCAGTTG
AGGCTTACACTTTCTCTTGGAGTTTCCGTTTATAATTTTTACACACACAAAAGCACAAACTACACTTTGT
CTTCACAGTGTATAACAGATACCACAGTATTACTAAGGGGGAAAACTAACCTAACCAAAGGGACTGACAA
AATAAGTGGAAAGACTACAAATGACGCCCTTAATATACGAGAGAGAATTGAAAAGACATACACATAATGT
TCGCTATAGAGAGATTTCCTAGCCGGAATGCACGACAATCCTGAGACGGAAGTCGATCGTCGATGCCCAT
GGTGCGTGGTGAAAAATTTTCTTAGAAAATTTGTTCTTTCCTTCAACTGCTTTTAAGAAAGGGAGGTTCA
AGTGGTTTAAGTACGACGGTCACAAAGATTGCGGCTTATGAGGCCCGAACTGAGTTGAAATACAAAATCA
AGATATAATTATATACCTTACTTGTCCATATTGTTTTATAATACATTCTTCAGATATTTAAATTTCTGTG
TATCAACCTATAAAACAGAGATACATTCAGTGCATTTAGTATACTGAGTGAACTGGTACCTGTGACATTC
AAGATAACTGTTTCGCGCACGCTGGCAGACGAACAATTGCGGCGAAAAAAAAAGAGGTCGCCAAAACTA
AACTGTTGGGACGATTTGCTGCCAATCACAATGAAAAAAAAAAAGAACAGTTGGTTTGAAACTTCTTCCT
CTAATACAGAATTAACTGATCTTTCTATCACTGTTTAAACTATTCATTACTCTCAAGAACTTACCATG
>retrotransposon_08 1385bp Incyte: 1..1385; Tca2-like LTR: 49..328
AATAAGTGGATTTATCATTACTATTATCGTAATGCTCAATCAGGGGAGTGTTGGTTTGTGCACTATTTTG
TGTCAGAAACTGATCAATGAAAATGATGGTTATTATGAGAATGGAAAATTTTTCCATCACACATCAGGTG
ATGACAGAACTAAACTATATTGTGTAGTATAAATAAGGGTATGAAATACCAACATCCCAGAATATCAACG
AGATAGAAGGGAGGAGTTTCAATATATATCTTGTGAATAATAACTTCGTTCTAATTCACTATACACAACT
AGACGTGTACACGCTCAATCTCAGGTAAAGAAAGTTTATATTCCATCAACAGTACTAGTATTAGTATTAG
TAGTTGCTTTGTCATATACAAATAGATTAATTAAACTAACTAACAACCTATATCAAATCAAATCATCAGT
TATATCATCATCAACATATTCATCATCTTTATTCATTCTATAAATTGTCATTGCCATACTTGCAAAATTC
AATAAACTCATAATCCAATCCGGCAAAGCAATTCCATATAATTCAATGAGATTAAATGTTAAATCTAAGA
AATTCCCAATTAATTCAATAATAAGCATCATTTTATCAAATCGTAAATCTTTTAATACTTTTTTGTATTT
TTTATTTAAATCTTCATTTATAAAATTTATTCCAGTCTTGTTTTAGTGGTGGTAGTAGAATTTAATAAA
TCAACTTCAATATTAACTTTTCTAATTTTACGTATTACATTTAGTAATTGAGATATGGTTTTCCTGATTA
AAAAAACCAATATTAATACCCAAATTTTATTGGTTTGTTTAAAAATCGATTTAAAAATTGTGGGAACAT
TGGTAAATTTGATAATAAATGTAAATTATCTAATAAATTGGCAAGATTTCTAAAATATTAACAAACATA
AATTCTATTTTTTCAAACTAAATGTATTTGGTCTATAGTATTTTATAGGTTTTATTATTATTATTAGGTT
TACTCCCTGACTTGGGTTTCTTCACTGGAGATTGACCTCGTTCTTGTCGATTGTTGTGAGATGATTTATT
AATATCAAATTTATTAAATACTGAAGGGTATTTTGGTTTTGGAGGTAATTTAGCCTTAGTAGGGGTTGAT
AATGGTTGTGATCGACTTTGTAACTTTTGTTGTTGTTGTTGTGCTAGTAAAATGGTTAATTTATCAA
GTTTATCTGATGTGATTGAAGTATTACCCTGTTGTTGTTCTTTTGAGCTAGAAGAAGTAAATTATTGAT
AATTTATTGTTGACGTGAGTCAGGATTAGGATCAATTGAAGTATGTTTAAGTTTAATTTTTGAATTAAA
TCAATATTCTCCTGTATTGTTGTAGTGAACATTACGGATATTAATAATAAATAAA
>retrotransposon_09 1483bp public: 1..525, Incyte: 526..1483; Tca2-like LTR: 871..1150
TGAATAATCAGGGGATGCAAGTTATTGATTTTGCCAGTATCCAATTTTACTTGTGGTTTCGAGAAAGTTC
TTTCTCTCATTGGTAGTTTAAAGTTAACTGAAATTCAAATTATAGGAGTTTTTGAACATAAAAAGCATAT
ACAACTTGAGTAGCATGTATATATTGCATATAAAGATTCTTTTTTTTTGTAATTGAGTTTGCCAAACATT
TTAGTCACTCCCAATATATCGTCAACTCGTAAATGTGATAATTCAGGTCAAGTGCCTACCTCTAACGATT
AGCCAACATTTTTTGAAACAAAAATATATTTCAAAGGAACACAGTGAAAACCTCTCTATGTAGGCTGACA
GGTGAAAATTATGAATTAATTGCATTGGCCAATGACAAATGAATAGACAAAACAGCAAATAAGGTTGCAA
AAGTAGCCCAAACAAACTAGATTTCGGTTACGAATTTTCCATCTTTCAAAACAATGAATTTGTTTAGAGC
TCTGTGCCATTTATTGCAACTAAAATGAATATGCAATTAAACAATCAGAGATGTATTGGATTATCCCCGT
GGTATACTTTTGAGTTCACCATTTGTTTTTTTTTGGGGTTAAATTAGTGCTCCTACTAAAAATCGCATT
TATCTTACACTCACCATTTTGATAAGTTATCTCTGGTCAATCGCAAATACTATGCTTCTAATTAAGAGTT
CTATGTAAATCCCATTTATTTTGATCAATCTATTGGTTTGAAGTAAGAGTTGATTTTCTGTAAAGATTTA
TTTGACAGTGTAGTTCGGTGTCAAAAATATATTATGATGTACACTAAAAAACACTAAATTTCAAGTCAAT
GGGGAACACAAAACTGAATTAATTACTATATGTTGGTTTGTGCACTATTTTGTGTCAGAAACTGATCAAT
GAAAATGATGGTTATTATGAGAATGGAAAATTTTTCCATCACACATCAGGTGATGACAGAACTAAACTAT
ATTGTGTAGTATAAATAAGGGTATGAAATACCAACATCCCAGAATATCAACGAGATAGAAGAGAGGAGTT
TCAATATATATCTTGTGAATAATAACTTCGTTCTAATTCACTATACACAACTAGACGTGTACACGCTGAA
TCTCAGGTAAAGAAAGTTTATATTCCATCACTATATAACAACATCAGGCTTTGCAAAAAAACATTTAAA
ACTAATACTGGTAATATGGAAATATAACGCCTCGTAGTTCTACGCACGTGGCATCCTTTATCTATTTATT
CAATTTACCCCTAATTTATGAATTAGCTTAATAAGAGCAGTCAAATTAACACGGCTCAATTAATAGTACT
TAATAATATGAAGCCGATCAATTAACCGATCCTTTGAATAATTTGAAAATAAAATAAAGTAATATAAATA
GGTATGCATTTTCCCTACATTTATTTCCTCTTTCTATTTTAATTTGTTTCCTAAACAGCAACAACAACAA
TTGAAATTCAAAA
>retrotransposon_10 879bp public: 1..879; Tca2-like LTR: 326..605
```

FIG. 71F

```
GGCTCGTAGATTCGGTATACTTGTCTAGAATAAAAATGAAAATGAATGTTAGTTGAAATGTCAGGTGGTG
GTGGTGGTTTTTTTTTAGATTTCAAAAACTATACATACTCCTATGAGATCAATTTTCTTGATTGAATATC
TTGGTAAAATGGTTATGAGTTCATTTTCTGCCAAAAAGGTAATTTCTGATGGCATAAGATTCCCTTGAAG
GTTTTTTGGGAGTACCATGACGGGTTAAGGATTATTTGTTAATGGTTAAAACTAGATAGTAGTAGTCTAT
ATTTAATTTATTTTTTTTTTTTGACACCTTGTGCGAAAGATCTCTGTTGGTTTGTACACTATTTTGTGT
CAGAAACTGATCAATGAAATGATGGTTATTATGAGAATGGAAATTTTCCATCACACATCAGGTGATG
ACAGAACTAAACTATATTGTGTAGTATAAATAAGGGTATGAAATACCAACATCCCAGAATATCAACTATA
TAGAAGGGAGGAGTTTCAATATATATCTTGTGAATAATAACTTCGTTCTAATTCACTATACACAACTAGA
CGTGTACACGCTCAATCTCAGGTAAAGAAAGTTTATATTCCATCAATCTCTCGATGTTGTAAAGAGAC
GCGTCAATTAACAATAAACTCTAATTTTGTTTTTCTTCTACAAAACTACCAAACATAATCATGTCAAGGT
AAATTACAATGATATTTAATTACGTAAATACTTCTATACCCTTATTGATATTCAATCATTTTCTTCTTAT
ACGTGGAAGTTCTTCCAGATGTCATGGCCTTGGCCCTTCTAGCAGGTTTTGGACCGTCACTATCTCTACT
ATACGGGTCAAATCCACGTCTCTGTCTACCATTAGTCTA
>retrotransposon_11 974bp Incyte: 1..974; CTA2 (transcription factor):
join(<974..>778,<223..>1), Tca2-like LTR: 483..761
ACCCGTCTAGTATCAGCTCGTCGTTTTCAAGTATGTTGTTCATGTCCAGGTTGTTGTCTGTGGTGGCAGG
TACTTTGTCGTCCAATTTTAGGTCCTCGTAGTCCATGTTGGACAACATGTCTTCGTCGGTATTGCCGTTG
ATGTCAAAGCCAATAAAGTCGTCAAAGTTGTCAAACTTTTGTGGGGCGGTCTCTGCTTTCTTTCTGGCCT
CTGCTTTCTGTTTGTTTTACACTTTTCGTCTTTAATTATAGTTTCGAAGAATTTCCTAGGAACTTAAGAA
TTTGTAGGAGAATGCTAATAAGAAGTTGTATTTCTTAATTGAAAGTTATAATTGTAAGAATATATTGTAT
AAAAGATGAGTTGATAAAGAAAAGATATAAAAAGTCCTATAAAAAAGTATTGTAAAATAAAAGTATATAA
AAATCAAGTAAAATAGAATATTTGCACACAAATTAAAAGTAGTGCAAATTTGACAGAAAAGTTGTTGGTT
TGTGCACTATTTTGTGTCAGAAACTGATCTATGAAAATGATGGTTATTATGAGAATGAAAAATTTTTCTT
TCACACATCAGGTGATGACAGAACTAAACTATATTGTGTAGTATAAGGGATGAAATACCAACATCC
CAGAATATCAACTATATAGAAGGCAGGAGTTTCAATATATATCTTGTGAATAATAACTTCGTTCTAATTC
ACTATACACAACTAGGCGTGTACACGCTCAATCTCAGGTAAAGAAAGTTTATATTCCATCAAAAGTAAAA
TAAAACACTTCTTCGCTTCCTCTGCTTTCTTGGCTTGCTCTGCCTTCTTGGCCTCTTCTTCCTTCTTTCT
TGCCGCTTCTTCTTTGACTTTCAATTCGTCAAGTTTCTTTTTCTTTTCAACCATAACGCCGAGACACCAC
TCTGCATCATTGAGTTTCGACACTGTTTGGTCTAGAATAGCATGGAAGTTTTGGATTTCGCCGT
>retrotransposon_12 3868bp Incyte: 1..1295, public: 1296..3868; Tca2-like
LTR: 127..407
AATGAAGTAACTTTTTTCAAGGCAACATCTATTCTTTTATTAATCTCGACGTCTGTTTGATTAAGTTGCT
CTAACATTTTATTTAGATCCTTCTCTATATTTTCTGCAATATCAAACACCGATTGCTTTTTGTCTGAAGT
TGCTGGTATATCACCACTTCCGCCAATTGTCGTATTTCCACTGTCCTTTGTTACTGACAGATTGGCACTG
ACATTACCTGAATTGTTCATGTTTGCTGTTGAAAGAGCAGGAACTGTACTTGGATAAGCAGCCGATTCAA
AAGAAGATGTGGACATGAGTGTCAAGAAAATGTGTAGAATCAGTACAAGACTGGAAAACAGAAGGAACAA
AGTGAACTGGATATTGTAGTTTTGTTGATAGTACTCGCGAGCTTTAATTTTTTTTTGTAACTGGCGGAAT
CAGATCTTATGCAATACTCAAATCCAAAGAAACAGTCAATCCAGATGAAAGGCATGTAATCGCTAGTTTT
CATAAACAGAATCATGTTACTAGTCATATTTTCTATAAAAATTCAATACTTCATTCTTTTTGTTCAATAC
TAACTATAAATGCTTACAAATAGATTCAAATTTCAACCAGATCCACCACTTCATTAGGCTCAACCAATTC
TTCATAAATAGAAACGTCTTCCTCAGCCAAGCTTAATTGATGGGAAACCCTAGCTTGCATTGAAGGAAAA
ATACATAATCCAAATAANCAACTGTCTTTCCAAATATTCTCAAAATTCAACTTCACCGTCTTTCACCAAG
CAGGATCTCGTGATTGGACCAATTCTAATTCAGAAGTTCTTCTCACACAAGTCCGAACGACTCGATCCAT
CATAATGGATACATCGTTCACGTTGCCACCAAATCGAATGACTCTGTTTGCACCTGTACAAAGTAGAACA
TATGCATGGAAAAGTAAAACTAGTAAAACCGCATAATGAAACCAATAATTCATCATATGTTGATTGAGTC
TGAACCCCATCAAATATAAAACAAAAGTGAGTTTAACCATAGTTATAAGAAGCAGTCTTCCGTTGGTGTA
TAATCTATCCATAAGATCGTCAATTTCAGCATCTTCAACATCAATGTTATTAGCGTCACCTGGAACGGCT
TGTTCATTAGATTCTGATTCCAGGTCACTACCAATATCATACATCATTACTAGTACTTTTTGAATCAATG
GCTCACCAGAAGCCAGTTTAAACACCTTGTGAACTTTTGCTGCACCCATAGGACCGAGTAGTAGATAAGG
ATCGTGCAAGCCGTTATCCACAACAATGCATTGTGCTGTACCCAAGCTTACTTTCTTCACAATATTGTCT
ACTTTCAAAGTAAGTTCATACTCAACATTAGACAAGTCATCCTGTTTCACTAGAATTTTTTTCCCTGAAT
GCTGTTCAACCATAGTATCGTACGATGTTCCCTCCATTTCCCATGTGGATCCACCACGTACCTGAATACT
GGCAGGTTTAATGGGGTCTATGTTAGGAGTTGAAGACTCTGATGGATTATTGACAAATGGAATAGAGTCT
TGTTGACTTGGCACCAGCGTTTCATAATTTGAAGGTGAAGGTACTGGGTTAGCCGAGGTTGGTGATGTTG
AAATATCACTATCAATTCCTTGTTCTGAGGATGAGCTAGTAGCAGTTGGATTGTTGTGCTTCTTGCAGC
AGACAAATCTGATGTTGATTCTAATGGCACTGAATTCGACAGCGCCAAATTGGGTTGCTGTAAAGAGTCA
TTGGTGGCAGGGAGAAATCTAAATCTATCATTTGACTGAAAGTCCTTCCAAAATTCTCTGCTCAACAACC
CACCAGTTCCATTTACATGTTCATGCTTTGTAAGTTTCAATTTTATGACACTGTTATTCTGTTCCAAAAG
```

FIG. 71G

```
CTCTTGATTCAATCCCAACAATTCATAAACACTAGCTTCCTCTTCTTGAAATGAGGTTGGTATTATATTC
CCTTCGTATGATAGTTTTATTTGTTCTATAAATGTACGTGTGACAGAACCTTCGTCATTCTTAGCTATTA
TTAATTGCTTGAGTTGCTTAACCGTAGTTCGGTCATTTATTTCAATCATTGACTTTTCATTCTGTAAATT
AGGAAGATTTGACTCCAACAAAACCCGGAATCTTTTGAAATTACTATTCATTTCTAAAGGTTTGGGTTGT
GTGATTGAAGCTAATGGTGTGTGTACTAAGTGGTTTTTCAATTATAAATATTGATGAACTACACTATATA
TACACTGAGAAAAACACGACCAAAATTGACACCGCACTAAAAACACGGAATTACCGTATTCTTTTTGTTA
ACGATTTTGTTTCATTACACGACTGTCGTTATACACACATTTAGAGCAAATTATTTTAGATTGATCAGTG
TTAGCAACTGGCTATCGATAATAGAGTACCTTCCGAGTTAGAATGTCTTATTAGAACAACAATTGTTTC
ATATAAATTTGTCGCAAAGCACACGTAATATACTATATGGAAGGGGCTAAGTAAAAATGTCCCGTTTCTT
CTTAATATGAGAACTCGTGTACGACACAATTTGCTGTGTTGTTAATCGAGTATGCTACAACCTGAAAATG
GACCATAGACCCAAACTACTTCTCTCTTTCTAGCACCACAAACCCCACAATTAGCACAACAATGAATTGG
ACTTCACTTGTATATCTATGGTTCATTTTCAAAAGCATATTTGCTGACTTAACATCACACCAACTCAAGA
GCAAAGTGGTATTCCTAGATACTACTATCCTGGATGAAGTGGCCCGAAGCTATTTGGGATCAGAGGACGG
AAATGTTACACATGGTAATTATGAAATATTGTCAATTGCAAATGGGCGCCAATGACGGAAACATCACATC
ATATTTATGCCAGTTGCCAAGAACCAAAAAAATGGCACCAACAAAACCCAAGCCCACCATGTCAGTTCAT
GAATTGAAATCGCGAGCTATTGACTTGATATCGGAATCCTTTGTCGAAGGTACCAGTTGCGTATTTCTT
TCAACTTGCATGCAAATTATTGGACTATAGGCTATTGCCATGGAATCAACGTTATTCAATTCCATGAGAA
TTTGGATGATTTTATAAGCGGAATTCATAAACCCCATTCTCCAAATCATGTATATACATTAGGCAATTTC
CTGAAGCAAACACTGCCATTAGAATTCGAGTTTGATACTAAAGAACGCACAATAAGTCAAAGATTGTTAG
GAGAAGTTTGTGATTTGACAGGAGAACCACGTACCATTGACACCATTTATAGATGTGACCATATACTTGA
AATTGTTGAATTAACAGAGATAAGAACATGTCAATATGAGTTACACATAAACGTTCCTAAGTTGTGCCTG
TTGCCGGAATTTAAAAGGACTAACCTTGAAGAAGGTGTCTCAGAAATACTCTGTACAAGAATTGAATAAG
CATTAAATTTAATAAAAAACATCAAAAAGTGTATGTCAAAGTATTTTTACCTTTGTAATTAGTAGTTTGT
CAGTTTCTATATAAACATAGGGTAGTTCGTATATACGATATCGGAGCGATTCTAAATAAGTCGTGGAAAT
TGGCCGACAATGGGATTTGAATTTTACTTGTGTGTGTGTGTGTGATCTGAATAATAGTAGTGCTAAACAA
CTTAAATTAAAGAAAAAAAGACAAAACAAAAAAAATTAAATCTGCTTATTGAAAATTTTTCGAAATAGGC
TAACCCGTGTTTATTAGATATTAGATAGTACGATTTGTTCAAGTGTCAAAGATAGCAAATTTTTATTGTT
TCTTCTTTTTTATATACAGCTTGTTTTAATTTCAGGATCATTTTACACTAACCTACTCATCAGCCTATTT
TAATTTATCCTTTTGGCT
>retrotransposon_13 469bp Incyte: 1..301, public: 302..469; Tca2-like LTR:
75..355
TAACGAATGAATATAAAATACTTGTATTATGTAGTGCCAATAAAAGTTGAAACGGTCGCACTACTTTTTA
GTCCTGTTGGTTTGTGCACTATTTTGTGTCAGAAACTGATCTATGAAAATGATGGTTATTATGAGAATGG
AAAACTTTTCCATCACACATCAGGTGATGACAGAACTAAACTATATTGTATAGTATAAATAAGGGTATGA
ATACCAACATCCCAGAATATTAATTATATAGAAGGGAAGGAGTTTTAATATATATCTTGTGAATAACAA
CTTCGGTCTAATTCACTATACACAACTAGGCGTGTACACGCTCAATCTCAAGTAAAGAAAGTTTATATTC
CATCAAGTCCCATCTGTTAAATATTTTGTATCTTTTTATTTTTATTTTTTTTCTTTTAATTTCATTTA
CATACATTAACACATCTACTAACCATATATCACGAGATACAAAGGCAAG
>retrotransposon_14 (direct) 4545bp Incyte: 1..4545; Tca3 LTR: 1..314,
4234..4545, POL fragment 1: 577..>3324, POL fragment 2: <3443..4201
TGACGATCCTGTATATTTCGTCATAATTCACACATTCTTAAAATTATGCACACATCCTTGAAATGTGTTA
ATATTCCCAACATTATCAATTATATGTGTTCAGAATTGGTTGCAAAGTTATCAACTCAATTCACGCTATA
TAAACCTTACAAATTCTCTACATTTTTATATTTTTTATATTGGCTTTTCTTTTAGAATCAATCAATACT
TTTTTTATCATTTAGATACATCTTTCATCTATTAATAGATTATCTTTCTATATATCAAAACACGACACAG
TCACGTGCCAAAAAGGATATAAGAAGGACTTCAGAAAATTAATTTTCTGATTATACTACTTACTAGATT
GCATAAAGTCAATATCTGATTGATACAACTTGGTTCATTATTCATAAAACTTAACAACTAATTCAACAAG
GAAACCCAACAAAAAAATCCAAATAAAATAATCAGGAAAATATTTATAATTAATTAATTACAAAAAAAAAC
AAAAAAATACACACACACATACACACACAAAATCTTGTTGCAAAAAAAAAAAAAATAATAATAATATAA
TAAGAATTAATTAACAATGTCGTTTCCACGGACACATTCACCAAGACCATCTGGTTCACGAGAACAGGAA
GATCTCACACTGATGATTAAAGCTTTTAGAGATTCAATGGAAGCTAAGCTTGACTTGCATTCGCAGAAGC
TTACTGCTTTGGTAGCAAACATTCCCAGAACGGACGAAGGGTTTGAAGATTATCACAAAGGATCACTGT
TCTTAAAAATCATCAAAAAGCATTTTTGCCCAAACAAGAAAAAGAAATCGGAAGTCTTCTCCACAGACAA
AGAGAGGAAGAAGGTGATATTAAGGATTTCAAAACAGTCGTTGGTGAAGAAAAGAAGAATTGCACCAGG
TTGAAGATTTCGTTTTAAAAGATCAAGAAGAATTACGAAACGTCGAAAAGAAAGTTTGAAAGAAGAAGA
AGAATTGCAAAAAGTGGAAGAGTCAATGGAAAAGGAAAAACAAGAGTTATACCAGGTTGAAGACTTTATT
TTGCAAAGAGATGAGACGGTAAAGAAACTTGGAGAAAGCAATCAATCTCAACAGGAACCATATACACCTG
CAACTTCTGGTTCGGATCAGAGATTCAGATCTCAACAACCTAACATTGGAAATACCTTAGCGCAGGATCT
AGCATTAATTCCAAAATTAGATCTGGAAATTTGCAAAATTGCAGTCAAATATCCAAAATTATTTGAAACA
```

FIG. 71H

```
AAATTAAGACCACCACCACCCAGAGACTTTCAATATAAAATTCAACTCACAGACCACACTCAAATTTATT
CAAAACCATATAAATGCAATCAAGAAGAACAAGCTCTCATTAAGGATTTCATCAATGAAAAATTAGAAGC
AGGCGTTTTGGTACCAGCTCCAATTGATGCTTGGTTACACCCAATATTTCCAATCAGAAAAACCAATGCC
AACCAATCCTCCACCAAAATAGCAGTTGATTTAAGACGTCTCAATAAGGTCACAGTACGAATGTACACTT
ATCCAACAGACACAAAAGACCTCTTATCCTCACTAACAGATTCCCACTATTTTAGCGCTTTAGACTTAAA
GAATGCGTTCTATCAGGTAAGCATACACAAGGATAGTATAAAATATTTTGGGATTTCAACATCCGAGGGG
AATTATTGCTTTACAACTTTACCGTTTGGAGCAATCAATTCCCCAACCATCTTTACTAACTTTGTGAGAC
AGATTTTAGAGGGGATCCCATGTATATTTATATACATGGATGATATCCTCATCCATACTAAAACCTTACA
TGACCACATGTCATTACTCAGGAGAATCATGGAGAAACTAAATGAGCATCAGTTTCAAATGAATTATAAC
AAGATGCAATTATTAACAACAAAAATCAATTTCTTAGGGTACAGCATTCAAGCGAACAAAATATCACCAG
ATATTTCCAAAATTCAAGCAATACAAAATTGGGAATTGCCCACGACCACTACTCAAATCAGAGCATTTGT
CAATTTCAGCAACCACTTTCGCATCTTCATCCCAGAAATAGCAAAATTTACTAATCCATTAAATGAATTA
TTGAAGAACAACAATGGTAAAAACATAAAGATTGAACACACCCAAGCATCCATTGATGGTTACAAGGCAT
TAAAAGCCGCCATCATTGGATTGCCGACGCTTCAACTTTACAATCCAAACTACCAACCATCATTTTCAC
AGATGCTAGCCACATGGTAGTAGGAGGATATTTATGTCAACCAACATTCAGAAATGACAAGAAGTCCTT
GTCCCAATTGCATTTTCATCACATAAATTAACAGAAACACAAAGCAGATATGCTGCTATGGAAAAGGAAC
TTTTGGCAATTATTGTGATATTGGAAAAATTTAGATATCACTGCAGCAATACGGTAGAGATCTATACAGA
TTATCAAAGTTTGGCATCATATTTAGATAAGAAAACTACTCCACCACCGAGAATTGCTAGGTTTTTAGAT
CTAATTGGATCATTTTCCCCAAAAGTGTACTATTTAAGTGGAAAGAAAAATTTCGTTGCTGATATCATTA
CAAGATATCAAACTCAAAATATTAAGGAATTGGTAGATGAAGACAAGATACTAGGACAGACTTTTACAGT
CAAGAGAAATTTGAAACAACAACTATTACCAAGATTGGAAGCAATTGAATTGGAAAATCTTAATGAATCA
CAGGTTCACAAAATCCAAACTTCATTAGAACAACAACAACAACATGATTTGGAAGACAATGATGAAGAGT
TACCTCTCCAACTGTTTAAATTAATGAATGATGAGTTATTTGTAATCATTAACAACCAACTTTTAAAATA
CCTTCCAAGACTGGAATACAATGATATTTGTCAAACAATCCATGACAAACACCATCCATCAACTAGAGTA
ACAGACTACTTATGCACACTCGCATATTGGCATCCTGACCATCTATTAATTGCTACAAACATTACGAGAA
AGTGTCACTATTGTCAACTAAACACGTCAATTCGTGAGGCCATTAGACCATACCGACCACTTGAACCACT
CAAGGCATTTAGCAGATGGGAATGGACTACTCTGGACCATACTTTAACACAGTCCAACACAGGTACATA
TTAGTAGCCGTGGAATATGTCACTGGTTTAACTATTGCAGTACCAACATTGCACAAAGACGCAGATAACG
CAATCAGTCTTTTACAATCAATCATTCTGATCATGTCAGCACCTACAGAATTAGTTACAGATCAAGGTAA
AAAAATTTTCATCACAAGCTTTGGCTACCCTATGTGACCAGAATAACATACAACACCATATTACCTCCGC
CCACCACCCACGTGGGAATGGTCGGGTTGAGAAGGTGAACCACCTATTGAAGAAAATATTGAAAGCATTA
ACTAACGATACGATGCAAGACTGGGATTTAAAACTATATGACGCTTTAAGAATCTACAATGCTACACCTA
CAATTTTTAACTACACTCCACTTTATCTTGCACTTGGAATTGAACCACACCATAATTTAAATCAATTACA
AAAAGATTTAATTGAAAATTTGCAAAAAGAATTGCCCCCAGAGGTCCAATCCACAGAAGAACACGAAGAA
AACCCAAATGATGAACAACAAGAAGAGGGCAGAGAACAACAAATTTCAAGAGAAGAACAACAGGACGGCA
GAGATCTTGTACACTTAAGAATTTACGAATTGGAAGCAATTAAGAAAGCTCGCAAGTTACACACAAATTT
GAAAACACGAAGAAACGCAGTCCAAAATATGTTAAAGGAACCATATGGCATTCCAGCACCTTTTACAAAA
GGACAATGGGTATACAGAATTAGAGCTAAAGCACGAAAATATGAACCAAATTTCGATGGTCCATATCAAG
TTCAAGAAGTATTAGGTAAAGGTGCTTATAAATTGAGAGACATCACTGGAAGAGAAAAAGGAATCTACAA
TCAGGATCAATTGAAGTTAGCATATTCAGCAGACAACGACCCAATACAGGTTTTTAGTTCTTTCAATAAA
GAATATGATCGAGTACAACAAAAATTGTTAGACAAAATTCAATCGGAAAGAGATCATCAATTAAATTGTT
TGTCAGTCCAACATTTACACAGACAAAGAAGGTTACTCGATATATCCAGCTGTCTTGAGCAAATTCTGCA
ATAATTTCGCTAATCATTGGAGGAAAGGGTAGATGACGATCCTGCATATTTCGTCATAATTCACACATTC
TTAAAATTATGCACACATCCTTGAAATGTGTTAATATTCCCAACATTATCAATTATATGTGTTCAGAATT
GGTTGCAAAGTTATCAACTCAATTCACGCTATATAAACCTTACAATTTCTCTACATTTTATATTTTTTA
TATTGGCTTTTCTTTTAGAATCAATCAATACTTTTTATCATTTAGATACATCTTTCATCTATTAATAGA
TTATCTTTCTATATATCAAAACACGACACAGTCACGTGCCAAAAAGGATATAAGAAGGAACTTCA
>retrotransposon_14 POL fragment 1 916aa
MSFPRTHSPRPSGSREQEDLTSMIKAFRDSMEAKLDLHSQKLTALVANIPRTDEGFEDLSQRITVLKNHQ
KAFLPKQEKEIGSLLHRQREEEGDIKDFKTVVGEEKEELHQVEDFVLKDQEELRNVEKKVLKEEEELQKV
EESMEKEKQELYQVEDFILQRDETVKKLGESNQSQQEPYTPATSGSDQRFRSQQPNIGNTLAQDLALIPK
LDSEICKIAVKYPKLFETKLRPPPPRDFQYKIQLTDHTQIYSKPYKCNQEEQALIKDFINEKLEAGVLVP
APIDAWLHPIFPIRKTNANQSSTKIAVDLRRLNKVTVRMYTYPTDTKDLLSSLTDSHYFSALDLKNAFYQ
VSIHKDSIKYFGISTSEGNYCFTTLPFGAINSPTIFTNFVRQILEGIPCIFIYMDDILIHTKTLHDHMSL
LRRIMEKLNEHQFQMNYNKMQLLTTKINFLGYSIQANKISPDISKIQAIQNWELPTTTTQIRAFVNFSNH
FRIFIPEIAKFTNPLNELLKNNNGKNIKIEHTQASIDGYKALKAAIIGLPTLQLYNPKLPTIIFTDASHM
VVGGYLCQPTFRNDKEVLVPIAFSSHKLTETQSRYAAMEKELLAIIVILEKFRYHCSNTVEIYTDYQSLA
SYLDKKTTPPPRIARFLDLIGSFSPKVYYLSGKKNFVADIITRYQTQNIKELVDEDKILGQTFTVKRNLK
```

FIG. 7II

```
QQLLPRLEAIELENLNESQVHKIQTSLEQQQQHDLEDNDEELPLQSFKLMNDELFVIINNQLLKYLPRSE
YNDICQTIHDKHHPSTRVTDYLCTLAYWHPDHLLIATNITRKCHYCQLNTSIREAIRPYRPLEPLKAFSR
WGMDYSGPYFNTVQHRYILVAVEYVTGLTIAVPTLHKDADNAISLLQSIISIMSAPTELVTDQGKKIFIT
SFGYPM
>retrotransposon_14 POL fragment 2 253aa
MQDWDLKLYDALRIYNATPTIFNYTPLYLALGIEPHHNLNQLQKDLIENLQKELPPEVQSTEEHEENPND
EQQEEGREQQISREEQQDGRDLVHLRIYELEAIKKARKLHTNLKTRRNAVQNMLKEPYGIPAPFTKGQWV
YRIRAKARKYEPNFDGPYQVQEVLGKGAYKLRDITGREKGIYNQDQLKLAYSADNDPIQVFSSFNKEYDR
VQQKLLDKIQSERDHQLNCLSVQHLHRQRRLLDISSCLEQISQ
>retrotransposon_15 2093bp Incyte: 1..2093; Tca3-like LTR: 1509..1822
TTTTCCCACAAATAATATCAACAATATTTCATATTTTCCATCATGCTAGAGAAGATCAAGTTATAACTAC
ATTAATTGGTTATGTTTATAAATTGACTCAAATTTGTTTAAAATTTGAATTACATTCTGAAATTAGAAAA
ATCATTGATAAATTAATTAAATTTACTACTTTAACTCACACACCTAAAAACCTTAATGAAATTTTAATTA
CTGAAGTCAAATTAGATAATAAAACCGAAATTTATGTTAGTGATTATGCTTGTTCATTTGGTCGTGATTT
TAAAGCTCAATTATCAACGGTGGTTTTATTTAAAATAATCAAGAAAAATAATCTTAAATTGAAAAATTGG
GATAAAATTGTGGAAATTATTGAAAAATTATATCAATATTCATTGATTATTGATGAGAAGGATACTACTA
CTACTACTACTACCAATGATAATAAGGAAGGTGATGATGAAAAGGATAATAAGGAAGCCACTGTTGAGAC
TGACAACTCAATATTGAAATTATTGCCTTCAAAAGATATTAAAAAATTCCCTATTAAAAGAATAACTAAT
GATCTGTTTCTTTCAATATTGAAAAATTTAATTGATAATCAACCTACTGAAGAAGAAATTCAATCAACTT
TAGCAGCTATGGATTGTATTAAATCATTAGTATCTTGAATGTATTAAGAATTGTTGCTGAATCCAAGAA
ACAAGCTAACTAAATCTAAACAATCTAAACATCTAAACATCTAAATATATATATATATCTATTGTATTAT
TATATTTGTAAAATTTTGTAGTTTGCAGTGGTTGGAATAAATGATAGGAGGATGTTCCATTTGTGATACA
CTATTTCTACAAACTGTCAAATTCAATAATCAAACTTGTTGCCAAGAAAAGATAACAAAGAAGGCTATTT
GGTTTACAAGGTACAACAAGAACATGGGTATATCACCACGATAGTTTAGTAATTTTGTAAATCTTCTTTC
TCTGTTTTACTTAGCCTCATTTAGTCCTTTCTTTCAGTTCCAAAGTAGGATGTGCAACATGGCCAATTAT
CAACAATAAGCTAGCATTGCATAATGGTAGTGATTGTACTGAAGAGAACAATACACTAATCTATTCCATT
GACGACGGAATAAGTGGACTGATAATTCACATGGATAATTCAGTCCACTCTGAGAGGAATTTCCTCTTTA
TATAATAGAAAATTCCTCAAGGTATTAGATTGTATATTTTCTATAGATAACTAACCTTGAACACAAGAAT
ACTATCGCCTTTCGTTGCAGATTATCGCTCAAAACTTTTCAATAACTTTTGGGTCTTTTTTTAACAATAA
CCAATAAATCATTACAAAGAATTACAAAAAGGGCTATAATGACAAATTTCACATAGATAAGAAATATAGG
TTTTATTACTTTTTGCATAATTGCTGACTTCTATTTTTGGTTTGGAGATATTTAGAACGTTTGATTGTGG
GGGTATTACTTCCAAAAAAAACAAAAATTTGTAAACCCTGACGATCCTGTATATTTCGTCATAATTCACA
CATTCTTAAAATTATGCACACATCCTTGAAATGTGTTAATATTCCCAACATTATCAATTATATGTGTTCA
GAATTGGTTGCAAAGTTATCAACTCAATTCACGCTATATAAACCTTACAAATTCTCTACATTTTTATATT
TTTTTATATTGGCTTTTCTTTTAGAATCAATCAATACTTTTTTTATCATTTAGATACATCTTTCATCTAT
TAATAGATTATCTTTCTATATATCAAAACACGACACAGTCACGTGCCAAAAAGGATATAAGAAGGAACTT
CACCCCCTTGCTCTTCTTATTATTGTGTGTGGTGTAAGTTCAGCGGGTAGTCCTACCTGATTTGAGGTCA
AAGTTTGAAGATATACGTGGTGGACGTTACCGCCGCAAGCAATGTTTTTGGTTAGACCTAAGCCATTGTC
AAAGCGATCCCGCCTTACCACTACCGTCTTTCAAGCAAACCCAAGTCGTATTGCTCAACACCAAACCCAG
CGGTTTGAGGGAGAAACGACGCTCAAACAGGCATGCCCTCCGGAATACCAGAGGGCGCAATGT
>retrotransposon_16 2099bp public: 1..2099; Tca3-like LTR: 1565..1878
ACATTTTTCAATATTGAAAGATAAATATAGCATTCCAAAAAAAAAGTGACTTCTGTGTTCACATTTAAT
CAACAAATTCCCACAACAGCTTGCACAAACTGCTATCTACTAGGCTTACGAGACACAAGTGTTACCAAAT
AGTGATACACTTATACTTTAACTCATAGAAGAGAATTAGATACTCGGAATATTACTCAACATATTCCCAA
AATAATCGTAAAGATAAATCTTTGAGAGTTAATACTAGAGAGCTCAATTCTAGGCACAAATACCACACTT
TTTACGAGTAGTGGGTAAGAGTTCGTACACATGATGCAACAACTTTCTAGTACCTACTTGCACAAAGTGT
AGTTTGCAAAAAACTTTGCTTCCTCCCATAGCATGTGTATCTCAATACTCCAGAAAATCCGATAAAGCAACTCT
CCGATGGTCATGCAAGTATTCGCCTTTCTCTTTTGTAGATTTATGTAGTTTCAAGATGACACTGAACTCC
TGAGTATTAAAGTAGATTAATAATAGAAGGTATTGCCTAATGCCGAGAAAGTAAACACCAGATCAAATAT
ATGCTTTACTATGAAACTTGTTTGTGTTGTGTGGATTGGCCAAACAAAGATCATGCTGATATCTGTAAAT
CTCTGGAACGGGGATAGGAATAAACTTGAAACAATATAAACGAGGTGTTTTCCTTTTCTGGTGCTTGAT
TTGAAACGTGTACATTCCCTCTTTTTCTCTTAGTTAACAATATTGCATAATAGTGAGGATGTGAGCGTAA
GACAGAAAGCAGCAGCATGGGAATAGTTCAGCCTATTATTGTCGCAAAGCTGCATATTGCTTCTTCTATT
AAACTTTTGAATCTTCTCTTTTAAGTAAATTAATTAATAACTTGATTGTTCCATTTACATCCATTTTCTA
TTTCTGTGTAATCTTCGTTTATTTTGCGGTTTGAATACTTCCAAATTTAATTAAATTTGTTCCTAAAATA
GAAGCTGTTATACTTGCGCCGCCAAACCCATTTTAATAGTGATCCTTATTTCAATTTAATTTGTTCACGT
TATATCTCTGAATTTGATTAATACTTGCTACAGATATTTGGAAATCATAATTTATGATTTCTCCGGAATG
TAACTGAGTGGCCAGAAGATATATAGTAACACATAAATACGTACACAACACCAGAACAACCGCAACATTC
```

FIG. 71J

```
AAGTGGAACTAGTATGTGTTGAAAAAACAGACAAATTAATCGGGATAGGAAGAGATGGGAAAGGGGGTG
AGAGAAAAGCAAAGAAAAAAAAAAAAGAAAAAAAAGAACAAAAATCAAATGGTACAAAAAAAAAGACACA
TCTTCTACACAATTAACAAAAACTGCCTTCTGATGGCAAGAAATCTACCTCACATACATACTTAAATGGA
ATAAAGAAAGTAATCTATAAAAATAATTTAACATGACTAACGTATTTCAAGTAAAAAGGTCAAAATTAGA
GAACCCACCACAATCAACTATTTTCTACTCTCAATTGTTTTTTCTTTTTAGTTCTTATAATTATCAACAT
TTTCCTTACTCAAATCTTTCACCTTGACGATCCTGCATATTTCGTCATAATTCACACATTCTTAAAATTA
TTCACACATCCTTGAAATGTGTTAATATTCCCAACATTATCAATTATATGTGTTCAGAATTGGTTGCAAA
GTTATCAACTCAATTCACGCTATATAAACCTTACAATTTCTCTACATTTTTATATTTTTTATATTGGCT
TTTCTTTTAGAATCAATCAATACTTTTTTTATCATTTAGATACATCTTTCATCTATTAATAGATTATCTT
TCTATATATCAAAACACGACACAGTCACGTGCCAAAAAGGATATAAGAAGGAACTTCAACCTGTTCTTTT
CTTTTTTATTTTTAAATTTGATTATTATTAATTTTTTTTCCTTTCTTTCCTTACCAATTTTTCTTTGCT
TGACTTATTCAAAAGGTGAAACAGGGATTTTCCAATTCACATAGCCAAAAGTATTTTTGGTTTCCACATT
CCTTCAAAACAATATTTGTGCTACCTCCCCCTTCCCACCAAAAGTATCCGATTCCAACCATAAAGCAGC
>retrotransposon_17 3284bp Incyte: 1..2749, public: 2750..3284; Tca3-like
LTR: 2750..3063
TAATAAGTACCAACTAAATCAAAACAAGCGACCAAATTGAATAATAGGAAGACAAAAAAAAAAGAGAGAA
AACAGTACCAAAATAGATATAGTATGTAGTTACATTTACTCAACATAGTTATTAGGTACAAATCCAATTC
TGTAGCTCTCATCATCAATTCTTGAGACTCCAATCAACCAATTTAACTCATCTGAATGATACAATGTATC
AATATTCTGAAAATCTAATAAAATTTCAATATTATCGCCTGTTTAAATGACAAATCACCTGGTTCATAA
CCACTAAAATCGTATTTTGCAGTTTTCAAAACTTTATTATCGGTGTTAATGTTCAACTTTTCAAAAAGC
TTTGTATCAAATTCAACTTGTAAGTCAAACTCATAGGCTTTTCAAACGTAAAAGGTTCATACTGGATTGG
CTTGGTTGTGATTGGGCTTTCCTTAATCTCATTCTTTACTGCCATTGTATATCCTTCTTAATTTAGCTTCG
GATGAATCATGGTTTGAGTACGAAACACTTGACATGGAGCTAATTGATGAAGCTTCTGACATAATAGTTG
CGCTCTCGTCTTCAAAATCTGATAGCAGTATAGAATCCATAGAATCTGTAGAAATAGAATATAACCGTGA
GGCACCTGCAGAAGACATTGGCGAGACAAGAACAGAATGCCTCATAATAGCAGTGTTTGACCTAGGTGGC
AATTCAGGACCATCTTTCTTCGGCACTGCTGGTACCTTTATATCTTCCTCATCGACTAATTTCCGTGGAT
GATATGTTCCGATGGGTTCATCGATGGATCTTGGTACTGTTTGTATGCCACCAAGGGATCGATTTCTAA
AGTATCATTGAATATGCCATTTACCTTGTCTTTTGTATTCACAACATGTTTCTTTTCAACAAATTTATTA
CTCATATTACGCCAAAATCTGTAATAGTTCAGCAGCGAATCTTCATCATTGATCTCCTTATCAAGCAAAT
CCGGGTGTTTCTCGTGCACAATTGTTAGAAGAGACTCTATCTGCAACCTTGTAGCTGTACTGTTCAGTTC
CCAATCGTCTATTATTTCAGTATACGATTTTGGTGAATTTTCTTTAATCAATCCATAAAACTCTGTAAAA
TATTGAAAAGTATCAGTTAGCTTTTTAAACGTCTCCAATTGTTGACATAATATCATCTTGGTAATATTTT
CAACAAACTCATCAAGAAATGAAACTATGTTAGGCAATAATTCAATACACTTTTTATTCAAGCTGTTGAA
CGCAGCATCAACTGTCTGATATGTTGTTTCTAATTTCTCAAGTTTGTCATTATCTTTCTCGTCCAATGGA
ATCGCTTTCTGGTTCAATTTCTCAATTTTGCGATGCAAATGATCCTGTTCTGTTCGTTTCATATTACGCT
TTTTAATCAATTTCAAAGTTTTCTTCAAGTATTTCTTCATTTCGTCAATTCTATATTTGAGAGATTCGTC
ATATGCTTCCCAATTATTTTCCAAATCAAATTTTAAGTTCTCCACCGTGATCAAATAATTATTCAACTCT
TCATTTATAGATTCATTCAAAAATTGCATCTCCTTTGGGTGTACATGTGGGATTTCTTGTGTTGCTTGCC
ATGAATCAAATTCTTGGTAATACTCGTTGATTTATCAAAACGCAAAGAGTCTTGACCAATCAAGTTGAT
AAATCCTTTAATAATTTTAATATTCAGGCCGAGCACATGTGGCAAGAAACTCTTGGACAAATGGTGATTC
TGCGATGTGATGTACTTCAAACCAGAAACTGATTGTTTGATATCGTGATAATAAATCTCAACAAGTTCAT
CATCCTTATCGTAATCTCTGGTGTGGAATGTAACTGTGTCTTCAATGTTGTAGGATATATTTTTGAATTC
TGATTCAGTGTACTTGTACCCGTCCTTAATATGAGTTCCAATATTAGACGATATCAGAACAATATTATTT
TTCAATTGATCCACAACCATCGTTGTCTTTTATCTATCAGTAGTAAATTGAAAGGTGGGGGGATAGAAAA
TGAACTAGAAAAAGAAAGTGATGATTCTAAAAAAAAAATTTCTCAAATACAAATACTAAGATAAGTGTTG
ATTATATGACAACAGGGTTGGAAAGTCAATTATTAATTAAGGACCATTGTAGTTAAGCTGCGCATAGAAG
CAGAAATGTGTGCAAGACAGGAACGGACGGGAAAATAATAAGCTATTTGAATTAACACGAAATAACGT
GACCTAAATTAAAATAAGAATAAGGAAAAAAAAAAAGATAGGCTTTGAATTAATGGTTTAGTCACTTTT
GAACTGATAATTGTTGATCTTGAACTAGTAATGATTAGTTTAAAAACCCAACAGGAACACTTAGTTTGGA
AAATATGAGTCTCCATAGATCTTCTCTTTAACTTATGCACGGAGCTTAAAAGTACAGTTAGACTCAAAAA
CGAATATTTTAGTGCAATCTCTACAGTATTGGGGTCTGCTCACAATCAAGAAGAATAACCATTTAAAGGC
GCTCTGTTGTAGAAATTGTTTGTCTCTACAAACGACCACGATTAGTAGAGAGGGGAGGAAAGACAAGAA
AAAAGGGGGTAATCATGATAATTGCTAAAAAGTTGAATTTTTGTAAAGTCCACCCGAGAGTTGGTAGCTT
TTTAGATTCTAGATCTAACAGCAGTTCTCTGTACCGTGTCAAAATATCAATTGTGGATCCAATACAGCTA
TTGTAGTGGTACTTACTGATGACGATCCTGCATATTTCGTCATAATTCACACATTCTTAAAATTATTCAC
ACATCCTTGAAATGTGTTAATATTCCCAACATTATCAATTATATGTGTTCAGAATTGGTTGCAAAGTTAT
CAACTCAATTCACGCTATATAAACCTTACAATTTCTCTACATTTTTATATTTTTTATATTGGCTTTTCT
TTTAGAATCAATCAATACTTTTTTATCATTTAGATACATCTTTCATCTATTAATAGATTATCTTTCTAT
```

FIG. 71K

```
ATATCAAAACACGACACAGTCACGTGCCAAAAAGGATATAAGAAGGAACTTCAACCTGTTCTTTTCTTTT
TTATTTTTAAATTTGATTATTATTAATTTTTTTTCCTTTCTTTCCTTACCAATTTTTCTTTGCTTGACT
TATTCAAAAGGTGAAACAGGGATTTTCCAATTCACATAGCCAAAAGTATTTTGGTTTCCACATTCCTTC
AAAACAATATTTGTGCTACCTCCCCCTTCCCACCAAAAGTATCCGATTCCAACCATAAAGCAGC
>retrotransposon_18 791bp Incyte: 1..791; Tca3-like LTR: 277..590
AATAATGTCAATTTATTACCAAGTTTCCAAAGTTGTCTTGTTGGTAGATTATATTGTTTACAGATTATGG
TACGTTATAAAGGTACTAATAATGATCAAAATGAATTTGCTGATAATATAGTTAAACTAGATGTACCAAT
ATTAGTAGGATAAATAAAGAATCAATAACCATGGCACGTGAATATGAAAAGGTAGGGGCTAATATAAGTG
TAAGTGTAGTGTATAAATTACAAAACAAAAAAGGCTGTTGTTATTAAGATGAGTCAACTGTGTAAGTGAC
GATCCTGCATATTTCGTCATAATTCACACATTCTTAAAATTATTCACACATCCTTGAAATGTGTTAATAT
TCCCAACATTATCAATTATATGTGTTCAGAATTGGTTGCAAAGTTATCAACTCAATTCACGCTATATAAA
CCTTACAATTTCTCTACATTTTTATATTTTTTATATTGGCTTTTCTTTTAGAATCAATCAATACTTTTT
TTATCATTTAGATACATCTTTCATCTATTAATAGATTATCTTTCTATATATCAAAACACGACACAGTCAC
GTGCCAAAAGGATATAAGAAGGAACTTCATCTTGATTGCGCCGCAAGCAACAAACAATAAGCCAAGGAA
AGTATATACTCCAGATCTACTATGAGTATGACACAGCTTATTAATGATCAAGTCTACAACTTCTACTACT
AAACACGTTCTTAACAAATCAAACAGTATTCAATTGTTTTAAAAAACACTATACAAAATTAATCAATAAA
AAACAACTAAAGCTAATTCTA
>retrotransposon_19 4581bp Incyte: 1..4581; Tca3-like LTR: 2725..3037
TGGGAATTATTAGAGGATTCTTTTTCAGTGGATATATAAATAACGAATAAATTCCTTGTTTAATTATTTT
AAGGGAAGAAAAAAAAAATAATCAAACAACCAACCCTCTTTATAATTAACAAGACTACAACTTAATAAAA
ATGGGATATCCACCAAATTTCAAAATTGTTACTAAATCATTAACAGAAAACATTTTATTAGCATCAACGG
CTTTTTCAAGAGTTGATAAATTCAATTTTGGTGCTCGTATGGCGGTATTTAAATTTCCTCAATCAAATAA
AATCATTTTATGGTCACCATTACCTTATACACCACAAGTAATTGATGTTTTGACAAAATTTACCAATAAT
ACCAATGAATCAAATTTAAATATTGCTTATGTGATAATTCCTGATCGTGAACATAATTTAGCTGCTAAAT
CATATAAAGAAAATTTCCCGGGTGTAAATTAATTGGAATGGAAGGATTAGATGAAAATTCATTGAAATT
GGATTATAAATTTATAAAACTGATGGGTAATAAAGTTTTAAAAAATGATGAATTAAAACAAATCTTTAAT
GACAGTGACAGTGGCTTGATTGTTGATAATTTTGAATTTGTTTATTTACCAAATCATGCAAATCAAGAAT
TGGTTGTATTTGATAAATCATCATCAACATTATTTGAAGCCGATTTATTATTCAATTTAGGTGTACCGGG
GTCAACTCTGGGTGAAACCATTTTAGAACAATATTCACCAGAGTTGGGGTTCCCTAAAGGGTTTAATCCT
CATTCTGGTTGGTCATTTATAACTAGATATTTACAACCATATTCTAAAGTTGGTCGTTTCTTATTTAGAA
AAATTGTTGATATAAATCATAGTAAACCTGGATTAGAAGCTATTTATAATTCATGGGATTTTAAAACTAT
TGTTATGTGTCATGGAAATATTATAACTAAAGATGCTAAAGAAGCATTTAAACATGTTTTTGTATAAAAG
TAAAAGAATTGAAGAAGATAGTCAAATAGTAATAATCAGAATATATGTATGTTTTTTTTGAAGAAAATT
AAAGAATATATTCACGAAATAATAATAATAAAAATAAAAGACTAACTATTTTGAATAGAAAAAAAAGGT
GGCACTATTTCAATGAGATAAACCAATTGTGAATATACGTAGATGCCTTGCAGCAGACAATATAACCAAA
TGTTGAACAATATGTGGGATAAATAGCATTTTCATCTGTGCCATTGATATTGCATTTATATCCTATTGTT
GAACAGTGACAGCACCTGTGGCGGTGGCTATTACATAACAGAACAAGTGGAACAGCAGTTACCAGTCAGA
ACAGATCTAACAGCATTGTTTTAGCAGCAGCATCTTTATCTTTGGTTTGACCAGATCCAGTTTTTTTAG
ATTGTTGTTGAGCAGCCATTTTTTATTTGAATTTGTTGATTGAGTTAATATAGTTTATAAGAATTGAGAG
TTACTTGTTTGAGTTGTTGATTAAGAATAGATTAAACAAAAATATACAAGAGAATCTGTAGACATATTTA
TACTCATGAATTTATATATATATCTATGCTTATATTCATTTGATGTATAAATTGACATGATTATGAACTG
CAAGAGGTTTGATTTTGATTTGTCTGCAAAAAAAATATGCTCTATTTTTCGCAATTACCCCCCAACCCCC
CCCTCACAAAGTTCCGAGTTTAGTTGGAAAAATGTTTCGATAGAGTAAAATTTCAGGAACAAAATTGACT
AATTGGGAGATGACAATGAGAAACAGTTTTGAGACTTGATCATACTTCCCCATACGCTCACCTCTTTACG
TTAAATATAGCTCTTTTACGTCTCTCTACAATAATTTTTTTGACTTATTGATATTTCTTAAAATGGTTACAT
GAAATAAAACAAAGAGATTCATAGGAATATTACTTTTTCAGGTAGACACAATGCAGCTAAGGTTGGATTT
CTCAGGAAATATCATTCAAGCTTTATCTGTTAGTTAGTGCTGTTATTTATTACTGGTGAACTACACCAAA
GCATACTGAAGGCATTTTACGAGGTTTTTGAAAGCTCTTACTATGTAGCAACTCATCTAGTACTTAGTAG
AGGAAGTGCATCAAGTATGGATCAACCAAGTGTTACCTTATATCATTGGTTTAAACATTGTAAGACTCAG
TTCGAAAAAAAAATTAAGGTTTCTACTTACCACTTTCATGTGGCTTAAAGTTGTGGATGTGATATTGAAT
ATGTTTCAGATTTGTCATGAAACAATAAGAACAATAATAAAGAAGAAATCAAATCAATCTTCAATGTATG
TATGTTTCTGTATGGCGCATGTGGGTTCTTTGTTTTAAAAAAAAAACTTTAAATTGAGTTTGTTTTTTCT
TTCTTTGTTAGTCAATCAAACTTTAAAAAAGAAGAACAAGTAGAAATAGTATAGTAAATTGATATAGATA
CTTTTATTACTAATAACAAATCTTTAATGGAATTTATCTGAAATTAATTGTCAAGTTTTAATTCAGTAAT
GATTGATATTACTCTAAAACAAATGCTGTGTGGGGTTGTTTTGTTTGACCTGAAGTGTCCAAGCTTTCCT
GCTTCATGATCTAACTCTTTGTACTGCTACACCTACATTGGGAAATATTGACCTTATAGTAACACTTACT
TTCTTTTATTAATTGTCTAAACTATGCTTTTGATCAATTCACACGTACTTCATTTCTTCTCCCCTGACGA
TCCTGCATATTTCGTCATAATTCACACATTCTTAAAATTATGCACACATCCTTGAAATGTGTTAATATTC
```

FIG. 71L

```
CCAACATTATCAATTATATGTGTTCAGAATTGGTTGCAAAGTTATCAACTCAATTCACGCTATATAAACC
TTACAATTTCTCTACATTTTTATATTTTTTATATTGGCTTTCTTTTAGAATCAATCAATACTTTTTTA
TCATTTAGATACATCTTTCATCTATTAATAGATTATCTTTCTATATATCAAAACACGACACAGTCACGTG
CCAAAAAGGATATAAGAAGGAACTTCACCCCCTTGCTCTTCTTATTATTGTGTGTGGTGTAATAGTTTAT
GGTGTGGTGTATGATTGCGTGTGTGGGTGCAAAAAAAGGTGAAGAAAAAAATACCTCAAAATAAAAACA
ACTTCAAACATTCCCCTCATTTTCTTTCACAGTCATTTGGTTTCAATCTCTATTGGTCTTCTTTAATCAT
CACTATTTATTCCAGTTTATAAGTCGAAAAAAGTTAGTTCATTGTTCAATTGGGTTTATTTATATTTAAT
ACTATGCACTTGTTCTTCCTTGACTAACTCACATGAGAAAGAGAGAGTGAGGAGAGGGTGAATCTATTCT
TTCTATTGATTATGCATAATTTTCAATCAGGTGATAAATAACATTATCGATTGTTCTGTGTATACGTTTG
CATATCTTTCTTATCTATCTTCATAGTAAGAGAGAGATTAGATATCATGATATTGAATAGAGCGTGTAAT
TATCAATTCACTATCATTGTAGAACCACCCTCAGTTGATCTTGTAATTGAAAGTTACAGATGAGTTGATT
ATGCGTATAGGAAAGTATTGAAGTAAATAAAGTCCGTGTGTATTATCTCTTTTTCTCCGCATTTTATTGC
TTTATCATTCATCATCTCTTTTCTTTTCTTTTTATTCTTCCTTTAATACAATAGTGGTCAAGGGGGGGAG
GAGGAAGAAATTGCAATCTATAGTAACATTGATGTTCCCCTCTTTCTGATTAGTAATCCCCCTTTCACTA
TTAGCAACAATAAACTATATATATATGTATATCAAACCTACCTTCCTTCCGGTCTTCATTTTTGTTCTCT
TTTCGTTGACTAGAACTTTCTTAACAAACTTCAAAACTATCATGCCCGATTTATTTGATAATATTTTAA
TAAAATTGGTACAAAATTCACTGGTGGCAAAACCACTCATCATTATGGTGGTGCATCTCAAGTAAATACC
GGGAAATGGTATAGTTATACCAGTAGTGCCAGTAATAATAATTATTGGTTACCTCGAGAAAGTCAAACAA
AGACACCAGGTACTCAAGCAGAAGAACCAGAAACAGTTCAATTTAAAGTGGATCGATCAATGAGTGTTGG
ATCAATTACTGAAGATTCTGGTGCTGCTGGTGCTGGCGGTGATCGATCAAGAATGAATAGTATTACTGAA
TAATTGTATATACAACGTATATAAATAGGCTGGTCTTATTATTATTGCTTTTAATTTAGTATCTTTTGAA
AGATAAATTGGTTAGTGACGTTTTTTTTTTAATAAATTTGTTTCTATATTAATATAAAATTCAGTTATT
ATTATTAATAGTAATCCAATTGTAATTATTTATAATGATATATATAAATATATTTAATATACAGTTTGTT
ATTATTATTCTTTAGTTTTGCTTTAAAATTTATTTTACTTTACTTTACTTTATATGATATTATATCTGTA
TTAATGACGAACTGAAATTGGTGAAATCGGCATTAGATTATGGACTGAGGATAAAACAGTTGAATAAGGG
GGAGGAGGTTTGATGTGGTGGTGTCATATCA
>retrotransposon_20 5325bp Incyte: 1..2386/3779..4807, public:
2387..3778/4808..5325
AATGGGTTTATACAATCAAGGACACCGGTCGCTACAAGGCTCGCCTTGTGGCACTTGGTTATCGACAACA
GGCTGGTGTGGACTTTCTCGAAACGTATGCTCCCGTGATTCGTGGAGAATCAATCAAACTAATCTTTGCA
CTCGCGTCAAAATCCAAACTAAAGATTCATTCCATAGATGTTACCACAGCTTTCCTCAACGGGGAAATAC
TGGAACTCATATTTGTGAAACAACCTCCGGGATATGAAGATAAGAAGCGTCCTAATCATGTTTGTAAGCT
CAATCGCAGCTTATATGGGCTTAAGCAGCTGCCACTAATGTGGAACATTAAATTAAATGATGTACTTATA
AAGGAAGGTTTCCGTCGACTTGGTGGTGACTTAGGGATATACATTAGTAAGGACAAAAGAACAATAATGG
GAGTTTATGTTGACGACATTCTCATTTGTGGACCTTCTGACAGTGAAATTGAACAAGTAAAGAACAACGT
GAGAAAATACTTCTCAATAACTGATAATGGATTATGCCGAAAATTCCTTGGAATTAACGTCTATCAACAA
GCAAATGAAATAAGATTAAGTTTGAATGATTATATAAGGAGAATGATTGAGGAGTTAAAATTATCTGTCT
CAGAAACAAACCCAGTATCTATACCATCTGATGTCAATTATGAAATATTTAAAGTTAACGAAAATGATGA
TGAGAAACCATGTGATCAAACCAAATACCGAAGTTTGATAGGCAAGCTCTTGTTTGCCAGTAATACTATA
AGGTTTGACATCGCCTATTCTGTCAACTCCCTATCCAGGTTTATCAACGATCCCAAAGAAAAACATTGGA
TTGCAGCTGTCAAGGTGGTAAAATATCTCAGTGGTACTCAACGGTATGGTATTTGTTATAACGGTAACGG
TGACTTGAATATTTACGCTGATAGTGATTGGGCTTCCACTCCATCTGATCGAAAGTCTATTACGGGGTAC
ATTGTTACCTATGCTGGAGCGCCGATAAGTTGGCGTTCCAAGAAGCAGAACGTGATAGCCTTGAGTACGA
CAGAAGCGGAGTTTATGGCTCTCACAGAGTCCATAAAGGAAGCCCTTTGGCTAATATACATTTTTCGAGA
TATTAATGTGATATTGAAATTACCAATTGTGATATATGAAGACAACCTACTGTGTCAGAAATTACTTGAA
AATCCTCGATTCCATAATAGGACAAAACACATTGACTTGAAATATAAATTTACCAAAGACCATATAGAAG
CTGGTACAATCAAAGTGGAATCAACTAATTCAGCAGATAACTTAGCCGACATGCTAACTAAACCTTTACC
AAAAATTAAATTTAAACATTTAAGATGGCTAGCAGGATTAAGACCTTTAGATTGATTAGATAATGATAAA
ATGAAATAAAGATTAATTTGGAGATGCAGGTTGATGGGGAGGATGTTGGAAAAATGAAATATGATCAATC
CTGCATCTAGAACCTGTGGCAGAATGAAACCTACGAGTTATGAATGACTTGTGAATACAAGTTGAATGT
TACAGAATGTTACCAAGAAGGTTACACTTGAATATATGAATGACTAGAAAGTGAATTGAATGTTACAGAA
CCTGAATAACAATGTTACACGAATGTGTGAATGATATGAGTTTATCTATAGTAATGTGACATATACACAA
AGGTGTGAATGACCGAGAAAACAGATGTTACATTACGGGCACTGGAGAGTGCAAGTCTAAAGAATCTTGG
AGTAGAAATAAGTAATATAAAAAGGACCAAAGATTCTTTAGAGAAAAGTAAATGAAACTATATTAGATTT
TATATAACTAACTAACAAATAAATAAAAAATATAATATGTCTACAATGCCACCAACTTCCAAACGTACTA
GAAAGAGAACTAGAACCGATGATAATGCTGAACCAACTATTCAAGATCCTTCACCGCCACTTGCTAATGT
TGAACCCACAATTCAAGAGACTCCACCGCTGGTTGAAGTTAGTGATGAGACTAATTCAACTGAAATCAAT
GAGACAAATAGTAATACTCATGAAGAAACAAATGTATTAACTAATGTGCACTCCTCTCCAATCGAGACAG
```

FIG. 71M

```
TTACTGAGAGGAACTTCAATTTTCAACAGGTTATTGCCTCTATCTCCACTGTGGACAATCAAAGTCTCTT
GAAGGATAAAATTTCTTATGATCATTGGTTCAGTACCTTGAAAGAAAATGCAATCATGATTAGTCCAGAT
TTTCTTGACTTTATTAACAAAGACACCATGGATCTCCAACAGTACCCAACTGTCTACCAAACATTCTTAG
ATCGTCTTATTTGTGCCACAATTGACCCACATATCAAACAATCTTTAAAATATCGGAAGTTATCAGGAAA
GAAAATGCTTAGTGAAATTATCTCTCAATTTGGTTCTATGACTATTAAAGACAAGGTTAACTACTCCATA
ATTATGGCTACCAAAATTCATTCTGATGTCACCACTCATTTAGACAAAATGAATTTACTGGCTCAATTTT
ACGCATTTCTTATGCGTCAACCTCAGGACCTTAAACCTGCCCTTTTACTTATTGCGGGTATCAATGACTC
ACGTTTCAATGAAACATACTTTCACGATAACAAAGAATTAACGATCTCTAAGTTGGAACGGTATATCATT
AATCAAAACTCCAAAATTACTCCGTCGGTACCAACACCTTCTCCACGTGACGCTGTTACGGGTTTACTGG
TTACCCAGCCTACGTCCGCTCTGGGACAAAGTGAAGTGTTTAATACACAATGTTTTAATTGCTTTGGGTT
GGGCCACACTGCACGTCGCTGTGCCTCTCCGAAACGTCTTGGCCAAATAAACAACCTTAGATCTAAATTA
CTTGCGTTTGAAACTCGATCCAAATCCAGAAAGCGTTTTCCACCTCAACCTCCTCCTACGAATCGGTCGG
CAAACTCAACAATAATAACTAATCCCTCACCTACTGACGATACCATCTCGTCCACCACTGAAGATTCTTT
TCCACGGGACGTCTTTGGATGGGCGGCATCATCTGACCAAATCAAATCAAAGGACAACCTTTCTTTATTT
TTTGACACAGGTGCCTCGGCACATCTTATCAATAATCTCAATCTACTTCATGATTACAAACCCTCTAAAG
AAAACAAACATGTGATCACTGCGAACGGTGATAAAATTCCTATCTTAGGAACTGGAACTGTGAAACTCCA
ACATGGTCAACACAAGATATCACTTCGCAATTGCCAATATTCTCCACATCTACACATCAATCTTATCTCA
CCCAGACTCTTACTTGATGATTCCACTAGCATGACTATCACCCAATCCGGGATTTATCACTCCAAAATTG
GACAAATTGGGTATTATTCGACTGAAGATGGTAATCTAATCAAGTGTATGTTCCGTCCCATTACCATTCC
TCATCTTTCGTTATATTCTCAATATGTCGAAATGGGTCTTCAATCTAACAATGTACTACGTAACATTCCA
GCTTTCACGGTCCATATTCCTCAACTACATGACTCCCTTGGACACACATCTACTCAACAAGTTTCAAATG
TCATGAAACGTTTCAATGTCACTACTGACAACATTGGTACGGACTGCGAAACTTGTCGGCTTGGAAAAGC
CATTACTCAGATTCCCAAGATCTCAACCCATACCATCTCTAGTCATTGCTTAGAACTACTTCACGTTGAT
GTTCATGGACCAATATCCGTTCCTAGTATATTTCAAGAACGTTATTTTCTTGTGATCCTTGATGACTACT
CAAAATACTTGACAGTTCAACCACTATGCAACAAATCTGATGCTACTGCCGAAATTATCGAATTCATCAA
TCATTGGGAAAAGTTCTTTCTGGGAAATGGCAATTACCATACGAAAATTCTCCGGTCGGATAATGGAGGG
GAATTCTTAAACAAAACATTGACTACCTATCTTGATTCAAAATATATTACTCACCAAACCTCCAATGCCT
ATGAACATCATGAGAATGGCGCTGCAGAACGAGCTATTAGATCGGTTAAAGACATGGCTCGAGTAATATT
GCTTCAATCCAAATTACCAGTGCCGTTTTGGTCCCTAGCAACCCGATGTGCTGCGTTTGTTATGAATCGT
CTTCCTCATAAAACAATAAATGGTAAGATTCCTTATGAAGTATGGACTAAACAACTTGTCAATCTCAAAA
TGATGAAACCGTTTGGCTCTCAAGTATATGTGAAAATTCCTATTGGAGTCAAAAGTTTTTCTGCACAAGC
ACTTTCTGGAATCATGGTGGGATATGCCACTAATAAGAAAGGCTACCTTGTATATGATCCCACACAAAAT
CGAATATTCACATCCTCACAAATAATATGTCATCCGAGCATTTATCCAGCAGCCAACCTTACGTTTAACG
AACCCTTAATTATCTCATCGAAAGTCACGGCTGCTCATCTTCACCCCCTTACCATTTCCAATTTAGTTAT
TCCACCTACCAATGCTGTATCTGAGACACCTCTGCAAATTGTGTGCTCTCCTCAAATTCGTCAGTATGTC
CCAAAGTTTGCCAATTACAAACTGTCTTGGAACATGGGGAGGATAAAATATATGCACTGATTATACCAAT
ATCGATCGGCAATATGAAACGCACAAGAACAAATGAAAACAAAATATGCCAGCTAGATGAATCGAACAAT
ACCACCATACCAGATAGTGTAATTTTATCGGCTAACAATGTGTTATTAAACTTAGAATCGAGATCTTCCA
TTCCCAAAAGTTATAAGGAAGCTATAACATCTAATGAAAAATCCAAATGGGCTGATGCTATGGATAGCGA
GTTTAATTCATTACAATCCAACAACACGTGGTCACTTGAACCACTACCGGAGGGACGCAAAGCTATTGGT
GTCAAATGGGTTTATACAATCAAGGACACCGGTCGCTACAAGGCTCGCCTTGTGGCACTTGGTTATCGAC
AACAGGCTGGTGTGGACTTTCTCGAAACGTATGCTCCCGTGATTCGTGGAGAATCAATCAAACTAATCTT
TGCACTCGCGTCAAAATCCAAACTAAAGATTCATTCCATAGATGTTACCACAGCTTTCCTCAACGGGGAA
ATACTGGAACTCATATTTGTGACACAACCCTCCGGGATATGAAGATAAGAAGCGTCCTAATCATGTTTGT
AAGCTCAATCGCAGCTTATATGGGCTTAAGCAGCTGCCACTAATGTGGAACATTAAATTAAATGATGTAC
TTATAAAGGAAGGTTCCGTCGACTTGGTGGTGACTTAGGGATATACATTAGTAAGGACAAAAGAACAATA
ATGGG
>retrotransposon_21 2027bp public: 1..624, Incyte: 625..2027; zeta-like LTR:
1384..1891
TTTGTTTGATAAAGAAAATAAAAAAAAGAAACAAGGGTAGTAAATGAGTACAGTAGCCCTGTTGAACAAA
GTCTGCGATAACTTAATTATGGGTGAACTCAAGGGGACAGTGTCTTTGTCTATCATCCGATCCTTAATCA
AGTCTATTACTGAATATCAATTATTTGGACACCTGTTTATAAATTACTATCCAATCTATGTTCTTTCAAT
TCTTTCCTTCAATATTTTGCCAGCCAATAAGACCAAACATAATCCAAATATACATACCAGTGAATTCTAA
ATTGTTTGGTGAAACATCCATTTTTGATCTATTTCAAATTGTATTTCTTTTAGTAGTAGTAGTAGTAGC
AGTAATTGATTAATTATTATCAATATCCGAAATGATGATAAGAATAATAATTATATATATAAGAAAGAGA
AAAAGAGAAAAGAAGAAGAAGAAGTATAAAAGAAGTTGTTATGGGTTTAATTAAAAAAGAAAAAATTCAA
TGAAATTTGTGTTGTGTTGTTGGGTTTGAATTTCTGTATAACTCAATTTGGAGATTTTTTTTTTTTTT
TTTTTTTGAAATTTTTATTAGTCGTGTACATTGTTACAATTGTTTCTCGTTCCCTTTTTTTTTTCCTTT
```

FIG. 71N

```
CTTTGTTTTGTTTTGTTTACCTTGTGATAATTTTATACGTGTTGAGAGGGCTCTCGTCGTGCCCGTGTCC
GTTTCCGTGTCCTGTTGGGTCCCCTCCGCCCATGCCGCACCGCACCGTACGGTAATGATATCTGATTGTT
GGAGCGTTCTTCGCTAACAGGTTCTTTATTTTTGTTCGGGGGTTTCGAAAGATAATGTAGAAACACCAGG
GCTTATAACTGAGAGTTAGAGTAGTGGAGATTAGTAGTAGTAGTACAATCCTATAGCCCAAACATTATTG
GAGAGATCTTACCAAATAGCAATCATCATGATGTATTTACTACTACATAAAGAATTTAAGACGATATTTA
CCAGCAATAAACAACATGACCAACTAATTAACAAACATTTGAAAAACATAAAGTAATTAGAAAGTTTAAA
AAGTGTACAACCAGTGTGGAAAAGAATGGAATTGGAATTGAACAAAGTTATTAATTACTGAAAAAGGAA
ATTTAATTTCTTGAAAGGCAAATCTTTGTTTGTTTTTTTTTTGGGTCTTTTCTTTCATTTAATAAGCGT
GGGGTATTAATAGATAATGATATTGTTGTTGTTATTGTGATATTGTTGTGAAATTTGACATATGATAAGA
TAAGTTTCTTTCTTTTCTTTCAACTAGTATAATTGAACTAAAGACCACCACCACCACCACCACATAGTTA
GCAACCTGATATGCTGTTCATGTAACAGTAAATTATCTTGGTACTATACCACTTGTTGTAATATAGCTAA
TGCTAATTCTTGATTAGTGTGGAAAGCCTAATAAGGTTATATTGTGCACAGGTTAACTACCTTAATATAG
TTATTGTTAATACAGTTATTGCTGTTGACTACTATTGTTATTGTTAAATTAAAGTGTTAGGTTGAGTTAA
TTGATTAGTGAAAACCAACTAACTACCGTATTAAATTATTGTATTAAGATTGATTCCTATTAAGGATAAA
ACAGAGAGTGTGTTAGAAAGAGAAAGGGTGGATTATAAATATGTGTAAAATCCCCTTTAGAGACTAACCA
CTAGAAATCTATTGATGGTTTCATATATAGAGATTAACGATTATATTTATAATATAAGTTGGTAGTTGCT
AGTATATTTGAAAGCACTACAGTATAGTATGTCAGAATCAGATCATTTAAACTCTACTAATAATACAGGA
AACACTTTCATTAGTCTAGATCAAGCCAGTACAATAATGGCAGATCAAACTCAAGGAGCTAACCCACAAC
AATGATAATTCATCTTTTTTGTCAAGACGATAGGTTAATGTTACAAGCACTTTATTGGGCTCGAAATAGT
GGTAAATAAGTCCATAGATATGACCTGTTACAAGTTATTTCGATGATCAAGCCGGCTCTGTGATTAC
>retrotransposon_22 2118bp Incyte: 1..2118; zeta-like LTR: 1419..1927
TTTTTTTAAAGAATTAATTAAATATGATGGATGATAGAAATTAAAGGAAAAAGAAGAAGAACAAAACAAA
AGTTTAATTGAAAAAAAAGGGAGAAATGAATATTGAATTATTCAGCTTTTATATTGCTGATAGATGTTGA
AAAAAAAAACGGAAGAATGGGGATAGCAAAACTGTGGGTGAGATTAACTCATCTATGGCGCTAAAAGTCT
TTTTTTTTCTCTTTTATTAGGGGGCACATAAATTATTCTTTTCATTGATAATCTCGAGTCCGTTTTTAG
TTCATTATTCGGAATATATTACCGTATTGGGAACGATAATTATTATTAGTTCTCCCCGATGGTTCGATTT
TGCTGGTGCAAAAATATAAATCCGATATTACTTTATTGGTGTTTTAATAAATCCGTTTTAAAAGTTCGTA
GACATATACAGGATGATAATAATTTAACCGATTTATAAGTTGGAATCATTTGGATGAATCCGCTTGGGGA
GACGTTTTCCAATTTTAGAAGTTTAACTATCAATTTTATGTGACATCCGAGTGTACACATTTTGTGAATT
TGATCTTATCAACTCACTTGGTGTACCATGGCATTTATAACAACACTTTTTAGAATCGGCTGAGTTACAT
GCATTTCCTCTATTTGTAGATTAATGGAAATTCATAAAATCGTTCACATTTTTTCTATAATGAGTACCA
TTCTGTTTCCATAAGTAGGGGACTAAAAAATAATTGATATCTCTAATCAGTGACAGCTCTAGTCAACTTG
ACCGTAATGTTTTGACGACCATTATATTTCTTGTTTGAACTATTGATTTATGAGTGTTGTCGTAACAAAA
GATCAATTCCCGTCAAAACGCATTTGGCACTTAATCTTTGATTGAACCGATTTTGATCTCAAAACATAGT
ACCAAGGTCAATTATGTTCGCTAATGAAAGAAAGCTGTGACGAAAACCTCAAATTCATGAAGAAAGAATT
ACTGTTGTGGAAAATAAAAAAGTCTTTCTTCTGATACTTTACAAGTCCCTCAACCACAAATACAAAAATG
AAAGTTACCCATCGATCTTTTTCATTGGTTAAGAATTAATACGAGAATATCAAATTATCTTAGAGAGGGT
CTCACAGAGCAACTTTCTGAGGCACACGGTCACCAACATGATTTGTTATAAAAAATTCAACCAAATTTTG
GAAAAAATGAAAACAAAACAAAACAAAATCTGAAACATCCCGAAAGTCACAAATGCTTGATTACTTAAAA
TTACTTATTTGCTTCAAGACGCTATTATTATTATTATGACATAATACTACTTGAATAACAGTGAACTGTA
ATTGTATTAAGAACAAATCATAACAAAGGAAGATGATGACGATGATGATGACCCCTTGAAATATCCAGGG
CACATGCATTGTGATGATTGTTGTAATATAGCTAATAGTTATTCTTGATTAGTGTGGAAAGCCTAATAAG
GTTATATTGTGCACAGGTTAACTACCTTAATATAGTTATTGTTAATACAGTTATTGCTGTTGACTACTAT
TGTTATTGTTAAATTAAAGTGTTAGGTTGAGTTAATTGATTAGTGAAAACCAACTAACTACCGTATTAAA
TTATTGTATTAAGATTGATTCCTATTAAGGATAAAACAGAGAGTGTGTTAGAAAGAGAAAGGGTGGATTA
TAAATATGTGTAAAATCCCCTTTAGAGACTAATCACTAGAAATCTATTGATGGTTTCATATATAGAGAT
TAACGATTATATTTATAATATAAGTTGGTAGTTGCTAGTATATTTGAAAGCACTACAGTATAGTATGTCA
GAATCAGATCATTTAAACTCTACTAATAATACAGGAAACACTTTCATTAGTCTAGATCAAGCCAGTACAA
TAATGGCAGATCAAACTCAAGGAGCTAACCCACAACAATTACCATATTATATGAAGAAGACTATAACAAA
ACTGTAGATAGTAGGGGATTGGTTATTTCCGGGGAGTAGAAGTATTGGGTTATCTAAGTCAATCTTTAAC
AACCAACAATCAACAACAACCAACAACGTTTTTCCTATTCTCGGAGATAACTTGATTAACTTAAAAATTT
TCTTGTCAAAAAATTTCT
>retrotransposon_23 4929bp public: 1..4929; zeta-like LTR: 2990..3497
TAATTCGCGTATGAATGAGATTGATGCCACTGTTGGTGCTGAAGTTTTAAAAAGAAACAAATGGAAGAT
ATGCAAAACAATAATAGTAATAATGGAGGGAAAAGATTTAAATCAGATCCAGTTTCTGATCAAGAAATAT
TAGATGCTTGGGAAAATAATCAATTGGATAGGTTTTCAGTGGATCAATTGAAGGCATTTAGAAGAAATA
TCCTGATGTCAAATCAGCTAATAAGAAAGCTGACTTGATTGAAAATATCAGTGAGTTTATAAGGACTCAT
AGAAAATGAGTTAATATGTAATAGTGATATGTTTATAGCTCTGTAAATACATGTAAATTTTTTGGTTGCC
```

FIG. 71O

```
AATGAATTGATTGAGACTGAAAATCGTTTGTGGTTTGCCAATGAACATTAAACTTATTACTTGATCTAGA
AGGCAGTTACTTGTTTAAAGAAGTGATGAGTCGTGATTAAGTAAAGTTTGCAGCACTAAATATTGTATGG
TATTTGACTTAATTTTTTCTGCAAAAAAAATTACAAATTTTTAATGAAAAAACAAAACACAAGATAATAA
CATTATAGAATAAAGATTATAGGATCCTACCAACATAGTTCCATTGCTGATCAGGACGTTTAATAAAAGA
GCTTCCCAACAGAGACATATCTTAATAATAACAGGCTATTTTCTGCCTTTAAAAAGCCATCTAGGCTCAA
AAACCTCAAAATAATTCATCTCCCACCTTGGCAGCAGAGTAGCCATAACACAGCCAAATCAATTTCTATA
GTTTACATAATATATAAAAGGTTTCTAATAGCCAGTAAGCTTATAGAAATTACCCTTTTCAAGTGATTTG
ATGAACAAATTATATTCTTGTACAAAATAGTATATTTAAAATTAAGAATTTGGCTTGCAAAAGAAACTCT
CGGTAGCTTAGTTGGTAAAGCATTAGACTGTAACTGAGTTATTGTTTGCAAACAAACAATTGGAATGCGA
TCTAAGGATCGGGTGTTCGACTCACTCCCGGGAGATTTTCTTTTTTACCACCACCATAGTTAACACGCTA
CCATATGAGACAGAAATCTAGCATGAATGGCTTATATACAAGTGGACCATTTAGAAGCATGAGCTGTGTC
CTAGTTTTTTATCATTTACAATTGAATTTCCCTCTGAAATTAAAATTCTAAGGTATTCATTTATCTCAAC
TTTCTTAGATGCTGTTAGTGGGTTAAAACTTGGTAATGAACCACTGACGGAAGTTATTTTTGTGAGAATT
AACTATAAATATATCAGCTTGGTTTTTTTTAACAACTTAGACAGCAATAACCAACACCCAACTAATTAAT
CAACATTGTTATAAAGTTGTTTTCATCTGTCAAACCAGGCACATGGTAGCACATCAAAATCACTCTCGAT
AGCTTAGTTGGTAAAGCATTAGACTGTAACTGTTCATTCTGGATATTGATATCTAAGGATCGGGTGTTCG
ACTCACCCTCGGGAGAAATATTTTTTTTTGCTTATAATTCCTTCAAATATTTACCTCCAGTATCGGTAT
TGAATTAAATACAGAGAGCAATTGGAAAGGTTATTTTTTTTGTTATTTATTCCAAAAATTTCAGGACTCA
AAGTTTAATAAGCCAAAGCCTATTTTGTACTGCGCTTCCCTTTAAAGCCCCTGCTAGCCCTGGGCTTGT
TGTTGTTGTTGTGTATGGAACAAGTTTATTAAATCCCATGACGACGATGATGTAATTGATTTTGAGAAAA
AAAAGGATGAACAATGGAAAAAGGTACAATGGGTTATATACTTTGCCATGTGGTTGAAAATATGTTTAAC
GGCTGTAGAACTTTTTTTATTTTGTGTTAGTGAGTGAATTTCGCTACAATTGTTATTATACTCCACAAT
TCAGATTTGTTGATAACGTTTAATTACTTAAATTTTAGTATGCATATTGATATATTTTTCTATGAGATT
GACGATTAATTATCGGTTTGTAAAATTCTATTGAAACACATTCACCAGTGCAACAATTAGACATTTCTC
AAAACCATGAATAGCTTGCAACTAAAACAAACAATAAGGCTGTACACTTTGCTGGCAATAAATCAGTGTC
AAGTCAATATAAACAGTCTTAAGAACAATGAGAAACTCAAAAGTTAGGGTAGTTAGTTGATTACAAAAGA
AAGAGACCACTTAGAGACAAAATAACAAGAAATGACATCACCATTGTAATAGATACATTTTCCAGTTATT
CAAGCAATTGATTGAATGTATTCATAGCAAAATACATTTAAGACATACAAGCTTAAACATGGGTTATTCT
CTAGTGGTGTTGTTGTTGCGATTCTAAGACTCCAATCTATGATTAATAATCGGATCACCATTTGCACATG
AACTACATTAAGTACTAAAAAATATGCAATTCGCCTGTTTTCTTATTGATTAAATTTAACAATAAACTTG
TCTTTAGCTTTGGCAAAAGCCTCCTTGAAAATCCTAACTAAGCACGTTGGAAGAGCAATGGAATTGTGGT
TAGTTATAGAAAGCAAAACAATCTGAATTGTAAAGTATTAGATGATGTGCAATGATATCAGAATAAAAT
AGTTGCTGTTGAAAATTTGTTCAAGACTCTTCACACAGCATAGCAAATAGTTATACATAAAGAGAAAAG
TTCAACGTGCTTTGTTGCCCGTGTCTATTTGTTTTTTTAAAGCCGAATTCACCACTAGAGGGAGTATATA
TGATTCAGAGTATCACCATCATCATCATCGAGCCCCCGTAAAAACTTACCAACTTTCGTCGACATTTCCG
ATGAGAAACTTGATTTTTTTTTCCTTCCGTTGAAATAATGTCAGATAGCTCGCAAATATCGGAACGAGCA
AATTCTTGGTCCAGCACCAATAATTCGGAAAATCACACTCAGTTAATATTTACTTACAAAATAAATTTAT
TTGTAATTTAATGGCTATAAAATGGGAACGTAGTAAGAAAATCAACAGCTGTTGTAATATAGCTAATGCT
AATTCTTGATTAGTGTGGAAAGCCTAATAAGGTTATATTGTGCACAGGTTAACTACCTTAATATAGTTAT
TGTTAATACAGTTATTGCTGTTGACTACTATTGTTATTGTTAAATTAAAGTGTTAGGTTGAGTTAATTGA
TTAGTGAAAACCAACTAACTACCGTATTAAATTAGTGATTAAGATTGATTCCTATTAAGGATAAAACAG
AGAGTGTGTTAGAAAGAGAAAGGGTGGATTATAAATATGTGTAAAATCCCCTTTAGAGACTAATCACTAG
AAATCTATTGATGGTTTCATATATAGAGATTAACGATTATATTTATAATATAAGTTGGTAGTTGCTAGTA
TATTTGAAAGCACTACAGTATAGTATGTCAGAATCAGATCATTTAAACTCTACTAATAATACAGGAAACA
CTTTCATTAGTCTAGATCAAGCCAGTACAATAATGGCAGATCAAACTCAAGGAGCTAACCCACAACAACA
GCCTAGTCTTCTTGACACTAAAAAAAAGAGATAAAAAACAATTTCAGCCAATCACATGTACTACATTTG
TAATAGATTTTATTACTTCAGCTGCTTATTACACAAACAAGGTTGAATTGATATTGTGTAGAGTAAATTT
TCGGAAATAGTTTGAATTGGGTGATCATTTTCTTTATTTTTTTATGTCTTGTTTCTGTGAAGATCGGAA
TGCCAGAGTGGAGCTCGTGAATTGCACCACTAATTGCAGCAGCACCATATTTCAAATAAAGTTTCTCATG
TTGTAGTAAGGATTGCTTGTCTCCATGAAACCAATCACTTAACTAAGCCCCAGGCTAATTAGTGTGTCTT
CAAACAGTTTTGTACTAGAGAAACTCAGACCTTCCCAGGGCAAGTAACAACCTAAAAAAATGCCACAAAA
CTAAATGCAATTTCAGTTTGATATGATAGGCAATGACATCAACACCTGGAAAAAAAAAAACTTTCAGGT
GATGAAACGATTAAGGATTAAAGTTTGCAACGAAAAACAAGTGGAACTAAACTTTGCCTTATTGTTTTGT
TCCGCTTACCTAATGATGTTTACTCCTTAGAACAAACAACATCAACTACTTTAATCCTGACGACGAAGA
AGAAGACCAAAAGAATAATTAGCCGCAGCTACGGTGGTGGCACTAGTAGTAGTGCTAGTGCTTGTTGTG
TCTCATCCAAGAGAAATGGAAAAACTGCAAAAATGCCGCAACTTTGAACATTTTGGAACACAATACAACT
TTTTTTTTCCTTTTGGATTTACGATTAGCGCGATAGACGTGACCATAAAATACCACACGATGTGTAGAT
CCTCTAAAAATAATGTACACATTTCCAGGCTTTTGTTTACTGCTTAATAATTTGTCATCATCGGTAACAA
```

FIG. 71P

```
TGATAGTCTCCCCACCCTAACTACAGTAGACGGAATTAGACACCAAAGATCTTATAAATCAACCCCAAAT
TTTCCCATTTTGATTTTTGATTTTTTCGTATTCCTTGTTGTTTCCATAATTTTTAGTTACTCCTCCTCA
ACTAAACTAGATAACTCGTCACAGTTAACAACAGAAAGGTATGTTAAATATTTATTTCGTTCTAAATTCA
AGTTTGGTATAGAATATTGCAAACAACAACAATCTGAAAAATGGACTTTAATTTGCTCTACAAAATGCAA
ACACATCTAGAATTAATATTTGGTCTGGAAACCGTATACGGAAGTTATGGATAATCACGTTATCCTGATA
TCTATTATTAACACCACCACAATATCTATTATTTCATGTATGGATTGCGGTGCCAAGATCAAAGAATCAT
TTTAACCCGATATCTTACATTTCACCTCGATCTAAATGTGATTCAGTATCACCGGCTCATTGTTTCACCA
CTCAACCTCCCCATACTGGGAGTACATAT
>retrotransposon_24 4954bp public: 1..4954; zeta-like LTR: 256..763
TGTTATAAAAAATTCAACCAAATTTTGGAAAAAATGAGAACAAAACAAAACAAAATCTGAAACATCCCGA
AAGTCACAAATGCTTGATTACTTAAAATTACTTATTTGCTTCAAGACGCTATTATTATTATTATGACATA
ATACTACTTGAATAACAGTGAACTGTAATTGTATTAAGAACAAATCATAACAAAGGAAGATGATGACGAT
GATGATGACCCCTTGAAATATCCAGGGCACATGCATTGTGATGATTGTTGTAATATAGCTAATGCTAATT
CTTGATTAGTGTGGAAAGCCTAATAAGGTTATATTGTGCACAGGTTAACTACCTTAATATAGTTATTGTT
AATACAGTTATTGCTGTTGACTACTATTGTTATTGTTAAATTAAAGTGTTAGGTTGAGTTAATTGATTAG
TGAAAACCAACTAACTACCGTATTAAATTATTGTATTAAGATTGATTCCTATTAAGGATAAAACAGAGAG
TGTGTTAGAAAGAGAAAGGGTGGATTATAAATATGTGTAAAATCCCCTTTAGAGACTAACCACTAGAAAT
CTATTGATGGTTTCATATATAGAGATTAACGATTATATTTATAATATAAGTTGGTAGTTGCTAGTATATT
TGAAAGCACTACAGTATAGTATGTCAGAATCAGATCATTTAAACTCTACTAATAATACAGGAAACACTTT
CATTAGTCTAGATCAAGCCAGTACAATAATGGCAGATCAAACTCAAGGAGCTAACCCACAACAATGATAA
TTCATCTTTTTTGTCAAGACGATAGTTAATGTTACAAGCACTTTATTGGGCTCGAAATAGTGGTAAATAG
GTCCATAGATATGACCTGTTACAAGTTTATTTCGATGATCAAGCCGCCTCTGTGATTACGGCAATTATTT
TACTATTGATAATGAGTAAAAGTTCACAACCAATAGAAGATATCCACCCAAGCAATTTCTCTCGACGAAC
ATCTTTAGAATAGTTGGTATAATAACCTTACGAAACATTAATAAAGAAATTGTACCCGATCTTGTTTTCG
AGTCAAAAACAAAGAAATCAAACCTAGAATCAACAATGTTCTAGCCATCATCTCCCGCCACCCAAGTGAT
GTACCCCTATTTCTTGATTCTATTATTTTCTGACCCTGTGAGGGAACAAAGATACTATCTTTAATAAAGA
AACAAAACCTCAACAACAACAACAACACACTAACACACTAAGAAACTAAAACTTGACGACAATATGATAT
TGTGATATATTAATACTGCCCAACATTCATCGTCGTCAAATCAGAATTCAGAGCAAAAAAGAGACGTTTA
CGTTACATTCCCCGATGTTTTTGTGACGTAACAAGCCGAAGAGAGGGAAAAAAAAAGTATGGTTATTGAA
AATCTAGTTAGGATCTACTTTCCTTTTTGTCTCATCTATTTATCAAACACTATCAACGCGTTTTGAATTG
ACGACCAGATCTATATCATCTAGTTTATAATATTCTTTGTCAGATCTGAATTGATCAATGTGTGGTTGTT
GTTTGTAGTTTTTTGTTGGATTTAAACTACTCACAAACATCAAGCTTTTGAGTAAGAATTGAATCAAATT
CAATATTGTCTTGTCACTTTTTTTCTGCGTGGTACACTACTACGAAACAAAATTTAAATTGTCGTGTTCT
TTTTGATAATTTGTTTGTTATAATTTTTTTGCTTGTGTGAAAAAAAAAGAGAAATGATAATTCGTTTTTT
TTATAGGGGTTTTTCTAATTCAACTCTTATAATAAATTAACTTATCAACACCGTAAATATAATTAAACCA
ACTGTGTTGCGCCATAAATAAATAAGTTGTTTCGGGATCAACACATCTCCAACAAATTGAATCGTAGGTG
AAAATTTTTTTTTTACTAGTAATTGGTAGTAATGGTGTTCACGAGTATTTTTTTTGGGGAGTATTTGTG
TCCCTTACAAGAAATAAAGCCAGGGCCATGAAAAAAAAATTAATACAAAACAAAATATTCGTATCAGCAC
AGCAGCACTTCCCCCCCTTTCCCCTTCGGCACGCCCTAAAAAGAATTTACTCATGTAGTCGTTATCACTT
CAACACCACACAAGAATACCTCGAGTGAAAGAAAATTGCTTGGGGAATGTGTGTAATTGGCTATGTAGAA
TTTGGTATTAATAACATTTCTACTGTTTTTCTTGTGCCATAACATACTTTTATCGCGATATATTGCAAAG
CCCCCCCTTCTAGCTCCTAATAAAAAAAACCCACATTACTATTATATTTAAAGTGTGAATTGGAGGGGAC
AAAAACAGAACAATGAGCAATTTATAATAGTGAATAACCTTTAGCAAAAAAAAAACATTGTAAATTCAAT
ATTTGACGATGGATTTAACAAACAATCAATCAAATTCTTAGTGTTGAACTGAACTGAAGTGATATTTTTT
GCCATATGCACAAAATCTTAAATATTCAAGTCTACACGAGAAAACCCAAAAAAAATGTTATTGTTTCAAA
AATTAATGCTTATGTAACACAACGCCAAATTTAAACCATTTTTTTTGGTTACTAAAAAAAAAAACAAA
CAAAACAAATAAAAAAAAGGATTACAAATTTCAGGCACATTGTTTAAATTTACTGACGCCAATTATTGT
TTGATTCAAGTATAAGTTGAGAATGATTTTCCCAATTTATTAAAACTACATACAAAAGAATATTAACCTT
TCTATTTTCTTTATTTTTTCAATTTAAAAGATATAAAATCGTTTCACCTTTTCTTTAAAATTATAATTTT
CAAGACTTACCTTATTTGCGTTTTCTAATCGCGTCCACTCCTTTATTACTACTATTAGCTTAAGTCTTTC
GTTCAAAAAACAACTACAATGCGTGCCAACTATTTGTTATTATTAGCTGCCACAGCTGTTCAAGCTGCTC
CATTCATTAAGAGATATGAAAACACTACTGCTCCAGCCAGTCAATTGTCCACTTCATTGGCTGATGGTTC
CACTACCATTCTTGGTTCTTCATCATCCAGTGTTGAAGAAGATGAAACCATCACTTCCACTATCGTTCAA
TATGTTACTGTCACTTCTTCTGACACCACTTACGTTTCTGCCACCAACACTTTGACTACTACTTTAACTA
CTAAACCAACCCCAGTTATCACCACTGAAGCTGAAGTGACGAAGAAGACAATGAAACCATTACTTCCAC
CATCCTCCAATACGTTACTGTTACTTCTTCTGACACCACTTACGTTTCTGCTACTAACACTTTGACTACT
ACTTTAACTACCAAAGCAGCCGAAGCTACTGAATCCGAAGAAGAAGAAACGAAACTATCACTTCCACCA
TTCTTCAATACGTCACCGTCACTTCTTCTGACACCACCTACGTTTCTGCCACCAACACTATAACCAGTGT
```

FIG. 71Q

```
TTTGACTACCAAAGCAGCAGTATCTACCAACGACGTCAGTGAAAATGCCAAGGCTGCTACTACTGAAGAT
GATGGTGAAACCACTACTTCAACCATTACTAGTATCGTTACTATTACTGATGCCAATGGTAACACCGAAG
TGTTGACCGAAGTTGCAGCTGAGACCAGTGGTGCAGAAGATGCTTCCTACTGTGTTCCTTCTACTGTCAC
TGTTACTGTCACTGCTGAACAAACTTCCGAAGTTGTTTCAACTATTGTTCACACTACCCAAGTTCCACTT
ACTGCTGAATTTACCCTTGATGATACCACTACTACCCTTACATCTTGGGTCGACTTGACTTCTACAGATC
TCGTTACTATAACTTCTACTTCAAGTGTCTATGATTCATACTCAACTGGCGTTTCTCAATCCCATCCAAT
TCCTCATACTCCAACTACACAATTTCGGACTATGCCCCACCAATCAGTTCTTACTACTCTTTGTAAAGAG
CTTGATATGAAAGTTTGTGATAGTGATACTACTACCGCCGCCACCACCACACCTTTAGAGTAAAGATTTG
TTTTTAAAAAAATCATTCTCATCATTTTTTTTTATTGGTTTTCCATTTTATGTCGTTTTTGACGTTACT
CATTTGTTTTATTGTATTTTGATAACTGGGTTTATTTGAATTTTTGCTTTTTTTATTTTTATTTTAA
CATTGTTATTCCTTTTTCCTTTGATTATTCCTTTAGTGGTTGGTGTTATTTTGATTTTGCTTACATTTT
TGCTTACATTGTTATATTTGTTATTCCTTTGTTAGAGTTTTTTTTATTTTTGCCCTTTTCCCTTTTGA
TTTTTTTATCATTGTCTGTCTTATTCAATGGTTTTCTAGTCTAAAAATTTGGTCTAGTTGCTATTTCAT
ATCTCTGTTCATTATCTCTATCCTTTTCTTAGAAACATCATTCTCTCTCTTTCTCTCTAACATTCCTCTC
TCTCATATTCTCTACAATTGTCTAGATAGATTTTTTATAGTCCTTATTGTTTTTTATTTCTCTAACTATA
TGTATCATTTTTTATTCTTTTACATATATCTTTACTCTTCTTTCTCTTTTTATTTTTTTGGATATAATA
AATAAATATACATTTGCCGTGTTATATTCAAAGATGGATTGATATTGGAATTGGAATTGAAATTGGTGTT
GCAAAAAAATAGCAACCAAAAAAATGACAACATCAACAACAACCACGAATAGGAGAAAAAATAAAAAA
AGAAAGGGAAAGAAAGAAAGGAAAACAATAGAGGTGGTTTGATTACATAAGCAACCAAAATTTCTCGCGT
CTTTCGCTCTGTTTGTTTTTCTGCCTTTGAAAGGGATGACAGCAGCAGAAAAGCAAGAAGAAAAAAACA
ACACCTACAATTCTTCATTTGTTTTGAGTTGGCCCTACATTCAAAGATCCAATTTAGCAGTCATCAAGAA
TAATTTACAATCGATCGACCTCAGTCATCACCAAATAGTCAAACCAATTATTAA
>retrotransposon_25 1047bp public: 1..1047; zeta-like LTR: 314..822
TAATAATTGATTGGGTTTTTGGGAAATCACCAATTGTCTACAAATCTATCCATATATAACTTAACACTAA
GGTTAACCTTGATCAAGAAGAAGGGAGTGGGGGGGGGGGTGCATTTATCCTTTATCTTGGCTATTGTGGC
GATGCATAATTCGTAATATAACGTAATTAATGAGCAATTAAATAAATAAATTGATCTGATACAACAAAAT
AAAAAGAAGAAATTTAATTAATACTGTGGCACGTGACAGTTGATTCTAGATCAATTCATAGTCCGCGTCC
CCGAACCGAACAAAAACAGGGCAAAATGATTACTGTTGTAATATAGCTAATGCTAATTCTTGATTAGTGT
GGAAAGCCTAATAAGGTTATATTGTGCACAGGTTAACTACCTTAATATAGTTATTGTTAATACAGTTATT
GCTGTTGACTACTATTGTTATTGTTAAATTAAAGTGTTAGGTTGAGTTAATTGATTAGTGAAAACCAACT
AACTACCGTATTAAATTATTGTATTAAGATTGATTCCTATTAAGGATAAAACAGAGAGTGTGTTAGAAAG
AGAAAGGGTGGATTATAAATATGTGTAAAAATCCCCTTTAGAGACTAATCACTAGAAATCTATTGATGGT
TTCATATATAGAGATTAACGATTATATTTATAATATAAGTTGGTAGTTGCTAGTATATTTGAAAGCACTA
CAGTATAGTATGTCAGAATCAGATCATTTAAACTCTACTAATAATACAGGAAACACTTTCATTAGTCTAG
ATCAAGCCAGTACAATAATGGCAGATCAAACTCAAGGAGCTAACCCACAACACCACTCAGATTTAGCCCC
TCTAAAATGCATATGGCACAATGATCTCACCTCGGTTGGTTAAACCTTTTTCTTCTTATTAAATCTATCT
TAGTTGTAGGTTGGTCTCCCCCCCCCTAACTAGTTTTACAATTCAATTATTAAACCAATTGTCAATTCTTG
GTATTTTGTAAACAAGACTCATTAATAATCAATCGTCAATGCATATGATCAAAACAAATAGAAACTT
>retrotransposon_26 7929bp Incyte: 1..7929; zeta-like LTR: 3346..3853
AAGAGATTGTAGTGAAGAATTCAGCTCATTATTACTGTTTGTCGTTGCTGGAAGGAGGAGGGATAATTC
AATGCGCCACAACAGTGTTACTATGCATGTGGTTCTGACTGACTGATATTGTTTAAAAATTAACCAGCTC
TCAAATAACAAAAGTTTAAATTTTCAAGGTTTGTAAACATGGCAGCTAGTAGTAGGATGGTTCATAATAT
TAATTAATTATTAGTAATAATGGCTAAGTTTTTGAAGCATTGTTTTAAATTTTCAAATTGAAATTCAATT
TCATTACAAATGGATTACTAACGGAATTCCTAAGCTCAACTGAATACCGTGATTGAAACATTTGAATTTG
TATCTTTTAGATTAGCTATTTTTACTTTTTTTGTCATTGTAGTTGGTTATGATAATTACAAGAAACTAA
GTTTAATATTTCATATTCATTTCTTTTTTGGCCAACTTGCAATAACACACAAACCCAAAATTAAATA
ATTAGATTTAATGCATGCATAATTTAACACAGATGTTTAGCCTTAACAAGTATTCTAGAAACAAGAAAGAA
AAAATGTCGTCTTGGCGTTTATCTTAATTGTATTCTGTAAACTGGGTTAATTCTTATTTCCAACTTTTCA
TTTTTTGGATCTTGTATGGATTAAAAATTAAATATGGTATGTTTAGGGTTGTATTAACAATACTTACA
ATTATCAATCATACAGCTTTACTATTTTATTTATCAGCAAATAGGGGAATTCAAGTTGCATGTGTTATT
CAGTGGCAGTGAATCATAAAACAGCCAACTTGCAGCTTATTTCACTCCAGGAGCAATCATCACGGAATTC
CGTTTCCCATCTCATTTTCATACTCTGTGGATTATGTATAGAGGCTATTTACAATATCACCAAGCAGTAA
AACATTCTCTCCTCAAAATAACAATAAGATTAGTCAAGATGAACGACTTGAATCTATTCATATGCATTAC
ACATTTAGTTTCTATTACAAATAGTGATGCAATGGTGCAAGATTACGTCTTGTCTGCACTAACTATTTGT
AACGATGATTATGTGATCAAGAATTGGAATTCTTATTATATTCAGTCGTGAGTGTAAGCTATTTCGTTAG
GGTTATCTTAACTCGAAGTTAAAGTTCCAAAACTATTCCATTTGGAGTTTCTGTTGTTGAGAAATACAAA
ATACTCTTCTTGGTGGGGAGGAAATCCATTAATGATTATAAAATGAAACTCTTGGTAACCTAATTGAAAC
ACCACATTCAGTACATTTTCAACCGTCACTATTATTATTGTGGCAAATGGATTAAACAATAGACCTAACT
```

FIG. 71R

```
TAATCTAATGGAAATTTTAAATCCATGAAAGGGGTGAAAATTTGAAATCAAAATAACTATCTGAACTGAA
ATACCCCATGGATCTGATATCTTATACAATCTATCAACTAAACAGGGAAGAGTACCTGGAATTCCAAATG
ACAATTCCTATTATAATTATTTAAACAGACTATGCCGTATTGTTTGTGACATTCATTGTTTTCCACAACT
CTAATGTCAAATTTTTGTTATTGTCATGTAATCCCGGTGTTTCTTTTTTCTTTTCGGTGTTGCGTTCCAT
GATATTTTGTTATCTCTTGTTTAGATTGAGATAAAGAATTGGTTAGCAGTGTAGCCATTTATGAGTGGTT
TGTAAAAACAAGAATTACAAGGTTTGAATGAATTCCAGGCAGGCAGTATTATAAAACCTCGAAATAACTA
ATCAAACCATCAGAAAAGAAAGCTTACTATGATGTACTGCTTAATCTCATATCTATCTTACAAACTTAAT
TCACTGATTGTGGCTTGTCCGTGAATAATTCGGAAACCTTGTCTTTTTCGGTCCAGTAGGGGGTGCCATA
GTCTTGGGTGGTGACAAAAAAAAAAAAATTATAGTTGGGGTGGTGGGGTGTACGTCTGAGTAAGTCAGG
GGAATGAACTCAAGACAAAAATAGAAGTTCTAAACATGGTACGTTCTGCTAAGTAATATCATCGATCTAT
CTATTTTGCTCTAAATTTTCATAAGCAAATCCAGAACTTCCTCGTCAGTTTCAATTTCAAGCATACGAAG
GGATAGTGATTAAATTATATTTTGAACCTTCTATTACTGATTAAGTGTTCCTATTAGTCTACGGATTAGA
CGGTTAGAATGGGATTTTCAAAAGCACAAAGGTCAAGACTTATAGGAAATTCATAGAAAAAACACTCTGA
AGTACTCGATGGTTGGATATATAATAGTTTTGCTAATTTAAACTCTTGCTGTTCGGCTAAGCTATTGTAC
CCAAATGCGGTACTCCGATAGTCTTATAAATAATACTTGGCAAAAGTTCAATAAATATATGTCAATGGTA
TTGCTTTCCAATTACCATTGACGAGGTTGTAAATTAATTCATACTTAGGTGACATCGATTAATTTAACAA
ATATGTCTGTTTCAACGCTTACATCATCAGTCTTGCAGGAAAAATGTTATTGCCACGACACCTCAAATTA
GCCCAACCCCTTCGTCTACCAAAACAATGTCAAAAACCCACTTAAAAGAAGTCGGACAAACCTGAACCCG
GTATTTTATAAAGTAGTTTTGTGAATAATATCAGTACATCGATTACACTTTCCGTCTCAAGACTGGAAGT
TGCAAAGCCATGACAATTGCTCAACCAAATGTGAATTTTTAGGTTCCATAGTCTTGATCGGGTAATGTAA
ACACTTTAACTTTTAGTAAATGATACCACCAAGAAGAAAGCACTATTTTAAGCTTTATTTAACACTATAC
ATTGGAAAATAAAAAAGTGGCTATGAGAATTAAACAAGATGACCGAGTAATTAAAATAGTGCTGTCGGTG
TTAAGCAATACCGCTAGGGTTCAATCAATTAAGTGCTGCTTTTTTTTGTCGTTGTATTTCCATTCCTCCA
CTCCTTTCTTTACTCTTGCAATCTAACATATTTTTTTAAAAAGAAAACATATTGATACTTACATGTGGT
AACTATTGTCTGATTCATCAATTCCGCTCTTCAATCTCGGTGTTCGGATAATTTCGATGAAATTATAATT
ACCTGCCGCAATTCTAGAAATTCCTTTTTTTTCTTTTCTTTTTCTCGGAGTTGGTTCCAATACAAAGATT
GAATTGAATTAGGTGAGAAGAAGAAGAGTCTTAACACCAGATGTATTACAGCTTTAAACTTTGTTTCTAA
TTTGACCACAAAAAGTTGTCTGGACGCCTCAGTTTGAAATTAGTTTTGGGAGATTTCTGTTTTCTCATTG
GCCTTACTCTATGGAAGTTTTTATACAAGAGCTTCCTTCTAAAATTAACTCTTTGTGTTGTAATATAGCT
AATGCTAATTCTTGATTAGTGTGGAAAGCCTAATAAGGTTATATTGTGCACAGGTTAACTACCTTAATAT
AGTTATTGTTAATACAGTTATTGCTGTTGACTACTATTGTTATTGTTAAATTAAAGTGTTAGGTTGAGTT
AATTGAATAGTGAAAACCAACTAACTACCGTATTAAATTATTGTATTAAGATTGATTCCTATTAAGGATA
AAACAGAGAGTGTGTTAGAAAGAGAAAGGGTGGATTATAAATATGTGTAAAATCCCCTTTAGAGACTAAC
CACTAGAAATCTATTGATGGTTTCATATATAGAGATTAACGATTATATTTATAATATAAGTTGGTAGTTG
CTAGTATATTTGAAAGCACTACAGTATAGTATGTCAGAATCAGATCATTTAAACTCTACTAATAATACAG
GAAACACTTTCATTAGTCTAGATCAAGCCAGTACAATAATGGCAGATCAAACTCAAGGAGCTAACCCACA
ACAACAGCCTAGTCTTCTTGACACTAAAAAAAAAGAGATAAAAAACAATTTCAGCCAATCACATGTACT
ACATTTGTAATAGATTTTATTACTTCAGCTGCTTATTACACAAACAAGGTTGAATTGATATTGTGTAGAG
TAAATTTTCGGAAATAGTTTGAATTGGGTGATCATTTTCTTTATTTTTTTTTGTCTTGTTTCTGTGAA
GATCGGAATGCCAGGGTGGAGCTCGTGAATTGCACCATAATTGCAGCAGCACCATATTTCAAATAAAGT
TTCTCATGTTGTAATAGGATTGCTTGTCTCCATGAAACCAATCACTTAACTAAGCCCCAGGCTGATTAGT
GTGTTTTCAAACAGTTTTGTACTAGAGAAACTCAGACCTTCTCAGGGCAAGTAATAACCTAAAAAAATGC
CACAAAACTAAATGCAATTTCAGTTTGATATGATAGGCAATGACATCAACACCTGGAAAAAAAAAAACT
TTCAGGTGATGAAACGATTAAGGATTAAAGTTTGCAACGAAAAACAAGTGGAACTAAACTTTGCCTTATT
GTTTTGTTCCGCTTACCTAATGATGTTTACTCCTTAGAACAAACAACATCAACTACTTTTAATCCTGACG
ACGAAGAAGAAGACCAAAAAGAATAATTAGCCGCAGCTACGGTGGTGGCACTAGTAGTAGTGCTAGTGCT
TGTTGTGTCTCATCCAAGAGAAATGGAAAAACTGCAAAAATGCCGCAACTTTGAACATTTGGAACACAA
TACAACTTTTTTTTCCTTTTGGATTTACGATTAGCGCGATAGACGTGACCATAAAAATACCACACGATG
TGTAGATCCTCTAAAAATAATGTACACATTTCCAGGCTTTTGTTTACTGCTTAATAATTTGTCATCATCG
GTAACAATGATAGTCTCCCCACCCTAACTACACAGTAGACGGAATTAGCACACCAAAGATCTTATAAATCAAC
CCCAAATTTTCCCATTTTGATTTTTCGTATTCCTTGTTGTTTCCATAATTTTTTAGTTACTC
CTCCTCAACTAAACTAGATAACTCGTCACAGTTAACAACAGAAAGGTATGTTAAATATTTATTTCGTTCT
AAATTCAAGTTTGGTATAGAATATTGCAAACAACAACAATTTGAAAAATGGACTTTAATTTGTTCTACAA
AATGCAAACACATCTAGAATTAATATTTGCTCTGGAAACCGTATACGGAAGTTATGGATAATCACGTTAT
CCTGATATCTATTATTAACACCACCACAATATCTATTATTTCTTGTATGGATTGCGGTGCCAAGATCAAA
GAATCATTTTAACCCGATATCTTACATTTCACCTCGATCTAAATGTGATTCAGTATCACCGCCTCATTGT
TTCACCACTCAACCTCCCCATACTGGCAGTACATATTTTTTTTTCATTTTAGAGAGTTTTAACATAACT
TATCGGCATTTTCAATAATGTTTATTTGGAAATTTAGTATATACCGATAAATCCTGAATTCTCGTATTGG
```

FIG. 71S

```
CGATGGATTTACCAAAAAAATGGGGAATGAGTGTACACCAAGAAAAAAAGAAAAATTCAAGAAAAAGCG
AGTGACTAAAAATGTCGTGGGAATTTAATTTATCCTGGAAAGATGCCCCGATTCAGAAGTAATGTCGAGT
ACTTTCACCCACATACAATGAACGACTTTTATTTATTCCTTCACCCCACACAGCAACAACTACATTTAAA
TTTCAGTATTTAAGCGACCATGAATTTAAATTACAATACTCCACAGATTAAAGCATTTTGTTTATAACTT
TTCTATTCTTATCAATTTTTTTGGTATAGTTGTGGTTTGCGTCACGGTTGTTTTCTTTTTTTCATTTTC
CTTAGTTTACTCCACATACACATACACGTACATTTCTATATATACCCCATGATTCCCCCCCCCATTTGATT
TTTGTTGTTGTTCAGCAATATCTACTTTATTTATTGGTTTTTATGTTTATATGATACTAACTTGTCT
TTGTTTGCTTTAGTCATGAACTCCGATATACCACCTCCACCACCACCTCCAGAATATACCCAGTCCCATG
AAGATTTACCAGCATACACTTCGTCGTTGAACTATTATGGATTATCATTGATTAAAACAGAATTCATAAC
CCCATATCAATACAATAGCGGTAACCGTTCCTGGAAACCAGTATTGCTTGAATTGAACTCTACTCAATTG
AAAATATACAACTTGAACATTGATAAGAAACTACAAGATTTGCTAATATGTTTATATTTTGAATTAAATT
GTTTAGATCAATTAACTAAAGACATCAATTCTCATTATAAAAGAGTAAAGGTTTTGACTTTAGTGAATT
ATCGTCTAATGATGCCGACGATGTCGGCGATTTGTTTTCCGGTGATGCATATGGTGGTACTGATAGCTCC
AAGTTATCTTTAAATGATTCCAAGTTTGGCAAATTGAAAAACAAATTGAGAAATCAAAAATCTAATAAAA
CCTTGCAATCAATAAAAGCTCATTACGATGAATTAAAAGATAACAAATTTTTCTTTGAACCAACATCCTC
AACAAAGGAATATAACCAATTCGCTAAAAAGTATAGAGGAAATTGTTGCACTGTTATTCTTTGGCAAAC
TTGCAGATTGGGGAAGCACCATCTTTGAACCAAATAATTTCAGCAATCTACAAGGAAGAGCATAATGGCA
ACACCAACAATTCATCACTCGTCAAATACAAAAACACATTGCGTCTTCGAATTGAATATAAACAAATCTT
ACTTCAATTTTGGTCTTTCTACGGTATGATCAGTTGGTTTAGGAATTTCACCATTGGAAGAGATTTGAGT
GTACCCGTCGAAGCAAGCAGACATGTATCGAAACTCAAATCTATACCCTCAAGAAACACTAGTCAAAACAATG
CATTATTGGCCGCTACTGCCGCAGCTGCAAACTATGGAAGAAACAGAGCCAATACTCCAGTGGACGGTGT
CGAAGAAGACATATCCATGTTTCGCTCCAACTATTTGACTATTAAAGATGAAGATAATACTCATTCTGAC
ACCAGTAGTGAGAATTCATCTGTGTTCGACAATGAGAGAAGAGGGTCCATAGTTTCAACAACTACGTCAA
TCGAACCAGTCGACTATGTTACTATTAACAATTACAAGTTTTATTCCCAAGAGTACACCTTTACCACTGT
TGAGAAACAATACATTTCCAATTGCATACCAGATTTGAACTCTTTTGATAAATGGAATGGCAAGTTAATC
ACCGTCAGTAACGTGGATCATTTTATTAGAGATAAGAGATCTTTTGAAGACAAAGATGACGTTTTCATTA
GTTATGCTGCATTGGGGAACTTGGTACAATCATATGATAAAAAATCACATAACGACTCATCCATGCTTAC
CACCCAAACTTTTATCATTCATCAAAAAGGGTTAGTTGGTTTAGGAACACAAGTTTGATTCTTAAAACAT
ATATAGATTGATAGATACCATTTAATATTTCTAAACATATCTTTACGAATTAATAAATACGACTTTTAAT
GATATAAGGTATTTTGGTTGTAATTGTAGATTTGGCAAAAAAAAAAAAAAATAAACAACCATCGTAGTAGT
TGTTGTTACAGTGGTTCAAGTTCACGCCCTAAATTCTTGTGGCTGTCTCGCCTTTAACTTTCTTTCTTCC
TCCCTTAACTTAACATGTACGTGTACTTAATATTATTTTGAAAAATTTTTTTTTCTGTCTGTTTCTCTC
TCTCCTTTGTTCCCAACACCAGTTGGTACTTTTAATTCTATTTTATTTTTACGTGATCTGATATTTATT
TATATATTTATATATTTCCATCAATTCTAAAACTTAATTACTTCAAAGACCAAGTTCTTGAATCTTCTTT
TGTTTTTGCTTGTTTGTATACCAAAACACTCTTTTTCAATTATTTCCCTGCTGTTTTTCTTTAGAAAAGC
ATTGTCCATTTGTCTATTAGTCTGTAACTGGAAATTTGTCCCGTCCTTAAATTATTTTTTTTTGAAGAA
TCTTTTCATTTGAATCATT
>retrotransposon_27 2292bp Incyte: 1..2292; zeta-like LTR: 1327..1834
GATATTAAGTCGTCTAATGCTATTTTTATTTGAAAAAAAAAAAACAAGAAAACAAATGTATAAAGGTGG
AAGGAAAATAAAAATTAAAAAAAAAAAAAACTCGAATATTAAATGAAAGTGGACAATTAATTGATTGAT
TAATAAATTGGTTTTATTAGTATTATGTAAGGGATTTCAAAGAAGTCATCTAAAAATTGTTAATGTAGAT
GTAGATGTAGATGTGGTTGTTGTTCTATGTGTTTACAGAAATTGATCATCAAAGTCCAAGATTTTACATT
GCCTCGCCAGTTCTATTTTTATAAATATTGGCTGTGTGTTTTGGGTGTGCTTGGGCCGGGCAGAGGGTGG
GAGAGAGGCATGAATGCGGAAGAGGAAGGAGGTCATTCCATTCCATTCCATCGCCTCATTCTTCTCCATC
GTTCATTCATTTAATTACGACAGCAGCAGAAGAAAAAAAAAAAAAGAATTCAGATGTAGATCACGTGCCAAT
ATTATGAAATATTCCATTTTGGGAAAGTCAGCTTCAATGGCTTACATGGTAGCGCATACTCATAGATTTT
AAAAAATCTGAATAATTTGTTAGTTCTCTATGAATGAATAAACAGATTACTGATAAGAACCAGATTAATT
ACTTAGAGGTTTTCTTATTTTTCTTTTTTGATAGCAAAAGTATTCATGAATTATTCGTATTCGTAAAAA
ATTTAAGAAGGAGGGAGAACAACAACTGTTAACCCAAATGGTGTTTTTGTTAAAACTCTATCTACTAAAT
TCAACATTTGTGAAGATAAAAGTGGTTCAAATTTTTGTATGAAAAAACAACATAGATTTATATAGCAAC
ATCACTACAGTAATATATCGAATACAATAAATATATATATATAATAAATTAAAATAAAAATAAAAATATA
CATCTACAATATGAAAAAATCATTTAACTATATAGTATGTCTAAATTATCGAATGAAAGTTAGTAATAC
AAACTCCATGTTTAGTGGGGAGCTTGGTAGAGCCTTCAAGGCAATTCATAGTAGGTTGGAGGAGGCCCT
AATCAGAGGGTCTGAGTTGAACAAAAGCGCCCAAAGCTTTGTTTGATTCATTGGAATATACTCTCGGTTA
TGTCGAAAGTATTGGAGCTGAAAATAGAAAAGAAAAAGTGAATAATTATGATAATTATTGGTGTGATTT
TGTCACCTTTTTATACCCAATTTTTTTTTATCAAGAGAGATTCTTAGATTTGCCATTTTGAGTGTTTCAA
ATTTCCCATGTGGATTGAATTTTCAAAATTGGTTACATATATCCTTGAAAGTGTTCATAATTTTTGTGTT
GTAATATAGCTAATGCTAATTCTTGATTAGTGTGGAAAGCCTAATAAGGTTATATTGTGCACAGGTTAAC
```

FIG. 71T

```
TACCTTAATATAGTTATTGTTAATACAGTTATTGCTGTTGACTACTATTGTTATTGTTAAATTAAAGTGT
TAGGTTGAGTTAATTGATTAGTGAAAACCAACTAACTACCGTATTAAATTATTGTATTAAGATTGATTCC
TATTAAGGATAAAACAGAGAGTGTGTTAGAAAGAGAAAGGGTGGATTATAAATATGTGTAAAATCCCCTT
TAGAGACTAATCACTAGAAATCTATTGATGGTTTCATATATAGAGTTTAACGATTATATTTATAATATAA
GTTGGTAGTTGCTAGTATATTTGAAAGCACTACAGTATAGTATGTCAGAATCAGATCATTTAAACTCTAC
TAATAATACAGGAAACACTTTCATTAGTCTAGATCAAGCCAGTACAATAATGGCAGATCAAACTCAAGGA
GTTAACCCACAACATTTTGTAGTCGTAAACTTGAAATTCAAAGAGAAGGGGGGGAATTAAATTGGGTGCA
ACGTGTTTGTCAAAAATTTGGTGTGAAAAAAATTAATTTAACACTCTGCATTGTACCATAGGGAATATAA
TACCCAGAAATAAGAGAAATTATCACGTGAGACTAAAACTAAATATAATAAATTAATATCACAATTGAGA
AAGACACTGAAACTAACTTCTTGGTGTATTAATTTTCAACACTTGATCACAAGTGCGGGGATTAATCATA
ATTGCAAAGAGTGTGTTAGAAAGAGCGAAGGTGGATTATGAATATTGGAGAATCCTCTTTAGAGACTATC
CGCTAACAAAATAGATGAACTTGCTCAACAGAAACAACTAATCGACTAACTGACTAAAATTAATATACTA
AGTATAGATTAAGTTATCACGTTAATATTCTATACTATCCATCTCCATCACT
>retrotransposon_28 2025bp Incyte: 1..2025; zeta-like LTR: <794...1294
TGGGGAGCAAATGTGAAATTAAAGAGTGTGGTGATATGTAATTTTTTTCAAAAAAGATTGGATTGACGA
AGCATTATATATTCGTCTAAAAACCATTTTTGCTGGTTCCGCAATAAATCTCGGAGATTATTTCTCGATT
ACCAATTTATGTTGTTTTGTGACATTTCTTATATTTTGTTCTATTTTACACGACTATTTATTGTTAATAA
ATATGTCACCTAAAGAATATTTCTATTTAGTTTTACATATGTTTTTGACGACAATCAACTATTACAAAT
TAACCTACATTTTTTAATTTGAATATATACAATTTATATTGAATTAACATTACCATTTAGTTTTTGATAA
GAATAGATTGCGCTATTTCAAACATTTGTTAAATTATTTATTGTGAAACAACTATGTAGAATAAAAGTAT
GAACAAATTCTACGTTCATCATGTGGGGTGTGCCTTCATATATATCTTTGGATGAGAATGCCAAGAAAAA
TGATGGCGTGACAATTCAATACGGCAAAACAAACTAATCCCCTCTAAGATTTTACTAGTGTGTTTCCCTA
TCGTCTGAGGAAAAGGTAACAAAACATCGTTTAACCAATTGGTGTTTGTTACGATGGTGACGTTGAGTAC
TGCATATAGTTGCAACGGCAAATTGCATCCAGCGAGTTAACAGCGAATGGCAAAGTGAAGCCTCCGACTT
GTGTTCATTGACTACTGGGATTGGACTGGGAATAACGACTTAACTAATTAATGTTCTCGTGGACTCGTTT
AGCTAGAACTAACATTTGTTATAATATAGCTAATGCTAATTCTTGATTAGTGTGGAAAGCCTAATAAGGT
TATATTGCGCACAGGTTAACTACCTTAATATAGTTATTGTTAATACAGTTATTGCTGTTGACTACTATTG
TTATTGTTAAATTAAAGTGTTAGGTTGAGTTAATTGATTAGTGAAAACCAACTAACTACCGTATTAAATT
ATTGTATTAAGATTGATTCCTATTAAGGATAAAACAGAGAGTGTGTTAGAAAGAGAAAGGGTGGATTATA
AATATGTGTAAAATCCCCTTTAGAGACTAACCACTAGAAATCTATTGATGGTTTCATATATAGAGATTAA
CGATTATATTTATAATATAAGTTGGTAGTTGCTAGTATATTTGAAAGCACTACAGTATAGTATGTCAGAA
TCAGATTATTTAAACTCTACTAATAATACAGGAAACACTTTCATTAGTCTAGATCAAGCCAGTACAATAA
TGGCAGATCAAACTCAAGGAGCTAACCCACAACAGCATTGATTATATAATCATCTATGTAGCCAATATAC
ACTACCGTCCAAACTCCCACTACACACTTGTAACAGTGTTTTACAAATCTATGAACGAATAACCGATTCA
AATGACACAATAAAGAACATTTCACCGATTTGAATTGCTAATCGGTACTATAATATTGATGGAAGGTTAA
GAGTTTAATGCTACCCTAGGTTTACCGGAGATCAACAGTTGCATATACAAAACGTGTTATCTGTCTACGA
ATGGCTTTCTATGTGTATAAAATGTTTCATCAATTGATAATTAATTATTAATCTGCTTACTGAGGTAAAC
CCCTTTTAATGCAATAGCAAATATGAGGTATTTTTTGCTATTGACATGCGTATATGAATCCATTTGTAT
CAAATTGCCGATATAATGAAATGGAAATTAAGGGAAAAAAAAAGTTTATATCCAAATTCATGCGATTAA
CAGGTTCTTGTGATTATAATTGGTAACCCCCTCCCCCCTAAAACTCATATCTGCCAAAAGAGGAGGATAT
TTGAATATGCTATTATGAACCCCATTGATTTTGACTACAATTGGATTTGTCGGGTATTGAAACCCAAACA
TATTATAATTTGCTATGCGTTTAAATCAACCGTTTACTGGTAGATCCTATACTATAAATACAGCCAACAA
TCCCCAATTGTTCAGATAAAGTAACACTCAATATCATTTGATCAATCAATCAAGAGGATTACAAA
>retrotransposon_29 2731bp public: 1..2731; zeta-like LTR: 380...887
ACATATTTTTTTTAAAAAGAAAACATATTGATACTTACATGTGGTACTATTGTCTGATTCATCAATTCC
GCTCTTCAATCTCGGTGTTCGGATAATTTCGATGAAATTATAATTACCTGCCGCAATTCTAGAAATTCCT
TTTTTTCTTTTCTTTTTCTCGGAGTTGGTTACAATACAAAGATTGAATTGAATTAGGTGAGAAGAAGAAG
AGTCTTAACACCAGATGTATTACAGCTTTAAACTTTGTTTCTAATTTGACCACAAAAAGTTGTCTGCACG
CCTCAGTTTGAAATTAGTTTTGGGAGATTTCTGTTTTCTCATTGGCCTTACTCTATGGAAGTTTTATAC
AAGAGCTTCCTTCTAAAATTAACTCTTTGTGTTGTAATATAGCTAATGCTAATTCTTGATTAGTGTGGAA
AGCCTAATAAGGTTATATTGTGCACAGGTTAACTACCTTAATATAGTTATTGTTAATACAGTTATTGCTG
TTGACTACTATTGTTATTGTTAAATTAAAGTGTTAGGTTGAGTTAATTGAATAGTGAAAACCAACTAACT
ACCGTATTAAATTATTGTATTAAGATTGATTCCTATTAAGGATAAAACAGAGAGTGTGTTAGAAAGAGAA
AGGGTGGATTATAAATATGTGTAAAATCCCCTTTAGAGACTAACCACTAGAAATCTATTGATGGTTTCAT
ATATAGAGATTAACGATTATATTTATAATATAAGTTGGTAGTTGCTAGTATATTTGAAAGCACTACAGTA
TAGTATGTCAGAATCAGATCAATTAAACTCTACTAATAATACAGGAAACACTTTCATTAGTCTAGATCAA
GCCAGTACAATAATGGCAGATCAAACTCAAGGAGGTAACCCACAACAGGTTATGAGCCTCGCCCGCTTAT
TGAATTTAGATAATATAGGGGCAATGAAAGCTTTTGAAAGTGTTGATTTTCCTGAATCATTAAAACTAGA
```

FIG. 71U

```
ATCCAAGATTAATTTTCAAGTGTGGAGAAATGAAATCCTTAGATATGCACGTGGTATTGGTGCTGAGTTT
GAAAACTTTGTATTGAATGAAACTCCAGCTCACCTGTATGATCTTAGATTGGGAAATATGCTTCATCAAT
TATTGATTCGCACTGTGAAAGAAAAAGTTAGAATGCCTAGGCAAGAACTTGGAAAATCAGGAAAAGAACT
TTATCTTGATCTTATTAAATCATTCGGTACTCAATACCCATACGATAAATTTGAGATAGTTAAATACTAT
TGGGATCAGTTAACAAACCCTTTAATTAATGTGAAGAGACGTTTTGAAATTGAAGAAGTATGGGTTCAAT
ACATTAATGCTCAAACTGCAACAGAGAGAGAAGTTCTTAATTCATTTGTTTGGTTACATTTGTCAAAATC
TATATTACCACAAGAGTACCTTAGAAGTGCCCATCCAGTTCTTGATAAAAATGTGATTAAAATATTTCTT
GATACCCATCCAAAATGTGATATTGATCAAATTATGTCATTTGTAAATAATGAACTGATTAATTATGTAG
GGAAAAATGATACAAGGGAAAATGATATGGGACAGAATTTAAGAGAGAGTGATTTAAGAGAGAGTGACTT
AAGTGAAAATGATATACAACAAAATGAGTTAAGCGAAAGCGATTCAAGTGAAAATGATTTAAGAGAAATA
GCAACAAAGAAACTGTTAGTGAACTTTTTGAAAATCAATGTCAGAATTGTTTTGGACTTGGTCATGATT
CATATGAATGTTCACTGGCATTTAGAAACAATCAGTATATTCCAGATTTATTTCTAGACTTCAGAGTTT
TCGTGGAAATAGAATTCAAAATAATAATAGAAATGTCTGGTCTAGATTCTCAGAACAAGATGAGTCAATT
GCAAATACAGAAAAAGGTAACTAGATCTAATGATAAAAATGAAAATCAGTGGCAGTCAAAACAATTTACA
TATTAAACAAGTTTGAATGTAAGTTGTTGTTGTTTAGATAAACTATGTCATGGTATCCAAAGTTTTATTT
TATATTTATTATTTAAGTGGTCATGTTTATTTACTTATAATTGTTATTTAGTTTTTCAAGTGTGAATTTT
ACTTACTTATAATTGTATTTAGTTTTCAAGTGTGAATTTTACTTACTTATAATTGTCATTTATTGTTCAA
GTGTTATTTTTACTTACTTATAATTGTTATTTAGTTTTCAAGTGTGAATTTTACTTACTTATAATTGTTA
TTTAGTTTTCAAGTGTTATCTTTACTTACTTATAATTGTCATTTATTGTTCAAGTGTTATTTTTACTTA
CTTATAATTGTTATTTATGTGTCCAAGTTTTAATATTATTTACTTATAATTGTTATTTATTGTATATGTG
TTAATTTAATTCAATTGTTAATTGTTATTTATTGTTCAAGTTTTAATTTTATTTACTTATAATTGTTATT
TATTGTTTATGTGTTAATTTAATTTAATTTAATTGTTATTTTTACTATTTAAATGTTGATTTTATTTATT
TAATGTTAACTTGTCATTTTTAATTTTACTTATTATATTTTACGTGTGACTATTATCTATGATAAAACAC
TAATAGTGGATATTGAGTGTTTATTTGTTTCATCGCAGAGGATATTTATTGGAGGAGGGAGAAAATGTCT
ATTTGGTATAAGGAAGACCATAAAAGTTGGTTCCAAATAGTCAACCAACCAATAAACATTCCCTCATGCT
T
>retrotransposon_30 2858bp Incyte: 1..2858; zeta-like LTR: 814..1321,
reverse transcriptase fragment (contains stop codon): 635..>537
CCTCCGGGCGTCTATTTACAAGCTGCTTTATTATTTGTTATTACCTGGGTGTAAAAGCCCTCTTGCATTT
GAGCTATTTCTATTCCCACTTCGGTATTTTTTTACAGCCTCGTTAGACGAGTTCTTGATATTACTAAAT
TAGTTGTTTACTGAGTGGCCTGATGGTTCCTCGTCACTCTAGTTTTGGTCTATATAAGGGTCAGAAATT
TCCCTTCTCCTTAGGTCCATCAAGTCAAGATATACATTAGTTGGTAGCATCGTATGGAATTTTCGTATGA
ACGGCATACCAAGTATTAATTTCCGATCGAAATTTTTAGGACGTCTTGATAATCAGGACAAACATCATG
AAAGGTCTATACGACGAAAGTTTACTTTACACAAGGGGAGACCATATGTCTTCTTTATTAACAACTAGTT
ATATAGCGAACAAATAAGTTTATACAGAAATATATGTACACAAACAAAGTTATTGTTTATTAATTATTTA
ATTAGCTCGGAAGAATAACTCTGTGATACTGCATACATTCAAACAAAATCAATCTAGTTTCCAACATCTT
TTTCACTTGGTAATGTAATTATTCTTGTTCTGGCACCGACAATGGGTATTGTTTTGTAGCTGGAGGACTA
ATATGGGGTACCACCTCAATTTTTGGATCCAGCTCCCACGCAGGGGTGGCTTCTGATCTAACTCACTTT
CGAAAATATCCTGATAGTTTCCAATTAATTCAGCAAAATAGCTCTTGTTTGTACCCTTAACCAATGACAT
GATATCCTTTTTATTATCACCGATACCACCTGTGTCTTCGTCTTGTTGTAATATAGCTAATGCTAATTCT
TGATTAGTGTGGAAAGCCTAATAAGGTTATATTGTGCACAGGTTAACTACCTTAATATAGTTATTGTTAA
TACAGTTATTGCTGTTGACTACTATTGTTATTGTTAAATTAAAGTGTTAGGTTGAGTTAATTGATTAGTG
AAAACCAACTAACTACCGTATTAAATTATTGTATTAAGATTGATTCCTATTAAGGATAAAACAGAGAGTG
TGTTAGAAAGAGAAAGGGTGGATTATAAATACGTGTAAAATCCCCTTTAGAGACTAACCACTAGAAATCT
ATTGATGGTTTCATAGATAGAGATTAACGATTATATTTATAATATAAGTTGGTAGTTGCTAGTATATTTG
AAAGCACTACAGTATAGTATGTCAGAATCAGATCATTTAAATTCTACTAATAATACAGGAAACACTTTCA
TTAGTCTAGATCAAGCCAGTACAATAATGGCAGATCAAACTCAAGGAGCTAACCCACAACACGTCTTCTT
CAGTATTAGGGAACAACATACTAACTTGACCTTTTCTAGCTTCAACCAAAAATTCCTCTATATCCATTAA
TGGAATTTCATCAAACTGAGCAGCCCCAAAAAACGTTTTGCTTCCAAAGTCTAAATGAGCATGGAATTTC
CTTATGAAAGGTATACCAAGTATTAATTTCTTATGGAAGCTGTCCACTACAGCAAAATTCTCTTGGAATG
TAATACCATTAAACTGGAACTTGAGGTTAATTATTTGGTTAAAGTTTCTGTTGATTTTTGGTCCAATAAA
GTACCCAAACTACTAGAGCTCCAACAACATTTTCAGAAAATGGCCAATAATACAATAAGTGGGTATATTT
TATCAAAAGTTTATATTATGGTTACTCGACGGTATTATTCTCTGTTGATTTAAGGCATTCTGGTCGAC
CAGTGGACAAAATTCAAGAGTAGTGTTTGTTTAGACTTTACAGGACATGATAGTATATATAACAAAATG
AAATACATTAATCAAAACTAACTAAATCCTAAATTAATGCCAATTTCTATTGAATTGGTTTGCTACTTTG
TAAAATTTGTGAGTAATCTTAAGTACTTATATGGAAATCAACAATGGCAAAAATACAAGAGAATGACCCC
ATGACACATTCAGTGCACAATTCATAGTAACTGCTTGGTCACTTGCACATGACTCTGCTAGTATACTCAA
CCACTCTTGTGACTTCCATATAGATACTCTCGATGAAATGTCTCAAATTAGAGGACAAACAATCTGCTAT
```

FIG. 71V

```
AATCTTGGCTAATCACCCATGTAACATGGAGGAACCAAACACATAGATATACGGTACCATTTCATACAGA
ATTTATCACTAAAGAAATTAAGAAAAACTTGTGTTATCAAAGTGGTTTGCGAACTTTGTAGTAAGGGAGA
GTGTTGAGAATTAGAGATTCTAAGTTCCAGAAAAATATCTATATTTATATATATATAGGTAGTGCAACAC
TACATAAAAGGGACTGATTTGAATGTATGTATGTCAAATGACACCCTTATAATGTTGAGTGACATCATAT
CAAAATGGAAATCTACTGTATCAATTAAGAGATTACTAAAAGCAATATACTTAATATGAGGTCGTACTTT
AAGATTGTGAATAGTATCAGTAGCGAGTGGCTATGTGTTGTGATGGAGCATCACTGGTAGTTTCTTAGAT
GTAAATCTCAGTGACTATAAGCATACTAAATTAGTTATGAAGATATGTTCCATTAAAGTATTTAAAAAAT
AATAGACAGGCTATCAATTTCTAATAGATTTACCGTCCAGATTATAAAAAAATTATCGAGATACATATTA
CACCGATTGAATTAATAATGTCTACTACAAACCCATCACGGAACTTGATGCAATTGATTGAATAAGTG
TCTCTCTAACGATGACATGTCCAATTCTAATCAAAATAATTATTATTCTAATTGTAATATCTGGTATTTA
ATTATTTATAATTCACGAAACAGTTTGATTGGTTTCTGATTCTTCTGACAAAAATAAG
>retrotransposon_31 1636bp Incyte: 1..1636; zeta-like LTR: <595..1098
ATGTTTATTTAATAATTAAACCCCAGTTGACCAACTATGAAATAGTATAATGATAAATGCAAATAAATA
TAGTATGAACAATATGATAGTTTTAGTGTGAATTTTGAATAAGAAAAAGAAGGGATAAGGATATTTTAC
TAGGAAACTCAATTATAATTACTAATGATAAAAACTCCATCAGCTACTATTATTACTCAAATTTTAAATC
ATTTGTTTATCACCTACACAAACAGGGATTGTCCAATATTGATTACTAAAATTAGAACAAATAAGAGAAT
ATAATTGAAGTTAAATAATTCTTTTACTAAATCTATTGACCAAGAACTACATCAAGGGAAAGTGTTGCAT
ATACATCTAATGTTTATTCTTGGTTAGAGTATTGATACAAAATTATATCATCACCAACGAATCACATTAA
GGGAAAGTGTTGTGCATATACCTGATGCTTAGTCTTGGTTAAAGTATTTGTGTGAAAGGTTATCGTGACC
AAAGATTATAGTAAGGGAAAGTATTATGAATAAATCCAATGTCTACTTTTACAGAAGTATTGACATGAGA
GATTATAACTATCAAGAATTGCATTAAGGGAAAGTGTTGTAATATAGCTAATGCTAATTCTTGATTAGTG
TGGAAAGCCTAATAAGGTTATATTGTGCACAGGTTAACTACCTTAATATAGTTATTGTTAATACAGTTAT
TGCTGTTGACTACTATTGTTATTGTTAAATTAAAGTGTTAGGTTGAGTTAATTGATTAGTGAAACCAAC
TAACTACCGTATTAAATTATTGTATTAAGATTGATTCCTATTAAGGATAAAACAGAGAGTGTGTTAGAAA
GAGAAAGGGTGGATTATAAATATGTGTAAAATCCCCTTTAGAGACTAACCACTAGAAATCTATTGATGGT
TTCATATATAGAGATTAACGATTATATTTATAATATAAGTTGGTAGTTGCTAGTATATTTGAAAGCACTA
CAGTATAGTATGTCAGAATCAGATCAATTAAACTCTACTAATAATACAGGAAACACTTTCATTAGTCTAG
ATCAAGCCAGTACAATAATGGCAGATCAAACTCAAGGAGGTAACCCACTACAGGTTATGAGCCTCGCCCG
CTTATTGAATTTAGATAATATAGGGGCAATGAAAGCTTTTGAAAGTGTTGATTTTCCTGAATCATTAAAA
CTAGAATCCAAGATTAATTTTCAAGTGTGGAGAAATGAAATCCTTAGATATGCACGTGGTATTGGTGCTG
AGTTTGAAAACTTTGTATTGAATGAAACTCCAGCTCACCTGTATGATCTTAGATTGGGAAATATGCTTCA
TCAATTATTGATTCGCACTGTGAAAGAAAAAGTTAGAATGCCTAGGCAAGAACTTGGAAAATCAGGAAAA
GAACTTTATCTTGATCTTATTAAATCATTCGGTACTCAATACCCATACGATAAATTTGAGATAGTTAAAT
ACTATTGGGATCAGTTAACAAACCCTTTAATTAATGTGAAGAGACGTTTTGAAATTGAAGAAGTATGGGT
TCAATACATTAATGCTCAAACTGCAACAGAGAGAGAAGTTCTTAATTCATTTGTTTGGTTACATTTGTCA
AAATCTATATTACCACAAGAGTACCT
>retrotransposon_32 2125bp Incyte: 1..2125; zeta-like LTR: 1105..1612
TGAGTAGCCTTTTCTTGGGCGACTTTATTAGCTTCATCAACAAGACGTTTATCTTCAGCTTCCTTTTCCA
TAATAATTCTCTTCCATTCTGGAATTGGTTTTGGTTTCTTTTTATTTATCTCCTCTTCTTTCATAGCCAA
CAAAAGAGTACCCAATAATAATATAATGGTGATACCTTGTGCGTACATTCTTGCTTGAACAGCTTTTTGT
GCGGTATCCATAATTTTGTCTCTGTTAACCAATACCCAAGAACCATATAAGGAACCAGCCCAAGCACTTA
TGATAATTTTATATTTATTGTCATTCAATACGGTGAAACATTTGTCACTAAGCGATAATCTGTTCCATTC
ACGGTATTCTTCCAAATATTTAGCTTCCTGATACTCCGATTGATGCATCTTTCTATCGAATTCAACAGAA
CCTTGATCAGCGAAAAAGGCAGCCACAGAAATTGTTGGCATAGCAATTATGGCTGCTTTGATACTTGGAT
TGAATGTTGCAAATCTTGCTGGATGTCTATGCTTTAAATATTGGTACAAACCGACTGAAAGTGCACCACC
ATAAAACAACCCTTTGGCACCTTCTGAAATAATATGTGAAATGTGAGCGTCTTTTTCTTCTTTGGATAAG
ATCTTCATTGTGGAATTAAGATGACTTTGTGATTAAATTGTTGACTTCTTTAAGCCTTTTAATGTGGAGG
AAAAAGAAAATCTATAATTAAAAAAAAAAAAGATAAAGCAGATAATTCTTTGATCTTTATATACTTGGT
CTATATGTAGTAGGGGAAAGTCGGAGTCGGAATTTGAAAAAAAAAGAGAAAAAGAACGAATATTTAGAC
TGTAAAATTCAAACCCCTGCTGATTAGTATATAAAAAAAATGAGTTCATTTTTCCTTTCTTTTTTTTTT
TTCGCGCGGATAGCAACGGTCATTAAGTTAACGAGATAAAAAGAAACAACCAGATAATTATGAAAAGTT
GTGATGGTGTCACGTGCGAACATGAGAGTCATGAATTTTGACGAAAACGTCAAGCTTCAGTTTACAAAAG
ACCTCTTTATTAAAATCGAATTGCTTATAGGGTCGTCGATGATGAGAAGGTGTATGTTGTAATATAGCTA
ATGCTAATTCTTGATTAGTGTGGAAAGCCTAATAAGGTTATATTGTGCACAGGTTAACTACCTTAATATA
GTTATTGTTAATACAGTTATTGCTGTTGACTACTATTGTTATTGTTAAATTAAAGTGTTAGGTTGAGTTA
ATTGATTAGTGAAACCAACTAACTACCGTATTAAATTATTGTATTAAGATTGATTCCTATTAAGGATAA
AACAGAGAGTGTGTTAGAAAGAGAAAGGGTGGATTATAAATATGTGTAAAATCCCCTTTAGAGACTAACC
ACTAGAAATCTATTGATGGTTTCATATATAGAGATTAAAGATTATATTCATAATATAAGTTGGTAGTTGC
```

FIG. 71W

```
TAGTATATTTGAAAGCACTACAGTATAGTATGTCAGAATCAGATCAATTAAACTCTACTAATAATACAGG
AAACACTTTCATTAGTCTAGATCAAGCCAGTACAATAATAGCAGATCAAACTCAAGGAGGTAACCCACAA
CATAGAATACGTTTTCAACTACTTAAGTATCCACTAACCTAAATTTTTTTTTAATAAAATTTCATTGTA
TTAGTCTTTCTTACTGCTTTTAATCAACTATAAGTATAGGTTTCCGTTTTTTTTGCAGTAAAATTTATCG
TTCAGGAGAAATAACAAAATGTACACGACTTATTCGCAGCATTTTTTTTTTGTTTTGGGTTTTTGTATC
AAATTGTTACAACAACAACAACAACCTCAATTCTTAACCAAATCTACCCCTCCTATTTTTTTTCTCATA
CACACAATACATCTTACACTATCTTTTGATAGGCTTTATTGAAGAAGTATTTAAGGAGTGTAATGACAAT
CTGCTTAACTCATATATATATATATAGATAGTAGTCAACAATAGCTTTATCTACTTTTTTTTTTGGCGA
CCCCTGCAACTTCAGGCCCACCAGTTTGCCCATTTGGTGCCCCCATTGAGTAAACATGGGGATTTGGAG
CACACTTTTTTTTAGGTAAAAATGG
>retrotransposon_33 1292bp Incyte: 1..1292; san-like LTR: 369..749, CTA2
(transcription factor): join(974..>234,<888..1292)
CTAATCCAAAAATCCATAACCCAACTGCTCAACGGCGAAATCCAAAACTTCCATGCTATTCTAGACCAAA
CAGTGTCGAAACTCAATGATGCAGAGTGGTGTCTCGGCGTTATGGTTGAAAAGAAAAAGAAACTTGACGA
ATTGAAAGTCAAAGAAGAAGCGGCAAGAAAGAAGGAAGAAGGGGCAAAGAAAAAGGAAGAAGAGGCAAAG
AAAAAGGCAGAGGAAGCGAAGAAGTGTTTTATTTTACTTTTCTGTCAAATTTGCACTACTTTTAATTTGT
GTGCAAATATTCTATTTTACTTGATTTTTATATACTTTTATTTTACAATACTTTTTTATAGGACTTTTTA
TATCTTTTCTTTATCAACTGTTCGCTATAGGGTAGGTCTTCCAAGCTAATTTTACCCGACACAAGATGAA
ATATTTTCTGTTGAGCACTCGTTGTCGACAGTGAAAAATTTTCACTCAAGAAAATATTTTATCATCACTT
TTTCTAGAAGGGAGGTTCAAGTGTTGGAGAATAGACAGCGAACACCTGATATTCCCAAGGTCGAATTAGA
TTGAAAGATAAATAATAGTCATATTTATTTTGTATTTAGTCAATAAATTATCTTTTTATATTTAAATTCT
TAGTATTGTCATACCACGTAGATTGATACGGACATACTTAGCACATTTAACATATATTAAGCACCGATTA
CCTGTGACATTCCGGAGTTTACTGTTTCGCGCACGCTGGCAGACGAACATCAACTCATCTTTTATACAAT
ATATTCTTACGATTATAACTTTCAATTAAGAAATACAACTTCTTATTAGCATTCTCCTACAAGTTCTTAA
GTTCCTAGGAATTTCTTCGAAACTATAATTAAAGACGAAAAGTGTAAAACAAACAGAAAGCAGAGGAGGC
CCAGAAGAAGGCAGAGGAGGCCGTCCCACAAAAGTTTGACAACTTTGACGACTTTATTGGCTTTGACATC
AACGACATGCAGAACGACGATACCATCGACGATACCATCGACGATACCATCGACGAAACCATCGATGAAA
CCATCGACGATACCAACGACGAAGACATGTTGTCCAACATGGACTACGAAAATCTAGATCCGGACGAGAC
CATCGACGAAGTACCTGCCACCACAGACAGCGACTTGGACATGAACAACATACTTGAAAACAACGAGCTG
ATATTAGACGGGTTGAACATGACATTCCTCGACAATGGCAACAACACCAACCACGTAAACGAAGAGTTTG
ATGTAGACGGCTTTTTAAACCAGTTTGGTAAT
>retrotransposon_34 568bp Incyte: 1..568; san-like LTR: 113..493
GATTGTATAGTGGTGTGGTTGATCGACTTCAATATAACAAGAGAGAGATGAGATGAGATGCTTTTATCGC
GTATATATTTTTTTTTCCATTGACAATTCTGATTTCACAAATTGTTCGCTATAGGGTAGGTCTTCCAAGC
TAATTTTACCCGACACAAGATGAAATATTTTCTGTTGAGCACTCGTTGTCGACAGTGAAAAATTTTCACT
CAAGAAAATATTTTATCATCACTTTTTCTAGAATGGAGGTTCAAGTGTTGGAGAATAGACAGCGAACACC
TGATATTCCCAAGGTCGAATTAGATTGAAAGATAAATAATAGTCATATTTATTTTGTATTTAGTCAATAA
ATTATCTTTTTATATTTAAATTCTTAGTATTGTCATACCACGTAGATTGATACGGACATACTTAGCACAT
TTAACATATATTAAGCACCGATTACCTGTGACATTCCGGAGTTTACTGTTTCGCGCACGCTGGCAGACGA
ACAGATTAGAAGCTTGGTAAATCTTTGGTTATTCATCACGTCTTGAGAATAATACAAAGTTTAATATAGT
ATTTTCAA
>retrotransposon_35 946bp public: 1..946; san-like LTR: 113..493, CTA2
(transcription factor) C-terminus: <632..946
GATTGTATAGTGGTGTGGTTGATCGACTTCAATATAACAAGAGAGAGATGAGATGAGATGCTTTTATCGC
GTATATATTTTTTTTTCCATTGACAATTCTGATTTCACAAATTGTTCGCTATAGGGTAGGTCTTCCAAGC
TAATTTTACCCGACACAAGATGAAATATTTTCTGTTGAGCACTCGTTGTCGACAGTGAAAAATTTTCACT
CAAGAAAATATTTTATCATCACTTTTTCTAGAATGGAGGTTCAAGTGTTGGAGAATAGACAGCGAACACC
TGATATTCCCAAGGTCGAATTAGATTGAAAGATAAATAATAGTCATATTTATTTTGTATTTAGTCAATAA
ATTATCTTTTTATATTTAAATTCTTAGTATTGTCATACCACGTAGATTGATACGGACATACTTAGCACAT
TTAACATATATTAAGCACCGATTACCTGTGACATTCCGGAGTTTACTGTTTCGCGCACGCTGGCAGACGA
ACATCAACTCATCTTTTATACAATATATTCTTACGATTATAACTTTCAATTAAGAAATACAACTTCTTAT
TAGCATTCTCCTACAAGTTCTTAAGTTCCTAGGAAATTCTTCGAAACTATAATTAAAGACGAAAAGTGTA
AAACAAACAGAAAGCAGAGGAGGCCAAGAAGAAAGCAGAGGAGGCCGCCCCACAAAAGTTTGACAACTTT
GACGACTTTATTGGCTTTGACATCAACGACAATACCAACGACGAAGACATGTTGTCCAACATGGACTACG
AGGACCTAAAATTGGACGACAAAGTACATGCCACCACAGACAACAACTTGGACATGAACAACATACTTGA
AAACGACGAGCTGATACTAGACGGGTTGAACATGACATTGCTCGACAATGGCGACCACGCAAACGAAGAG
TTTGATGTAGACAGCTTTTTAAACCAGTTTGGCAAT
```

FIG. 71X

```
>retrotransposon_36 951bp Incyte: 1..951; san-like LTR: 389..769; POL
protein: <1..321
GATTTGAGAAATACCATTGAAGATCTAGAGTTAAAAATAAGGAATTTGCATGTACATGAGGATAATCAAG
CGGTCATTACAATCTTAAAGAATGATAATTTCCACCCACATAGACCGATTGATATATGTTACAAATTTCT
CAGACAAAAATTGAAAGATGGATTTTTTTCAATATCATATGTTGAATCTGGAGATAATTTAGCTGACTCA
TTCACGAAAGCTTTAGGAAGAAATAAATTGATTGAACATACCAAAAGGATTAGAGAAAGAAAGGATTATG
ATAATAATGCTACACTGATAGTGGACGTTAGGACGCTCGAAGAGATTAAGATAAACAAGAAATTGGTACA
TCATTAATTAATTTAGCTGTTTACCTGAATCAGGGGAGTGTTCGCTATAGGGTAGGTCTTCCAAGCTAAT
TTTACCCGACACAAGATGAAATATTTTCTGTTGAGCACTCGTTGTCGACAGTGAAAAATTTTCACTCAAG
AAAATATTTTATCATCACTTTTTCTAGAATGGAGGTTCAAGTGTTGGAGAATAGACAGCGAACACCTGAT
ATTCCCAAGGTCGAATTAGATTGAAAGATAAATAATAGTCATATTTATTTTGTATTTAGTCAATAAATTA
TCTTTTTATATTTAAATTCTTAGTATTGTCATACCACGTAGATTGATACGGACATACTTAGCACATTTAA
CATATATTAAGCACCGATTACCTGTGACATTCCGGAGTTTACTGTTTCGCGCACGCTGGCAGACGAACAC
AAATGCTTGAACTATCTGCCGACTTTTTTTTATTTATGGCGTGAGACATTGTTCTCGCACACGGTTGTGA
TTTATCTACCAGGCTCTCATATTTAGAGCGACAACTACTTTGAGCAAGCAAAACGCATATCTCACCACAC
ACCAATTGTAGGCTATTCTCAACCGGAAAGTACAACTAGCA
>retrotransposon_36 POL protein 107aa
DLRNTIEDLELKIRNLHVHEDNQAVITILKNDNFHPHRPIDICYKFLRQKLKDGFFSISYVESGDNLADS
FTKALGRNKLIEHTKRIRERKDYDNNATSIVDVRTLE
>retrotransposon_37 9850bp public: 1..9850; san-like LTR: 369..769; CTA2 N-
terminus: 1..>234, GAG protein: 939..1853, POL protein fragment 1:
1896..2360, POL protein fragment 2: 2509..4893, POL protein fragment 3
(reverse transcriptase): 4953..5723
CTAATCCAAAAATCCATAACCCAACTGCTCAACGGCGAAATCCAAAACTTCCATGCTATTCTAGACCAAA
CAGTGTCGAAACTCAATGATGCAGAGTGGTGTCTCGGCGTTATGGTTGAAAAGAAAAAGAAACTTGACGA
ATTGAAAGTCAAAGAAGAAGCGGCAAGAAAGAAGGAAGAAGGGGCAAAGAAAAAAGGAAGAAGGAGGCAAAG
AAAAAGGCAGAGGAAGCGAAGAAGTGTTTTATTTTACTTTTCTGTCAAATTTGCACTACTTTTAATTTGT
GTGCAAATATTCTATTTTACTTGATTTTTATATACTTTTATTTTACAATACTTTTTTATAGGACTTTTTA
TATCTTTTCTTTATCAACTGTTCGCTATAGGGTAGGTCTTCCAAGCTAATTTTACCCGACACAAGATGAA
ATATTTTCTGTTGAGCACTCGTTGTCGACAGTGAAAAATTTTCACTCAAGAAAATATTTTATCATCACTT
TTTCTAGAAGGGAGGTTCAAGTGTTGGAGAATAGACAGCGAACACCTGATATTCCCAAGGTCGAATTAGA
TTGAAAGATAAATAATAGTCATATTTATTTTGTATTTAGTCAATAAATTATCTTTTTATATTTAAATTCT
TAGTATTGTCATACCACGTAGATTGATACGGACATACTTAGCACATTTAACATATATTAAGCCCCGATTA
CCTGTGACATTCCGGAGTTTCTTGTTTCGCGCACGCTGGCAGACGAACAGATTAGAAGCTTGGTAAATCT
TTGGTTATTCATCACGTCTTGAGAATAATACAAAGTTTAATATAGTATTTTCAAATTTTGGAATACAAAA
GTTGCTAATTGGTAAATAAGTTATTGATTTATTTCATAAATCTTTTTTGGTATCATATTTCAAAGAGTTG
CAATTGAAAGCTAAAGACATCCTTATAAATGGCTGAATTTAGCGATGCTGAGCTCAGAAAGATGATGGGT
ACACTTTCACTCTTGGTACAAGATTCCAGGAGAGAAATTAACCACTTGCATGATAAGTTGGAGAACAATA
GTGACTCAAAATATCAATCTTTAGAAACGTACATCAACTCAAAGTATGCAGATACTATAAAATCATTTGA
AAAATTAAAATATTTGGACATTGATAATTCAGAGTTGGTTAATACCTGGATCATGTGTTTAATCAGGTT
AAAAGGTTTCACCCTCAGGTTTTTGATGCTTTCATGGAGGCAGAGAACGAGGACGAAATTGGAATCGAAA
AGATCCAATATACGCCATACACAGGTAAACACTTGAATGATATGATCAGAATCTTCTACATGAAGATATC
CGAATTAATAGAAAGAAAAGTTAGTCCAAATGTTTCTAGAGAGATGAATGATGGACAGCCACAATTTGTT
CCGAATTTGTTTAAAAAAGTTTACGAGATGATTATTTCAAAACCAGATGTTTCTGCTGCTGAAAGAATTG
GAAAAGCTCTTTTCAAGTTACAATCTAAACTGAGAGAACTTGAAAGAGAATCAGTCATTTTTGTTATGTCA
ACATTTAATGACCAATGACCACCAGCACGATGATATTATTCTTAAATTTCTCGTTAGCGGTGTCTCACCA
TGGTACTTACATCTGCAAATTTACATGCTGTCATATAAACTTGGATTCTCAAATTTGTTTTTAGAGATTT
ATGCTCAACATTATGAATTGTATAAAGCAGATCCCATTTACAAATTGCCAGATAGTATGACATTGTTGAA
TGAAATAAGATCAAATAGAGATTATCCTAAAGTGGTAAATGCTGCAAAAAATACAGTACAAGTCAATAAT
GTTTCATCCAAGAACAATAAAAAGAAGGATGAATGACAACAATTAGCCAATAAAATTGAGGAAGTAGGAC
GTTATAGCGAAATAAACGCAACATCTACATATCATGAAATTGGCGATACCAACAAAAACAAAGAACAATT
AATATTGAATTTGAAAAATCATACAAAATTAAGTGAACAAAAGAAGAAAACAAACCTATTGGTATATGAT
CTGGGAGCCACAGTATCCGTGGTGAATGATAAGACTTTACTTAACGACATTAAAGAATCAAATATCGAAA
TTGCAACTGCTGAAGGGGAGACATCTACGGCTTATGCTTTAGGTACTCTAACCATATCTGTGAATGGATT
GAATGCGAAATTAGATGGTGTTCTATACTTGCCATCTATTCAATTAAACTTAATATCTATAAAACAATTT
GAAGATTTATGCTACGCAATTTTGATTTCCGAAAATCTAATGTGTCTAGTTCACAGTGACCACGGACCTA
CGGTCATTGCGAAATATTCACCTAAAGATGACTTATACTCAGGCCCAAGTCGGGAACCTTTTTTAAAA
GAATTCATAATGACCAAACCCATTTTTTGCTTGCCNCTGCTAAAAAACTTTTAGAATCAGAGACCATATT
```

FIG. 71Y

```
TCTGGAGAATCCCTGAAAAATCCAATGGATTGATCAAGAAAAATTAGATCCGTTGAAAATGACCAATAAA
GTAGAAAGAGTTACCTATGTCAGCATACGCAACATCAAACAAGAAGTGGCAGACAAATATATGATAAAAG
ATCTTTACTACTATCATTTATTAATTAATCACCTTTCACATGAAAAACTACAATTATTAGTAAAAAGGGG
AGTGATTAAACCAGTCAAATCTACTTCGGCTGAGTCGGCCATTTTAAATTGTCAGATATGTGTTGCAGCC
CATGCAAAATTAGCTAGCCATAATCACACTCAACAACGGGAATTGGAGCGACCATTACAACGCCTCCATT
TGGATACCGCCGGACCATTTACCTCAAATAAAACTAAGAGCTATCTTACAACCGTGATTGATCAATTTTC
CAGATATACTGAAGTTATTGTATCTGACACCAAAGCAGTCAAACAAAGCATATTGCATAGACTTAGGGTC
TGGAACAATAGATTTCAGTTTAAGATCGCGGAGATAAGATATGATAATGCATTGGAGTATCCATCGGCTG
AGGAGTTAGAGGAGTTAGGAATTTATAAACACCTTCTCCCAAACTACTCTCCTATGCTTAACGGTACAGC
TGAAGCAACCAACCGCCCCATTGTCCAAGGTATTTATAAGGTAGTGTTAAATTTTAGTTGTCAAGTATTA
ATACTTTTCCCATTTATAGTGGAGTATGCGGTTCATATCCGGAATCATACACCTATAAAAGAATTTGATG
GTGCTACTCCTTATGAACGTTACTATGTTTATCTAAATACGTCATACCATTTTTCAGTTTGGAACCGA
CGTTTTGATAAAATGTGCTAGTGTACAAGAAGCTATTTCATTAAAACTACCATCTTCAAGAGATAAAGCT
TTTCCTACAGTGATGTTTGGTGCTTTTCTCGGTTACGGCTCAGATTCCTTTACCTTCAGAGTTTTAGTTT
CCACGAAAGGATATCCAGTTATTACAACATCAAACATCCGTCCAATAGCGACGATGCAAGTACTCAATGA
CTATTTGGCATACATATCGGAGAATAGCTCAATAAGCTATGACGATACATTCTTATCACCTTTGAATCAC
CCAATGATTCGCACAAACCAACATGATAGACGTGGAGACAATATAAATGTCGAATATGAAAACCGTCCAA
ATGTACCATTTGAATATCATGCTGAACCTCCTCGTACAAATTCATCGACGGGAATTATCGATCGACCAGA
TATTAGACCTAGAGCTGATCCCACCTGGCAACGTATGCCTGATGCCAACATACATCAGGAAACAACAACT
GTACAGACTCCTGATCATGGGGAGTTAGATACCATGATCAACAACGAACACCAACTACCACGATCTGGGG
AGGGTAATTACCCCGGGCAACAGGTGCGCACCGATATTATTGGGCAATTTCGAGATCGCGGGCCTACCAC
TCTAAACACTCCGATCGATCTAGGTGTACCCGATGAAACAGACGATATTAGTATGACATCAGAGAATCCA
ATTGATTCCCCAAATTCCGAGATGATCATATCCCCATCTTTACCCACAAATGAATTGGAACATCAAATCG
ATATCAGTTCAGGGGAGATGTCGTTATTGCAAACGAATATGGAAGCAGATAACGAATTGAAAACAAATGA
AATGGTATTATACAAATCAAAAAATGATGGTATTATCATTCAACAACAACAATTCACTGAAAATTTGTCA
GATGAAAATGAAGAAGATTCATCAACAGATGAGGAAACATTGGAAGACAAAAACAACAGCGATTGGAAT
ATAATATTTCACCAAACGATGAGTGGATAAATAATGACGTTCAGAACGAAGATGACACACAAGTGCCACA
TGTTAAGGAACCAATCAATTATGAAACTCAAAGTAGAAATGAAACAAACATGCCACGAATTGAAATGGGC
ATAATAGAAAACTTAAGTGATGATGGAAAGAATACACCACGTGAATTACGTATCGTCACCTACGATAATA
ATAAAGAAATTGAAAAGTACCAAGACAGTAATATCGAGATCCTGGAACCCAGAAACGAAAATGAAAACCA
GACATTCATTGAAAGCAACTTAGAATTACTTGACAATCAAGAAATGTTTCAAGAAGATCCTCAAGTTGAA
GATATTCGATTGACAACTCCAAAAAAGGACAAATCGTTATCACCTGATTTCAATCAAACCCATAATGAAA
TACAACTATTCATGGCAGATATCAATGAAGATATGCTAGAAGAATATGATGAAAATATAAATATGAATGA
AGTGTTAGCTGACTCCACGGAGACGTTGGACAAAGAATTAGATTTAGATGAAGAAAGTGGAAGGATCGAA
TATATTGCTGATAGAGTTAGAAAAAAGACAGAGGTACTGATGGTGCGCCACACGGGAAATATTTAAAGAA
AAATGATAAAGATTTTGGTTCAATAAAAAGTCAGAAAAAATCTGACGCACAAATGGATGATGAAGTTGGA
ATTGCTATTTCGAAGATCAGAAACTTTCCATTTAGATTGAAGGATGGACGAGCAAGTTTCTTCCCTCCAT
ATAAAACAAATTTGGAAGATCAGTGCATCCACCTAAAAGATATTTAAATGCCATTGTTAAGAAAATAGA
TTACAATCAAAAAGAATGGCGTCAAAGTATGGAAGAAGAAATCGAAAAATTTAAGGCTAACCAAGTTTAC
ACCGTTGAAAAAACACCAAAGAACGTTGTCCCATTGAAAACCATGTGGGTACATACTTACAAAACCAATG
ACCTCAAAAATCATAATTACAAAAGCCGTTGCGTGGTAATGGGAAACTATATGGTCGAAAATCGTGATTT
TGATCCCCATGCCATCTCCTCCCGGTAGTAGATCTCACAAGTATACGACTATTATCTGCCATAGCTGTT
GAAAATAACTTGGTTATGCACCAATTGGACATCGCCTCAGCTTATTTGAACGCCAGTTTGGAGGATGGAA
GAGTAATCTTTGTGAGACCACCGCGTGGTTTTGAGGTTAAACCTGGCTATAGTTGGCGTTTACACAAGTC
TGTGTACGGTCTTAGGCAGAGTGCCCATAATTGGTACTCACATTTTAAGAATGTGTTGGAGGCAAATGGT
TTAAAACAAACACTACACAATGATGGCATTTTTTGGAAAAATTATGAAAATGGAGATGTATTATATGTGA
GTGTATATGTGGATGATGTTTTTATCAAAGCGAATTCAATGAGTTTGTGCAACTAAATTTAGAGTTGCTT
TTAGTTTACTAAACAAATTTTATCCTTGCTAATCAATACTATCTATTATGCACGATCTAGCAACCTTAAA
ACAACCAATGGAAAATTAAAAAAATTCCCTCATCAATCTGGCATGTTCGAATTGAAAAAAAAAAAAGAA
AACAATAGAAATTCAATACAATAGAGCATAGAACTGGCCAGAATGTGAGACAATAAGTCAGAACAAGTGA
TTGCCAGTATAGGTAGGGAGAAGCAACAAAGAGAGTTTACACAGCTGAAAACAATCATATCGACGGTTAT
TGCAACTTGGTTGCTATTTCAACTATTCGTAATGGTCCCATTTTTAGCCAACACAATTTCAGAGAAGACG
CGAAAAAGGACTTGGAAACTTCATAGTTTAGAGCCACAAACTATAAGAAATAATAGTACGATCTAAATTG
GTTCCCTAGGATAATGCCCAACAAAGAAATCCCCCAAATAATTGTAAATTGTTCAACCTTAGTAACTCTA
TCTAGCATTGCGGAGTTCCTTGAAAATGAATTGGTTTGGTGTTCCTACCTGTTCAGTACTTAATCACTAA
CTAGACAAATTCTTTGGCGAAAGCTCAACTTTTGTGAAGGTCTTTCTCTACTATGAACATGACTCCCAGC
AAGTCTAGGTTTGGCTGCACTATGAGTTTAATTTAGTTTTATCGGGCTAATACTACTTATTTCCGTTATC
GGTGTGACCCCCGAAGAAAGGGTATTACGGGGCTCATAATTTTTTTTTTTTTGGCAAGTAGAGTGAGATT
```

FIG. 71Z

```
CAAAAAAGAAAAGTGAACCAGAGCAATAATTGCTATTAATTTTAGTTTTTTACTCACTAGCTATACTTGG
CTCCCAAACTGATTTTGTAACCCTTTGAGCAAGGTTGTTGGTCAACTGCAAGATCAACTAAGCAAGATCA
CGCCTTATACGCAAGCCCTGCCAAAAATAATTCACTCTTGAAACAAGGAATTAGCAGCTATTAGGTAGA
CTTTTTTTTGTACCTGTATTTCGTTACCAACACTAACCGAGGCACTACCCAAACTCATATAAACATGACT
AAGAGAAAACAATAGAGAAGGGGTTTAGTTGATTTTCCAATACATTTTAGTGCTGAATTACATTTATCTA
TTTAGTTTAGTTCCATAATCTTTCTAATATTGTTGAACCATTAGCAAACTTTTTAGATTAAAAGCTCTTT
TGTAACTGTTTTTTTTCTGTAGTTATCGCGTAACCTTTCCCCCTCAGAATTTCTAAACCCTCCCCCCCCT
TTCTTCAAAACATTAAAGACTTTGAACTTTATCATCACCACAAAAACTTATTAAGCTCCAGCAAATTTCA
GGTGACACCAAGGAAAACAACAATTAACATTCTTGGAGTTAAGAGTATATGCTGGTGCATGGATTAAATA
TGCCTGTTCTTAACCCCAGCGAAAAGAATATGTTATTTTTGAACAAAAAAATAGAATATCTCAAATAAAT
TTGTTCTCCCCTTTTGTCTATCTATCCCTTTAGCTTTTTGCCAAATTCCAACACAAAATGCTTTAGTCTG
CAGAAATGATGACTAAAATATTCCTTTTCTTCAAAATTCATATTTTCAAAATTTAGCAAATGGTTGTACT
AGATATCAGAATTTTATCTGGTGAGTTTACTCAACCATAGTAGTCTTTTTTTAGATCAAAAATTAGACTT
ATGAACCCTATATTGAATAAAGTTAGTGTTCCCCACAGCTATTCATAATAAAAAGCTTAACAAAAAGTT
GAGATTATCAGCGACGATCGATCATGTCGTTCCAGAGATTGTGTTATAGCGCCTCCTTATGAACAGGTAA
ACTATTAGTTGCATGTAGATCTATTGTGTTCAAATTTAAATTTAAGAATTGTTAGCTCAAAACAAAGAC
GACCTGAAATTCCAAAAATCATAAAGTTTACCCCCAAAAAAGTAACGACAATAAAGGTGCACCAAGAAAT
AATGGTTGTAGTTTTTCCTTTATCTGTTTTAGATTGCTTTATTAGGGGGTATCACTAATTAGCAATTGTA
GCCCTTGCTCGTTATTGTTGCTTGATTTTTTCTAAAAACATTTGCTTAGCATTATTGTTGTAAGACATAT
TTATCTATTGTTTCTCACCCTTTTAGACAAATGATTAGCGCCCCTTGACACGATCACAGCCTATTGTTTG
GTGCACTATTTGAGCTTTAAAGTACTAACTTGTTTTCAGACTATCAATCTATGTGTTTGTTCAAAGCCAG
GCACTCGAGTCATTAGTCAACAATAGGCTGTATGTTGCTATCCATGTAGTGCCTTGTCTACAGAAATTTG
CTTTTTTAATTCACAAGCATGAGATTTTTGTTTGTGTGGTATTTGACGTAAATGTAACATGATTACTTG
AAATTCGATACGATCTTTTCGTCGTCTATACAAAATTTATCAAGTGCTACTCTGTGATATTTTGCAAAA
CCAATCTCATTGTTCCTTGCATGAGAATGATTTCGTTGTCATCAAAGAAATATAAGCTTTCATTACCACA
ACAAATAGCACATGGTACTACCTTCCCAATTAAAGTATGATGTAACCGTCGTTGTCCCCTTATGTCAAAT
GCAAAGTGAACATTCAAACTTAAATGCGAGCAAGAGCAATTATAATATTACTTCTTCTAGCTTTACAAAA
TAATATTTTCATCATTTCTGAGTTTATTAGTAGAAACGTTAATATTATTTCAGAAAAGACTACAATAAAT
TATTGGGGTAATTCTTAGCGGTAGGTTCTCCTGCCCACGAGTGCTTTGCACTGTAGGTTAAATTTATTTC
TTCAGGATATTCCTACCCCTCTAGGTTGTACTAACCATTGATAATTACTTGCAAATATTTTTTCAAAAA
AAGAAAACCCTTTACATAAATAAGCTTTATATAATTATACGTTGAAAAATGACCCTAATTAGTGTGCAGT
TTTCAAATCTTAAATGTTTCTCTACCCAATGATTACAGAGATCATCAACACTTGTGAATGGACATCATAT
CTGTACGCTTTTCTAGGCTGCGAAATTATGTAACTTCTTGGTGTACAAAAAATTGCAACCCCTAAGAAAA
TCATAAGTTTATATCCAAGAAAAAATGGTTTATAAGCGTATAATGAAAATAATAATATTATTAACCACG
ATGGCCAAAAGAAATCTAAAGTTGGCAATAATTCGCTAGTTGGGGGGAAGTTGCCAATAATAAATGAGCA
GGCGTTTTGATATTTATAATAATAGGTCACCTGTTTTGAGTATTTCCTACAGGGACTTTTATTTTCATAA
GGTGGATATGCTATCACTTGGTGAAACAACTTCAAATTCGTGTACTTTGCTTATGCCAGATACTTAGCAC
TGGGAAATTGTTACAACCCCATTTCTGGAAATGTAACGTCACCTGAAACCATCTTATGGTCCTGCCATTG
GTGTTTCATCGTGTTACAATGCTAGGTTTTTAAATGTCTACAAGTCAATATTATATTCAAGATAAACTT
TTCAAAACATCTGATTTATTATGACATTATTCTTGTTGACATTTTTTGGGGTAGACAAGAAATAATTGC
AGATAATATAGAACACTTATGCCACGTGGGTGGATTTAATAGAATCCTTGTAAAATATTATCTCTAGAGA
ATTATAAGGGGAGGAGAGAAGATCTATGGCAATGCAAGAAAATGCAAGATCATCGTAAAAAAGTATAAG
AATGACTCCATAAGATATATAAACCCACTTGTTTGAAGAGCGCTTACTACACGGGGTTGTCTTAATACAA
AGGCGGCAGGGTTGCAGTACTTCTGTAGTTTCTAACCTTTGTATTCCTTAGGCCCTGGAATATAATACTT
CCTGTAGTAAATGTCGGAGTTTAAATTGCTGACATTGCAAGAAAATAAAACCAATATAATATTTTTATG
TCACGAAAGAAATGGAACAACAATGTAGCACCAAAAGGGGTAGAGACTAGGCAGTACTATATTTGGAGGT
AAAAGTATATTAGAAAAGAACCTATACATGAACCAGTAACCATAACAAAAAAAACTAAACCCAAGCAA
TTAACCATCCAAATTTAACCCGTTTTATAATACAATTTTGACCACATCTA
>retrotransposon_37 GAG 305aa
MAEFSDAELRKMMGTLSLLVQDSRREINHLHDKLENNSDSKYQSLETYINSKYADTIKSFEKLKYLDIDN
SELVNTWIMCFNQVKRFHPQVFDAFMEAENEDEIGIEKIQYTPYTGKHLNDMIRIFYMKISELIERKVSP
NVSREMNDGQPQFVPNLFKKVYEMIISKPDVSAAERIGKALFKLQSKSRELERESAFLLCQHLMTNDHQH
DDIILKFLVSGVSPWYLHSQIYMSSYKLGFSNLFLEIYAQHYELYKADPIYKLPDSMTLLNEIRSNRDYP
KVVNAAKNTVQVNNVSSKNNKKKDE
>retrotransposon_37 POL fragment 1 155aa
SEINATSTYHEIGDTNKNKEQLILNLKNHTKLSEQKKKTNLLVYDSGATVSVVNDKTLLNDIKESNIEIA
TAEGETSTAYALGTLTISVNGLNAKLDGVLYLPSIQLNLISIKQFEDLCYAILISENLMCLVHSDHGPTV
IAKYSPKDDLYSGPR
```

FIG. 71Z2

```
>retrotransposon_37 POL fragment 2 795aa
MTNKVERVTYVSIRNIKQEVADKYMIKDLYYYHLLINHLSHEKLQLLVKRGVIKPVKSTSAESAILNCQI
CVAAHAKLASHNHTQQRELERPLQRLHLDTAGPFTSNKTKSYLTTVIDQFSRYTEVIVSDTKAVKQSILH
RLRVWNNRFQFKIAEIRYDNALEYPSAEELEELGIYKHLLPNYSPMLNGTAEATNRPIVQGIYKVVLNFS
CQVLILFPFIVEYAVHIRNHTPIKEFDGATPYERYYGLSKYVIPFFQFGTDVLIKCASVQEAISLKLPSS
RDKAFPTVMFGAFLGYGSDSFTFRVLVSTKGYPVITTSNIRPIATMQVLNDYLAYISENSSISYDDTFLS
PLNHPMIRTNQHDRRGDNINVEYENRPNVPFEYHAEPPRTNSSTGIIDRPDIRPRADPTWQRMPDANIHQ
ETTTVQTPDHGELDTMINNEHQLPRSGEGNYPGQQVRTDIIGQFRDRGPTTLNTPIDLGVPDETDDISMT
SENPIDSPNSEMIISPSLPTNELEHQIDISSGEMSLLQTNMEADNELKTNEMVLYKSKNDGIIIQQQQFT
ENLSDENEEDSSTDEETLEDKKQQRLEYNISPNDEWINNDVQNEDDTQVPHVKEPINYETQSRNETNMPR
IEMGIIENLSDDGKNTPRELRIVTYDNNKEIEKYQDSNIEISEPRNENENQTFIESNLELLDNQEMFQED
PQVEDIRLTTPKKDKSLSPDFNQTHNEIQLFMADINEDMLEEYDENINMNEVLADSTETLDKELDLDEES
GRIEYIADRVRKKTEVSMVRHTGNI
>retrotransposon_37 POL fragment 2 (reverse transcriptase) 257aa
MDDEVGIAISKIRNFPFRLKDGRASFFPPYKTKFGRSVHPPKRYLNAIVKKIDYNQKEWRQSMEEEIEKF
KANQVYTVEKTPKNVVPLKTMWVHTYKTNDLKNHNYKSRCVVMGNYMVENRDFDPHAISSPVVDLTSIRL
LSAIAVENNLVMHQLDIASAYLNASLEDGRVIFVRPPRGFEVKPGYSWRLHKSVYGLRQSAHNWYSHFKN
VLEANGLKQTLHNDGIFWKNYENGDVLYVSVYVDDVFIKANSMSLCN
>retrotransposon_38 3159bp public: 1..2084, Incyte: 2085...3159; san-like
LTR: 2638..3019
AATCTGTCCACCTCGTTTTGAGAGGTTCTCAAAATTCTTTGTAATTTTCAAACTTCACCTTTGGCTTTGT
AAAGTTGGTTTTTTAAGGAATAGCTTTGATTATTTGACATTGCAAACAGTATAGTCAAGATGCACACAGA
TTGGACCTGAAATTATTCCTTCGCAAAAACTTAAAATAACCCAAATATTAAACATCCACTCGGATTCAA
TACCTCAGCACTCTTTTATAGGCACTTGTATAATTTGTTATATGAATCATTTCCAGCTTCCTTGTAGAAC
CGCCAAATATTTGAATCACATGGGAAACAGATTTGACCATCTAACTTTCATGGTTCTTATGAAAAAGATC
TGGAAATGGTGATATAGCTTGATTGTCTAGCATATTCAGCGATTACCCTATTTTGTGGTTGCCTGGGATA
ACCCCTGGCTGTTGTTGGAAAAGACTCGTGACAAGTATTTTTGCCCACGAGTTTCTAATTACTGCGATAT
TATCCAGTTACATTTTCGCAACTCGTTCTACTTGAGCTCCTTCTATGAATCAACTAGCTGGCTATTTCCC
TGGATAGAAAACCTTCATTCTTCTTCTCCTGGTTGAGTATCACCGACTTGTGGCCGTACCGTTCAACCCC
CTACAATACACCATCAACTTTATACTTGTAATACTCGGCTTTGCCACTCCCCAAACTAACCACTATAAGT
TCATACTCCTTGGCTTGCTTGACTTTCCTATTTCTTAACCCACTACTCTTCTGTACCACTCCGATCATCA
GATTGACAGAGGTTACTTCATACCCAACAACATTTTCATACCAGTCGACCTTCTCCTCTGCACCACCAAA
CCCAACACATCGGATTTCCCTGGGATCTCTCTCAACTCTCAAACATATTGCTTTCTTATCTACCCTGAAC
GTGTGCACCACTACCACCCCTTCTATCTCATATACCACACTGAACGATGAGATCGCAGCACTCCCACAAA
ACCGACAATGCAGCGGCTCAGGATACGACACCCTCAACGAGTTCACCTTCATATTCCCGACCCCAAACAG
TTTGATGACCACCCCCGTGTTCACATCTATAAGCTGACACTCTAACCCGTCAACACGTATAAAGAACCCC
ACAAACTCAACCGGAAATATCCCACACAGTTTCAGGGGCGCCACCTCTAGCTTTCTGCTCTTCATGCTGT
TGTTGACGATGTTCACCACAATAATATCCAACTCCTTCGTCTGCACAACAATTCTATCCATCACCCTTGG
TGTTCTTATCTTTATTGCACAGACCAACTGCTGCTTCACATCATAACTCTGTACTTTCCCATCATTACAC
GACACAACAAGTATCTCCCCACTATCCATGACCATCACAAACTCTTCCCTACTAGTCCTCTCACGCTGTT
TCTGTCCAAACGATTTCATCTGTATTGGTGGCGGAAAGTTCGCATTGATCAGCGAATTTACCGACGACAT
TGACGCATCACTGCCCCTCCTCTTTCTAATCATTTTACGTGCTAAAAACCCCGGCACAGTTCTCCGCCTG
AAAAACGACTCCAACACTTTACCTCGAAAGTGCACCGACAGTGTCCACTTCAACTCCCGCTTGTCATAAC
CCTGTATGACACCCTGTCTAGTACTCACCAACACAACCATACTCCCATCATCATTGAGCCCCACATGGCT
GACCGGCCACATCTGACAGGGTATGGCTAGTGGTTCAGGGTCGTAACAGTACTCGACATCTTGGGGTTGG
TAGTGATATATCTGAACTCGTATCCATCATATAACTCTTCCTCAGCAAACTCAATGGCCTGGGTTTTT
GCCGGAACCACTAGTGCAACCACCAACAAGAGGTACTCCACATAGTAAATGTACGTGTTAGACTGGGAAA
CAACCACACTGGTTTGGTCGACTCAGCACGCTATTCATCAACAATACCCCAACAGAATCACCAAGTTAT
TTGTCAGCCTCAGTTTGTACTTCCACCACTGACCCCACCACCGCATAGTTCACCAAAAGGGTCTTGCATA
ATCCACGTCCCACCATATCACTTCAACTCCCATATTCCTCGATGCAAGAATAACCACAATAATCGGCTTT
CGTAAACGTCGTCAGTGGCTCAAACACATTGCTGCACCTTGAGCTCTAGAACAACCCCACACTCACTAGC
CATCGCCACACCAACAACCAAATTGCTGATCCAGAAAAAATACCACCCCGTAGTCCGGCTTGTATGAA
TAATTGCTTGGCCAGGTACGTCCCCACCTCATCGTGTCTTTTCTGGTTGAAATATGTCATCTCCCGGGCT
AACAGTACCGTATCTCTGTGGCTGGGGCATCTATACTCTTTCATTCTCGGCTTACAAATCTATCTTGTTC
ACACATTTCATATATCTGGGACTTGTCGAACTCTCTGCACTCTATCATAAACTGGAACTCGCTTGCATTC
TGGGACACACACTGGAGCTGGAATCCATGGTCAGGAAATGTGAAAATTTTCTTCTCGGGAAATATTTGTG
ACAATTAGTCCTAGTACACGATAGTTTCATTACGCCCACTAAAAGTGTCTACTGAAACTCGGTCTCTATA
TCGTCAATATCTTTCATTTCTCTTCCTGGCTTTTCACTGCGACTTATTGTTCGCTATAGGGTAGGTCTTC
```

FIG. 71Z3

```
CAAGCTAATTTTACCCGACACAAGATGAAATATTTTCTGTTGAGCACTCGTTGTCGACAGTGAAAAATTT
TCACTCAAGAAAATATTTTCATCATCACTTTTTCTAGAAAGGAGGTTCAAGTGTTGGAGAATAGACAGCG
AACACCTGATATTCCCAAGGTCGAATTAGATTGAAAGATAAATAATAGTCATATTTATTTTGTATTTAGT
CAATAAATTATCTTTTTATATTTAAATTCTTAGTATTGTCATACCACGTAGATTGATACGGACATACTTA
GCACATTTAACATATATTAAGCACCGATTACCTGTGACATTCCGAAGTTTACTGTTTCGCGCACGCTGGC
AGACGAACACTTATCAAGGTGCTACTCCCGCGCATCAGTTTCCTCTGGGTTCTCTTTTTGATCTTGGTGA
ACTACCTTTTTTCCCACTCGCGTGAGAAGTTCAACACTTTTTTTACCCATCCACCAAACTTTATTCTT
TTCCCCACC
```

FIG. 72A

| Name | Length (bp) | Regions of interest | Remarks | Novelty |
|---|---|---|---|---|
| AF041469 (280 bp) *Candida albicans* retrotransposon long terminal repeat kappa, complete sequence | | | | |
| retrotransposon_01 | 994 | LTR kappa: 548..927 | | *partial* sequence present in public domain |
| retrotransposon_02 | 1348 | LTR kappa: 764..1043, POL (contains stop codons): <136..714 | | *partial* sequence present in public domain |
| retrotransposon_03 | 3034 | LTR kappa: 75..354 | | *complete* sequence present in public domain, identity 99% |
| AF043301 (5624 bp) *Candida albicans* retrotransposon-like element Tca1, complete sequence | | | | |
| retrotransposon_04 | 3504 | Tca1-like LTR:688..1075 | | *complete* sequence present in public domain, identity 99% |
| retrotransposon_05 | 3955 | Tca1-like LTR: 2656..3043 | | *complete* sequence present in public domain, identity 99% |
| retrotransposon_06 | 1434 | Tca1-like LTR: 87..475 | | *complete* sequence present in public domain, identity 100% |
| retrotransposon_07 | 1606 | Tca1-like LTR: 1046..1433 | | *complete* sequence present in public domain, identity 98% |
| AF050215 (6980 bp) *Candida albicans* Tca2 retrotransposon gag polyprotein (gag) and pol polyprotein (pol) genes, complete cds | | | | |
| retrotransposon_08 | 1385 | Tca2-like LTR: 49..328 | | *partial* sequence present in public domain |
| retrotransposon_09 | 1483 | Tca2-like LTR: 871..1150 | | *complete* sequence present in public domain, identity 99% |
| retrotransposon_10 | 879 | Tca2-like LTR: 326..605 | | *complete* sequence present in public domain, identity 100% |
| retrotransposon_11 | 974 | Tca2-like LTR: 483..761, CTA2 (transcription factor): join(<974..>778,<223..>1) | | *partial* sequence present in public domain |
| retrotransposon_12 | 3868 | Tca2-like LTR: 127..407 | | *complete* sequence present in public domain, identity 99% |
| retrotransposon_13 | 469 | Tca2-like LTR: 75..355 | | *complete* sequence present in public domain, identity 99% |
| AF061575 (583 bp) *Candida albicans* retrotransposon Tca3 reverse transcriptase (pol) gene, partial cds | | | | |
| retrotransposon_14 | 4545 | Tca3 LTR: 1..314, 4234..4545, POL fragment 1: 577..>3324, POL fragment 2: <3443..4201 | complete retrotransposon | *partial* sequence present in public domain |
| retrotransposon_15 | 2093 | Tca3-like LTR: 1509..1822 | | *partial* sequence present in public domain |
| retrotransposon_16 | 2099 | Tca3-like LTR: 1565..1878 | | *complete* sequence present in public domain, identity 100% |
| retrotransposon_17 | 3284 | Tca3-like LTR: 2750..3063 | | *partial* sequence present in public domain |
| retrotransposon_18 | 791 | Tca3-like LTR: 277..590 | | *partial* sequence present in public domain |
| retrotransposon_19 | 4581 | Tca3-like LTR: 2725..3037 | | *partial* sequence present in public domain |
| AF065434 (1145 bp) *Candida albicans* retrotransposon Tca5 reverse transcriptase (pol) gene, partial cds | | | | |

FIG. 72B

| | | | | |
|---|---|---|---|---|
| retrotransposon_20 | 5325 | POL protein: rearranged CDS | | partial sequence present in public domain |

AF069450 (508) *Candida albicans* retrotransposon long terminal repeat zeta, complete sequence

| | | | | |
|---|---|---|---|---|
| retrotransposon_21 | 2027 | LTR zeta: 1384..1891 | | partial sequence present in public domain |
| retrotransposon_22 | 2118 | LTR zeta: 1419..1927 | | partial sequence present in public domain |
| retrotransposon_23 | 4929 | LTR zeta: 2990..3497 | | complete sequence present in public domain, identity 100% |
| retrotransposon_24 | 4954 | LTR zeta: 256..763 | | complete sequence present in public domain, identity 100% |
| retrotransposon_25 | 1047 | LTR zeta: 314..822 | | complete sequence present in public domain, identity 100% |
| retrotransposon_26 | 7929 | LTR zeta: 3346..3853 | | partial sequence present in public domain |
| retrotransposon_27 | 2292 | LTR zeta: 1327..1834 | | partial sequence present in public domain |
| retrotransposon_28 | 2025 | LTR zeta: <794..1294 | | partial sequence present in public domain |
| retrotransposon_29 | 2731 | LTR zeta: 380..887 | | complete sequence present in public domain, identity 100% |
| retrotransposon_30 | 2858 | LTR zeta: 814..1321 reverse transcriptase fragment (contains stop codon): 635..>537 | | partial sequence present in public domain |
| retrotransposon_31 | 1636 | LTR zeta: <595..1098 | | partial sequence present in public domain |
| retrotransposon_32 | 2125 | LTR zeta: 1105..1612 | | partial sequence present in public domain |

AF074943 (381 bp) *Candida albicans* retrotransposon long terminal repeat san, complete sequence

| | | | | |
|---|---|---|---|---|
| retrotransposon_33 | 1292 | LTR san: 369..749, CTA2 (transcription factor): join(974..>234,<888..1292) | | partial sequence present in public domain |
| retrotransposon_34 | 568 | LTR san: 113..493 | | partial sequence present in public domain |
| retrotransposon_35 | 946 | LTR san: 113..493, CTA2 (transcription factor) C-terminus: <632..946 | | complete sequence present in public domain, identity 100% |
| retrotransposon_36 | 951 | POL protein: <1..321, LTR san: 389..769 | contains also POL | partial sequence present in public domain |
| retrotransposon_37 | 9850 | GAG protein: 939..1853; POL protein fragment 1: 1896..2360; POL protein fragment 2: 2509..4893; POL protein fragment 3 (reverse transcriptase): 4953..5723 | contains also GAG/POL | complete sequence present in public domain, identity 100% |
| retrotransposon_38 | 3159 | LTR san: 2638..3019 | | complete sequence present in public domain, identity 99% |

AF078809 (1470 bp) *Candida albicans* Tca4 retrotransposon reverse transcriptase (pol) gene, partial cds

| | | | | |
|---|---|---|---|---|
| retrotransposon_36 | | (see above) | | |
| retrotransposon_37 | | (see above) | | |

FIG. 73A
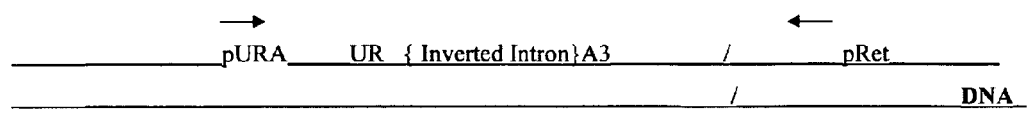
Initial DNA construct.
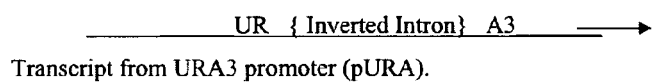
Transcript from URA3 promoter (pURA).
FIG. 73B
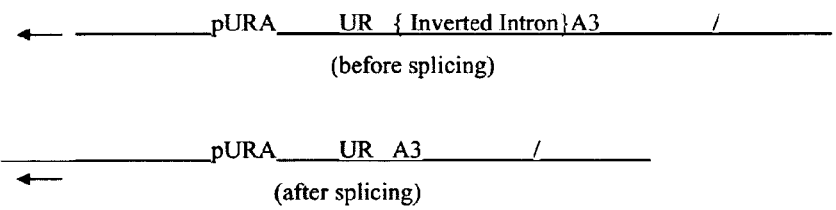
FIG. 73C
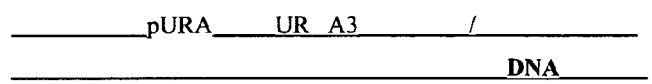
Integrated spliced construct.

URA3 gene with forward Intron

Initial Transcript

Spliced transcript

URA3 gene with Inverted Intron

Initial Transcript (cannot be spliced)

Integrated into genome following retrotransposition

UNUSUAL RETROTRANSPOSON FROM THE YEAST *CANDIDA ALBICANS*

RELATED APPLICATIONS

Reference is made to U.S. application Ser. No. 60/106,342, filed Oct. 30, 1998. U.S. application Ser. No. 60/106,342 and all documents cited therein ("U.S. Ser. No. 60/106,342 cited documents") and all documents referenced or cited in U.S. Ser. No. 60/106,342 cited documents are hereby incorporated herein by reference. In addition all documents cited herein ("herein cited documents") and all documents cited or referenced in herein cited documents are likewise incorporated herein by reference.

FIELD OF INVENTION

The invention relates to a novel retrotransposon. The novel retrotransposon is from the yeast *Candida albicans*. In particular, the invention relates to a retrotransposon pCal which belongs to the Ty1/copia group.

INTRODUCTION

*Candida albicans* is an asexual yeast species which is the major fungal pathogen of humans. Although it is commonly found as a harmless commensal organism, inhabiting mucosal membranes and the digestive tract, it can cause superficial infections, such as oral thrush, in otherwise healthy people and can cause severe, often fatal, systemic infections in immuno-compromised patients. The recent increased use of immunosuppressive treatments and the increased incidence of immunosuppressive diseases, such as HIV infections, have meant that *C. albicans* infections are of increasing medical significance (Odds 1988). There is significant strain variation within this species, potentially affecting virulence, and mobile retroelements have been suggested as one source of this.

Retroelements are a widespread family of sequences that can replicate via the reverse transcription of single-stranded RNA into double-stranded DNA, or are assumed to have arisen in this way. Two major types of retroelement are the retroviruses, such as HIV1 and Moloney murine leukaemia virus, and the retrotransposons such as Ty1 and Ty3 from *Saccharomyces cerevisiae* (Boeke and Sandmeyer 1991). The structures and lifecycles of retrotransposons and retroviruses are very similar. The major difference between the two groups is that the retroviruses can form infectious virus particles which can be transmitted between cells and between individuals. Retrotransposons can form intracellular virus-like particles (VLPs) but they lack the genes coding for the viral envelope so the VLPs are usually confined to the one cell.

Similarly to retroviruses, retrotransposons consist of an internal domain flanked by long terminal direct repeats (LTRs). In Ty1, for example, the LTRs are about 335 bp in length and the internal domain is about 5.3 kb long. The internal region has two long open reading frames (ORFs) homologous to the gag and pol ORFs of retroviruses. The gag gene encodes the structural proteins which make up the VLP while, downstream, the pol gene encodes the enzymes required for reverse transcription and integration—protease, integrase, reverse transcriptase and RNase H. The LTRs contain the promoter and the transcription termination signals and are functionally divided into three regions—$U_3$, R and $U_5$. Transcription proceeds from the $U_3$/R boundary in the left LTR to the R/$U_5$ boundary in the right LTR to produce an RNA molecule which has the R region repeated at each end. Translation of this terminally redundant mRNA is usually regulated to ensure that the structural proteins of the VLP (gag) are produced in much higher quantities than the enzymes (pol). This is because large quantities of the gag proteins are required for the assembly of the VLP but only catalytic quantities of the pol enzymes are required.

The most common method of down-regulating the translation of the pol ORF is to have it out of frame relative to the upstream gag ORF. A rare, programmed ribosomal frameshift is thus required for translation of the pol ORF. A number of retrotransposons employ a +1 frameshift. Ty1 achieves this by tRNA slippage while the Ty3 mechanism involves the 'skipping' of a base. The Ty1-slippage mechanism involves a seven base sequence, CUU AGG C. It is thought that a tRNA$^{LeuUAG}$, which can recognise all six leucine codons, slips forward one base from CUU-Leu to UUA-Leu, during a translational pause caused by a rare tRNA$^{ArgCCU}$(2). The Ty3 +1 frameshift also involves a seven base sequence, GCG AGU U. An alanine-valine sequence (encoded by GCG-GUU) is produced but tRNA slippage is not involved. It is thought that out-of-frame aminoacyl-tRNA binding or four-base decoding is responsible. Frameshifting is stimulated by the low availability of the tRNA decoding the AGU-Ser codon and also by the 12 nucleotides downstream of the AGU codon. Retrotransposons have also been found to use a −1 frameshift; an example is CfT-I of *Cladosporium fulvum*. Here the ribosome is thought to slip back one base on the sequence AAAA slightly upstream of the gag termination codon.

An alternative method of down-regulation has been found in the copia retrotransposon. Here the gag and pol ORFs are fused into one long continuous ORF, but a splicing reaction usually occurs prior to translation to excise most of the pol region from the mRNA. Only occasionally is a full-length RNA translated with the concomitant production of the pol enzymes.

Following translation the retrotransposon proteins and RNA can form into a VLP. This consists of a shell of gag proteins with the pol enzymes and genomic RNA packaged inside. The VLP is the site of reverse transcription. In general, the process of reverse transcription in retrotransposons is very similar to the well-characterised process of retroviral reverse transcription. Two important steps in the reverse transcription process are the priming of minus- and of plus-strand DNA synthesis. Minus-strand synthesis is most commonly primed by a cytoplasmic tRNA (often initiator methionine tRNA) which is packaged within the VLP along with the mRNA of the retrotransposon. The retrotransposon has a region adjacent to the left LTR, known as the minus-strand primer binding site [(−)PBS], which is complementary to the 3' end of this tRNA. The tRNA binds to the retrotransposon RNA at the (−)PBS and can then be used by reverse transcriptase as a primer for the synthesis of minus-strand DNA. Plus-strand synthesis is primed by a short purine-rich sequence, known as a polypurine tract (PPT), located just upstream of the right LTR. After minus-strand DNA synthesis has passed this sequence the RNA is nicked between the PPT and the LTR. The PPT RNA can then be used as a primer for the synthesis of the plus-strand. Reverse transcription is generally very inefficient; greater than 10% of cellular mRNA can be retrotransposon RNA yet the dsDNA form is not usually detectable by Southern blotting.

Following the synthesis of the dsDNA form of the retrotransposon it may integrate at a new site within the host genome. This process is likely to involve a complex of the integrase enzyme associated with the two ends of the retrotransposon DNA. In a process which is not well understood the integrase complex must be released from the VLP, move into the nucleus and then insert the DNA into a new genomic site. Studies with Ty1 and Ty3 have shown that the integration site-selection mechanisms of these retrotransposons are non-random and appear to be specifically adapted to avoid causing disruption to the host genome.

Retrotransposons can be divided into three major groups based on their reverse transcriptase sequences and the order of the genes within their pol ORFs. Members of the Ty3/gypsy group are the most closely related to the retroviruses and share a similar pol gene order—protease, reverse transcriptase, RNase H and integrase. Examples of these elements are Ty3 of *S. cerevisiae*, gypsy of *Drosophila melanogaster*, Tf1 of *Schizosaccharomyces pombe* and del of *Lilium henryi*. Members of the Pao group, for example Pao of *Bombyx mori* and Tas of *Ascaris lumbricoides*, have a similar pol gene order to Ty3/gypsy retrotransposons but can be distinguished from them by their reverse transcriptase sequence. Ty1/copia elements are most easily distinguished from Ty3/gypsy and Pao retrotransposons and retroviruses by the gene order of the pol protein-protease, integrase, reverse transcriptase, RNase H. This group includes Ty1 and Ty2 of *S. cerevisiae*, copia and 1731 of *D. melanogaster*, Tst1 of *Solanum tuberosum* and Tnt1 of *Nicotiana tabacum*.

The first *Candida* retroelement, TCa 1, was identified through the discovery of multiple-copy isolated LTRs dispersed around the genome (1). These LTRs were discovered in an analysis of moderate repeat elements. Subsequently, composite elements, named TCa1, consisting of two LTRs flanking a 5.5 kb internal domain were also found. In the *C. albicans* strains tested, one to two TCa1 loci were found, indicating between one and four copies of TCa1 depending on whether the loci were homozygous or not. TCa1 has many features of a typical retrotransposon including 388 bp LTRs, beginning TG and ending CA, with six nucleotide inverted repeats, TGTTCGAACA (SEQ ID NO. 1) at either end. The element is flanked by 5 bp duplications of the host DNA and is transcribed to give an approximately unit length mRNA. Within the 5.5 kb internal domain a (−)PBS and a plus-strand priming site are evident. The (−)PBS was not immediately obvious: no complementarily to tRNA$^{iMet}$(as used by Ty1 and Ty3) could be found. Bases 31 to 39 of tRNA$^{Arg}$ of *S. cerevisiae*, however, perfectly complemented the nine bases immediately adjacent to the left LTR (GATTAGAAG). There is, for some tRNA, a high degree of conservation between S. cerevisiae and *C. albicans* leading to the suggestion that a cleavage product of a *C. albicans* tRNA$^{Arg}$ might serve as the primer. This suggestion is supported by the knowledge that the primer used by the copia retrotransposon is a cleavage product of tRNA$^{iMet}$ containing only the first 39 nucleotides.

TCa1 has been shown to be transcriptionally active, but an analysis of 1200 bp of its internal sequence has indicated that it is defective, there being multiple stop codons in all three reading frames. It is remarkable, given the clearly non-functional nature of this element, that the LTRs remain identical and that the plus- and minus-strand priming sites remain in apparently functional form. It is possible that the defective TCa1 retrotransposon has been maintained via the passive reverse transcription of its RNA by the products of a functional *C. albicans* retrotransposon. This passive replication would require that the element has identical LTRs and functional plus- and minus-strand priming sites but would be independent of the element's internal sequence.

The object of the invention is to provide a novel retrotransposon, in particular the isolation and sequencing of pCal, an unusual, novel Ty1/copia retrotransposon from *C. albicans*. The free, linear, double-stranded DNA form of this element is so highly expressed that it can be seen as a distinct band when uncut genomic *C. albicans* DNA is simply analysed on an agarose gel. It contains features conserved in TCa1 and other retrotransposons and has additional features previously unreported in the retrotransposon family.

The sequence of another *C. albicans* element, potentially retrotransposon-like in nature, has recently been submitted to the databases by a group in the U.K. (accession no. Y08494). This element has been named beta and is defined as an LTR. It consists of a repeated sequence about 400 bp in length, flanked by 5 bp direct repeats of the host DNA, and associated with tRNA genes. The borders of the element consist of short, imperfect, inverted repeats: 5'-TAATGTA-TANTATACAACA (SEQ ID NO. 2). Such an element is reminiscent of the isolated LTRs of other retrotransposons which are the result of homologous recombination between the ends of a retrotransposon with the concomitant deletion of the internal region. No significant similarity is detectable between the beta sequence and the LTRs of TCa1 or pCal of the present invention.

SUMMARY OF THE INVENTION

The invention provides an isolated and purified retrotransposon having a copy number of between 40–150 (preferably 50–100) copies of free DNA of itself per genome (preferably 10–25 megabases, more preferably substantially 15 megabases). The DNA is preferably linear and is more preferably double stranded.

The retrotransposon may be isolated from fungi or yeast, preferably *Candida* and more preferably from *Candida albicans*.

The invention also provides a novel retrotransposon comprising at least one polypeptide positioned between at least two long terminal repeats, and wherein the retrotransposon is capable of integrating into the DNA in a genome providing a copy number of between 40–150 copies per genome. The copy number is preferably 50–100 copies.

The retrotransposon does not necessarily integrate into the DNA.

The retrotransposon preferably belongs to the Ty1/copia group.

The retrotransposon is preferably isolated from fungi or yeast, preferably *Candida* and more preferably from *Candida albicans*.

The retrotransposon designated pCAL includes two long terminal repeats (LTR's) flanking an internal domain comprising at least two open reading frames. Advantageously, the LTR regions as identified in the sequence illustrated in FIG. 2B (SEQ ID NOS. 3–5) may be used to introduce DNA into the genome of a cell.

Accordingly, there is also provided by the present invention a method of introducing DNA into the genome of a cell which method comprises introducing a transposable element comprising a nucleotide sequence encoding a desired protein located between two long terminal repeats sequences having the sequences illustrated in FIG. 2B, which element is such that it can insert into the genome of said cell in the presence of an appropriate integration factor. Preferably, said integration factor comprises an integrase which preferably is itself included in said transposable element and which integrase is derived from the POL region of said pCAL retrotransposon.

The transposable element for introducing a desired DNA sequence into the genome of the cell also forms part of the present invention. This transposable element comprises an internal domain for receiving a nucleotide sequence encoding a desired protein flanked by two long terminal repeat regions having the sequences identified in FIG. 2B. The transposable element may advantageously also be included in a DNA transfer system comprising said transposable element, which is capable of integrating into the genome of said cell in the presence of an appropriate integration factor and, said integration factor. In a preferred embodiment, the transposable element comprises an open reading frame encoding said integration factor which is an integrase protein, which preferably is encoded by nucleotide sequence within the POL region of the retrotransposon of FIG. 2B.

The invention provides an isolated and purified retrotransposon comprising a nucleotide sequence selected from the group comprising:
  (a) The sequence illustrated in FIG. 2B;
  (b) A nucleotide sequence with at least 65% similarity with the LTR and POL region of FIG. 2B;
  (c) A nucleotide sequence that hybridizes under conditions of standard stringency to the nucleotide sequence shown in FIG. 2B; and
  (d) A functional fragment of (a), (b) or (c).

The retrotransposon is preferably pCal.

The invention also provides the integrated form of the retrotransposon of the retrotransposon pCal, which has been designated TCa2 or sequences capable of hybridising thereto under standard hybridisation conditions.

The invention also provides an expression vector including any of the aforementioned retrotransposons or fragments thereof. The expression vector may be used to transform the cell into which the DNA is to be introduced. The expression vector may be introduced by any suitable means such as micro injection or electroporation or the like. The discovered promoter of RNA transcription is temperature regulated such that comparatively high levels of transcription occur at up to 37° C. Thus, levels of transcription may be regulated as required by altering the temperature.

The invention also provides the use of any of the aforementioned retrotransposons in a gene disruption system and in a gene discovery system. Upon active retrotransposition the retrotransposon can integrate into new sites in the fungi/yeast (preferably *Candida*) genome causing gene disruption which is preferably non-revertible. The retrotransposon can be 'tagged' with a selectable marker gene carrying its own promoter. This disruption system permits discovery (isolation and characterisation) of the disrupted gene.

The invention also provides a retroviral-like carrier system comprising any of the aforementioned retrotransposons, preferably pCal. The invention gives rise to virus-like particles in the yeast which can be modified to contain novel proteins such as enzymes.

The invention also provides a transformation and expression system for fungi/yeast (preferably *Candida*) comprising any of the aforementioned retrotransposons. The discovered promoter functions in a variety of yeasts including *Saccharomyces cerevisiae* and *Candida maltosa* and *Candida albicans*.

The invention also provides nucleic acid encoding a retrotransposon having a copy number of between 40–150 (preferably 50–100) copies per cell. The invention also provides the nucleic acid vector. The vector may be a gene expression vector. The vector may be a plasmid.

The invention also provides cells containing the nucleic acid including transposable elements and retrotransposons according to the invention. The cells may be contacted with a desired compound to identify its effect on the phenotype of the cell conferred by expression of the protein encoded by the nucleotide sequence provided in the transposable element.

The invention also provides the linear or circular, double stranded DNA copy of the retrotransposon.

Also provided by the present invention is a method of assigning a function to a nucleotide sequence which method comprise providing said sequence between the long terminal repeat sequences of the transposable element according to claim 1, 5 or 12 and introducing it into said cell and monitoring for the presence of an altered phenotype of said cell compared to a cell which has not had said nucleotide sequence introduced therein.

The invention also provides a nucleic acid fragment selected from the group comprising:
  a) a nucleic acid sequence positioned between at least two long terminal repeats of the sequence of PCal as described in GenBank accession number AF007776;
  b) a nucleic acid sequence with at least 65% similarity with the LTR and POL region of the sequence of (a);
  c) a nucleic acid sequence that hybridizes under conditions of standard stringency to the nucleotide sequence of (a); and
  d) a functional fragment of (a), (b) or (c).

The nucleic acid sequence preferably comprises a functional POL gene.

More preferably the nucleic acid sequence comprises two long terminal direct repeats flanking a series of genes in the order gag (group antigen), pol (polyprotein) where the pol sequence comprises an aspartic protease, an integrase and a reverse transcriptase/RNAseH, particularly as seen in FIG. 2B.

The invention also comprises a functional (preferably temperature) inducible promoter isolated from a retrotransposon according to the invention. The promoter is preferably temperature inducible.

The invention also provides novel retrotransposons isolated from fungi/yeast, preferably *Candida*. In particular the invention provides retrotransposons 1–28 and more particularly retrotransposon 15.

The invention provides the use of the SEQ ID NOS: 6–37 probes and also provides use of the SEQ ID NOS. 6–37 in any of the gene disruption systems, gene discovery systems, retroviral-like carrier systems, transformation and expression systems above.

The invention also provides the use of the SEQ ID NOS: 6–37 in an expression vector as above.

The invention provides amino acid sequence equivalents to the nucleic acid sequences herein described.

Furthermore, the invention comprehends uses of the retrotransposons, the nucleic acid, e.g., DNA, RNA and amino acids of the invention, such as methods employing and/or compositions containing and/or comprising one or more a retrotransposon, nucleic acid, e.g., DNA, RNA and/or amino acid of the invention, including, for instance, wherein the retrotransposon is a vector containing and/or expressing an exogenous nucleic acid molecule.

BRIEF DESCRIPTION OF THE DRAWINGS

Embodiments of the invention are now described, by way of example only, with reference to the drawings, in which:

FIG. 4 shows the conserved motifs in the pol ORF of pCal compared to those of other Ty1/copia retrotransposons (SEQ ID NOS: 43–65) Absolutely conserved amino acids are indicated by an asterisk (*). Positions containing 4 or 5 identical amino acids or in which there are only two types of amino acids present are indicated by a caret (^). The numbers in brackets indicate the positions of the motifs from the start of the gag/pol fusion proteins.

FIG. 9 shows the comparison of the 5' regions of TCa2 retrotransposons from the various strains. The first ~400 bp of TCa2 retrotransposons from each of the seven strains, except hOG1042, were amplified by PCR and cloned into a plasmid vector. The inserts of two clones from each strain were then sequenced and the sequences are compared above. The clones are labelled according to the strain they were derived from, for example, the first clone from ATCC10261 is ATC-1, the second clone from SC5314 is SC5-2 etc. Also shown are the sequences of p30 and p36, two of the original clones of pCal from hOG1042. The 5' half of the published pCal sequence was derived from p36. The sequences of the clones are listed in order corresponding to the amount of TCa2 RNA produced by the host strain, i.e. SGY269, (SEQ ID NO: 68–82) produces the least and hOG1042 the most. The 6 bp inverted repeats at the ends of the LTRs are overlined.

High molecular weight chromosomal DNA from each of the strains was purified away from the extrachromosomal copies of pCal as described in Materials and methods and then subjected to Southern analysis using the pCal internal probe. The DNA was digested with PstI (lanes 1 and 2), EcoRI (lanes 3 and 4) or ClaI (lanes 5 and 6). Lanes 1, 3, and 5, hOG759; lanes 2, 4, 6, hOG1042. Sizes in kb are indicated to the left.

Figure 13:
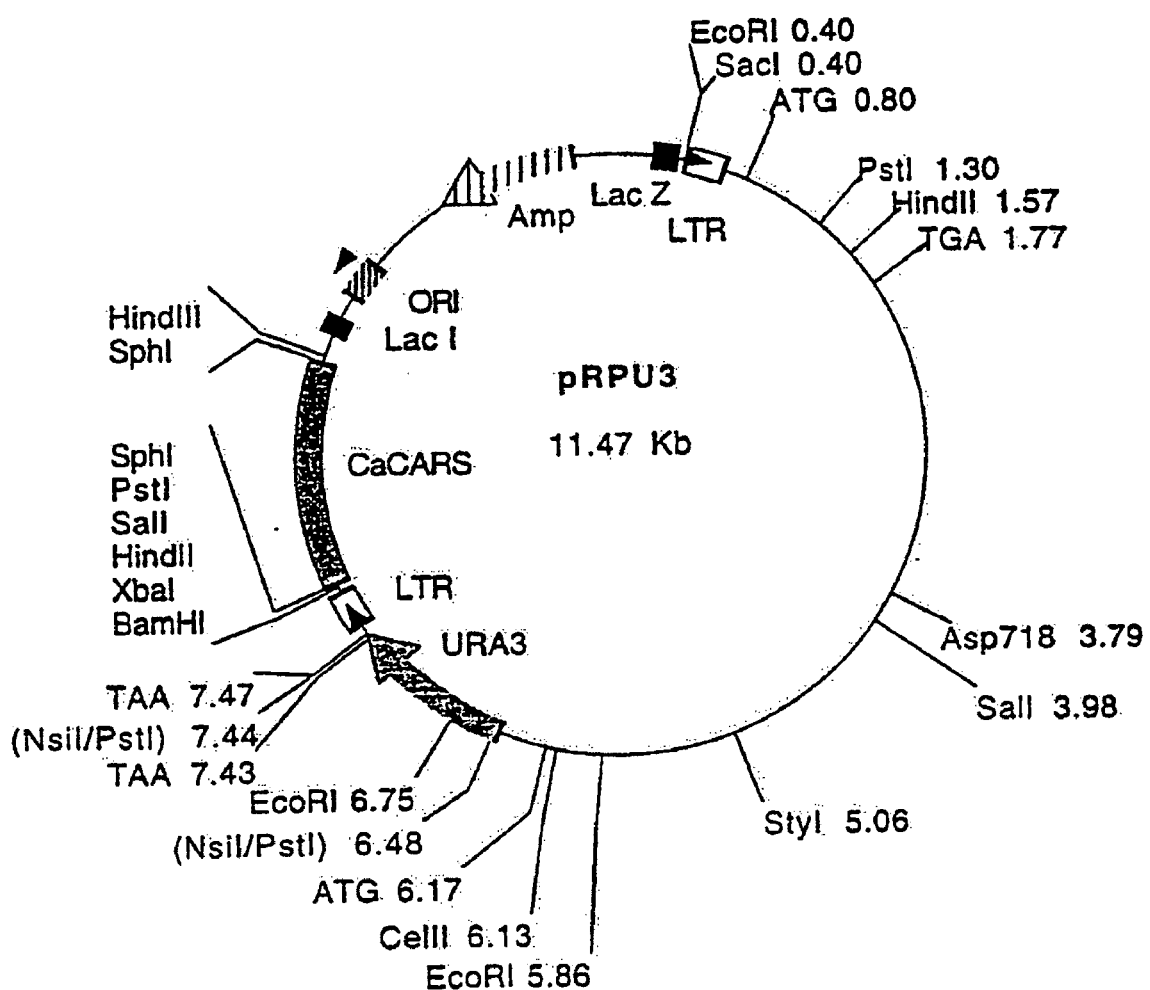

FIG. 13 shows the plasmid pRPU3. The CaARS from pCARS (originally the SphI fragment from pRC2312) was ligated in as a HindIII/BamHI fragment into pRPU2.

Figure 14:
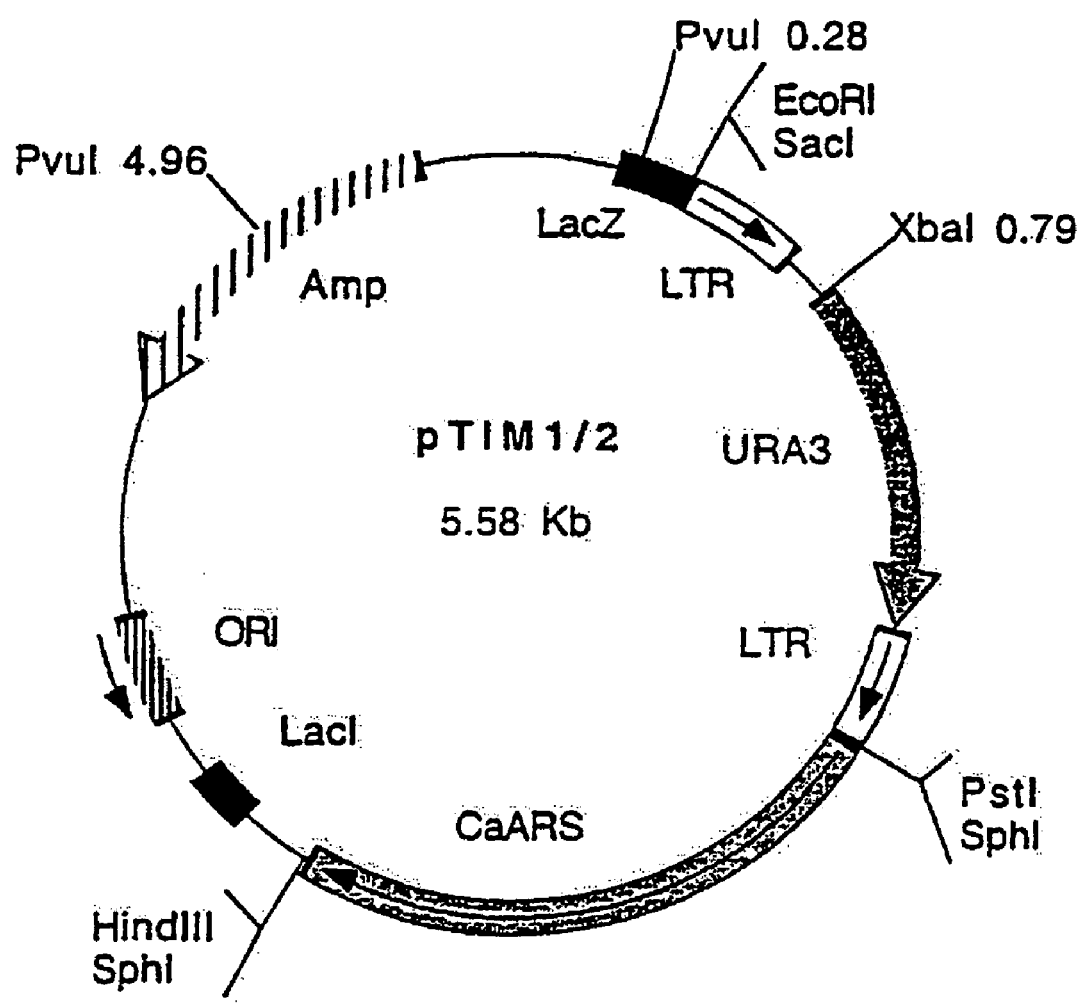

FIG. 14 shows the plasmid pTIM1/2. Using CAL1 and CAL2 primers on p36 template the SacI/XbaI products were cloned into p36K (creating p36Kf1) and then into pUXLC (creating pTIM1/p36flUXLC) and pUXILC (creating pTIM2/p36flUX1LC).

Figure 15:
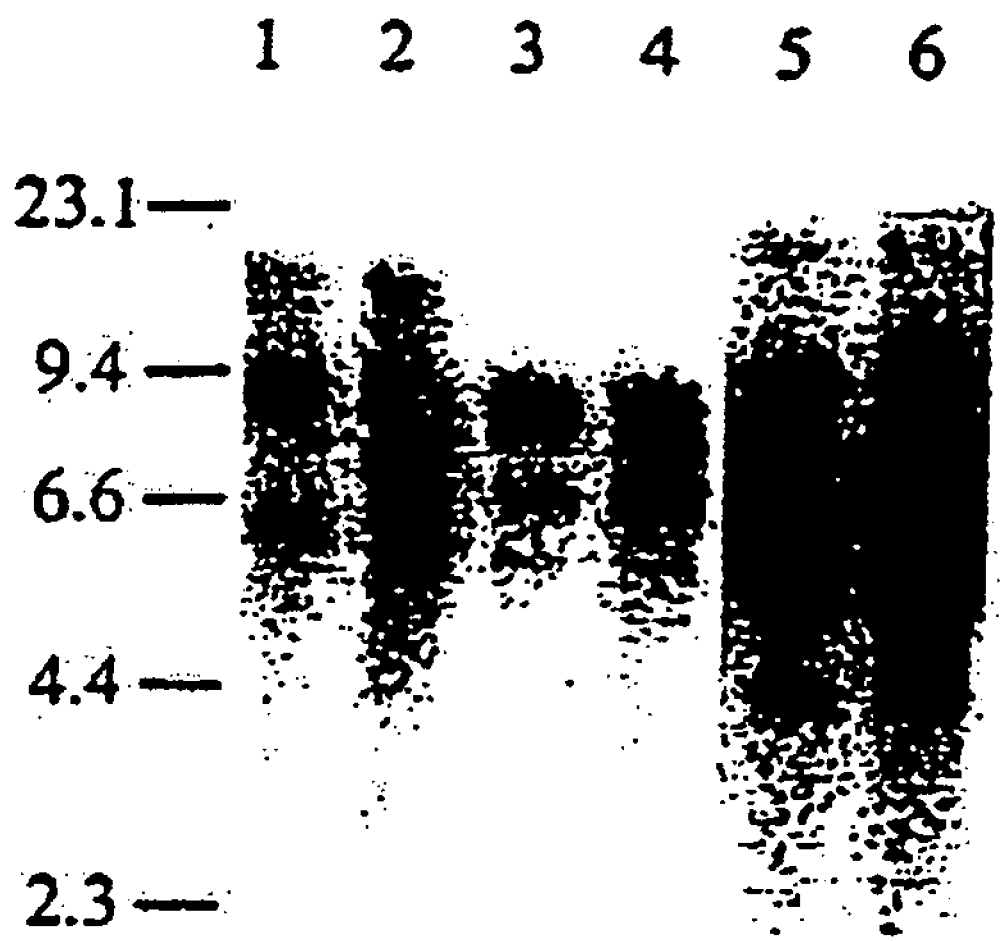

FIG. 15 shows a Southern analysis of the TCa2 probe;
Lane 1 hOG759 Pst1 cut TCa2 probe
Lane 2 hOG1042 Pst1 cut TCa2 probe
Lane 3 hOG759 EcoR1 cut TCa2 probe
Lane 4 hOG1042 EcoR1 cut TCa2 probe
Lane 5 hOG759 Cla1 cut TCa2 probe
Lane 6 hOG1042 Cla1 cut TCa2 probe.

Figure 16:

FIG. 16 shows the generation of additional bands hybridising to TCa2 after culture. hOG1042 was grown for approximately 30 days in rich medium at 37° C. by continually transferring cells between flasks. Nine independent colonies were isolated from the final passage. Genomic DNA was isolated from each of these colonies, and also from hOG1042 and hOG762 (a precursor of hOG1042). EcoRI-digested samples of DNA from each strain were then subjected to Southern blotting using as a probe a 2 kb fragment of TCa2 corresponding to the reverse transcriptase coding sequence. The results are shown in the figure. Lanes: 1, hOG762; 2, hOG1042, 3 to 11, 9 independent strains derived from hOG1042 after growth for approximately 30 days at 37° C. In several of the strains which had been subjected to passage at 37° TCa2 hybridised to more bands than in the parent hOG1042, for instance additional high molecular weight bands can be seen in lanes 4, 6 and 11. Additional bands of various sizes were also visible in these and other strains when the DNA was digested with other enzymes (not shown). Gain of bands was never found to be associated with the loss of any of the original bands, suggesting that the new bands represent additional copies of TCa2.

FIG. 17 shows the nucleic acid sequence of retrotransposon 1 of 1309 base pairs (SEQ ID NO: 6).

FIG. 18 shows the nucleic acid sequence of retrotransposon 2 (SEQ ID NO: 7).

FIG. 19 shows the nucleic acid sequence of retrotransposon 3 (SEQ ID NO: 8).

FIG. 20 shows the nucleic acid sequence of retrotransposon 4 (SEQ ID NO: 9).

FIG. 21 shows the nucleic acid sequence of retrotransposon 5 (SEQ ID NO: 10).

FIG. 22 shows the nucleic acid sequence of retrotransposon 6 (SEQ ID NO: 11).

FIG. 23 shows the nucleic acid sequence of retrotransposon 7 (SEQ ID NO: 12).

FIG. 24 shows the nucleic acid sequence of retrotransposon 8 (SEQ ID NO: 13)

FIG. 25 shows the amino acid sequence of the pol protein of retrotransposon 8 (SEQ ID NO: 14)

FIG. 26 shows the nucleic acid sequence of retrotransposon 9 (SEQ ID NO: 15). This has TCa2-like LTR.

FIG. 27 shows the nucleic acid sequence of retrotransposon 10 (SEQ ID NO: 16) This has a TCa2-like LTR.

FIG. 28 shows the nucleic acid sequence of retrotransposon 11 (SEQ ID NO: 17). This also has a TCa2-like LTR.

FIG. 29 shows the DNA sequence of retrotransposon 12 (SEQ ID NO: 18). This also has a TCa2-like LTR.

FIG. 30 is the nucleic acid sequence of retrotransposon 13 (SEQ ID NO: 19). This also has a TCa2like LTR.

FIG. 31 shows the nucleic acid sequence of retrotransposon 14 (SEQ ID NO: 20). The pol protein is from nucleic acids 1169–1839.

FIG. 32 shows the nucleic acid sequence of retrotransposon 15 (SEQ ID NO: 21). The pol protein is from 1555–4302 base pairs. The LTR regions are from 979–1292 and 5212–5525 base pairs.

FIG. 33 shows the amino acid sequence of retrotransposon 15 (SEQ ID NO: 22). The pol protein is from 916 amino acids.

FIG. 34 shows the nucleic acid sequence of retrotransposon 16 (SEQ ID NO: 23). The pol protein is from 309–2332 base pairs.

FIG. 35 shows the amino acid sequence of retrotransposon 16 (SEQ ID NO: 24). The pol protein is 748 amino acids.

FIG. 36 shows the DNA sequence of retrotransposon 17 (SEQ ID NO: 25). The LTR zeta is from 887–1394 base pairs.

FIG. 37 shows the nuclei acid sequence of retrotransposon 18 (SEQ ID NO: 26). The LTR zeta is from 1418–1926 base pairs.

FIG. 38 shows the nucleic acid sequence of retrotransposon 19 (SEQ ID NO: 27). The LTR zeta is from 767–1274 base pairs.

FIG. 39 shows the nucleic acid sequence of retrotransposon 20 (SEQ ID NO: 28). The LTR zeta is from 3344–3851 base pairs.

FIG. 40 shows the nucleic acid sequence of retrotransposon 21 (SEQ ID NO: 29). The LTR zeta is from 812–1319 base pairs.

FIG. 41 shows the nucleic acid sequence of retrotransposon 22 (SEQ ID NO: 30) The LTR zeta is from 672–1179 base pairs.

FIG. 42 shows the nucleic acid sequence of retrotransposon 23 (SEQ ID NO: 31). The LTR zeta is from 467–974 base pairs.

FIG. 43 shows the nucleic acid sequence of retrotransposon 24 (SEQ ID NO: 32). The LTR zeta is from 787–1294 base pairs.

FIG. 44 shows the nucleic acid sequence of retrotransposon 25 (SEQ ID NO: 33).

FIG. 45 shows the nucleic acid sequence of retrotransposon 26 (SEQ ID NO: 34) The pol protein is from 2–322 base pairs. The LTR san is from 390–377 base pairs.

FIG. 46 shows the amino acid sequence of retrotransposon 26 (SEQ ID NO: 35). The pol protein of 106 amino acids.

FIG. 47 shows the nucleic acid sequence of retrotransposon 27 (SEQ ID NO: 36). The LTR san is from 143–523 base pairs.

FIG. 48 shows the nucleic acid sequence of retrotransposon 28 (SEQ ID NO: 37). The LTR san is from 558–939 base pairs.

Figure 49:
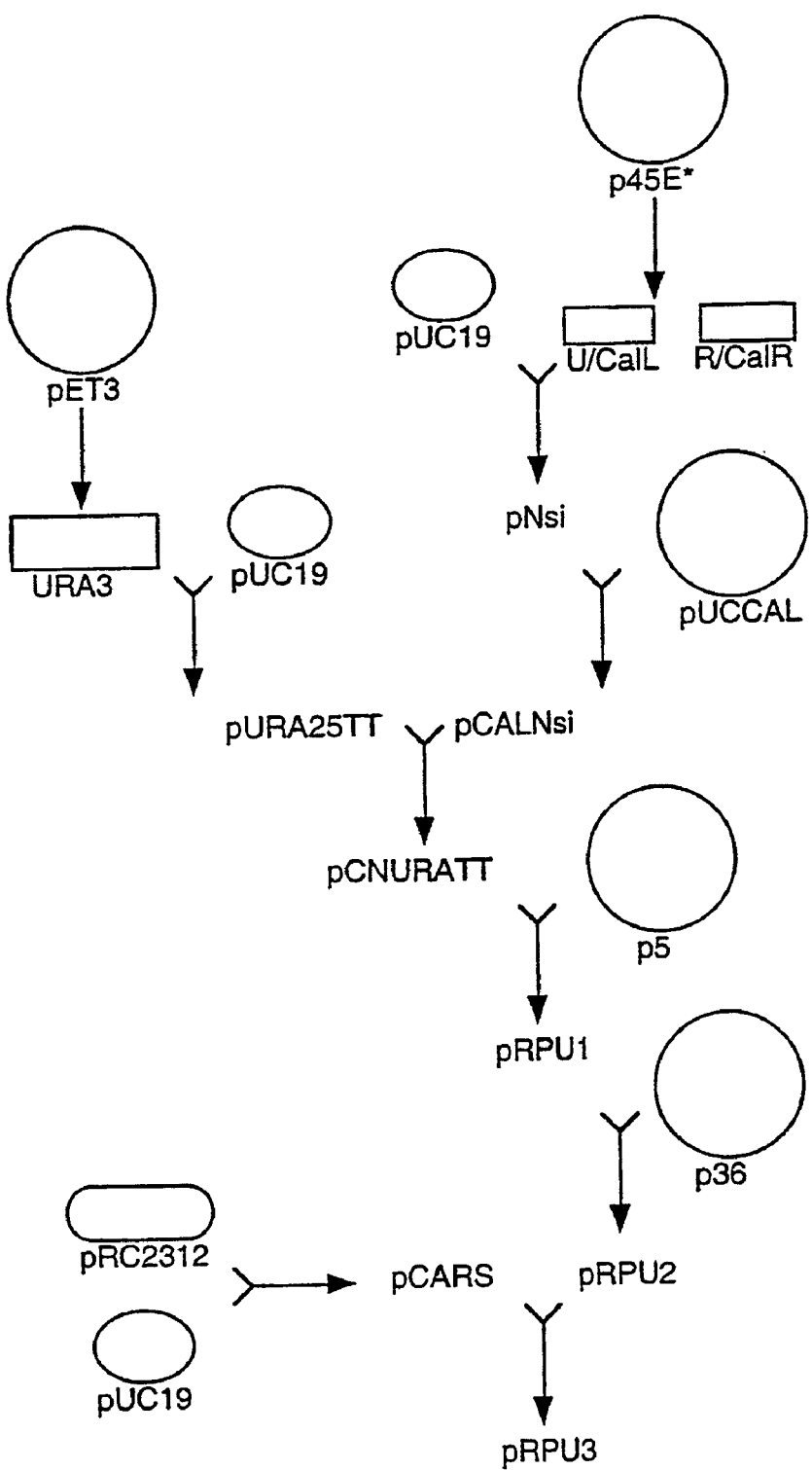

FIG. 49 shows the outline of the construction of the plasmid pRPU3. Plasmids from which DNA was derived from in this work are accompanied by a circle. The rectangular boxes indicate PCR products.

Figure 50:
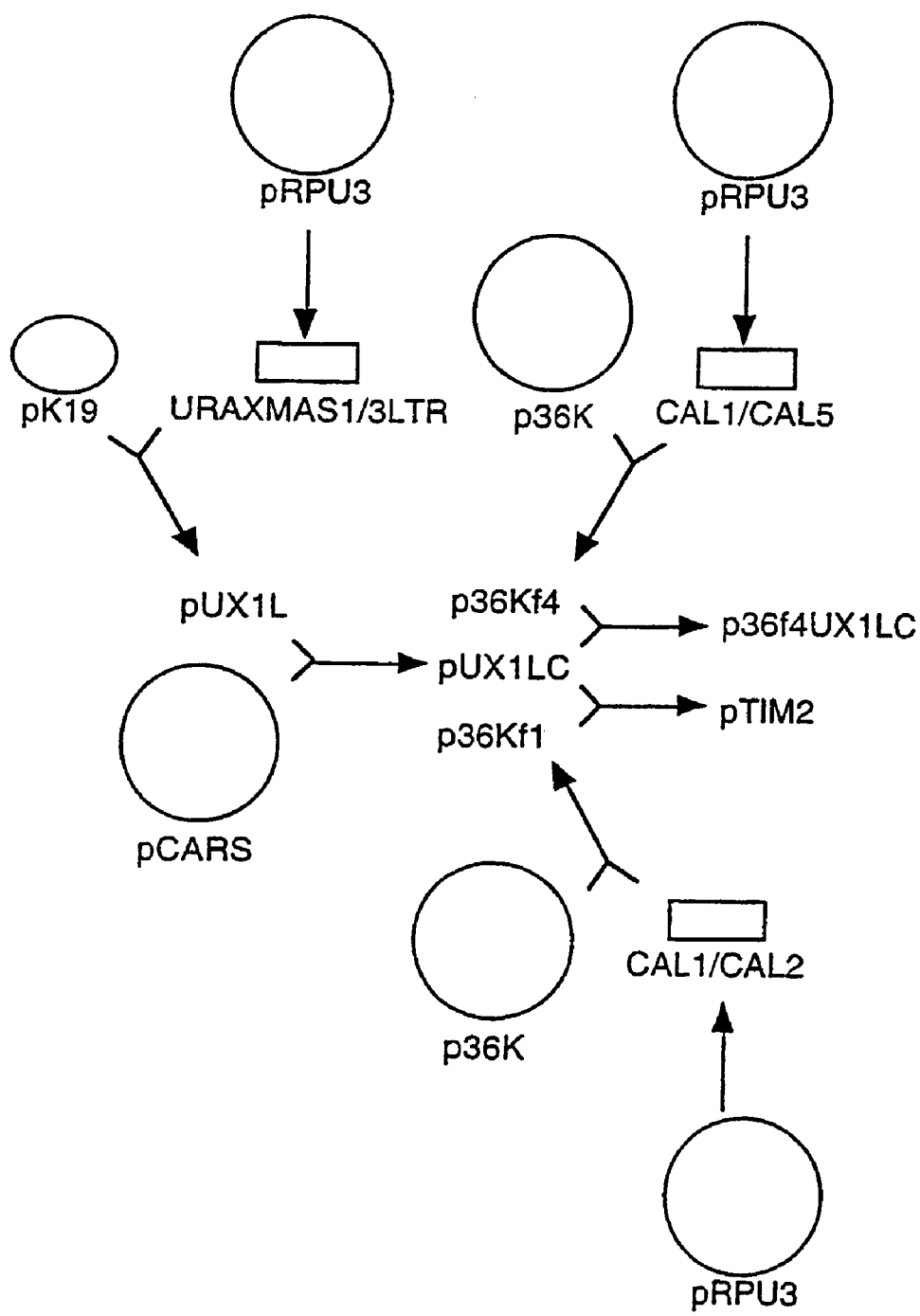

FIG. 50 shows the construction of pTIM2 and p36f4UX1LC. These plasmids contain a yeast autonomously replicating sequence (CARS) and the *C. albicans* URA3 gene. In both plasmids the URA3 gene uses the promoter in the left LTR and relies on the transcription termination signals in the right LTR. P36f4UX1LC also contains the gag ORF of pCAL as a fusion product with the URA3 gene. The rectangular boxes represent PCR products and the circles the original plasmids from which DNA was obtained.

Figure 51:
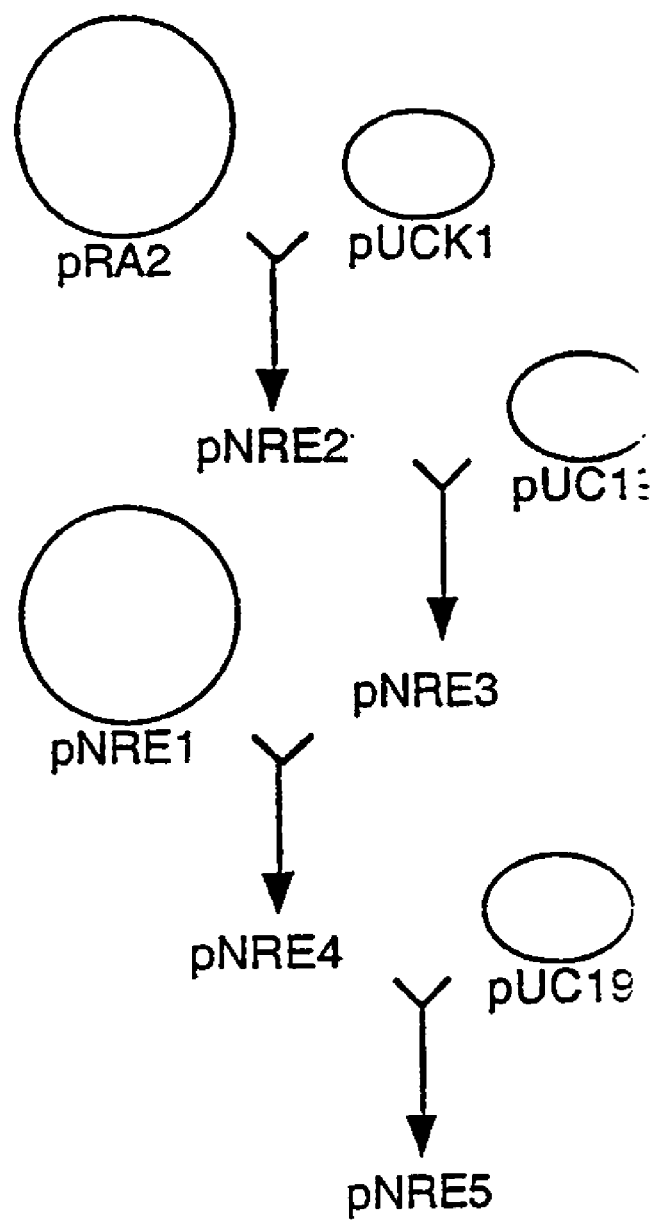

FIG. 51 shows the outline of the construction of the plasmid pNRE5 used in an in vivo construction in the *C. maltosa* strain CHAU1.

FIG. 52 shows the results of transformed colonies per µg DNA.

Figure 53:
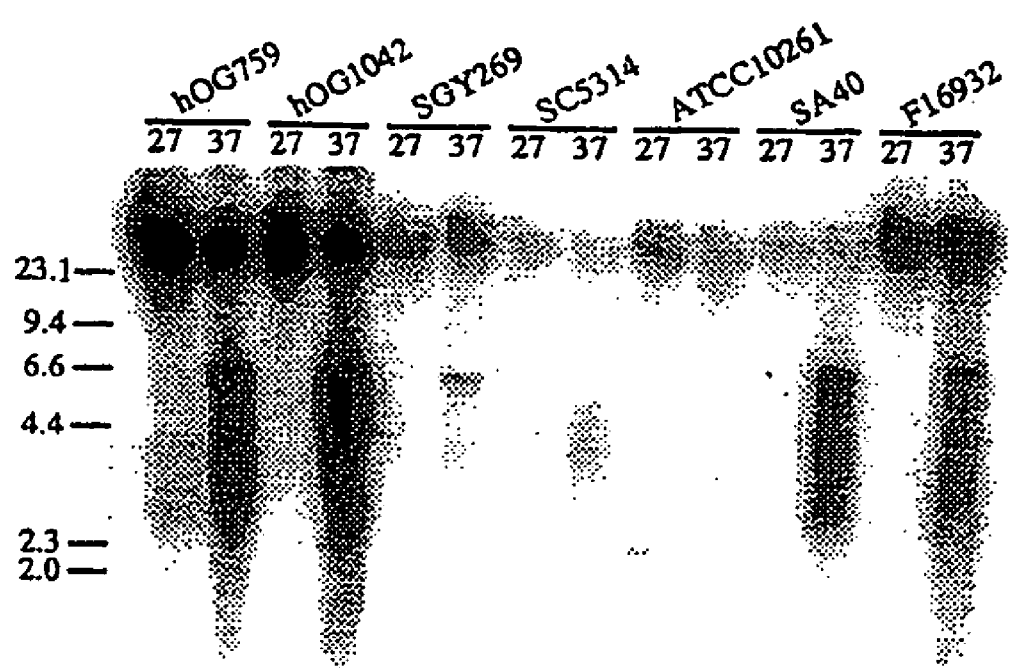

FIG. 53 shows the expression of pCal DNA occurs in a temperature- and strain-dependent manner. Cultures of the seven indicated *C. albicans* strains were grown at 27° C. and 37° C. to late log/early stationary phase following which total DNA was isolated. Approximately equal amounts of undigested DNA samples from each culture were then electrophoresed on an agarose gel and transferred to a nylon membrane. The membrane was then probed with an internal fragment of pCal. In the gel-blot shown above, the extra-chromosomal pCal forms appear as a band running at about 6.5 kb and a smear of shorter forms running between 3 and 6.5 kb. The integrated chromosomal copies of TCa2 appear as a band at >20 kb.

Figure 54:
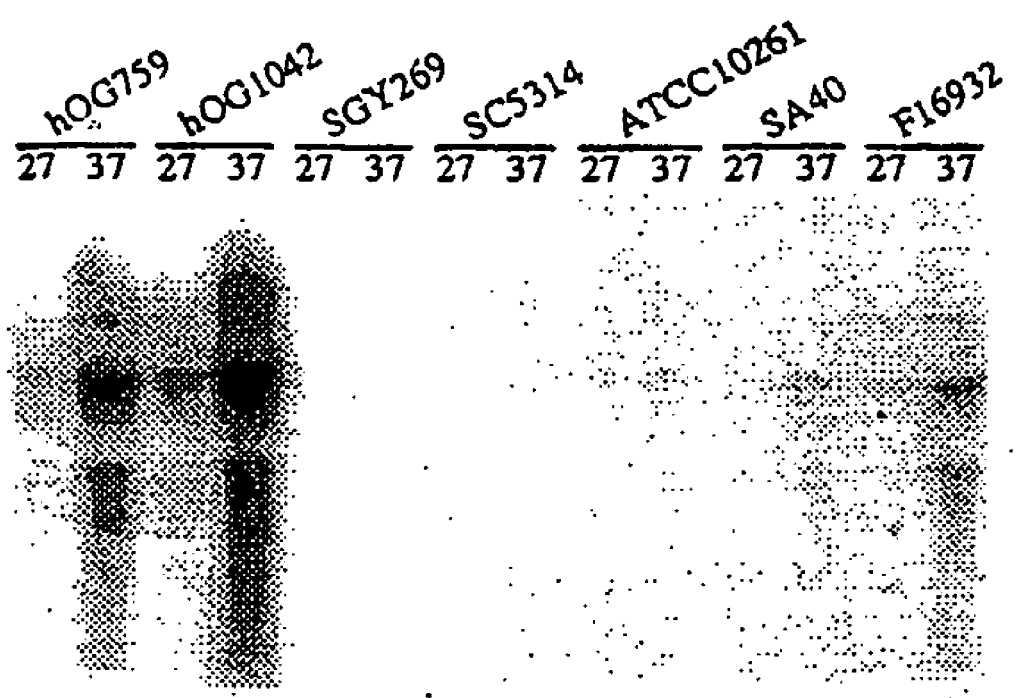

FIG. 54 shows TCa2 RNA expression occurs in a similar pattern to the expression of pCal DNA. Total RNA was isolated from cultures of the seven *C. albicans* strains, grown at 27° C. or 37° C., as for the DNA in FIG. 1. Approximately equal amounts of RNA from each culture were then separated on agarose gels, transferred to nylon membranes and probed with the pCal internal probe. With longer exposures, TCa2 RNA could be detected in all of the strains.

Figure 55:
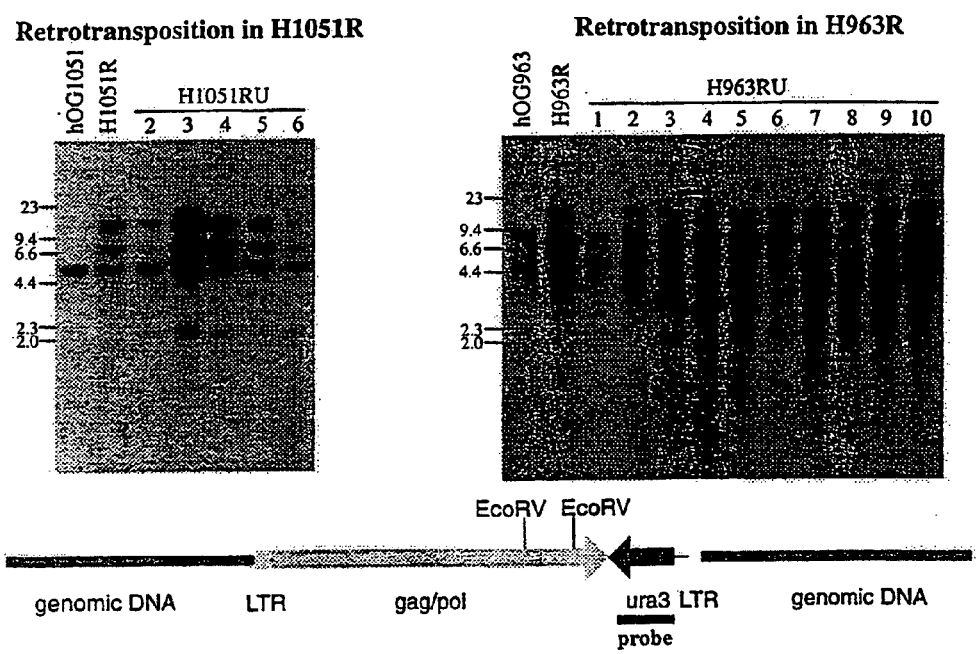

FIG. 55 is a Southern analysis of URA3* colonies derived from two *Candida* strains, hOG1051 and hOG963. Genomic DNA from URA3* colonies and their parental strains was digested with Eco RV and probed with the URA3* gene (shown in the schematic diagram).

Figure 56:
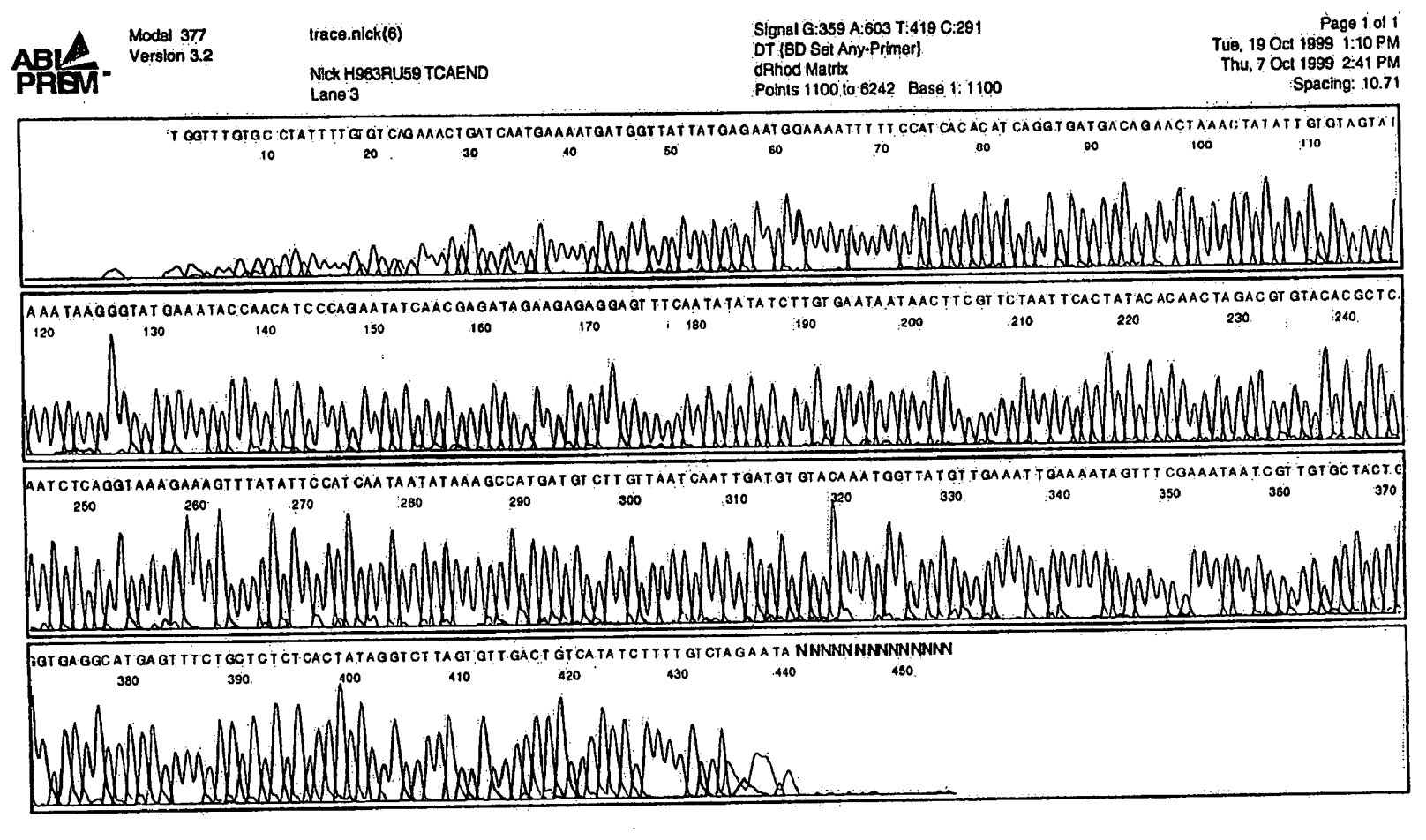

FIG. 56 shows ABI PRISM chromatogram H963RU59; that is, sequence surrounding a TCa2/URA3 element integrated into a new position in the *Candida* genome. Position 291 shows the start codon of an ORF corresponding to a probable membrane protein. Position 276 represents the insertion site of TCa2/URA3, within the ORF.

FIG. 57 is a summary of the integration sites of TCa2/URA3 and the sequences around the integration sites.

Figure 58:
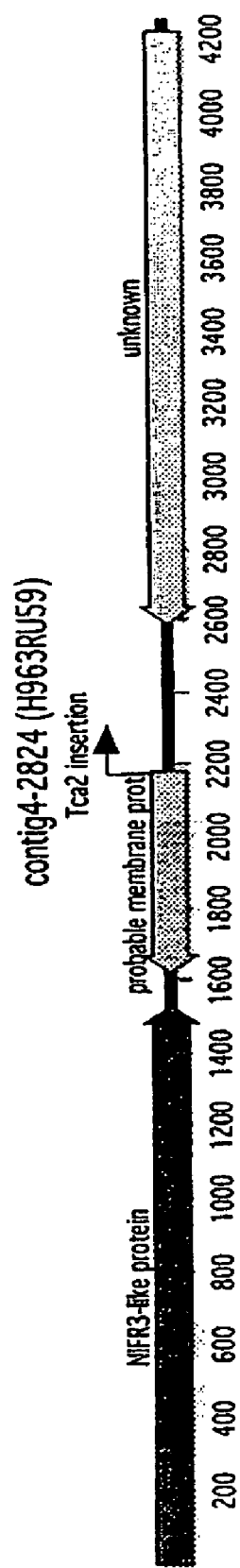

FIG. 58 is an ORF map of contig 4-2824 and shows the integration site in H963RU59 (URA*).

Figure 59:
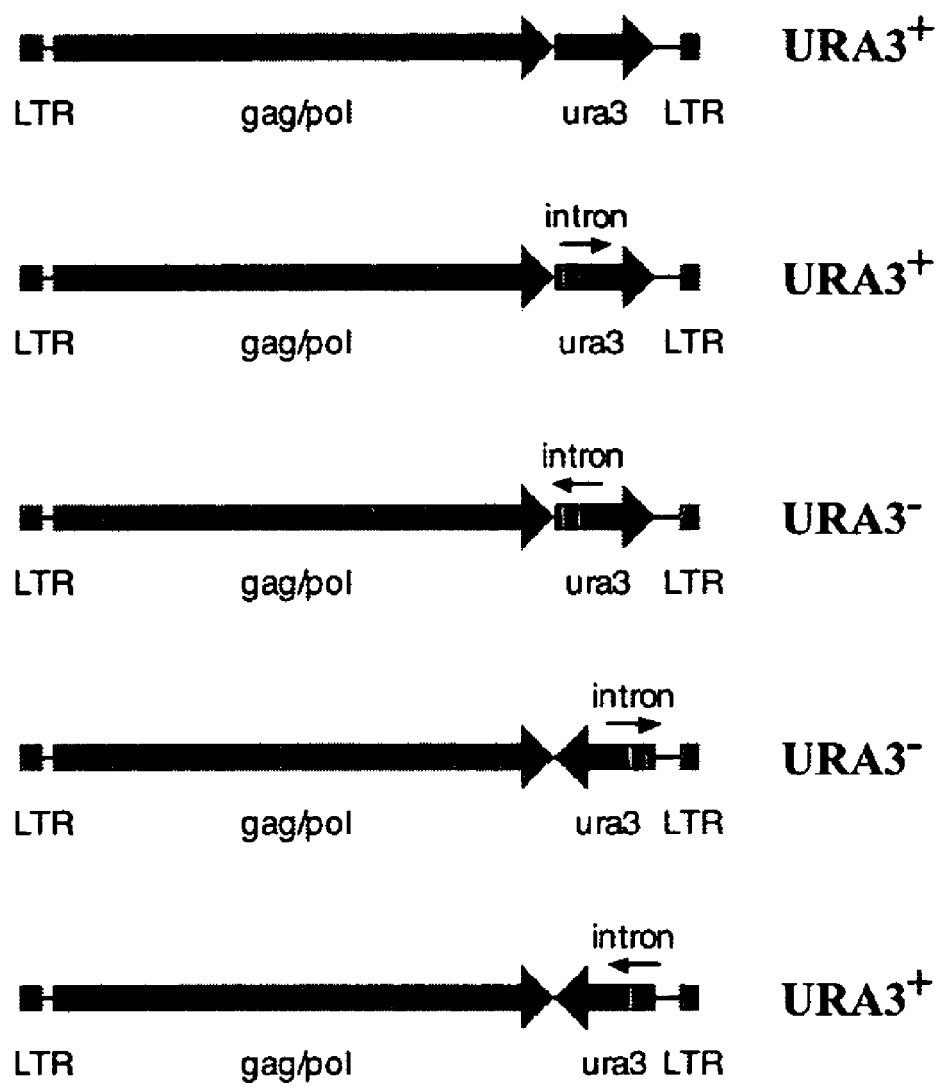

FIG. 59 shows an analysis of intron processing from the ura3 gene. The URA3 gene was placed into TCa2 in all possible combinations. The vector was then transformed into *C. albicans* CA1-4 and URA3+transformants were selected. Constructs, which gave rise to URA3+colonies, are indicated.

Figure 60:
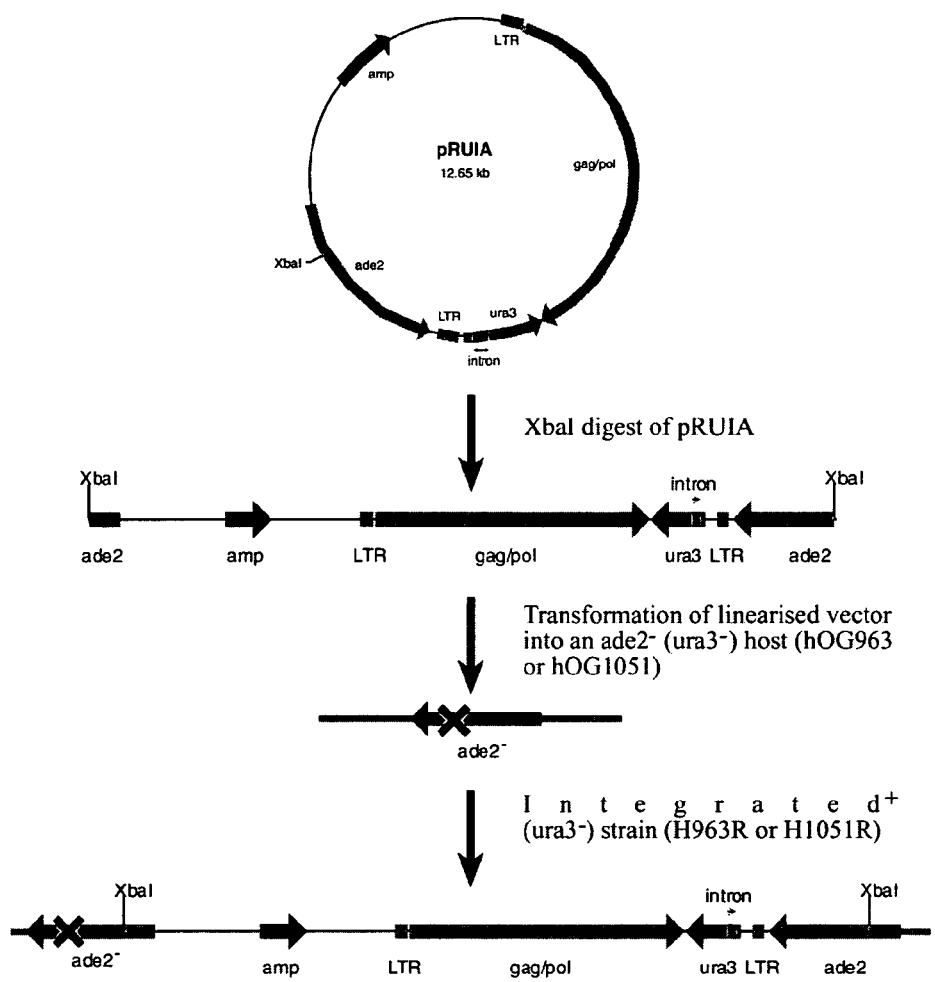

FIG. 60 shows the Integration of pRUIA. Integration of pRUIA results in the formation of a functional ADE2 gene.

FIG. 61 shows a Southern analysis of pRUIA integrated into hOG1051 and hOG963. Southern analysis was performed using a URA3 probe, shown in the schematic diagram. Genomic DNA has been digested with Eco RI (E), Hind III (H) or Xba I (X). H1051R appears to contain two copies of pRUIA.

Figure 62:
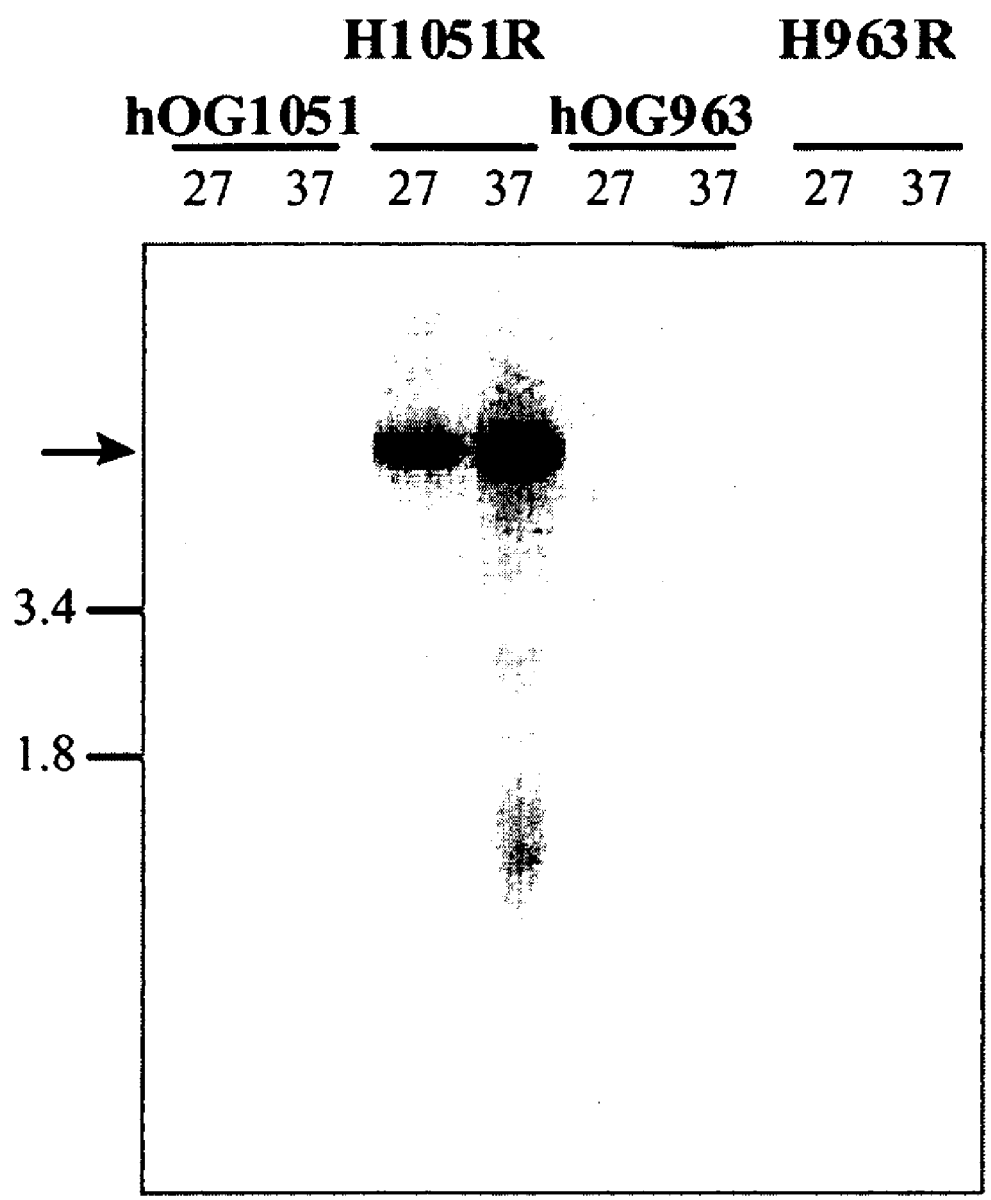

FIG. 62 shows a Northern analysis of tagged TCa2. RNA was isolated from cultures grown at 27° C. and 37° C. AURA3 gene probe was used in this analysis. The arrow indicates the transcript containing the tagged TCa2 (approximately 7 kb).

Figure 63:
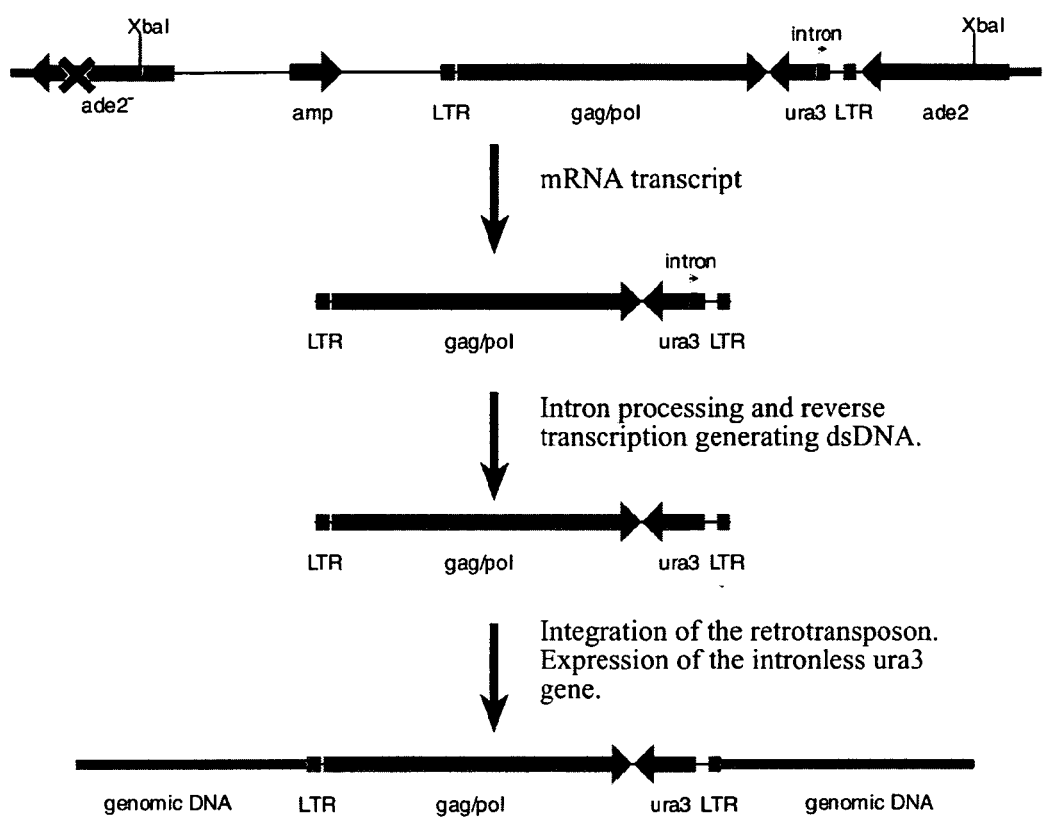

FIG. 63 shows a tagged retrotransposition.

Figure 64:
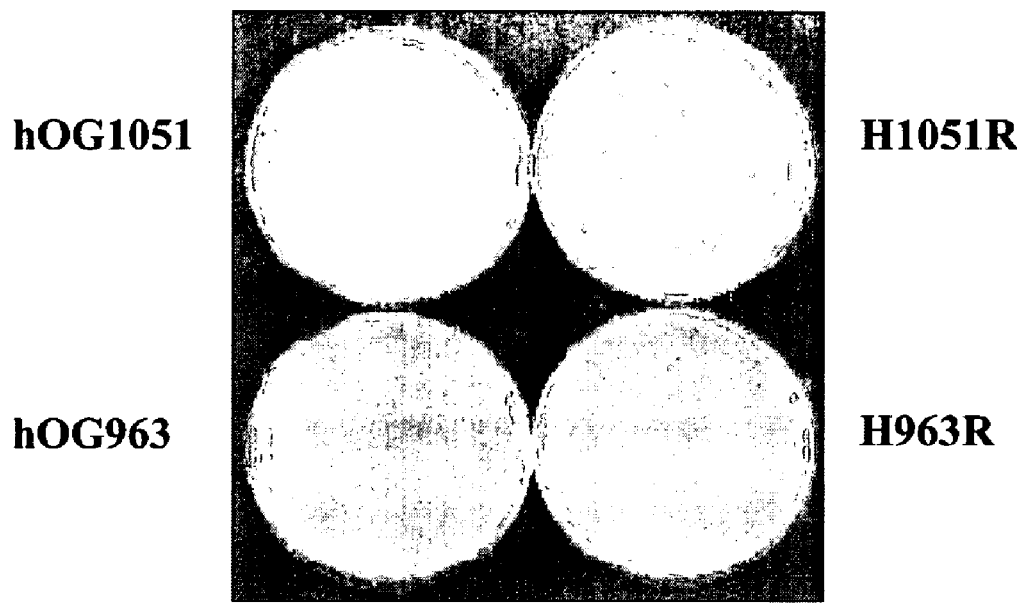

FIG. 64 shows the production of URA3+colonies. Approximately $10^7$ cells were plated on each of the four plates. Only strains containing pRUIA give rise to URA3+ colonies.

FIG. 65 shows a Southern analysis of URA3+ colonies. Genomic DNA from URA3+ colonies and their parental strains was digested with Eco RV and probed with the URA3+ gene (shown in the schematic diagram).

Figure 66A:
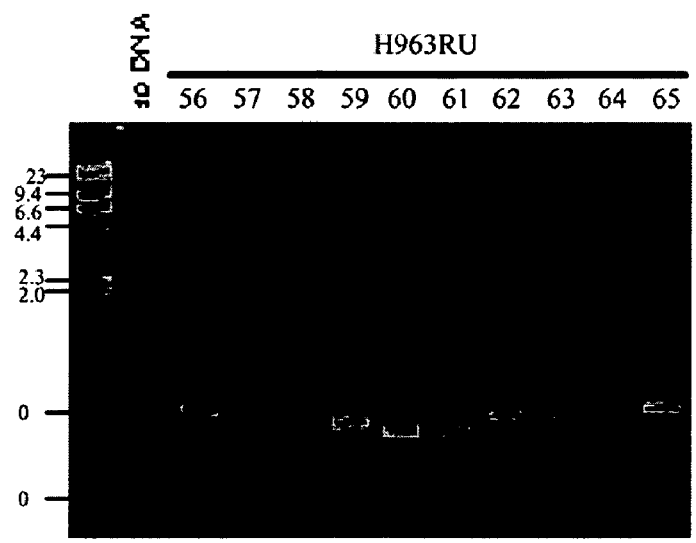
Figure 66B:
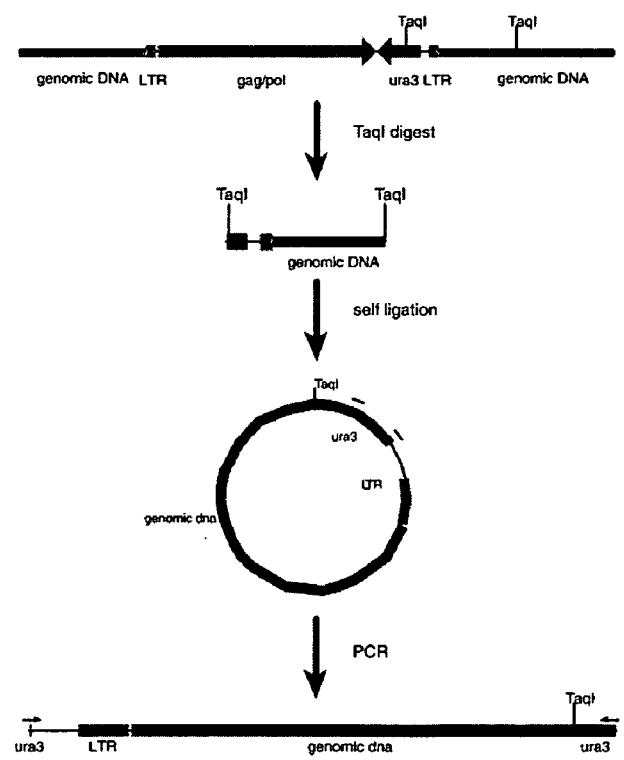

FIG. 66 shows the general principle of inverse PCR as applied in this analysis. The agarose gel shows the result of inverse PCR on 10 independent tagged retrotransposition events.

Figure 67A:
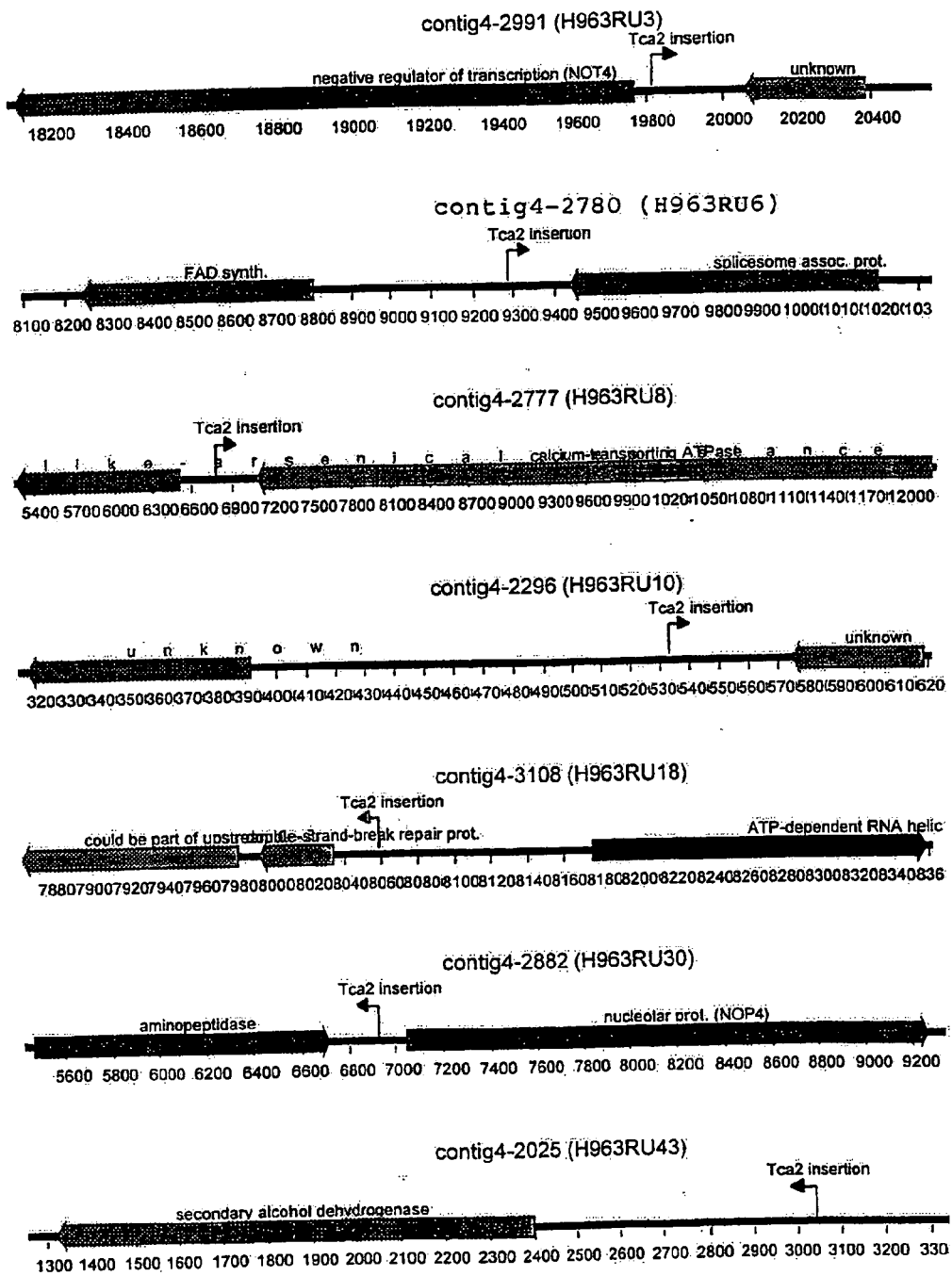
Figure 67B:
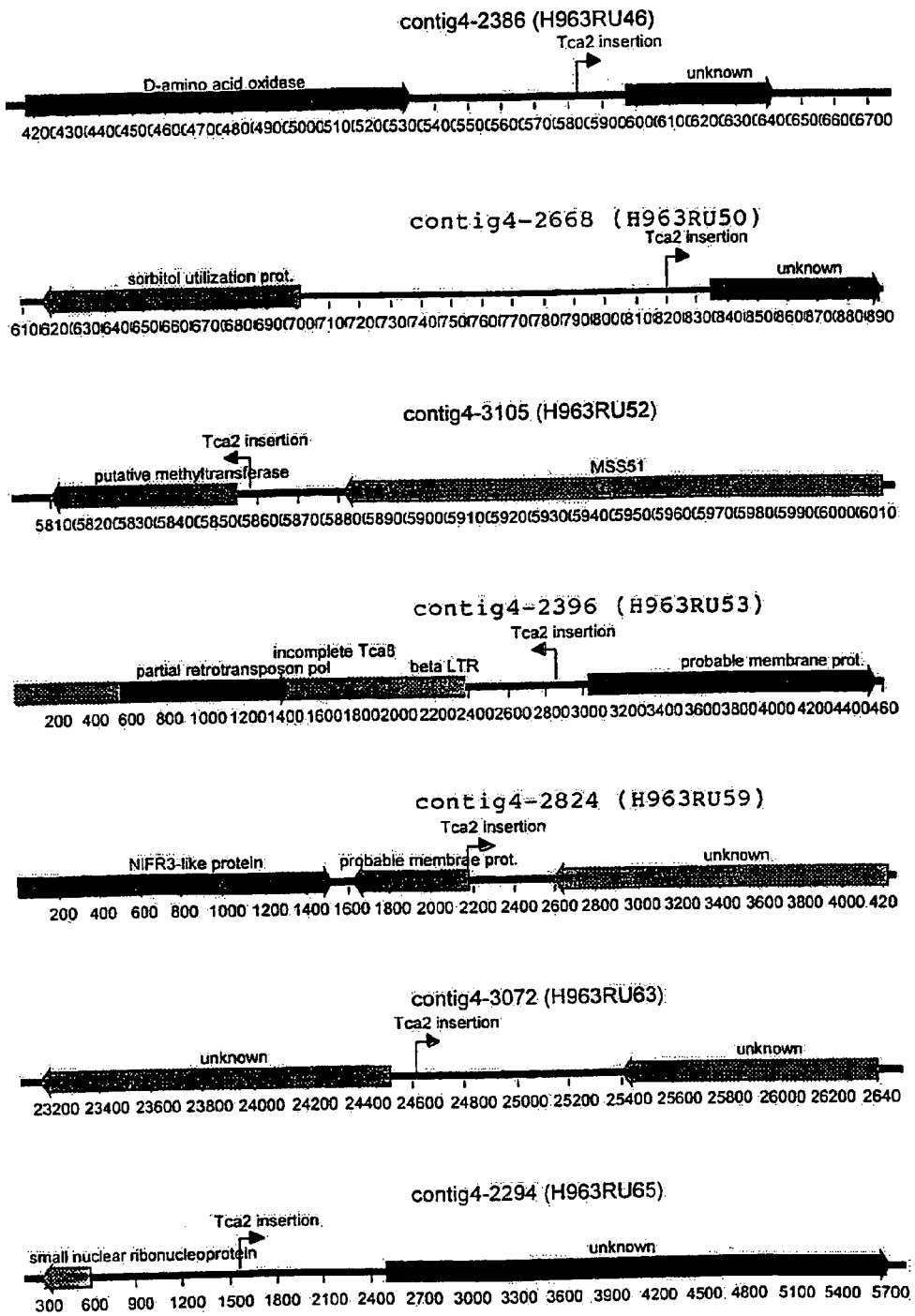

FIG. 67 shows ORF maps of tagged retrotransposition events. The arrow at the integration site indicates the direction of the TCa2 element. Tentative annotations of ORF have been made. Only the ORFs closest to the insertion site are shown.

Figure 68:
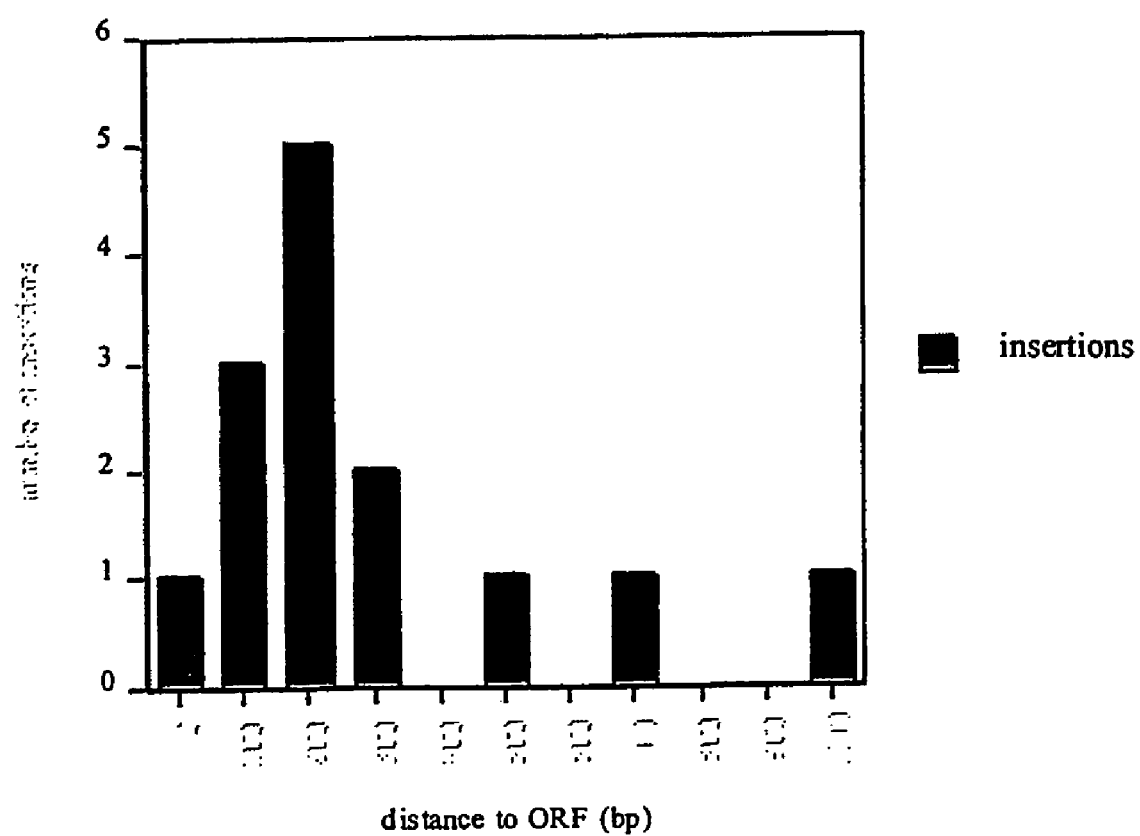

FIG. 68 shows the distribution of TCa2 insertions in relation to the nearest ORF.

FIG. 69 is an analysis of the sequence around the insertion site. All sequences are shown in the same orientation with respect to the integrated TCa2.

Figure 70:
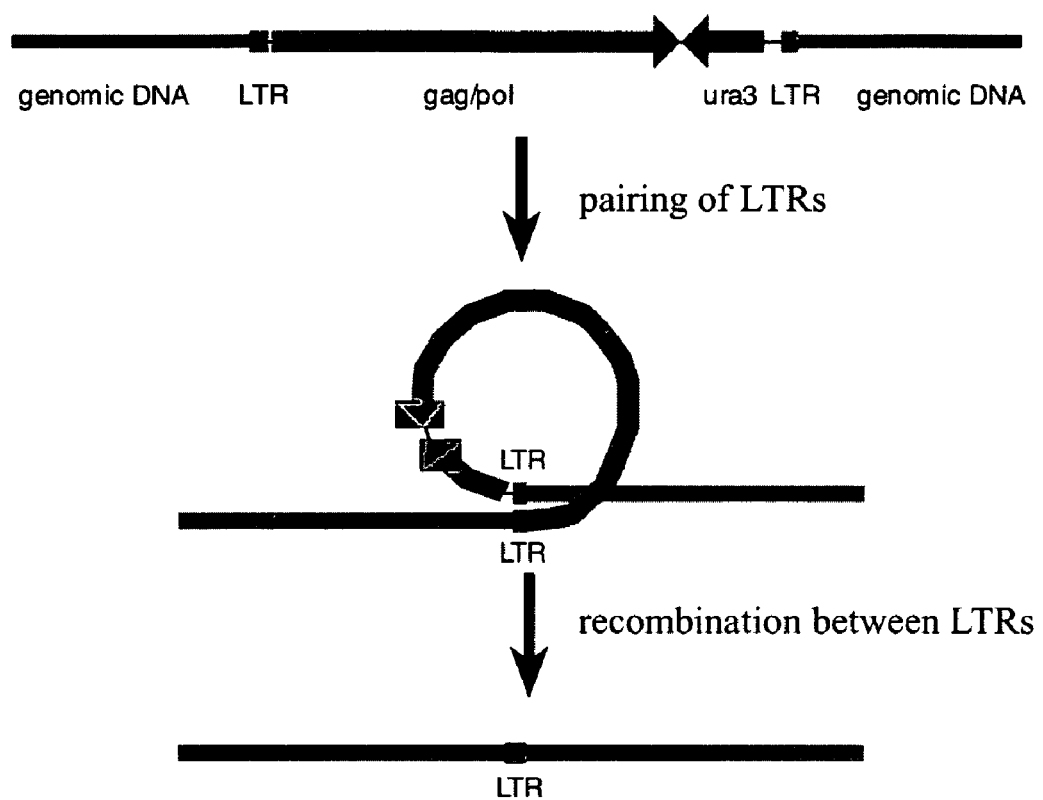

FIG. 70 shows the removal of an integrated retrotransposon. Recombination between LTR sequences results in the loss of the URA3 gene. The result of this recombination is a solo LTR.

FIG. 71 shows the nucleotide sequence of a further 38 retrotransposons.

FIG. 72 is an overview table of SEQ ID NOs: 100–144.

FIG. 73 is a schematic representation of an inverted intron inserted within the reporter gene, URA3. A) The transcript is not able to code for the URA3 gene product because the intron cannot be removed (it is in backwards). B) The transcript before and after splicing from Retrotransposon promoter (pRet). The transcript is not able to code for the URA3 gene product because, although the intron can be removed (processed or spliced), the URA3 sequence is backwards. C) Reverse transcriptase/integrase functions of the retrotransposon may act on the spliced pRet transcript converting it to a double stranded integrated DNA. Once integrated, the copy in the genome will provide a functional pURA3.

Figure 74A:
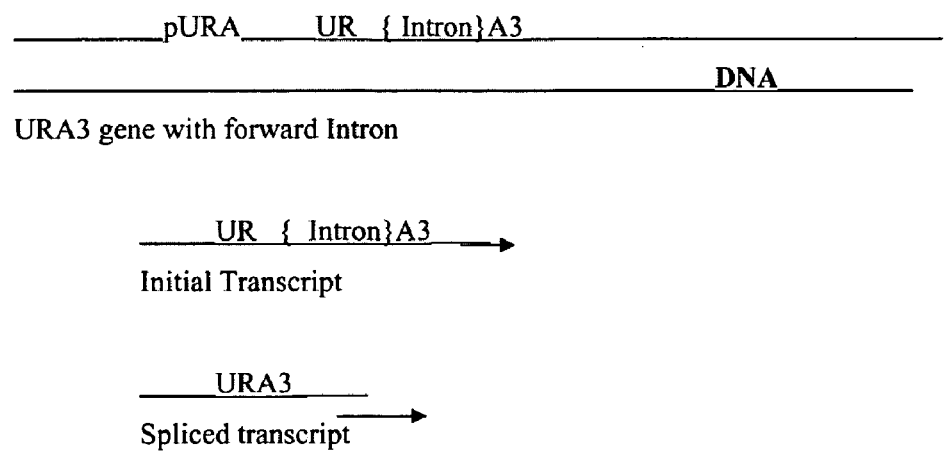
Figure 74B:
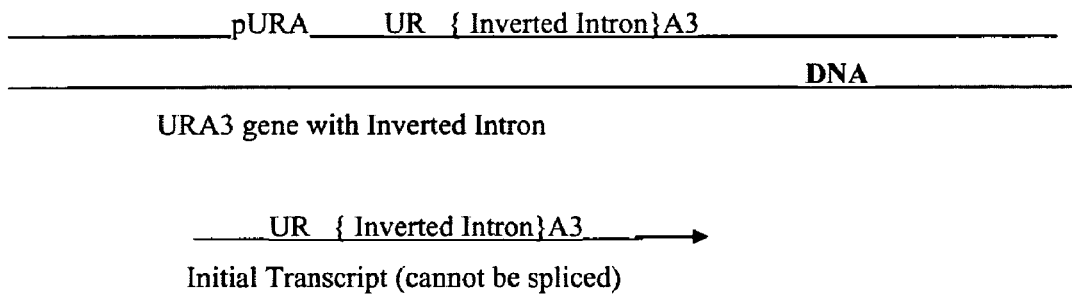

FIG. 74 shows the URA3 gene with the mini-intron from the peptide transporter gene inserted in the forward (A) and inverted (B) directions, and the resulting transcripts.

Figure 75:
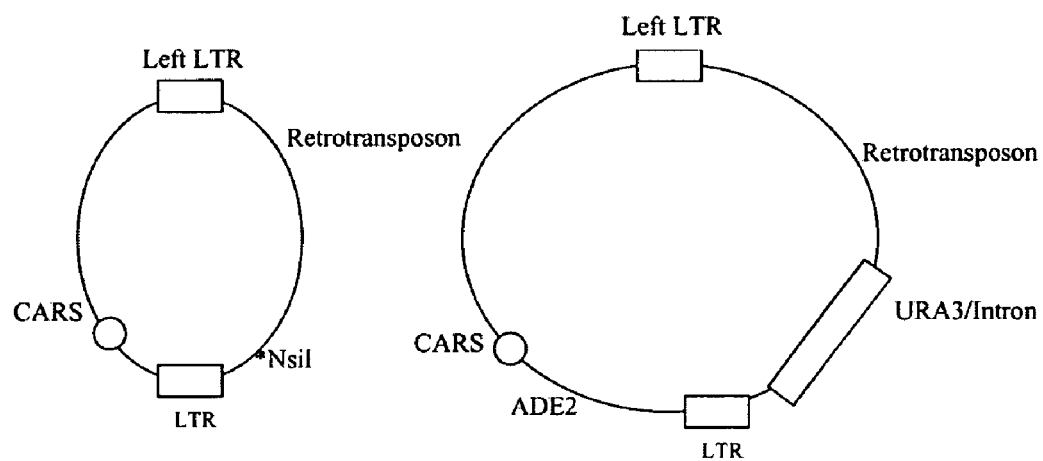

FIG. 75 shows the URA3/inverted intron element mounted onto a retrotransposon plasmid in a synthetic Nsi1 site at the 3' end of the coding sequence. An ADE2 element was also inserted between the right LTR and the *Candida* ARS.

Figure 76A:
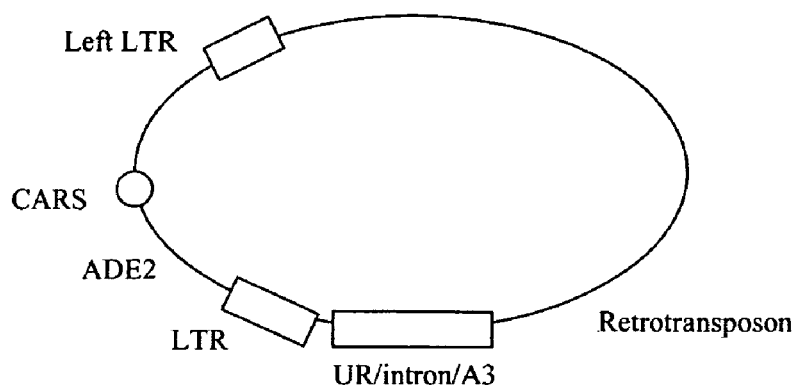
Figure 76B:
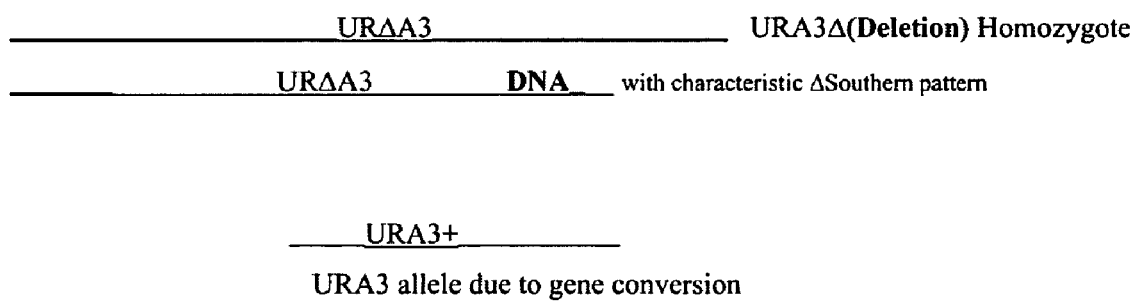

FIG. 76 shows the retrotransposon plasmid containing a mutated form of URA3 (URΔA3) (A), and a schematic of the URΔA3 and URA3+ DNA (B).

Figure 77:
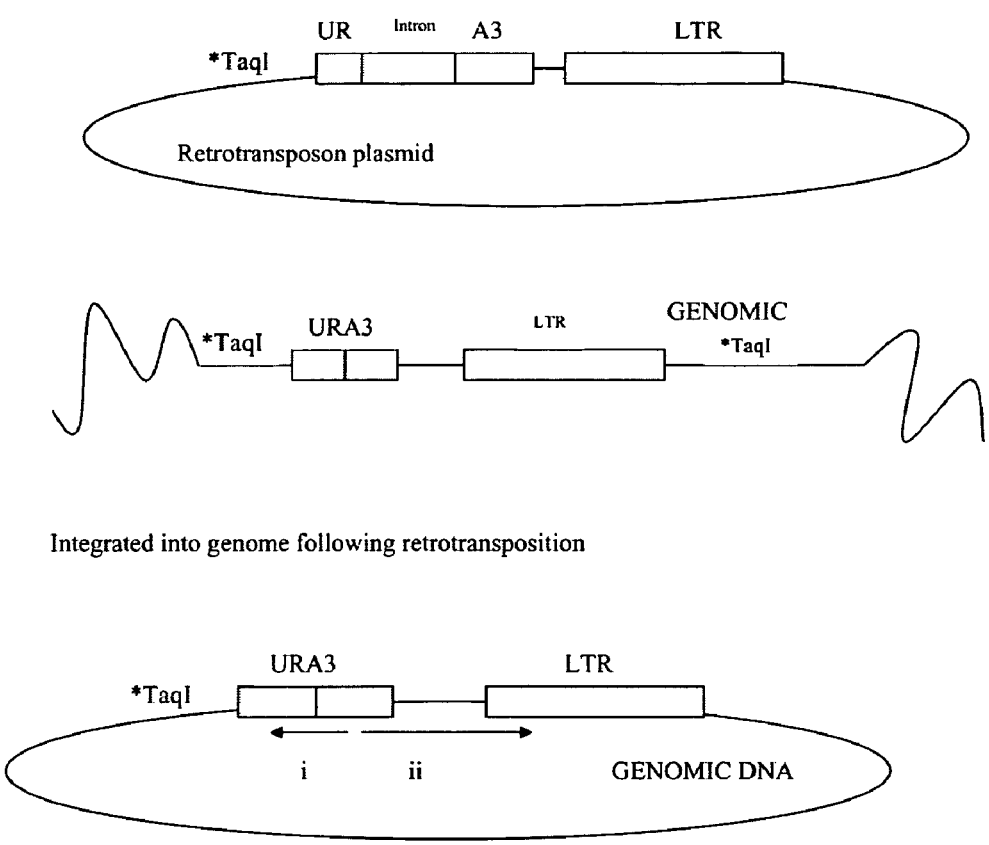

FIG. 77 schematically represents the results of inverse PCR to analyze and confirm retrotransposition into the genome.

DETAILED DESCRIPTION OF THE INVENTION

Retrotransposons have many uses. Retrotransposons can be used as vectors for expression—either in vivo or in vitro of exogenous nucleic acid molecules. Retrotransposons thus can also be used for immunological, immunogenic or vaccine compositions, as well as for therapeutic compositions. Further, retrotransposons can be used for eliciting an immunological or immunogenic or protective immunological (vaccine) response, as well as a therapeutic response. Retrotransposons can be used for gene insertion and expression studies in cell culture, gene therapy, for the generation of transgenic animals, and in where traditional RNA retroviral vectors may be used (as well as in instances where such RNA retroviral vectors theoretically may be employed but may be considered unsafe or undesirable).

For instance, reference is made to: Gilbert et al., Biol Chem 380 (3):299–303 (March 1999), Plebanski et al. Eur J Immunol 28(12):4345–55 (December 1998), Garcia-Valcarcel et al. Vaccine 15(6–7):709–10 (April–May 1997), Poggeler et al. Biochem Biophys Res Commun 219(3): 890–9 (February 1996); Kingsman et al. Ann NY Acad Sci 754:202–13 (May 1995); Adams et al. Mol Biotechnol 1(2):125–35 (April 1994); Adams et al. Int. Rev. Immunol 11(2):133–41 (1994); Kingsman et al. Trends Biotechnol 9(9):303–9 (September 1991); Cook et al. Biotechnology 9(8):748–51 (August 1991); Kingsman et al. Vaccine 6(4): 304–6 (1988); Malim et al. Nucleic Acids Res 15(18): 7571–80 (1987); WO88/03169; WO92/07950; WO94/20608; and U.S. Pat. Nos. 5,041,385, 5,354,674, 5,879,933, 5,969,126, 5,925,565, 5,885,971, 5,916,804, and 5,292,662 relate to retrotransposons and uses thereof, such as in introducing nucleotide sequences or nucleic acid molecules of interest into certain cells (expression systems, e.g. 72-kDa mitochondrial polypeptide), gene transfer, position-specific insertion vectors, vaccines (or immunological or immunogenic or therapeutic compositions; in vivo presentation of antigen or therapeutic or antigen or therapeutic delivery systems such as for antigens from *Plasmodium*, varicella zoster, HIV antigens, other viral antigens or for therapeutics such as interferon), purification or presentation or targeting vehicles, and in carriers or adjuvants, and the like. Indeed, these documents demonstrate that retrotransposons "can be administered safely in humans" (Plebanski et al., supra). Inventive nucleic acid molecules (DNA, RNA), amino acids, and retrotransposons can be used in the same fashion as previous retrotransposons; and thus, can be formulated and used in the fashion that retrotransposons are formulated in herein cited documents.

Thus, for instance, retrotransposons of the invention can be used to express nucleic acid molecules and can be formulated in compositions such as immunogenic, immunological or vaccine compositions. An immunological composition elicits an immunological response—local or systemic. The response can, but need not be, protective. An immunogenic composition likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

Figures 2A, 2B:
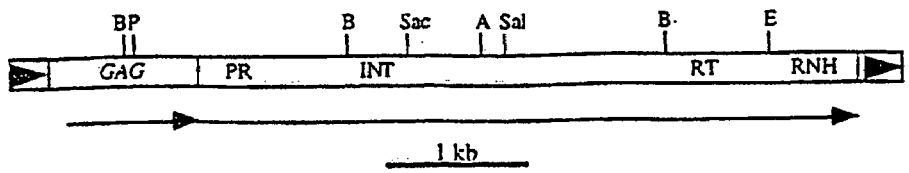
FIG. 2(A) shows the general structure of pCal. The boxed triangles represent the LTRs. The long boxes represent the internal region. The arrows below the boxes indicate the extent of the two long open reading frames. The positions of the encoded products are indicated: GAG, structural protein of the virus-like particle; PR, protease; INT, integrase; RT, reverse transcriptase; RNH, RNaseH. The termination codon at the end of each ORF is indicated by a vertical line. Selected restriction sites are shown above the diagram: B, Bg/II; P, PstI; Sac, SacI; A, Asp718; SaI, SalI; E, EcoRI.
FIG. 2(B) shows the complete nucleotide sequence (SEQ ID NO: 3) of pCal and deduced amino acid sequence (SEQ ID NO: 79) of the two long ORFs (SEQ ID NOS: 4 and 5) translated using the non-standard C. albicans genetic code). Every tenth nucleotide is indicated by a dot above the sequence. The terminal inverted repeats of the LTRs are underlined. The putative poly-A signal and TATA boxes are highlighted in bold and labelled above the sequence. The minus-strand primer-binding site [(−)PBS] and the additional region complementary to the tRNA$^{Arg}$ fragment are in italics. The stop codon at the end of the gag ORF, the adjacent purine-rich tract (PRT) and the stems of the pseudoknot are highlighted in bold. The PRT is also in italics. The 5' and 3' limits of the pseudoknot are indicated by <and >, respectively. The 3' polypurine tract (PPT1) and internal polypurine tract (PPT2) are highlighted in bold.

With respect to nucleic acid molecules and polypeptides of the invention, the nucleic acid molecules and polypeptides advantageously have at least about 65% or greater homology or identity or similarity with herein disclosed sequences, e.g., at least 70%, such as at least 75%, or at least 80% or advantageously at least 85%, for instance at least 90%, such as at least 95% or even 97% or 100%, similarity or homology or identity with herein disclosed sequences, such as (a) the LTR and/or POL region of FIG. 2B, or (b) the sequence illustrated in FIG. 2B, or (c) a nucleic acid sequence positioned between at least two long terminal repeats of the sequence of pCal as in GenBank accession number AF007776, or (d) a LTR and/or POL region of (c), or (e) any of sequences 1–28, or (f) any of retrotransposons 1–28, or (g) a sequence which hybridizes under standard stringent conditions to any of (a)–(f), or (h) a functional fragment of any of (a)–(g) (including subsequences discussed below).

Nucleotide sequence homology or identity or similarity can be determined using the "Align" program of Myers and Miller, ("Optimal Alignments in Linear Space", CABIOS 4, 11–17, 1988, incorporated herein by reference) and available at NCBI. Alternatively or additionally, the term "homology" or "identity", for instance, with respect to a nucleotide or amino acid sequence, can indicate a quantitative measure of homology between two sequences. The percent sequence homology can be calculated as $(N^{ref}-N^{dif})*100/N^{ref}$, wherein $N^{dif}$ is the total number of non-identical residues in the two sequences when aligned and wherein $N^{ref}$ is the number of residues in one of the sequences. Hence, the DNA sequence AGTCAGTC will have a sequence similarity of 75% with the sequence AATCAATC ($N^{ref}$=8; $N^{dif}$=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. RNA sequences within the scope of the invention can be derived from DNA sequences, by thymidine (T) in the DNA sequence being considered equal to uracil (U) in RNA sequences.

Additionally or alternatively, nucleotide and/or amino acid sequence similarity or identity or homology can be determined using the BlastP program (Altschul et al., Nucl. Acids Res. 25, 3389–3402, incorporated herein by reference) and available at NCBI. The following references (each incorporated herein by reference) also provide algorithms for comparing the relative identity or homology or similarity of amino acid residues of two proteins, and additionally or alternatively with respect to the foregoing, the teachings in these references can be used for determining percent homology or identity: Needleman S B and Wunsch C D, "A general method applicable to the search for similarities in the amino acid sequences of two proteins," J. Mol. Biol. 48:444–453 (1970); Smith T F and Waterman Miss., "Comparison of Bio-sequences," Advances in Applied Mathematics 2:482–489 (1981); Smith T F, Waterman Miss. and Sadler J R, "Statistical characterization of nucleic acid sequence functional domains," Nucleic Acids Res., 11:2205–2220 (1983); Feng D F and Dolittle R F, "Progressive sequence alignment as a prerequisite to correct phylogenetic trees," J. of Molec. Evol., 25:351–360 (1987); Higgins D G and Sharp P M, "Fast and sensitive multiple sequence alignment on a microcomputer," CABIOS, 5: 151–153 (1989); Thompson J D, Higgins D G and Gibson T J, "Cluster W: improving the sensitivity of progressive multiple sequence alignment through sequence weighing, positions-specific gap penalties and weight matrix choice, Nucleic Acid Res., 22:4673–480 (1994); and, Devereux J, Haeberlie P and Smithies O, "A comprehensive set of sequence analysis program for the VAX," Nucl. Acids Res., 12: 387–395 (1984).

Furthermore, as to inventive nucleic acid molecules, the invention comprehends codon equivalent nucleic acid molecules. For instance, if the invention comprehends "X" protein having amino acid sequence "A" and nucleic acid molecule "N" encoding protein X, the invention comprehends nucleic acid molecules that also encode protein X via one or more different codons than in nucleic acid molecule N.

In addition, as to inventive nucleic acid molecules, the invention comprehends nucleic acid molecules that hybridize under stringent conditions to herein disclosed nucleic acid molecules.

As to herein disclosed amino acid sequences, the invention comprehends nucleic acid molecules encoding the herein disclosed amino acid sequences, as well as nucleic acid molecules that hybridize under stringent conditions to nucleic acid molecules encoding herein disclosed amino acid sequences, as these nucleic acid molecules that hybridize under stringent conditions to nucleic acid molecules encoding herein disclosed amino acid sequences can provide proteins having similarity, homology or identity as herein discussed.

The disclosed nucleic acid sequences or portions or fragments thereof, e.g., subsequences comprising at least about 12 nucleotides in length, for instance, at least about 15, about 18, about 21, about 24 or about 27 nucleotides in length, such as at least about 30, about 33, about 36, about 39 or about 42 nucleotides in length, for example, a nucleic acid molecule of at least about 12 nucleotides in length such as about 12 to about 30, about 12 to about 50 or about 12 to about 60, or about 12 to about 75 or about 12 to about 100 or more nucleotides in length may be useful in hybridization, e.g., as probes or primers; for instance, to detect the presence or absence of Candida albicans in a sample or to determine the presence or absence of retrotransposons of the invention in a sample (amplification or detection of Candida albicans and/or inventive retrotransposons). The diagnostic applicability of nucleic acid molecules of the invention is a very real world use of the inventive nucleic acid molecules.

Further, the invention comprehends use of nucleic acid molecules and/or retrotransposons as vectors e.g., containing and/or expressing such an exogenous or heterologous (as to Candida albicans or as to the cell) or homologous (e.g., as to an organism or animal or cell) nucleic acid molecule, e.g., the use of a recombinant retrotransposon of the invention as a vector for delivery of a nucleic acid molecule that is exogenous or heterologous or even homologous to a cell, organism or animal, for instance, to elicit an immunogenic, immunological or protective immune response (e.g., from expression of an exogenous or heterologous nucleic acid molecule encoding an epitope of interest or an antigen) or as a therapeutic (e.g., to express a homologous nucleic acid molecule such as interferon or a gene that may need to be expressed in a particular individual).

Even further still, the invention comprehends use of the retrotransposons to contain and/or express a nucleic acid molecule deleterious to Candida albicans, e.g., so that the retrotransposon can become integrated into the Candida albicans genome and be lethal to Candida albicans; for instance, as a form of treatment against Candida albicans. The therapeutic, immunogenic, immunological or vaccine compositions can contain the retrotransposon in amounts and in carriers or vehicles analogous to those employed in herein cited documents.

The nucleic acids used for hybridization can, of course, be conveniently labelled by incorporating or attaching a marker, e.g., a radioactive or other marker. Such markers are well known in the art. The labelling of said nucleic acid molecules can be effected by conventional methods. The presence or expression of Candida albicans or of retrotransposons thereof (such as inventive retrotransposons) can be monitored by using a primer pair that specifically hybridizes and by carrying out a PCR reaction according to standard procedures. Specific hybridization of the above mentioned probes or primers preferably occurs at stringent hybridization conditions. A probe or primer can be any stretch of at least 8, preferably at least 10, more preferably at least 12, 13, 14, or 15, such as at least 20, e.g., at least 23 or 25, for instance at least 27 or 30 nucleotides in a herein defined nucleic acid molecule which are unique thereto. As to PCR or hybridization primers or probes and optimal lengths therefor, reference is also made to Kajimura et al., GATA 7(4):71–79 (1990), incorporated herein by reference.

With respect to hybridization, it is advantageously under high stringency conditions; and, hybridizing or hybridization under high stringency conditions can be synonymous with stringent hybridization conditions, terms which are well known in the art; see, for example, Sambrook, "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985; both incorporated herein by reference.

With respect to therapeutic, immunogenic, immunological and vaccine formulations, in addition and/or as an alternative to employing compositions and amounts of retrotransposon and routes of administration as in herein cited documents, it is noted that in classical formulations, e.g., classical immunogenic, immunological or vaccine or therapeutic formulations containing an antigen or epitope of interest (e.g., subunit formulations) or containing a biologically active therapeutic, typically contain the active ingredient in in an amount on the order of micrograms to milligrams, such as 5 micrograms to 500 milligrams, or, about 0.001 to about 20 wt %, preferably about 0.01 to about 10 wt %, and most preferably about 0.05 to about 5 wt %; and, in compositions involving a recombinant such as a recombinant viral vector expressing an antigen, epitope of interest or biologically active molecule, the vector is administered in an amount of about at least $10^3$ pfu; more preferably about $10^4$ pfu to about $10^{10}$ pfu, e.g., about $10^5$ pfu to about $10^9$ pfu, for instance about $10^6$ pfu to about $10^8$ pfu; and, in DNA plasmid compositions, suitable quantities of plasmid DNA such compositions can be 1 ug to 100 mg, preferably 0.1 to 10 mg, e.g., 500 micrograms, but lower levels such as 0.1 to 2 mg or preferably 1–10 ug may be employed. Accordingly, the recombinant retrotransposons of the invention can be administered in dosages sufficient to elicit a response analogous to compositions wherein the antigen, epitope of interest or biologically active molecule are directly present; or to have expression analogous to dosages in such compositions; or to have expression analogous to expression obtained in vivo by recombinant viral or DNA plasmid compositions.

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response, e.g., a suitable immunological or therapeutic response, such as by titrations of sera and analysis thereof, e.g., for antibodies or antigens or epitopes of interest or the therapeutic molecule. Such determinations do not require undue experimentation from the knowledge of the skilled artisan, this disclosure and the documents cited herein. And, the time for sequential administrations can be ascertained without undue experimentation using similar analyses. Thus, the amount of retrotransposon in the inventive compositions and the dosages administered can be determined by techniques well known to those skilled in the medical or veterinary arts and taking into consideration such factors as the particular antigen, eptitope of interest or therapeutic being expressed, the carrier, or diluent, any adjuvant (if present), the age, sex, weight, species and condition of the particular patient, and the route of administration.

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the retrotransposon. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the retrotransposon. This will present no problem to those skilled in chemical and pharmaceutical principles, or problems can be readily avoided by reference to standard texts or by simple experiments (not involving undue experimentation), from this disclosure and the documents cited herein.

The compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below.

The inventive retrotransposons can contain and preferably express at least one nucleic acid molecule encoding an antigen or epitope of interest. An epitope of interest is an immunologically relevant region of an antigen or immunogen or immunologically active fragment thereof, e.g., from a pathogen or toxin of veterinary or human interest. An epitope of interest can be from an antigen of a pathogen or toxin, or from another antigen or toxin which elicits a response with respect to the pathogen or toxin, e.g., from an antigen of a first human or veterinary pathogen or toxin that elicits a response with respect to the pathogen or toxin in question (such as a measles virus antigen or epitope of interest eliciting an immunological response against canine distemper). Thus, for instance, an epitope of interest can be from: a Morbillivirus antigen, e.g., a canine distemper virus or measles or rinderpest antigen such as HA or F; a rabies glycoprotein, e.g., rabies glycoprotein G; an avian influenza antigen, e.g., turkey influenza HA, Chicken/Pennsylvania/1/83 influenza antigen such as a nucleoprotein (NP) or influenza A/Jalisco/95H5 hemagglutinin; a human influenza antigen such as HA and/or NA; a bovine leukemia virus antigen, e.g., gp51, 30 envelope; a Newcastle Disease Virus (NDV) antigen, e.g., HN or F; a feline leukemia virus antigen (FeLV), e.g., FeLV envelope protein; a rous associated virus antigen such as RAV-1 env; matrix and/or preplomer of infectious bronchitis virus; a Herpesvirus glycoprotein, e.g., a glycoprotein, for instance from feline herpesvirus, equine herpesvirus, bovine herpesvirus, pseudorabies virus, canine herpesvirus, HSV, Marek's Disease Virus, herpesvirus of turkeys (HVT) or cytomegalovirus; a flavivirus antigen, e.g., a Japanese encephalitis virus (JEV) antigen, a Yellow Fever antigen, or a Dengue virus antigen; a malaria (*Plasmodium*) antigen, an immunodeficiency virus antigen, e.g., a feline immunodeficiency virus (FIV) antigen or a simian immunodeficiency virus (SIV) antigen or a human immunodeficiency virus antigen (HIV) such as gp120, gp160; a parvovirus antigen, e.g., canine parvovirus; an equine influenza antigen; a poxvirus antigen, e.g., an ectromelia antigen, a canary pox virus antigen or a fowl pox virus antigen; an infectious bursal disease virus antigen, e.g., VP2, VP3, VP4; a Hepatitis virus antigen, e.g., HBsAg; a Hantaan virus antigen; a *C. tetani* antigen; a mumps antigen; a pneumococcal antigen, e.g., PspA; a *Borrelia* antigen, e.g., OspA, OspB, OspC of *Borrelia* associated with Lyme disease such as *Borrelia burgdorferi, Borrelia afzelli* and *Borrelia garinii*; a chicken pox (varicella zoster) antigen. Of course, this is intended as exemplary, as the epitope of interest expressed by an inventive retrotransposon can be derived from any antigen of any veterinary or human pathogen or toxin; and, the recombinant retrotransposon can express express an antigen of any veterinary or human pathogen or toxin. Thus, it is envisioned that the inventive recombinant retrotransposon contain at least one nucleic acid molecule encoding at least one antigen or epitope of interest.

With respect to DNA encoding epitopes of interest, antigens and/or therapeutics, attention is directed to documents cited herein, see, e.g., documents cited supra and documents cited infra, for instance: U.S. Pat. Nos. 5,174,993 and 5,505,941 (e.g., rabies glycoprotein (G), gene, turkey influenza hemagglutinin gene, gp51,30 envelope gene of bovine leukemia virus, Newcastle Disease Virus (NDV) antigen, FeLV envelope gene, RAV-1 env gene, NP (nucleoprotein gene of Chicken/Pennsylvania/1/83 influenza virus), matrix and preplomer gene of infectious bronchitis virus; HSV gD); U.S. Pat. No. 5,338,683 (e.g., DNA encoding Herpesvirus glycoproteins, inter alia); U.S. Pat. Nos. 5,494,807, 5,756,103, 5,762,938 and 5,766,599 (e.g., DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, *C. tetani*, avian influenza, mumps, NDV, inter alia); U.S. Pat. Nos. 5,503,834 and 5,759,841 (e.g., Morbillivirus, e.g., measles F, hemagglutinin, inter alia); U.S. Pat. No. 4,722,848 (e.g., HSV tk, HSV glycoproteins, e.g., gB, gD, influenza HA, Hepatitis B, e.g., HBsAg, inter alia); U.S. Pat. Nos. 5,514,375, 5,744,140 and 5,744,141 (e.g., flavivirus structural proteins); U.S. Pat. Nos. 5,766,598 and 5,863,542 (e.g., Lentivirus antigens such as immunodeficiency virus antigens, inter alia); U.S. Pat. Nos. 5,658,572 and 5,641,490 (e.g., IBDV antigens, inter alia); U.S. Pat. No. 5,833,975 (e.g., cytokine and/or tumor associated antigens, inter alia); U.S. Pat. Nos. 5,688,920, and 5,529,780 (e.g., canine herpesvirus antigens), PCT publication WO 96/3941 (e.g., cytomegalovirus antigens); and U.S. Pat. Nos. 5,756,101 and 5,766,597 (*Plasmodium* antigens). Thus, the skilled artisan can obtain DNA or a nucleic acid molecule for including in an inventive retrotransposon, without any undue experimentation.

As to epitopes of interest, one skilled in the art can determine an epitope or immunodominant region of a peptide or polypeptide and ergo the coding nucleic acid molecule or DNA therefor from knowledge in the art, without undue experimentation, for instance, from the amino acid of the peptide or polypeptide and corresponding nucleic acid molecule or DNA sequences coding for the peptide or polypeptide, as well as from the nature of particular amino acids (e.g., size, charge, etc.) and the codon dictionary, inter alia; and, in respect to this, attention directed to documents cited herein, including U.S. Pat. No. 5,955,089. Accordingly, one skilled in the art can obtain an epitope of interest and a nucleic acid molecule coding therefor without any undue experimentation.

Thus, the invention comprehends an immunogenic, immunological, vaccine or therapeutic composition comprising an inventive retrotransposon of the invention wherein the retrotransposon includes a nucleic acid molecule encoding at least one antigen or epitope of interest or therapeutic molecule. The invention further comprehends a method for inducing an immunological or immune or protective immune or therapeutic response comprising administering to a host such as an animal or human an inventive retrotransposon of the invention wherein the retrotransposon includes a nucleic acid molecule encoding at least one antigen or epitope of interest or therapeutic molecule.

The retrotransposon can have expression in any suitable cell, such as a eukaryotic cell; for instance, fungus or yeast cells such as *Saccharamyces cerevisiae* cells, *Saccharamyces pastorianus* cells, *Candida albicans* cells, vertebrate cells such as fish cells (e.g., shark, salmon, rainbow trout, zebrafish, herring, mackerel cells), amphibian cells (e.g., frog, toad, salamander cells), bird or avian cells (e.g. chicken, turkey, duck, pigeon, dove cells), reptile cells (e.g. snake such as cobra), and mammalian cells (e.g., human, rabbit, hamster, mouse, rat, primate, cells such as VERO, HeLa cells, Chinese hamster ovary (CHO) cell lines, W138, BHK, COS-7293, MDCK; invertebrate cells such as land invertebrate cells, for instance, insect cells, e.g., lepidopteran cells such as *Spodoptera* (e.g., *Spodoptera frugiperda*, *Trichoplusia* (e.g., *Trichoplusia* ni), dipteran such as mosquito (e.g. *Culicidae*) cells, fly cells (e.g. *Drosophila*); e.g., typical cells that are used with eukaryotic replicable expression vectors such a *S. frugiperda* cells, VERO cells, MRC-5 cells, SCV-1 cells COS-1 cells, NIH3T3 cells, mouse L cells, HeLa cells and the like.

The invention further comprehends methods for treating *Candida albicans* comprising administering a recombinant retrotransposon of the invention that includes a nucleic acid molecule that is lethal or deleterious to *Candida albicans*, as well as recombinant retrotransposons that include a nucleic acid molecule that is lethat or deleterious to *Candida albicans*. For instance, a retrotransposon of the invention can disrupt or interfere with a gene essential to the viability of *Candida albicans*; for instance, an inventive retrotransposon can disrupt or interfere with CaSNF1 (Petter et al. Infect Immun 65(12):4909–17 (1997)) and/or H(+)-ATPase (Perlin et al. Ann NY Acad Sci 834:609–17 (1997)) and/or the *Candida albicans* 37 kDa polypeptide that appears to be a ribosomal protein (Montero et al. Microbiology 144(Pt4): 839–47 (1998) and/or a *Candida albicans* topoisomerase gene (Keller et al. Biochem J 324(Pt1):329–39 (1997) and/or a yeast essential gene (cf. Hanes et al. Yeast 5:55–72 (1989); and/or an inventive retrotransposon can express a candidacidal antibody (Conti et al. J Infect Dis 177(3): 807–11 (1998)) and/or an antifungal (Ben-Josef et al. J Antibiot (Tokyo) 50(11):937–43 (1997)) and/or an antibody-like molecule (Tournay et al. DNA Cell Biol 15(8):617–24 (1996)).

Furthermore, in view of the foregoing and the documents cited herein, the invention comprehends a process for the transfer and expression of at least one gene into a cell in vitro or in vivo comprising the steps of: (a) isolating the gene; (b) introducing the gene into an inventive retrotransposon (a retrotransposon as herein described); (c) introducing said hybrid retrotransposon into a donor cell and allowing the donor cell to package and transmit said hybrid retrotransposon into a virion; (d) transferring said virion to a recipient cell wherein said hybrid retrotransposon replicates by reverse transcription and may also be integrated into the recipient cell's genome; (e) expressing said hybrid retrotransposon as RNA and/or protein from either at least one internal promoter and/or from said retrotransposon long terminal repeat promoter or both (or a promoter as herein described); and (f) screening or selecting for the phenotype of said hybrid retrotransposon. The retrotransposon can contain genetic material encoding at least one dominant selectable marker; e.g., a selectable marker is selected from the group consisting of aminoglycoside phosphotransferase (neo, G418, APH), dihydrofolate reductase (DHFR), hygromycin-B-phosphotransferase (HPH), thymidine kinase (TK), xanthine-guanine phosphoribosyltransferase (XG-PRT, gpt), chloramphenicol acetyltransferase (CAT) and luciferase. In the process multiple cellular movable genetic elements can be introduced and expressed as RNA; for instance, the multiple cellular movable genetic elements can be introduced and expressed in tandem in RNA; or, the multiple cellular movable genetic elements can be introduced and expressed as separate transcriptional units within a single cell or organism. And, the gene can encode a peptide, antibody, antigen, hormone, or drug not normally expressed in the cell, at biologically significant levels. (Cf. U.S. Pat. No. 5,354,674.)

Similarly, the invention can comprehend polycistronic vector for the expression of one or more or a plurality, e.g., at least two or three polynucleotide sequences comprising a promoter operably linked to a nucleotide sequence comprising elements encoding one, or two or three, or more proteins, and an inventive retrotransposon or portion thereof; the retrotransposon or portion thereof can act as an internal ribosome entry site. The invention thus further comprehends a method of incorporating a DNA encoding a protein of interest into a cell in vitro comprising transforming said cell with this vector. The vector can be a plasmid vector or a viral vector; for instance, a vector from a virus selected from the group consisting of poxvirus, adenovirus, baculovirus, herpesvirus, adeno-associated virus, and retrovirus. The vector can include an an encapsidation sequence. A viral particle can comprise the vector. An isolated cell can comprise the vector. And, the vector can be in a composition. (Cf. U.S. Pat. No. 5,925,565.) Likewise, the invention comprehends other methods, products, compositions and the like that are analogous to those in documents cited herein, but wherein retrotransposons, nucleic acid molecules, amino acid molecules (proteins, polypeptides) and promoters disclosed herein are employed.

Further, as discussed, the invention can include an immunological, or immunogenic, or vaccine or therapeutic composition comprisng a carrier or diluent and an inventive expression vector wherein the vector expresses an antigen, or an epitope of interest or a therapeutic. The composition can be an immunological, immunogenic or vaccine composition when the vector expresses an antigen or an epitope of interest (see supra). The composition can be a therapeutic composition when the vector expresses a therapeutic (e.g., interferon, a cytokine, a tumor associated antigen, etc.; see supra). And, the invention can include a method for inducing an immunological response in a host including an animal (e.g., mammal) or a human comprising administering to the host the immunological, immunogenic or vaccine composition; as well as a method for inducing a therapeutic response in a host including an animal (e.g., mammal) or human comprising administering to the host the therapeutic composition. As noted in many documents cited herein, an immunological or immunogenic response can be useful; for instance, in generating antibodies which are themselves useful in diagnostic and other uses.

Accordingly the invention has many embodiments and uses that can be practised without undue experimentation from this disclosure and the knowledge in the art, for instance as exemplified by documents cited and incorporated herein by reference.

A better understanding of the present invention and of its many advantages will be had from the following non-limiting Examples, given as a further description of the invention and as illustration of it.

Plasmids carrying both the retrotransposon and other genetic elements can be assembled by in vitro molecular genetic manipulations. Such plasmids should, for ease of manipulation, be capable of growing both in E. coli and in yeasts. Such plasmids should carry some suitable marker (such as ADE2) which can be selected for following yeast transformation. The presence of such plasmids can be detected and selected for following transformation into an Ade-(Adenine auxotrophic) yeast. Detection or selection consists of allowing the yeasts to attempt to grow on media without say adenine. The parental auxotrophic yeast will not grow whereas a transformant carrying say a plasmid with the ADE2 gene will grow. The transformed culture can be maintained on a medium without adenine and this will select for the retention of the plasmid strains carrying the plasmid (maintained by say selection on medium without adenine) can be used to perform the various activities described in this patent. For example they could be plated on a medium which would select for integration events (say by selecting for URA3+).

EXAMPLES

Materials and Methods

Strains and Culture Conditions

The isolate iB65, precursor to the *Candida albicans* strain currently under investigation (hOG1042), was isolated as a met2 heterozygote from an Otago University intermediate biology student in 1983. It was subsequently mutagenised with UV radiation (2) and N-methyl-N-nitro-N nitrosoguanidine (Poulter et al 1981) to produce five strains—hOG758, hOG759, hOG760, hOG761 and hOG762—which are all met2 homozygotes and also auxotrophic for adenine. hOG1042 is an ade2/ade2 MET2/met2 revertant of hOG762. The strains were grown at 27° C. or 37° C. in YPD medium (1% yeast extract, 2% peptone and 2% glucose).

Other *Candida albicans* strains analyzed were F16932 (Poulter, unpublished), SA40 (Agatensi et al 1991), SC5314 (Gillum et al 1984), and SGY269 (Kelly et al 1987). Other *Candida* species analyzed were *C. pseudotropicalis* (CDC B2455), *C. tropicalis* (CDC B397), *C. parapsilosis* (CDC MCC 499), all from the National Health Institute, Porirua, New Zealand, and *C. maltosa* (CHAU1).

Enzymes

Agarase (GELase™) and phosphatase (HK™ Phosphatase) were purchased from Epicentre Technologies, USA. T4 DNA ligase, Expand high fidelity PCR system, RNase A, and DNase I, Proteinase K, Klenow, and restriction endonucleases were purchased from Boehringer Mannheim GmbH, Biochemica, West Germany. Vent® polymerase was purchased from New England Biolabs, USA. Zymolyase 100T was from Seikagaku Corporation, Tokyo.

Nucleic Acid Manipulations

*C. albicans* genomic DNA was prepared essentially by the method of Cryer et al. (1975). DNA was separated on 1% agarose gels using TAE buffer. Gel purification of DNA was from low melting point agarose using agarase. Bacterial plasmids were prepared by a modified alkaline lysis/PEG precipitation from Applied Biosystems, Inc. Polymerase chain reactions were performed using an Autogene II Programmable cycling water bath from Grant Instruments (Cambridge) Ltd. Temperature cycling consisted of 35 cycles of 95° C. for 1 min, 45° C. for 1 min and 72° C. for 1 min. PCR products were purified for sequencing using the QIAquick PCR Purification Kit from QIAGEN GmbH, Hilden.

Sequencing and Nucleotide Analysis

Sequencing was performed using a combination of subcloning and specifically designed oligonucleotide primers. The sequences were determined on an automated DNA sequencer (Applied Biosystems 373A DNA sequencer). Oligonucleotides were purchased from Macromolecular Resources, Fort Collins or from the DNA Synthesiser, Dunedin. Sequences were edited using SeqEd 1.0.3 (Applied Biosystems). Sequence contigs were assembled using VTUTIN 5.21 (Stockwell 1985) and HOMED 5.14 (Stockwell and Petersen 1987). Other sequence analysis was carried out using version 8 of the University of Wisconsin GCG Sequence Analysis Package (Devereux et al 1984). The open reading frames were translated using the nonstandard *C. albicans* genetic code (CUG codes for serine instead of leucine) (Santos and Tuite 1995 and White et al 1995). Sequences for the alignments in FIG. 4 and for the phylogenetic analysis were obtained from the Genbank database using the following accession numbers: 17.6—A03971, 1731—S00954, CfT-1—Z11866, copia—A03324, dong-L08889, gypsy-B25666, HIV1—K02013, Hopscotch-U12626, jockey-JT0396, MMLV-A03956, Osser—S32437, RSV-S26418, Ta1—S05465, Tf1—A36373, Tnt1—SO4273, Tom S34639, Tst1—X52387, Tx1-B32494, Ty1—B28097, Ty2—S45842, Ty3—S53577, Ty4—P47024 and Ty5—U19263. The trees were constructed using the UPGMA (unweighted pair group method using arithmetic averages), Neighbor-Joining and Parsimony methods available in the PHYLIP package (Felsenstein 1989). Bootstrapping was performed using SEQBOOT and consensus trees were derived using CONSENSE, both programs also from PHYLIP.

The nucleotide sequence of pCal has been submitted to Genbank and assigned the accession number AF007776.

*Candida* nucleic acid isolations. For DNA isolations, cells were grown at 27° C. or 37° C. to late log/early stationary phase. DNA for the hOG759 library was then prepared essentially as in Cryer et al. 1975. DNA for the Southern blots and PCRs was prepared as described by Philippsen et al. 1991. To determine the copy number of TCa2 in hOG759 and hOG1042 it was found to be necessary to purify the chromosomal DNA away from the abundant pCal molecules. To do this DNA samples from cells grown at 27° C. were electrophoresed on 0.7% agarose gels. The high molecular weight chromosomal DNA was then cut out of the gel under long wavelength UV light. The DNA was then extracted from the gel by spinning through siliconized glass wool in microcentrifuge tubes for 5 min at 6500 rpm and 2 min at 8000 rpm. DNA was precipitated by adding an equal volume of 5M ammonium acetate and 2 volumes of cold 96% ethanol. The tubes were mixed and then centrifuged at 13000 rpm for 30 min. Pellets were washed in 70% ethanol, dried, resuspended in 10 mM Tris-Cl, pH 7.5; 1 mM EDTA and stored at −80° C.

RNA extractions were performed as follows. Cells were grown in YPD medium overnight at either 27° C. or 37° C. then a volume of culture containing ~$2.5 \times 10^8$ cells was transferred to Falcon tubes. The cells were spun down, washed once in 1 ml RNA buffer [0,5M NaCl; 200 mM Tris-Cl, pH 7.5; 10 mM EDTA—treated with diethyl pyrocarbonate (DEPC)], then resuspended in 300 µl RNA buffer and transferred to eppendorf tubes. To these tubes was added 200 µl RNase-free glass beads (425 to 600 µm diameter), 150 µl phenol equilibrated with RNA buffer and 150 µl chloroform-isoamylalcohol (24:1). The tubes were then vortexed in 30 sec bursts, with intervals on ice, for a total of 5 min vortexing. 30 µl of 10% SDS was then added and the tubes were vortexed for a further 2 min. The organic and aqueous phases were then separated by centrifuging for 1 min at 13000 rpm. The aqueous phase was then extracted once more from 150 µl phenol, 150 µl chloroform-isoamylalcohol. RNA was precipitated by adding 2 volumes of cold absolute ethanol and holding at −80° C. for 20 min. The tubes were then centrifuged for 10 min at 13000 rpm; the resulting RNA was washed in 70% ethanol, dried, resuspended in 50 µl DEPC-treated $H_2O$ and stored at −80° C.

RNA preparations were tested for RNase-sensitivity by treating them with 0.2 mg.ml$^{-1}$ RNase A for 30 min at 37° C.

Figure 11A:
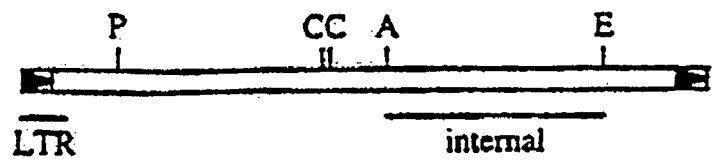
FIG. 11(A) shows the location of the TCa2 probes and some important restriction sites. The structure of TCa2 is represented as the long box and the LTRs are the boxed triangles. The locations of the LTR and internal probes and certain restriction sites are indicated. P, PstI; C, ClaI; A, Asp718; E, EcoRI. (B) Copy number of TCa2. DNA was isolated from cells grown at 27° C. then digested with EcoRI. The resulting fragments were separated on an agarose gel then transferred to a nylon membrane. The DNA immobilized on the membrane was then hybridized to the TCa2 internal probe. Lane 1, hOG1042; lane 2, SGY269; lane 3, SC5314; lane 4, ATCC10261; lane 5, SA40; lane 6, F16932; lane 7, *C. maltosa*; lane 8, *C. parapsilosis*; lane 9, *C. tropicalis*; lane 10, *C. pseudotropicalis*. Sizes in kb are indicated at the left of the picture. (C) Copy number of the TCa2 LTR. The membrane used in panel B was stripped and then reprobed with the TCa2 LTR.

Southern blotting. DNA was electrophoresed in 0.75% agarose with TAE buffer in the presence of 0.5 µg.ml$^{-1}$ ethidium bromide. When the DNA fragments were sufficiently separated, the gels were photographed under UV light followed by a 5 min wash in sterile $H_2O$. The DNA was then capillary transferred to Hybond-N+ nylon membranes (Amersham) using 0.4M NaOH as the transfer solution. Following transfer the membranes were rinsed in 2XSSC and stored at 4° C. until hybridization. DNA fragments to be used as probes were isolated by restriction digestion of plasmid clones followed by gel purification of the appropriate fragment as described above for genomic DNA. The locations of the probes used are shown in FIG. 11A. Probes were radiolabelled with $\lambda^{32}$PdCTP by random-primed labelling using Hexanucleotide Mix from Boehringer Mannheim. Prior to hybridization, probes were denatured by heating in a boiling water bath for 10 min. Hybridization was carried out in sealed plastic bags in a shaking water bath. Most hybridizations were performed at 65° C., but some lower stringency ones were at 55° C. The hybridization buffer was similar to that of Church and Gilbert 1984, but without the BSA (0.36M Na2HPO$_4$, 0.12M NaH$_2$PO$_4$, 1 mM EDTA, 7% SDS). Membranes were prehybridized in this buffer for 2 hours, the denatured probe was then added in 5 ml of fresh buffer and hybridization was allowed to proceed for 16–20 hours. Post-hybridization washes consisted of two rinses in 2XSSC at room temperature followed by stringency washes in 0.2XSSC (or 0.4XSSC for low stringency), 0.1% SDS at the hybridization temperature. Finally membranes were rinsed in 2XSSC then exposed to Kodak X-Omat AR film at −80° C. using an intensifying screen. Membranes were stripped for reprobing by rinsing in $H_2O$ for 1 min, followed by two washes in 0.2M NaOH, 0.1% SDS at 37° C., and then a final rinse in 2XSSC.

Northern blotting. Briefly, approximately equal amounts of total RNA were denatured in formamide-formaldehyde at 65° C. then separated on 1% agarose, 2.2M formaldehyde gels in MOPS running buffer (40 mM 3-[N-Morpholino] propanesulfonic acid, pH 7.0; 10 mM sodium acetate; 1 mM EDTA). Following electrophoresis, gels were washed twice, 20 min per wash, in RNase-free $H_2O$. RNA was then capillary transferred for 5 hours to Hybond-N+ membranes using 8 mM NaOH as the transfer solution. The membranes were then rinsed in 2XSSC, 0.1% SDS for 5 min. The RNA sides of the membranes were then exposed to UV light for 45–60 sec and the membranes were stored at 4° C. until hybridization. Probes were radiolabelled double-stranded DNAs prepared as described above for Southern blotting. Hybridization was performed at 42° C. in FPH buffer (5XSSC, 5° Denhardt's solution, 50% formamide and 1% SDS). Membranes were prehybridized for 2 hours in this buffer; the denatured probe was then added in 5 ml of fresh FPH buffer and hybridization was left to proceed for about 20 hours. After hybridization the membranes were washed twice, 5 min per wash, in 2XSSC at room temperature, twice, 5 min per wash, in 0.2XSSC, 0.1% SDS at room temperature and twice, 15 min per wash, in 0.2XSSC, 0.1% SDS at 42° C. Finally, the membranes were rinsed in 2XSSC and exposed to x-ray film at—80° C.

The films from the Southerns and Northerns were scanned using a Bio-Rad GS-670 imaging densitometer. Relative band intensities were determined using Molecular Analyst version 2.1. The brightness/contrast of the scans was adjusted for printing using Adobe Photoshop 3.0.

Recombinant DNA manipulations. A λ-library of BamHI-digested hOG759 DNA was constructed using the Lambda-GEM-11 BamHI Arms Cloning System from Promega, according to the manufacturer's instructions. The library was screened using the DIG DNA Labelling and Detection Kit from Boehringer Mannheim. Probes were derived from clones of pCal. Recombinant λ DNA was prepared according to the protocol accompanying the lambda cloning system from Promega. Bacterial plasmids were prepared using an alkaline lysis-polyethylene glycol precipitation method from Applied BioSystems. Sequencing was performed using a combination of subcloning and specifically designed oligonucleotide primers. Sequences were determined on an ABI 373A DNA Sequencer and edited using SeqEd 1.0.3. Sequences were aligned and assembled into contigs using the programs available in the University of Wisconsin GCG package and HOMED 5. PCRs were performed on an Autogene II programmable cycling water bath from Grant Instruments, Cambridge. Primers were synthesized on an ABI 380B oligonucleotide synthesizer. Primers used for the amplification of the 5' regions of TCa2 retrotransposons from various *C. albicans* strains were as follows:

Cal1.2 5'-AGTGAGCTCTGTTGGTTTGTGCACT-3'; Cal2.2 5'-GCGTCTAGAAATTCTGTACCTTC-3'. Together these primers can amplify the first 400 bp of the retrotransposon including the complete left LTR. Primers from the genomic regions flanking the integrated copy of TCa2 were: TGFS-L, 5'-CTACATAGGATGACTCAC-3'; and TGFS-R, 5'-ATCCAAGTCTGAAAGATC-3'. Temperature cycling consisted of 35 cycles of 95° C. for 1 min, 45° C. for 1 min, and 72° C. for 1 min. PCR products were purified prior to cloning using Strataclean resin (Stratagene, La Jolla, Calif.).

Nucleotide sequence accession numbers. The nucleotide sequence of the TCa2 fragment from hOG759 with the perfect 32-bp minus-strand primer-binding site, and that of the integrated TCa2 element, have been submitted to GenBank and assigned accession numbers AF030556 and AF050215, respectively.

Example 1

Cloning and Mapping

Figure 1:
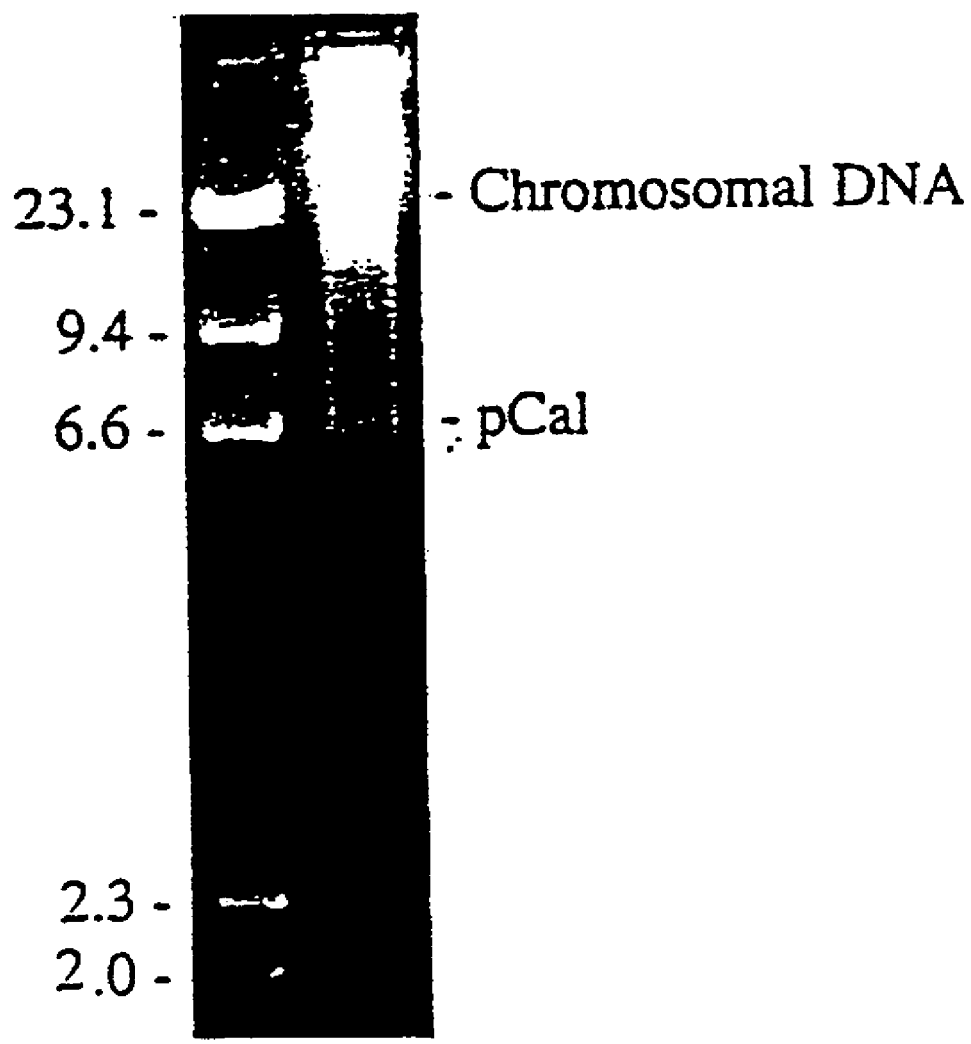
FIG. 1 shows the presence of a high copy number, extrachromosomal element in *C. albicans* strain hOG1042. An uncut sample of hOG1042 DNA was electrophoresed on a 1% agarose gel alongside some marker DNA (sizes in kb indicated at left). A distinct band of about 6.5 kb running ahead of the bulk of the chromosomal DNA (>20 kb) indicates the presence of an extrachromosomal element in this strain. The relative intensity of the band suggests that the element exists at about 50–100 copies per cell (see text). The gel photo was scanned using a BIO-RAD GS-670 Imaging Densitometer and annotated using Adobe Photoshop™ 4.0.

Some uncut genomic DNA prepared from *Candida albicans* strain hOG1042 was analysed on an agarose gel and a distinct band running at about 6.5 kb was found (FIG. 1). Such a band had never previously been reported from any *Candida* strain or species. To analyse this feature the band was extracted from an agarose gel and tested to see if it could be cut with restriction enzymes. A number of enzymes cut the band into smaller fragments which indicated that it was made up of double-stranded DNA. At this point the band was named pCal (plasmid of *Candida albicans*). The restriction digests allowed the construction of a simple restriction map of pCal. This work revealed that pCal was linear, with a Pst1 site about 1 kb from one end, an EcoR1 site about 1 kb from the opposite end and an Asp718 site near the middle. To permit further analysis the fragments of pCal produced with Asp 718 were cloned into the Asp718 site of pUC19. Five clones were isolated and each was found to contain just a single Asp718 site, the other apparently destroyed during the cloning, as expected. Three of the clones contained a Pst1 site and two contained an EcoR1 site.

Example 2

Nucleotide Sequence of pCal

The five plasmids containing the pCal fragments were all sequenced from both ends in the hope of finding an identifiable feature which would provide an insight into the nature of pCal. The first remarkable features to be found were 280 bp direct repeats.

The existence of these direct repeats suggested that pCal was likely to be a retrotransposon. As no other retrotransposon had ever been found existing at a high copy number in a free, linear, dsDNA form we determined the complete sequence of pCal. Therefore, the three clones of pCal carrying the Pst1 site and one of the two clones carrying the EcoR1 site were completely sequenced. In addition a region of pCal spanning the central Asp718 site used in the cloning was amplified by PCR and each strand was sequenced. This analysis confirmed that there was only one Asp718 site and that therefore the clones that we had of each half of pCal truly represented adjacent fragments.

Assembly of the 6426 bp pCal sequence revealed many characteristics typical of a retrotransposon. An obvious feature was the identical 280 bp long terminal direct repeats (LTRs). The borders of these LTRs are short, imperfect, inverted repeats 6 bp long—TGTTGGNCCATCA (SEQ ID NO: 145). This repeat is very similar to that found in the LTRs of TCa1 (TGTTCG), Ty3 (TGTTGTAT), 1731 (TGTTG) and copia (TGTTGGAAT). Within the LTRs putative TATA boxes and a polyadenylation signal were identified. These and other features are highlighted on the sequence of pCal in FIG. 2.

Figures 3A, 3B:
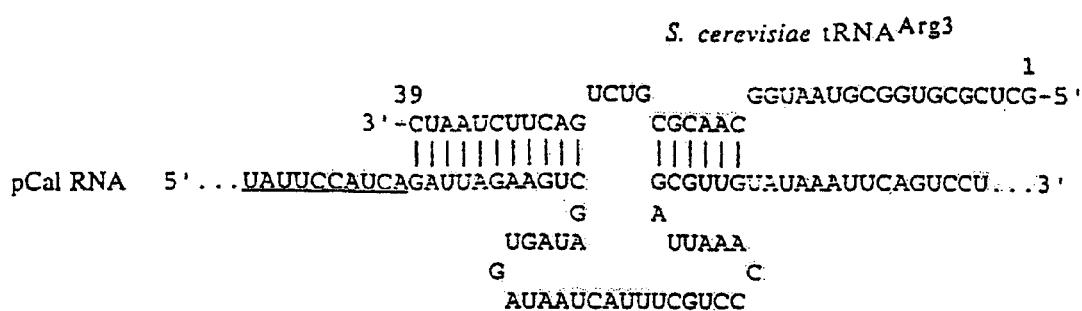
FIG. 3 shows the plus- and minus-strand priming sites of pCal. (A) Minus-strand primer-binding site. The region of pCal around the (−)PBS(SEQ ID NO: 38) (bottom) is shown compared to the first 39 bases of tRNA$^{Arg}$3 of S. cerevisiae (SEQ ID NO: 39)(top). The region of pCal shown here extends from base 271 to 341. The bases of pCal within the LTR are underlined. For clarity, the bases of the tRNA molecule are shown in their unmodified form. (B) A comparison of the polypurine tracts of pCal and TCa1(SEQ ID NOS: 40–42); The TCa1 and pCal 3' PPTs are adjacent to the right LTRs. The pCal internal PPT (bases 3455–3465) is from within the presumed integrase coding region.

The minus-strand primer-binding [(−)PBS] was found adjacent to the left LTR and consists of the sequence GATTAGAAGTC (SEQ ID NO: 146). This is very similar to the (−)PBS of TCa1, GATTAGAAG, but complements 11 bases, rather than 9 of a possible tRNA$^{Arg}$ cleavage product. The *S. cerevisiae* retrotransposons Ty1, Ty2 and Ty3 have been found to contain additional sequences 3' to the (−)PBS which complement additional regions of the primer tRNA. These additional sequences are likely to be involved in the packaging of the primer tRNA within the VLP. An additional region of complementarity is also apparent in pCal—the sequence GCGTTG, approximately 30 nucleotides 3' of the (−)PBS, perfectly complements the sequence CAACGC (bases 19–24) in the primer tRNA$^{Arg}$ fragment (FIG. 3).

A plus-strand priming site or polypurine tract (PPT) was found immediately upstream of the right LTR. It is very similar to the PPT described for TCa1. A second sequence very similar to the 3' PPT was found near the middle of pCal (bases 3455–3465). Internal PPTs which function as plus-strand priming sites have been identified in Ty1 and HIV1 and may serve to speed up the reverse transcription process. The two pCal PPTs and that of TCa1 are compared in FIG. 3. We believe that the internal PPT of pCal may also be serving as a site for plus-strand initiation during the reverse transcription process. TCa1 and pCal have very similar (−)PBSs and PPTs and very similar borders to their LTRs. A comparison of the remainder of the LTRs, however, revealed that the similarity did not extend beyond these regions.

Example 3

The Open Reading Frames

Two long open reading frames were found in pCal, the first 972 bp (324aa) and the second 4728 bp (1576aa) long. Conserved motifs from the four pol proteins— protease, integrase, reverse transcriptase and RNase H—were identified in the second ORF. The order of these motifs (as listed above) places pCal within the Ty1/copia group of retrotransposons. The pCal motifs are shown compared to those of other Ty1/copia elements in FIG. 4. No conserved motifs were found in the first ORF but it is similar in size and position to the gag genes of other retroelements. Retroelement gag genes in general are known to be extremely variable and it is not uncommon for no identifiable conserved features to be present.

Figure 5A:
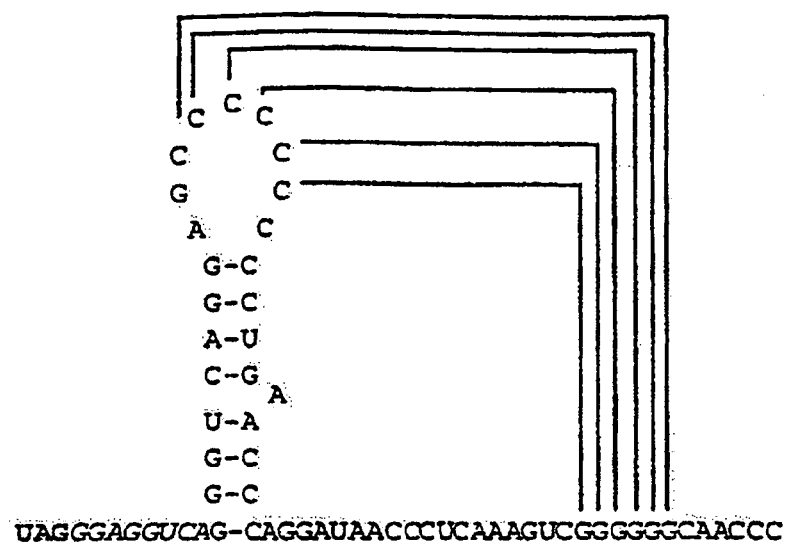
FIG. 5 shows the comparison of the putative pseudoknot structures of Moloney murine leukemia virus (A)(SEQ ID NO: 66) and pCal (B)(SEQ ID NO: 67) at the boundary of their gag and pol ORFs. The stop codons are shown in bold and the 8 bp purine-rich tract in italics. The long lines represent the base pairings in the second stems. Note that in pCal there are two downstream regions to which the first loop of the pseudoknot can anneal. The nucleotides in the bulge of the first stem of pCal also have a downstream region to which they can potentially anneal (bases marked *). Base pairing between these sequences could lead to the formation of an alternative pseudoknot.
Figure 5B:
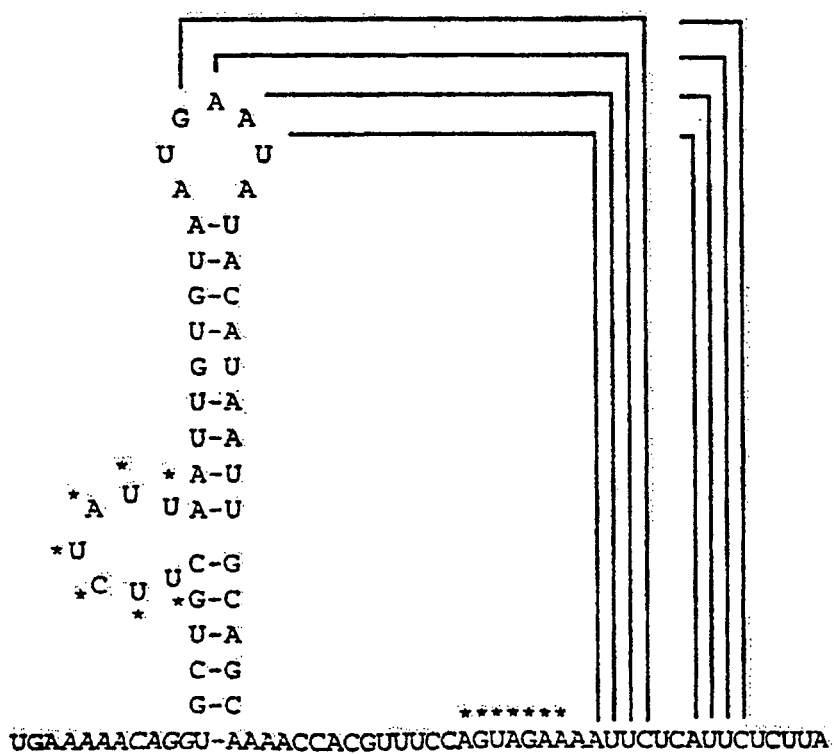

Unlike other retrotransposons, the gag and pol ORFs of pCal are in the same phase separated only by a UGA termination codon. This arrangement is similar to what has been found for mammalian type C retroviruses such as Moloney murine leukemia virus (MMLV). In MMLV a UAG termination codon separates the gag and pol ORFs. Translation of the pol ORF occurs via the occasional read-through suppression of the UAG codon. This suppression requires an 8 bp purine-rich sequence immediately downstream of the stop codon and an adjacent pseudoknot (a pseudoknot being a structural element of RNA formed upon the annealing of the nucleotides of a loop region with nucleotides outside of that loop) (ten Dam et al 1982). In pCal, an 8 bp purine-rich sequence, AAAACAGG, lies immediately downstream of the UGA codon and this is followed immediately by a potential pseudoknot. These features are illustrated in FIG. 5. A further unusual feature is apparent slightly upstream of the UGA codon. It consists of four tandem repeats of the sequence GAAAAA. The role, if any, of this distinctive sequence in the ribosomal gag-pol transition is unclear.

Example 4

Copy Number of pCal

The copy numbers of other extrachromosomal elements from lower eukaryotes have been determined. For instance, the 2 micron circle plasmids of *Saccharomyces* species exist at 50–100 copies per cell and the Ddp elements of Dictyostelium discoideum exist at 50–300 copies per cell. When uncut genomic DNA from the *Saccharomyces* and Dictyostelium species containing these elements is run out on agarose gels the extrachromosomal elements appear as distinct bands running ahead of the chromosomal DNA. The intensity of the bands relative to that of the chromosomal DNA is indicative of the elements' copy numbers. These elements are comparable in size to pCal and the host genomes are similar in size to that of *C. albicans*. Therefore, using the relative intensity of extrachromosomal and chromosomal DNA in *Saccharomyces* and Dictyostelium as a guide, we estimated, from the relative intensity of pCal and hOG1042 chromosomal DNA, that pCal exists at 50–100 copies per cell.

Example 5

Phylogenetic Analysis

Figure 6:
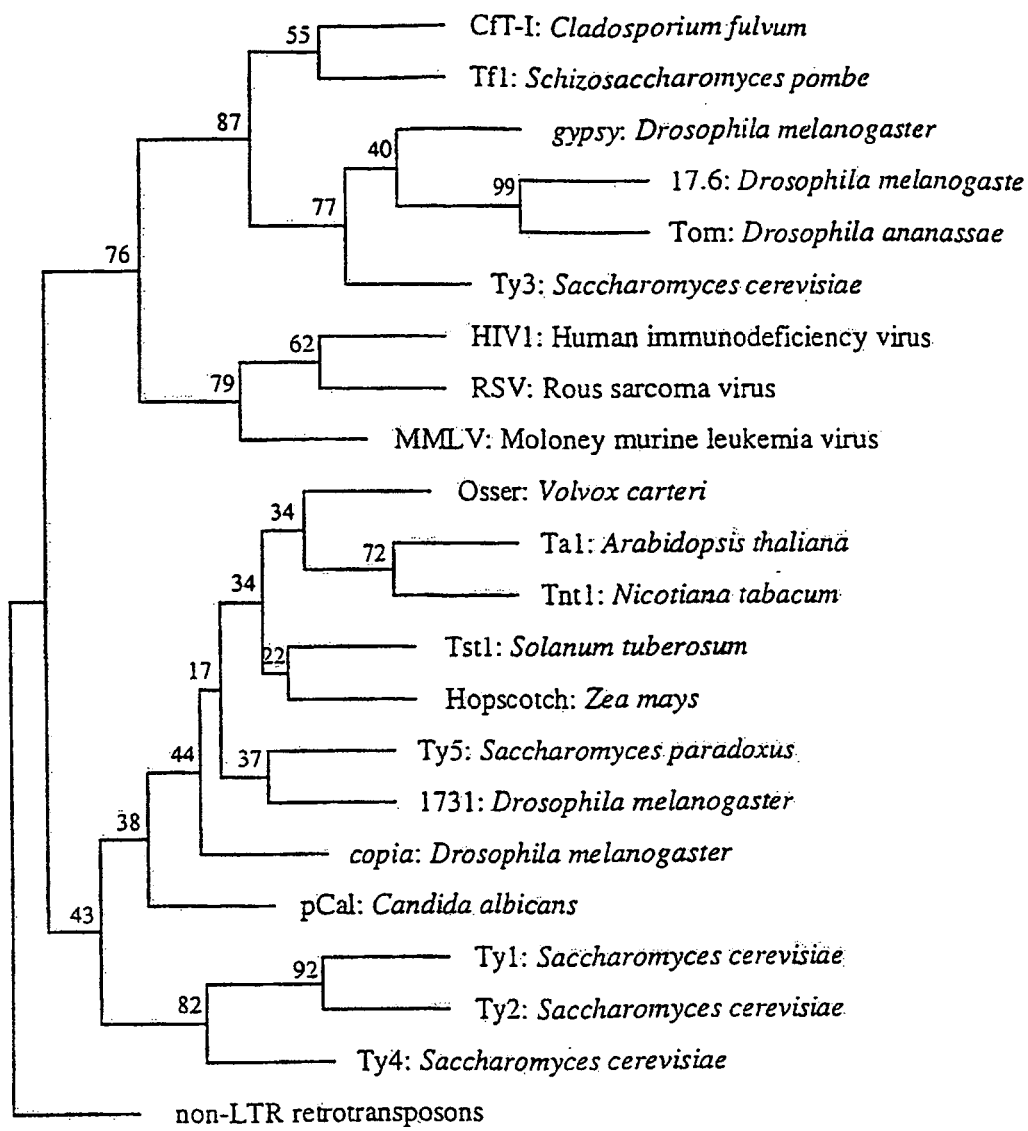
FIG. 6 shows the phylogenetic tree of some LTR retroelements. The data used in the tree construction were the predicted amino acids of the seven conserved domains of reverse transcriptase identified by Xiong and Eickbush (1990). The tree was constructed using the UPGMA method available within the PHYLIP package (Felsenstein (1989). The percentages of trees, from 500 bootstrap replications, supporting each branch are indicated. Non-LTR retrotransposons were used as an outgroup to root the tree. The accession numbers for the sequences of the elements can be found in the Materials and Methods section of the Detailed Description.

In an attempt to gain a better understanding of the relationship of pCal to other retroelements a phylogenetic tree of a number of retrotransposons and retroviruses was constructed. The data used in the analysis were the predicted amino acids of the seven conserved domains of reverse transcriptase identified by Xiong and Eickbush. The tree was constructed using the UPGMA method within the PHYLIP package and is shown in FIG. 6. It is generally consistent with the trees constructed earlier by Xiong and Eickbush. For instance, the retroviruses and the gypsy-type retrotransposons are closer to each other than to the Ty1/copia retrotransposons. Within the retroviral group HIV1 and RSV are closer to each other than to MMLV and within the Ty3/gypsy group CfT-1 and Tf1 form a group as do the *Drosophila* elements 17.6, Tom and gypsy. The tree placed pCal with the Ty1/copia elements. This placement of pCal is in agreement with the fact that pCal has the pol gene order protease—integrase—reverse transcriptase —RNase H. Such an order is diagnostic for Ty1/copia elements. Within the Ty1/copia division two broad groups are apparent. One group contains the *Saccharomyces* elements Ty1, Ty2 and Ty4 and the other contains copia and 1731 of *Drosophila*, Ty5 of *Saccharomyces*, the plant elements Hopscotch, Tst1, Ta1 and Tnt1, Osser from the green alga *Volvox carteri* and pCal. Within this second group pCal is the most divergent element. Similar results were obtained using Neighbor-Joining and Parsimony methods of tree construction.

Example 6

Partial Sequencing of Additional Clones of pCal

At the start of this work all five of the clones of pCal were partially sequenced. When the partial sequences of the three clones carrying the Pst1 site, which represent the left half of pCal, were compared it was found that one clone differed from the other two at a small number of sites. To determine the full extent of these differences, it was decided to completely sequence each of these three clones. When the sequences were compared it was found that two of the clones were identical, but differed from the third clone at twelve sites. The differences were all base substitutions. This finding suggested the possibility that the total population of pCal within a cell might be made up of a number of subpopulations with different sequences. Such a situation could arise in a number ways. For instance, there could be a number of integrated retrotransposons, varying in sequence, each contributing to the pCal population. Alternatively, pCal could be a self-sustaining molecule (ie. independent of any integrated copies) and the inherent inaccuracy of reverse transcriptase could be introducing variation into the system. To investigate this idea further we obtained four additional clones of pCal from a region which differed among the original clones (from the 5' border of the 5' LTR to the Pst1 site at position 905). The region of greatest variability was then sequenced in each of these new clones. Analysis of the sequences revealed that the four new clones were identical in sequence to each other and to the two original clones which had been found to be identical. This result suggests that the majority of the pCal molecules in the total pCal population are likely to be very similar, if not identical, in sequence. One cannot, however, rule out the possibility that more than one integrated retrotransposon is contributing to the pCal population or that pCal is a self-sustaining system.

Example 7

Expression of pCal Extrachromosomal DNA.

Figure 7:
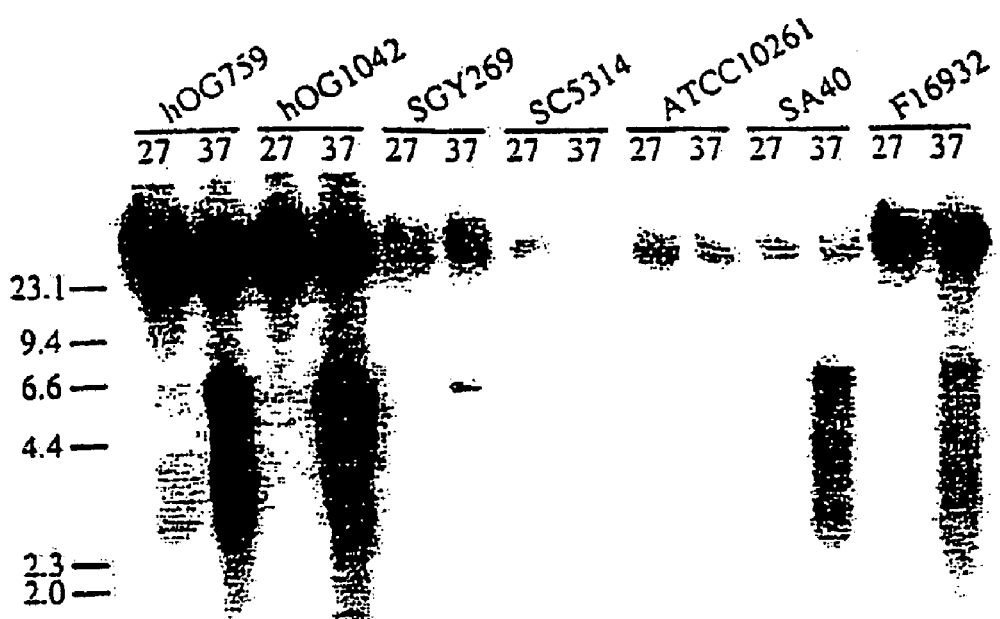
FIG. 7 shows that the expression of pCal DNA occurs in a temperature- and strain-dependent manner. Cultures of the seven indicated C. albicans strains were grown at 27° C. and 37° C. to late log/early stationary phase following which total DNA was isolated. Approximately equal amounts of undigested DNA samples from each culture were then electrophoresed on an agarose gel and transferred to a nylon membrane. The membrane was then probed with an internal fragment of pCal. In the gel-blot shown above, the extrachromosomal pCal forms appear as a band running at about 6.5 kb and a smear of shorter forms running between 3 and 6.5 kb. The integrated chromosomal copies of TCa2 appear as a band at >20 kb.

The TCa2 retrotransposon was originally found as an abundant, linear, extrachromosomal DNA molecule, referred to as pCal, in *C. albicans* strain hOG1042. The level of expression of pCal was so high that it could be seen as a distinct band of about 6.5 kb when uncut hOG1042 DNA was analyzed by agarose gel electrophoresis. The fact that such a band had not been reported in any other *C. albicans* strains suggested that the level of expression of pCal extrachromosomal DNA is much higher in hOG1042 than in any other strain. To examine this idea further we used Southern analysis to compare the level of expression of pCal amongst a variety of *C. albicans* strains. The strains examined included hOG1042 and its close relative hOG759, two recent clinical isolates (SA40 and F16932), and three common laboratory strains (SGY269, SC5314, and ATCC10261). In addition, to see if pCal expression exhibits any temperature-dependence, pCal levels were compared between cells grown at 27° C. and cells grown at 37° C. The results are shown in FIG. 7. The upper bands in the figure, running at >20 kb, represent the integrated forms of the retrotransposon (TCa2). The differences in hybridization intensity of these bands reflect the differences in the copy number of the integrated form (see below). Also, the extrachromosomal, pCal molecules are seen as a band at about 6.5 kb with a smear trailing off below. On other blots distinct bands can be seen in the smears, suggesting that the smears represent incomplete or subgenomic reverse transcripts rather than them being the result of degradation during the DNA isolation procedure. A broad range of fragment sizes, as well as molecules of discrete lengths, have similarly been reported for reverse transcripts isolated from Ty1 particles (Garfinkel et al 1985). With these points in mind it can be seen that pCal expression varies greatly amongst the various strains and that it is strongly dependent on temperature. As expected the highest levels of pCal were found in hOG1042 and the closely related strain hOG759. An abundance of pCal molecules was also found in two other strains, SA40 and F16932. Densitometric analysis indicated that the level of expression in these two strains is approximately a fifth that in hOG1042 and hOG759. A low level of pCal expression was found in two strains, SGY269 and SC5314 (about 50- to 100-fold lower than in hOG1042 and hOG759). The majority of pCal molecules in SC5314 appear to be less than full-length. This seems to be a characteristic of this strain, rather than being the result of degradation of this particular sample, as it was seen consistently with different DNA preparations. The last strain, ATCC10261, produced no detectable extrachromosomal pCal molecules at all. In each strain that produces pCal, a much higher level of pCal expression was found at 37° than at 27°. Densitometric analysis indicated a 10- to 20-fold difference in expression between the two temperatures.

Example 8

TCa2 RNA Expression.

Figure 8:
FIG. 8 shows that TCa2 RNA expression occurs in a similar pattern to the expression of pCal DNA. Total RNA was isolated from cultures of the seven C. albicans strains, grown at 27° C. or 37° C., as for the DNA in FIG. 1. Approximately equal amounts of RNA from each culture were then separated on agarose gels, transferred to nylon membranes and probed with the pCal internal probe. With longer exposures, TCa2 RNA could be detected in all of the strains.

The results showed that the number of pCal molecules per cell varies greatly amongst different strains. This strain-dependent expression could arise in a number of different ways. It could result from strain-specific differences in the efficiency of reverse transcription of the retrotransposon RNA molecules. Alternatively, each of the strains could have a similar potential for reverse-transcription, but there could be widely varying amounts of RNA for the reverse transcriptases to act upon. A combination of these two possibilities could also be responsible. In an attempt to distinguish between these three scenarios, RNA was extracted from each of the seven *C. albicans* strains using cells grown at either 27° C. or 37° C. The RNA was then subjected to Northern analysis using the same probe as in the Southern shown in FIG. 7. The results are presented in FIG. 8. It can be seen, by comparing FIG. 7 and FIG. 8, that the pattern of TCa2 RNA expression is very similar to the pattern of pCal DNA expression. In each strain there is a greater amount of TCa2 RNA in cells grown at 37° C. than in cells grown at 27° C. Densitometric analysis indicates a 5- to 10-fold difference between the two temperatures. Also the strains which produce the largest amounts of pCal DNA, in general, also have the largest amounts of TCa2 RNA. This finding that the observed patterns of pCal DNA and TCa2 RNA expression are very similar, and the fact that pCal is a small, linear, extrachromosomal DNA molecule, however, suggests the possibility that the signals seen on the Northern blot in FIG. 8 may not represent the RNA at all; instead, they might be the result of hybridization to some pCal DNA contaminating the RNA preparations. To test this possibility, RNA samples were treated with DNase-free RNase A for 30 minutes and then compared to untreated RNA samples by Northern blotting using the TCa2 probe (not shown). We found that after the RNase A treatment less than 10% of the hybridization signal remained, indicating that the great majority of the signals seen in FIG. 8 does truly represent hybridization to RNA. In addition, pCal DNA samples were denatured under the same conditions as the RNA, and then also examined by an identical Northern blotting procedure (not shown). We found that, under the Northern blotting conditions, pCal DNA gave only a very weak signal. This suggests that even the hybridization signal that remains after RNase A treatment of the RNA samples is unlikely to be due to contaminating DNA, but rather, is likely to represent incompletely digested RNA.

The similarity in the patterns of TCa2 RNA and pCal DNA expression suggests that the strain-dependent variations in the levels of pCal DNA are largely the result of similar inter-strain variations in the levels of TCa2 RNA. Or put another way, the inter-strain variations in the levels of pCal DNA are introduced mainly at the level of transcription rather than reverse transcription. The inter-strain variations in pCal expression, however, are unlikely to be produced exclusively at the transcriptional stage. It can be seen from FIGS. 7 and 8 that the patterns of TCa2 RNA and pCal DNA expression, though very similar, are not exactly the same. For instance, SGY269 and SC5314 produce significantly more pCal than ATCC10261 yet both of these strains have lower levels of TCa2 RNA than ATCC10261. In addition, F16932 and SA40 have similar amounts of pCal, but F16932 has approximately 5-fold more TCa2 RNA. These differences probably are the result of variations introduced at the level of reverse transcription.

Example 9

Comparison of TCa2 LTRs From Various Strains.

Figure 9:
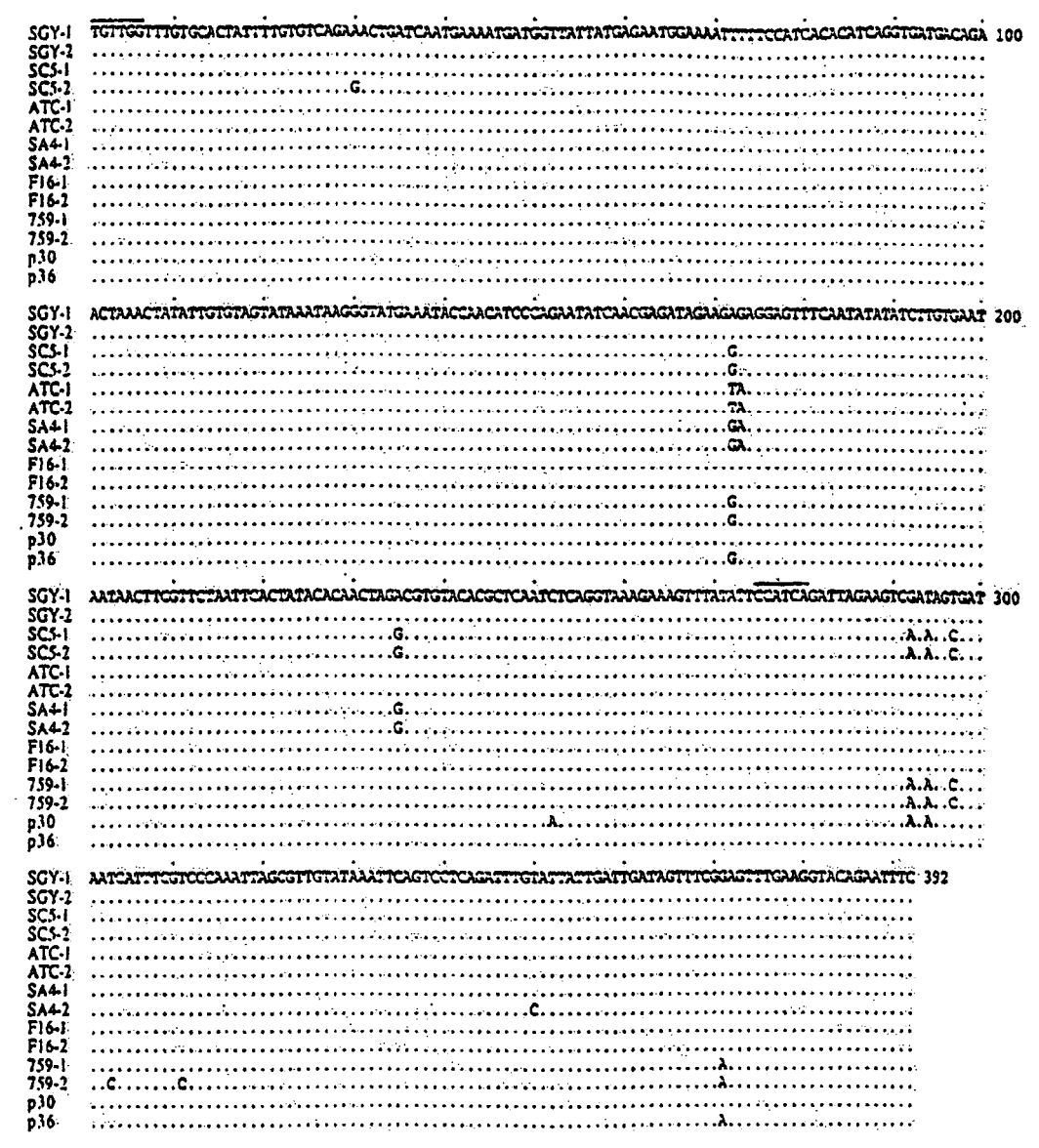

It is possible that the differences in the levels of TCa2 RNA seen in the different strains result from differences in the promoters of the retrotransposons in those strains. As an initial means of testing this possibility we cloned and sequenced the first 400 bp, including the entire left LTR, of TCa2 retrotransposons from each of the various strains. By analogy with other retrotransposons, this region should contain all the major sequences regulating transcription. The sequences are shown compared to each other in FIG. 9. It can be seen that the sequences are all remarkably similar to one another, there being no insertions or deletions and very few base substitutions. The few differences that there are do not seem to fall into a pattern that can be easily explained by relatedness of the various elements. The variations appear to be located in a non-random manner, some sites seeming more prone to variation than others. These variable sites may represent hotspots for mutation during reverse transcription. Within the LTRs, the sequences are identical at 275 out of 280 sites and there is no obvious correlation between the differences and the abundance of TCa2 RNA in the host strains. It therefore seems unlikely that differences in the promoters of the TCa2 retrotransposons in the various strains could account for the observed differences in RNA expression.

Figure 10:
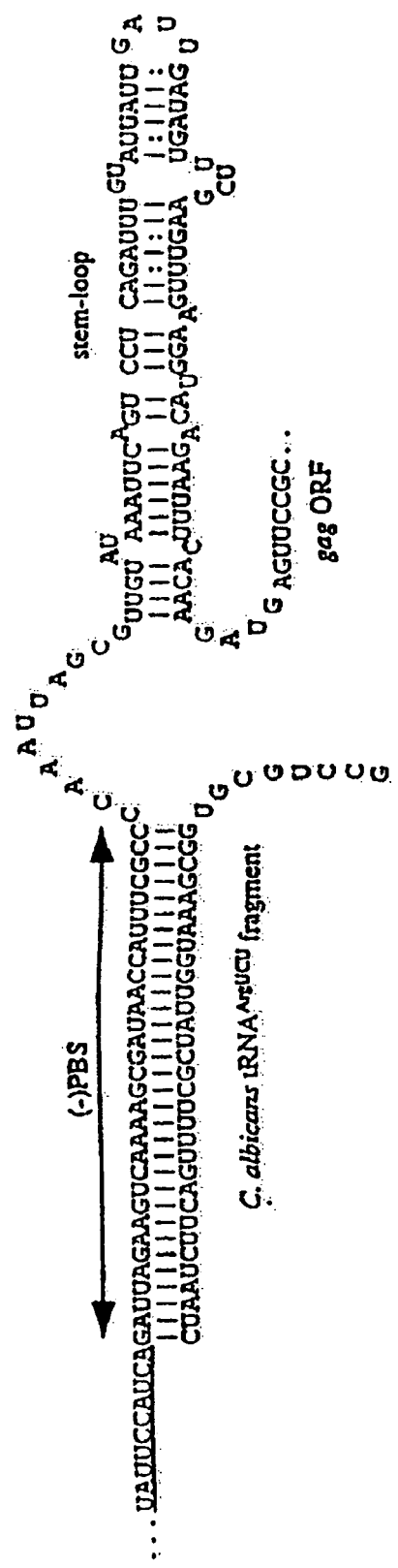
FIG. 10 shows the possible secondary structure of the minus-strand priming complex (SEQ ID NO: 83) The sequence of clone p759-2 is shown as it might appear bound to the C. albicans tRNA$^{Arg(UCU)}$ fragment (SEQ ID NO: 84). The PBS of this clone is a perfect 32 bp match to the tRNA fragment. The remainder of the 5' untranslated region has the potential to form a stem-loop structure. The nucleotides of the retrotransposon from within the LTR are underlined. The AUG codon at the start of the gag ORF is shown in boldface.

An interesting finding that did emerge from this work, though, is that there is variation in the sequence of the minus-strand primer-binding site (PBS). The PBS is a short sequence adjacent to the left LTR which is complementary to part of a cytoplasmic tRNA. The tRNA binds to the retrotransposon RNA at this site and its 3'OH can then be used by RT to prime minus-strand DNA synthesis. In most retrotransposons and retroviruses, the PBS complements the 3' end of the primer tRNA. TCa2, and a few other Ty1/copia retrotransposons, for example Ty5 and copia are exceptions to this general rule in that their PBSs complement an internal region of the primer tRNA and the primer is not a complete tRNA, but rather, a 39- or 40-nucleotide fragment of one. In the original description of the pCal sequence, the PBS was predicted to be 11 bases long, by comparison to tRNA$^{Arg(UCU)}$ of *S. cerevisiae*. Since then the sequence of tRNA$^{Arg(UCU)}$ of *C. albicans* has become available. A comparison of the pCal sequence to this tRNA showed that the homology between the pCal RNA and the tRNA primer extends over 32 bp, although there would be a number of unpaired bases in the PBS-tRNA primer duplex. Comparison of the sequences obtained here, however, shows that the variations found in the PBS region actually give some clones a better match to the tRNA primer fragment than that found in the original pCal sequence. One LTR in particular, isolated from hOG759, has base substitutions relative to the original pCal sequence and these result in a perfect 32-bp match to the primer tRNA. In addition, the region between the PBS and the start of the gag ORF was found to have the potential to form into a stem-loop. The possible secondary structure of the tRNA primer fragment and the 5' region of the TCa2 RNA, as they might appear in the minus-strand priming complex, is depicted in FIG. 10.

Example 10

TCa2 is a Moderately Repetitive Element and May Still be Active.

Figure 11B:
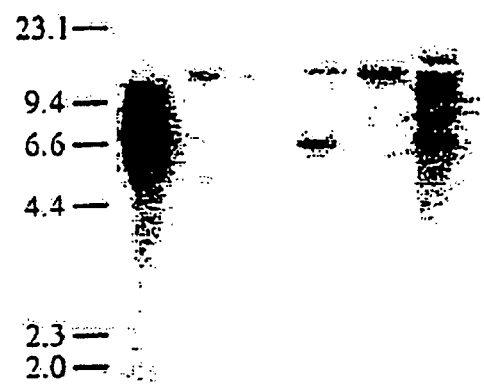
Figure 11C:
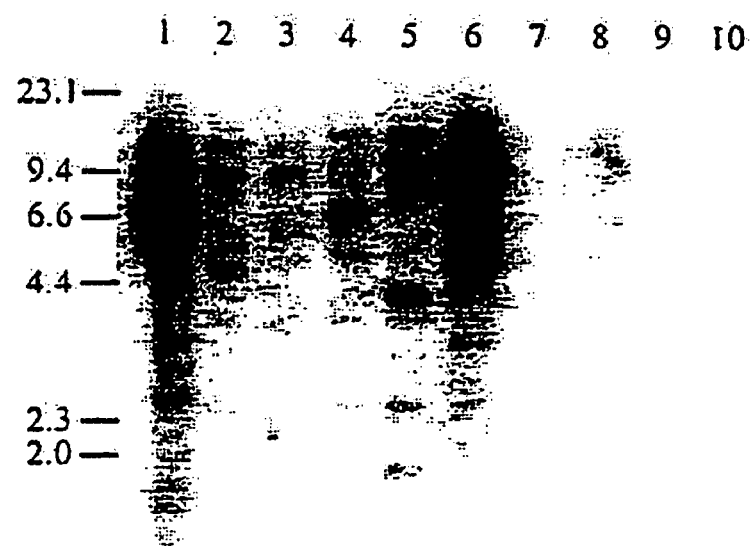

An important unanswered question, which may have implications for the regulation of this system, is: how abundant are the integrated chromosomal copies in the various strains? To answer this question we subjected genomic DNA samples from each strain to Southern analysis using either the internal TCa2 fragment, or the LTR, as a probe (FIG. 11). The DNA samples used were isolated from cells grown at 27° C. to minimize interference from the extrachromosomal copies. Also, to see if TCa2 is specific to *C. albicans* or whether it is also found in other *Candida* species, we analyzed the closely related species *C. maltosa*, *C. parapsilosis*, and *C. tropicalis* and the more distantly related *C. pseudotropicalis*. The locations of the internal and LTR probes and some important restriction sites are shown in FIG. 11A. In FIG. 11B it can be seen that in SGY269, SC5314, ATCC10261 and SA40 the element TCa2 is present at a low copy number—just one or two copies per cell. In F16932 five bands were found that hybridized to TCa2, indicating a moderate copy number in this strain. No hybridization to DNA from any of the other *Candida* species analyzed was detected suggesting that TCa2 is specific to *C. albicans*. This was true even when the blot was reprobed at lower stringency and exposed for a long period of time (not shown). In FIG. 11C it can be seen that the TCa2 LTR is more abundant in SGY269, SC5314, ATCC10261, and SA40 (5 to 7 copies per cell) than the full-length retrotransposon. The number of LTRs in F16932 is hard to tell from this exposure because the bands are close together. Analysis of a variety of different exposures, however, revealed about 12 bands hybridizing to the LTR in this strain (not shown).

Figure 12:
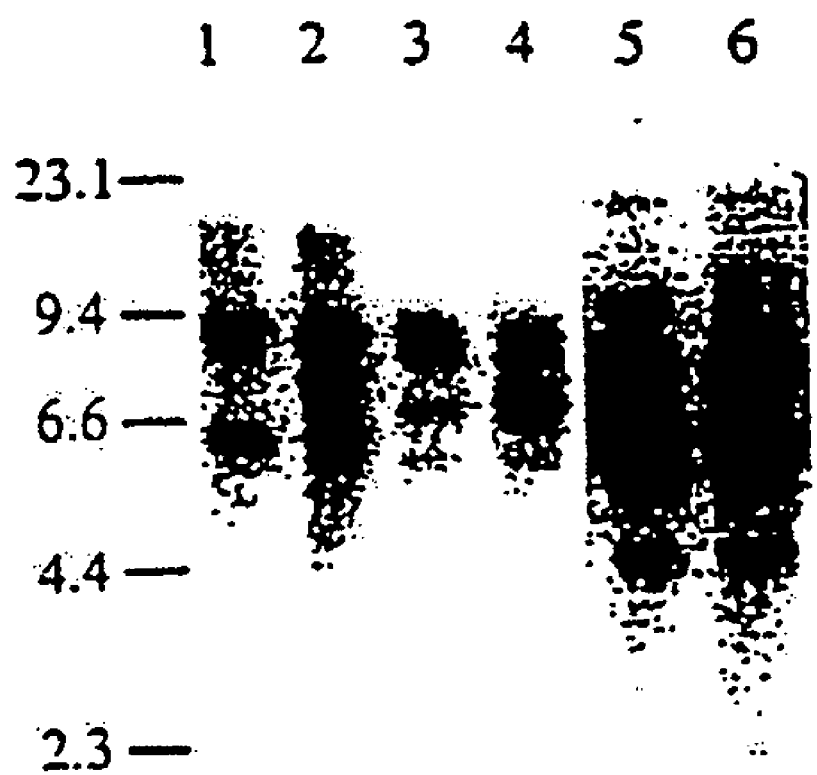
FIG. 12 shows the determination of TCa2 copy number in hOG759 and hOG1042.

Determining the copy number of TCa2 in hOG1042 proved to be more problematic. Even though the DNA used was isolated from cells grown at 27° C. (in which the expression of pCal is 10- to 20-fold lower than in cells grown at 37° C.—FIG. 7), it was found that the signal from the extrachromosomal copies overwhelmed any signal from the integrated copies to such an extent that no bands could be distinguished (lanes 1, FIGS. 11B and 11C). To get around this problem we purified the intact chromosomal DNA away from the extrachromosomal copies of pCal by separating the two on agarose gels, then extracting the chromosomal DNA from the gels. This was done for both hOG1042 and the closely related strain hOG759. The copy number of TCa2 in each strain was then determined by Southern analysis (FIG. 12). Three different enzymes, PstI, EcoRI, and ClaI, were used to cleave the DNA prior to electrophoresis. The number of bands detected varied depending on which enzyme had been used. Four or five bands were detected in PstI-cut DNA. Four bands were found when EcoRI had been used and eight or nine were detected in ClaI-cut DNA. Each of these enzymes cuts TCa2 on just one side of the probe so the bands detected should represent DNA molecules containing a fragment of TCa2 and the flanking DNA out to the nearest cleavage site for each enzyme. These fragments will generally be of different sizes and so will appear as separate bands. However, in the situation where the distance out to the nearest flanking restriction site is similar for retrotransposons at two different genomic loci, then the resulting fragments will comigrate in the gel and give a single band of increased intensity. The finding that the TCa2 probe hybridizes to different numbers of bands depending on the enzyme used, as shown in FIG. 12, and that the bands vary in intensity (for example, FIG. 12, lane 1) suggests that the brighter bands represent more than one integrated TCa2 retrotransposon. In such a situation the digest giving the greatest number of bands, and bands the most similar in intensity, is the most reliable indicator of copy number. Here this is the ClaI digests. Even in the ClaI digests, however, some bands appear at greater intensity than others suggesting that they may also represent more than one integrated copy of TCa2. Taking this into account, and given that the ClaI digests give 8 or 9 bands, we estimate that there are 10 to 12 integrated copies of TCa2 in hOG759 and hOG1042. Overall, the hyridization patterns found for hOG759 and hOG1042 are very similar. Interestingly, however, they are not identical. In the PstI digests (FIG. 12, lanes 1 and 2) hOG1042 has a band at about 7.5 kb that is not found in hOG759. In the EcoRI digests (lanes 3 and 4) the two strains give the same bands, but the band at about 7 kb is brighter in hOG1042. Again, in the ClaI digests (lanes 5 and 6) hOG1042 has a band at about 11 kb that is not found in hOG759. Together, these findings suggest that there is at least one more copy of TCa2 in hOG1042 than in its close relative hOG759. Given the abundance of full-length copies of the retrotransposon in these strains, the most likely explanation for this finding is that a copy of TCa2 has integrated into the hOG1042 genome in the short time since the divergence of this strain from hOG759.

It is interesting to note that the number of integrated copies of TCa2 in each strain correlates fairly well with the levels of TCa2 RNA produced by each strain. For instance, the highest amounts of TCa2 RNA are found in hOG759 and hOG1042, which also have the greatest number of integrated copies. F16932, with about 5 integrated copies of TCa2, has the next highest amount of RNA, and SGY269, SC5314, ATCC10261, and SA40, with 1 or 2 TCa2 elements apiece, have only low levels of TCa2 RNA. It is not a simple, or linear, correlation however: hOG759 and hOG1042 produce at least 50 times as much TCa2 RNA as SGY269, SC5314, etc. but they have just 10 times as many integrated copies. This indicates that additional factors, as well as TCa2 genomic copy number, are involved in generating the variable levels of TCa2 transcripts.

Example 11

An Integrated Copy of TCa2.

The sequence of pCal was primarily based on two clones that were derived from the pool of extrachromosomal copies in hOG1042. To determine if this sequence is typical of the TCa2 retrotransposon family, or if it differs in some important way from the integrated copies, we constructed a λ-library of hOG759 DNA and from it we cloned and sequenced a full-length, integrated copy of TCa2. The sequence of this copy of TCa2 (GenBank accession no. AF050215) is very similar to that of pCal. Over their entire length of 6426 bp the two elements differ at only three sites, each of these differences being the substitution of one base for another. Two of these base substitutions occur in the region encoding the RT and the other is in the RNase H coding region. The base changes do result in changes to the predicted amino acid sequence of the RT and RNase H proteins. It is possible that these amino acid alterations result in significant differences in the catalytic properties of the RTs and RNase Hs. Whether or not such changes play a role in the over-production of pCal in some strains is uncertain. It may be instructive to compare the sequences that we have determined of TCa2 and pCal with the sequence of a copy of TCa2 from a strain which produces only low amounts of pCal, such as SGY269 or SC5314. In any case, the finding that an integrated copy of TCa2 has an almost identical sequence to pCal indicates that there are no major sequence differences distinguishing the extrachromosomal forms of this retrotransposon from the integrated copies.

The DNA sequence of the regions flanking the integrated copy of TCa2 was also determined (not shown). Starting about 800 bp upstream of the retrotransposon is sequence virtually identical to that of the 5' regions of the *C. albicans* CDR1 gene (Prasad et al 1995), which has been assigned to chromosome 3. About 100 bp downstream is the start of an ORF that bears a strong resemblance to the 5' regions of cytoplasmic dynein heavy chain genes found in some other fungi. A *C. albicans* sequence containing an ORF that bears a strong resemblance to the central region of other fungal cytoplasmic dynein heavy chain genes has previously been assigned to chromosome 3. These findings indicate that the cloned copy of TCa2 is located on chromosome 3, between CDR1 and a gene encoding cytoplasmic dynein heavy chain. Using PCR and primers corresponding to sequences on either side of the TCa2 integration site we were able to amplify and sequence, from hOG759, another allele without an integrated retrotransposon. This work revealed, therefore, that this locus is heterozygous for the presence of TCa2, and it also showed that the insertion of TCa2 resulted in a duplication of 5 bp (ACACG) at the integration site, as is commonly found with other retrotransposons.

DISCUSSION OF RESULTS OF EXAMPLES 7–11

Expression of pCal DNA is strongly dependent on temperature and varies greatly among *C. albicans* strains. The expression of TCa2 RNA occurs in a similar pattern to that of the pCal DNA, suggesting that the variations in pCal expression are introduced predominantly at the level of transcription. A comparison of the 5' sequences of TCa2 retrotransposons from various strains, however, failed to identify any intrinsic differences which could account for the observed strain variations in expression. Some elements, though, were found to have very long tRNA primer-binding sites, which may predispose them to efficient reverse transcription. The integrated TCa2 form was found to be a moderately repetitive element, present at 1 to about 10 copies per genome. TCa2 copy number correlates well with TCa2 RNA expression, but is insufficient to account for all the strain variation, suggesting the involvement of other factors. Sequence analysis of an integrated copy of TCa2 showed that it is very similar to pCal and is inserted between two closely placed genes. Variation in TCa2 copy number between two closely related strains suggests that the element is still transpositionally active.

Example 12

Further retrotransposons have been found. These are shown in FIGS. 17–48.

Isolation of the *C. albicans* retrotransposon sequences began with a search for sequences similar to *C. albicans* retrotransposon sequences present in the EmbI Nucleotide Sequence Database (Stroger et al 1988) release 56, using the BLASTN program (Altschul et al 1990, 1997) version 2.0.4. A total of 28 similar sequences were identified in the proprietary Pathoseq™ database (Incyte Pharmaceuticals Inc Palto Alto Calif., USA). These are different from the complete retrotransposon sequences presently available, or extend the partial retrotransposon sequences presently available.

The majority of the retrotransposons are not complete. However these partial retrotransposons can, for example, be usefully used as probes to identify the full sequences.

The partial sequences can be used as probes for the complete sequence if one was screening a DNA library. The full length retrotransposon sequences are themselves potentially useful as variants of the described TCa2. As an example the LTR promoter of TCa2 shows a different activity pattern (eg, temperature inducibility) to another unrelated retrotransposon TCa1. The retrotransposon TCa1 is less transcriptionally active at 37° than 27° while TCa2 is more active at 37° than 27°.

Retrotransposon 15 (FIG. 32) is complete and can be used in an expression and disruption system. For example, it can be used to provide an expression vector which includes retrotransposon 15, and could be used in a gene disruption system in *Candida*.

It may also be used as a transformation and expression system for *Candida* comprising the retrotransposon.

Example 13

The Production of auxotrophic mutants from a strain iB65 (the original strain from which all the pCal carrying strains were derived) and its derivatives. This example shows the appearance of an auxotrophic mutant allele in the strains derived from iB65.

i) The strain was isolated from an undergraduate mouthwash (ib=intermediate Biology) in 1984. iB65 was heterozygous for a methionine auxotrophy and gave rise (following UV irradiation) to a number of homozygous methionine auxotrophs in 1984 including hOG-Met5;

ii) hOGMet5: (Met). This strain was exposed to N-methyl-N-nitro-nitrosoguanidine mutagenesis and gave rise to numerous red adenine auxotrophs (some termed hOG 758-hOG762). Some of these were ade1 and some ade2. An unusual feature was that some (for example hOG759:Ade1 Met) were completely non-revertible.

iii) Strain hOG762 (Ade2Met) was exposed to a further round of UV irradiation in 1988 and gave rise to numerous auxotrophs of a unique type. These auxotrophs required either aspartic acid or proline or alpha keto-glutarate. They are some kind of glyoxylate/TCA cycle mutant. We have never encountered TCA cycle mutants before or since. These auxotrophic mutants, like the ade1 mutant described above, were absolutely non-revertible even after mutagenesis. This is most unusual for *Candida* mutants. Strain hOG762 must have become heterozygous for the Asp/Pro mutant allele. It therefore acquired the characteristic of producing 'Asp/Pro' auxotrophic homozygous derivatives.

We believe that the non-revertible ade 1 and asp/pro mutant alleles produced in these strains were generated by insertions of TCa2. Such an insertion would give a non-revertible mutant allele.

The pCal carrying strains gave rise to non-revertible mutants (as would be expected given the abundance of linear retrotransposon DNA).

We have tested this hypothesis by comparing the Southerns of hOG1042 (a strain carrying the asp/pro mutant allele heterozygously) and hOG759 (FIG. 15). There is an additional band present in hOG1042 (EcoR1 Lane 4, Cla1 Lane 6) which is what would be expected if hOG1042 carries an additional copy of TCA2 integrated into the mutant asp/pro allele.

We have also tried to find evidence for TCA2 retrotransposition in strains of this family in the absence of any mutagenesis or phenotypic change. This is shown in FIG. 16, most obviously in Lanes 6 and 11. In general the strains that show extra bands following the EcoR1 digest also show bands following a Cla1 digest. This helps confirm the strains are carrying extra copies of the TCa2 retrotransposon.

These Southerns demonstrate that TCa2/pCal is retrotranspositionally active. If the element is transposing at this frequency in the absence of selection then in the presence of selection it should be relatively easy to isolate strains carrying disrupted alleles.

There are several ways of applying selection but the simplest would be to include a selectable gene within the retrotransposon.

The asp/pro allele is an example of gene disruption by the retrotransposon.

Examples 14–18 show the characterisation of the integrated form of TCa2 and a comparative analysis of its expression.

Example 14

The use of TCa2 as an Expression System and as a Transformation System: Construction of a Vector System with the Candida albicans Retrotransposon pCAL The aim was to create a vector system based around the C. albicans retrotransposon-like element. The plasmid pRPU3 was constructed in which a URA3 sequence was placed within the retrotransposon at the very end of the ORF2 coding sequence adjacent to the 3' untranslated region. The URA3 is on its own promoter and it functions to confer prototrophy on ura3 auxotrophs following transformation. This demonstrated that a selectable gene, such as URA3, can be placed in this position and still function.

Materials and Methods

Microbial Strains and Plasmids

For in vitro plasmid construction and for plasmid amplification the E. coli strain DH5∂ was used (Woodcock et al., 1989).

The strain from which pCAL was isolated was hOG1042, a C. albicans auxotrophic isolate, derived from an oral isolate by mutagenising the parental strain and selecting for red adenine auxotrophs.

Four other yeast strains were used in the transformation of the retrotransposon based plasmids. These were SGY269, GSY112, MIB1 and CHAU1. They were selected as recipients for the transforming DNA because of their uridine auxotrophies and defined genotypes. SGY269, a C. albicans strain derived from the parental strain A81-Pu by directed mutagenesis (Kelly et al., 1987) has the genotype ade2/ade2, ura3::ADE2/ura3::ADE2. GSY112 is a haploid ura3 and leu2 auxotrophic S. cerevisiae strain, Mat ura3 pep4::HIS3 prb1—DI.6R leu2::hisG can1 cir°(Wagenbach et al., 1991). MIB1 is a S. cerevisiae strain constructed for this work and is auxotrophic for both adenine and uridine. It was created by crossing a1.0 (Woods and Bevan, 1965) with GSY112. The diploids were sporulated and an ade1/ura3 was purified. CHAU1, a C. maltosa strain (Ohkuma et al., 1993) has the genotype his5/his5 ade1/ade 1 ura3/ura3.

Plasmid DNA used in the construction of the retrotransposon based plasmids were the kind donations of various labs. Plasmid pET3 was provided by E. Y. H. Tsay (Gillium et al., 1984), pSM7 was provided by M. B. Kurtz (Kurtz et al., 1987) and pRC2312 was provided by R. Cannon (Jenkinson et al., 1988). The E. coli plasmids pUC19 (Yannish-Perron et al., 1985) and pBluescript (Short et al., 1988) were used in the cloning exercises. pK19 and pUCK1 are plasmids in which the kanamycin cassette from M13 mp18–19 (Markie et al., 1986) was inserted into the ScaI site of pUC19. pUCK1 however lacks some of the restriction sites in the cloning cassette. pNRE1 is a plasmid containing the kanamycin cassette from M13 mp18–19 as an EcoRI fragment in pUC19 and made ampicillin sensitive by removing the PvuI portion of pUC19.

Oligonucleotides

Two primers, CalR and CalF were designed to create a unique NsiI restriction endonuclease recognition site (ATG-CAT) at the very end of the POL of pCAL. The overlapping primers match the pCAL sequence at all but one position to provide a site for the insertion of a selectable marker. The mismatch is a T instead of an A in the fourteenth position of CalR and the complementary A as the tenth residue of CalL. The sequence of CalR is 5' GATACAAAATGCATTAACG-GCAG3' (SEQ ID NO: 147) and the sequence of CalL is 5' CTGCCGTTAATGCATTTTGTATC3 (SEQ ID NO: 148, These primers were used in conjunction with the universal forward and reverse primers complementary to pUC19.

Another pair of primers was designed to amplify the C. albicans URA3 gene from the plasmid pET3 with PstI restriction sites on the ends. The underlined portion of (5'CGACGGCTGCAGTTCTTCAATGATGATTTCAAC3') (SEQ ID NO: 149), is complementary to the upstream region of the gene described by Losberger and Ernst (1989), and the underlined portion of 3URA (5'CGACGGCTGCAGCCT-TCACATTTATAATTGGC3') (SEQ ID NO: 150) is complementary to the 3' end of the gene but not including any non-coding regions. Primers were also designed to amplify the URA3 gene and the retrotransposon LTR after the two had been cloned adjacent to each other in the plasmid pRPU3 (described later). A primer corresponding to the 5' end of the URA3 gene, URAXMAS1, and a primer complementary to the 3' end of the right LTR, 3LTR, were synthesised. URAXMAS1 (5'GCGAGATCTAGATATGACAGT-CAACACTAAG3') (SEQ ID NO: 151) A contains a synthetic XbaI restriction site and allows a fusion construct to be made in frame with PCR products derived from CAL2 and CAL5 (described below). No promoter sequences are amplified with this primer. 3LTR (5'CGACGCCTGCAG-GTGATGGAATATAAACTTTC3')(SEQ ID NO: 152) contains a synthetic PstI restriction site. The underlined region is that which is complementary to the 3' end of the retroelements right LTR.

Three primers were designed to amplify portions of the retroelement for further analysis. CAL1 (5'AGTGAGCTCT-GTTGGTTTGTGCACT3') (SEQ ID NO: 153) contains a synthetic SacI restriction site and the underlined region complements the 5' end of the left LTR. CAL2 (5'GCGTCTAGAAATTCTGTACCTTC3') (SEQ ID NO: 154) is complementary to a region of the 5'LTR just upstream of the gag ORF. CAL2 in conjunction with CAL1 allows for the amplification of the left LTR. CAL5 (5'GCGTCTAGAACATTCCAGTGAAGT3 (SEQ ID NO: 155) complements the region spanning the UGA stop that separates the gag and pol ORFs. A single base mismatch changes the TGA stop to a TGT codon. Both CAL2and CAL5 contain XbaI restriction sites to allow the fusion of the URA3 gene (in frame in the case of CAL5). CAL5 in conjunction with 101F (TCTAAGCTACCAAAGCAC) (SEQ ID NO: 156) enables the amplification of a portion of the gag ORF and removal of the stop codon so that the gag and pol ORFs are contiguous.

DNA Manipulations

Plasmid DNA isolation and plasmid subcloning; recombinant plasmid construction; and restriction mapping were all performed according to Maniatis et al., (1982). Transformation of E coli DH5∂ was performed according to the method of Maniatis et al., (1982) with some modifications. Instead of recovering in SOC media, 500 μl of TB was used. Cells were plated onto BB plates (10 g/L Tryptone, 8 g/L NaCl) with antibiotic selection. DNA fragments were purified after electrophoresis in low melting point agarose (FMC Bioproducts, USA) using agarase (GELase™, Epicentre Technologies, USA) according to the manufacturers instructions.

Construction of pRPU3 (a Marked Element)

The pCAL retrotransposon was originally discovered as a linear extrachromosomal element in *C. albicans* strain hOG1042. It was cloned into pUC19 as two halves using a central Asp718 site. The resulting clones each had one Asp718 site, the other destroyed during the cloning procedure, as expected.

Two of these clones, p30 and p36, represent the 5' half of pCAL, whilst another two clones, p5 and p45, represent the 3' end of the element. An EcoRI site in the cloning cassette of p30 was subsequently destroyed by digesting the plasmid with EcoRI, filling in the ends with Klenow and religating. This plasmid, p30E*, was then digested with Asp718 and BamHI and the retrotransposon fragment from a similarly digested p45 was ligated in. The new plasmid, pUCCAL, was sequenced. pUCCAL has the same structure as the native retrotransposon. However further sequencing of p36, p5 and additional clones of pCal revealed that the two fragments used to create pUCCAL differed from all the others, presumably because of point mutations incurred in the reverse transcription.

The following describes the construction of a plasmid with DNA sequence that conforms to the most common form of pCAL; construction of a NsiI restriction site within this sequence; and the addition of a selectable marker and a *C. albicans* origin of replication. The cloning strategy is shown in FIG. 49. Separate PCR products were generated using the primer CalL and the universal primer of pUC19, and CalR and the reverse primer of pUC19. The template was p45E*, a plasmid containing 979 bp of the 3' end of the retrotransposon from p45. PCR products were joined using the new NsiI site, cloned into pUC19 and the plasmid was named pNsi. The EcoRI/HindIII fragment from pUCCAL was replaced with the EcoRI/HindIII fragment from pNsi. The presence of the NsiI site in the resulting plasmid, pCALNsi, was confirmed by restriction digest.

The plasmid containing the *C. albicans* URA3 gene, pET3, was used as the template for another PCR reaction. The primers 5URATT and 3URA were used to produce a URA3 gene with synthetic PstI restriction sites at each end. This was cloned into pUC19 and named pURA25TT. The URA3 gene was cut out of the pURA25TT using PstI and ligated into the NsiI site of pCALNsi creating pCNURATT. The orientation of the URA3 gene was confirmed by restriction analysis. pCNRUATT represents the complete pCal retrotransposon cloned into pUC19. It has a *C. albicans* URA3 gene cloned into a synthetic NsiI restriction site at the 3' end of the pol ORF. The URA3 gene is expressed off its own promoter.

The intention of this construction was that as the retrotransposon was tagged with a selectable marker it could be analysed in auxotrophic hosts. As analyses of the other clones representing the integrated form of pCAL progressed, some additional steps were required to replace portions of the plasmid represented by p30 or p45 that were not the most common sequence of pCal. There was four differences over some 3.5 kb between p45 and p5 and twelve differences over a similar area between the clones p30 and p36. One of the differences between p5 and p45 was an in frame stop in p45. The following changes were made to render the retrotransposon portion of the plasmid identical to the most common sequence of pCAL. A StyI/Asp718 fragment from pCNU-RATT was replaced with the same fragment from p5 creating pRPU1. All of the retrotransposon sequence from p30 and all of the pUC1 g sequence of pRPU1 was replaced with p36 resulting in pRPU2. This was achieved by linearising p36 with Asp718 and BamHI and ligating the Asp718/BamHI fragment from pRPU1 into this.

The last step in the construction of a plasmid that would be capable of replicating in both *E. coli* and *C. albicans* was to add the *Candida* Autonomously Replicating Sequence (CARS). This was done by first subcloning the CARS element as a SphI fragment from pRC2312 into pUC19. The CARS element was then transferred to pRPU2 as a HindIII/BamHI fragment, creating pRPU3.

Construction of Reporter Gene Plasmids

Two plasmids were constructed for use as reporter genes. Both of these contain a CARS element and the *C. albicans* URA3 gene (see FIG. 50). The URA3 gene and the right LTR were amplified by PCR using pRPU3 as the template. The primer URAXMAS1 was paired with 3LTR. The resulting PCR product was cloned into XbaI/PstI digested pK19 and named pUX1L. The XbaI/PstI fragment was then cloned into pCARS creating the plasmid pUX1LC. A fragment of the retroelement was amplified by PCR from p36. The primer CAL2 was used with the primer CAL1 to generate a 0.4 kb product. A kanamycin resistant clone of p36 (p36K) was used as the initial recipient for this PCR product. The product was cloned using the synthetic SacI and XbaI restriction sites designed as part of the plasmid. This plasmid was labelled p36Kf1. The XbaI/SacI fragment from this plasmid was then cloned into pUX1L and labelled pTIM2. Expression of the URA3 gene in pTIM2 is driven off the LTR promoter.

The plasmid p36f4UX1LC contains a CARS and the *C. albicans* URA3 gene which both function in *S. cerevisiae*. A PCR product was made using the 101F and CAL5 PCR primers and pRPU3 as a template. It was cloned into p36K using the synthetic XbaI restriction site of CAL5 and an internal Bg/II site. From this plasmid, p36Kf4, the SacI/XbaI fragment was cloned into SacI/XbaI digested pUX1LC creating p36f4UX1LC. The URA3 gene in p36f4UX1LC is present as an in frame fusion to the pCAL pol ORF.

Construction of Plasmids for In Vivo Recombination in *C. maltosa*

The *C. maltosa* ADE1 gene has been cloned in the plasmid pRA2 (Sasnauskas et al., 1991). The gene was cloned from pRA2 into pUCK1 as a BamHI fragment and labelled pNRE2 (see FIG. 51). From this plasmid it was cloned as a SspI fragment into HindII digested pUC19 and named pNRE3. The HindII fragment containing the kanamycin cassette from pNRE1 was ligated into SmaI digested pNRE3. The resulting plasmid, pNRE4, was restricted with Ecl136/DraI and the fragment containing the kanamycin cassette and the ADE1 gene was cloned into the SspI site of pUC19 to create the ampicillin sensitive, kanamycin resistant plasmid pNRE5. Thus pNRE5 is a pUC19 based plasmid containing the adjacent kanamycin resistance cassette and *C. maltosa* ADE1 gene inserted into the ampicillin resistance gene.

Construction of Plasmids for In Vivo Recombination in *S. cerevisiae*

The *C. albicans* ADE2 gene from pSM7 was excised using EcoRV and blunt-end ligated into SmaI digested pBluescript destroying these sites. The resulting plasmid, pBSAde2, was linearised with EcoRV and the kanamycin element from pNRE1 was blunt-end ligated in as a HindII fragment. The kanamycin element and the ADE2 gene are adjacent in this new plasmid, pBSKanAde2. A fragment containing the first 900 bp of pCal was cloned into SmaI/PstI digested pUC19 and labelled pSP2. The kanamycin element and the ADE2 gene was excised from pBSKanAde2 as an Asp718/SacI fragment and ligated into Asp718/SacI restricted pSP2. Thus the adjacent kanamycin resistance cassette and C. albicans ADE2 gene are flanked by pUC19 on one side and pCal on the other.

Transformations

The C. albicans, C. maltosa and S. cerevisiae strains were all transformed using the method of Kelly et al., (1988) with some modifications. A 50 mL YPD culture was grown to an $OD_{600}$ of 0.7–1.3 After washing the cells in 1 M sorbitol they were resuspended in 20 mL SCE, 22 µl β-mercaptoethanol and 150 µl of 1 mg/mL zymolyase 20T (Seikagaku Kogyo Co., Ltd, Tokyo). They were spheroplasted at 27° C. until the $OD_{600}$ of 50 µl of cells in 1 mL of water showed a 50% drop compared to the 1 M sorbitol reference. After washing the cells they were suspended in 1 mL STC and incubated with the transforming DNA at room temperature for 10 minutes. 1 mL of PEG solution was added and the cells were incubated at room temperature for a further 10 minutes. The cells were pelleted and recovered in 1 mL of SOS at 27° C. for 90 minutes. This was then plated in an osmotically buffered overlay onto minimal media. Some incubation steps were performed at 37° C. for the C. albicans and C. maltosa strains.

Plasmid Extraction from Yeast Strains 50 mL YNB cultures supplemented with histidine were inoculated with the transformants and incubated at either 27° C. (S. cerevisiae) or 37° C. (C. maltosa). Confluent cultures were spun down and the pellet resuspended in 10 mL 10 mM Tris, 50 mM EDTA, pH 7.5. The cells were pelleted again and resuspended in 10 mL 50 mM EDTA, pH 9.5 and 200 µL β-mercaptoethanol. After incubation for 15 minutes at room temperature the cells were pelleted again and resuspended in 10 mL 1 M sorbitol, 100 mM EDTA, pH 7.5 (SE). To this 50 µL 1 mg/mL zymolyase 20T was added. After 90 minutes incubation at 37° C. the cells were pelleted. The pellet was resuspended in 10 mL SE with 100 µL 10 mg/mL pronase and 1 mL 10% SDS. This was incubated at 37° C. for 60 minutes. This was then extracted with an equal volume of phenol:chloroform (1:1) twice. Two volumes of 95% ethanol was added and the precipitate spun down. The DNA pellet was resuspended in 100 µL TE. This was transformed into E. coli from which transformants containing the yeast plasmid were purified according to Maniatis et al., (1982).

Results

Site Directed Mutagenesis

Using a plasmid containing the 5' end of the retrotransposon (p45E*) as the template, two PCR reactions were performed. One used the universal forward primer and CalL and the other the reverse primer and CalR. Each of the resultant PCR products were gel purified. The purified universal/CalL product was digested with Eco RI and NsiI and the reverse/CalR product was digested with BamHI and NsiI. The digested fragments were ligated into EcoRI/BamHI restricted pUC19. The resulting plasmid, pNsi, contained the NsiI restriction site as confirmed by restriction analysis. Sequencing of pNsi confirmed that there were no other changes. The A at position 6135 of pCAL was changed to a T, resulting in the change ATGCAA to ATGCAT.

In Vitro Plasmid Construction

The construction of pRPU3 was achieved by conventional cloning methods. The intermediate constructs were confirmed as being correct by restriction analysis.

Steps in which portions of the new plasmid were derived from PCR products or steps where the insert was replacing a fragment of similar size, were verified as being the desired product by sequencing the relevant region. Similarly the intermediates and final products in the construction of pTIM2, p36f4UX1LC, pNRE5 and pSPKanAde2 were analysed by restriction analysis and sequencing where appropriate.

Transformation of S.cerevisiae, C. maltosa and C. albicans

The three yeast strains transformed in this work represent the species from which the retrotransposon was isolated C. albicans (SGY269), a closely related species C. maltosa (CHAU1) and a more distantly related species S. cerevisiae (GSY112). Each of these yeasts were transformed with the newly constructed plasmid, pRPU3, and a plasmid known to transform efficiently both C. albicans and S. cerevisiae, pRC2312 (Jenkinson et al., 1988). The relative numbers of transformed cells per µg of transforming DNA are shown in FIG. 52. The efficiency of transformation was determined for each of the yeasts. One pRPU3 transformant was found for every 400 viable cells in each of the strains. There was more variation in the pRC2312 transformations ranging from 1/1300 successfully transformed cells for S. cerevisiae GSY112 down to 1/10 000 for C. albicans SGY269. The successful expression of the URA3 gene required the transcription termination signals from the right LTR of the retroelement. These results suggest that the signals for transcription termination are present in the LTR and function effectively in all three yeasts.

In addition the C. maltosa strain CHAU1 was transformed with pTIM2 and linearised pNRE5. When the cells were plated onto minimal media supplemented with histidine they required either exogenous adenine and uridine or the plasmids carrying the genes which enabled the cell to make these products. The URA3 gene was carried on the plasmid pTIM3 and this plasmid could stably maintain itself as it contained the CARS from pRC2312. The ADE1 gene however is carried on a plasmid that is not only linearised and hence unstable in yeasts, but also has no CARS and as such cannot be maintained as an independent DNA molecule in the cell. The ways in which a cell transformed with pTIM2 can survive on histidine supplemented media include recombining the plasmids with each other, recombining the linear DNA into the genome such that it is maintained by the hosts origins of replication, or alternatively have the adenine and uridine auxotrophies revert. Transformants were obtained that were able to survive on the histidine supplemented media. All of the transformants when purified onto complete media and grown overnight in 50 mL YEP media lost the ability to grow on media lacking uridine or adenine. This indicates that the function of prototrophy was carried by one plasmid which was lost when its maintenance was not required. The natural promoter signals and the transcription termination signals for the ADE1 gene are contained within the plasmid outside the retroelements LTRs. The URA3 gene in both pTIM2 and p36f4UX1LC (used in the S. cerevisiae in vivo transformation) is not driven off its own promoter as it is in pRPU3. It is driven by the promoter signals in the left LTR and in p36f4UX1LC it is part of a fusion construction with the gag gene of pCAL.

The S. cerevisiae strain MIB1 was transformed with the linearised pSPKanAde2 and p36f4UX1LC. As with the C.

*maltosa* transformation described above, the linearised DNA must recombine with genomic DNA or with a plasmid carrying an origin of replication in order to complement both auxotrophies. pSPKanAde2 has extensive homology to the pCAL and pUC19 portions of p36f4UX1LC which allows preferential recombination with between the plasmids rather than illegitimate recombination into the chromosomes. p36f4UX1LC transformants were obtained on media supplemented with adenine. Similar numbers were obtained from a p36f4UX1LC/pSPKanAde2 transformation on adenine supplemented media. Of these transformants up to 10% were also able to grow on minimal media, indicating that the in vivo recombination occurs with some efficiency even without selection. Growth of these transformants on complete media results in the inability to grow on media lacking either uridine or adenine indicating that recombination has occurred between the plasmids.

In Vivo Plasmid Construction

The Ade1/Ura3I auxotrophic yeast *C. maltosa* CHAU1 was transformed with pTIM2 and linearised pNRE5. pTIM2 contains the *Candida* Autonomously Replicating Sequence (CARS) and the URA3 gene, and as such is maintained in Ura3 auxotrophic yeasts as a multi-copy plasmid. pNRE5 will complement the Ade1 auxotrophy but is unable to maintain itself as an independent element. To confer the functionality of the gene it must recombine with some other DNA that is stably maintained. After selecting transformants that were able to complement both auxotrophies we passaged colonies on complete media and repurified them on media lacking adenine and/or uridine. The colonies were unable to grow under these conditions indicating that the function conferred by the ADE1 and URA3 genes was found on a plasmid or plasmids. Genomic DNA preparations were performed and plasmids rescued by *E. coli* transformation. The plasmids were selected for their ability to confer resistance to kanamycin and replica plating showed that they were ampicillin resistant. Plasmid preparations showed that there was only one plasmid and that it was larger than either of the parental plasmids, pNRE5 or pTIM2. Restriction analysis showed that this new plasmid contained restriction fragments unique to each of the parental plasmids and hence was a chimera of the two.

Similarly the Ade2/Ura3 auxotrophic yeast *S. cerevisiae* MIB1 was transformed with a plasmid containing a CARS and the *C. albicans* URA3 gene, p36f4UX1LC, and a linearised plasmid containing the *C. albicans* ADE2 gene, pSPKanAde2. Transformants were selected that complemented the Ura3 auxotrophy and were subsequently purified onto medium lacking adenine. About 10% of the transformants that grew on the medium lacking uridine also grew on medium lacking adenine. After plating the cells on complete medium they lost their ability to grow on media lacking adenine and/or uridine indicating that this ability was conferred by plasmid DNA. Genomic DNA preparations from these cells were made and the plasmids rescued by *E. coli* transformation. Plasmids were selected for their ability to confer resistance to both ampicillin and kanamycin. Plasmid preparations showed that there was a single plasmid larger than either parental plasmid. Restriction analysis showed that the new plasmid, contained restriction fragments unique to both p36f4UX1LC and pSPKanAde2.

DISCUSSION

Transformations

By constructing and transforming plasmids with different features we have been able to demonstrate that the new *C. albicans* retrotransposon like element, pCAL, contains promoter and transcription termination signals. In the plasmid pRPU3, a marker gene, URA3, was ligated into the 3' end of the pol gene of pCAL. The URA3 gene contained its own promoter sequence but no transcription termination signals. Thus to be successfully expressed when transformed into the yeasts a message could be driven off either its own promoter or that of the retroelement, but it was reliant on the polyadenylation signal in the right LTR to terminate transcription. The successful transformation of three Ura3 auxotrophs, *C. albicans* SGY269, *C. maltosa* CHAU1 and *S. cerevisiae* GSY112, indicates that not only is the polyadenylation signal functional in the host species but that it works in at least two other yeast species. pTIM2 and p36f4UX1LC also contain the *C. albicans* URA3 gene, however neither of these plasmids contain the URA3 promoter sequence. pTIM2 has the left LTR and non-coding sequence of pCAL immediately upstream of the URA3 gene while p36f4UX1LC has the URA3 gene as a fusion product with the gag gene of pCAL. pTIM2 and p36f4UX1LC where shown to function in *C. maltosa* CHAU1 and *S. cerevisiae* MIB1 respectively. In addition they both function in *C. albicans* (data not shown).

In Vivo Recombination

We report the in vivo recombination of two plasmids in both *S. cerevisiae* and *C. maltosa* as a method for constructing plasmids too large to be easily constructed in E. coli or for constructing plasmids where there are no unique restriction sites available. Selection of recombinant plasmids only requires that one plasmid contain a autonomously replicating sequence and that the other plasmid contains a selectable marker. As both of the plasmids are reliant on each other for expression and maintenance there is positive selection for legitimate recombination. In the *C. maltosa* CHAU1 transformation the homology between the pUC 19 derived portions of pNRE5 and pTIM2 was used to direct recombination.

The MIB1 transformation results show that recombination occurs without selection in up to 10% of the transformants. This is significant because it suggests that the recombination machinery preferentially associates with naked DNA rather than chromosomal DNA.

The plasmids constructed by in vivo recombination are potentially useful for the analysis of the frequency of transposition under various conditions. By including a marker gene (URA3) within the LTRs and one external to the LTRs (ADE) of a complete retrotransposon or a functional portion of it, the frequency of transposition can be determined by analysing the preparation of cells which maintain prototrophy after growth on complete media. The majority of cells will lose the functionality with plasmid loss. Others will become prototrophic for one or both of the defects due either to retrotranspositoin or recombination. Transposition will integrate everything between the LTRs including the URA3 gene. These colonies will be auxotrohpic for adenine and prototrophic for uridine. Recombination between homologous regions of the plasmid and the genome (such as the LTRs or the marker genes) will result in the incorporation of plasmid information from both within the LTRs and outside of them. The resulting colony would be prototrophic for both adenine and uridine. The possibility of reversion of the phenotypic markers becomes increasingly important when analysing rare events such as retrotransposition. Where transposition occurs there will be an increase in the number of LTRs which can be detected by Southerns, whereas reversion of the phenotypic markers will result in no increase in LTR numbers.

The presence of a strong promoter within the LTRs is not repressing expression of the adjacent URA3 promoter. Such repression has been encountered in other systems extending over several kilobases (the "Temin" effect). The most effective way to use selection is to have the prototrophic gene (such as URA3) placed on its own promoter backwards with respect to the retrotransposon (adjacent to the 3'UTR). The prototrophic gene is disrupted with an intron which is aligned forwards with respect to the retrotransposon. In this situation the URA3 gene is non-functional (because of the intron) unless the whole element has been transcribed, the intron removed and the retrotranscript reintegrated. In other words all the URA transformants are due to retrotransposition (rather than say random integration of the plasmid). This is the system used in *Saccharomyces* and *Schizosaccharomyces*.

Taken together we believe that these results demonstrate that TCa2 is an active retrotransposon. This is further supported by the observation that the Southern pattern of strains differs—suggesting an active retrotransposon. If TCa2 is active it follows naturally that it should function to disrupt genes at the new integration site. The pRPU3 results indicate th at TCa2 can be 'tagged' with a URA3 gene expressed from its own promoter.

Example 15

Use of TCa2 as an Expression System and as a Transformation System

We have demonstrated that there is a very strong, temperature regulated promoter in the LTRs of TCa2. This is established by the abundant RNA as measured by northern blots. This is of considerable value as there is no other strong inducible promoter in *Candida*. Most genes from *S. cerevisiae* do not function in *Candida* and this is probably due to a promoter specificity (the reverse does not hold, most *Candida* genes do work in *S. cerevisiae*). This means that one can not use the *S. cerevisiae* expression systems in *Candida*. In addition we have demonstrated that the LTR promoter will work in *Candida* by placing a *Candida* URA3 gene in phase and adjacent (just 5') to the initiator methionine of ORF1. Such plasmids (pTIM1/2) function in *Candida* and confer URA3 prototrophy on Ura-auxotrophs. This establishes that the promoter is working. Such transformations are, we think, reasonably efficient and the transformants are reasonably stable. A curious and interesting observation may explain this. Strains transformed with pTIM plasmids show an obvious band on agarose gels. This DNA is not pTIM. It does not hybridise with TCa2. It is in fact circular extrachromosomal copies of the ribosomal repeat element. The *Candida* replication origin used in pTIM is called CARS. It was derived from *Candida*. It is a part of the ribosomal repeat structure. We believe that the abundant RNA transcribed from the LTR promoter in pTIM (and similar) is resulting in the cell 'up regulating' the ribosomal system by producing free circular replicating rDNA plasmids. This would explain the circular DNA in pTIM transformants. If the upregulation is also acting on the CARS element carried by pTIM then the system will up regulate itself in a positive feed back loop. That is to say; the LTR driven RNA transcription up regulates the pTIM CARS which results in more replication of pTIM and more copies of pTIM. This will result in more transcripts from the LTRs and therefore even greater up regulation of pTIM. The bottom line is you get an efficient transformation and stable (more or less) transformants.

Example 16

Use of a pCal Construct to Induce Random Mutagenesis

In order to 'tag' the retrotransposon the intention was to use an inverted ('back to front') intron inserted within a reporter gene (URA3). Such an inverted intron would prevent URA3 phenotypic function unless the intron is removed from the transcript (FIG. 73).

There is no experimental work on introns in *Candida*. So we selected one possible candidate, the very small intron (mini-intron) from the peptide transporter gene (Basrai et al 1995). This was amplified by PCR and inserted into the URA3 gene in both the forward and backward direction (FIG. 74). The forward was a control to make sure the peptide transporter intron would splice. As expected, it did.

Again, as expected, the backward intron failed to splice, even though it was the identical sequence put into the identical URA3 site.

We have now mounted this URA3/inverted intron element onto a retrotransposon plasmid putting the element into a (synthetic) Nsi1 site at the 3' end of the coding sequence. We have also added an ADE2 element between the right LTR and the *Candida* ARS (CARS). This is summarised in FIG. 75.

In theory the retrotransposon will transcribe from the left LTR to the right LTR, the transcript will have the intron spliced out and the spliced elements will be converted into DNA by reverse transcriptase and integrated. The URA3 element will then be transcribed off its own promoter to give a URA$^+$ phenotype. There are possible problems to do with the pURA3 element interfering with transcription of the retrotransposon or the reverse transcriptase but these can only be found, and fixed empirically. The ADE2 was added to the plasmid to give positive selection (as the URA3/intron is non-functional in the plasmid).

The plasmid is quite large and therefore not that easy to work with but it has been completed. The plasmid has been transformed into two ADE2$^-$URA$^-$ strains, one carrying a URA3 point mutation and the other a URA3 deletion (a small deletion) (FIG. 76). ADE2$^+$ transformants were selected and grown at 37° C. to encourage retrotransposition. Cultures were then plated on minimal medium+adenine. The plasmid is lost under these conditions and only URA$^+$ variants (retrotranspositions?) can grow. Both strains gave URA$^+$ derivatives. The URA$^-$ point mutation is reasonably stable and the URA$^-$ deletion completely so. We, therefore, are sure that these URA$^+$ variants are not revertants. They are, we believe, a mixture of retrotransposition and gene conversion. There is very little literature on gene conversion in *Candida*.

Gene conversion between the URA3 and the URA3/inverted intron allele can generate a URA$^+$ allele that will have the wild-type Southern allele pattern.

The URA3+ colonies generated in these experiments were analysed by Southern analysis to confirm the presence of a new copy of TCa2 containing the URA3+ gene (FIG. 55). The URA3+ colonies derived from L11051R all appear to contain the same putative retrotransposition event. The clones derived from L1963R appear to contain different events, since several different sized bands are observed. However, some of the URA3+ colonies appear not to contain extra bands.

Some of the URA+ variants are clearly due to gene conversion. Some are clearly not due to gene conversion. They give new and various bands which we think indicates retrotransposition into random sites.

Example 17

Further Analysis of URA3+

We have done further analysis of the URA3+strains thought to be carrying a new retrotransposition (URA3+ and having 'unusual' Southerns when probed with a URA3 probe) (FIG. 55).

Specifically we have done 'inverse PCR' (IPCR) after a TaqI (4base cutter) digest of the DNA and self-ligation. The IPCR primers correspond to:

i) the URA3 gene (interrupted by the peptide transporter intron); and ii) the boundary of the URA3 and TCa2 LTR.

These should only give a product following a retrotransposition event since the intron must be removed before primer i) will work (FIG. 77).

The inverse PCR products have been sequenced from several independent URA3+ and the sequence confirms that there has been a retrotransposition (the intron has gone) and that there is an additional retrotransposon integrated into a novel site in the genome.

In summary the system works. So far all the integrations are in different sites.

Results are shown in FIGS. 59–62.

The ABI PRISM DNA sequence chromatograms of FIGS. 59 and 60 show that the URA+ tagged retrotransposon has undergone retrotransposition and integrated into a new site in the *Candida* genome. In other words it is an actual example of a random tagged integration/mutation event.

Specifically:

DNA was isolated from the URA+ *C. albicans*, digested with the restriction enzyme TaqI, self-ligated and subjected to inverse PCR. The resulting PCR product was cloned and sequenced from the 'universal' forward and reverse primers.

The sequence H963RU59 defines the exact integration site of the retrotransposon.

This integration site falls within the ORF of a membrane protein. This is not a unique event, the table (FIG. 58) describes other integration events.

These integration sites do not seem to be associated with tRNA genes or LTR sequences from Tca2 or other retrotransposons. The integrations seem to have occurred at a wide variety of sites. The integration site sequences show no obvious homology to each other. In as far as a generalisation can be made on the present data, the Tca2 integrase seems to prefer to integrate near to the 5 end of coding sequences (ORFs). This may be within the ORF (as in strain H963RU59) or within several hundred base pairs 5 to the ORF. Such integration will potentially inactivate the ORF expression, down-regulate or up-regulate the ORF expression or alter the regulation of expression (for example, make expression of the ORF temperature sensitive).

This pattern of integration is unlike that of any previously described retrotransposon integrase. For example, in *Saccharomyces cerevisiae* Ty1, Ty2, Ty3 and Ty4 integrate near tRNA sites, while Ty5 integrates into telomeric DNA. The Tca2 integration pattern is unlike those integrases previously described and therefore could not be predicted. The use of Tca2 as a random integration system is therefore a non-obvious application of this retrotransposon.

Example 18

Evidence of Temperature Dependent Retrotransposition

Strain hOG 1042, which contains TCa2, was grown in liquid culture (Yeast extract, Peptone,Glucose) at 37° C. Serial subcultures were made every day for 3 weeks. A number of single colonies from this liquid culture were isolated on solid medium and DNA extracted from them. These DNA samples were included in a Southern analysis, where the probe used would hybridise to the 3' region of the POL gene of the integrated retrotransposon.

The results of this Southern (FIG. 16) indicate the presence of one or more new bands in many of the strains cultured over the 3 weeks as compared to the original hOG 1042. It is assumed that these new bands represent the presence of TCa2 integrated at new genomic loci. This implies that TCa2 has actively retrotransposed to generate new copies of itself at new positions. The size of the new band(s) vary from strain to strain, indicating that the new integration sites are different in each individual strain.

Example 19

Vector Construction

The initial phase of the project involved the construction of a vector that could be used to characterise retrotransposition events in *C. albicans*. This vector contains the retrotransposon TCa2 and a selectable marker gene with an intron inserted. The URA3 gene, from *C. albicans*, was chosen as the selectable marker. Since the URA3 gene does not contain a native intron, a small intron from a *C. albicans* peptide transporter gene was used.

Insertion of an Intron into the ura3 Gene

The intron of the peptide transporter gene was inserted into the URA3 gene, close to the start of the open reading frame (ORF). This location was used since most *C. albicans* introns are located near the front of ORFs. The URA3 gene used contains only a short promoter region (130 bp) and no transcription termination signal so as not to interfere with the transcription of the retrotransposon. The intron was inserted in both forward and reverse orientations (with respect to the URA3 gene) to allow analysis of the intron processing. The intron-containing URA3 gene was placed into TCa2 near the end of the pol gene, in both orientations (FIG. 59).

It was found that the URA3 gene in these constructs was functional only when the intron was placed in the normal orientation with respect to the URA3 gene. In addition the URA3 gene was functional in either orientation with respect to TCa2. Therefore the intron is capable of being processed correctly.

A construct was then produced which contains the URA3 gene in the reverse orientation with respect to TCa2 and an intron inserted into this gene in the forward direction with respect to TCa2. In addition an ADE2 gene and *Candida* autonomously replicating sequence (CARS) were also present on this vector. The resultant vector was transformed into an ura3' ade2° *C. albicans* strain (hOG963). Transformants were selected using the ADE2 marker. Transformants were grown overnight in minimal media supplemented with uridine and then plated on minimal media containing adenine but lacking uridine. If retrotransposition had occurred then URA3+ colonies would be produced as a result of splicing of the reverse intron from the URA3 gene and therefore restoration of a functional gene (FIG. 63). Several such colonies were produced, however they all appeared to be the result of gene conversion of the plasmid borne URA3 gene with the native URA3 gene. It was therefore decided to integrate the vector in the hope that this would reduce the frequency of gene conversion.

Integration of the Retrotransposition Vector

The CARS from the plasmid used in the previous analysis was removed resulting in the plasmid pRUIA (FIG. 60). This plasmid was digested at the unique Xba I site (within the ADE2 gene) and transformed into two ura3− ade2− strains of C. albicans, hOG963 and hOG1051, giving rise to the strains H963R and H1051R, respectively. A schematic diagram of the integration is shown in FIG. 60. Southern analysis of strains containing the integrated pRUIA is shown in FIG. 61.

Expression of the Tagged TCa2 is Temperature Sensitive

It is known that in some C. albicans strains (for example hOG1051) TCa2 is expressed at higher levels at 37° C., as compared to cultures grown at 27° C. To insure that the full tagged TCa2 was being expressed Northern analysis was performed (FIG. 62). Results of this analysis indicate that the TCa2 construct containing the URA3 gene is expressed as one long transcript.

Retrotransposition in C. albicans

The strains H1051R and H963R (containing the integrated pRUIA) were used to analyse retrotransposition of TCa2. Since retrotransposition occurs via a mRNA intermediate the intron inserted into the URA3 gene can be processed before reverse transcription of TCa2. The double stranded DNA copy of the retrotransposon is then integrated into the host genome. Since the URA3 gene has had the intron removed it can produce a functional protein. A diagram of this process is shown in FIG. 63.

C. albicans strains containing integrated pRUIA (H1051R and H963R) were grown overnight in rich medium (YPD) then plated on minimal media. If retrotransposition has occurred then URA3+ colonies are produced. An example of a typical experiment is shown in FIG. 64.

The strain hOG1051 is known to overexpress TCa2 (FIG. 62). The derivative H1051R gave rise to approximately 10-fold more URA3+ colonies than H963R. The estimated rate of URA3+production for H1051R is approximately $10^{-5}$ URA3+ colonies/cell plated.

The URA3+ colonies generated in these experiments were analysed by Southern analysis to confirm the presence of a new copy of the TCa2 containing the URA3+ gene (FIG. 65).

The URA3+ colonies derived from H1051R all appear to contain the same putative retrotransposition event. The clones derived from H963R appear to contain different events, since several different sized bands are observed. However, some of the URA3+ colonies appear not to contain extra bands.

Inverse PCR of Tagged Retrotranspositions

In order to analyse the putative retrotransposition events further inverse PCR was used to determine the sequence flanking the 3' end of the tagged TCa2. A PCR primer was designed to the boundary of the URA3/TCa2 and another primer to the site of intron insertion in the URA3 gene. These two primers are specific for the tagged retrotransposon, since the URA3/TCa2 boundary is unique to the integrated vector and any retrotransposon insertions which result. The second primer requires that the intron is removed, thereby only allowing the generation of PCR products from retrotransposition events. Primers were designed so inverse PCR could be performed with the restriction enzymes Taq I or Nla III. Both of these enzymes have a four base pair recognition sequences. It was expected that this would allow inverse PCR of any integration events since these enzymes cut frequently in the genome. A schematic diagram of the inverse PCR strategy is shown in FIG. 66.

Initially the inverse PCR products were cloned and sequenced, however once the inverse PCR was optimised the PCR products could be directly sequenced.

Analysis of Insertion Sites of the Tagged TCa2

Analysis of the Ty retrotransposons of S. cerevisiae indicates the presence of some target site specificity. Ty3, for example integrates 1–4 nucleotides from the start site of RNA polymerase III transcription start sites; Ty1 integrates close to tRNA genes while Ty5 inserts near telomeres. Although Ty1 tends to integrate close to tRNA genes, insertions into coding sequences have also been observed. From analysis of pre-existing TCa2 insertions in the public database a target-site preference similar to those of the Ty elements is not observed. Instead, the data suggest that TCa2 has a preference for inserting into the noncoding DNA adjacent to ORFs.

Analysis of tagged TCa2 retrotranspositions reveals the occurrence of two main types of events, in this system. Insertion site sequences obtained from URA3+ colonies of H1051R all appear to be the result of homologous recombination with TCa2 LTRs. The parental strain of H1051R is known to contain an abundance of TCa2 linear DNA, it is possible therefore that homologous recombination is occurring since there may not be a sufficient level of the retrotransposon integrase.

Target site sequences obtained from H963R URA3+ colonies again show some events which appear to be the result of homologous recombination into LTRs, however these account for only about 40% of the events analysed. It should be noted that the proportion of recombination events appears to vary between experiments. The remainder of sequences analysed have target site sequences not previously found next to TCa2 elements; these events are thought to be genuine retrotransposition events. To date the genomic location of 14 insertions have been determined by comparison of the flanking sequences with the assembled C. albicans genomic sequence from the Stanford sequencing project. In addition one insertion was found in a repeat sequence, and three other insertions could not be assigned to a contig because the sequence obtained was too short, or that region had not been sequenced. These sequences have not been included in the analysis presented. Open reading frame maps of the regions flanking the TCa2 insertions are shown in FIG. 67. With the exception of one insertion into a gene (H963RU59) all other events are in the intergenic regions between ORFs. No evidence could be seen for an association with tRNAs or RNA polymerase III transcription sequences, as is seen for Ty1 and Ty3.

In order to determine the target site preference of TCa2 various analyses have been performed. There appears to be a strong preference for intergenic regions. FIG. 68 shows the distribution of insertion sites in relation to the nearest ORF. This may be the result of integration occurring via an interaction with transcription factors. If this were the case then it would be expected that there would be a preference for the control regions of promoters. In support of this argument most insertions are closest to the 5' end of ORFs, rather than in the 3' region (FIG. 67).

An attempt was made to determine if there is any sequence specificity for the insertion site. A region 500 bp either side of the insertion site was analysed for sequence patterns, however no consistent pattern was observed, indicating that there is no absolute sequence specificity of the TCa2 integrase. The only sequence pattern that could be determined for the integration site is a preference for AT rich sequences close to the insertion site (FIG. 69), however this observation may be biased by the AT richness of *C. albicans* intergenic sequences.

These findings are consistent with the above proposal that TCa2 integration sites are determined by the distribution of transcription factors, rather than by the integrase interacting directly in a sequence-specific manner with the target site DNA.

Removal of Marker Genes Following Retrotransposition

In order to construct further gene disruptions in strains which have undergone tagged retrotransposition it would be desirable to have selectable marker in these strains. Both the ADE2 and URA3 genes used as markers in these experiments are able to be removed, allowing reuse of these markers. Removal of the URA3 gene should be possible through homologous recombination between the LTR sequences. Such an event should result in the presence of a single LTR (solo LTR) at the site of insertion (FIG. 70). It has been demonstrated in one of the H963R URA3$^+$ strains that the URA3 gene can be removed by selection with 5-fluoroorotic acid (5-FOA). Analysis of these ura3' revertants is currently in progress.

In a similar way recombination between ADE2 genes surrounding the integrated pRUIA results in the loss of the vector. These cells are now ade2$^-$ and can be selected by their red colour on selective media. This event can be seen in H963RU1 (FIG. 65). Note the loss of the band which corresponds to the integrated pRUIA.

Discussion

Analysis of the complete 6426 bp sequence of pCal revealed that it is a free (i.e. unintegrated), double-stranded DNA form of a new retrotransposon belonging to the Ty1/copia group. Initially, no significant similarity at the nucleotide level was found between pCal and any other sequence in the databases. This was not considered surprising, however, because reverse transcriptase has no editing function, so reverse transcriptase-based elements have a higher mutation rate than those utilising other polymerases. A more appropriate and useful analysis was to look for the conserved functional motifs expected to be present. Such areas have tight evolutionary constraints and are often similar, even in highly divergent elements such as copia and gypsy. A close examination of the sequence revealed that pCal has many of the features commonly found in retrotransposons. Such features include the 280 bp long terminal direct repeats (LTRs) with short inverted repeats and putative transcriptional initiation and termination signals, a (−)PBS adjacent to the left LTR, a PPT adjacent to the right LTR and two long ORFs, the first similar in size and position to the gag ORFs of other retroelements and the second containing motifs homologous to pol ORFs. Within the gag ORF of pCal no nucleic acid binding motif could be identified. A $CX_2CX_4HX_4C$ nucleic acid binding motif is found within the gag ORF of some retrotransposons of the Ty1/copia group, for example Ta1, copia, 1731 and Tp1. However, this motif is not found in the functional retrotransposon Ty1. Taken together, all the features required for retrotransposition appear to be intact in pCal suggesting that it is likely to be a functional retrotransposon.

The order of the motifs within the pol gene of pCal (protease—integrase—reverse transcriptase —RNase H) suggests that pCal is a member of the Ty1/copia group. In agreement with this a phylogenetic analysis, based on the reverse transcriptase genes of a diverse range of retroelements, also placed pCal within the Ty1/copia group (FIG. 12). This analysis, however, also revealed that pCal has no close relatives within the known set of Ty1/copia retrotransposons: pCal was placed as the most divergent element in a large group of retrotransposons containing representatives from plants (Ta1, Tnt1, Hopscotch and Tst1), insects (copia and 1731), a green alga (Osser) and yeast (Ty5). It is probable that the reverse transcriptase of pCal is functional and so, therefore, this placement of pCal is probably a genuine reflection of the divergent nature of this element, rather than being the result of the unselected accumulation of random mutations.

Within the LTRs of pCal there was no extended DNA sequence homology to the other *C. albicans* retroelements, TCa1 and beta. TCa1 and pCal do, however, share features such as similar inverted terminal repeats on their LTRs, a very similar PPT sequence and they potentially utilise the same tRNA$^{Arg}$ fragment as a primer. The TCa1 (−)PBS complements nine nucleotides at the 3' end of the tRNA$^{Arg}$ fragment (bases 31–39). The pCal (−)PBS complements eleven nucleotides of the tRNA$^{Arg}$ fragment (bases 29–39) and, similarly to what has been found in Ty1, Ty2 and Ty3, pCal has an additional sequence downstream of the (−)PBS which complements a further 6 bases (19–24) of the TRNA$^{Arg}$ fragment.

Given that pCal and TCa1 are believed to use an internal fragment of the tRNA$^{Arg}$ (nucleotides 1–39), it is of great interest to note that the retrotransposon copia uses the first 39 nucleotides of tRNA$^{iMet}$ as a primer. It is not clear if the fragment is the result of normal tRNA degradation. The copia primer may be a product of 'hyperprocessing' of tRNA$^{iMet}$ by *Drosophila* RNase P. Hyperprocessing was defined as the processing of a mature tRNA to produce another functional RNA molecule, although, to date, the only assigned function of these tRNA fragments is as primers for retrotransposons. The RNA component of E. coli RNase P was shown to cleave a number of sites in the tRNA$^{iMet}$, one of these being between nucleotides 39 and 40. The *Drosophila* tRNA$^{iMet}$ and yeast tRNA$^{Arg}$3 have a very similar physical structure in terms of numbers and positions of loops and stems, residues in each loop, number of base pairs in each stem and total number of nucleotides in the tRNA. It is therefore possible that a similar hyperprocessing reaction is occurring with a tRNA$^{Arg}$ in *C. albicans* to produce the primers for pCal and TCa1.

If pCal is using a tRNA fragment for priming, there are implications for control of replication. An element using a whole tRNA as a primer has a pool of normal, functional tRNAs to draw on, even if the tRNA in question is a rare one. Elements using a fragment, however, have to contend with the stability of tRNAs and the possibility that once a tRNA starts degrading, it may be rapidly further degraded. The elements using a fragment as a primer will have to bind the tRNA after only partial degradation. This process could be a limiting step in the reverse transcription process and consequently control copy number of pCal.

Most retrotransposons and retroviruses have been found to have their gag and pol ORFs lying in different phases on the mRNA. The necessary down-regulation of the pol gene with respect to the gag gene is thus brought about by the fairly low frequency of ribosomal frameshifting from the gag reading frame to the pol reading frame. There are, however, exceptions to this finding. For instance, the gypsy-type retrotransposon Tf1 from *Schizosaccharomyces pombe* has its gag and pol ORFs fused into one long ORF. The gag and pol gene products are thus produced in equal amounts. The required excess of gag protein to pol enzyme is produced post-translationally, via an enhanced rate of degradation of the pol enzymes. Some insect and plant retrotransposons of the Ty1/copia group, for example copia, Ta1 and Tnt1 also have their gag and pol ORFs fused into one long ORF. In copia, at least, the down-regulation of pol occurs by the frequent splicing of the mRNA to remove most of the pol ORF. The fact that the gag and pol ORFs of pCal are in the same phase implies that pCal is another retrotransposon that doesn't use frameshifting to down-regulate pol. Instead it seems likely that some form of stop codon suppression is required for translation of the pol ORF and this would also be likely to result in the down-regulation of pol relative to gag. It is therefore interesting to note that pCal has some structural similarities with mammalian type C retroviruses, such as Moloney murine leukemia virus (MMLV), in the vicinity of the gag/pol boundary. In MMLV a UAG stop codon which separates the gag and pol ORFs is suppressed with an efficiency of about 5%, being translated as glutamine. An 8 bp purine-rich sequence immediately 3' to the stop codon and an adjacent pseudoknot structure are both necessary and sufficient for stop codon suppression. Mutations disrupting the stems of the pseudoknot impaired suppression and compensatory mutations restored suppression. Also the sequence of the purine-rich tract between the stop codon and the pseudoknot was found to be critical and it is likely that the length of this sequence is important. The MMLV read-through mechanism is not yet fully understood, but a pseudoknot-induced ribosomal pause at the suppressed UAG codon is likely to be involved. Similarly to MMLV, pCal has an 8 bp purine-rich sequence immediately 3' to the UGA stop codon, although not the same sequence as in MMLV, and it has a putative pseudoknot (FIG. 5). There is only the 8 bp purine-rich sequence between the termination signal and the start of the putative pseudoknot. It is therefore likely that a similar form of read-through suppression is occurring in pCal and MMLV.

It has been reported that *C. albicans* and some other closely related *Candida* species contain a tRNA capable of suppressing UAG and UGA stop codons. This tRNA, tRNA$^{SerCAG}$, was originally identified as being responsible for the translation of the universal CUG-leucine codon as serine in certain *Candida* species. The tRNA$^{SerCAG}$ has some unusual structural features and a recent report has even shown that tRNA$^{SerCAG}$ can be charged to a low degree (about 3%) with leucine and can incorporate this leucine into proteins during translation. This is one of the first examples of the assignment of a single tRNA species to two amino acids. This strange tRNA was also implicated in some aberrant translational events. It was found that when *C. albicans* tRNAs were added to in vitro translation systems, proteins which migrated more slowly than expected on SDS-PAGE gels were produced. These results were interpreted as evidence that *C. albicans* contains a tRNA capable of suppressing UAG and UGA stop codons. The tRNA responsible for the unusual translational events has been identified as tRNA$^{SerCAG}$. However, results could not be simply explained by tRNA$^{SerCAG}$ being an omnipotent nonsense suppressor: The amino-terminal regions of proteins synthesised in the presence of tRNA$^{SerCAG}$ also migrated more slowly than expected with SDS-PAGE. At present it is unclear what the actual effects of tRNA$^{SerCAG}$ are, aside from incorporation of serine at CUG codons. This leaves open the question of what molecule it is that mediates the suppression of the UGA termination codon at the gag/pol boundary of pCal. Sequencing the gag and the gag/pol fusion proteins and mutational analyses of the regions surrounding the stop codon could be used to determine the mechanism by which the pol genes of pCal are translated.

The pCal system is producing much more free dsDNA—estimated at 50–100 copies per cell—than any other reported retrotransposon system. This is true even of the system in which Ty1 of *S. cerevisiae* is expressed off a high copy number plasmid under the control of the highly inducible GAL 1 promoter. Such a GAL promoter system is capable of producing about 10 dsDNA copies per cell and the DNA requires Southern blotting before it can be detected. We have detected integrated retrotransposons, similar in sequence to pCal, which we have named TCa2. This integrated form has been detected in a diverse range of *C. albicans* strains. Extremely high levels of the free, linear, dsDNA form (pCal), however, have only been detected in hOG1042 and its close relatives (descendants of iB65).

Overall, pCal presents itself as a highly unusual retrotransposon. While having many of the features conserved among retrotransposons, it has a number of features which set it apart from other elements of its class. For instance, the translation of the pol ORF seems to be dependent upon the pseudoknot-assisted read-through of a UGA stop codon. This is similar to the mechanism used by mammalian type C retroviruses, but has not been previously reported in retrotransposons. A phylogenetic analysis of the reverse transcriptase sequences of a number of LTR-retroelements showed that, while pCal lies within the Ty1/copia group of retrotransposons, it is one of the most divergent elements within this group. The most distinctive feature of pCal, however, is that it exists at a high copy number as a free, linear, double-stranded DNA molecule.

The TCa2 retrotransposon was originally discovered due to its appearance as an abundant, extrachromosomal DNA molecule in *Candida albicans* strain hOG1042. Sequence analysis of some clones of this extrachromosomal form of TCa2 (referred to as pCal) showed it to be basal member of the Ty1/copia class of retrotransposon. Here we have extended the characterization of this element to include an analysis of its integrated forms, and a comparison of the expression of its RNA and extrachromosomal DNA forms, in a variety of *C. albicans* strains.

An important finding to emerge from this work is that there is a large amount of variation amongst different *C. albicans* strains, in both the amount of TCa2 RNA and extrachromosomal pCal DNA produced, and in the genomic copy number of TCa2. It is of interest that the number of integrated copies of TCa2 in the different strains correlates with the amount of TCa2 RNA produced by each strain, and again, that the amount of TCa2 RNA in each strain is related to the amount of extrachromosomal pCal DNA. The greatest numbers of integrated copies of TCa2, 10 to 12, occur in the closely related strains hOG759 and hOG1042. About 5 copies are found in F16932, and the other strains examined, SGY269, SC5314, ATCC10261, and SA40 each have 1 or 2 copies. The highest levels of TCa2 RNA are also found in hOG759 and hOG1042. The next highest level occurs in F16932, and the other four strains each have a relatively low level. The greatest amounts of pCal extrachromosomal DNA are, once again, found in hOG759 and hOG1042. Moderate levels of pCal are found in F16932, and also in SA40. Low levels occur in SGY269 and SC5314, and, lastly, no extrachromosomal copies of pCal, at all, were detected in ATCC10261. These correlations between genomic copy number and abundance of RNA, and between the abundance of RNA and the abundance of extrachromosomal DNA, suggest that a large amount of the variation seen among strains, in the amount of pCal DNA and TCa2 RNA that they produce, is simply a consequence of variations in the number of integrated copies. Or, to put this another way, the genomic copy number of TCa2 is a major determinant of TCa2 RNA levels, and the TCa2 RNA levels are a major determinant of pCal DNA levels. As mentioned in the results, however, the correlations are not perfect which suggests that other factors are also involved. To reiterate: hOG759 and hOG1042 have roughly twice as many integrated TCa2 copies as F16932 and ten times as many as the other four strains, yet they produce about 5 times and 50 to 100 times as much RNA, respectively; SA40 has about a fifth the TCa2 RNA found in F16932 and only slightly more than SGY269 and SC5314, yet it produces similar quantities of pCal to F16932 and 10 to 20 times as much as the other two strains; and ATCC10261 produces a slightly larger amount of TCa2 RNA than SGY269 and SC5314, and a similar amount to SA40, yet it doesn't produce any detectable extrachromosomal copies of pCal.

A simple explanation for the result with ATCC10261 is that the TCa2 elements in this strain have suffered mutations that corrupt their RT gene or render inactive other sequences required for reverse transcription, for example the polypurine tract. Such an occurrence would account for the lack of extrachromosomal pCal molecules in this strain. Accounting for the relative overproduction of TCa2 RNA in hOG759 and hOG1042, and the relative overproduction of pCal DNA in SA40 is, however, not so simple. In hOG759 and hOG1042 there is roughly five times as much TCa2 RNA as would have been expected from a comparison with TCa2 copy number and RNA expression in other strains. This suggests that one or more TCa2 elements in these strains are being transcribed at a very high rate. There are a number of possible explanations for this. Firstly, it is possible that an element in these strains has suffered an alteration to its promoter region such that it becomes hyperactive and produces an abundance of transcripts. A comparison of the 5' regions of TCa2 elements from various strains (FIG. 9), however, failed to identify any significant differences between the LTRs of hOG759 and hOG1042 and the LTRs of other strains, although this does not rule out the possibility that such an element exists. Another possible factor that could be involved is the genomic location of the TCa2 elements. It is possible, for instance, that TCa2 retrotransposons are normally integrated in regions of silent chromatin, as is the case with the Ty5 element of *Saccharomyces*. If, for some reason, a copy of the retrotransposon became integrated at an open or transcriptionally active region of the genome then this might result in the overexpression of its RNA. Strain variation in proteins involved in regulating transcription could also be involved in the overproduction of TCa2 RNA in hOG759 and hOG1042. These strains have been subjected to mutagenesis with UV radiation and N-methyl-N-nitro-N-nitrosoguanidine. It is possible that in the course of this mutagenesis these strains have, for instance, lost some repressor of TCa2 transcription or suffered a mutation in some other transcription factor, with the result that the TCa2 retrotransposons are subsequently transcribed at a higher than normal rate. Finally, it is conceivable that the higher copy number in hOG759 and hOG1042 acts to titrate out a repressor molecule, with the result that there are unrepressed elements which are then transcribed at a high rate. As can be seen, further experiments will be required to determine which, if any, of these factors are involved.

Strain SA40 produces about 5 to 6 times as much pCal DNA as might have been predicted from a comparison of TCa2 RNA and pCal DNA levels in the other strains. This suggests that reverse transcription of TCa2 RNA is proceeding more efficiently in this strain than in other strains. Again, there are a number of possible explanations. For instance, the retrotransposon in this strain could have a superior RT or the genomic RNA may be more efficiently packaged into the virus-like particle where reverse transcription occurs. Alternatively, it could result from some host factor, such as increased availability of the primer tRNA fragment, which may be limiting for reverse transcription. Whatever the cause, it is interesting that strain SA40 manages to produce abundant amounts of pCal DNA from, apparently, just one integrated copy of the element. This may make it a useful strain for further dissection of this system.

Determination of the number of integrated elements in the closely related strains hOG759 and hOG1042 revealed that hOG1042 has at least one more copy than hOG759. There are at least three possible explanations for this: (1) a recombination between the two LTRs of a retrotransposon in hOG759 resulting in the deletion of an element, (2) a non-homologous chromosomal recombination resulting in either the duplication of an element in hOG1042 or in the deletion of an element in hOG759, and (3) a transposition event in hOG1042 resulting in an additional copy in this strain. Intra-element recombination and non-homologous recombinations are both likely to be relatively rare events and so, given the abundance of full-length pCal molecules in hOG1042, and the fact that the elements encode a potential integrase enzyme, the most likely explanation of the extra copy in hOG1042 is that it is the result of a transposition event since the divergence of this strain from hOG759. Since the divergence of hOG1042 from hOG759, the strains have spent most of their time stored at $-80°$ C., with no more than a week or two of active growth. The discovery of what is likely to be a transposition in hOG1042, in just a short period of time since its divergence from hOG759, suggests that the retrotransposon may be transposing at a high rate, which is perhaps not surprising given the abundance of apparently full-length reverse transcripts. If this element is still actively transposing then it may make a useful system for insertional mutagenesis in *C. albicans*, as has been the case with Ty1 and *Saccharomyces*. Regarding this last point, it is of interest that hOG1042, not only has more integrated copies of TCa2 than hOG759, but also has suffered a de novo auxotrophic mutation (resulting in a requirement for aspartate or proline when brought to homozygosity) that is not found in hOG759. It is possible that this spontaneous mutation is the result of a TCa2 transposition event.

The expression of TCa2 RNA was found to be 5 to 10 times higher at $37°$ C. than at $27°$ C. This contrasts with the expression of the *C. albicans* retrotransposon-like element TCa1, in which the RNA was found to be 20- to 30-fold more abundant at $25°$ C. than at $37°$ C. The temperature-dependent expression of these retrotransposons does not appear to be the result of a general temperature-dependent variation in transcription rate, so it is probably a specific retrotransposon effect. It is not clear what advantage it confers on the retrotransposons to regulate their expression in this manner. It has been suggested that TCa1 could play a role in, for instance, up-regulating genes which improve the chances of the survival outside of the host, or, alternatively, down-regulating genes which trigger host defences. Similar effects could be proposed for TCa2. For example, transposition of TCa2 could up-regulate genes required for maintaining an infection, or could down-regulate genes not required outside the host. It would be interesting to identify the sequences within TCa1 and TCa2 that are responsible for their temperature-dependent expression. Such sequences may be widely used in *C. albicans* as a means of regulating the expression of specific genes. The TCa1 and TCa2 promoters may also make useful temperature-inducible promoters in transformation studies analyzing other *C. albicans* genes.

In our original description of pCal we estimated that it appears at 50–100 extrachromosomal copies per cell in hOG1042 (30). In FIG. 7, however, the TCa2 probe can be seen to hybridize to the extrachromosomal and chromosomal DNA from hOG1042 (37° C.) to a similar degree. The number of integrated copies in hOG1042 is 10 to 12, suggesting that, at 37° C., pCal is also present at 10 to 12 copies per cell. This estimate may be misleading, however, because at least some of the pCal molecules are likely to be located in the interior of a large, proteinaceous particle, and therefore may be lost during the DNA isolation procedure. In agreement with this, we have found that the amount of pCal obtained, relative to chromosomal DNA, varies with different DNA extraction protocols (not shown). The method used to isolate the DNA for the Southern shown in FIG. 7 gives a lower amount of pCal than some other methods. An unbiased technique will be required to accurately determine the absolute number of extrachromosomal pCal molecules per cell. The technique that we have used in FIG. 7 should, however, be a reliable indicator of the relative amounts of pCal in the different strains and at the different temperatures.

An analysis of the 5' regions of TCa2 retrotranposons from the various strains showed that some of these elements have minus-strand primer-binding sites which are very long. One clone from hOG759 has a perfect 32 bp match to the primer tRNA$^{Arg(UCU)}$ fragment. The other clone from hOG759 and the two clones from SC5314 also have 32-bp matches to the tRNA primer, allowing for 2 G-U base pairs. The p30 clone of pCal from hOG1042 also has a 32-bp match but with 3 G-U base pairs. All the other clones have 31 out of 32-bp matches to the tRNA primer with 4 G-U base pairs. To the best of our knowledge, these 32-base PBSs are the longest described. Most retrotransposons have PBSs that are 10 to 12 nucleotides long, for example Ty1 (10 nucleotides). Retroviruses, for example, Moloney murine leukemia virus have 18 nucleotide PBSs. After the TCa2 PBS, the next longest PBS of which we are aware is 24 nucleotides long and is found in the magellan element of maize. It has been shown that introducing a mismatch into the Ty1 PBS reduces the Ty1 transposition frequency at higher temperatures while increasing the length of the PBS results in an increase in the transposition frequency at higher temperatures. These differences in transposition frequency are most likely due to differences in the efficiency of the initiation of the reverse transcription process. This suggests that long PBSs are more efficient than short PBSs at high temperatures. The very long PBSs found in TCa2 elements, may thus predispose these retrotransposons to high levels of reverse transcription at 37° C. On the other hand, it has recently been shown that there are regions, in addition to the PBS, where Ty1 binds to its tRNA primer, such that 30 bases of Ty1 RNA are paired with primer tRNA. Disruption of as few as two of these base pairs was found to have a drastic effect on transposition frequency. It may be that a long PBS is necessary for efficient reverse transcription at 37° C., especially for elements, such as TCa2, utilising a tRNA fragment that is just 40 nucleotides long and to which there would be little opportunity for additional regions of base-pairing.

No hybridization of either the TCa2 internal or LTR probes was observed to DNA of *C. maltosa, C. tropicalis*, or *C. parapsilosis* which are all close relatives of *C. albicans*, nor to DNA of the more distantly related *C. pseudotropicalis*. This suggests that TCa2 is specific to *C. albicans*. Given the apparent ubiquity of retrotransposons in the eukaryotes, it is likely that these species have retrotransposons, but that these retrotransposons have diverged sufficiently since speciation that they are no longer detectable by hybridization to TCa2.

In most of the *C. albicans* strains that we have examined here, there is a fairly low number of integrated copies of TCa2 (5 or fewer per genome). The full-length TCa1 element is also present at low copy numbers (just 1 or 2 per genome) and all the retroelement LTRs found in *C. albicans* to date, and those of TCa1 and TCa2, appear at a similar low copy number of about 5 to 15 per genome. These low copy numbers are suggestive of a mechanism whereby transposition of retroelements in *C. albicans* is held in check. In hOG759 and hOG1042, however, the copy number of TCa2 is higher (about 10 full-length elements per genome) and appears to be capable of increase. It may be that in these strains the TCa2 retrotransposons have escaped the normal constraints on their replication and are thus transposing at rates much above normal. If, as is most likely, the majority of newly transposed copies are themselves capable of transposition they may serve to increase the rate of transposition still further. It would therefore be interesting to see what would happen in these strains if they were continuously grown for an extended period.

REFERENCES

Agatensi, L., F. Franchi, F. Mondello, R. L Bevilacqua, T. Ceddia, F. De Bernardis, and A. Cassone 1991. Vaginopathic and proteolytic *Candida* species in outpatients attending a gynaecology clinic. J. Clin. Pathol. 44:826–830.

Altschul, S. F., Gish, W., Miller W., Myers, E. W., Lipman, D. J. 1990. Basic local alignment search tool. J. Mol. Biol. 215:403–410.

Altschul, S. F., Madden, T. L., Schaffter, A. A., Zhang, J., Zhang, Z., Miller, W., Lipman, D. J. 1997. Gapped BLAST and PSI-BLAST: a new generation of protein database search programs. Nucleic Acids Res. 25:3389–3402.

Boeke, J. D., and S. Sandmeyer 1991. Yeast transposable elements. In the molecular and cellular biology of the yeast *Saccharomyces cerevisiae*. (eds. J. R. Broach, E. W. Jones, and J. Pringle), pp193–261. Cold Spring Harbor Laboratory Press, Cold Spring Harbor, N.Y.

Basrai, M. A., Lubkowitz, M. A., Perry, J. R., Miller, D., Krainer, E., Naider, F. and Becker, J. M. (1995) Cloning of a *Candida albicans* peptide transport gene. Microbiology 141:1147–1156.

Chen, J-Y., and W. A. Fonzi. 1992. A Temperature-Regulated, Retrotransposon-Like Element from *Candida albicans*. J. Bacteriol. 174:5624–5632.

Church, G. M., and W. Gilbert. 1984. Genomic sequencing. Proc. Natl. Acad. Sci. USA 81:1991–1995.

Cryer, D. R., R. Eccleshall, and J. Marmur. 1975. Isolation of Yeast DNA. Methods Cell Biol. 12:39–44.

Devereux, J., P. Haerberli, and O. Smithies. 1984. A comprehensive set of sequence analysis programs for the VAX. Nucleic Acids Res. 12:387–395.

Felsenstein, J. 1989. PHYLIP-Phylogeny inference package (version 3.2). Cladistics 5:164–166

Fourcade-Peronnet, F., L. d'Auriol, J. Becker, F. Galibert, and M. Best-Belpomme.

1988. Primary structure and functional organization of *Drosophila* 1731 retrotranposon. Nucleic Acids Res. 16:6113–6125.

Garfinkel, D. J., J. D. Boeke, and G. R. Fink. 1985. Ty element transposition: reverse transcriptase and virus-like particles. Cell 42:507–517.

Gillium, A. M., E. Y. H. Tsay and D. R. Kirsch. 1984. Isolation of the *Candida albicans* gene for orotidine-5'-phosphate decarbosylase by complementation of *S.cerevisiae* ura3 and *E. coli* pyrF mutations. Mol. Gen. Genet. 198: 179–182.

Hansen, L. J., D. L. Chalker, and S. B. Sandmeyer. 1988. Ty3, a Yeast Retrotransposon Associated with tRNA Genes, Has Homology to Animal Retroviruses. Mol. Cell. Biol. 8:5245–5256.

Jenkinson, H. F., Schep, G. P., and M. G. Shepherd. 1988. Cloning and expression of the 3-isopropylmalate dehydrogenase gene from *Candida albicans*. FEMS Microbiol. Lett. 49: 285–288.

Kelly, R., S. M. Miller, M. B. Kurtz and D. R. Kirsch. 1987. Directed mutagenesis in Candid albicans: one-step gene disruption to isolate ura3 mutants. Mol. Cell. Biol. 7: 199–208.

Kelly, R., S. M. Miller, M. B. Kurtz and D. R. Kirsch. 1988. One-step gene disruption by cotransformation to isolate double auxotrophs in *Candida albicans*. Mol. Gen. Genet. 214:24–31.

Kurtz, M. B, Cortelyou, M. W, Miller, S. M., Lai, M and D. R. Kirsch. 1987. Development of Autonomously Replicating Plasmids for *Candida albicans* Mol Cell Biol 7:209–217.

Kelly, R., Miller, S. M and M. B. Kurts. 1988. One-step gene disruption by cotransformation to isolate double auxotrophs in *Candida albicans*. Mol Gen. Genet. 214:24–31.

Losberger, C., and Ernst, J. F. 1989. Sequence and transcript analysis of the *C. albicans* URA3 gene encoding orotidine-t'-phosphate decarboxylase. Current Genetics. 16: 153–157 Markie, D., Hill, D. F and R Poulter. 1986. The Construction of a Modified Drug Resistance Cassette Proc. Univ. Otago Med Sch 64:69–70.

Maniatis, T., Fritsch, E. F., and J. Sambrook. 1982. Molecular Cloning: a laboratory manual, Cola Spring Harbor Laboratory, Cola Spring Harbor, N.Y.

Matthews, G. D., T. J. D Goodwin, M. I. Butler, T. A. Berryman, and R. T. M Poulter. 1997. PCal, a highly unusual Ty1/copia retrotransposon from the pathogenic yeast *Candida albicans*. J. Bacteriol 179: 7118–7128.

Mount, S. M., and G. M. Rubin. 1985. Complete Nucleotide Sequence of the *Drosophila Transposable Element Copia: Homology Between Copia and Retroviral Proteins. Mol. Cell. Biol.* 5:1630–1638.

Odds, F. C. 1988. *Candida* and candidosis. A review and bibliography. Balliere Tindall, London, UK Ohkuma, M., Muraoka, S., Hwang, C. W., Ohta, A. and Takagi, M. 1993. Cloning of the C-URA3 gene and construction of a triple auxotroph (his5, ade 1, ura3) as a useful host for the genetic engineering of *Candida maltosa*. Current Genetics 23:205–210.

Perreau, V. M., Santos M. A., Tuite, M. F. 1997. Beta, a novel repetitive DNA element associated with tRNA genes in the pathogenic yeast *Candida albicans*. Mol. Microbiol July 25(2):229–236.

Philippsen, P., A. Stotz and C. Scherf. 1991. DNA of *Saccharomyces cerevisiae*. Methods enzymol. 194: 169–182.

Poulter, R., K. Jeffrey, M. J. Hubbard, M. G. Shepherd, and P. A. Sullivan. 1981. Parasexual Genetic Analysis of *Candida albicans* by Spheroplast Fusion. J. Bacteriol. 146:833–840.

Prasad, R., P. De Wergifosse, A. Goffeau, and E. Balzi. 1995. Molecular cloning and characterization of a novel gene of *Candida Albicans*, CDR1, conferring multiple resistance to drugs and antifungals. Curr. Genet. 27:230–329.

Santos M A., Tuite M F (1995) The CUG codon is decoded in vivo as serine and not leucine in *Candida albicans*. Nucleic Acids Res 23:1481–6

Sasnauskas. K., Jomantiene, R., Geneviciute, E., Januska, A. and J. Lebedys. 1991. Molecular cloning of the *Candida maltosa* ADE1 gene. Gene 107: 161–164.

Short, J. M., Fernandez, J. M. Sorge, J. A. and W. D Huse. 1988. λZAP: a bacteriophage λ expression vector with in vivo excision properties. Nucl. Acids Res 16: 7583–7600.

Stockwell Pa. (1985) VTUTIN: a full screen gel management editor. Comput Appl Biosci. 1:253–9.

Stockwell, P. A., and G. B. Petersen. 1987. HOMED: a homologous sequence editor. Comp. Appl. Biosci. 3:37–43.

Stoesser, G., Moseley, M. A., Sleep, J., McGowran, M., Garcia-Pa stor, M., Sterk, P. 1998. The EMBL nucleotide sequence database. Nucleic Acids Res. 26:8–15.

ten Dam, E., Pleij, K., and Draper, D. 1992. Structural and functional aspects of RNA pseudoknots. Biochemistry 31:11665–11676.

Wagenbach, M. O'Rourke, K., Vitez, L., Wieczorek, A., Hoffman, S., Durfee, S., Tedesco, J. and G Stetler. 1991. Synthesis of Wild Type and Mutant Human Hemoglobins in *Saccharomyces cerevisiae* Bio Tech 9:57–61.

Woodcock, D. M., Crowther, P. J., Doherty, J., DeCruz, E., Noyer-Weidner, M., Smith, S. S., Michael, M. Z., and M. W. Graham. 1989. Quantitative evaluation of *Escherichia coli* lest strains for tolerance to cytosine methylation in plasmid and phage recombinants Nucleic Acid Res 17:3469–3478.

Woods, R. A. and E. A Bevan. 1965. Interallelic Complementation at the ad-2 Locus of *Saccaromyces* cerevisiae. Heredity 21: 121–130.

Xiong, Y., and T. H. Eickbush. 1990. Origin and evolution of retroelements based upon their reverse transcriptase sequences. EMBO J. 9:3353–3362.

Yanish-Perron, C., Viera, J. and J. Messing. 1985. Improved M13 phage cloning vectors and host strains: nucleotide sequences of M13 mp18 and pUC19 vectors. Gene 33: 103–119.

What is claimed is:

1. An isolated retrotransposon consisting of SEQ ID NO:3.

2. An isolated and purified retrotransposon comprising a nucleotide sequence which has at least 95% sequence similarity with a nucleotide sequence selected from the group consisting of:
   (a) SEQ ID NO:3; and
   (b) the LTR and POL region of SEQ ID NO:3.

3. A cell transformed with an isolated retrotransposon comprising a nucleotide sequence which has at least 95% sequence similarity with SEQ ID NO:3, wherein the retrotransposon is integrated into the genome of the cell.

4. An expression vector comprising the retrotransposon of claim 2.

5. A DNA transfer construct comprising the retrotransposon of claim 2.

6. An isolated nucleic acid fragment selected from the group consisting of:
   (a) a nucleic acid sequence comprising the two terminal repeats of SEQ ID NO:3 and a nucleic acid molecule of interest, wherein the nucleic acid molecule of interest is positioned between the two terminal repeats; and
   (b) a nucleic acid sequence consisting of the LTR and POL region of SEQ ID NO:3.

7. The nucleic acid fragment according to claim 6 in which the nucleic acid sequence comprises a functional POL gene.

8. The nucleic acid fragment according to claim 6 in which the nucleic acid sequence comprises a series of genes in the order gag (group antigen), pol (polyprotein) where the pol sequence comprises an aspartic protease, an integrase and a reverse transcriptase/RNAseH.

9. The retrotransposon of claim 2, wherein the retrotransposon comprises a nucleotide sequence having four tandem repeats of the sequence GAAAAA.

10. The DNA transfer vector of claim 5, wherein the transposable element comprises a nucleotide sequence having four tandem repeats of the sequence GAAAAA.

11. The retrotransposon of claim 2, wherein the nucleotide sequence of (b) has at least 97% similarity with the LTR and POL region of SEQ ID NO:3.

12. The DNA transfer construct of claim 5, further comprising a dominant selectable marker.

13. The DNA transfer construct according to claim 5 comprising:
   a) a transposable element for introducing a desired DNA sequence into the genome of a cell, having the sequence identified in SEQ ID NO:3 comprising an internal domain for receiving a nucleotide sequence encoding a desired protein, said internal domain comprising the gag and pol ORF in the same phase and flanked by two terminal repeat regions, said transposable element being capable of integrating into the genome of a cell in the presence of an integration factor; and
   b) a nucleotide sequence encoding an integration factor.

14. The DNA transfer construct according to claim 13, wherein the integration factor is an integrase protein encoded by a nucleotide sequence within the pol ORF of the DNA transfer construct.

* * * * *

SEQUENCE LISTING

<160> NUMBER OF SEQ ID NOS: 156

<210> SEQ ID NO 1
<211> LENGTH: 388
<212> TYPE: DNA
<213> ORGANISM: Candida albicans
<300> PUBLICATION INFORMATION:
<308> DATABASE ACCESSION NUMBER: AF043301
<309> DATABASE ENTRY DATE: 1998-07-21
<313> RELEVANT RESIDUES: (1)..(388)

<400> SEQUENCE: 1

```
tgttcgctat agagagattt cctagccgga atgcacgaca atcctgagac ggaagtcgat      60
cgtcgatgcc catggtgcgt ggtgaaaaat tttcttagaa aatttgttct ttccttcaac     120
tgcttttaag aaagagaggt tcaagtggtt taagtacgac ggtcacaaag attgcggctt     180
atgaggcccg aactgagttg aaatacaaaa tcaagatata attatatacc ttacttgtcc     240
atattgtttt ataatacatt cttcagatat ttaaatttct gtgtatcaac ctataaaaca     300
gagatacatt cagtgcattt agtatactga gtgaactggt acctgtgaca ttcaagataa     360
ctgtttcgcg cacgctggca gacgaaca                                        388
```

<210> SEQ ID NO 2
<211> LENGTH: 400
<212> TYPE: DNA
<213> ORGANISM: Candida albicans
<300> PUBLICATION INFORMATION:
<308> DATABASE ACCESSION NUMBER: Y08494
<309> DATABASE ENTRY DATE: 1997-08-27
<313> RELEVANT RESIDUES: (1)..(400)

<400> SEQUENCE: 2

```
cgggttaatg tatatttcga cttgcaggac ctatagaaca gctgtagatg taaacactaa      60
tatgaagaac tgggaaaaca ataacttcta ttctgactct gattctgtat gaaaactaac     120
tgaagaaaag aatataaaaa tataaaatat ataagaagac aaaggagaat ctctgaccct     180
tatatagacc gaaaactaga gtgacgatga accatcagac cagtcaataa ccaactaatt     240
taataatatc aataactcgt ctaacgaggt gtaaacaaaa taccgaaaat agaaatataa     300
ataactcaat gccaagatgg tgcgcaacca ccaaggtaat aaacaaccaa tagaaccaag     360
aattgtaaat cagacaacga gcaaggctga ttatacaaca                           400
```

<210> SEQ ID NO 3
<211> LENGTH: 6426
<212> TYPE: DNA
<213> ORGANISM: Candida albicans
<220> FEATURE:
<221> NAME/KEY: CDS
<222> LOCATION: (398)..(1372)
<223> OTHER INFORMATION: ORF1 coding sequence for gag
<221> NAME/KEY: CDS
<222> LOCATION: (1373)..(6103)
<223> OTHER INFORMATION: ORF2 - coding sequence for pol

<400> SEQUENCE: 3

```
tgttggtttg tgcactattt tgtgtcagaa actgatcaat gaaaatgatg gttattatga      60
gaatggaaaa ttttccatc acacatcagg tgatgacaga actaaactat attgtgtagt     120
ataaataagg gtatgaaata ccaacatccc agaatatcaa cgagatagaa gggaggagtt     180
tcaatatata tcttgtgaat aataacttcg ttctaattca ctatacacaa ctagacgtgt     240
```

```
                                                          -continued acacgctcaa tctcaggtaa agaaagttta tattccatca gattagaagt cgatagtgat      300
aatcatttcg tcccaaatta gcgttgtata aattcagtcc tcagatttgt attattgatt      360
gatagtttcg aagtttgaag gtacagaatt tcacaag atg agt tcc gca aag aat      415
                                        Met Ser Ser Ala Lys Asn
                                         1               5 gat gat aac gaa ggg aag gtc atg gaa agt gtt gat caa gct aat gct      463
Asp Asp Asn Glu Gly Lys Val Met Glu Ser Val Asp Gln Ala Asn Ala
             10                  15                  20 att agt aag gtg gat gaa cat atc aag gct aga ttc aat atg ctt ttc      511
Ile Ser Lys Val Asp Glu His Ile Lys Ala Arg Phe Asn Met Leu Phe
         25                  30                  35 ata aaa ttt aat gac tta cct aag ttg gcc gtc ggt aat cag aaa agc      559
Ile Lys Phe Asn Asp Leu Pro Lys Leu Ala Val Gly Asn Gln Lys Ser
     40                  45                  50 gtg gat aaa tgg aat gaa gaa ttt aaa tat ttc cac gtt gct tac ccc      607
Val Asp Lys Trp Asn Glu Glu Phe Lys Tyr Phe His Val Ala Tyr Pro
 55                  60                  65                  70 gat gtt ttg gaa ttt ttg ctt gac tat aat cct aaa gat aaa ttc aag      655
Asp Val Leu Glu Phe Leu Leu Asp Tyr Asn Pro Lys Asp Lys Phe Lys
                 75                  80                  85 gtt aaa aag gta gaa ggt att tat ttt act ggt tgg tgt tta caa atg      703
Val Lys Lys Val Glu Gly Ile Tyr Phe Thr Gly Trp Cys Leu Gln Met
             90                  95                 100 tgt tta cag tcc att ttt gat agg ttc aga ttg atc atg att tct aag      751
Cys Leu Gln Ser Ile Phe Asp Arg Phe Arg Leu Ile Met Ile Ser Lys
        105                 110                 115 cta cca aag cac ttg caa aag gaa gca aac tta atc aaa gct gct tat      799
Leu Pro Lys His Leu Gln Lys Glu Ala Asn Leu Ile Lys Ala Ala Tyr
    120                 125                 130 gat gct gtt act aaa tct aaa gat tat acc att act agt aag atc ttg      847
Asp Ala Val Thr Lys Ser Lys Asp Tyr Thr Ile Thr Ser Lys Ile Leu
135                 140                 145                 150 ctg aag ttt gta aac gtt gaa cat gag tta gtg gtt tgc tat aac ctt      895
Ser Lys Phe Val Asn Val Glu His Glu Leu Val Val Cys Tyr Asn Leu
                155                 160                 165 cca tat ttg ctg cag gtg gaa gag aaa ctt gag gaa ata ctc tac aac      943
Pro Tyr Leu Leu Gln Val Glu Glu Lys Leu Glu Glu Ile Leu Tyr Asn
            170                 175                 180 act tca aac gtt gtc gat gag tat gtc cgt agt ctt cca aat ctc ata      991
Thr Ser Asn Val Val Asp Glu Tyr Val Arg Ser Leu Pro Asn Leu Ile
        185                 190                 195 ggt caa gtc ttg tac ttc aat cat gtg aag aaa tca gag gct tta agt     1039
Gly Gln Val Leu Tyr Phe Asn His Val Lys Lys Ser Glu Ala Leu Ser
    200                 205                 210 ttg ttt ttg aat att cat gcc tca tac tac tca aag tgg att caa gct     1087
Leu Phe Leu Asn Ile His Ala Ser Tyr Tyr Ser Lys Trp Ile Gln Ala
215                 220                 225                 230 gac aat gat aca tca gta ctc cca agt tgc tct acc ata gct gaa gaa     1135
Asp Asn Asp Thr Ser Val Leu Pro Ser Cys Ser Thr Ile Ala Glu Glu
                235                 240                 245 atg tgt gat cat cct gat tat gct aga ttg gtt gac att cca agc aac     1183
Met Cys Asp His Pro Asp Tyr Ala Arg Leu Val Asp Ile Pro Ser Asn
            250                 255                 260 aaa tat gaa ctt aat ctt att gtt agt tta cca gca cca gag aaa cca     1231
Lys Tyr Glu Leu Asn Leu Ile Val Ser Leu Pro Ala Pro Glu Lys Pro
        265                 270                 275 aaa gga aaa cca gag gag aac tca ctg gaa caa tct caa aag aag aac     1279
Lys Gly Lys Pro Glu Glu Asn Ser Ser Glu Gln Ser Gln Lys Lys Asn
    280                 285                 290
```

```
ctg aaa tca aga aag aga aat aag aaa cat cca aaa tca gat aac gat       1327
Ser Lys Ser Arg Lys Arg Asn Lys Lys His Pro Lys Ser Asp Asn Asp
295                 300                 305                 310 aaa ggt gaa aaa gaa aaa gaa aaa gaa aaa act tca ctg gaa tga aaa       1375
Lys Gly Glu Lys Glu Lys Glu Lys Glu Lys Thr Ser Ser Glu         Lys
                315                 320                         325 aca ggt gct gct tct att aat tgt gta atg aat ata cat aat tgc agc       1423
Thr Gly Ala Ala Ser Ile Asn Cys Val Met Asn Ile His Asn Cys Ser
                330                 335                 340 aaa acc acg ttt cca gta gaa aat tct cat tct ctt aat gct tct ttg       1471
Lys Thr Thr Phe Pro Val Glu Asn Ser His Ser Leu Asn Ala Ser Leu
                345                 350                 355 aac gta atg aat ttt aaa ggt tta agg ttt aac aag tat cta gtg tat       1519
Asn Val Met Asn Phe Lys Gly Leu Arg Phe Asn Lys Tyr Leu Val Tyr
                360                 365                 370 gat act ggt gcc aca ata tct gtt gtg aac aat aaa gat ata ttg ctg       1567
Asp Thr Gly Ala Thr Ile Ser Val Val Asn Asn Lys Asp Ile Leu Ser
            375                 380                 385 aat gtt aag gac gca aca att gaa gtt tct gtt gct gat ggt gct aca       1615
Asn Val Lys Asp Ala Thr Ile Glu Val Ser Val Ala Asp Gly Ala Thr
390                 395                 400                 405 tta gaa gca gat tgt att ggt gat cta att atc aga gtc ggt att gtc       1663
Leu Glu Ala Asp Cys Ile Gly Asp Leu Ile Ile Arg Val Gly Ile Val
                410                 415                 420 tcg att acg tta gag aat aca ttg tat tta cca gaa agt tcc ttt aat       1711
Ser Ile Thr Leu Glu Asn Thr Leu Tyr Leu Pro Glu Ser Ser Phe Asn
                425                 430                 435 ctt gtg agt ttg aaa caa att gaa gaa cga gga ttt aat gtt ctt att       1759
Leu Val Ser Leu Lys Gln Ile Glu Glu Arg Gly Phe Asn Val Leu Ile
                440                 445                 450 act aaa gaa tca gtg att gta ttt aac caa aat gtg gct cct act att       1807
Thr Lys Glu Ser Val Ile Val Phe Asn Gln Asn Val Ala Pro Thr Ile
455                 460                 465 att gct tca agg aag aat gct gct gat ctt tat atg ggt cct caa ttc       1855
Ile Ala Ser Arg Lys Asn Ala Ala Asp Leu Tyr Met Gly Pro Gln Phe
470                 475                 480                 485 agt gaa gaa tct tta gaa tgt gat ttt gat tat gat ggt ttg gca gat       1903
Ser Glu Glu Ser Leu Glu Cys Asp Phe Asp Tyr Asp Gly Leu Ala Asp
                490                 495                 500 atg ttg tcc aat gct aac caa gat gac aaa gat aaa tca agt atg aat       1951
Met Leu Ser Asn Ala Asn Gln Asp Asp Lys Asp Lys Ser Ser Met Asn
                505                 510                 515 gaa atg tca gaa tat caa gaa cat gat tat agt tct cga gca tta ata       1999
Glu Met Ser Glu Tyr Gln Glu His Asp Tyr Ser Ser Arg Ala Leu Ile
                520                 525                 530 aat tct ttg acg gag gtt gat gtt tta gat gtt gaa att tcc cca tat       2047
Asn Ser Leu Thr Glu Val Asp Val Leu Asp Val Glu Ile Ser Pro Tyr
535                 540                 545 gga gtt gaa caa ttg cta cca act gga gat aag aac gat att tat aat       2095
Gly Val Glu Gln Leu Leu Pro Thr Gly Asp Lys Asn Asp Ile Tyr Asn
550                 555                 560                 565 ttc cat ttg atg tca aat cat atg tcc att gag aaa atc ttg ttg tta       2143
Phe His Leu Met Ser Asn His Met Ser Ile Glu Lys Ile Leu Leu Leu
                570                 575                 580 caa aaa tac cag ggt ctc gta ctt cac act tca aaa gag agt ctt caa       2191
Gln Lys Tyr Gln Gly Leu Val Leu His Thr Ser Lys Glu Ser Leu Gln
                585                 590                 595 aag att gct gat tgt aag gta tgt cta tta tcg aat gcc aaa cag aga       2239
Lys Ile Ala Asp Cys Lys Val Cys Leu Leu Ser Asn Ala Lys Gln Arg
```

-continued

```
                600                     605                     610
agt cac aat cat cat tca gaa aga aaa gcc tcg aga aga cat gag aga          2287
Ser His Asn His His Ser Glu Arg Lys Ala Ser Arg Arg His Glu Arg
    615                     620                     625 ctt cat tgt gat act ctc ggt cca ttt agg tcc gaa aat aac aag tgg          2335
Leu His Cys Asp Thr Leu Gly Pro Phe Arg Ser Glu Asn Asn Lys Trp
630                     635                     640                 645 tat tta acg tct gtt ata gat gaa cat acg ggt tac att gaa gga att          2383
Tyr Leu Thr Ser Val Ile Asp Glu His Thr Gly Tyr Ile Glu Gly Ile
                650                     655                     660 att act aaa gac aga aag gta aag gat ctc tta att caa cga tta aag          2431
Ile Thr Lys Asp Arg Lys Val Lys Asp Leu Leu Ile Gln Arg Leu Lys
            665                     670                     675 atc tgg aat aat cgg ttt aac gat aag gtg gca tac ttc aga agt gat          2479
Ile Trp Asn Asn Arg Phe Asn Asp Lys Val Ala Tyr Phe Arg Ser Asp
        680                     685                     690 aat gct cct gag ttc cca caa cct tct gat tta gct gag ttc ggt att          2527
Asn Ala Pro Glu Phe Pro Gln Pro Ser Asp Leu Ala Glu Phe Gly Ile
    695                     700                     705 tgg agg gag act ata gcg gca tat ctg cct gag ctt aat ggt ctc gcc          2575
Trp Arg Glu Thr Ile Ala Ala Tyr Ser Pro Glu Leu Asn Gly Leu Ala
710                     715                     720                 725 gag gtt gtt aat aaa ttg att tta caa cag att tac agg atc gtt gtg          2623
Glu Val Val Asn Lys Leu Ile Leu Gln Gln Ile Tyr Arg Ile Val Val
                730                     735                     740 aca ctt ggt cca caa ata ctc aag ttg att tat tat gtg att caa tat          2671
Thr Leu Gly Pro Gln Ile Leu Lys Leu Ile Tyr Tyr Val Ile Gln Tyr
            745                     750                     755 tct att aca atg atc aac cac act cca cgt cgt tca ctc aag gga caa          2719
Ser Ile Thr Met Ile Asn His Thr Pro Arg Arg Ser Leu Lys Gly Gln
        760                     765                     770 acc cct tat ggt tgc tat tat caa tta agt gag gga aat ttc tac cgg          2767
Thr Pro Tyr Gly Cys Tyr Tyr Gln Leu Ser Glu Gly Asn Phe Tyr Arg
775                     780                     785 ttt cct ttt gcc atc gat tgt gtc gtt aca ttt agt aat gcc atc gaa          2815
Phe Pro Phe Ala Ile Asp Cys Val Val Thr Phe Ser Asn Ala Ile Glu
790                     795                     800                 805 aag aac cgt tac gga gtt aca tca act aaa gga gct cct tca tcg atc          2863
Lys Asn Arg Tyr Gly Val Thr Ser Thr Lys Gly Ala Pro Ser Ser Ile
                810                     815                     820 atg ggt gct gtg att ggc tac gct agc gat tgt ttt agt tat tac gtg          2911
Met Gly Ala Val Ile Gly Tyr Ala Ser Asp Cys Phe Ser Tyr Tyr Val
            825                     830                     835 ttg cta aaa aat atg cgg tgt gat att atc ctt agc cct aat gtc cgt          2959
Leu Leu Lys Asn Met Arg Cys Asp Ile Ile Leu Ser Pro Asn Val Arg
        840                     845                     850 ata ttg cga agc tat gag gtt att aac tcc tat ctc aaa aac tta tcc          3007
Ile Leu Arg Ser Tyr Glu Val Ile Asn Ser Tyr Leu Lys Asn Leu Ser
855                     860                     865 act aca cct atg tca cac att gtt cct atg gct gaa ggt atc cag gga          3055
Thr Thr Pro Met Ser His Ile Val Pro Met Ala Glu Gly Ile Gln Gly
870                     875                     880                 885 agg caa ctg ggc gct cag tac gag gta cgc gga aca tat gtg gaa agt          3103
Arg Gln Leu Gly Ala Gln Tyr Glu Val Arg Gly Thr Tyr Val Glu Ser
                890                     895                     900 gaa tat gac aat aca aat gac gtg atg cac atg ccc aaa gag tca tat          3151
Glu Tyr Asp Asn Thr Asn Asp Val Met His Met Pro Lys Glu Ser Tyr
            905                     910                     915 tca gtt cag cca gca tcg ttt act tta act acg ggt aac agt tct aac          3199
```

```
                          Ser Val Gln Pro Ala Ser Phe Thr Leu Thr Thr Gly Asn Ser Ser Asn
                                  920                 925                 930 gaa tat gtt ata aat gat gat cca gta cag att acc att gag aat ccc              3247
Glu Tyr Val Ile Asn Asp Asp Pro Val Gln Ile Thr Ile Glu Asn Pro
        935                 940                 945 gat gat ttt tct aac cct ctt caa cta act gaa gaa tca cac gat atg              3295
Asp Asp Phe Ser Asn Pro Leu Gln Leu Thr Glu Glu Ser His Asp Met
950                 955                 960                 965 gta tcc gaa gta aaa tcg gat gag aat cct aaa ccc agt ctc cac gag              3343
Val Ser Glu Val Lys Ser Asp Glu Asn Pro Lys Pro Ser Leu His Glu
                970                 975                 980 cta aca cct ggg gat aat ccg gtg tct aaa cct cct caa ctt ggt acc              3391
Leu Thr Pro Gly Asp Asn Pro Val Ser Lys Pro Pro Gln Leu Gly Thr
            985                 990                 995 gag act tca gta ata ggg aag tct aaa gag cct att aca aac cac                  3436
Glu Thr Ser Val Ile Gly Lys Ser Lys Glu Pro Ile Thr Asn His
        1000                1005                1010 aca aag gac gcc cct tcc atc cag ggg agg gac cat aaa cgc ctg                  3481
Thr Lys Asp Ala Pro Ser Ile Gln Gly Arg Asp His Lys Arg Ser
    1015                1020                1025 gaa tct act gct cag gtt gga cta tca cac caa ccc cag act ggt                  3526
Glu Ser Thr Ala Gln Val Gly Leu Ser His Gln Pro Gln Thr Gly
1030                1035                1040 act ccc gct tcg gag gag tca aaa ttg tca gga aca gat cat ttc                  3571
Thr Pro Ala Ser Glu Glu Ser Lys Leu Ser Gly Thr Asp His Phe
        1045                1050                1055 ggt gtc gac gtt gtt aaa gaa aca gtc tca gaa gat tgg cat act                  3616
Gly Val Asp Val Val Lys Glu Thr Val Ser Glu Asp Trp His Thr
    1060                1065                1070 tct gac tac cca gaa act agt gct gaa gat gaa cag caa aat ccc                  3661
Ser Asp Tyr Pro Glu Thr Ser Ala Glu Asp Glu Gln Gln Asn Pro
1075                1080                1085 tcg tta ctg gct aat aag aat cgg gta act gaa aaa ata gat gag                  3706
Ser Leu Ser Ala Asn Lys Asn Arg Val Thr Glu Lys Ile Asp Glu
        1090                1095                1100 gga gaa aat att tca ttt ccg ggg ggt gat gat gat tct gtc gtg                  3751
Gly Glu Asn Ile Ser Phe Pro Gly Gly Asp Asp Asp Ser Val Val
    1105                1110                1115 atc aac tca aat gtt gag caa tct aat gtt gaa aca gag gat gct                  3796
Ile Asn Ser Asn Val Glu Gln Ser Asn Val Glu Thr Glu Asp Ala
1120                1125                1130 ggt aac agt cca att caa gac gaa gtt tct caa gag gga aga ata                  3841
Gly Asn Ser Pro Ile Gln Asp Glu Val Ser Gln Glu Gly Arg Ile
        1135                1140                1145 ctt aat gaa caa act gat ata gtt gat act gtt gct aaa gtt att                  3886
Leu Asn Glu Gln Thr Asp Ile Val Asp Thr Val Ala Lys Val Ile
    1150                1155                1160 gag aat gaa aaa atc tct cct att aat tca tta gat gat cat act                  3931
Glu Asn Glu Lys Ile Ser Pro Ile Asn Ser Leu Asp Asp His Thr
1165                1170                1175 gaa ctt gct aca gac tcg gga aat gat agc aat tca aca gaa tcc                  3976
Glu Leu Ala Thr Asp Ser Gly Asn Asp Ser Asn Ser Thr Glu Ser
        1180                1185                1190 gac att caa tcg aaa aat gaa ata tca cca gtg att aat gag aaa                  4021
Asp Ile Gln Ser Lys Asn Glu Ile Ser Pro Val Ile Asn Glu Lys
    1195                1200                1205 aat act gaa ata atc caa aaa cac att gaa agt atc ctt gct gat                  4066
Asn Thr Glu Ile Ile Gln Lys His Ile Glu Ser Ile Leu Ala Asp
1210                1215                1220
```

```
aag aga ttg gat gaa ttt gaa acg tat aat gtt gat gaa att gag       4111
Lys Arg Leu Asp Glu Phe Glu Thr Tyr Asn Val Asp Glu Ile Glu
        1225                1230                1235 aat gtg att aat gac gat gac att gct gaa gct aat cca cta cca       4156
Asn Val Ile Asn Asp Asp Asp Ile Ala Glu Ala Asn Pro Leu Pro
        1240                1245                1250 gat gaa aat aat gat gtt cag atg aat gag agt ttt gat aat aat       4201
Asp Glu Asn Asn Asp Val Gln Met Asn Glu Ser Phe Asp Asn Asn
        1255                1260                1265 cat agc atg tca cga gca aag aag aaa tac aca ttt gag aaa gaa       4246
His Ser Met Ser Arg Ala Lys Lys Lys Tyr Thr Phe Glu Lys Glu
        1270                1275                1280 gtt aac gaa aaa att gct ggt act aaa cat tca ctt gat aca act       4291
Val Asn Glu Lys Ile Ala Gly Thr Lys His Ser Leu Asp Thr Thr
        1285                1290                1295 gat cca aga gaa gca atc aga gtg tta aat act ggt gaa acc aag       4336
Asp Pro Arg Glu Ala Ile Arg Val Leu Asn Thr Gly Glu Thr Lys
        1300                1305                1310 aga atc gaa ccc aag aaa aga gag gtg cct atc act gtg aaa tta       4381
Arg Ile Glu Pro Lys Lys Arg Glu Val Pro Ile Thr Val Lys Leu
        1315                1320                1325 aac aaa aga tcg caa tac aag tca cca tat gtt aca aga agt ggt       4426
Asn Lys Arg Ser Gln Tyr Lys Ser Pro Tyr Val Thr Arg Ser Gly
        1330                1335                1340 aga acg gtt ata aac ccc aag agg tat tta cat gcg gtc gtc aac       4471
Arg Thr Val Ile Asn Pro Lys Arg Tyr Leu His Ala Val Val Asn
        1345                1350                1355 aaa atc gac tat aat gat ccg gga tgg ata aag tca atg aat gct       4516
Lys Ile Asp Tyr Asn Asp Pro Gly Trp Ile Lys Ser Met Asn Ala
        1360                1365                1370 gaa cta gag aaa ttt aga tca aaa gat gtt tac gaa gaa gtt cca       4561
Glu Leu Glu Lys Phe Arg Ser Lys Asp Val Tyr Glu Glu Val Pro
        1375                1380                1385 att ccc acc ggt gtg aag cct ata tct atg ggt tgg gta cat act       4606
Ile Pro Thr Gly Val Lys Pro Ile Ser Met Gly Trp Val His Thr
        1390                1395                1400 gag aaa att gat tct ctc aaa ggt gtt gtt cgg aaa tca cgt tgt       4651
Glu Lys Ile Asp Ser Leu Lys Gly Val Val Arg Lys Ser Arg Cys
        1405                1410                1415 gtt gtc cat ggc aac aga caa aag gaa aaa ttg gat tat gac cct       4696
Val Val His Gly Asn Arg Gln Lys Glu Lys Leu Asp Tyr Asp Pro
        1420                1425                1430 ttt agt gtt agt tca cct gtt ata gat ctt gtg act ata aga tta       4741
Phe Ser Val Ser Ser Pro Val Ile Asp Leu Val Thr Ile Arg Leu
        1435                1440                1445 ttg aca ata ata ggt tgt gaa tta gga atg aca att caa cat tta       4786
Leu Thr Ile Ile Gly Cys Glu Leu Gly Met Thr Ile Gln His Leu
        1450                1455                1460 gac gtc gag tcg gcg tat cta aat gcc tct att act cat tca aat       4831
Asp Val Glu Ser Ala Tyr Leu Asn Ala Ser Ile Thr His Ser Asn
        1465                1470                1475 cca att tat gtc ttt cct cct aaa tca gta cct ttg aag aaa aac       4876
Pro Ile Tyr Val Phe Pro Pro Lys Ser Val Pro Leu Lys Lys Asn
        1480                1485                1490 cat tgt tgg tta ttg aaa cgt tct gtc tat ggg tta aaa cag tcg       4921
His Cys Trp Leu Leu Lys Arg Ser Val Tyr Gly Leu Lys Gln Ser
        1495                1500                1505 ggt ttg gaa tgg tat cac act atc aaa aga gta ttg gaa gac att       4966
Gly Leu Glu Trp Tyr His Thr Ile Lys Arg Val Leu Glu Asp Ile
        1510                1515                1520
```

-continued

| | | | | | | | | | | | | |
|---|---|---|---|---|---|---|---|---|---|---|---|---|
| ggt | ttt | act | caa | gtt | tta | cac | aat | gat | ggt | tta | ttt | cac | att | gaa | 5011 |
| Gly | Phe | Thr | Gln | Val | Leu | His | Asn | Asp | Gly | Leu | Phe | His | Ile | Glu | |
| | | 1525 | | | | 1530 | | | | | 1535 | | | | |

```
ggt ttt act caa gtt tta cac aat gat ggt tta ttt cac att gaa       5011
Gly Phe Thr Gln Val Leu His Asn Asp Gly Leu Phe His Ile Glu
        1525                1530                    1535 tat gaa gag gga tca gta ata tat tta ggt tta tat gtt gat gat       5056
Tyr Glu Glu Gly Ser Val Ile Tyr Leu Gly Leu Tyr Val Asp Asp
        1540                1545                    1550 att ctt atg gtt gga agt tca caa aaa gtt att gat aat ttt gtg       5101
Ile Leu Met Val Gly Ser Ser Gln Lys Val Ile Asp Asn Phe Val
        1555                1560                    1565 gat caa ttg aga gat cat ttt gaa gtt aaa gtg ttt ggt gaa ata       5146
Asp Gln Leu Arg Asp His Phe Glu Val Lys Val Phe Gly Glu Ile
        1570                1575                    1580 tca aat tat ctt ggt att gaa ttt cgt aaa acc gaa tct ggt tat       5191
Ser Asn Tyr Leu Gly Ile Glu Phe Arg Lys Thr Glu Ser Gly Tyr
        1585                1590                    1595 att tta tct caa gaa aaa ttt ctc aag aaa tta ctt aag gat ttc       5236
Ile Leu Ser Gln Glu Lys Phe Leu Lys Lys Leu Leu Lys Asp Phe
        1600                1605                    1610 aaa cta gat gac tca tat ggg aaa aac ata ccc tgg att ccg aat       5281
Lys Leu Asp Asp Ser Tyr Gly Lys Asn Ile Pro Trp Ile Pro Asn
        1615                1620                    1625 gac aaa tat gaa aag gtt gca ata att cgt gaa aac gtt aat cca       5326
Asp Lys Tyr Glu Lys Val Ala Ile Ile Arg Glu Asn Val Asn Pro
        1630                1635                    1640 gag aat gat ttt gaa aag gtt ccg aat gag aca ttg ctt gac cct       5371
Glu Asn Asp Phe Glu Lys Val Pro Asn Glu Thr Leu Leu Asp Pro
        1645                1650                    1655 gat gct aaa aaa cta tac caa agt ggt gtt ggc ctg ctt tta tgg       5416
Asp Ala Lys Lys Leu Tyr Gln Ser Gly Val Gly Ser Leu Leu Trp
        1660                1665                    1670 gct gcc aca aac aca cgt cca gat ata tcg gtc gta gtg aat tcg       5461
Ala Ala Thr Asn Thr Arg Pro Asp Ile Ser Val Val Val Asn Ser
        1675                1680                    1685 ttg ggt tct aaa tct gca aat cca aat gtc cat gat tat gag aaa       5506
Leu Gly Ser Lys Ser Ala Asn Pro Asn Val His Asp Tyr Glu Lys
        1690                1695                    1700 ttg att tat tgt ctt agg tat atc aaa aat agc atg gga tat cac       5551
Leu Ile Tyr Cys Leu Arg Tyr Ile Lys Asn Ser Met Gly Tyr His
        1705                1710                    1715 att gag tac aaa aga aac aga ttg aat ata cca cca aaa tca ttt       5596
Ile Glu Tyr Lys Arg Asn Arg Leu Asn Ile Pro Pro Lys Ser Phe
        1720                1725                    1730 gtt atc gaa tgt ttc agt gat gcg tca ttt gca cca gga ttg gat       5641
Val Ile Glu Cys Phe Ser Asp Ala Ser Phe Ala Pro Gly Leu Asp
        1735                1740                    1745 aga aaa tct att agt gga act ttg att tat gtg aat gga aat ttg       5686
Arg Lys Ser Ile Ser Gly Thr Leu Ile Tyr Val Asn Gly Asn Leu
        1750                1755                    1760 gtg caa tgg gcg acc aaa aaa caa acg gtc ata gca caa agc tca       5731
Val Gln Trp Ala Thr Lys Lys Gln Thr Val Ile Ala Gln Ser Ser
        1765                1770                    1775 gca gct tgt gaa atg ttg gct cta aat tat aca atg ttg aaa gct       5776
Ala Ala Cys Glu Met Leu Ala Leu Asn Tyr Thr Met Leu Lys Ala
        1780                1785                    1790 atc gaa ata aaa aac cat tta atg gat ttg ggt ttt gaa gta ggt       5821
Ile Glu Ile Lys Asn His Leu Met Asp Leu Gly Phe Glu Val Gly
        1795                1800                    1805 aag ata cat tgt cat caa gac aac caa gct gtg att aaa gtt ttg       5866
Lys Ile His Cys His Gln Asp Asn Gln Ala Val Ile Lys Val Leu
```

-continued

```
        1810                1815                1820
aga aat aac tat tgt cac cca cat cga cca ata gat atc tgc tat       5911
Arg Asn Asn Tyr Cys His Pro His Arg Pro Ile Asp Ile Cys Tyr
        1825                1830                1835 aag ttt cta cgc caa ttg atc aat gat aaa gta ttt tca ata tcc       5956
Lys Phe Leu Arg Gln Leu Ile Asn Asp Lys Val Phe Ser Ile Ser
        1840                1845                1850 tat gtg aag aca aat gat aat tac gcc gat tgt atg act aag tgt       6001
Tyr Val Lys Thr Asn Asp Asn Tyr Ala Asp Cys Met Thr Lys Cys
        1855                1860                1865 cta agt cgt gct aaa ttc aaa gca ttc gtt gag ggt atg ata aaa       6046
Leu Ser Arg Ala Lys Phe Lys Ala Phe Val Glu Gly Met Ile Lys
        1870                1875                1880 cgg tta gac cta gaa gat aat caa aca ctg ata caa aat gca ata       6091
Arg Leu Asp Leu Glu Asp Asn Gln Thr Ser Ile Gln Asn Ala Ile
        1885                1890                1895 acg gca gaa taa gtggatttat cattactatt atcgtaatgc tcaatcaggg       6143
Thr Ala Glu
        1900 gagtgttggt ttgtgcacta ttttgtgtca gaaactgatc aatgaaaatg atggttatta   6203 tgagaatgga aaattttttcc atcacacatc aggtgatgac agaactaaac tatattgtgt   6263 agtataaata agggtatgaa ataccaacat cccagaatat caacgagata gaagggagga   6323 gtttcaatat atatcttgtg aataataact tcgttctaat tcactataca caactagacg   6383 tgtacacgct caatctcagg taaagaaagt ttatattcca tca                    6426
```

<210> SEQ ID NO 4
<211> LENGTH: 324
<212> TYPE: PRT
<213> ORGANISM: Candida albicans

<400> SEQUENCE: 4

```
Met Ser Ser Ala Lys Asn Asp Asp Asn Glu Gly Lys Val Met Glu Ser
1               5                   10                  15

Val Asp Gln Ala Asn Ala Ile Ser Lys Val Asp Glu His Ile Lys Ala
            20                  25                  30

Arg Phe Asn Met Leu Phe Ile Lys Phe Asn Asp Leu Pro Lys Leu Ala
        35                  40                  45

Val Gly Asn Gln Lys Ser Val Asp Lys Trp Asn Glu Glu Phe Lys Tyr
    50                  55                  60

Phe His Val Ala Tyr Pro Asp Val Leu Glu Phe Leu Leu Asp Tyr Asn
65                  70                  75                  80

Pro Lys Asp Lys Phe Lys Val Lys Lys Val Glu Gly Ile Tyr Phe Thr
                85                  90                  95

Gly Trp Cys Leu Gln Met Cys Leu Gln Ser Ile Phe Asp Arg Phe Arg
            100                 105                 110

Leu Ile Met Ile Ser Lys Leu Pro Lys His Leu Gln Lys Glu Ala Asn
        115                 120                 125

Leu Ile Lys Ala Ala Tyr Asp Ala Val Thr Lys Ser Lys Asp Tyr Thr
    130                 135                 140

Ile Thr Ser Lys Ile Leu Ser Lys Phe Val Asn Val Glu His Glu Leu
145                 150                 155                 160

Val Val Cys Tyr Asn Leu Pro Tyr Leu Ser Gln Val Glu Glu Lys Leu
                165                 170                 175

Glu Glu Ile Leu Tyr Asn Thr Ser Asn Val Val Asp Glu Tyr Val Arg
            180                 185                 190
```

```
Ser Leu Pro Asn Leu Ile Gly Gln Val Leu Tyr Phe Asn His Val Lys
        195                 200                 205

Lys Ser Glu Ala Leu Ser Leu Phe Leu Asn Ile His Ala Ser Tyr Tyr
    210                 215                 220

Ser Lys Trp Ile Gln Ala Asp Asn Asp Thr Ser Val Leu Pro Ser Cys
225                 230                 235                 240

Ser Thr Ile Ala Glu Glu Met Cys Asp His Pro Asp Tyr Ala Arg Leu
                245                 250                 255

Val Asp Ile Pro Ser Asn Lys Tyr Glu Leu Asn Leu Ile Val Ser Leu
            260                 265                 270

Pro Ala Pro Glu Lys Pro Lys Gly Lys Pro Glu Glu Asn Ser Ser Glu
        275                 280                 285

Gln Ser Gln Lys Lys Asn Ser Lys Ser Arg Lys Arg Asn Lys Lys His
        290                 295                 300

Pro Lys Ser Asp Asn Asp Lys Gly Glu Lys Glu Lys Glu Lys Glu Lys
305                 310                 315                 320

Thr Ser Ser Glu
```

<210> SEQ ID NO 5
<211> LENGTH: 1576
<212> TYPE: PRT
<213> ORGANISM: Candida albicans

<400> SEQUENCE: 5

```
Lys Thr Gly Ala Ala Ser Ile Asn Cys Val Met Asn Ile His Asn Cys
1               5                   10                  15

Ser Lys Thr Thr Phe Pro Val Glu Asn Ser His Ser Leu Asn Ala Ser
            20                  25                  30

Leu Asn Val Met Asn Phe Lys Gly Leu Arg Phe Asn Lys Tyr Leu Val
        35                  40                  45

Tyr Asp Thr Gly Ala Thr Ile Ser Val Val Asn Asn Lys Asp Ile Leu
    50                  55                  60

Ser Asn Val Lys Asp Ala Thr Ile Glu Val Ser Val Ala Asp Gly Ala
65                  70                  75                  80

Thr Leu Glu Ala Asp Cys Ile Gly Asp Leu Ile Arg Val Gly Ile
                85                  90                  95

Val Ser Ile Thr Leu Glu Asn Thr Leu Tyr Leu Pro Glu Ser Ser Phe
            100                 105                 110

Asn Leu Val Ser Leu Lys Gln Ile Glu Glu Arg Gly Phe Asn Val Leu
        115                 120                 125

Ile Thr Lys Glu Ser Val Ile Val Phe Asn Gln Asn Val Ala Pro Thr
    130                 135                 140

Ile Ile Ala Ser Arg Lys Asn Ala Ala Asp Leu Tyr Met Gly Pro Gln
145                 150                 155                 160

Phe Ser Glu Glu Ser Leu Glu Cys Asp Phe Asp Tyr Asp Gly Leu Ala
                165                 170                 175

Asp Met Leu Ser Asn Ala Asn Gln Asp Asp Lys Asp Lys Ser Ser Met
            180                 185                 190

Asn Glu Met Ser Glu Tyr Gln Glu His Asp Tyr Ser Ser Arg Ala Leu
        195                 200                 205

Ile Asn Ser Leu Thr Glu Val Asp Val Leu Asp Val Glu Ile Ser Pro
    210                 215                 220

Tyr Gly Val Glu Gln Leu Leu Pro Thr Gly Asp Lys Asn Asp Ile Tyr
225                 230                 235                 240
```

-continued

```
Asn Phe His Leu Met Ser Asn His Met Ser Ile Glu Lys Ile Leu Leu
            245                 250                 255

Leu Gln Lys Tyr Gln Gly Leu Val Leu His Thr Ser Lys Glu Ser Leu
            260                 265                 270

Gln Lys Ile Ala Asp Cys Lys Val Cys Leu Leu Ser Asn Ala Lys Gln
            275                 280                 285

Arg Ser His Asn His His Ser Glu Arg Lys Ala Ser Arg Arg His Glu
            290                 295                 300

Arg Leu His Cys Asp Thr Leu Gly Pro Phe Arg Ser Glu Asn Asn Lys
305                 310                 315                 320

Trp Tyr Leu Thr Ser Val Ile Asp Glu His Thr Gly Tyr Ile Glu Gly
                325                 330                 335

Ile Ile Thr Lys Asp Arg Lys Val Lys Asp Leu Leu Ile Gln Arg Leu
            340                 345                 350

Lys Ile Trp Asn Asn Arg Phe Asn Asp Lys Val Ala Tyr Phe Arg Ser
            355                 360                 365

Asp Asn Ala Pro Glu Phe Pro Gln Pro Ser Asp Leu Ala Glu Phe Gly
370                 375                 380

Ile Trp Arg Glu Thr Ile Ala Ala Tyr Ser Pro Glu Leu Asn Gly Leu
385                 390                 395                 400

Ala Glu Val Val Asn Lys Leu Ile Leu Gln Gln Ile Tyr Arg Ile Val
                405                 410                 415

Val Thr Leu Gly Pro Gln Ile Leu Lys Leu Ile Tyr Tyr Val Ile Gln
            420                 425                 430

Tyr Ser Ile Thr Met Ile Asn His Thr Pro Arg Arg Ser Leu Lys Gly
            435                 440                 445

Gln Thr Pro Tyr Gly Cys Tyr Tyr Gln Leu Ser Glu Gly Asn Phe Tyr
            450                 455                 460

Arg Phe Pro Phe Ala Ile Asp Cys Val Val Thr Phe Ser Asn Ala Ile
465                 470                 475                 480

Glu Lys Asn Arg Tyr Gly Val Thr Ser Thr Lys Gly Ala Pro Ser Ser
                485                 490                 495

Ile Met Gly Ala Val Ile Gly Tyr Ala Ser Asp Cys Phe Ser Tyr Tyr
            500                 505                 510

Val Leu Leu Lys Asn Met Arg Cys Asp Ile Ile Leu Ser Pro Asn Val
            515                 520                 525

Arg Ile Leu Arg Ser Tyr Glu Val Ile Asn Ser Tyr Leu Lys Asn Leu
            530                 535                 540

Ser Thr Thr Pro Met Ser His Ile Val Pro Met Ala Glu Gly Ile Gln
545                 550                 555                 560

Gly Arg Gln Ser Gly Ala Gln Tyr Glu Val Arg Gly Thr Tyr Val Glu
                565                 570                 575

Ser Glu Tyr Asp Asn Thr Asn Asp Val Met His Met Pro Lys Glu Ser
            580                 585                 590

Tyr Ser Val Gln Pro Ala Ser Phe Thr Leu Thr Thr Gly Asn Ser Ser
            595                 600                 605

Asn Glu Tyr Val Ile Asn Asp Pro Val Gln Ile Thr Ile Glu Asn
            610                 615                 620

Pro Asp Asp Phe Ser Asn Pro Leu Gln Leu Thr Glu Glu Ser His Asp
625                 630                 635                 640

Met Val Ser Glu Val Lys Ser Asp Glu Asn Pro Lys Pro Ser Leu His
                645                 650                 655
```

-continued

```
Glu Leu Thr Pro Gly Asp Asn Pro Val Ser Lys Pro Pro Gln Leu Gly
                660                 665                 670

Thr Glu Thr Ser Val Ile Gly Lys Ser Lys Glu Pro Ile Thr Asn His
        675                 680                 685

Thr Lys Asp Ala Pro Ser Ile Gln Gly Arg Asp His Lys Arg Ser Glu
        690                 695                 700

Ser Thr Ala Gln Val Gly Leu Ser His Gln Pro Gln Thr Gly Thr Pro
705                 710                 715                 720

Ala Ser Glu Glu Ser Lys Leu Ser Gly Thr Asp His Phe Gly Val Asp
                725                 730                 735

Val Val Lys Glu Thr Val Ser Glu Asp Trp His Thr Ser Asp Tyr Pro
                740                 745                 750

Glu Thr Ser Ala Glu Asp Glu Gln Gln Asn Pro Ser Leu Ser Ala Asn
                755                 760                 765

Lys Asn Arg Val Thr Glu Lys Ile Asp Glu Gly Glu Asn Ile Ser Phe
        770                 775                 780

Pro Gly Gly Asp Asp Asp Ser Val Val Ile Asn Ser Asn Val Glu Gln
785                 790                 795                 800

Ser Asn Val Glu Thr Glu Asp Ala Gly Asn Ser Pro Ile Gln Asp Glu
                805                 810                 815

Val Ser Gln Glu Gly Arg Ile Leu Asn Glu Gln Thr Asp Ile Val Asp
                820                 825                 830

Thr Val Ala Lys Val Ile Glu Asn Glu Lys Ile Ser Pro Ile Asn Ser
        835                 840                 845

Leu Asp Asp His Thr Glu Leu Ala Thr Asp Ser Gly Asn Asp Ser Asn
        850                 855                 860

Ser Thr Glu Ser Asp Ile Gln Ser Lys Asn Glu Ile Ser Pro Val Ile
865                 870                 875                 880

Asn Glu Lys Asn Thr Glu Ile Ile Gln Lys His Ile Glu Ser Ile Leu
                885                 890                 895

Ala Asp Lys Arg Leu Asp Glu Phe Glu Thr Tyr Asn Val Asp Glu Ile
                900                 905                 910

Glu Asn Val Ile Asn Asp Asp Ile Ala Glu Ala Asn Pro Leu Pro
        915                 920                 925

Asp Glu Asn Asn Asp Val Gln Met Asn Glu Ser Phe Asp Asn Asn His
        930                 935                 940

Ser Met Ser Arg Ala Lys Lys Lys Tyr Thr Phe Glu Lys Glu Val Asn
945                 950                 955                 960

Glu Lys Ile Ala Gly Thr Lys His Ser Leu Asp Thr Asp Pro Arg
                965                 970                 975

Glu Ala Ile Arg Val Leu Asn Thr Gly Glu Thr Lys Arg Ile Glu Pro
                980                 985                 990

Lys Lys Arg Glu Val Pro Ile Thr Val Lys Leu Asn Lys Arg Ser Gln
        995                 1000                1005

Tyr Lys Ser Pro Tyr Val Thr Arg Ser Gly Arg Thr Val Ile Asn
        1010                1015                1020

Pro Lys Arg Tyr Leu His Ala Val Val Asn Lys Ile Asp Tyr Asn
        1025                1030                1035

Asp Pro Gly Trp Ile Lys Ser Met Asn Ala Glu Leu Glu Lys Phe
        1040                1045                1050

Arg Ser Lys Asp Val Tyr Glu Glu Val Pro Ile Pro Thr Gly Val
        1055                1060                1065

Lys Pro Ile Ser Met Gly Trp Val His Thr Glu Lys Ile Asp Ser
```

-continued

```
              1070                1075                1080
    Leu Lys Gly Val Val Arg Lys Ser Arg Cys Val Val His Gly Asn
        1085                1090                1095
    Arg Gln Lys Glu Lys Leu Asp Tyr Asp Pro Phe Ser Val Ser Ser
        1100                1105                1110
    Pro Val Ile Asp Leu Val Thr Ile Arg Leu Leu Thr Ile Ile Gly
        1115                1120                1125
    Cys Glu Leu Gly Met Thr Ile Gln His Leu Asp Val Glu Ser Ala
        1130                1135                1140
    Tyr Leu Asn Ala Ser Ile Thr His Ser Asn Pro Ile Tyr Val Phe
        1145                1150                1155
    Pro Pro Lys Ser Val Pro Leu Lys Lys Asn His Cys Trp Leu Leu
        1160                1165                1170
    Lys Arg Ser Val Tyr Gly Leu Lys Gln Ser Gly Leu Glu Trp Tyr
        1175                1180                1185
    His Thr Ile Lys Arg Val Leu Glu Asp Ile Gly Phe Thr Gln Val
        1190                1195                1200
    Leu His Asn Asp Gly Leu Phe His Ile Glu Tyr Glu Glu Gly Ser
        1205                1210                1215
    Val Ile Tyr Leu Gly Leu Tyr Val Asp Asp Ile Leu Met Val Gly
        1220                1225                1230
    Ser Ser Gln Lys Val Ile Asp Asn Phe Val Asp Gln Leu Arg Asp
        1235                1240                1245
    His Phe Glu Val Lys Val Phe Gly Glu Ile Ser Asn Tyr Leu Gly
        1250                1255                1260
    Ile Glu Phe Arg Lys Thr Glu Ser Gly Tyr Ile Leu Ser Gln Glu
        1265                1270                1275
    Lys Phe Leu Lys Lys Leu Leu Lys Asp Phe Lys Leu Asp Asp Ser
        1280                1285                1290
    Tyr Gly Lys Asn Ile Pro Trp Ile Pro Asn Asp Lys Tyr Glu Lys
        1295                1300                1305
    Val Ala Ile Ile Arg Glu Asn Val Asn Pro Glu Asn Asp Phe Glu
        1310                1315                1320
    Lys Val Pro Asn Glu Thr Leu Leu Asp Pro Asp Ala Lys Lys Leu
        1325                1330                1335
    Tyr Gln Ser Gly Val Gly Ser Leu Leu Trp Ala Ala Thr Asn Thr
        1340                1345                1350
    Arg Pro Asp Ile Ser Val Val Val Asn Ser Leu Gly Ser Lys Ser
        1355                1360                1365
    Ala Asn Pro Asn Val His Asp Tyr Glu Lys Leu Ile Tyr Cys Leu
        1370                1375                1380
    Arg Tyr Ile Lys Asn Ser Met Gly Tyr His Ile Glu Tyr Lys Arg
        1385                1390                1395
    Asn Arg Leu Asn Ile Pro Pro Lys Ser Phe Val Ile Glu Cys Phe
        1400                1405                1410
    Ser Asp Ala Ser Phe Ala Pro Gly Leu Asp Arg Lys Ser Ile Ser
        1415                1420                1425
    Gly Thr Leu Ile Tyr Val Asn Gly Asn Leu Val Gln Trp Ala Thr
        1430                1435                1440
    Lys Lys Gln Thr Val Ile Ala Gln Ser Ser Ala Ala Cys Glu Met
        1445                1450                1455
    Leu Ala Leu Asn Tyr Thr Met Leu Lys Ala Ile Glu Ile Lys Asn
        1460                1465                1470
```

```
His Leu Met Asp Leu Gly Phe Glu Val Gly Lys Ile His Cys His
    1475            1480                1485

Gln Asp Asn Gln Ala Val Ile Lys Val Leu Arg Asn Asn Tyr Cys
    1490            1495                1500

His Pro His Arg Pro Ile Asp Ile Cys Tyr Lys Phe Leu Arg Gln
    1505            1510                1515

Leu Ile Asn Asp Lys Val Phe Ser Ile Ser Tyr Val Lys Thr Asn
    1520            1525                1530

Asp Asn Tyr Ala Asp Cys Met Thr Lys Cys Leu Ser Arg Ala Lys
    1535            1540                1545

Phe Lys Ala Phe Val Glu Gly Met Ile Lys Arg Leu Asp Leu Glu
    1550            1555                1560

Asp Asn Gln Thr Ser Ile Gln Asn Ala Ile Thr Ala Glu
    1565            1570                1575
```

<210> SEQ ID NO 6
<211> LENGTH: 1309
<212> TYPE: DNA
<213> ORGANISM: Unknown
<220> FEATURE:
<223> OTHER INFORMATION: sequence of retrotransposon from unknown organism
<221> NAME/KEY: misc_feature
<222> LOCATION: (1)..(1309)
<223> OTHER INFORMATION: 'n' can be any nucleotide 'a', 'c', 'g' or 't'

<400> SEQUENCE: 6

```
ctggataaag aaatcagaaa agagatagca ggaaaaccag gaaaaggtga cgatgatgac      60
gacgacagtt ggggatctgt gcctgtttca attcgagtat ttgctgaagt tgaaaagaag     120
ttgaagcaaa agaaaagttt ggcatcaagc tagatattta tatatgtata tgattagacc     180
aacataaaac tagacgtcca aatatttatt tatttattta ttgatatata ttcttattta     240
ttactgttat gatcttttga ttcacacaga gatttaatcc aaatcaatac cttttgtttt     300
gtagaaatct tttgcttctt caatttgtat tttcaattct ttgtatttat gttctttgtc     360
tttgaatgta acaattcccc aacctaacgt tgataaggca taagacccaa atgtgactaa     420
tccccaccat ggcaagtatg gcaatatttc atcgtgtatt ttagctggag ttggaatcac     480
acctgtgata agagcaaaat aaatagctga taaggcaaaa attgttaatc ctgtttcagt     540
agctttagtc attcttatag ttagacttgt taaagggtag ttgtgttaat tgaagatatg     600
ctggaaaact atacttttcg ttgtttttt ttttcaatct aggtcgggtg tgctgttatt     660
ttttttctct cttcttggtt cttagtattg gattatatgt tggtttatgc gacgtttgtg     720
tcagggaaat aacaccttga tataagtcgt gcgtattagg tcaacattgg tgaaaaattt     780
gcactcatcg agagccagga attagtataa aagaagaga aagaaagat atttaggata     840
tttattatat agggaccgag tttcaggaga cactttagt gggcgtaaac ttcattcact     900
ctgtttttg cttattacaa attatcacct atcgtgtact aggactaatt ctcacgaata     960
ttccgtgtat acaaacactt attgccaact tatggtgcgg aactttattt gtctgaacca    1020
aaatcaaagt cacatcattt aaatgaacgt tgacataaat agattcttta ttcaatagaa    1080
acaatttctt cctttntctt ttctttgtat tantggttag atttccattc catatacaca    1140
caagatgtca acgaaatcag caaattcaac tgctgtcaat tcatttaatg caaaccactc    1200
caactatgac gttttagac cttcattcac cccagttttg gtcaatacat tcttagtaca    1260
tcttggatta gctacgaaaa acccagatga cactttcact tttgacata                1309
```

<210> SEQ ID NO 7
<211> LENGTH: 1340
<212> TYPE: DNA
<213> ORGANISM: Unknown
<220> FEATURE:
<223> OTHER INFORMATION: sequence of retrotransposon from unknown organism
<221> NAME/KEY: misc_feature
<222> LOCATION: (1)..(1340)
<223> OTHER INFORMATION: 'n' can be any nucleotide 'a', 'c', 'g' or 't'

<400> SEQUENCE: 7

| | | | | | |
|---|---|---|---|---|---|
| cccntttgtn | tggtacatgt | tagacaggcc | caaaaaatgg | tatcatttag | aactgtatgg | 60 |
| agaacattag | ttttggtcca | acattgcgtg | atgatggtat | ntntttcgta | ttatagtaca | 120 |
| atgatggctc | aatgattnat | tttaggttta | tatgtggatg | atatcttaat | ggacagaatc | 180 |
| tcagatggaa | tcgttatcag | atttgttgaa | caagagagag | tttatttcgc | gtnaaaatca | 240 |
| atttaggtct | catgacagaa | tatgtgagat | aaaatgtcca | cgtaagcaaa | actgggtgat | 300 |
| actntgaatt | aagagatact | cctaaataag | caaaccaagg | atnttaaact | acacaantcg | 360 |
| tatggtaaaa | cgtgctttga | gtnccaaatg | atagatgcga | gataccaaca | aaatagnact | 420 |
| gtcgcaaatg | ctgaanacaa | tttcactgag | gttcgaaatg | naaaatnact | taantcaatt | 480 |
| aaaaaattta | taccaaaagg | tggtctggaa | gtgctgatat | gaacacgaaa | tttaangcat | 540 |
| tctgtggaaa | attcgtttaa | gctcacantc | ggaaaatact | accattctac | atttgcagaa | 600 |
| aattaaaatt | gtgttgtgaa | atatctacat | cctacaaagt | tcaagacatt | tattgatggt | 660 |
| atattcaaag | gactcgatgt | tgagaatgat | aataacctga | accaagacgc | tacaaatgct | 720 |
| aattgagtaa | ttcgtaattg | ctaaacaacg | ccatttcgaa | tcaggggagt | gttggtttat | 780 |
| gcgacgtttg | tgtcagggaa | ataacacctt | gatataagtc | gtgcgtatta | ggtcaacatt | 840 |
| ggtgaaaaat | ttgcactcat | cgagagccag | gaattagtat | aaaaagaaga | gaaagaaag | 900 |
| atatttagga | tatttattat | atagggaccg | agtttcagga | gacactttta | gtgggcgtaa | 960 |
| actncattac | tntgtttttt | gcttattgca | aataatccct | atcgtgtact | aggactaatt | 1020 |
| ctcacgaata | ttccgtgtat | acaaacaaaa | tcagacttct | tggtaagccc | agccgaaaca | 1080 |
| gccatacttc | tagtggatct | ttctatacta | caacattcac | actgcttgac | ctacaactac | 1140 |
| acatattcct | tgttataagg | gcaatctatc | acacaaaaga | tttactgttg | actcacaaga | 1200 |
| tatcaactgt | actaataaag | gagtgcattc | tatgacccttt | ggagaggaac | tatgtataat | 1260 |
| ataagagaga | agggactaaa | gatctatata | taatgagcag | gatgggtaac | ccggtggggt | 1320 |
| attagcacgc | acacgacctg | | | | | 1340 |

<210> SEQ ID NO 8
<211> LENGTH: 556
<212> TYPE: DNA
<213> ORGANISM: Unknown
<220> FEATURE:
<223> OTHER INFORMATION: sequence of retrotransposon from unknown organism

<400> SEQUENCE: 8

| | | | | | |
|---|---|---|---|---|---|
| caacattggg | tgaaaaaatt | tgcactcatc | gagagccagg | aattagtata | aaagaggag | 60 |
| aaagaaggta | tttaggatat | ttattatata | gggaccgagt | tcaggagac | acttttagtg | 120 |
| ggcgtaaact | tcattcactc | tgttttttgc | ttattacaaa | ttatcaccta | tcgtgtacta | 180 |
| ggactaattc | tcacgaatat | tccgtgtata | caaacattat | acgtgtctgt | aactacgcga | 240 |

-continued

```
aactacttcg tctcagtttt ttgttacaaa caactttccg tatagacctg agattttgtc    300
agcttgattg aatggaagag tttactaaag taccagaaag gtgttttata gataacatgt    360
agatatataa aaatgttata ttacaaatga cttccaaaag aaactgtacg aattttgctg    420
tttattaaaa accagttcct gaaaactagt atcttagctt cagtacattt agcccaccta    480
aattggacct atgacaagtt ctactttccc gacaatgcta atatagagca gtttcttctt    540
cttcttcttc ctcgtc                                                    556
```

<210> SEQ ID NO 9
<211> LENGTH: 2112
<212> TYPE: DNA
<213> ORGANISM: Unknown
<220> FEATURE:
<223> OTHER INFORMATION: sequence of retrotransposon from unknown
      organism

<400> SEQUENCE: 9

```
atttaatatg ttggtattgg ctactgccaa cttcttagct gatgcagatg ccattgttaa     60
tattgttaaa ttgggtaaat agtatgaagg aagctttggc aggcgttgtt attttttca    120 ccaattatta tcatcacctg cggaggttag tcaatttgag attgtgcgag ggaaaaaaaa    180
cgacctccat acactacctc aagtataagt ccagtccaat tgttcgctat agagagattt    240
cctagccgga atgcacgaca atcctgagac ggaagtcgat cgtcgatgcc catggtgcgt    300
ggtgaaaaat tttcttagaa aatttgttct ttccttcaac tgctttgaag agagggaggt    360
tcaagtggtt taagtacgac ggtcacaaag attgcggctt atgaggcccg aactgagttg    420
aaatacaaaa tcaagatata attatatacc ttacttgtct atattgtttt ataatacatt    480
cttcagatat ttaaatttct gtgtatcatc ctataaaaca gagatacatt cagtgcattt    540
agtatactga gtgaactggt acctgtgaca ttcaagataa ctgtttcacg cacgctggca    600
gacgaacacc aatagtatga tgaagaactg accatggtgt aagaggtttg atggagtttc    660 tttttttag aagaggttga taagccaaca gatgaggagt aacaagtaac tcgcaacatt    720
gtataacata agtttacatc aaatcagaat ttactaagaa aatcaatcca ttcaaaaggc    780
actcaatcat tgaaaaaacg agcttaatga gtagacggtc tgttcatatg aaacaattga    840
aagggttgaa tattgtttgg aaaattatat aattcatgtc aaactgggag cttaaatta    900 tggtcactcc acagattatg aaacgtagtt acacaattct tggacctgga atcccacaa    960 gagagcgtta gttagtttgc actctcctca ccagttaaac tacccatgat tctccaatgt   1020
ggcttattta agtatcagac aacagataca tggtttccaa gtggtctcat ttttggttta   1080
ctggagtctg cattccccac aaaagtacct ttcaaaacta attaatgtag cttctatttg   1140
atagcctctg ttatggaaat agatttgctc tgcccagtgg gtgtaattat tcccagctgg   1200
aactattccg atagatatgt tttaatgtca atttaaatct tgtaataata gtaaggatgc   1260
ggtttatccg cgatcttctt aatacctgtg gagttactcc agaacagagg ttcaattttt   1320
tcttggttgg taaattatcc gagtaacacg gggtagcttg gttactccag ttgagaatgt   1380
aaactataga tgaagatttc aacacgcaat tattacccca ccttggcgaa ttactaatcg   1440
actatttgtt aatccagaaa aaattataca caaacactgc ctttttttaa aaaagcgtt   1500 attttgatgg aacgataatt aacgatggtt ctgcacaaaa atgtggtcca aagccccaga   1560
ctattctgaa gtatgatttg ttacttaatt tagtgaataa ttaaacataa aatctggaga   1620 aaaattttt ttttgctctc atgaccagtg gcaaattctt ggtaacgagg cttaacatta   1680
```

-continued

```
atccgcaaat tacctggcaa cagagaaaac acccagaaag ttctgtcgta tgagaaaacc   1740
tacagttgtt tccgatttct ccgagcacta acataaaga gaccagtaat gctaaaaaaa    1800 ttttattc tgcattactg ttttagcaa atacacgtct aatttattgt atttgttaaa      1860
cattcttttc ctgaaatttt aagaaaatgt tttggtttgt tggaattcca tttaaacggt   1920
actttggggt gcagacagca atccatttgg agagtggcaa gtctacacga atttagctaa   1980
ggttcactat atcgtgtaac aagaaatttc tataccaaat aaacagcact tgattgaact   2040
acaatatgta aaaacttgct tttattacca gtcttcatac ataccccggt cttctctttt   2100
caatattctg ta                                                       2112
```

<210> SEQ ID NO 10
<211> LENGTH: 3742
<212> TYPE: DNA
<213> ORGANISM: Unknown
<220> FEATURE:
<223> OTHER INFORMATION: sequence of retrotransposon from unknown
      organism

<400> SEQUENCE: 10

```
ttagaaaaca ggaaacagca atagagagca ataattgaaa aatagtgttg tcaacaatag     60
aacaaattgg tcaaacttta aatgcaaaac atgaaattcc caatttccag aataaataat    120
atcagcatac atggccccga aaactacttt accgtgtcgc tttaaccccc cccttcctaa    180
aacgagacaa ttagacatac attccacaat tatcataatc ccctttttt tccttacaaa     240 acactttatt tttgtcgttt tcgttatttg cttcgacgac attgtaaact ctttggattt    300
gcagtagtag tgctcctggt gtaaggtggg tttggttgta gagtaaaaga acgacaatt     360 gattacacct cgatatgcat acgcatggca aagagaatac cgagttaata gtgagtctat    420
tagtgttgca ggaaaagtta tacgaacaac attttgttta gtgtggatat tccagatcaa    480
caacaatatg actaaaatca tagctctaat tttcagttta cctttgttta ttacgatact    540
gccacagtcg tgctgtacca gggtcagttt tagaaaaact attctagaaa tgatgagtag    600
aaatgtacta ttatgagcaa tatttcaaaa agtgaaatta taattgctgc tgacaacacc    660
aacaatacat acaaatttgg aaacgagcaa atcgagaaaa tttcaatccg tttagcaagt    720
tgttcgttgt cgtcattgtc gattagtttc agtttctaga ggtgaaattt tctatggcac    780
caaaaccaaa gcctcaattt taatttactc tgtgtggtac aaaatacatt agagaggatc    840
ctctccaaac aggattgcag gaagttttac acgagaatga tttactacac gacgttgaat    900
taaaaagctc aaccagtttg tcagcaattt tgttctatct gttcaatttc ttgtataaaa    960
taaagcaata tgagagagca tctaaatcaa taatgtcaac acaatattaa actttgagaa    1020
ggattgttca acaaaacaat ccgatgaata gaagaagaat aatatcaaat tgttcctgat    1080
tgattgttgt tatttatttt ttatctccga attcctgcac aatggctcaa caacagccaa    1140
cacggatcac acattaaatt ttttttcgt gcaggacccc gtggtggtgg ctgtggctgt     1200
gattgtgatc attgtagttt ctgccttgat gatgacaaaa aatgatagag ttcagtatga    1260
ggaagaaatt aagcgatatc ggtttatgat gtgtttagtt attaattgct ctcaatggtt    1320
ttcaacaacg tatacaaaac tggtggtgct tgaaacgaat gagtaataca gatctaatta    1380
agctgtgatt ttctaagttt gccttgtctc tacagttcaa aaaaaagaa cagaacacct     1440 cagaggctgt tgtgatgcaa ttttaggaa cctcaacaac aaccactgac tgatctaagc    1500
cagcatctgt ttaatgggtt ttcaaaaaga atggggcaaa cggggaattg aaccccgggc    1560
```

-continued

```
ctcctcgaat tttgtgtttg gtgaacaacc caaacgagga atcataccac tagaccattc    1620
gcccaattcg atgacttgga attattctag ttattttga catacaaagc tcagctttat     1680
tacagatagt catgtttgca tggatgaatt agtactacta ataataag aaaactagtt      1740
aattggagtc aatgtcttat acatgtcttc tgatgggtta tgcattgatt aattatgaat   1800
ttcttttaaa tacaatctat tgctattatt tgtatgtaaa actttaccca aaaaccaaca   1860
aaaagagtg gtcttggata aagattaaag taattccaaa aagatttggt aattagctat    1920
attgttttga cgtacatcta taactacaaa tagccattca gtttgattat gtatattgac  1980
atagttggat ttgtaatttc tgttaaaatg gaaaaccta atcaaatgta tatgttgaat   2040
aggtagttaa attgtacaac ctactacttg ttgtcaattg aattcagagc caatacttat  2100
atctcctgga aactgataca caaacgaatt gttaaactat aacactcgac gttcacatct   2160
aaggattcat cgtcgttaag atttatactc attagcaaac tcacttgcca tattaaacac   2220
ttctcaatct atttcccaca atccaattaa tcagcacgaa aactaagata ctatatatat  2280
ctgcctatac ctgatataca catggcacat ggcgtatccc acaaaaaacc gtcaagacaa   2340
caccaatatg acaatgccaa ttatacaatt gcatatacca cgtgacttca ttttatggtc   2400
atgagaaatt aacttatcat ggggttaggc gagaatatca actgttcgct atagagagat   2460
ttcctagccg gaatgcacga caatcctgag acggaagtcg atcgacgatg cccatggtgc   2520
gtggtgaaaa atttcttag aaatttgtt ctttccttca actgctttga agaaagggag    2580
gttcaagtgg tttaagtacg acggtcacaa agattgcggc ttatgaggcc cgaactgagt  2640
tgaaatacaa aatcaagata taattatata ccttacttgt ctatattgtt ttataataca  2700
ttcttcagat atttaaattt ctgtgtatca ttctataaaa cagagataca ttcagtacat  2760
ttagtatact gagtgaactg gtacctgtga cattcaagat aactgtttcg cgcacgctgg  2820
cagacgaaca tcaacactga tcatttgttt ttttttatt tctcctttt ctcctttttc    2880
tttctttttt cttctttctt cagacgttgt tgatttattt tatcgacagc atcctttct   2940
ttggccacat atccaagcga tatactggcc aaagcgaagt cctttataa agcaatgcta   3000
ccaaatgtaa cagttcgagg tcagaagatt aagcgggtat gttcacacgg atattttatg 3060
gggtatcact tgtaccaaac actttgatac gataagaata tttgtaatac taacttcagt  3120
gtctttcata atcagctcat aacctgttgg aattaaatt cgtatgttgt tcattcaaaa   3180
ttttgataaa tgggacgaga atcatcgtt gcctcctaat tagattatga cttagtacta   3240
actaaactgt ttatcatttt ttaaagcgtt gggctccatg ttagaataga ttattagggc  3300
ggtacgtatt tcataattta tatataggta cttattttta ctaatttatt gcacaggaaa   3360
agataaaagg tatcgattat acctatcagc aaggtttaag caaaatgaag tattttacc    3420
atattttcc attttatat agatacatca agaggttat tttaagttca cctggataaa   3480
ccattcaact aacccaattg aattgaatga caattgatc tccaaagagg gattcatttc    3540
tattctggag agataaacgt cattgtttag gaaagagcaa gagataagaa atcttttgta  3600
tattgtatat atattattaa tgttatatta cactattgtt tgtttgtttg ttataattat   3660
atgtgagatt tcatatgtaa gatgttgtta tctctttcca ttatttagct tttttgaaaa   3720
agctatcaat ggctccacgt tt                                            3742
```

<210> SEQ ID NO 11
<211> LENGTH: 1438
<212> TYPE: DNA

```
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(1438)
<223> OTHER INFORMATION: 'n' can be any nucleotide 'a', 'c', 'g' or 't'

<400> SEQUENCE: 11
gtgtagatgc aataggtgta tgaaatgtat ctagattata tcatgaagcc cttgccaata     60
aaatctagcc aaaaatttgt gtactgcaat tgttcgctat agagagatat cctagccgga    120
atgcacgaca atcctgagac ggaagtcgat cgtcgatgcc catggtgcgt ggtgaaaaat    180
tntcttagaa aatttgttct ttccttcaac tgcttttaag agaagggagg ttcaagtggt    240
ttaagtacga cggtcacaaa gattgcggct tatgaggccc gaactgagtt gaaatacaaa    300
atcaagatat aattatatac cttacttgtc tatattgttt tataatacat tcttcagata    360
tttaaatttc tgtgtatcat cctataaaac agagatacat tcagtacatt tagtatactg    420
agtgaactgg tacctgtgac attcaagata actgtttcgc gcacgctggc agacgaacag    480
caattctgta attgtcgtag agtagcaaca aatcttcccg atgattggta cttgtgttag    540
tctacacgac atgtgttttg gtacacttga actgtatgtc caagaatgga aacatatgcg    600
ggaaggacgc gaaagatgag tttggtatag aagggataag aactgtaaaa tatattatgt    660
agttatatat tttaattatg ggaaattgag tgtttattct gttcaacaag tttcaaccgt    720
agagattaca tttaaagtct gtggtcgaaa tccacaagat acagcaaatt catgaattca    780
cctatttaaa tcaagtttac caagcaccat tgcctagaac ttgccatatc atcaattaag    840
tcagacatta ctaatttgag caaagctttt agcttaatgg gccaactaat ttaagtcgaa    900
ttggtaatgc aatctgttct tcatttgagt cgcttgctac ggctccatga cacatccatt    960
tgattgtttt aattcgagca attatccacc ataactctca gtaatatcat taacagtttt   1020
acgcttaata agcatagaaa gttgtatgaa gttgtctcct aggtatgcta gagagatttg   1080
tatatacgac cagtaaagag tgtgatgagg tgtttactgt agggtaaatt gcaattgact   1140
tgagttgata gcggttatta caaaagtata gattcaacaa attaagacaa gtaccaaacg   1200
ataggccgaa tgtgacttat accgttgaag ttcaagcgtt tttaacaaat agaaatgtga   1260
gattaatgag ttcgacaaat gttttactag atactattaa tttcgatgta ctatataagt   1320
ttaaccagct ataaccggca gagcagactt cctgaaactc aaattggttg tgtttggact   1380
tgagttacac cacaaagttt gacaatcgtg aggacatagc aacctatcaa gccactca    1438

<210> SEQ ID NO 12
<211> LENGTH: 1304
<212> TYPE: DNA
<213> ORGANISM: Unknown
<220> FEATURE:
<223> OTHER INFORMATION: sequence of retrotransposon from unknown
      organism

<400> SEQUENCE: 12
tgaagatctg gctttggcca agtatcagc tgcattagat actgtcattg gcattggctt      60
gaacccactg gctgtggatg taactgtgga gccaaaagct cgtaaagctt tggcgttcat    120
ggagaaaaat ctttttaacag acattgtata aacgttgaag attaaagaaa aaaaaaacag   180
aaagattacg aataatttgt ttttaattgg tgggtatgag gtgttgcgca gtcgactcaa    240
caattctctt ttggtgcaca aagttggttt tatggtcaac aattacggag tactgtctgt    300
```

```
agtgatgttg aatctaagac ggaaatgcct cctttacatt tgtttctatt ctcttaaaat      360
acatattcaa ttgtgtgttt taattgaaaa tttgttcatc ttcatctgat gattgtgtaa      420
tctttgcggg ggggggggcgt gtcatgaacc aatctctttg agtcatagga cgagtcatcc      480
tattgtgact catggctcat cttactctct tactaatctc ttacttcatc tgtttactat      540
aaatatgtct actactcctc tattttatta cctcgtttac tattttttatt caatatatga     600 tcttatcttt aaatttcttt tgacaaatac aatcaactta caaaacaaaa gaaaaaagac      660
taataaaata gaattaatga aaaaaaaaaa agactaataa agaaaaaga aagaagacta       720 acaaaagaaa aaacaaaccg gagaacccctt cgctgtagag gaatttccta gccggattgc    780
acgacaatcc tgagacggaa ttcgatcgtt gatgaccgtg gtgcgaggtg aaaagttttc     840
gtagaaattt tgttctctct ttcaaactgc ttttaagaaa atgaggttca agtggtttaa     900
gtacgacggt cacaaagatt gcgacttatg aggaccgaac taagttgaaa tacaaaatca     960
agatataatt atataccctta cttgtctata ttgtttttata atacattctt cagatatttta  1020 aattcctgtg tatcatccta taaaacagac atacattcag tacatttaat atactgagtg     1080
agcttgtatc tgtgacattc aagatatgtt tcgcgcacgc tgacagacaa acatttggtt     1140
gtaaaaaaaa aaatattgaa gaacctcatc accaagatgt ttgaaaaaaa aaaaaatcaa     1200
atacttaatc gcaagctttt caattttattg attgtttgaa ttaattgaat ataaacaaaa    1260
aaaaaaagaa ttcaaattca tttgacatgt cagtggaagt taga                      1304
```

<210> SEQ ID NO 13
<211> LENGTH: 3604
<212> TYPE: DNA
<213> ORGANISM: Unknown
<220> FEATURE:
<223> OTHER INFORMATION: sequence of retrotransposon from unknown organism
<221> NAME/KEY: misc_feature
<222> LOCATION: (1)..(3604)
<223> OTHER INFORMATION: 'n' can be any nucleotide 'a', 'c', 'g' or 't'

<400> SEQUENCE: 13

```
agccccaaaa tggttttcct agnggaggat ggaatggatg ggaccaccca ccaatttggt      60
tcccggaatt tggtttaaaa aaaagtttac ggggatgatt tatttccaaa cccagatgtt     120
tcctgctgct gaaagaattg gaaaagctct tttcagtnac aatctaactg agagaacttg    180
aaagggatca gcatttttgt tatgtcaaca tttaatgacc aatgaccacc agcacgatga    240
tattattctt aaatttctcg ttagcggtgt ctcaccatgg tacttacatc tgcaaattta    300
catgctgtca tataaacttg gattctcaaa tttgttttta gagatttatg ctcaacatta    360
tgaattgtat aaagcagatc ccatttacaa attgccagat agtatgacat tgttgaatga    420
aataagatca aatagagatt atcctaaagt ggtaaatgct gcaaaaaata cagtacaagt    480
caataatgtt tcatccaaga acaataaaaa gaaggatgaa tgcaacaat tagccaataa    540 aattgaggaa gtaggacgtt atagcgaaat aaacgcaaca tctacatatc atgaaattgg    600
cgataccaac aaaaaccaaa ggacaattaa tattgaattt gaaaaatcat acaaaattaa    660
gtgaacaaaa gaagaaaaca aacctattgg tatatgatct gggagccaca gtatccgtgg    720
tgaatgataa gactttactt aacgacatta agaatcaaa tatcgaaatt gcaactgctg     780
aaggggagac atctacggct tatgctttag gtactctaac catatctgtg aatggattga    840
atgcgaaatt agatggtgtt ctatacttgc catctattca attaaactta atatctataa    900
aacaatttga agatttatgc tacgcaattt tgatttccga aaatttaatg tttctagttc    960
```

-continued

```
acagtgacca cgaacctacg gtcattgcga aatattcacc taaagatgac ttatactcag      1020
gcccaagatc gggaaacttt cttaagaaga atcataatga acaaaaccaa attttgcttg      1080
acactgctaa aaaactatta ggatcagaga acatatttct ggagaaatca ctgaaaaatc      1140
caatgattga tcaaggaaaa ttagatccgt tgaaaatgaa caataaagta gaaagagtta      1200
actatgtcag catacacaac atcaaacaag aagtggcaga caaatatatg ataaaagatc      1260
tttactacta tcatttatta attaatcacc tttcacatga aaaactacaa ttattagtaa      1320 aaagggagt gattaaacca gtcaaatcta cttcggctga gtcggccatt ttaaattgtc       1380
agatatgtgt tgcagcccat gcaaaattag ctagccataa tcacactcaa caacgggaat     1440
tggagcgacc attacaacgc ctccatttgg ataccgccgg accatttacc tcaaataaaa     1500
ctaagagcta tcttacaacc gtgattgatc aatttttccag atatactgaa gttattgtat    1560
ctgacaccaa agcagtcaaa caaagcatat tgcatagact tagggtctgg aacaatagat    1620
ttcagtttaa gatcgcggag ataagatatg ataatgcatt ggagtatcca tcggctgagg    1680
agttagagga gttaggaatt tataaacacc ttctcccaaa ctactctcct atgcttaacg    1740
gtacagctga agcaaccaac cgccccattg tccaaggtat ttataaggta gtgttaaatt    1800
ttagttgtca agtattaata cttttcccat ttatagtgga gtatgcggtt catatccgga    1860
atcatacacc tataaaagaa tttgatggtg ctactcctta tgaacgttac tatggtttat    1920
ctaaatacgt cataccattt tttcagtttg gaaccgacgt tttgataaaa tgtgctagtg   1980
tacaagaagc tatttcatta aaactaccat cttcaagaga taaagctttt cctacagtga   2040
tgtttggtgc ttttctcggt tacggctcag attcctttac cttcagagtt ttagtttcca    2100
cgaaaggata tccagttatt acaacatcaa acatccgtcc aatagcgacg atgcaagtac    2160
tcaatgacta tttggcatac atatcggaga atagctcaat aagctatgac gatacattct    2220 tatcacctt gaatcaccca atgattcgca caaaccaaca tgatagacgt ggagacaata    2280
taaatgtcga atatgaaaac cgtccaaatg taccatttga atatcatgct gaacctcctc    2340
gtacaaattc atcgacggga attatcgatc gaccagatat tagacctaga gctgatccca    2400
cctggcaacg tatgcctgat gccaacatac atcaggaaac aacaactgta cagactcctg    2460
atcatgggga gttagatacc atgatcaaca acgaacacca actaccacga tctgggagg     2520 gtaattaccc cgggcaacag gtgcgcaccg atattattgg gcaatttcga gatcgcgggc    2580
ctaccactct aaacactccg atcgatctag gtgtacccga tgaaacagac gatattagta    2640
tgacatcaga gaatccaatt gattccccaa attccgagat gatcatatcc ccatctttac    2700
ccacaaatga attggaacat caaatcgata tcagttcagg ggagatgtcg ttattgcaaa    2760
cgaatatgga agcagataac gaattgaaaa caaatgaaat ggtattatac aaatcaaaaa    2820
atgatggtat tatcattcaa caacaacaat tcactgaaaa tttgtcagat gaaaatgaag    2880
aagattcatc aacagatgag gaaacattgg aagacaaaaa acaacagcga ttggaatata    2940
atatttcacc aaacgatgag tggataaata atgacgttca gaacgaagat gacacacaag    3000
tgccacatgt taaggaacca atcaattatg aaactcaaag tagaaatgga acaaacatgc    3060
cacgaattga aatgggcata atagaaaact taagtgatga tggaaagaat acaccacgtg    3120
aattacgtat ggtcacctac gataataata aaaaaattca aaagtaccaa acagtaata    3180 tcgagatcct ggaacccaga aacgaaaata aaaccacac attcattgaa agcaacttag    3240
aattacttga caatcaagaa atgtttcaag aagatcctca agttgaagat attcgattga    3300
```

-continued

```
caactccaaa aaaggacaaa tcgttatcac ctgatttcaa tcaaacccat aatgaaatac     3360
aactattcat ggcagatatc aatgaagata tgctagaaga atatgatgaa aatataaata     3420
tgaatgaagt gttagctgac tccacggaga cgttggacaa agaattagat ttagatgaag     3480
aaagtggaag gatcgaatat attgctgata gagttagaaa aagacagag gtactgatgg      3540 tgcgccacac ggggaattnt ttacagaaaa atggataaag atttttgggt ccattaaaaa     3600
ggcc                                                                  3604
```

<210> SEQ ID NO 14
<211> LENGTH: 995
<212> TYPE: PRT
<213> ORGANISM: Unknown
<220> FEATURE:
<223> OTHER INFORMATION: sequence of retrotransposon from unknown organism
<221> NAME/KEY: UNSURE
<222> LOCATION: (1)..(995)
<223> OTHER INFORMATION: 'XAA' can be any amino acid

<400> SEQUENCE: 14

```
Met Lys Leu Ala Ile Pro Thr Lys Thr Lys Gly Gln Leu Ile Leu Asn
1               5                   10                  15

Leu Lys Asn His Thr Lys Leu Ser Glu Gln Lys Lys Thr Asn Leu
            20                  25                  30

Leu Val Tyr Asp Ser Gly Ala Thr Val Ser Val Val Asn Asp Lys Thr
        35                  40                  45

Leu Leu Asn Asp Ile Lys Glu Ser Asn Ile Glu Ile Ala Thr Ala Glu
    50                  55                  60

Gly Glu Thr Ser Thr Ala Tyr Ala Leu Gly Thr Leu Thr Ile Ser Val
65                  70                  75                  80

Asn Gly Leu Asn Ala Lys Leu Asp Gly Val Leu Tyr Leu Pro Ser Ile
                85                  90                  95

Gln Leu Asn Leu Ile Ser Ile Lys Gln Phe Glu Asp Leu Cys Tyr Ala
            100                 105                 110

Ile Leu Ile Ser Glu Asn Leu Met Phe Leu Val His Ser Asp His Glu
        115                 120                 125

Pro Thr Val Ile Ala Lys Tyr Ser Pro Lys Asp Asp Leu Tyr Ser Gly
    130                 135                 140

Pro Arg Ser Gly Asn Phe Leu Lys Lys Asn His Asn Glu Gln Asn Gln
145                 150                 155                 160

Ile Leu Leu Asp Thr Ala Lys Lys Leu Leu Gly Ser Glu Asn Ile Phe
                165                 170                 175

Ser Glu Lys Ser Ser Lys Asn Pro Met Ile Asp Gln Gly Lys Leu Asp
            180                 185                 190

Pro Leu Lys Met Asn Asn Lys Val Glu Arg Val Asn Tyr Val Ser Ile
        195                 200                 205

His Asn Ile Lys Gln Glu Val Ala Asp Lys Tyr Met Ile Lys Asp Leu
    210                 215                 220

Tyr Tyr Tyr His Leu Leu Ile Asn His Leu Ser His Glu Lys Leu Gln
225                 230                 235                 240

Leu Leu Val Lys Arg Gly Val Ile Lys Pro Val Lys Ser Thr Ser Ala
                245                 250                 255

Glu Ser Ala Ile Leu Asn Cys Gln Ile Cys Val Ala Ala His Ala Lys
            260                 265                 270

Leu Ala Ser His Asn His Thr Gln Gln Arg Glu Leu Glu Arg Pro Leu
        275                 280                 285
```

-continued

```
Gln Arg Leu His Leu Asp Thr Ala Gly Pro Phe Thr Ser Asn Lys Thr
    290                 295                 300
Lys Ser Tyr Leu Thr Thr Val Ile Asp Gln Phe Ser Arg Tyr Thr Glu
305                 310                 315                 320
Val Ile Val Ser Asp Thr Lys Ala Val Lys Gln Ser Ile Leu His Arg
                325                 330                 335
Leu Arg Val Trp Asn Asn Arg Phe Gln Phe Lys Ile Ala Glu Ile Arg
            340                 345                 350
Tyr Asp Asn Ala Leu Glu Tyr Pro Ser Ala Glu Glu Leu Glu Glu Leu
        355                 360                 365
Gly Ile Tyr Lys His Leu Leu Pro Asn Tyr Ser Pro Met Leu Asn Gly
    370                 375                 380
Thr Ala Glu Ala Thr Asn Arg Pro Ile Val Gln Gly Ile Tyr Lys Val
385                 390                 395                 400
Val Leu Asn Phe Ser Cys Gln Val Leu Ile Leu Phe Pro Phe Ile Val
                405                 410                 415
Glu Tyr Ala Val His Ile Arg Asn His Thr Pro Ile Lys Glu Phe Asp
                420                 425                 430
Gly Ala Thr Pro Tyr Glu Arg Tyr Gly Leu Ser Lys Tyr Val Ile
        435                 440                 445
Pro Phe Phe Gln Phe Gly Thr Asp Val Leu Ile Lys Cys Ala Ser Val
    450                 455                 460
Gln Glu Ala Ile Ser Leu Lys Leu Pro Ser Ser Arg Asp Lys Ala Phe
465                 470                 475                 480
Pro Thr Val Met Phe Gly Ala Phe Leu Gly Tyr Gly Ser Asp Ser Phe
                485                 490                 495
Thr Phe Arg Val Leu Val Ser Thr Lys Gly Tyr Pro Val Ile Thr Thr
                500                 505                 510
Ser Asn Ile Arg Pro Ile Ala Thr Met Gln Val Leu Asn Asp Tyr Leu
            515                 520                 525
Ala Tyr Ile Ser Glu Asn Ser Ser Ile Ser Tyr Asp Asp Thr Phe Leu
        530                 535                 540
Ser Pro Leu Asn His Pro Met Ile Arg Thr Asn Gln His Asp Arg Arg
545                 550                 555                 560
Gly Asp Asn Ile Asn Val Glu Tyr Glu Asn Arg Pro Asn Val Pro Phe
                565                 570                 575
Glu Tyr His Ala Glu Pro Pro Arg Thr Asn Ser Ser Thr Gly Ile Ile
            580                 585                 590
Asp Arg Pro Asp Ile Arg Pro Arg Ala Asp Pro Thr Trp Gln Arg Met
        595                 600                 605
Pro Asp Ala Asn Ile His Gln Glu Thr Thr Val Gln Thr Pro Asp
    610                 615                 620
His Gly Glu Leu Asp Thr Met Ile Asn Asn Glu His Gln Leu Pro Arg
625                 630                 635                 640
Ser Gly Glu Gly Asn Tyr Pro Gly Gln Gln Val Arg Thr Asp Ile Ile
                645                 650                 655
Gly Gln Phe Arg Asp Arg Gly Pro Thr Thr Leu Asn Thr Pro Ile Asp
            660                 665                 670
Leu Gly Val Pro Asp Glu Thr Asp Asp Ile Ser Met Thr Ser Glu Asn
        675                 680                 685
Pro Ile Asp Ser Pro Asn Ser Glu Met Ile Ile Ser Pro Ser Leu Pro
    690                 695                 700
```

```
Thr Asn Glu Leu Glu His Gln Ile Asp Ile Ser Ser Gly Glu Met Ser
705                 710                 715                 720
Leu Leu Gln Thr Asn Met Glu Ala Asp Asn Glu Leu Lys Thr Asn Glu
            725                 730                 735
Met Val Leu Tyr Lys Ser Lys Asn Asp Gly Ile Ile Ile Gln Gln Gln
        740                 745                 750
Gln Phe Thr Glu Asn Leu Ser Asp Glu Asn Glu Glu Asp Ser Ser Thr
    755                 760                 765
Asp Glu Glu Thr Leu Glu Asp Lys Lys Gln Gln Arg Leu Glu Tyr Asn
770                 775                 780
Ile Ser Pro Asn Asp Glu Trp Ile Asn Asn Asp Val Gln Asn Glu Asp
785                 790                 795                 800
Asp Thr Gln Val Pro His Val Lys Glu Pro Ile Asn Tyr Glu Thr Gln
            805                 810                 815
Ser Arg Asn Gly Thr Asn Met Pro Arg Ile Glu Met Gly Ile Ile Glu
        820                 825                 830
Asn Leu Ser Asp Asp Gly Lys Asn Thr Pro Arg Glu Leu Arg Met Val
    835                 840                 845
Thr Tyr Asp Asn Asn Lys Lys Ile Gln Lys Tyr Gln Asn Ser Asn Ile
850                 855                 860
Glu Ile Ser Glu Pro Arg Asn Glu Asn Lys Asn His Thr Phe Ile Glu
865                 870                 875                 880
Ser Asn Leu Glu Leu Leu Asp Asn Gln Glu Met Phe Gln Glu Asp Pro
            885                 890                 895
Gln Val Glu Asp Ile Arg Leu Thr Thr Pro Lys Lys Asp Lys Ser Leu
        900                 905                 910
Ser Pro Asp Phe Asn Gln Thr His Asn Glu Ile Gln Leu Phe Met Ala
    915                 920                 925
Asp Ile Asn Glu Asp Met Leu Glu Glu Tyr Asp Glu Asn Ile Asn Met
930                 935                 940
Asn Glu Val Leu Ala Asp Ser Thr Glu Thr Leu Asp Lys Glu Leu Asp
945                 950                 955                 960
Leu Asp Glu Glu Ser Gly Arg Ile Glu Tyr Ile Ala Asp Arg Val Arg
            965                 970                 975
Xaa Lys Thr Glu Val Ser Met Val Arg His Thr Gly Asn Xaa Leu Gln
        980                 985                 990
Lys Asn Gly
        995

<210> SEQ ID NO 15
<211> LENGTH: 1249
<212> TYPE: DNA
<213> ORGANISM: Unknown
<220> FEATURE:
<223> OTHER INFORMATION: sequence of retrotransposon from unknown
      organism

<400> SEQUENCE: 15
tctctatgta ggctgacagg tgaaaattat gaattaattg cattggccaa tgacaaatga       60
atagacaaaa cagcaaataa ggttgcaaaa gtagcccaaa caaactagat ttcggttacg      120
aattttccat ctttcaaaac aatgaatttg tttagagctc tgtgccattt attgcaacta      180
aaatgaatat gcaattaaac aatcagagat gtattggatt atccccgtgg tatacttttg      240
agttcaccat ttgttttttt tttggggtta aattagtgct cctactaaaa atcgcattta      300
tcttacactc accattttga taagttatct ctggtcaatc gcaaatacta tgcttctaat      360
```

```
taagagttct atgtaaatcc catttaattt tgatcaatct attggtttga agtaagagtt      420
gattttctgt aaagatttat ttggccagtg tagttcggtg tcaaaaatat attatgatgt      480
acactaaaaa acactaaatt tcaagtcaat ggggaacaca aaactgaatt aattactata      540
tgttggtttg tgcactattt tgtgtcagaa actgatcaat gaaaatgatg gttattatga      600
gaatggaaaa tttttccatc acacatcagg tgatgacaga actaaactat attgtgtagt      660
ataaataagg gtatgaaata ccaacatccc agaatatcaa cgagatagaa gagaggagtt      720
tcaatatata tcttgtgaat aataacttcg ttctaattca ctatacacaa ctagacgtgt      780
acacgctcaa tctcaggtaa agaaagttta tattccatca ctatataaca acaatcaggc      840
tttgcaaaaa aacatttaaa actaatactg gtaatatgga aatataacgc ctcgtagttc      900
tacgcacgtg gcatcccttta tctatttatt caatttaccc ctaatttatg aattagctta    960
ataagagcag tcaaattaac acggctcaat taatagtact taataatatg aagccgatca    1020
attaaccgat cctttgaata atttgaaaat aaaataaagt aatataaata ggtatgcatt    1080
ttccctacat ttatttcctc tttctattt aatttgtttc ctaaacagca acaacaacaa     1140
ttgaaattca aaaatggttt ctgtttctaa attattgaac aatggattgt tattagctgg    1200
tcaaagtgtc ttccaagatg ttgctactcc acagcaagct tctgtgcaa                1249
```

<210> SEQ ID NO 16
<211> LENGTH: 5611
<212> TYPE: DNA
<213> ORGANISM: Unknown
<220> FEATURE:
<223> OTHER INFORMATION: sequence of retrotsequence of retrotransposon
      from unknown organism
<221> NAME/KEY: misc_feature
<222> LOCATION: (1)..(5611)
<223> OTHER INFORMATION: 'n' can be any nucleotide 'a', 'c', 'g' or 't'

<400> SEQUENCE: 16

```
tctctatgta ggctgacagg tgaaaattat gaattaattg cattggccaa tgacaaatga       60
atagacaaaa cagcaaataa ggttgcaaaa gtagcccaaa caaactagat ttcggttacg      120
aattttccat ctttcaaaac aatgaatttg tttagagctc tgtgccattt attgcaacta     180
aaatgaatat gcaattaaac aatcagagat gtattggatt atccccgtgg tatacttttg    240
agttcaccat ttgttttttt tttggggtta aattagtgct cctactaaaa atcgcattta    300
tcttacactc accattttga taagttatct ctggtcaatc gcaaatacta tgcttctaat   360
taagagttct atgtaaatcc catttaattt tgatcaatct attggtttga agtaagagtt    420
gattttctgt aaagatttat ttggccagtg tagttcggtg tcaaaaatat attatgatgt    480
acactaaaaa acactaaatt tcaagtcaat ggggaacaca aaactgaatt aattactata    540
tgttggtttg tgcactattt tgtgtcagaa actgatcaat gaaaatgatg gttattatga    600
gaatggaaaa tttttccatc acacatcagg tgatgacaga actaaactat attgtgtagt    660
ataaataagg gtatgaaata ccaacatccc agaatatcaa cgagatagaa gagaggagtt    720
tcaatatata tcttgtgaat aataacttcg ttctaattca ctatacacaa ctagacgtgt    780
acacgctcaa tctcaggtaa agaaagttta tattccatca ctatataaca acaatcaggc    840
tttgcaaaaa aacatttaaa actaatactg gtaatatgga aatataacgc ctcgtagttc    900
tacgcacgtg gcatccttta tctatttatt caatttaccc ctaatttatg aattagctta    960
ataagagcag tcaaattaac acggctcaat taatagtact taataatatg aagccgatca   1020
```

-continued

```
attaaccgat cctttgaata atttgaaaat aaaataaagt aatataaata ggtatgcatt    1080
ttccctacat ttatttcctc tttctatttt aatttgtttc ctaaacagca acaacaacaa    1140
ttgaaattca aaaatggttt ctgtttctaa attattgaac aatggattgt tattagctgg    1200
tcaaagtgtc ttccaagatg ttgctactcc acagcaagct tctgtgcaac aatataacat    1260
cgtcaattct cttggcggta gtgcccctta tattcaaaga aacggatatg ggatttctac    1320
tgatatccct gctggttgtg aaattgctca aattcaattg tattcaagac atggtgaaag    1380
atacccaagt aaaagtaatg gtaaaagttt agaagcaatt tatgctaaat ttgaaaacta    1440
caaaggtact tttaaaggtg atttggcttt cttaaatgat tatacttatt ttgttactga    1500
taaaaacaat tacgaaaagg aaactagccc aaaaaattct gaaggaaccct atgccggtac    1560 aaccaatgcc ttgcgtcacg gtgctgcgtt tagagccaaa tatggatcct tatcaaagga    1620
aaattcaaca ttaccagttt tctcttccaa ttcaggtaga tgttaccaaa cttcaagata    1680
ttttgctaga ggattttag gtgatgactt taaagaaggt aaaactgtca agtttaacat    1740
catttctgaa gatgctgatg ttggtgccaa tagtttgact ccaagaagtg catgttccaa    1800
gaacaaagaa cggagcagta gtactgccaa aaaatataac acaacatatt taaatgctat    1860
tgctgaaaga ttagttaaac caaacccagg tttgaatttg actacaagtg atgtcaacaa    1920
tttattcagt tggtgtgctt atgaaatcaa cgtcagagga agttcaccat tctgtgattt    1980
attcaccaat gaagaattca ttaagaactc ttatggtaat gatctttcca aatattattc    2040
taatggtgct ggtaataatt acaccagaat cattggttca gtgattttga attcatcctt    2100
ggaactttta aaagacaccg agaactctaa tcaagtatgg ttatcatttg ctcatgatac    2160
tgatttagaa attttccatt ctgctttagg attattggaa ccagctgaag atttaccaac    2220
atcttacatc ccattcccta acccatacgt ccattcttct attgttccac aaggtgccag    2280
aatatacaca gaaaaacttc aatgtggaaa cgatgcttat gttagataca ttatcaacga    2340
tgctgtcgtg ccaattccaa aatgtgctac tggtccaggg ttctcttgta aacttgatga    2400
ttttgaaaat ttcgttaaag aaagaattgg agatgttgac tttattaaac aatgtggtgt    2460
caatagtacc tacccatctg agcttacttt ctactgggat tataaaaatg tcacttacaa    2520 tgctcccttta gaattgtaag acatcattag atcaatttag atatccaaac atttattcgt    2580
tattctcttc gtatattatt tatattcttc cttttcttga aaaaaaaat agacaattta    2640 tttagacttt ataacttta cttcgtgttg caacaaattg agcatttac acgaaacttt    2700 aaataattga atccttcgaa aaccaaagtt ttattggtcg acgggttggt taacatggaa    2760
tatatcactt tctaataact atgtcacacc aacaaatatc aatatgagtg tttcagacaa    2820
atacccagaa cttgttagac aattttcct tcttgatgaa gtgaaggaaa ttttgccgaa    2880
ctatccaaaa tacaaaattt tactgcaaac tcctgaagtc gatcgtgaat actacaaaaa    2940
catcaccagt cctgaattca ttagacaatg gcagccagaa gtcctcaatc actaccgaaa    3000
taactggacc gaagtcactc ctctttgtgc tattgtacat gatagaacca ttgatgccgg    3060
tttgagaatc caaaagtttt tccatccatc catcttaccg aatgaacttc atggcgatgt    3120
ttggatactg gtaaaagaga acaaagaaga actcgatgcc tttatagaaa atgtgcaatg    3180
tcttcaaaat tatgttagag atagctccaa cagtaaatac acttattatc gttgtgagta    3240
ttgcaaaaag aataaaggtg ttaaaagtaa aaaaactgat tgcaagcata aaattgcagt    3300
acatgctctt gaaggtggaa aatacaaaat agtctggcac tttcagcata accatgcttt    3360
cgatccaaga aggattacaa aggcaaccag aaactggttg atggacttag cttcaacaaa    3420
```

-continued

```
tataccaagg gcaagttctg acagcaggag atcagtgact aaattcaaac tgagttcatt    3480
tttactttct gacaaattta aaatttccaa caaggtattt aattattata aaaacaaaaa    3540
taaagagagc caggcacatc ttgacaaaaa tgttatcaaa agtttaaaaa tatgggtttc    3600
atatataaat acccttaatg aatttgccgt gtttaaaaag agatcaacaa atactgaaaa    3660
tgntgaattc tgtgacgtgg aaggcgatgc tctgaatcct gagtctacgt ggtattttgg    3720
aattattctt ttgagcaatc tccaatatat gctgagccca caaactgttt tccttgatag    3780
tacacataaa ttaggccacg gccctcacaa cgaggacata ataacatata tctttatcac    3840
aaaaagctct ttatctggag gagggatacc aataggttac ttaataacaa atagagagtc    3900
tcatgagccg ttagcatcat ttttgagatt ttttgttgaa aagaaaatac aaatcaaaag    3960
attcgtgata gattgttcag ctactgaaat aaaagctatt gaagaaggat ataatgttgg    4020
tatcattgaa cccacagatg gatcatcaag tgctggtgat aaatttgaag ctatcataac    4080
gttttgcact tggcattgtt tgagagcttt taataagacc attaacaaac ttattacaat    4140
acaaaataga acaaataatg agcaaatatc cccaaatgaa attatcacag aagttgacgg    4200
agaaatgaca gatgaagaat tcataaatca gatagccact caaggggttg ttgcacaatc    4260
aaacttaact gcaggtagga ataaggaaga gataattgca aatcaaagaa ttgctctttc    4320
atatatggta gaattaaaac ggaaaaaagc cattgaagaa gctaatgatt ttttgcatgt    4380
aatcgaagcc acgtttcggg aatacccgga ctttgttgca tacgcccaga aaacattcaa    4440
aaccacaggg aaatactggt taaactgcca ttttggtaat tacagagaac ttacaaataa    4500
ttgtgtgaaa agttatcacc aagttttaaa aaccaaatat ttcgaaagac gcagaaaata    4560
ccgagttgac cgagtaattt ggatgtttat tgaacccatt gctaagtact atgagtatta    4620
ccattcagct gttattgtta catccctgtt aaggtacatt gataaagctg aagaagcttc    4680
caaactcaaa gcagaagcag tttcagatga ggacatgagg caaatgattg ttgaccttcc    4740
aggttatatt gcagttaaat cgttcaatgg atcaaattat tacaagatta gttttggtga    4800
acgtggaatc ttttcctgcg aatgtccgta caacgagtat tcaattgatt ggtgcaaaca    4860
cattttctta tataagcgtt ataaggtggc taaaggattg gacataccta ttgtcgagct    4920
tgaaagaaac cctttggctg acttaagtgg ttttaaacggt actaatgaga tagttgaacg    4980
agaaacagat actattggaa atgaatcaga agacgaagaa ttagttgata gtgagtcagg    5040
atttaagaat gccacctata tgagagtgat ttttggtgac gataatttg attctatgga    5100 aaatgatcca gatggtgacg aaccagattt tagtattgaa aacacagaac caactgaagt    5160
atcccaagaa gagaccgaag aagaaattgg tgccaggctt gcacgcgaca gagttgatcc    5220
tgggttctcc atagatgacg acaatattgg aaacgacttc gaactcgctg actcttctca    5280
agtttttaca gacggtggaa cagcttatta cacacaaaac acagaatcag acccatttat    5340
tgaatggcct ataagtgaaa caattgatct gcaagaaagt gctgatgtta ttttagaaat    5400
cgaaagcata gaaggggttt atgctaagaa agctgctaga aatattaagc aacgggaaga    5460
gaattatagt agtttagata cagaggttaa aagaattcaa gatgaggaga atctcaaag    5520 ggagaaggtt aaaaagctaa gggcattaat taaaaaagaa gagatggaac ataaaaagaa    5580
aatggcggca gtgaatagga ttcaaaagaa a                                    5611
```

<210> SEQ ID NO 17
<211> LENGTH: 1308
<212> TYPE: DNA

```
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(1308)
<223> OTHER INFORMATION: 'n' can be any nucleotide 'a', 'c', 'g' or 't'

<400> SEQUENCE: 17
tggtgccatt tttagaattg atgtctgaaa tagaatatga ggtccagaga agttttattt      60
ttgttataca tcattttttt tttttgcttt gtctcaccga atattatttg attcctaaaa     120
aattgtaata ccctgtgttg gtttgtgcac tattttgtgt cagaaactga tctatgaaaa     180
tgatggttat tatgagaatg gaaaatttt ccatcacaca tcaggtgatg acagaactaa      240
attatattgt gtagtataat aaagggtatg aaataccaac atcccaggat atcaattata     300
tagaagggaa ggagtttcaa tatatatctt gtgaataata acttcgttct aattcactat     360
tcacaactag gcgtgtacac gctgaatctc aggtaaagaa agtttatatt ccatcactct     420
gaagtcatac attaatatta aataaacaat ctaacactag catgcattca taacctatag     480
atcattctaa acaagctgtt aacacaaatc caatcaattg aatttatcat ataatgaagt     540
aacttttttc aaggcaacat ctattctttt attaatctcg acgtctgttt gattaagttg     600
ctctaacatt ttatttagat ccttctctat attttctgca atatcaaaca ccgattgctt     660
tttgtctgaa gttgctggta tatcaccact tccgccaatt gtcgtatttc cactgtcctt     720
tgttactgac agattggcac tgacattacc tgaattgttc atgtttgctg ttgaaagagc     780
aggaactgta cttggataag cagccgattc aaaagaagat gtggacatga gtgtcaagaa     840
aatgtgtaga atcagtacaa gactggaaaa cagaaggaac aaagtgaact ggatattgta     900
gttttgttga tagtactcgc gagctttaat ttttttttgt aactggcgga atcagatctt     960
atgcaatact caaatccaaa gaaacagtca atccagatga aaggcatgta atcgctagtt    1020
ttcataaaca gaatcatgtt actagtcata ttttctataa aaattcaata cttcattctt    1080
tttgttcaat actaactata aatgcttaca aatagattca aatttcaacc agatccacca    1140
cttcattagg ctcaaccaat tcttcataaa tagaaacgtc ttcctcagcc aagcttaatt    1200
gatgggaaac cctagcttgc attgaaggaa aaatacataa tccaaataac aaactgtctt    1260
tccnaatatt ctcaaaattc gacttcaccg tcttccaacc aagcaggt                 1308

<210> SEQ ID NO 18
<211> LENGTH: 1672
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(1672)
<223> OTHER INFORMATION: 'n' can be any nucleotide 'a', 'c', 'g' or 't'

<400> SEQUENCE: 18
cctatcaggt acttccccac ttggattggc ttctgcctct cttcttctcc caaccatcat      60
cccaatatca ttccacccat cgtcttcatc gttgtcgtct tttgttggtn tctcttcttg     120
tttttctagt ttaccactat aaaaatcaat caattcagtt tgttttatgg catcagattt     180
ataaattttt ttaatttat caacataatt atcaacaatc caatcaagat gtaatttatt     240 caattttct tgtaaagaat caccaccacc atttcctatt ccttccattc ttgataatat     300
attccaatta gtttcatgac ataatttcgt taattcatct aaatcattca attgttgttt     360
```

```
atcattaata atttgattta tattgatgga aattttatca attaaatttt tagaaatttt       420
agaatttaaa taatttttga ttataggata ttgtaattca tttataaatc taattaaatt       480
agtaattgat ttaataaaat tgttgtcctc gttgtctgat acaatttcta atttaatagt       540
atcttccaat tcatcaacaa tcaaactaag ttgttttgaa ggggtggggg tggagtcccc       600
caatattgaa tccactaatt tatcccaatt ttccttatat ttatcgtatg cattcatatt       660
attatgtcca tttttcaata aaaccgatt gaaatcttgt aaaattgcta tattagtaat        720
agtcaatgga tcaggaatta aaagaatagt taaatattca ttcaattgat taacaaaatt       780
ttcataaagt gaatcgactc gtttcttgat ttgtttatat ataatatatt gagaatttgt       840
atcaatgatg atttgtttaa ataaattatt taaatattgt aaatctaata tactttgtaa       900
tgttttcggt ttccccaaat acgtttcaat ttctttaat ttagaattga tctcttgtaa       960
ttcattcaat tgttgtaaat tgtcagtaac gatttcaaat ttattattca attcagtaat       1020
tgttaaatca gttaaattgt tactttcagt ggtatttgaa tcttgaggaa tttcttcaaa       1080
ttgttttcgg aaatcattat cattttcaag ggttgttttg tttattttgg ataatgtttt      1140
atttatgttc tgttcaatat cttttaaata taattcttga tcttctaatt gttgttcaat      1200
cgatggcatt attggtgttg tataaaaatg gaattttgta aagttgaatg tgttggcaac      1260
acttgtgttt gtatgggcgt atatttttg aggagatcaa agcaaaaat attttgagac        1320 ttatacacgc aacatacaga acagttgttg gtttgtgcac tattttgtgt cagaaactga      1380
tcaatgaaaa tgatggttat tatgagaatg gaaaattttt ccatcacaca tcaggtgatg      1440
acagaactaa actatattgt gtagtataaa taagggtatg aaataccaac atcccagaat      1500
atcaacgagg atagaanggg anggagtttc aattanaata atcctgtnga ataaataaac      1560
ttccggntcc taaattcnnc taataccnac caaaccttag naccgtngta acancgcctc      1620
caatcctcca ngggaaaaag aaaangtttt aataatttcc cnatcccgga tt              1672
```

<210> SEQ ID NO 19
<211> LENGTH: 690
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(690)
<223> OTHER INFORMATION: 'n' can be any nucleotide 'a', 'c', 'g' or 't'

<400> SEQUENCE: 19

```
tgatacgatt gaatggtgga gacaaaatat ccgatgtgtt gaaagataaa attgtactcg       60
aatatcccac aatatatgtt gctgcaaatg acgagtgttt acaagataga attatagata      120
gccttcaatt ggccgaggag gaagaagatg acaccactga ctcaagtgag gatgattcta      180
gtgactcaga gagtgatgat gatgatagtg atagtggtag tgaaaccagt agtattggag      240
acggttcagg tgaagataac gattctgatt cggcaccgga agagacatct ctgaaactac      300 caccttttc acagaaattc tttgaagcgt cagctgagcc aaaaccaata atagaagaga       360
taggatctaa caagactgta gaagaaccat aacgaatgaa tataaaatac ttgtattatg      420
tagtgccaat aaaagttgaa acggtcgcac tactttttag tcctgttggt ttgtgcacta      480
ttttgtgtca gaaactgatc tatgaaaatg atggttatta tgagaatgga aaactttttcc     540 atcacacatc aggtgatgac agaactaaac tatattgtat agtataaata agggtatgaa     600
```

```
ataccaacat cccagaatat taattatata gaanggaagg agtttaatat atatcctgtg    660
gaataacaac ttcggtctaa ttcactatac                                     690

<210> SEQ ID NO 20
<211> LENGTH: 1912
<212> TYPE: DNA
<213> ORGANISM: Unknown
<220> FEATURE:
<223> OTHER INFORMATION: sequence of retrotransposon from unknown
      organism

<400> SEQUENCE: 20
ctaggtttta attcactatc ataaagatca atggttagcc caaaattaaa atatggaagc     60
caaaacttcc gtggtcaaaa aatgaactaa gaagctaaag tcttttttgaa acagtatgcc   120 attatgtttt tcagatgttt ttacttggtt gttatattaa aatccaaagc tctggctctt   180
atcaagaatt tgtcagtcaa ctcatcatca aatgagtgga tatattactt tcaagaatca   240
tcattaccaa gttgtcaaac gattgctaag caaatgttga agaatactga ttatttcagt   300
tttgagaaac ctaaccccaa agataattta aggagaatca aaatttgaaa gaaaaggatg   360
aaaagttgga gaaagaaacc ctattgaaaa tttaagtact gattgtttca gaaaatcatt   420
gaatatgaaa caacagaaag gatattttac caactaatga acattttcct cccttataca   480
ccttaaaata cattaaatcc ttctggaata gttttttctc acaagacatt ttggtgtata   540
acattggtac tatttgttgct gtcatgacaa ataaggaatg ctacaaaacg tcaaggtaga   600
agctatcgat gttttttcca gctaatgaca ggacaacgtt agaaacgaag tgtgcagacg   660
atttggttac aaagattgca agtgtatcaa ttatgctagc atataccttat tattttcgtt   720 gagagtattt ttatcatcgt tggtctgcaa aacttcaaag aagggtgct atatgtgtta    780 aatgctgaga atcgaacact gtatctcatg gcgataaaat tcaaatatt gtcgttagta    840 tgagaagatt ttgctgatat ttacttatat ttcacaatgt tcagtaaaga tccttatgac   900
ggtggtacaa tatgggacat gctatctgac acgttgacaa ccactaaaat cagctgttac   960
cgatagagac catacagatt gacgcaacac ataagtatac tcgaaaagct aacccaccat  1020
atcaggcatc aagccaaaaa tcaattttga ctgaaaatgg acgtcattaa ctctgagtcg  1080
ctaaaatcaa ggtatgaaat atttgccaaa gaggaaatcg atcagagtcg caatttctgt  1140
tcaatattca accaaataca attttccaac ctataaatct ccaccatctg tgttatgtgc  1200
tgtcattgag tttgcaactg atattttttgc tatatcttta cgttgcaaaa atgcgggggt  1260
gatgttaaac ttacccgaat tctccgtgta tcacatgtta ttatgccaaa tatgcatatc  1320
taggaaaaca gtctcaacca tctaacacac acattttctc accactgaag ctatgaagat  1380
agcccattcg ggaacggtaa acgacgtagc gggaaaaatg tgcttaaaag aatatgggaa  1440
aataaacggg tagacgtcat ttcccagtac catattctat tcagtcgaac gtcttcattc  1500
ttatcaacgg gggactggtc cagagaccct tcttatttta ttgtgattca gtagcgtcta  1560
ccatatacaa tgatattgta acttccgatc aagtggaaac accggagct tccaaagtat   1620 ggtatccgaa tataaagcca cccaaaatcc aattcaccac gagctaacac ctggggaaaa  1680
cgaggtgtct aaacctcctc aacttgattt cgagacttcg gtagtaggga agtttaaagg  1740
gcctattaca accacaaaag tggcaccacc accctccatg ggaggtctat taagtacatg  1800
gaaacgcatg ctctggttga tacatcacct caatcaaaaa aattggtgtt ccacattcga  1860
aggaactaaa accgacgaga acctatcaca cggtgtcgac gatgataaga aa          1912
```

```
<210> SEQ ID NO 21
<211> LENGTH: 6140
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(6140)
<223> OTHER INFORMATION: 'n' can be any nucleotide 'a', 'c', 'g' or 't'

<400> SEQUENCE: 21
```

| | | | | | |
|---|---|---|---|---|---|
| agtaaaaaaa | gaagaaaaaa | aagctaaaat | tgggacaata | tgctaagtat | atataggga      60 |
| agacgtcgaa | cagcaaccac | ggaaaaataa | tagtgattgt | ctttatccgt | tattggctgg    120 |
| atggcgacgc | cacaacctga | aatttggttc | caactgttga | ggatgattta | tgtttgtgat    180 |
| tagaactaaa | atcattcgag | aaaaaggaa  | taggagagaa | ccaactttag | tcgtgtaaaa    240 |
| agtaacatct | gccaattata | aactatacgt | agtccaaata | atttacggta | tatttctgta    300 |
| ccccttcttg | gcaatatcac | aagaatatca | taatgttcat | gaaccctctt | tgaacacgta    360 |
| gacaagtaaa | cccaatgagg | gggcagtgtt | ctattcttgt | aaactgcgca | ccaaaaacgg    420 |
| ggcttaaaaa | ataagttatg | aaaactataa | ataaccatga | aaatcaccct | actcccttcc    480 |
| tcccttcctt | ccttccttcc | ttccttttct | cttttcctct | acccacacta | ctcacaatgt    540 |
| tcggtatttt | tgaggaaaac | tacgattctg | tttacaaagg | caaccacgaa | gccaagttct    600 |
| ctcacgaagc | agttgctggt | gctgcttcat | ttgctgctgt | caagttgttt | gaagatagac    660 |
| aaagaagaga | agggaaacca | gttagtcacg | cctttgctaa | agaagcttta | gctgctattg    720 |
| ctggtggaga | agtcgacaaa | ttatttgaaa | ccaaagggtt | ggactatttg | gatagagaga    780 |
| gacttagaga | tcaagctatc | aacaacgctc | aaagaggtta | cgacgaccat | tacggtcaac    840 |
| acgaagaatg | gtctccagaa | cacagaccac | cttttgacta | ccaaagatat | taagtagaaa    900 |
| ctgtgtagtg | aatttacaat | ttttttgaca | agaattaact | taaacctcgt | ttttaggttt    960 |
| tgtgcggctt | ttgtcaattg | acgatcctgt | atatttcgtc | ataattcaca | cattcttaaa   1020 |
| attatgcaca | catccttgaa | atgtgttaat | attcccaaca | ttatcaatta | tatgtgttca   1080 |
| gaattggttg | caaagttatc | aactcaattc | acgctatata | aaccttacaa | attctctaca   1140 |
| ttttatatt  | ttttatatt  | ggcttttctt | ttagaatcaa | tcaatacttt | ttttatcatt   1200 |
| tagatacatc | tttcatctat | taatagatta | tctttctata | tatcaaaaca | cgacacagtc   1260 |
| acgtgccaaa | aaggatataa | gaaggaactt | cagaaaatta | attttctgat | tatactactt   1320 |
| actagatttc | ataaagtcaa | tatctgattg | atacaacttg | gttcattatt | cataaaactt   1380 |
| tacaactaat | tcnacaagna | aacccnacaa | aaaaatccna | atnaaataat | cnnnnnaata   1440 |
| ttataattaa | ttaattacaa | aaaaaaacaa | aaaaatacac | acacacatac | acacacacaa   1500 |
| aatcttgttg | caaaaaaaaa | aaaataataa | taatataata | agaattaatt | aacaatgtcg   1560 |
| tttccacgga | cacattcacc | aagaccatct | ggttcacgag | aacaggaaga | tctcacactg   1620 |
| atgattaaag | cttttagaga | ttcaatggaa | gctaagcttg | acttgcattc | gcagaagctt   1680 |
| actgctttgg | tagcaaacat | tcccagaacg | gacgaagggt | ttgaagattt | atcacaaagg   1740 |
| atcactgttc | ttaaaaatca | tcaaaaagca | ttttgcccca | acaagaaaaa | agaaatcgga   1800 |
| agtcttctcc | acagacaaag | agaggaagaa | ggtgatatta | aggatttcaa | aacagtcgtt   1860 |
| ggtgaagaaa | aagaagaatt | gcaccaggtt | gaagatttcg | ttttaaaaga | tcaagaagaa   1920 |
| ttacgaaacg | tcgaaaagaa | agttttgaaa | gaagaagaag | aattgcaaaa | agtggaagag   1980 |

```
tcaatggaaa aggaaaaaca agagttatac caggttgaag actttatttt gcaaagagat    2040
gagacggtaa agaaacttgg agaaagcaat caatctcaac aggaaccata tacacctgca    2100
acttctggtt cggatcagag attcagatct caacaaccta acattggaaa taccttagcg    2160
caggatctag cattaattcc aaaattagat ctggaaattt gcaaaattgc agtcaaatat    2220
ccaaaattat ttgaaacaaa attaagacca ccaccaccca gagactttca atataaaatt    2280
caactcacag accacactca aatttattca aaccatata aatgcaatca agaagaacaa    2340
gctctcatca aggatttcat caatgaaaaa ttagaagcag gcgttttggt accagctcca    2400
attgatgctt ggttacaccc aatatttcca atcagaaaaa ccaatgccaa ccaatcctcc    2460
accaaaatag cagttgattt aagacgtctc aataaggtca cagtacgaat gtacacttat    2520
ccaacagaca caaaagacct cttatcctca ctaacagatt cccactattt tagcgcttta    2580
gacttaaaga atgcgttcta tcaggtaagc atacacaagg atagtataaa atattttggg    2640
atttcaacat ccgaggggaa ttattgcttt acaactttac cgtttggagc aatcaattcc    2700
ccaaccatct ttactaactt tgtgagacag attttagagg ggatcccatg tatatttata    2760
tacatggatg atatcctcat ccatactaaa accttacatg accacatgtc attactcagg    2820
agaatcatgg agaaactaaa tgagcatcag tttcaaatga attataacaa gatgcaatta    2880
ttaacaacaa aaatcaattt cttagggtac agcattcaag cgaacaaaat atcaccagat    2940
atttccaaaa ttcaagcaat acaaaattgg gaattgccca cgaccactac tcaaatcaga    3000
gcatttgtca atttcagcaa ccactttcgc atcttcatcc cagaaatagc aaaatttact    3060
aatccattaa atgaattatt gaagaacaac aatggtaaaa acataaagat tgaacacacc    3120
caagcatcca ttgatggtta caaggcatta aaagccgcca tcattggatt gccgacgctt    3180
caactttaca atccaaaact accaaccatc attttcacag atgctagcca catggtagta    3240
ggaggatatt tatgtcaacc aacattcaga atgacaaag aagtccttgt cccaattgca    3300
ttttcatcac ataaattaac agaaacacaa agcagatatg ctgctatgga aaaggaactt    3360
ttggcaatta ttgtgatatt ggaaaaattt agatatcact gcagcaatac ggtagagatc    3420
tatacagatt atcaaagttt ggcatcatat ttagataaga aaactactcc accaccgaga    3480
attgctaggt ttttagatct aattggatca ttttccccaa aagtgtacta tttaagtgga    3540
aagaaaaatt tcgttgctga tatcattaca agatatcaaa ctcaaaatat taaggaattg    3600
gtagatgaag acaagatact aggacagact tttacagtca agagaaattt gaacaacaa    3660 ctattaccaa gattggaagc aattgaattg gaaaatctta atgaatcaca ggttcacaaa    3720
atccaaactt cattagaaca acaacaacaa catgatttgg aagacaatga tgaagagtta    3780
cctctccaac tgtttaaatt aatgaatgat gagttatttg taatcattaa caaccaactt    3840
ttaaaatacc ttccaagact ggaatacaat gatatttgtc aaacaatcca tgacaaacac    3900
catccatcaa ctagagtaac agactactta tgcacactcg catattggca tcctgaccat    3960
ctattaattg ctacaaacat tacgagaaag tgtcactatt gtcaactaaa cacgtcaatt    4020
cgtgaggcca ttagaccata ccgaccactt gaaccactca aggcatttag cagatgggga    4080
atggactact ctggaccata ctttaacaca gtccaacaca ggtacatatt agtagccgtg    4140
gaatatgtca ctggtttaac tattgcagta ccaacattgc acaaagacgc agataacgca    4200
atcagtcttt tacaatcaat cattctgatc atgtcagcac ctacagaatt agttacagat    4260
caaggtaaaa aaattttcat cacaagcttt ggctacccta tgtgaccaga ataacataca    4320
```

```
acaccatatt acctccgccc accacccacg tgggaatggt cgggttgaga aggtgaacca    4380
cctattgaag aaaatattga aagcattaac taacgatacg atgcaagact gggatttaaa    4440
actatatgac gctttaagaa tctacaatgc tacacctaca attttttaact acactccact    4500 ttatcttgca cttggaattg aaccacacca taatttaaat caattacaaa aagatttaat    4560
tgaaaatttg caaaaagaat tgcccccaga ggtccaatcc acagaagaac acgaagaaaa    4620
cccaaatgat gaacaacaag aagagggcag agaacaacaa atttcaagag aagaacaaca    4680
ggacggcaga gatcttgtac acttaagaat ttacgaattg gaagcaatta agaaagctcg    4740
caagttacac acaaatttga aaacacgaag aaacgcagtc caaaatatgt taaaggaacc    4800
atatggcatt ccagcacttt ttacaaaggg acaatgggta tacagaatta gagctaaagc    4860
acgaaaatat gaatcaaatt ttgatggtcc atatcaagtt caagaagtat taggtaaagg    4920
tgcttataaa ttgagagaca tcactggaag agaaaaagga atctacaatc aggatcagtt    4980
gaagttagca tattcagcag acaacgatcc aatacaggtt tttagttctt ttaataaaga    5040
atatgatcga gtacaacaaa aattgttaga caaaattcaa tcagaaagag atcatcaatt    5100
aaattgtttg tcagtccaac atttacacag acaaagaagg ttactcgata tatccagctg    5160
tcttgagcaa attctgcaat aatttcgcta atcattggag gaaagggtag atgacgatcc    5220
tgcatatttc gtcataattc acacattctt aaaattattc acacatcctt gaaatgtgtt    5280
aatattccca acattatcaa ttatatgtgt tcagaattgg ttgcaaagtt atcaactcaa    5340
ttcacgctat ataaaccta caatttctct acatttttat attttttat attggctttt    5400 cttttagaat caatcaatac ttttttatc atttagatac atctttcatc tattaataga    5460
ttatctttct atatatcaaa acacgacaca gtcacgtgcc aaaaaggata taagaaggaa    5520
cttcactgaa atgcaatcac ttcgcattat tcaagatctt tttctattgt ggctggtttt    5580
tggtgattgc tatgtttggt tttttttttc tggaacacaa gcaaccaaat ttttcaactg    5640
ttacgtcaca catttactgt cacactcact tactggcaca caaagaacaa agcaatcatc    5700
cggcgtaaac ttttggtctt tgagatgcaa agttgcaaa gcaattggca cttctactaa    5760
gatggttcca gtaaaaattg tgttttatag tacatcaata atcaaacaat acttaatgat    5820
gtaacaatac cttaaaaagc ccccactata tttcttttt ttttaagttt gctatataat    5880
ttattatgtg ttattattat tgacttaatt gttagcattt tattgcttga gatcgtttgc    5940
ttgtcactcc accctgaaga aaatttgaat aattgctatt aatttattta tttcttggac    6000 acacccgta ttgtcgtatg ggtataaatt ccgtttcatt tctcctccct atttcatatt    6060
tcataacttc ttaaatcaat attcaaacca actccaaatt ataaactatc aaacaaagaa    6120
acaaaaaaac acacaacaca                                                6140
```

<210> SEQ ID NO 22
<211> LENGTH: 916
<212> TYPE: PRT
<213> ORGANISM: Unknown
<220> FEATURE:
<223> OTHER INFORMATION: sequence of retrotransposon from unknown organism

<400> SEQUENCE: 22

```
Met Ser Phe Pro Arg Thr His Ser Pro Arg Pro Ser Gly Ser Arg Glu
1               5                   10                  15

Gln Glu Asp Leu Thr Ser Met Ile Lys Ala Phe Arg Asp Ser Met Glu
            20                  25                  30
```

-continued

```
Ala Lys Leu Asp Leu His Ser Gln Lys Leu Thr Ala Leu Val Ala Asn
         35                  40                  45
Ile Pro Arg Thr Asp Glu Gly Phe Glu Asp Leu Ser Gln Arg Ile Thr
 50                  55                  60
Val Leu Lys Asn His Gln Lys Ala Phe Leu Pro Lys Gln Glu Lys Glu
 65                  70                  75                  80
Ile Gly Ser Leu Leu His Arg Gln Arg Glu Glu Gly Asp Ile Lys
             85                  90                  95
Asp Phe Lys Thr Val Val Gly Glu Glu Lys Glu Glu Leu His Gln Val
            100                 105                 110
Glu Asp Phe Val Leu Lys Asp Gln Glu Glu Leu Arg Asn Val Glu Lys
            115                 120                 125
Lys Val Leu Lys Glu Glu Glu Leu Gln Lys Val Glu Glu Ser Met
            130                 135                 140
Glu Lys Glu Lys Gln Glu Leu Tyr Gln Val Glu Asp Phe Ile Leu Gln
145                 150                 155                 160
Arg Asp Glu Thr Val Lys Lys Leu Gly Glu Ser Asn Gln Ser Gln Gln
                165                 170                 175
Glu Pro Tyr Thr Pro Ala Thr Ser Gly Ser Asp Gln Arg Phe Arg Ser
            180                 185                 190
Gln Gln Pro Asn Ile Gly Asn Thr Leu Ala Gln Asp Leu Ala Leu Ile
            195                 200                 205
Pro Lys Leu Asp Ser Glu Ile Cys Lys Ile Ala Val Lys Tyr Pro Lys
            210                 215                 220
Leu Phe Glu Thr Lys Leu Arg Pro Pro Pro Arg Asp Phe Gln Tyr
225                 230                 235                 240
Lys Ile Gln Leu Thr Asp His Thr Gln Ile Tyr Ser Lys Pro Tyr Lys
                245                 250                 255
Cys Asn Gln Glu Glu Gln Ala Leu Ile Lys Asp Phe Ile Asn Glu Lys
            260                 265                 270
Leu Glu Ala Gly Val Leu Val Pro Ala Pro Ile Asp Ala Trp Leu His
            275                 280                 285
Pro Ile Phe Pro Ile Arg Lys Thr Asn Ala Asn Gln Ser Ser Thr Lys
290                 295                 300
Ile Ala Val Asp Leu Arg Arg Leu Asn Lys Val Thr Val Arg Met Tyr
305                 310                 315                 320
Thr Tyr Pro Thr Asp Thr Lys Asp Leu Leu Ser Ser Leu Thr Asp Ser
                325                 330                 335
His Tyr Phe Ser Ala Leu Asp Leu Lys Asn Ala Phe Tyr Gln Val Ser
            340                 345                 350
Ile His Lys Asp Ser Ile Lys Tyr Phe Gly Ile Ser Thr Ser Glu Gly
            355                 360                 365
Asn Tyr Cys Phe Thr Thr Leu Pro Phe Gly Ala Ile Asn Ser Pro Thr
            370                 375                 380
Ile Phe Thr Asn Phe Val Arg Gln Ile Leu Glu Gly Ile Pro Cys Ile
385                 390                 395                 400
Phe Ile Tyr Met Asp Asp Ile Leu Ile His Thr Lys Thr Leu His Asp
                405                 410                 415
His Met Ser Leu Leu Arg Arg Ile Met Glu Lys Leu Asn Glu His Gln
            420                 425                 430
Phe Gln Met Asn Tyr Asn Lys Met Gln Leu Leu Thr Thr Lys Ile Asn
            435                 440                 445
Phe Leu Gly Tyr Ser Ile Gln Ala Asn Lys Ile Ser Pro Asp Ile Ser
```

-continued

```
            450                 455                 460
Lys Ile Gln Ala Ile Gln Asn Trp Glu Leu Pro Thr Thr Thr Thr Gln
465                 470                 475                 480

Ile Arg Ala Phe Val Asn Phe Ser Asn His Phe Arg Ile Phe Ile Pro
                485                 490                 495

Glu Ile Ala Lys Phe Thr Asn Pro Leu Asn Glu Leu Leu Lys Asn Asn
            500                 505                 510

Asn Gly Lys Asn Ile Lys Ile Glu His Thr Gln Ala Ser Ile Asp Gly
            515                 520                 525

Tyr Lys Ala Leu Lys Ala Ala Ile Ile Gly Leu Pro Thr Leu Gln Leu
530                 535                 540

Tyr Asn Pro Lys Leu Pro Thr Ile Ile Phe Thr Asp Ala Ser His Met
545                 550                 555                 560

Val Val Gly Gly Tyr Leu Cys Gln Pro Thr Phe Arg Asn Asp Lys Glu
                565                 570                 575

Val Leu Val Pro Ile Ala Phe Ser Ser His Lys Leu Thr Glu Thr Gln
                580                 585                 590

Ser Arg Tyr Ala Ala Met Glu Lys Glu Leu Leu Ala Ile Ile Val Ile
            595                 600                 605

Leu Glu Lys Phe Arg Tyr His Cys Ser Asn Thr Val Glu Ile Tyr Thr
            610                 615                 620

Asp Tyr Gln Ser Leu Ala Ser Tyr Leu Asp Lys Lys Thr Pro Pro
625                 630                 635                 640

Pro Arg Ile Ala Arg Phe Leu Asp Leu Ile Gly Ser Phe Ser Pro Lys
                645                 650                 655

Val Tyr Tyr Leu Ser Gly Lys Lys Asn Phe Val Ala Asp Ile Ile Thr
                660                 665                 670

Arg Tyr Gln Thr Gln Asn Ile Lys Glu Leu Val Asp Glu Asp Lys Ile
            675                 680                 685

Leu Gly Gln Thr Phe Thr Val Lys Arg Asn Leu Lys Gln Gln Leu Leu
            690                 695                 700

Pro Arg Leu Glu Ala Ile Glu Leu Glu Asn Leu Asn Glu Ser Gln Val
705                 710                 715                 720

His Lys Ile Gln Thr Ser Leu Glu Gln Gln Gln His Asp Leu Glu
                725                 730                 735

Asp Asn Asp Glu Glu Leu Pro Leu Gln Ser Phe Lys Leu Met Asn Asp
            740                 745                 750

Glu Leu Phe Val Ile Ile Asn Asn Gln Leu Leu Lys Tyr Leu Pro Arg
            755                 760                 765

Ser Glu Tyr Asn Asp Ile Cys Gln Thr Ile His Asp Lys His His Pro
770                 775                 780

Ser Thr Arg Val Thr Asp Tyr Leu Cys Thr Leu Ala Tyr Trp His Pro
785                 790                 795                 800

Asp His Leu Leu Ile Ala Thr Asn Ile Thr Arg Lys Cys His Tyr Cys
                805                 810                 815

Gln Leu Asn Thr Ser Ile Arg Glu Ala Ile Arg Pro Tyr Arg Pro Leu
            820                 825                 830

Glu Pro Leu Lys Ala Phe Ser Arg Trp Gly Met Asp Tyr Ser Gly Pro
            835                 840                 845

Tyr Phe Asn Thr Val Gln His Arg Tyr Ile Leu Val Ala Val Glu Tyr
            850                 855                 860

Val Thr Gly Leu Thr Ile Ala Val Pro Thr Leu His Lys Asp Ala Asp
865                 870                 875                 880
```

```
Asn Ala Ile Ser Leu Leu Gln Ser Ile Ile Ser Ile Met Ser Ala Pro
            885                 890                 895

Thr Glu Leu Val Thr Asp Gln Gly Lys Lys Ile Phe Ile Thr Ser Phe
            900                 905                 910

Gly Tyr Pro Met
        915

<210> SEQ ID NO 23
<211> LENGTH: 3470
<212> TYPE: DNA
<213> ORGANISM: Unknown
<220> FEATURE:
<223> OTHER INFORMATION: sequence of retrotransposon from unknown
      organism

<400> SEQUENCE: 23
```

| | | | | | |
|---|---|---|---|---|---|
| gtatatttca | agacgttatt | tcttgtgacc | cttggatgac | tactcaaaat | acttgacagt | 60 |
| tcaacccact | atgcaacaaa | tctgatgcta | ctgccgaaat | tatcgaattc | atcaatcatt | 120 |
| gggaaaagtt | ctttctggga | aatggcaatt | accatacgaa | aattctccgg | tcggataatg | 180 |
| gagggaatt | cttaaacaaa | acattgacta | cctatcttga | ttcaaaatat | attactcacc | 240 |
| aaacctccaa | tgcctatgaa | catcatgaga | atggcgctgc | agaacgagct | attagatcgg | 300 |
| ttaaagacat | ggctcgagta | atattgcttc | aatccaaatt | accagtgccg | ttttggtccc | 360 |
| tagcaacccg | atgtgctgcg | tttgttatga | atcgtcttcc | tcataaaaca | ataaatggta | 420 |
| agattccta | tgaagtatgg | actaaacaac | ttgtcaatct | caaaatgatg | aaaccgtttg | 480 |
| gctctcaagt | atatgtgaaa | attcctattg | gagtcaaaag | tttttctgca | caagcacttt | 540 |
| ctggaatcat | ggtgggatat | gccactaata | agaaaggcta | ccttgtatat | gatcccacac | 600 |
| aaaatcgaat | attcacatcc | tcacaaataa | tatgtcatcc | gagcatttat | ccagcagcca | 660 |
| accttacgtt | taacgaaccc | ttaattatct | catcgaaagt | cacggctgct | catcttcacc | 720 |
| cccttaccat | ttccaattta | gttattccac | ctaccaatgc | tgtatctgag | acacctcttg | 780 |
| caaattgtgt | gctctcctca | aattcgtcag | tatgtcccaa | agtttgccaa | ttacaaactg | 840 |
| tcttggaaca | tggggaggat | aaaatatatg | cactgattat | accaatatcg | atcggcaata | 900 |
| tgaaacgcac | aagaacaaat | gaaaacaaaa | tatgccagct | agatgaatcg | aacaatacca | 960 |
| ccataccaga | tagtgtaatt | ttatcggcta | acaatgtgtt | attaaactta | gaatcgagat | 1020 |
| cttccattcc | caaaagttat | aaggaagcta | taacatctaa | tgaaaatcc | aaatgggctg | 1080 |
| atgctatgga | tagcgagttt | aattcattac | aatccaacaa | cacgtggtca | cttgaaccac | 1140 |
| taccggaggg | acgcaaagct | attggtgtca | aatgggttta | tacaatcaag | gacaccggtc | 1200 |
| gctacaaggc | tcgccttgtg | gcacttggtt | atcgacaaca | ggctggtgtg | gactttctcg | 1260 |
| aaacgtatgc | tcccgtgatt | cgtggagaat | caatcaaact | aatctttgca | ctcgcgtcaa | 1320 |
| aatccaaact | aaagattcat | tccatagatg | ttaccacagc | tttcctcaac | ggggaaatac | 1380 |
| tggaactcat | atttgtgaaa | caacctccgg | gatatgaaga | taagaagcgt | cctaatcatg | 1440 |
| tttgtaagct | caatcgcagc | ttatatgggc | ttaagcagct | gccactaatg | tggaacatta | 1500 |
| aattaaatga | tgtacttata | aaggaaggtt | tccgtcgact | tggtggtgac | ttagggatat | 1560 |
| acattagtaa | ggacaaaaga | acaataatgg | gagtttatgt | tgacgacatt | ctcatttgtg | 1620 |
| gaccttctga | cagtgaaatt | gaacaagtaa | agaacaacgt | gagaaaatac | ttctcaataa | 1680 |
| ctgataatgg | attatgccga | aaattccttg | gaattaacgt | ctatcaacaa | gcaaatgaaa | 1740 |

```
taagattaag tttgaatgat tatataagga gaatgattga ggagttaaaa ttatctgtct   1800
cagaaacaaa cccagtatct ataccatctg atgtcaatta tgaaatattt aaagttaacg   1860
aaaatgatga tgagaaacca tgtgatcaaa ccaaataccg aagtttgata ggcaagctct   1920
tgtttgccag taatactata aggtttgaca tcgcctattc tgtcaactcc ctatccaggt   1980
ttatcaacga tcccaaagaa aaacattgga ttgcagctgt caaggtggta aaatatctca   2040
gtggtactca acggtatggt atttgttata acggtaacgg tgacttgaat atttacgctg   2100
atagtgattg ggcttccact ccatctgatc gaaagtctat tacggggtac attgttacct   2160
atgctggagc gccgataagt tggcgttcca agaagcagaa cgtgatagcc ttgagtacga   2220
cagaagcgga gtttatggct ctcacagagt ccataaagga agccctttgg ctaatataca   2280
tttttcgaga tattaatgtg atattgaaat taccaattgt gatatatgaa acaacctac   2340 tgtgtcagaa attacttgaa atcctcgat tccataatag acaaaacac attgacttga   2400 aatataaatt taccaaagac catatagaag ctggtacaat caaagtggaa tcaactaatt   2460
cagcagataa cttagccgac atgctaacta aacctttacc aaaaattaaa tttaaacatt   2520
taagatggct agcaggatta agacctttag attgattaga taatgataaa atgaaataaa   2580
gattaatttg gagatgcagg ttgatgggga ggatgttgga aaaatgaaat atgatcaatc   2640
ctgcatctag aacctgtggc agaatgaaac ctacgagatt atgaatgact tgtgaataca   2700
agttgaatgt tacagaatgt taccaagaag gttacacttg aatatatgaa tgactagaaa   2760
gtgaattgaa tgttcagaa cctgaataac aatgttacac gaatgtgtga atgatatgag   2820
tttatctata gtaatgtgac atatacacaa aggtgtgaat gaccgagaaa acagatgtta   2880
cattacgggc actggagagt gcaagtctaa agaatcttgg agtagaaata agtaatataa   2940
aaaggaccaa agattcttta gagaaaagta atgaaacta tattagattt tatataacta   3000
actaacaaat aaataaaaaa tataatatgt ctacaatgcc accaacttcc aaacgtacta   3060
gaaagagaac tagaaccgat gataatgctg aaccaactat tcaagatcct tcaccgccac   3120
ttgctaatgt tgaacccaca attcaagaga ctccaccgct ggttgaagtt agtgatgaga   3180
ctaattcaac tgaaatcaat gagacaaata gtaatactca tgaagaaaca aatgtattaa   3240
ctaatgtgca ctcctctcca atcgagacag ttactgagag gaacttcaat tttcaacaat   3300
aataatattg gttggattta cacgtacgtt gttgttacaa agacgtgagc agagtgagag   3360
agatcaacct tcatattcaa tctcatctca atcaacgctc aatttttttt tcttctccct   3420
ctctttgttg tttaactaag tttgttccct tccatccaag caagttagaa              3470
```

<210> SEQ ID NO 24
<211> LENGTH: 748
<212> TYPE: PRT
<213> ORGANISM: Unknown
<220> FEATURE:
<223> OTHER INFORMATION: sequence of retrotransposon from unknown
      organism

<400> SEQUENCE: 24

Met Ala Arg Val Ile Leu Leu Gln Ser Lys Leu Pro Val Pro Phe Trp
1               5                   10                  15

Ser Leu Ala Thr Arg Cys Ala Ala Phe Val Met Asn Arg Leu Pro His
            20                  25                  30

Lys Thr Ile Asn Gly Lys Ile Pro Tyr Glu Val Trp Thr Lys Gln Leu
        35                  40                  45

Val Asn Leu Lys Met Met Lys Pro Phe Gly Ser Gln Val Tyr Val Lys

```
                50                  55                  60
Ile Pro Ile Gly Val Lys Ser Phe Ser Ala Gln Ala Leu Ser Gly Ile
 65                  70                  75                  80

Met Val Gly Tyr Ala Thr Asn Lys Lys Gly Tyr Leu Val Tyr Asp Pro
                     85                  90                  95

Thr Gln Asn Arg Ile Phe Thr Ser Ser Gln Ile Ile Cys His Pro Ser
                100                 105                 110

Ile Tyr Pro Ala Ala Asn Leu Thr Phe Asn Glu Pro Leu Ile Ile Ser
            115                 120                 125

Ser Lys Val Thr Ala Ala His Leu His Pro Leu Thr Ile Ser Asn Leu
130                 135                 140

Val Ile Pro Pro Thr Asn Ala Val Ser Glu Thr Pro Leu Ala Asn Cys
145                 150                 155                 160

Val Leu Ser Ser Asn Ser Ser Val Cys Pro Lys Val Cys Gln Leu Gln
                165                 170                 175

Thr Val Leu Glu His Gly Glu Asp Lys Ile Tyr Ala Ser Ile Ile Pro
                180                 185                 190

Ile Ser Ile Gly Asn Met Lys Arg Thr Arg Thr Asn Glu Asn Lys Ile
            195                 200                 205

Cys Gln Leu Asp Glu Ser Asn Asn Thr Thr Ile Pro Asp Ser Val Ile
210                 215                 220

Leu Ser Ala Asn Asn Val Leu Leu Asn Leu Glu Ser Arg Ser Ser Ile
225                 230                 235                 240

Pro Lys Ser Tyr Lys Glu Ala Ile Thr Ser Asn Glu Lys Ser Lys Trp
                245                 250                 255

Ala Asp Ala Met Asp Ser Glu Phe Asn Ser Leu Gln Ser Asn Asn Thr
                260                 265                 270

Trp Ser Leu Glu Pro Leu Pro Glu Gly Arg Lys Ala Ile Gly Val Lys
            275                 280                 285

Trp Val Tyr Thr Ile Lys Asp Thr Gly Arg Tyr Lys Ala Arg Leu Val
290                 295                 300

Ala Leu Gly Tyr Arg Gln Gln Ala Gly Val Asp Phe Leu Glu Thr Tyr
305                 310                 315                 320

Ala Pro Val Ile Arg Gly Glu Ser Ile Lys Leu Ile Phe Ala Leu Ala
                325                 330                 335

Ser Lys Ser Lys Leu Lys Ile His Ser Ile Asp Val Thr Thr Ala Phe
                340                 345                 350

Leu Asn Gly Glu Ile Ser Glu Leu Ile Phe Val Lys Gln Pro Pro Gly
            355                 360                 365

Tyr Glu Asp Lys Lys Arg Pro Asn His Val Cys Lys Leu Asn Arg Ser
370                 375                 380

Leu Tyr Gly Leu Lys Gln Ser Pro Leu Met Trp Asn Ile Lys Leu Asn
385                 390                 395                 400

Asp Val Leu Ile Lys Glu Gly Phe Arg Arg Leu Gly Gly Asp Leu Gly
                405                 410                 415

Ile Tyr Ile Ser Lys Asp Lys Arg Thr Ile Met Gly Val Tyr Val Asp
                420                 425                 430

Asp Ile Leu Ile Cys Gly Pro Ser Asp Ser Glu Ile Glu Gln Val Lys
            435                 440                 445

Asn Asn Val Arg Lys Tyr Phe Ser Ile Thr Asp Asn Gly Leu Cys Arg
            450                 455                 460

Lys Phe Leu Gly Ile Asn Val Tyr Gln Gln Ala Asn Glu Ile Arg Leu
465                 470                 475                 480
```

Ser Leu Asn Asp Tyr Ile Arg Arg Met Ile Glu Glu Leu Lys Leu Ser
            485                 490                 495

Val Ser Glu Thr Asn Pro Val Ser Ile Pro Ser Asp Val Asn Tyr Glu
        500                 505                 510

Ile Phe Lys Val Asn Glu Asn Asp Glu Lys Pro Cys Asp Gln Thr
            515                 520                 525

Lys Tyr Arg Ser Leu Ile Gly Lys Leu Leu Phe Ala Ser Asn Thr Ile
        530                 535                 540

Arg Phe Asp Ile Ala Tyr Ser Val Asn Ser Leu Ser Arg Phe Ile Asn
545                 550                 555                 560

Asp Pro Lys Glu Lys His Trp Ile Ala Ala Val Lys Val Val Lys Tyr
            565                 570                 575

Leu Ser Gly Thr Gln Arg Tyr Gly Ile Cys Tyr Asn Gly Asn Gly Asp
            580                 585                 590

Leu Asn Ile Tyr Ala Asp Ser Asp Trp Ala Ser Thr Pro Ser Asp Arg
        595                 600                 605

Lys Ser Ile Thr Gly Tyr Ile Val Thr Tyr Ala Gly Ala Pro Ile Ser
    610                 615                 620

Trp Arg Ser Lys Lys Gln Asn Val Ile Ala Leu Ser Thr Thr Glu Ala
625                 630                 635                 640

Glu Phe Met Ala Leu Thr Glu Ser Ile Lys Glu Ala Leu Trp Leu Ile
            645                 650                 655

Tyr Ile Phe Arg Asp Ile Asn Val Ile Leu Lys Leu Pro Ile Val Ile
            660                 665                 670

Tyr Glu Asp Asn Leu Ser Cys Gln Lys Leu Leu Glu Asn Pro Arg Phe
            675                 680                 685

His Asn Arg Thr Lys His Ile Asp Leu Lys Tyr Lys Phe Thr Lys Asp
        690                 695                 700

His Ile Glu Ala Gly Thr Ile Lys Val Glu Ser Thr Asn Ser Ala Asp
705                 710                 715                 720

Asn Leu Ala Asp Met Leu Thr Lys Pro Leu Pro Lys Ile Lys Phe Lys
            725                 730                 735

His Leu Arg Trp Leu Ala Gly Leu Arg Pro Leu Asp
            740                 745

<210> SEQ ID NO 25
<211> LENGTH: 1550
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(1550)
<223> OTHER INFORMATION: 'n' can be any nucleotide 'a', 'c', 'g' or 't'

<400> SEQUENCE: 25
gtgttgtgtt gggtttgaat ttctgtataa ctcaatttgg agattttttt ttttttttttt    60 ttgaaatttt tattagtcgt gtacattgtt acaattgttt ctcgttcccc ttttttttttc   120 ctttctttgt tttgttttgt ttaccttgtg ataatttat acgtgttgag agggctctcg   180
tcgtgcccgt gtccgtttcc gtttccgtgt cctgttgggt cccctccgcc catgccgcac    240
cgcaccgtac ggtaatgata tctgattgtt gttggagcgt tcttcgctaa caggttcttt    300 cttttttgttc aggggtttcg aaagataatg tagaaacacc agggcttata actgagagtt    360
agagtagtgg agattagtag tagtagtaca atcctatagc ccaaacatta ttggagagat    420

```
cttaccaaat agcaatcatc atgatgtatt tactactaca taaatnattt aagacgacat    480
ttaccagcaa taaacaacat gaccaactaa ttaacaaaca tttgaaaaac ataaagtaat    540
tagaaagttt aaaaagtgta caaccagtgt ggaaaaagaa tggaattgga attgaacaaa    600
gttattaatt actgaaaaag gaaatttaat ttcttgaaag gcaaatcttt gtttgttttt    660 tttttttgggt cttttctttc atttaataag cgtggggtat taatagataa tgatattgtt    720
gttgttattg tgatattgtt gtgaaatttg acatatgata agataagttt ctttcttttc    780
tttcaactag tataattgaa ctaaagacca ccaccaccac caccacatag ttagcaacct    840
gatatgctgt tcatgtaaca gtaaattatc ttggtactat accacttgtt gtaatatagc    900
taatgctaat tcttgattag tgtggaaagc ctaataaggt tatattgtgc acaggttaac    960
taccttaata tagttattgt taatacagtt attgctgttg actactattg ttattgttaa   1020
attaaagtgt taggttgagt taattgatta gtgaaaacca actaactacc gtattaaatt   1080
attgtattaa gattgattcc tattaaggat aaaacagaga gtgtgttaga aagagaaagg   1140
gtggattata aatatgtgta aaatcccctt tagagactaa ccactagaaa tctattgatg   1200
gtttcatata tagagattaa cgattatatt tataatataa gttggtagtt gctagtatat   1260
ntgaaagcac tacagtatag tatgtcagaa tcagatcatt taaactctac taataataca   1320
ggaaacactt tcattagtct agatcaagcc agtacaataa tggcagatca aactcaagga   1380
gctaacccac aacaatgata attcatcttt tttgtcaaga cgatagttaa tgttacaagc   1440
actttnattg ggctcgaaat agtggtaaat agggtccata ggatatgacc tgttacaagt   1500
ttatttcgat gatcnagccg gcctctgtga ttacggcaat tattttttacc              1550

<210> SEQ ID NO 26
<211> LENGTH: 2132
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(2132)
<223> OTHER INFORMATION: 'n' can be any nucleotide 'a', 'c', 'g' or 't'

<400> SEQUENCE: 26
tttttaaaag aattaattaa atatgatgga tgatagaaat taaaggaaaa agaagaagaa     60
caaaacaaaa gtttaattga aaaaaaaggg agaaatgaat attgaattat tcagctttta    120
tattgctgat agatgttgaa aaaaaaacgg aagaatgggg atagcaaaac tgtgggtgag   180
attaactcat ctatggcgct aaaagtcttt tttttttctc ttttattagg gggcacataa    240
attattcttt tcattgataa tcccgagtcc gttttttgtt cattattcgg aatatattac    300
cgtattggga acgataatta ttattagttc tccccgatgg ttcgattttg ctggtgcaaa    360
aatataaatc cgatataact ttattggtgc tttgataaat ccgttttata agttggtaga    420
catatacagg atgataataa tttaacggat ttataagttg gaatcatttg gatgaatccg    480
cttggggagg cgttttccaa ttttagaagt ttaactatca attttatgtg acatccgagt    540
atacacattt tgtgaatttg atcttgtaaa ctcacttggt gtaccatggc attttataaca   600 acactttcta gaatcggctg agttacatgc atttcctcta tttgtagatt aatggaaatt    660
catgaaatcg ttcacatttt tttctataat gagtatcgtt cggtttccat aagtaggga    720 ctaaaaaata attgatatct ctaatcagtg acagctctag tcaacttgac cgtaatgttt    780
```

```
tgacgaccat tatatttctt gtttgaacta ttgatttatg agtgttgtcg taacaaaaga    840
tcaattcccg tcaaaacgca tttggcactt aatctttgat tgaaccgatt ttgatctcaa    900
aacatagtac caaggtcaat tatgttcgct aatgaaagaa agctgtgacg aaaacctcaa    960
attcatgaag aaagaattac tgttgtggaa aataaaaaag tctttcttct gatactttac   1020
aagtccctca accacaaata caaaaatgaa agttacccat cgatctttt cattggttaa   1080 gaattaatac gagaatatca aattatctta gagagggtct cacagagcaa ctttctgagg   1140
cacacggtca ccaacatgat ttgttataaa aaattcaacc aaattttgga aaaaatgaaa   1200
acaaaacaaa acaaaatctg aaacatcccg aaagtcacaa atgcttgatt acttaaaatt   1260
acttatttgc ttcaagacgc tattattatt attatgacat aatactactt gaataacagt   1320
gaactgtaat tgtattaaga acaaatcata caaaggaag atgatgacga tgatgatgac   1380
cccttgaaat atcccagggc acatgcattg tgatgattgt tgtaatatag ctaatgctaa   1440
ttcttgatta gtgtggaaag cctaataagg ttatattgtg cacaggttaa ctaccttaat   1500
atagttattg ttaatacagt tattgctgtt gactactatt gttattgtta aattaaagtg   1560
ttaggttgag ttaattgatt agtgaaaacc aactaactac cgtattaaat tattgtatta   1620
agattgattc ctattaagga taaaacagag agtgtgttag aaagagaaag ggtggattat   1680
aaatatgtgt aaaaatcccc tttagagact aatcactaga aatctattga tggtttcata   1740
tatagagatt aacgattata tttataatat aagttggtag ttgctagtat atttgaaagc   1800
actacagtat agtatgtcag aatcagatca tttaaactct actaataata caggaaacac   1860
tttcattagt ctagatcaag ccagtacaat aatggcagat caaactcaag gagctaaccc   1920
acaacaatta ccatattata tgaagaagac tataacaaaa ctgtagatag taggggattg   1980
ggtatttccg ggggagtaga agtattgggg ttatctaagt ccatctttaa ccacccaaca   2040
atccaacaac aacccaacna cgttttttccc caattctcng gagatnactt gattaactt n   2100 aaatttttcc ntggccaaaa aatttccttt tc                                 2132
```

<210> SEQ ID NO 27
<211> LENGTH: 1734
<212> TYPE: DNA
<213> ORGANISM: Unknown
<220> FEATURE:
<223> OTHER INFORMATION: sequence of retrotransposon from unknown
      organism

<400> SEQUENCE: 27

```
aataaccaac cagctgctca ttttttagatg tatgtatttt ataggaaaat tgaataactt     60
gttattacta tggcctgttt tctaaagcca agttgtttct tcttatattt tttttttcta    120
aacaccgttt gttgaagatg gctttatccg tatactattg ggcgtcgatt ttcgcacaaa    180
agcttttatc cacggaatat ttgcgataat atagtacaaa agtgtgttct agtcttgtaa    240
atgtccaata tttttagtac aacgatggaa acccgtatag cgcagacaca gtttggatag    300
atttacgtag gtgatgagga gttaaattga atattcttgt ataatttcaa gagctgtgac    360
tactatttaa attttttcca cttcactttc tttctcttct ttgacattca agttagtctt    420
tctgtatttg aataatacta catttatcat gtctcacgtc tcaattgtaa ctggtgcttc    480
tagaggtacg ttttaatgaa caaaatctat gatgttgaga cttccaattt gaactttagt    540
actaactcaa ataaaggcat tggtaaggct atcgccgaaa ttcttttaaa aactccatct    600
tcaaaagttg tgattgttgc tagatctcaa gctccattgg aatctttcca aaagcaacac    660
```

```
ggctcggaca gagtagcatt tgttgctggt gatattacag atccagcaac gtctaagact    720
gctgttgaaa ctgccatctc caaatttggt caattaaatg ctgtcatgtt gtaatatagc    780
taatgctaat tcttgattag tgtggaaagc ctaataaggt tatattgtgc acaggttaac    840
taccttaata tagttattgt taatacagtt attgctgttg actactattg ttattgttaa    900
attaaagtgt taggttgagt taattgatta gtgaaaacca actaactacc gtattaaatt    960
attgtattaa gattgattcc tattaaggat aaaacagaga gtgtgttaga aagagaaagg   1020
gtggattata aatatgtgta aaatcccctt tagagactaa tcactagaaa tctattgatg   1080
gtttcatata tagagtttaa cgattatatt tataatataa gttggtagtt gctagtatat   1140
ttgaaagcac tacagtatag tatgtcagaa tcagatcatt taaactctac taataataca   1200
ggaaacactt tcattagtct agatcaagcc agtacaataa tggcagatca aactcaagga   1260
gttaacccac aacattttgt agtcgtaaac ttgaaattca agagaaggg ggggaattaa   1320 attgggtgca acgtgtttgt caaaaatttg gtgtgaaaaa aattaattta acactctgca   1380
ttgtaccata gggaatataa tacccagaaa taagagaaat tatcacgtga gactaaaact   1440
aaatataata aattaatatc acaattgaga agacactga aactaacttc ttggtgtatt   1500
aattttcaac acttgatcac aagtgcgggg attaatcata attgcaaaga gtgtgttaga   1560
aagagcgaag gtggattatg aatattggag aatcctcttt agagactatc cgctaacaaa   1620
atagatgaac ttgctcaaca gaaacaacta atcgactaac tgactaaaat taatatacta   1680
agtatagatt aagttatcac gttaatattc tatactatcc atctccatca cttt          1734
```

<210> SEQ ID NO 28
<211> LENGTH: 5734
<212> TYPE: DNA
<213> ORGANISM: Unknown
<220> FEATURE:
<223> OTHER INFORMATION: sequence of retrotransposon from unknown
organism
<221> NAME/KEY: misc_feature
<222> LOCATION: (1)..(5734)
<223> OTHER INFORMATION: 'n' can be any nucleotide 'a', 'c', 'g' or 't'

<400> SEQUENCE: 28

```
gagattgtag tgaagaattc agctcattat tactgttttg tcgttgctgg aaggaggagg     60
gataattcaa tgcgccacaa cagtgttact atgcatgtgg ttctgactga ctgatattgt    120
ttaaaaatta accagctctc aaataacaaa agtttaaatt ttcaaggttt gtaaacatgg    180
cagctagtag taggatggtt cataatatta attaattatt agtaataatg gctaagtttt    240
tgaagcattg ttttaaattt tcaaattgaa attcaatttc attacaaatg gattactaac    300
ggaattccta agctcaactg aataccgtga ttgaaacatt tgaatttgta tcttttagat    360
tagctatttt tactttttttt gtcattgtag ttggttatga taattacaag aaactaaagt    420
ttaatatttt aatattcatt ttctttttg gccaacttgc aaataacaca caacccaaa     480 attaaataat tagatttaat gcatgcataa ttacacagaa tgtttagcct taacaagtat    540
tctagaaaca agaagaaaa aatgtcgtct tggcgtttat cttaattgta ttctgtaaac    600
tgggttaatt cttatttcca acttttcatt ttttggatc ttgtatggaa taaaaattaa    660
atatggtatg ttttagggtt gtattaacaa tacttacaat tatcaatcat acagctttac    720
tatttttatt tatcagcaaa taggggaatt caagttgcat gtgttattca gtggcagtga    780
atcataaaac agccaacttg cagcttattt cactccagga gcaatcatca cggaattccg    840
tttcccatct cattttcata ctctgtggat tatgtataga ggctatttac aatatcacca    900
```

-continued

```
agcagtaaaa cattctctcc tcaaaataac aataagatta gtcaagatga acgacttgaa    960
tctattcata tgcattacac atttagtttc tattacaaat agtgatgcaa tggtgcaaga   1020
ttacgtcttg tctgcactaa ctatttgtaa cgatgattat gtgatcaaga attggaattc   1080
ttattatatt cagtcgtgag tgtaagctat ttcgttaggg ttatcttaac tcgaagttaa   1140
agttccaaaa ctattccatt tggagttttct gttgttgaga atacaaaat actcttcttg   1200
gtggggagga atccattaa tgattataaa atgaaactct tggtaaccta attgaaacac   1260
cacattcagt acattttcaa ccgtcactat tattattgtg gcaaatggat taaacaatag   1320
acctaactta atctaatgga aattttaaat ccatgaaagg ggtgaaaatt tgaaatcaaa   1380
ataactatct gaactgaaat accccatgga tctgatatct tatacaatct atcaactaaa   1440
cagggaagag tacctggaat tccaaatgac aattcctatt ataattattt aaacagacta   1500
tgccgtattg tttgtgacat tcattgtttt ccacaactct aatgtcaaat ttttgttatt   1560
gtcatgtaat cccggtgttt cttttttctt ttcggtgttg cgttccatga tattttgtta   1620
tctcttgttt agattgagat aaagaattgg ttagcagtgt agccatttat gagtggtttg   1680
taaaaacaag aattacaagg tttgaatgaa ttccaggcag gcagtattat aaaacctcga   1740
aataactaat caaaccatca gaaaagaaag cttactatga tgtactgctt aatctccatat   1800
ctatcttaca aacttaattc actgattgtg gcttgtccgt gaataattcg gaaaccttgt   1860
cttttttcggt ccagtagggg gtgccatagt cttgggtggt gacaaaaaaa aaaaaaatta   1920
tagttggggt ggtggggtgt acgtctgagt aagtcagggg aatgaactca agacaaaaat   1980
agaagttcta aacatggtac gttctgctaa gtaatatcat cgatctatct attttgctct   2040
aaattttcat aagcaaatcc agaacttcct cgtcagtttc aatttcaagc atacgaaggg   2100
atagtgatta aattatattt tgaaccttct attactgatt aagtgttcct attagtctac   2160
ggattagacg gttagaatgg gatttncaaa agcacaaagg tcaagactta taggaaattc   2220
atagaaaaaa cactctgaag tactcgatgg ttggatatat aatagttttg ctaatttaaa   2280
ctcttgctgt tcggctaagc tattgtaccc aaatgcggta ctccgatagt cttataaata   2340
atacttggca aaagttcaat aaatatatgt caatggtatt gctttccaat taccattgac   2400
gaggttgtaa attaattcat acttaggtga catcgattaa tttaacaaat atgtctgttt   2460
caacgcttac atcatcagtc ttgcaggaaa atgttattg ccacgacacc tcaaattagc   2520
ccaaccccctt cgtctaccaa aacaatgtca aaaacccact taaagaagt cggacaaacc   2580
tgaacccggt attttataaa gtagttttgt gaataatatc agtacaacga ttacactttc   2640
cgtctcaaga ctggaagttg caaagccatg acaattgctc aaccaaatgt gaattttag   2700
gttccatagt cttgatcggg taatgtaaac actttaactt ttagtaaatg ataccaccaa   2760
gaagaaagca ctattttaag ctttatttaa cactatacat tggaaaataa aaaagtggct   2820
atgagaatta acaagatga ccgagtaatt aaaatagtgc tgtcggtgtt aagcaatacc   2880
gctagggttc aatcaattaa gtgctgcttt tttttgtcgt tgtatttcca ttcctccact   2940
cctttctttta ctcttgcaat ctaacatatt ttttttaaaa agaaaacata ttgatactta   3000
catgtggtaa ctattgtctg attcatcaat tccgctcttc aatctcggtg ttcggataat   3060
ttcgatgaaa ttataattac ctgccgcaat tctagaaatt cctttttttt cttttctttt   3120
tctcggagtt ggttccaata caaagattga attgaattag gtgagaagaa gaagagtctt   3180
aacaccagat gtattacagc tttaaacttt gtttctaatt tgaccacaaa aagttgtctg   3240
```

```
gacgcctcag tttgaaatta gttttgggag atttctgttt tctcattggc cttactctat    3300
ggaagttttt atacaagagc ttccttctaa aattaactct ttgtgttgta atatagctaa    3360
tgctaattct tgattagtgt ggaaagccta ataaggttat attgtgcaca ggttaactac    3420
cttaatatag ttattgttaa tacagttatt gctgttgact actattgtta ttgttaaatt    3480
aaagtgttag gttgagttaa ttgaatagtg aaaaccaact aactaccgta ttaaattatt    3540
gtattaagat tgattcctat taaggataaa acagagagtg tgttagaaag agaaagggtg    3600
gattataaat atgtgtaaaa tcccctttag agactaacca ctagaaatct attgatggtt    3660
tcatatatag agattaacga ttatatttat aatataagtt ggtagttgct agtatatttg    3720
aaagcactac agtttagtat gtcagaatca gatcatttaa actctactaa taatacagga    3780
aacactttca ttagtctaga tcaagccagt acaataatgg cagatcaaac tcaaggagct    3840
aacccacaac acattcttct tgtaaaatta attctattat aattcaggtc ttagtcgacg    3900
caaaatacca tgttgcaatt gtccgtaaac aattatacaa caatttaacc aatgcaacat    3960
caattgaaat caagaattca acacttgaac attttttcttg ttttcagatc tcgtcaaaac    4020
accagtcaat aaagcttgga aagttttagc acaaccatca aagtagaaag cctaacttat    4080
aggttcgaat tacgtgaatt ttggtttcac taatcacgcc ccaaaaaaat tcanaaaagc    4140
ttagtatgta acatttattg caaattttt attgttcgtc ataaatgata attagtaaat    4200
gaggttacag aatagttatg ttttacttca taaccaattc tactattttt ttttgtatta    4260
taacctcgga taacacaaac aaaaaaaaag tactactacc aattaatgtt tagtagattc    4320
tacacaaact tgataatgcg ggagttattt tttttttgaag ccactttatt ttcagccgac    4380
ttatctagct acgagacaga acaatactta gcactaattc ttaaaattcc atactatttc    4440
tatcattcaa aatgcatttt aacaatcaat tgtcaaatgt gaatgcaaca aagtcctgaa    4500
tttataaaaa aaagtagatc attgatgcaa aaagtgaatt ctttggaaag ctttactttg    4560
aaccgaaagg agaaggcaag tcgtgcaaca agttattatt tcgtgtacag tatccaattt    4620 tggttttttcg acactaggtc tagactccag aaacaaagtc ctaataagaa aggtgttcaa    4680 aaacaatttta atttttagtaa aaaaacacaa cctgcatttc gcaatttatg accaaattga    4740
gttagctaat tatagggcat caacaataat atccagcctc acacaaatca gaaacagtca    4800
tataacaact cgaatgcaaa tatcaagact atgttatgat aagagtagtt gggccaataa    4860
gataaaacag aaaagaaaa ttttatattc tttaaatctt tgggtgacag atcagctcca    4920
attctcttga aattggcaca aatacttcgt cttttttcat tcatcagtat atcacgtgta    4980
gaattgatgc tgatattcaa aaattacccc taaagttgct tatcaacgca acttaagatt    5040
tcatacaagt cgataacgaa tctgaatttc agcttgctct tagattaaac aaaatggtag    5100
attcaatcaa ttagataacg ccaaataaca tttgatgttt tgcggcaata tttggatggt    5160
gtcaactagg agaaaattga ttccccgcca tatctcataa gcctctagct gtccactttt    5220
ctaaataatt gatatggatc accacattgg ggtctaaatg aaacaacgta acccgaaaac    5280
gtgtcaaatt cggaattcgt atgtataatt caaacaatac aagaaatatg gagaaagcag    5340
atacacacat acacactcaa agagcttggt agaataacaa taacttgata taatacgtac    5400
tattcataca caattactta attgatttgc aatcattcct aaaaaaattc tctttttattt    5460 ttttttttaat tggtaatatc ggtggtatac aatgatttac ctagttaaac aattgaaaac    5520
aagaaagtat aaaatttctt catttatttt gcttaccctc taccttggta attacaccga    5580
tgtgagtttg gaaatctgat aatcccagaa attggatcta attggntcat atttagattt    5640
```

-continued

```
caacaaatca taaacagttc tagactccat gtatttcttt tggtgtgtgt atattttgc      5700 caatgtctcc aaagcaaatg gaactcgtca cttg                                 5734
```

<210> SEQ ID NO 29
<211> LENGTH: 1875
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(1875)
<223> OTHER INFORMATION: 'n' can be any nucleotide 'a', 'c', 'g'  or 't'

<400> SEQUENCE: 29

```
cctccggccg ctaattacaa ggctgcttta tattgttata ccttggggta aatgccctct       60
ggcattgagc tatttccaat tcccacttcg gtatttttttt ttacagcctc gttagacgag      120
ttcttgatat tactaaatta gttgtttact gagtggcctg atggttcctc gtcactctag      180
tttttggtct atataagggt cagaaatttc ccttctcctt aggtccatca agtcaagata      240
tacattagtt ggtagcatcg tatggaattt tcgtatgaac ggcataccaa gtattaattt      300
ccgatcgaaa ttttttagga cgtcttgata atcaggacaa acatcatgaa aggtctatac      360
gacgaaagtt tactttacac aaggggagac catatgtctt ctttattaac aactagttat      420
atagcgaaca aataagttta tacagaaata tatgtacaca acaaagtta ttgtttatta      480 attatttaat tagctcggaa gaataactct gtgatactgc atacattcaa acaaaatcaa      540
tctagtttcc aacatctttt tcacttggta atgtaattat tcttgttctg gcaccgacaa      600
tgggtattgt tttgtagctg gaggactaat atggggtacc acctcaattt ttggatccca      660
gctcccacgc aggggtggct tctgatctaa ctcactttcg aaaatatcct gatagtttcc      720
aattaattca gcaaaatagc tcttgtttgt acccttaacc aatgacatga tatccttttt      780
attatcaccg ataccacctg tgtcttcgtc ttgttgtaat atagctaatg ctaattcttg      840
attagtgtgg aaagcctaat aaggttatat tgtgcacagg ttaactacct taatatagtt      900
attgttaata cagttattgc tgttgactac tattgttatt gttaaattaa agtgttaggt      960
tgagttaatt gattagtgaa aaccaactaa ctaccgtatt aaattattgt attaagattg     1020
attcctatta aggataaaac agagagtgtg ttagaaagag aaagggtgga ttataaatac     1080
gtgtaaaatc cccttagag actaaccact agaaatctat tgatggtttc atagatagag      1140
attaacgatt atatttataa tataagttgg tagttgctag tatatttgaa agcactacag     1200
tatagtatgt cagaatcaga tcatttaaat tctactaata atacaggaaa cactttcatt     1260
agtctagatc aagccagtac aataatggca gatcaaactc aaggagctaa cccacaacac     1320
gtcttcttca gtattaggga acaacatact aacttgacct tttctagctt caaccaaaaa     1380
ttcctctata tccattaatg gaatttcatc aaactgagca gccccaaaaa acgttttgct     1440
tccaaagtct aaatgagcat ggaatttcct tatgaaaggt ataccaagta ttaatttctt     1500
atggaagctg tccactacag caaaattctc ttggaatgta ataccattaa actggaactt     1560
gaggttaatt atttgttaa agtttctgtt gattttggt ccaataaagt acccaaacta      1620
ctagagctcc aacaacattt tcagaaaatg gccaataata caataagtgg gtatatttta     1680
tcaaaagagt ttatattatg gttactcgac gggtattatt ctctgttgga ttaaggcatc     1740
tgggcgaccc agtgggacca aaattccaga gtagtggttt ggtttaggac tttaccaagg     1800
```

-continued

| nccatgatta gggaatattn taaccaaaaa attaaaatta ccatttaatt cnaaaaccta | 1860 |
| acctaaattc cctaa | 1875 |

<210> SEQ ID NO 30
<211> LENGTH: 1712
<212> TYPE: DNA
<213> ORGANISM: Unknown
<220> FEATURE:
<223> OTHER INFORMATION: sequence of retrotransposon from unknown organism
<221> NAME/KEY: misc_feature
<222> LOCATION: (1)..(1712)
<223> OTHER INFORMATION: 'n' can be any nucleotide 'a', 'c', 'g' or 't'

<400> SEQUENCE: 30

| taaccatgga attcctngaa ttantnataa ttaaccaaat tttttagggn ttattaggac | 60 |
| ctaggattga attccatgtt tatttaataa ttaancccca gtttggccaa ctatgaaata | 120 |
| gtataatggt taaatgcaaa ataaatatag tatgaacaat atgatagttt tagtgtgaat | 180 |
| tttgaataag aaaaagaagg gataaggata tttttactag gaaactcaat tataattact | 240 |
| aatgataaaa actccatcag ctactattat tactcaaatt ttaaatcatt tgtttatcac | 300 |
| ctacacaaac agggattgtc caatattgat tactaaaatt agaacaaata agagaatata | 360 |
| attgaagtta aataattctt ttactaaatc tattgaccaa gaactacatc aagggaaagt | 420 |
| gttgcatata catctaatgt ttattcttgg ttagagtatt gatacaaaat tatatcatca | 480 |
| ccaacgaatc acattaaggg aaagtgttgt gcatatacct gatgcttagt cttggttaaa | 540 |
| gtatttgtgt gaaaggttat cgtgaccaaa gattatagta agggaaagta ttatgaataa | 600 |
| atccaatgtc tactttttaca gaagtattga catgagagat tataactatc aagaattgca | 660 |
| ttaagggaaa gtgttgtaat atagctaatg ctaattcttg attagtgtgg aaagcctaat | 720 |
| aaggttatat tgtgcacagg ttaactacct taatatagtt attgttaata cagttattgc | 780 |
| tgttgactac tattgttatt gttaaattaa agtgttaggt tgagttaatt gattagtgaa | 840 |
| aaccaactaa ctaccgtatt aaattattgt attaagattg attcctatta aggataaaac | 900 |
| agagagtgtg ttagaaagag aaagggtgga ttataaatat gtgtaaaatc cccttttagag | 960 |
| actaaccact agaaatctat tgatggtttc atatatagag attaacgatt atatttataa | 1020 |
| tataagttgg tagttgctag tatatttgaa agcactacag tatagtatgt cagaatcaga | 1080 |
| tcaattaaac tctactaata atacaggaaa cactttcatt agtctagatc aagccagtac | 1140 |
| aataatggca gatcaaactc aaggaggtaa cccactacag gttatgagcc tcgcccgctt | 1200 |
| attgaattta gataatatag gggcaatgaa agcttttgaa agtgttgatt ttcctgaatc | 1260 |
| attaaaacta gaatccaaga ttaattttca agtgtggaga aatgaaatcc ttagatatgc | 1320 |
| acgtggtatt ggtgctgagt ttgaaaactt tgtattgaat gaaactccag ctcacctgta | 1380 |
| tgatcttaga ttgggaaata tgcttcatca attattgatt cgcactgtga aagaaaaagt | 1440 |
| tagaatgcct aggcaagaac ttggaaaatc aggaaaagaa ctttatcttg atcttattaa | 1500 |
| atcattcggt actcaatacc catacgataa atttgagata gttaaatact attgggatca | 1560 |
| gttaacaaac cctttaatta atgtgaagag acgttttgaa attgaagaag tatgggttca | 1620 |
| atacattaat gctcaaactg caacagagag agaagttctt aattcatttg tttggttaca | 1680 |
| tttgtcaaaa tctatattac cacaagagta cc | 1712 |

<210> SEQ ID NO 31
<211> LENGTH: 1540

```
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(1540)
<223> OTHER INFORMATION: 'n' can be any nucleotide 'a', 'c', 'g' or 't'

<400> SEQUENCE: 31
tgtggaatta agatgactttt gtgattaaat tgttgacttc tttaagcctt ttaatgtgga      60
ggaaaaagaa aaatctataa ttaaaaaaaa aaaagataaa gcagataatt ctttgatctt     120
tatatacttg gtctatatgt agtaggggaa agtcggagtc ggaatttgaa aaaaaagag      180
aaaaagaac gaatatttag actgtaaaat tcaaacccct gctgattagt atataaaaaa     240
aatgagttca tttttccttt ctttttttt ttttcgcgcg gatagcaacg gtcattaagt     300
taacgagata aaaagaaac aaccagataa ttatgaaaag ttgtgatggt gtcacgtgcg     360
aacatgagag tcatgaattt tgacgaaaac gtcaagcttc agtttacaaa agacctcttt     420
attaaaatcg aattgcttat agggtcgtcg atgatgagaa ggtgtatgtt gtaatatagc     480
taatgctaat tcttgattag tgtggaaagc ctaataaggt tatattgtgc acaggttaac     540
taccttaata tagttattgt taatacagtt attgctgttg actactattg ttattgttaa     600
attaaagtgt taggttgagt taattgatta gtgaaaacca actaactacc gtattaaatt     660
attgtattaa gattgattcc tattaaggat aaaacagaga gtgtgttaga aagagaaagg     720
gtggattata aatatgtgta aaatccccct tagagactaa ccactagaaa tctattgatg     780
gttcatata tagagattaa agattatatt cataatataa gttggtagtt gctagtatat      840
ttgaaagcac tacagtatag tatgtcagaa tcagatcaat taaactctac taataataca     900
ggaaacactt tcattagtct agatcaagcc agtacaataa tagcagatca aactcaagga     960
ggtaacccac aacatagaat acgttttcaa ctacttaagt atccactaac ctaaattttt    1020
tttttaataa aatttcattg tattagtctt tcttactgct tttaatcaac tataagtata    1080
ggtttccgtt ttttttgcag taaaatttat cgttcaggag aaataacaaa atgtacacga    1140
cttattcgca gcatttttt ttttgtttg ggttttgta tcaaattgtt acaacaacaa       1200
caacaacctc aattcttaac caaatctacc cctcctattt ttttncnca tacacacaat     1260
acatcttaca ctatcttttg ataggctta tngaagangt atttanggng tgtaatgaca     1320
atctgcttaa cncatatatn tatntanngn nngtngtcaa caatagcttt atctactttt     1380
tttttttggn nacnccngna acttcaggnc cacnnntttg ccnattttgg ggccccnatt    1440
nggaaaacat gggnattggg annacagctt tttttaggnn naaangggtn ttnccntttn    1500
tggtgggctt ggaaagnaac agcntntaaa nnaatgggct                          1540

<210> SEQ ID NO 32
<211> LENGTH: 2025
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(2025)
<223> OTHER INFORMATION: 'n' can be any nucleotide 'a', 'c', 'g' or 't'
<221> NAME/KEY: misc_feature
<222> LOCATION: (1)..(2025)
<223> OTHER INFORMATION: sequence of retrotransposon from unknown
      organism
```

<400> SEQUENCE: 32

```
tggggagcaa atgtgaaatt aaagagtgtg gtgatatgta attttttttc aaaaaagatt      60
ggattgacga agcattatat attcgtctaa aaaccatttt tgctggttcc gcaataaatc     120
tcggagatta tttctcgatt accaatttat gttgttttgt gacatttctt atattttgtt     180
ctattttaca cgactattta ttgttaataa atatgtcacc taaagaatat ttctatttag     240
ttttacatat gttttttgac gacaatcaac tattacaaat taacctacat tttttaattt     300
gaatatatac aatttatatt gaattaacat taccatttag tttttgataa gaatagattg     360
cgctatttca aacatttgtt aaattattta ttgtgaaaca actatgtaga ataaaagtat     420
gaacaaattc tacgttcatc atgtggggtg tgccttcata tatatctttg gatgagaatg     480
ccaagaaaaa tgatggcgtg acaattcaat acggcaaaac aaactaatcc cctctaagat     540
tttactagtg tgtttcccta tcgtctgagg aaaaggtaac aaaacatcgt ttaaccaatt     600
ggtgtttgtt acgatggtga cgttgagtac tgcatatagt tgcaacggca aattgcatcc     660
agcgagttaa cagcgaatgg caaagtgaag cctccgactt gtgttcattg actactggga     720
ttggactggg aataacgact taactaatta atgttctcgt ggactcgttt agctagaact     780
aacatttgtt ataatatagc taatgctaat tcttgattag tgtggaaagc ctaataaggt     840
tatattgcgc acaggttaac tcccttaata tagttattgt taanncagtt attgttgttg     900
actactattg ttattgttaa attaaagtgt tagggttagt taattgatta gtgaaaacca     960
actaactacc gtattaaatt attgtattaa gattgattcc tattaaggat aaaacagaga    1020
gtgtgttaga aagagaaagg gtggattata aatatgtgta aaatcccctt tagagactaa    1080
ccactagaaa tctattgatg gtttcatata tagagattaa cgattatatt tataatataa    1140
gttggtagtt gctagtatat ttgaaagcac tacagtatag tatgtcagaa tcagattatt    1200
taaactctac taataataca ggaaacactt tcattagtct agatcaagcc agtacaataa    1260
tggcagatca aactcaagga gctaacccac aacagcattg attatataat catctatgta    1320
gccaatatac actaccgtcc aaactcccac tacacacttg taacagtgtt ttacaaatct    1380
atgaacgaat aaccgattca aatgacacaa taaagaacat ttcaccgatt tgaattgcta    1440
atcggtacta taatattgat ggaaggttaa gagtttaatg ctaccctagg tttaccggag    1500
atcaacagtt gcatatacaa aacgtgttat ctgtctacga atggctttct atgtgtataa    1560
aatgtttcat caattgataa ttaattatta atctgcttac tgaggtaaac ccctttaat    1620
gcaatagcaa atatgaggta tttttttgct attgacatgc gtatatgaat ccatttgtat    1680
caaattgccg atataatgaa atggaaatta agggaaaaaa aaagtttat atccaaattc    1740
atgcgattaa caggttcttg tgattataat tggtaacccc ctccccccta aaactcatat    1800
ctgccaaaag aggaggatat ttgaatatgc tattatgaac cccattgatt ttgactacaa    1860
ttggatttgt cgggtattga aacccaaaca tattataatt tgctatgcgt ttaaatcaac    1920
cgtttactgg tagatcctat actataaata cagccaacaa tccccaattg ttcagataaa    1980
gtaacactca atatcatttg atcaatcaat caagaggatt acaaa                   2025
```

<210> SEQ ID NO 33
<211> LENGTH: 3583
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(3583)
<223> OTHER INFORMATION: 'n' can be any nucleotide 'a', 'c', 'g' or 't'

<400> SEQUENCE: 33

```
aaaannttcc ccatngccta ttcctaggnc ccaaaaccag ttgtccgaaa ctccatggat      60
gccagaagtg gtggtcctcc gccgttatgg ttggaaaaga aaagaaaact tgacgaattg     120
aaagtcaaag aagagcggca agaaagaagg aagaagggc aaagaaaaag gaagaagagg      180
caaagaaaaa ggcagaggaa gcgaagaagt gttttatttt acttttctgt caaatttgca     240
ctacttttaa tttgtgtgca aatattctat tttacttgat ttttatatac ttttatttta    300
caatactttt ttataggact ttttatatct tttctttatc aactgttcgc tatagggtag    360
gtcttccaag ctaattttac ccgacacaag atgaaatatt ttctgttgag cactcgttgt    420
cgacagtgaa aaattttcac tcaagaaaat attttatcat cacttttcct agaagggagg    480
ttcaagtgtt ggagaataga cagcgaacac ctgatattcc caaggtcgaa ttagattgaa    540
agataaataa tagtcatatt tattttgtat ttagtcaata aattatcttt ttatatttaa    600
attcttagta ttgtcatacc acgtagatta atacggacat acttagcaca tttaacatat    660
attaagcacc gattacctgt gacattccgg agtttactgt ttcgcgcacg ctggcagacg    720
aacatcaact catcttttat acaatatatt cttacgatta taactttcaa ttaagaaata    780
caacttctta ttagcattct cctacaagtt cttaagttcc taggaatttc ttcgaaacta    840
taattaaaga cggaaaagtg taaaacaaac agaaagcaga ggaggccaag aagaaagcag    900
aggaggccgc cccacaaaag tttgacaact ttgacgactt tattggcttt gacatcaacg    960
acaataccaa cgacgaagac atgttgtcca acatggacta cgaggaccta aaattggacg   1020
acaaagtacc tgccaccaca gacaacaact tggacatgaa caacatactt gaaaacgacg   1080
agctgatact agacgggttg aacatgacat tgctcgacaa tggcgaccac gtaaacgaag   1140
agtttgatgt agacagcttt ttaaaccagt ttggtaatta ggggctctgt tctacaagac   1200
atatacagat agtgcaggaa taagaaaaga aatattttat atagctatat atttcaagtg   1260
tttattctgt tcaacaagtt ctaaccgtag atacaccaaa tcaccaagtc agacattact   1320
gagctagctt aacggtccaa ctactttaaa ttgcaatccg ttctttactt gagtcagtcg   1380
actctacaac aactatcctg aggtgattat tttttggtgg aaattttgac caaattctta   1440
agcaaaaatc tagtttctac tgataaataa atacacattg ctctacttct gtactccaca   1500
ctctgctatt gcttgatagc catccttaaa tcaacagaat ccactaattc tgctacttcc   1560
agaaccatga ctactctaca ttttaacca tctcaattaa ttaccatctt tttctctcat     1620
tatttggcac tatggccgag ttggtctaag gcggtagact caagaattat tcttctcctg   1680
cgatccaggg gtttctacta tcgtaagatg caggagttcg aatctccttg gtgtcattat   1740
ttttttttttt ccaagaacct ctcattttt ttttcaaaa attatttcta caatttcctc    1800
tattcttaaa aatctttggt attaaactaa aaatgtacct aactaaacta ctaggctgga   1860
aaataataaa tctaacgtta acgaaataag caaaagtaat ttttttttt caagacaatt    1920
ccatgtttgg ggatgaaaac tgcctgcaat tatatatcct gtaacaatcc ccttatatca   1980
acaacaaccc gagaacaaca aaaagtccac tggcagaaac cttaccacca atattctcaa   2040
tttgtgtcac tgattgggca gtttgtgtcg atatccatga tgtggtcaaa ctggcagcag   2100
tggtagatgg ataaacactt tcagcagcaa cagtaaccga gttgacaact tcccttagcag  2160
cttgtgtatc acactcttca tcatcatccc agctatcatc ctcatcgtca cactctggtt   2220
```

-continued

```
caggagtttg atcatcttca tcatcgtagc catcttcacc agggcaaaca taatcgttac    2280
cagatccacc ccaccagctt ccagacgatc caccagtaac tgaagaagaa ccggaatcac    2340
ctgaactaac accagaactg atccagaaag tagtaccacc acttgatcca gcaccagaac    2400
cccaccaaga gcctgtgcca gatccagaac ttgatccacc tgttggcaca cattcgccat    2460
catcttcttc ataccattcc cattcaccat catcagagga gccactggca gaaccaccgg    2520
cattgtcttc cccttcatag ccatcatctt cccagtcatc tggatagaca gtgtgtgtgg    2580
taataacagt cacagtcgtg gtatatagct gtccacctgg agcaacagtt gtcagtggac    2640
atgtggttgt gattgtcaac gtaacagttt catcacagat ttcaccagat tgtgtgagat    2700
aagtggtaaa tgtctgacca ccaccagtat atgtgataga acaacttcc gtttcagtat     2760 gttgattagt ggttggaggt aattttgtgg tgagtgtttg agttgttggc accccatcgg    2820
aagtaaatgt tctagtggtt gacacagttg gatggatagt aggaatttca gtttcacaat    2880
cagtctcgtc atcgtcgtca tcagaagtgg ttgactttgt tggagaaca gtaatagatc     2940 ctgacccagt tggaataata gttggaagaa cagacgttgt tggaagaact gacccacttg    3000
gaatgatggt tggaacgtct gtctcacaat cagtctcaat tatcttctgt agtggctttt    3060
tgaaacaact gacgagacac ttgtcttact ttgactggtg attggaaggg ttggaattgt    3120
aggaccaaaa tttggggctt ccattggatc tttacactct ccaccactgc acaactttaa    3180
tttggaacca caactggaac tagtttctgt ttcaaggctt taccagttga cctgatcgta    3240
ataagccacg gggttaccaa cttgttgcat cttcactgat cagccatcaa tctttgataa    3300
gccctgattt ctctcatcta tgcaacaatc ttctattgtg aatcatttgt tttgctaaac    3360
ttgtagttgg tgtccaaaaa aaaagtgat gtaaaattta aattttttctg aacttgtcgt    3420 gtaaaaaagt ctccagaaaa agggacaaca cacacaccaa ttttttcacca taccacacaa    3480 ttcaccaata agctctctca tatccatcna ataattacag tacagcctcc tattcncaat    3540
ttttggnatt taaaccagtt cccttggcag gtcaccagtt cat                      3583
```

<210> SEQ ID NO 34
<211> LENGTH: 770
<212> TYPE: DNA
<213> ORGANISM: Unknown
<220> FEATURE:
<223> OTHER INFORMATION: sequence of retrotransposon from unknown
      organism

<400> SEQUENCE: 34

```
tgatttgaga aataccattg aagatctaga gttaaaaata aggaatttgc atgtacatga     60
ggataatcaa gcggtcatta caatcttaaa gaatgataat ttccacccac atagaccgat   120
tgatatatgt tacaaatttc tcagacaaaa attgaaagat ggattttttt caatatcata   180
tgttgaatct ggagataatt tagctgactc attcacgaaa gctttaggaa gaaataaatt   240
gattgaacat accaaaagga ttagagaaag aaaggattat gataataatg ctacactgat   300
agtggacgtt aggacgctcg aagagattaa gataaacaag aaattggtac atcattaatt   360
aatttagctg tttacctgaa tcaggggagt gttcgctata gggtaggtct tccaagctaa   420
ttttacccga cacaagatga aatatttct gttgagcact cgttgtcgac agtgaaaaat    480
tttcactcaa gaaaatattt tatcatcact ttttctagaa tggaggttca agtgttggag   540
aatagacagc gaacacctga tattcccaag gtcgaattag attgaaagat aaataatagt   600
catatttatt ttgtatttag tcaataaatt atctttttat atttaaattc ttagtattgt   660
```

-continued

```
cataccacgt agattgatac ggacatactt agcacattta acatatatta agcaccgatt    720
acctgtgaca ttccggagtt tactgtttcg cgcacgctgg cagacgaaca              770
```

<210> SEQ ID NO 35
<211> LENGTH: 106
<212> TYPE: PRT
<213> ORGANISM: Unknown
<220> FEATURE:
<223> OTHER INFORMATION: sequence of retrotransposon from unknown
      organism

<400> SEQUENCE: 35

```
Asp Leu Arg Asn Thr Ile Glu Asp Leu Glu Leu Lys Ile Arg Asn Leu
1               5                   10                  15

His Val His Glu Asp Asn Gln Ala Val Ile Thr Ile Leu Lys Asn Asp
            20                  25                  30

Asn Phe His Pro His Arg Pro Ile Asp Ile Cys Tyr Lys Phe Leu Arg
        35                  40                  45

Gln Lys Leu Lys Asp Gly Phe Phe Ser Ile Ser Tyr Val Glu Ser Gly
    50                  55                  60

Asp Asn Leu Ala Asp Ser Phe Thr Lys Ala Leu Gly Arg Asn Lys Leu
65                  70                  75                  80

Ile Glu His Thr Lys Arg Ile Arg Glu Arg Lys Asp Tyr Asp Asn Asn
                85                  90                  95

Ala Thr Ser Ile Val Asp Val Arg Thr Leu
            100                 105
```

<210> SEQ ID NO 36
<211> LENGTH: 598
<212> TYPE: DNA
<213> ORGANISM: Unknown
<220> FEATURE:
<223> OTHER INFORMATION: sequence of retrotransposon from unknown
      organism

<400> SEQUENCE: 36

```
cttcaatgct tcacttgtac tagtacccat gattgtatag tggtgtggtt gatcgacttc    60
aatataacaa gagagagatg agatgagatg cttttatcgc gtatatattt ttttttccat   120
tgacaattct gatttcacaa attgttcgct atagggtagg tcttccaagc taattttacc   180
cgacacaaga tgaaatattt tctgttgagc actcgttgtc gacagtgaaa aattttcact   240
caagaaaata ttttatcatc acttttttcta gaatggaggt tcaagtgttg agaatagac    300 agcgaacacc tgatattccc aaggtcgaat tagattgaaa gataaataat agtcatattt   360
attttgtatt tagtcaataa attatctttt tatatttaaa ttcttagtat tgtcatacca   420
cgtagattga tacggacata cttagcacat ttaacatata ttaagcaccg attacctgtg   480
acattccgga gtttactgtt tcgcgcacgc tggcagacga acagattaga agcttggtaa   540
atctttggtt attcatcacg tcttgagaat aatacaaagt ttaatatagt attttcaa     598
```

<210> SEQ ID NO 37
<211> LENGTH: 1082
<212> TYPE: DNA
<213> ORGANISM: Unknown
<220> FEATURE:
<223> OTHER INFORMATION: sequence of retrotransposon from unknown
      organism

<400> SEQUENCE: 37

```
ataaccacaa taatcggcct cgtaaacgtc gtcagtggct caaacacatt gctgcacctt    60
```

-continued

```
gagctctaga acaaccccac actcactagc catcgccaca ccaacaacca aattgctgat      120
ccagaaaaaa taccaccccc gtagtccggc ttgtatggaa taattgcttg gccaggtacg      180
tccccacctc atcgtgtctt ttctggttga aatatgtcat ctcccgggct aacagtaccg      240
tatctctgtg gctggggcat ctatactctt tcattctcgg cttacaaatc tatcttgttc      300
acacatttca tatatctggg acttgtcgaa ctctctgcac tctatcataa actggaactc      360
gcttgcattc tgggacacac actggagctg gaatccatgg tcaggaaatg tgaaaatttt      420
cttctcggga aatatttgtg acaattagtc ctagtacacg atagtttcat tacgcccact      480
aaaagtgtct actgaaactc ggtctctata tcgtcaatat ctttcatttc tcttcctggc      540
ttttcactgc gacttattgt tcgctatagg gtaggtcttc caagctaatt ttacccgaca      600
caagatgaaa tattttctgt tgagcactcg ttgtcgacag tgaaaaattt tcactcaaga      660
aaatattttc atcatcactt tttctagaaa ggaggttcaa gtgttggaga atagacagcg      720
aacacctgat attcccaagg tcgaattaga ttgaaagata aataatagtc atatttattt      780
tgtatttagt caataaatta tcttttttata tttaaattct tagtattgtc ataccacgta      840
gattgatacg gacatactta gcacatttaa catatattaa gcaccgatta cctgtgacat      900
tccgaagttt actgtttcgc gcacgctggc agacgaacac ttatcaaggt gctactcccg      960
cgcatcagtt tcctctgggt tctcttttttg atcttggtga actacctttt tttcccactc     1020
gcgtgagaag ttcaacactt ttttttaccc atccaccaaa ctttattctt ttccccacca     1080
tg                                                                    1082
```

<210> SEQ ID NO 38
<211> LENGTH: 39
<212> TYPE: RNA
<213> ORGANISM: Candida albicans
<220> FEATURE:
<221> NAME/KEY: primer_bind
<222> LOCATION: (11)..(21)
<223> OTHER INFORMATION: minus strand primer binding site

<400> SEQUENCE: 38

```
gcucgcgugg cguaauggca acgcgucuga cuucuaauc                             39
```

<210> SEQ ID NO 39
<211> LENGTH: 71
<212> TYPE: RNA
<213> ORGANISM: Candida albicans

<400> SEQUENCE: 39

```
uauuccauca gauuagaagu cgauagugau aaucauuucg ucccaaauua gcguuguaua      60
aauucagucc u                                                          71
```

<210> SEQ ID NO 40
<211> LENGTH: 11
<212> TYPE: DNA
<213> ORGANISM: Candida albicans

<400> SEQUENCE: 40

```
gaatcaggga g                                                          11
```

<210> SEQ ID NO 41
<211> LENGTH: 11
<212> TYPE: DNA
<213> ORGANISM: Candida albicans -continued

```
<400> SEQUENCE: 41
aatcagggga g                                                      11

<210> SEQ ID NO 42
<211> LENGTH: 11
<212> TYPE: DNA
<213> ORGANISM: Candida albicans

<400> SEQUENCE: 42
atccagggga g                                                      11

<210> SEQ ID NO 43
<211> LENGTH: 14
<212> TYPE: PRT
<213> ORGANISM: Unknown
<220> FEATURE:
<223> OTHER INFORMATION: protease sequence of 1731 retrotransposon

<400> SEQUENCE: 43

Thr Gln Trp Cys Leu Asp Ser Gly Ala Thr Ser His Met Cys
1               5                   10

<210> SEQ ID NO 44
<211> LENGTH: 14
<212> TYPE: PRT
<213> ORGANISM: Unknown
<220> FEATURE:
<223> OTHER INFORMATION: protease sequence of copia retrotransposon

<400> SEQUENCE: 44

Cys Gly Phe Val Leu Asp Ser Gly Ala Ser Asp His Leu Ile
1               5                   10

<210> SEQ ID NO 45
<211> LENGTH: 14
<212> TYPE: PRT
<213> ORGANISM: Unknown
<220> FEATURE:
<223> OTHER INFORMATION: protease sequence of Tn1 retrotransposon

<400> SEQUENCE: 45

Ser Glu Trp Val Val Asp Thr Ala Ala Ser His His Ala Thr
1               5                   10

<210> SEQ ID NO 46
<211> LENGTH: 14
<212> TYPE: PRT
<213> ORGANISM: Unknown
<220> FEATURE:
<223> OTHER INFORMATION: protease sequence of Ty1 retrotransposon

<400> SEQUENCE: 46

Gly His Leu Leu Leu Asp Ser Gly Ala Ser Arg Thr Leu Ile
1               5                   10

<210> SEQ ID NO 47
<211> LENGTH: 14
<212> TYPE: PRT
<213> ORGANISM: Unknown
<220> FEATURE:
<223> OTHER INFORMATION: protease sequence of Ty4 retrotransposon

<400> SEQUENCE: 47

Lys Leu Val Ile Ile Asp Thr Gly Ser Gly Val Asn Ile Thr
1               5                   10
```

```
<210> SEQ ID NO 48
<211> LENGTH: 14
<212> TYPE: PRT
<213> ORGANISM: Candida albicans
<220> FEATURE:
<221> NAME/KEY: UNSURE
<222> LOCATION: (1)..(14)
<223> OTHER INFORMATION: protease sequence of pCal retrotransposon

<400> SEQUENCE: 48

Lys Tyr Leu Val Tyr Asp Thr Gly Ala Thr Ile Ser Val Val
 1               5                  10

<210> SEQ ID NO 49
<211> LENGTH: 63
<212> TYPE: PRT
<213> ORGANISM: Unknown
<220> FEATURE:
<223> OTHER INFORMATION: integrase of retrotransposon 1731

<400> SEQUENCE: 49

His Lys Arg Asn Gly His Cys Lys Thr Cys Lys Ile Lys Cys Ile Arg
 1               5                  10                  15

Ser Asp Asn Gly Gly Glu Phe Val Asn Asn Val Phe Asp Asp Tyr Leu
            20                  25                  30

Lys Ala His Gly Ile Ala Arg Gln Leu Thr Ile Pro His Thr Pro Gln
        35                  40                  45

Gln Asn Gly Val Ala Glu Arg Ala Asn Arg Thr Leu Val Glu Met
    50                  55                  60

<210> SEQ ID NO 50
<211> LENGTH: 63
<212> TYPE: PRT
<213> ORGANISM: Unknown
<220> FEATURE:
<223> OTHER INFORMATION: Integrase sequence of copia retrotransposon

<400> SEQUENCE: 50

His Glu Arg Phe Gly His Cys Glu Pro Cys Lys Val Val Tyr Leu Tyr
 1               5                  10                  15

Ile Asp Asn Gly Arg Glu Tyr Leu Ser Asn Glu Met Arg Gln Phe Cys
            20                  25                  30

Val Lys Lys Gly Ile Ser Tyr His Leu Thr Val Pro His Thr Pro Gln
        35                  40                  45

Leu Asn Gly Val Ser Glu Arg Met Ile Arg Thr Ile Thr Glu Lys
    50                  55                  60

<210> SEQ ID NO 51
<211> LENGTH: 63
<212> TYPE: PRT
<213> ORGANISM: Unknown
<220> FEATURE:
<223> OTHER INFORMATION: Integrase sequence of Tnt1 retrotransposon

<400> SEQUENCE: 51

His Lys Arg Met Gly His Cys Asp Tyr Cys Lys Leu Lys Arg Leu Arg
 1               5                  10                  15

Ser Asp Asn Gly Gly Glu Tyr Thr Ser Arg Glu Phe Glu Tyr Cys
            20                  25                  30

Ser Ser His Gly Ile Arg His Glu Lys Thr Val Pro Gly Thr Pro Gln
        35                  40                  45

His Asn Gly Val Ala Glu Arg Met Asn Arg Thr Ile Val Glu Lys
```

```
                    50                  55                  60

<210> SEQ ID NO 52
<211> LENGTH: 62
<212> TYPE: PRT
<213> ORGANISM: Unknown
<220> FEATURE:
<223> OTHER INFORMATION: Integrase sequence of Ty1 retrotransposon

<400> SEQUENCE: 52

His Arg Met Leu Ala His Cys Pro Asp Cys Ser Val Leu Val Ile Gln
1               5                   10                  15

Met Asp Arg Gly Ser Glu Tyr Thr Asn Arg Thr Leu His Lys Phe Leu
            20                  25                  30

Glu Lys Asn Gly Ile Thr Pro Cys Tyr Thr Thr Ala Asp Ser Arg
        35                  40                  45

Ala His Gly Val Ala Glu Arg Leu Asn Arg Thr Leu Leu Asp
    50                  55                  60

<210> SEQ ID NO 53
<211> LENGTH: 59
<212> TYPE: PRT
<213> ORGANISM: Unknown
<220> FEATURE:
<223> OTHER INFORMATION: Integrase sequence of Ty4 retrotransposon

<400> SEQUENCE: 53

His Lys Arg Met Gly His Lys Val Arg Glu Ile Asn Ser Asp Arg Gly
1               5                   10                  15

Thr Glu Phe Thr Asn Asp Gln Ile Glu Glu Tyr Phe Ile Ser Lys Gly
            20                  25                  30

Ile His His Ile Leu Thr Ser Thr Gln Asp His Ala Ala Asn Gly Arg
        35                  40                  45

Ala Glu Arg Tyr Ile Arg Thr Ile Ile Thr Asp
    50                  55

<210> SEQ ID NO 54
<211> LENGTH: 60
<212> TYPE: PRT
<213> ORGANISM: Candida albicans

<400> SEQUENCE: 54

His Leu Met Ser Asn His Cys Lys Val Cys Lys Val Ala Tyr Phe Arg
1               5                   10                  15

Ser Asp Asn Ala Pro Glu Phe Pro Gln Pro Ser Asp Leu Ala Glu Phe
            20                  25                  30

Gly Ile Trp Arg Glu Thr Ile Ala Ala Tyr Ser Pro Glu Leu Asn Gly
        35                  40                  45

Leu Ala Glu Val Val Asn Lys Leu Ile Leu Gln Gln
    50                  55                  60

<210> SEQ ID NO 55
<211> LENGTH: 63
<212> TYPE: PRT
<213> ORGANISM: Unknown
<220> FEATURE:
<223> OTHER INFORMATION: Reverse Transcriptase sequence of 1731
      retrotransposon

<400> SEQUENCE: 55

His His Met Asp Val Cys Thr Ala Tyr Leu Asn Ser Glu Leu Lys Asp
1               5                   10                  15
```

```
Thr Val Tyr Met Lys Gln Pro Gln Gly Phe Thr Asp Ala Ala Asn Pro
             20                  25                  30

Asp Gln Val Leu Leu Leu Arg Lys Ala Ile Tyr Gly Leu Lys Gln Ser
         35                  40                  45

Gly Arg Glu Trp Asn Ile Leu Val Tyr Val Asp Leu Ile Leu
     50                  55                  60

<210> SEQ ID NO 56
<211> LENGTH: 61
<212> TYPE: PRT
<213> ORGANISM: Unknown
<220> FEATURE:
<223> OTHER INFORMATION: Reverse Transcriptase sequence of copia
      retrotransposon

<400> SEQUENCE: 56

His Gln Met Asp Val Lys Thr Ala Phe Leu Asn Gly Thr Leu Lys Glu
1               5                   10                  15

Glu Ile Tyr Met Arg Leu Pro Gln Gly Ile Ser Cys Asn Ser Asp Asn
             20                  25                  30

Val Cys Lys Leu Asn Lys Ala Ile Tyr Gly Leu Lys Gln Ala Ala Arg
         35                  40                  45

Cys Trp Phe Val Leu Leu Tyr Val Asp Asp Val Val Ile
     50                  55                  60

<210> SEQ ID NO 57
<211> LENGTH: 63
<212> TYPE: PRT
<213> ORGANISM: Unknown
<220> FEATURE:
<223> OTHER INFORMATION: Reverse Transcriptase sequence of Tnt1
      retrotransposon

<400> SEQUENCE: 57

Glu Gln Leu Asp Val Lys Thr Ala Phe Leu His Gly Asp Leu Glu Glu
1               5                   10                  15

Glu Ile Tyr Met Glu Gln Pro Glu Gly Phe Glu Val Ala Gly Lys Lys
             20                  25                  30

His Met Val Cys Lys Leu Asn Lys Ser Leu Tyr Gly Leu Lys Gln Ala
         35                  40                  45

Pro Arg Gln Trp Tyr Leu Leu Leu Tyr Val Asp Asp Met Leu Ile
     50                  55                  60

<210> SEQ ID NO 58
<211> LENGTH: 60
<212> TYPE: PRT
<213> ORGANISM: Unknown
<220> FEATURE:
<223> OTHER INFORMATION: Reverse Transcriptase sequence of Ty1
      retrotransposon

<400> SEQUENCE: 58

Thr Gln Leu Asp Ile Ser Ser Ala Tyr Leu Tyr Ala Asp Ile Lys Glu
1               5                   10                  15

Glu Leu Tyr Ile Arg Pro Pro His Leu Gly Met Asn Asp Lys Leu
             20                  25                  30

Ile Arg Leu Lys Lys Ser Leu Tyr Gly Leu Lys Gln Ser Gly Ala Asn
         35                  40                  45

Trp Tyr Ile Cys Leu Phe Val Asp Asp Met Val Leu
     50                  55                  60
```

-continued

```
<210> SEQ ID NO 59
<211> LENGTH: 47
<212> TYPE: PRT
<213> ORGANISM: Unknown
<220> FEATURE:
<223> OTHER INFORMATION: Reverse Transcriptase sequence of Ty4
      retrotransposon

<400> SEQUENCE: 59

Lys Thr Leu Asp Ile Asn His Ala Phe Leu Tyr Ala Lys Leu Glu Glu
1               5                   10                  15

Glu Ile Tyr Ile Pro His Pro His Asp Arg Arg Cys Val Val Lys Leu
            20                  25                  30

Asn Lys Ala Leu Tyr Gly Leu Lys Gln Ser Pro Lys Glu Trp Asn
        35                  40                  45

<210> SEQ ID NO 60
<211> LENGTH: 63
<212> TYPE: PRT
<213> ORGANISM: Candida albicans

<400> SEQUENCE: 60

Gln His Leu Asp Val Glu Ser Ala Tyr Leu Asn Ala Ser Ile Thr His
1               5                   10                  15

Ser Asn Pro Ile Tyr Val Phe Pro Pro Lys Ser Val Pro Leu Lys Lys
            20                  25                  30

Asn His Cys Trp Leu Leu Lys Arg Ser Val Tyr Gly Leu Lys Gln Ser
        35                  40                  45

Gly Leu Glu Trp Tyr Leu Gly Leu Tyr Val Asp Asp Ile Leu Met
    50                  55                  60

<210> SEQ ID NO 61
<211> LENGTH: 24
<212> TYPE: PRT
<213> ORGANISM: Unknown
<220> FEATURE:
<223> OTHER INFORMATION: RNAse H sequence of 1731 retrotransposon

<400> SEQUENCE: 61

Ala Phe Thr Gly Phe Val Asp Ala Asp Trp Gly Gly Asp Arg Leu Asp
1               5                   10                  15

Arg Lys Ser Tyr Thr Gly Tyr Val
            20

<210> SEQ ID NO 62
<211> LENGTH: 24
<212> TYPE: PRT
<213> ORGANISM: Unknown
<220> FEATURE:
<223> OTHER INFORMATION: RNAse H sequence of copia retrotransposon

<400> SEQUENCE: 62

Lys Ile Ile Gly Tyr Val Asp Ser Asp Trp Ala Gly Ser Glu Ile Asp
1               5                   10                  15

Arg Lys Ser Thr Thr Gly Tyr Leu
            20

<210> SEQ ID NO 63
<211> LENGTH: 24
<212> TYPE: PRT
<213> ORGANISM: Unknown
<220> FEATURE:
<223> OTHER INFORMATION: RNAse H sequence of Tnt1 retrotransposon
```

-continued

```
<400> SEQUENCE: 63

Ile Leu Lys Gly Tyr Thr Asp Ala Asp Met Ala Gly Asp Ile Asp Asn
1               5                   10                  15
Arg Lys Ser Ser Thr Gly Tyr Leu
            20

<210> SEQ ID NO 64
<211> LENGTH: 23
<212> TYPE: PRT
<213> ORGANISM: Unknown
<220> FEATURE:
<223> OTHER INFORMATION: RNAse H sequence of Ty1 retrotransposon

<400> SEQUENCE: 64

Lys Leu Val Ala Ile Ser Asp Ala Ser Tyr Gly Asn Gln Pro Tyr Tyr
1               5                   10                  15
Lys Ser Gln Ile Gly Asn Ile
            20

<210> SEQ ID NO 65
<211> LENGTH: 23
<212> TYPE: PRT
<213> ORGANISM: Unknown
<220> FEATURE:
<223> OTHER INFORMATION: RNAse H sequence of Ty4 retrotransposon

<400> SEQUENCE: 65

Lys Val Ile Ala Ile Thr Asp Ala Ser Val Gly Ser Glu Tyr Asp Ala
1               5                   10                  15
Gln Ser Arg Ile Gly Val Ile
            20

<210> SEQ ID NO 66
<211> LENGTH: 23
<212> TYPE: PRT
<213> ORGANISM: Candida albicans

<400> SEQUENCE: 66

Val Ile Glu Cys Phe Ser Asp Ala Ser Phe Ala Pro Gly Leu Asp Arg
1               5                   10                  15
Lys Ser Ile Ser Gly Thr Leu
            20

<210> SEQ ID NO 67
<211> LENGTH: 67
<212> TYPE: RNA
<213> ORGANISM: Candida albicans

<400> SEQUENCE: 67
uagggagguc aggucagga gcccccccc ugaacccagg auaacccuca aagucggggg      60
gcaaccc                                                             67

<210> SEQ ID NO 68
<211> LENGTH: 90
<212> TYPE: RNA
<213> ORGANISM: Candida albicans

<400> SEQUENCE: 68 ugaaaacag gugcugcuuc uauuaauugu guaaugaaua uacauaauug cagcaaaacc    60 acguuccag uagaaauucu cauucucuua                                    90
```

```
<210> SEQ ID NO 69
<211> LENGTH: 392
<212> TYPE: DNA
<213> ORGANISM: Candida albicans
<220> FEATURE:
<221> NAME/KEY: misc_feature
<222> LOCATION: (1)..(392)
<223> OTHER INFORMATION: sequence of clone SGY-1
<221> NAME/KEY: variation
<222> LOCATION: (30)..(30)
<223> OTHER INFORMATION: 'a' replaced by 'g' in SC5-2
<221> NAME/KEY: variation
<222> LOCATION: (172)..(172)
<223> OTHER INFORMATION: nucleotide 'a' is replaced by 'g' in SC5-1,
      SC5-2, SA4-1, SA4-2, 759-1, 759-2 and p36 or by 't' in ATC-1
      and ATC-2
<221> NAME/KEY: variation
<222> LOCATION: (173)..(173)
<223> OTHER INFORMATION: nucleotide 'g' is replaced by 'a' in ATC-1,
      ATC-2, SA4-1 and SA4-
<221> NAME/KEY: variation
<222> LOCATION: (235)..(235)
<223> OTHER INFORMATION: nucleotide 'a' is replaced by 'g' in SC5-1,
      SC5-2, SA4-1 and SA4-
<221> NAME/KEY: variation
<222> LOCATION: (292)..(292)
<223> OTHER INFORMATION: nucleotide 'g' is replaced by 'a' in SC5-1,
      SC5-2, 759-1, 759-2 and p3
<221> NAME/KEY: variation
<222> LOCATION: (294)..(294)
<223> OTHER INFORMATION: nucleotide 't' is replaced by 'a' in SC5-1,
      SC5-2, 759-1, 759-2 and p3
<221> NAME/KEY: variation
<222> LOCATION: (297)..(297)
<223> OTHER INFORMATION: nucleotide 't' is replaced by 'c' in SC5-1,
      SC5-2, 759-1 and 759-
<221> NAME/KEY: variation
<222> LOCATION: (303)..(303)
<223> OTHER INFORMATION: nucleotide 't' is replaced by 'c' in 759-2
<221> NAME/KEY: variation
<222> LOCATION: (311)..(311)
<223> OTHER INFORMATION: nucleotide 't' is replaced by 'c' in 759-2
<221> NAME/KEY: variation
<222> LOCATION: (350)..(350)
<223> OTHER INFORMATION: nucleotide 't' is replaced by 'c' in SA4-2
<221> NAME/KEY: variation
<222> LOCATION: (371)..(371)
<223> OTHER INFORMATION: nucleotide 'g' is replaced by 'a' in 759-1,
      759-2 and p36

<400> SEQUENCE: 69
tgttggtttg tgcactattt tgtgtcagaa actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgagatagaa gagaggagtt     180
tcaatatata tcttgtgaat aataacttcg ttctaattca ctatacacaa ctagacgtgt     240
acacgctcaa tctcaggtaa agaaagttta tattccatca gattagaagt cgatagtgat     300
aatcatttcg tcccaaatta gcgttgtata aattcagtcc tcagatttgt attattgatt     360
gatagtttcg gagtttgaag gtacagaatt tc                                   392

<210> SEQ ID NO 70
<211> LENGTH: 392
<212> TYPE: DNA
<213> ORGANISM: Candida albicans
<220> FEATURE:
<221> NAME/KEY: misc_feature
<222> LOCATION: (1)..(392)
<223> OTHER INFORMATION: sequence of clone SGY-2

<400> SEQUENCE: 70
```

```
tgttggtttg tgcactattt tgtgtcagaa actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgagatagaa gagaggagtt     180
tcaatatata tcttgtgaat aataacttcg ttctaattca ctatacacaa ctagacgtgt     240
acacgctcaa tctcaggtaa agaaagttta tattccatca gattagaagt cgatagtgat     300
aatcatttcg tcccaaatta gcgttgtata aattcagtcc tcagatttgt attattgatt     360
gatagtttcg gagtttgaag gtacagaatt tc                                   392
```

<210> SEQ ID NO 71
<211> LENGTH: 392
<212> TYPE: DNA
<213> ORGANISM: Candida albicans
<220> FEATURE:
<221> NAME/KEY: misc_feature
<222> LOCATION: (1)..(392)
<223> OTHER INFORMATION: sequence of clone SC5-1

<400> SEQUENCE: 71

```
tgttggtttg tgcactattt tgtgtcagag actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgagatagaa gggaggagtt     180
tcaatatata tcttgtgaat aataacttcg ttctaattca ctatacacaa ctaggcgtgt     240
acacgctcaa tctcaggtaa agaaagttta tattccatca gattagaagt caaaagcgat     300
aatcatttcg tcccaaatta gcgttgtata aattcagtcc tcagatttgt attattgatt     360
gatagtttcg gagtttgaag gtacagaatt tc                                   392
```

<210> SEQ ID NO 72
<211> LENGTH: 392
<212> TYPE: DNA
<213> ORGANISM: Candida albicans

<400> SEQUENCE: 72

```
tgttggtttg tgcactattt tgtgtcagag actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgagatagaa gggaggagtt     180
tcaatatata tcttgtgaat aataacttcg ttctaattca ctatacacaa ctaggcgtgt     240
acacgctcaa tctcaggtaa agaaagttta tattccatca gattagaagt caaaagcgat     300
aatcatttcg tcccaaatta gcgttgtata aattcagtcc tcagatttgt attattgatt     360
gatagtttcg gagtttgaag gtacagaatt tc                                   392
```

<210> SEQ ID NO 73
<211> LENGTH: 392
<212> TYPE: DNA
<213> ORGANISM: Candida albicans

<400> SEQUENCE: 73

```
tgttggtttg tgcactattt tgtgtcagaa actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgtaatagaa gagaggagtt     180
tcaatatata tcttgtgaat aataacttcg ttctaattca ctatacacaa ctagacgtgt     240
acacgctcaa tctcaggtaa agaaagttta tattccatca gattagaagt cgatagtgat     300
```

```
aatcatttcg tcccaaatta gcgttgtata aattcagtcc tcagatttgt attattgatt    360
gatagtttcg gagtttgaag gtacagaatt tc                                  392

<210> SEQ ID NO 74
<211> LENGTH: 392
<212> TYPE: DNA
<213> ORGANISM: Candida albicans

<400> SEQUENCE: 74
tgttggtttg tgcactattt tgtgtcagaa actgatcaat gaaaatgatg gttattatga     60
gaatggaaaa ttttccatc acacatcagg tgatgacaga actaaactat attgtgtagt    120
ataaataagg gtatgaaata ccaacatccc agaatatcaa cgtaatagaa gagaggagtt   180
tcaatatata tcttgtgaat aataacttcg ttctaattca ctatacacaa ctagacgtgt   240
acacgctcaa tctcaggtaa agaaagttta tattccatca gattagaagt cgatagtgat   300
aatcatttcg tcccaaatta gcgttgtata aattcagtcc tcagatttgt attattgatt   360
gatagtttcg gagtttgaag gtacagaatt tc                                  392

<210> SEQ ID NO 75
<211> LENGTH: 392
<212> TYPE: DNA
<213> ORGANISM: Candida albicans

<400> SEQUENCE: 75
tgttggtttg tgcactattt tgtgtcagaa actgatcaat gaaaatgatg gttattatga     60
gaatggaaaa ttttccatc acacatcagg tgatgacaga actaaactat attgtgtagt    120
ataaataagg gtatgaaata ccaacatccc agaatatcaa cggaatagaa gagaggagtt   180
tcaatatata tcttgtgaat aataacttcg ttctaattca ctatacacaa ctaggcgtgt   240
acacgctcaa tctcaggtaa agaaagttta tattccatca gattagaagt cgatagtgat   300
aatcatttcg tcccaaatta gcgttgtata aattcagtcc tcagatttgt attattgatt   360
gatagtttcg gagtttgaag gtacagaatt tc                                  392

<210> SEQ ID NO 76
<211> LENGTH: 392
<212> TYPE: DNA
<213> ORGANISM: Candida albicans

<400> SEQUENCE: 76
tgttggtttg tgcactattt tgtgtcagaa actgatcaat gaaaatgatg gttattatga     60
gaatggaaaa ttttccatc acacatcagg tgatgacaga actaaactat attgtgtagt    120
ataaataagg gtatgaaata ccaacatccc agaatatcaa cggaatagaa gagaggagtt   180
tcaatatata tcttgtgaat aataacttcg ttctaattca ctatacacaa ctaggcgtgt   240
acacgctcaa tctcaggtaa agaaagttta tattccatca gattagaagt cgatagtgat   300
aatcatttcg tcccaaatta gcgttgtata aattcagtcc tcagatttgc attattgatt   360
gatagtttcg gagtttgaag gtacagaatt tc                                  392

<210> SEQ ID NO 77
<211> LENGTH: 392
<212> TYPE: DNA
<213> ORGANISM: Candida albicans

<400> SEQUENCE: 77
```

```
tgttggtttg tgcactattt tgtgtcagaa actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgagatagaa gagaggagtt     180
tcaatatata tcttgtgaat aataacttcg ttctaattca ctatacacaa ctagacgtgt     240
acacgctcaa tctcaggtaa agaaagttta tattccatca gattagaagt cgatagtgat     300
aatcatttcg tcccaaatta gcgttgtata aattcagtcc tcagatttgt attattgatt     360
gatagtttcg gagtttgaag gtacagaatt tc                                   392
```

<210> SEQ ID NO 78
<211> LENGTH: 392
<212> TYPE: DNA
<213> ORGANISM: Candida albicans

<400> SEQUENCE: 78

```
tgttggtttg tgcactattt tgtgtcagaa actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgagatagaa gagaggagtt     180
tcaatatata tcttgtgaat aataacttcg ttctaattca ctatacacaa ctagacgtgt     240
acacgctcaa tctcaggtaa agaaagttta tattccatca gattagaagt cgatagtgat     300
aatcatttcg tcccaaatta gcgttgtata aattcagtcc tcagatttgt attattgatt     360
gatagtttcg gagtttgaag gtacagaatt tc                                   392
```

<210> SEQ ID NO 79
<211> LENGTH: 392
<212> TYPE: DNA
<213> ORGANISM: Candida albicans

<400> SEQUENCE: 79

```
tgttggtttg tgcactattt tgtgtcagaa actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgagatagaa gggaggagtt     180
tcaatatata tcttgtgaat aataacttcg ttctaattca ctatacacaa ctagacgtgt     240
acacgctcaa tctcaggtaa agaaagttta tattccatca gattagaagt caaaagcgat     300
aatcatttcg tcccaaatta gcgttgtata aattcagtcc tcagatttgt attattgatt     360
gatagtttcg aagtttgaag gtacagaatt tc                                   392
```

<210> SEQ ID NO 80
<211> LENGTH: 392
<212> TYPE: DNA
<213> ORGANISM: Candida albicans

<400> SEQUENCE: 80

```
tgttggtttg tgcactattt tgtgtcagaa actgatcaat gaaaatgatg gttattatga      60
gaatggaaaa tttttccatc acacatcagg tgatgacaga actaaactat attgtgtagt     120
ataaataagg gtatgaaata ccaacatccc agaatatcaa cgagatagaa gggaggagtt     180
tcaatatata tcttgtgaat aataacttcg ttctaattca ctatacacaa ctagacgtgt     240
acacgctcaa tctcaggtaa agaaagttta tattccatca gattagaagt caaaagcgat     300
aatcatttcg tcccaaatta gcgttgtata aattcagtcc tcagatttgt attattgatt     360
gacagtttcg cagtttgaag gtacagaatt tc                                   392
```

<210> SEQ ID NO 81
<211> LENGTH: 392
<212> TYPE: DNA
<213> ORGANISM: Candida albicans

<400> SEQUENCE: 81

| | | | | | |
|---|---|---|---|---|---|
| tgttggtttg | tgcactattt | tgtgtcagaa | actgatcaat | gaaaatgatg | gttattatga | 60 |
| gaatggaaaa | tttttccatc | acacatcagg | tgatgacaga | actaaactat | attgtgtagt | 120 |
| ataaataagg | gtatgaaata | ccaacatccc | agaatatcaa | cgagatagaa | gagaggagtt | 180 |
| tcaatatata | tcttgtgaat | aataacttcg | ttctaattca | ctatacacaa | ctagacgtgt | 240 |
| acacgctcaa | tctcaggtaa | agaaagttta | tattccatca | gattagaagt | caaaagtgat | 300 |
| aatcatttcg | tcccaaatta | gcgttgtata | aattcagtcc | tcagatttgt | attattgatt | 360 |
| gatagtttcg | gagtttgaag | gtacagaatt | tc | | | 392 |

<210> SEQ ID NO 82
<211> LENGTH: 392
<212> TYPE: DNA
<213> ORGANISM: Candida albicans

<400> SEQUENCE: 82

| | | | | | |
|---|---|---|---|---|---|
| tgttggtttg | tgcactattt | tgtgtcagaa | actgatcaat | gaaaatgatg | gttattatga | 60 |
| gaatggaaaa | tttttccatc | acacatcagg | tgatgacaga | actaaactat | attgtgtagt | 120 |
| ataaataagg | gtatgaaata | ccaacatccc | agaatatcaa | cgagatagaa | gggaggagtt | 180 |
| tcaatatata | tcttgtgaat | aataacttcg | ttctaattca | ctatacacaa | ctagacgtgt | 240 |
| acacgctcaa | tctcaggtaa | agaaagttta | tattccatca | gattagaagt | cgatagtgat | 300 |
| aatcatttcg | tcccaaatta | gcgttgtata | aattcagtcc | tcagatttgt | attattgatt | 360 |
| gatagtttcg | aagtttgaag | gtacagaatt | tc | | | 392 |

<210> SEQ ID NO 83
<211> LENGTH: 137
<212> TYPE: RNA
<213> ORGANISM: Candida albicans

<400> SEQUENCE: 83

| | | | | | |
|---|---|---|---|---|---|
| uauuccauca | gauuagaagu | caaaagcgau | aaccauuucg | ccccaaauua | gcguuguaua | 60 |
| aauucagucc | ucagauuugu | auuauugauu | gauaguucga | aguuugaagg | uacagaauuu | 120 |
| cacaagauga | guuccgc | | | | | 137 |

<210> SEQ ID NO 84
<211> LENGTH: 39
<212> TYPE: RNA
<213> ORGANISM: Candida albicans

<400> SEQUENCE: 84

| | | | |
|---|---|---|---|
| gccugcgugg | cgaaaugguu | aucgcuuuug | acuuuaauc | 39 |

<210> SEQ ID NO 85
<211> LENGTH: 455
<212> TYPE: DNA
<213> ORGANISM: Candida albicans
<220> FEATURE:
<221> NAME/KEY: misc_feature
<222> LOCATION: (1)..(455)
<223> OTHER INFORMATION: 'n' can be any nucleotide 'a', 'c', 'g' or 't'

```
<400> SEQUENCE: 85
tggtttgtgc ctattttgtg tcagaaactg atcaatgaaa atgatggtta ttatgagaat    60
ggaaaatttt tccatcacac atcaggtgat gacagaacta aactatattg tgtagtataa   120
ataagggtat gaaataccaa catcccagaa tatcaacgag atagaagaga ggagtttcaa   180
tatatatctt gtgaataata acttcgttct aattcactat acacaactag acgtgtacac   240
gctcaatctc aggtaaagaa agtttatatt ccatcaataa tataaagcca tgatgtcttg   300
ttaatcaatt gatgtgtaca aatggttatg ttgaaattga aaatagtttc gaataatcg    360 ttgtgctact gggtgaggca tgagtttctg ctctctcact ataggtctta gtgttgactg   420
tcatatcttt tgtctagaat annnnnnnnn nnnnn                              455

<210> SEQ ID NO 86
<211> LENGTH: 20
<212> TYPE: DNA
<213> ORGANISM: Candida albicans

<400> SEQUENCE: 86
tatatatgtt aatatacact                                                20

<210> SEQ ID NO 87
<211> LENGTH: 20
<212> TYPE: DNA
<213> ORGANISM: Candida albicans

<400> SEQUENCE: 87
gagtctgtaa gaaatcacca                                                20

<210> SEQ ID NO 88
<211> LENGTH: 20
<212> TYPE: DNA
<213> ORGANISM: Candida albicans

<400> SEQUENCE: 88
gccactttgg agtacattcg                                                20

<210> SEQ ID NO 89
<211> LENGTH: 20
<212> TYPE: DNA
<213> ORGANISM: Candida albicans

<400> SEQUENCE: 89
tattcggttt taaataaatt                                                20

<210> SEQ ID NO 90
<211> LENGTH: 20
<212> TYPE: DNA
<213> ORGANISM: Candida albicans

<400> SEQUENCE: 90
aaaaaataga gaacgcgctg                                                20

<210> SEQ ID NO 91
<211> LENGTH: 20
<212> TYPE: DNA
<213> ORGANISM: Candida albicans

<400> SEQUENCE: 91
tctttctttt tcttgacact                                                20
```

```
<210> SEQ ID NO 92
<211> LENGTH: 20
<212> TYPE: DNA
<213> ORGANISM: Candida albicans

<400> SEQUENCE: 92
ttctattttt ggttttcttg                                               20

<210> SEQ ID NO 93
<211> LENGTH: 20
<212> TYPE: DNA
<213> ORGANISM: Candida albicans

<400> SEQUENCE: 93
gtataacaac atttgtaaca                                               20

<210> SEQ ID NO 94
<211> LENGTH: 20
<212> TYPE: DNA
<213> ORGANISM: Candida albicans

<400> SEQUENCE: 94
gcctcctttg gatttctata                                               20

<210> SEQ ID NO 95
<211> LENGTH: 20
<212> TYPE: DNA
<213> ORGANISM: Candida albicans

<400> SEQUENCE: 95
attgttcatt aatttcttaa                                               20

<210> SEQ ID NO 96
<211> LENGTH: 20
<212> TYPE: DNA
<213> ORGANISM: Candida albicans

<400> SEQUENCE: 96
ctggagctaa aaataataca                                               20

<210> SEQ ID NO 97
<211> LENGTH: 20
<212> TYPE: DNA
<213> ORGANISM: Candida albicans

<400> SEQUENCE: 97
atactaaatt ataatataaa                                               20

<210> SEQ ID NO 98
<211> LENGTH: 20
<212> TYPE: DNA
<213> ORGANISM: Candida albicans

<400> SEQUENCE: 98
aatagagaag aaaaaaaata                                               20

<210> SEQ ID NO 99
<211> LENGTH: 20
<212> TYPE: DNA
<213> ORGANISM: Candida albicans

<400> SEQUENCE: 99
ttgtgtatcg tataccatcg                                               20
```

<210> SEQ ID NO 100
<211> LENGTH: 994
<212> TYPE: DNA
<213> ORGANISM: Unknown
<220> FEATURE:
<223> OTHER INFORMATION: sequence of retrotransposon from unknown
      organism

<400> SEQUENCE: 100

| | | | | | |
|---|---|---|---|---|---|
| tagatattta | tatatgtata | tgattagacc | aacataaaac | tagacgtcca | aatatttatt | 60 |
| tatttattta | ttgatatata | ttcttattta | ttactgttat | gatcttttga | ttcacacaga | 120 |
| gatttaatcc | aaatcaatac | cttttgtttt | gtagaaatct | tttgcttctt | caatttgtat | 180 |
| tttcaattct | ttgtatttat | gttctttgtc | tttgaatgta | acaattcccc | aacctaacgt | 240 |
| tgataaggca | taagacccaa | atgtgactaa | tccccaccat | ggcaagtatg | gcaatatttc | 300 |
| atcgtgtatt | ttagctggag | ttggaatcac | acctgtgata | agagcaaaat | aaatagctga | 360 |
| taaggcaaaa | attgttaatc | ctgtttcagt | agctttagtc | attcttatag | ttagacttgt | 420 |
| taaagggtag | ttgtgttaat | tgaagatatg | ctggaaaact | atacttttcg | ttgttttttt | 480 |
| ttttcaatct | aggtcgggtg | tgctgttatt | tttttctct | cttcttggtt | cttagtattg | 540 |
| gattatatgt | tggtttatgc | gacgtttgtg | tcagggaaat | aacaccttga | tataagtcgt | 600 |
| gcgtattagg | tcaacattgg | tgaaaaattt | gcactcatcg | agagccagga | attagtataa | 660 |
| aaagaagaga | aaagaaagat | atttaggata | tttattatat | agggaccgag | tttcaggaga | 720 |
| cacttttagt | gggcgtaaac | ttcattcact | ctgttttttg | cttattacaa | attatcacct | 780 |
| atcgtgtact | aggactaatt | ctcacgaata | ttccgtgtat | acaaacactt | attgccaact | 840 |
| tatggtgcgg | aactttattt | gtctgaacca | aaatcaaagt | cacatcattt | aaatgaacgt | 900 |
| tgacataaat | agattcttta | ttcaatagaa | acaatttctt | cctttttctt | ttctttgtat | 960 |
| tattggttag | atttccattc | catatacaca | caag | | | 994 |

<210> SEQ ID NO 101
<211> LENGTH: 1348
<212> TYPE: DNA
<213> ORGANISM: Unknown
<220> FEATURE:
<223> OTHER INFORMATION: sequence of retrotransposon from unknown
      organism

<400> SEQUENCE: 101

| | | | | | |
|---|---|---|---|---|---|
| tgtatggtac | atgtacgaca | gcccaaaaaa | tggtatcatt | tagaactgta | ttggagaaca | 60 |
| ttagttttgg | tccaacattg | cgtgatgatg | gtatgttttt | cgtattatag | tacaatgatg | 120 |
| gctcaatgat | ttattttagg | tttatatgtg | gatgatatct | taatggacag | aatctcagat | 180 |
| ggaatcgtta | tcagatttgt | tgaacaagag | agagtttatt | tcgcgtcaaa | atcaatttag | 240 |
| gtctcatgac | agaatatgtg | agataaaatg | tccacgtaag | caaaactggg | tgatactttg | 300 |
| aattaagaga | tactcctaaa | taagcaaacc | aaggatttta | aactacacaa | ttcgtatggt | 360 |
| aaaacgtgct | ttgagttcca | aatgatagat | gcgagatacc | aacaaaatag | aactgtcgca | 420 |
| aatgctgaag | acaatttcac | tgaggttcga | atgaaaaat | tacttaattc | aattaaaaaa | 480 |
| tttataccaa | aaggtggtct | ggaagtgctg | atatgaacac | gaaatttaat | gcattctgtg | 540 |
| gaaaattcgt | ttaagctcac | aatcggaaaa | tactaccatt | ctacatttgc | agaaaattaa | 600 |
| aattgtgttg | tgaatatct | acatcctaca | agttcaaga | catttattga | tggtatattc | 660 |
| aaaggactcg | atgttgagaa | tgataataac | ctgaaccaag | acgctacaaa | tgctaattga | 720 |

-continued

```
gtaattcgta attgctaaac aacgccattt cgaatcaggg gagtgttggt ttatgcgacg      780
tttgtgtcag ggaaataaca ccttgatata agtcgtgcgt attaggtcaa cattggtgaa      840
aaatttgcac tcatcgagag ccaggaatta gtataaaaag aagagaaaag aaagatattt      900
aggatattta ttatataggg accgagtttc aggagacact tttagtgggc gtaaacttca      960
ttcactctgt tttttgctta ttacaaatta tcacctatcg tgtactagga ctaattctca     1020
cgaatattcc gtgtatacaa acattatacg tgtctgtaac tacgcgaaac tacttcgtct     1080
cagttttttg ttacaaacaa ctttccgtat agacctgaga ttttgtcagc ttgattgaat     1140
ggaagagttt actaaagtac cagaaaggtg ttttatagat aacatgtaga tatataaaaa     1200
tgttatatta caaatgactt ccaaaagaaa ctgtacgaat tttgctgttt attaaaaacc     1260
agttcctgaa aactagtatc ttagcttcag tacatttagc ccacctaaat tggacctatg     1320
acaagttcta ctttcccgac aatgctaa                                        1348
```

<210> SEQ ID NO 102
<211> LENGTH: 3034
<212> TYPE: DNA
<213> ORGANISM: Unknown
<220> FEATURE:
<223> OTHER INFORMATION: sequence of retrotransposon from unknown
      organism

<400> SEQUENCE: 102

```
tggttggtct tatcagtaga ggagtgagta tcagttgctg tggttttttt ttttttttg       60 tcgtcttcaa attttgttgg tttatgcgac gtttgtgtca gggaaatatc accttgatat      120
aagtcgtgcg tattaggtca acattggtga aaaatttgca ctcatcgaga gccaggaatt      180
agtataaaaa gaagagaaaa gaaagatatt taggatattt attatataga gaccgagttt      240
caatagacac tttagtgggc cgtaaacttc atttactctg tttttgctt attacaaatt       300 atcacctatc gtgtactagg actaattctc acgaatattc cgtgtataca aacaaaattt      360
tcgaaactag tcaatcacaa caaatttgtt gagttcaac  tgaaacgata acaaccatca      420
taattcgatt gaatactttg tgtcgtctct ttctttctat gcattctact acttgtcgac      480
tacatatatc cagccatgtc ttgcatatat cctagcaact cctccctccc cctattgtt       540 gttgttttt ttaataatat ttagtatatg tatcaatggt aaaaactatt ttttgtattt       600 tttttggtt tgtaaatttt gatagttttt ttattgaaaa cttcaaatct caaaaatttc       660
taataacaac aacgacaaca attattaaat gatactctac tcaaaagaa  aatttgatga      720 aatgccaaga acaatataat ttagtcagta cattaatact caattacaac aacaacaaca      780
acaacaacaa caacaactgt tcaatgcaat aataagagag aaaccaatag aactaattta      840 gttttttcaaa tagccaacct tcaaaaaaaa ataaattatg tgaatgcata aaatatgtat      900
tattagtagt agtttgtagt tgttgtaacc agaattctca atacatactt tttcatatcg      960
atcctttttc ttcttcctcc tcgattttg  gattatatta actaaatttt gcatttacgt     1020
ttataatgat tttcaataca aaaaaaaaag cattataaac tatatattat cttgaatagt     1080
aaaaataaat tagtattgat agaaagtttt ttacatctga cattatttac taatttaagg     1140
aagaatggga cttaaaaaaa tatctaaaaa cccatgtgtt ctagttttc  atttgttatt     1200 agcttattat actttacatt attatttttg ctataatcta gaaaaaaaaa agtagacttt     1260
agatctaatg tataattggt atattgatag ttttttaatg ttttttttat taaatcattt     1320
catttatttg gtcttctttg ttttggtatt gtctatgtgg ggtggcggag ttgggtgcaa     1380
```

```
cgcaaacaaa aatatttttt agcaattaag ttttttgccgt actgtatgga aattagttcc    1440
attatgatag cattttgcat ctttgattaa tttttatcat tccatagcaa caattacttc    1500
tttctcctcc ggtgtcaatc aatcccatat aggtcttgca ttgttttgtc aaacgtttca    1560
aattgggaat tgtttagttt gaaaaactat agatttcctt atcttgattc agatctctct    1620
ctcagccatg cttatgtaac ttagctattg tttctgttat tgttattgtt gtttggtgat    1680
tatcgacatt tgggttcatt ttataaaagc aaacgagaga tcgatagcaa ttataaaaac    1740
cattacacac acccaaaaaa atcaaagtaa tatgttatct aataggacaa ctgatgtatc    1800 ctttaatttta aatattttgg aataaaagta caccccttc catcatattc atgtgcaatt    1860
taaaaggaat caattatcaa aaacccaact aaccaacaag tttctggtat atagcctttc    1920
tgtccaattt ttttttttttt tttgaaatct aaactactgg cctctttaaa ctaaaatcaa    1980
agatcacttc ttaattagtt ttgtagatcc agaatcgtta ccaatactgt taataaatga    2040
ttgaatgatg taatttcaaa tagcaatcgt tgagtatatt ataatcaatg aatagctaga    2100
tttagagaca attataataa taacgaatca tcacaaaaaa aaaagtggtg tacagaaaac    2160
gtatgtatgt aaactagata caatggaaag ggctgggagc ggagggggg ggggggggtt    2220 taattctgat taagaaaaaa agggggaagga catggaattt atccacatga gagaaagggt    2280
tcctaaaaga tgtcctttac ggtgggcccg gggaacccca attttcagaa atttcacctg    2340 tttgggcgc ataatgttca caacccaggg ttgccttaat gacgtattct ttacaatttc    2400
atcaaaccag ttgttgttgt ttaaataaaa gttgatagtt gtattgctca aattcaaggg    2460 gggaggggt ggtgaattca tatttctcat atatcacact catatttgcg aatacttgaa    2520
ttactctaca tttatgcttt tcacatggat caatttaata taagtacatc aatccaatat    2580
gaacatgaat gtaccaacta aaattaggtg ttagtctgaa ttcttgttca ccattgttta    2640
gttttgtttg tgatgaatct caagatacag attggttttta caataatacg tttgttgttg    2700
ctgtatgaac aggcagtcac ccttcctccc ccacaaaaac atattctgta taatctatgt    2760
aatattataa gatccaatca aaacatcacc accaaatat actgtagtaa tgcctaatct    2820
aattactaaa tagaaatata gaatggggta tggttgagat ttttgggtaa ggtccaatt    2880 gccaaaaaaa aaaaaatatg caaccttttt ccctcctcca cctccttcct atttcgtgaa    2940
attcggtaga atccgaaaga ctaatgaaga aaaaatcaag aaaaaaggtt aaggtcattg    3000
atcaattgat ggcaaatatg taagtaagtt cgat                                3034
```

<210> SEQ ID NO 103
<211> LENGTH: 3504
<212> TYPE: DNA
<213> ORGANISM: Unknown
<220> FEATURE:
<223> OTHER INFORMATION: sequence of retrotransposon from unknown organism

<400> SEQUENCE: 103

```
ttttctcttc tagcttgcaa ttttttgttga cgtttactag tagcagaatt ggtttgttta     60
gtttctgctt gttgttcctc tggtgtagag ccatttgatt tattcttttt aatgaatggt    120
aaaataaaat tactcaattt gtaaatagca aatccaggaa ttatcaagta cccataccat    180
actttattac ttccaaaaat aatcatcaaa atatcgaacc cccaagtcaa atagataaca    240
tcaaaataat attcatataa actccccagt aatctaatgt cttcaccact tgaaactaaa    300
gagttaccat tggtatattt gggacgacca aattttccca aagaatattg taaaaatata    360
```

```
cttgggatgg agaaaattat ccacggttta taggaagatg gacgatggaa aatggagata    420
attaaaaaca caataatgtt aattgatgcg gaaatgatta ataattgatt taatatgttg    480
gtattggcta ctgccaactt cttagctgat gcagatgcca ttgttaatat tgttaaattg    540
ggtaaatagt atgaaggaag ctttggcagg cgttgttatt tttttcacca attattatca    600
tcacctgcgg aggttagtca atttgagatt gtgcgaggga aaaaaaacga cctccataca    660
ctacctcaag tataagtcca gtccaattgt tcgctataga gagatttcct agccggaatg    720
cacgacaatc ctgagacgga agtcgatcgt cgatgcccat ggtgcgtggt gaaaaatttt    780
cttagaaaat ttgttctttc cttcaactgc tttgaagaga gggaggttca agtggtttaa    840
gtacgacggt cacaaagatt gcggcttatg aggcccgaac tgagttgaaa tacaaaatca    900
agatataatt atatacctta cttgtctata ttgttttata atacattctt cagatattta    960
aatttctgtg tatcatccta taaaacagag atacattcag tgcatttagt atactgagtg   1020
aactggtacc tgtgacattc aagataactg tttcacgcac gctggcagac gaacaccaat   1080
agtatgatga agaactgacc atggtgtaag aggtttgatg gagtttcttt ttttttagaag  1140 aggttgataa gccaacagat gaggagtaac aagtaactcg caacattgta taacataagt   1200
ttacatcaaa tcagaattta ctaagaaaat caatccattc aaaaggcact caatcattga   1260
aaaaacgagc ttaatgagta gacggtctgt tcatatgaaa caattgaaag ggttgaatat   1320
tgtttggaaa attatataat tcatgtcaaa ctgggaggct taaattatgg tcactccaca   1380
gattatgaaa cgtagttaca caattcttgg acctggaaat cccacaagag agcgttagtt   1440
agtttgcact ctcctcacca gttaaactac ccatgattct ccaatgtggc ttatttaagt   1500
atcagacaac agatacatgg tttccaagtg gtctcatttt tggtttactg gagtctgcat   1560
tccccacaaa agtacctttc aaaactaatt aatgtagctt ctatttgata gcctctgtta   1620
tggaaataga tttgctctgc ccagtgggtg taattattcc cagctggaac tattccgata   1680
gatatgtttt aatgtcaatt taaatcttgt aataatagta aggatgcggt ttatccgcga   1740
tcttcttaat acctgtggag ttactccaga acagaggttc aatttttttct tggttggtaa   1800 attatccgag taacacgggg tagcttggtt actccagttg agaatgtaaa ctatagatga   1860
agatttcaac acgcaattat taccccacct tggcgaatta ctaatcgact atttgttaat   1920
ccagaaaaaa ttatacacaa acactgcctt ttttttaaaaa aagcgttatt ttgatggaac   1980
gataattaac gatggttctg cacaaaaatg tggtccaaag ccccagacta ttctgaagta   2040
tgatttgtta cttaatttag tgaataatta acataaaat ctggagaaaa atttttttt    2100 tgctctcatg accagtggca aattcttggt aacgaggctt aacattaatc cgcaaattac   2160
ctggcaacag agaaaacacc cagaaagttc tgtcgtatga gaaacctac agttgtttcc   2220 gatttctccg agcactaaac ataaagagac cagtaatgct aaaaaaattt ttatttctgc   2280
attactgttt ttagcaaata cacgtctaat ttattgtatt tgttaaacat tctttttcctg  2340 aaattttaag aaaatgtttt ggtttgttgg aattccattt aaacggtact ttggggtgca   2400
gacagcaatc catttggaga gtggcaagtc tacacgaatt tagctaaggt tcactatatc   2460
gtgtaacaag aaatttctat accaaataaa cagcacttga ttgaactaca atatgtaaaa   2520
acttgctttt attaccagtc ttcatacata ccccggtctt ctcttttcaa tattctgtat   2580
atgtctttac aactcttaac actccgtaaa tgtgcctttc gaatactttt gcagctggat   2640 attttttccgg tgcacctttt cagttatctt ttgcaacttt tcgcgagcaa tgacaaaagt   2700
```

-continued

| | |
|---|---|
| ttggggcgtg aggcaacaaa atgcatggca ttaccagtac agtatcgcca caagtggttt | 2760 |
| tccttggcat ttcttgattg tttagtagaa caattcaata agactttttt gatcatgaat | 2820 |
| ttttttttgcc atgaaggtgc tttcattgtt caaggttgaa ggggaattga aaaatttgta | 2880 |
| gagtcacaat caaatgactt gataaatttga tagaaaaaaa aaagaaacct taaaaaatat | 2940 |
| tcataccaat gtatgcataa ccataaagaa cttactaatt atgcacctgc aatcagaaag | 3000 |
| tcatttctta cgatgatttg ccaaatgacc gtaaaacgac tagcaaaaac agtgacattt | 3060 |
| tttttgaaaa ggtggagatg aaaaccattc tggtttgttt cgtcatttac acaaatattc | 3120 |
| gacacaaaaa ctattaattc aatacaaaca aaaaatgtg caggaagtct tggaaccgat | 3180 |
| acaaaaattt ttacaaacca cgtcacactat tgttttgggg aagaattagt cggggaagaa | 3240 |
| ggcccagaaa cttgagtaaa gagtggattc aacactttat aatagtatca ttttgtaaca | 3300 |
| caaaatgaa atacacccaa taaaaactgt tgaaacattt atccgtcaag cttattcgat | 3360 |
| ggagtacaac actttacatt tcttccgaaa caataactat ataaacccat gtaagtctcc | 3420 |
| cctcttttgt ttcaaacgtc ttatcaattt ttctcttcac tacttttcca acttaacaat | 3480 |
| cttcacttat aatctcaacg aatc | 3504 |

<210> SEQ ID NO 104
<211> LENGTH: 3955
<212> TYPE: DNA
<213> ORGANISM: Unknown
<220> FEATURE:
<223> OTHER INFORMATION: sequence of retrotransposon from unknown
    organism

<400> SEQUENCE: 104

| | |
|---|---|
| tgttaattga tactaagtgt aattgattgg aatactagaa aaaaagaaa gaagaagaaa | 60 |
| agaaagaaga aaaaactcaa ctttctttcg aaaatcaagg atcaatgttg gtatttatat | 120 |
| acttttttt ttagtcaaac tctacgaaat gaaattcaaa gagaataatc cacagaagag | 180 |
| gagagagggc aaaagtgggg ggaccaaagg gggttagaaa acaggaaaca gcaatagaga | 240 |
| gcaataattg aaaaatagtg ttgtcaacaa tagaacaaat tggtcaaact ttaaatgcaa | 300 |
| aacatgaaat tcccaatttc cagaataaat aatatcagca tacatggccc cgaaaactac | 360 |
| tttaccgtgt cgctttaacc cccccttcc taaaacgaga caattagaca tacattccac | 420 |
| aattatcata atccccttt ttttccttac aaaacactt attttttgtcg ttttcgttat | 480 |
| ttgcttcgac gacattgtaa actctttgga tttgcagtag tagtgctcct ggtgtaaggt | 540 |
| gggtttggtt gtagagtaaa agaaacgaca attgattaca cctcgatatg catacgcatg | 600 |
| gcaaagagaa taccgagtta atagtgagtc tattagtgtt gcaggaaaag ttatacgaac | 660 |
| aacattttgt ttagtgtgga tattccagat caacaacaat atgactaaaa tcatagctct | 720 |
| aattttcagt ttacctttgt ttattacgat actgccacag tcgtgctgta ccagggtcag | 780 |
| ttttagaaaa actattctag aaatgatgag tagaaatgta ctattatgag caatatttca | 840 |
| aaaagtgaaa ttataattgc tgctgacaac accaacaata catacaaatt tggaaacgag | 900 |
| caaatcgaga aaatttcaat ccgtttagca agttgttcgt tgtcgtcatt gtcgattagt | 960 |
| ttcagtttct agaggtgaaa ttttctatgg caccaaaacc aaagcctcaa ttttaattta | 1020 |
| ctctgtgtgg tacaaaatac attagagagg atcctctcca aacaggattg caggaagttt | 1080 |
| tacacgagaa tgatttacta cacgacgttg aattaaaaag ctcaaccagt ttgtcagcaa | 1140 |
| ttttgttcta tctgttcaat ttcttgtata aaataaagca atatgagaga gcatctaaat | 1200 |

-continued

```
caataatgtc aacacaatat taaactttga gaaggattgt tcaacaaaac aatccgatga  1260
atagaagaag aataatatca aattgttcct gattgattgt tgttatttat tttttatctc  1320
cgaattcctg cacaatggct caacaacagc caacacggat cacacattaa atttttttt   1380 cgtgcaggac cccgtggtgg tggctgtggc tgtgattgtg atcattgtag tttctgcctt  1440
gatgatgaca aaaatgata gagttcagta tgaggaagaa attaagcgat atcggtttat  1500
gatgtgttta gttattaatt gctctcaatg gttttcaaca acgtatacaa aactggtggt  1560
gcttgaaacg aatgagtaat acagatctaa ttaagctgtg attttctaag tttgccttgt  1620
ctctacagtt caaaaaaaa gaacagaaca cctcagaggc tgttgtgatg caatttttag   1680
gaacctcaac aacaaccact gactgatcta agccagcatc tgtttaatgg gttttcaaaa  1740
agaatggggc aaacggggaa ttgaaccccg ggcctcctcg aattttgtgt ttggtgaaca  1800
acccaaacga ggaatcatac cactagacca ttcgcccaat tcgatgactt ggaattattc  1860
tagttatttt tgacatacaa agctcagctt tattacagat agtcatgttt gcatggatga  1920
attagtacta ctaataatat aagaaaacta gttaattgga gtcaatgtct tatacatgtc  1980
ttctgatggg ttatgcattg attaattatg aatttctttt aaatacaatc tattgctatt  2040
atttgtatgt aaaactttac ccaaaaacca acaaaaaaga gtggtcttgg ataaagatta  2100
aagtaattcc aaaaagattt ggtaattagc tatattgttt tgacgtacat ctataactac  2160
aaatagccat tcagtttgat tatgtatatt gacatagttg gatttgtaat ttctgttaaa  2220
atggaaaacc ctaatcaaat gtatatgttg aataggtagt taaattgtac aacctactac  2280
ttgttgtcaa ttgaattcag agccaatact tatatctcct ggaaactgat acacaaacga  2340
attgttaaac tataacactc gacgttcaca tctaaggatt catcgtcgtt aagatttata  2400
ctcattagca aactcacttg ccatattaaa cacttctcaa tctatttccc acaatccaat  2460
taatcagcac gaaaactaag atactatata tatctgccta tacctgatat acacatggca  2520
catggcgtat cccacaaaaa accgtcaaga caacaccaat atgacaatgc caattataca  2580
attgcatata ccacgtgact tcattttatg gtcatgagaa attaacttat catggggtta  2640
ggcgagaata tcaactgttc gctatagaga gatttcctag ccggaatgca cgacaatcct  2700
gagacggaag tcgatcgacg atgcccatgg tgcgtggtga aaaatttct tagaaaattt    2760 gttctttcct tcaactgctt tgaagaaagg gaggttcaag tggtttaagt acgacggtca  2820
caaagattgc ggcttatgag gcccgaactg agttgaaata caaatcaag atataattat    2880 ataccttact tgtctatatt gttttataat acattcttca gatatttaaa tttctgtgta  2940
tcattctata aaacagagat acattcagta catttagtat actgagtgaa ctggtacctg  3000
tgacattcaa gataactgtt tcgcgcacgc tggcagacga acatcaacac tgatcatttg  3060 ttttttttt atttctcctt tttctccttt ttctttcttt tttcttcttt cttcagacgt    3120
tgttgattta ttttatcgac agcatccttt tctttggcca catatccaag cgatatactg  3180
gccaaagcga agtccttta taaagcaatg ctaccaaatg taacagttcg aggtcagaag   3240
attaagcggg tatgttcaca cggatatttt atggggtatc acttgtacca aacactttga  3300
tacgataaga atatttgtaa tactaacttc agtgtctttc ataatcagct cataacctgt  3360 tggaattaa attcgtatgt tgttcattca aaatttgat aaatgggacg agaaatcatc     3420
gttgcctcct aattagatta tgacttagta ctaactaaac tgtttatcat tttttaaagc  3480
gttgggctcc atgttagaat agattattag ggcggtacgt atttcataat ttatatatag  3540 gtacttatt ttactaattt attgcacagg aaaagataaa aggtatcgat tataccctatc   3600
```

-continued

| | |
|---|---|
| agcaaggttt aagcaaaatg aagtatttt accatatttt tccatttta tatagataca | 3660 |
| tcaagaggtt tattttaagt tcacctggat aaaccattca actaacccaa ttgaattgaa | 3720 |
| tgacaatttg atctccaaag agggattcat ttctattctg gagagataaa cgtcattgtt | 3780 |
| taggaaagag caagagataa gaaatctttt gtatattgta tatatattat taatgttata | 3840 |
| ttacactatt gtttgtttgt ttgttataat tatatgtgag atttcatatg taagatgttg | 3900 |
| ttatctcttt ccattattta gcttttttga aaaagctatc aatggctcca cgttt | 3955 |

<210> SEQ ID NO 105
<211> LENGTH: 1434
<212> TYPE: DNA
<213> ORGANISM: Unknown
<220> FEATURE:
<223> OTHER INFORMATION: sequence of retrotransposon from unknown organism

<400> SEQUENCE: 105

| | |
|---|---|
| tagatgcaat aggtgtatga aatgtatcta gattatatca tgaagcccctt gcaataaaat | 60 |
| ctagccaaaa atttgtgtac tgcaattgtt cgctatagag agatatccta gccggaatgc | 120 |
| acgacaatcc tgagacggaa gtcgatcgtc gatgcccatg gtgcgtggtg aaaaattttc | 180 |
| ttagaaaatt tgttctttcc ttcaactgct tttaagagaa gggaggttca agtggtttaa | 240 |
| gtacgacggt cacaaagatt gcggcttatg aggcccgaac tgagttgaaa tacaaaatca | 300 |
| agatataatt atataccta cttgtctata ttgttttata atacattctt cagatattta | 360 |
| aatttctgtg tatcatccta taaaacagag atacattcag tacatttagt atactgagtg | 420 |
| aactggtacc tgtgacattc aagataactg tttcgcgcac gctggcagac gaacagcaat | 480 |
| tctgtaattg tcgtagagta gcaacaaatc ttcccgatga ttggtacttg tgttagtcta | 540 |
| cacgacatgt gttttggtac acttgaactg tatgtccaag aatggaaaca tatgcgggaa | 600 |
| ggacgcgaaa gatgagtttg gtatagaagg gataagaact gtaaaatata ttatgtagtt | 660 |
| atatatttta attatgggaa attgagtgtt tattctgttc aacaagtttc aaccgtagag | 720 |
| attacattta aagtctgtgg tcgaaatcca caagatacag caaattcatg aattcaccta | 780 |
| tttaaatcaa gtttaccaag caccattgcc tagaacttgc catatcatca attaagtcag | 840 |
| acattactaa ttgagcaaa gcttttagct taatgggcca actaatttaa gtcgaattgg | 900 |
| taatgcaatc tgttcttcat ttgagtcgct tgctacggct ccatgacaca tccatttgat | 960 |
| tgttttaatt cgagcaatta tccaccataa ctctcagtaa tatcattaac agttttacgc | 1020 |
| ttaataagca tagaaagttg tatgaagttg tctcctaggt atgctagaga gatttgtata | 1080 |
| tacgaccagt aaagagtgtg atgaggtgtt tactgtaggg taaattgcaa ttgacttgag | 1140 |
| ttgatagcgg ttattacaaa agtatagatt caacaaatta agacaagtac caaacgatag | 1200 |
| gccgaatgtg acttataccg ttgaagttca agcgttttta acaaatagaa atgtgagatt | 1260 |
| aatgagttcg acaaatgttt tactagatac tattaatttc gatgtactat ataagtttaa | 1320 |
| ccagctataa ccggcagagc agacttcctg aaactcaaat tggttgtgtt tggacttgag | 1380 |
| ttacaccaca aagtttgaca atcgtgagga catagcaacc tatcaagcca ctca | 1434 |

<210> SEQ ID NO 106
<211> LENGTH: 1608
<212> TYPE: DNA
<213> ORGANISM: Unknown
<220> FEATURE:
<223> OTHER INFORMATION: sequence of retrotransposon from unknown

<400> SEQUENCE: 106

```
tgctagtatg tattttggct ctttgatcct gaatgcgaca atgcaatacaa aatagtagaa      60
ataatgatgg tgatactact agtattaata ataatccgag aaacgatatc acaaaataaa     120
tcagtgccca atgaggttga tgcacaaata ttagtggtgt gtaaaactaa agagaatatc     180
tcgctatgat ttctattgat aagaaaagat gagagattaa ggaaatatct tctgtaaagt     240
tgtatcgcca ccttttttt ttgtagtagt agtatcggtt ttggttttgg ttttctcatt     300
agttaagatt cttgcgataa ggcacgacct tgatcatttg catgtttctc gtttaattgt     360
ttttatttct ttttttttta tggtgtgtgg tagtagttac agatatcgac ggttgcaagt     420
gcacgagtgc tgcgactgac cggatcgtca tgctaaaaga ttcaggggtg tgtaagagcg     480
tgccaagtcg aggaggaacc aacatttcac aactgcttca ggatagggca ttcttttct     540
tctttctatt tgatctagcc ttgcgtctat tcgtgttgtt ggttggtaca agcgaatatc     600
ccaataaggt ttttgttgcc tatgtgcatc gtgttgtagc atagtaacga gagatacgat     660
tcttcttctt ctccttcccc ttttctttgg attgctttat atttatatat atatattgtc     720
atcatcgtca cgaaattcac tatcattatc aattattttg tttttttctct atctttgtcc     780
tcctcgttta atccttatca cagttttggg ttgttgcaat ttctttttcat tctccagttg     840
aggcttacac tttctcttgg agtttccgtt tataatttt acacacacaa aagcacaaac     900
tacactttgt cttcacagtg tataacagat accacagtat tactaagggg gaaaactaac     960
ctaaccaaag ggactgacaa aataagtgga aagactacaa atgacgccct taatatacga    1020
gagagaattg aaaagacata cacataatgt tcgctataga gagatttcct agccggaatg    1080
cacgacaatc ctgagacgga agtcgatcgt cgatgcccat ggtgcgtggt gaaaaatttt    1140
cttagaaaat ttgttctttc cttcaactgc ttttaagaaa gggaggttca agtggtttaa    1200
gtacgacggt cacaaagatt gcggcttatg aggcccgaac tgagttgaaa tacaaaatca    1260
agatataatt atatacctta cttgtccata ttgttttata atacattctt cagatatta    1320
aatttctgtg tatcaaccta taaaacagag atacattcag tgcatttagt atactgagtg    1380
aactggtacc tgtgacattc aagataactg tttcgcgcac gctggcagac gaacaattgc    1440
ggcgaaaaaa aaaagaggtc gccaaaacta aactgttggg acgatttgct gccaatcaca    1500
atgaaaaaaa aaaagaacag ttggtttgaa acttcttcct ctaatacaga attaactgat    1560
ctttctatca ctgtttaaac tattcattac tctcaagaac ttaccatg                 1608
```

<210> SEQ ID NO 107
<211> LENGTH: 1385
<212> TYPE: DNA
<213> ORGANISM: Unknown
<220> FEATURE:
<223> OTHER INFORMATION: sequence of retrotransposon from unknown organism

<400> SEQUENCE: 107

```
ataagtgga tttatcatta ctattatcgt aatgctcaat caggggagtg ttggtttgtg       60
cactattttg tgtcagaaac tgatcaatga aaatgatggt tattatgaga atggaaaatt     120
tttccatcac acatcaggtg atgacagaac taaactatat tgtgtagtat aaataagggt     180
atgaaatacc aacatcccag aatatcaacg agatagaagg gaggagtttc aatatatatc     240
ttgtgaataa taacttcgtt ctaattcact atacacaact agacgtgtac acgctcaatc     300
```

-continued

```
tcaggtaaag aaagttttata ttccatcaac agtactagta ttagtattag tagttgcttt      360
gtcatataca aatagattaa ttaaactaac taacaaccta tatcaaatca aatcatcagt      420
tatatcatca tcaacatatt catcatcttt attcattcta taaattgtca ttgccatact      480
tgcaaaattc aataaactca taatccaatc cggcaaagca attccatata attcaatgag      540
attaaatgtt aaatctaaga aattcccaat taattcaata ataagcatca ttttatcaaa      600
tcgtaaatct tttaatactt ttttgtattt tttatttaaa tcttcattta taaaatttat      660
tccagtcttg tttttagtgg tggtagtaga atttaataaa tcaacttcaa tattaacttt      720
tctaatttta cgtattacat ttagtaattg agatatggtt ttcctgatta aaaaaaccaa      780
tattaatacc caaatttat tggtttgttt taaaaatcga tttaaaaatt gtgggaacat       840
tggtaaattt gataataaat gtaaattatc taataaattg gcaagatttt ctaaaatatt      900
aacaaacata aattctattt ttttcaaact aaatgtattt ggtctatagt attttatagg     960
tttattatta ttattaggtt tactccctga cttgggtttc ttcactggag attgacctcg   1020
ttcttgtcga ttgttgtgag atgatttatt aatatcaaat ttattaaata ctgaagggta   1080
ttttggtttt ggaggtaatt tagccttagt aggggttgat aatggttgtg atcgactttg    1140
taacttttgt tgttgttgtt gttgtgctag taaaatggtt aatttatcaa gtttatctga    1200
tgtgattgaa gtattaccct gttgttgttc ttttgagct agaagaagta aattattgat      1260
aatttattgt tgacgtgagt caggattagg atcaattgaa gtatgtttta agtttaatt     1320 ttgaattaaa tcaatattct cctgtattgt tgtagtgaac attacggata ttaataataa   1380
ataaa                                                                1385
```

<210> SEQ ID NO 108
<211> LENGTH: 1483
<212> TYPE: DNA
<213> ORGANISM: Unknown
<220> FEATURE:
<223> OTHER INFORMATION: sequence of retrotransposon from unknown
      organism

<400> SEQUENCE: 108

```
tgaataatca ggggatgcaa gttattgatt ttgccagtat ccaatttac ttgtggtttc        60 gagaaagttc tttctctcat tggtagttta aagttaactg aaattcaaat tataggagtt     120
tttgaacata aaaagcatat acaacttgag tagcatgtat atattgcata taaagattct     180
ttttttttgt aattgagttt gccaaacatt ttagtcactc ccaatatatc gtcaactcgt    240
aaatgtgata attcaggtca agtgcctacc tctaacgatt agccaacatt ttttgaaaca     300 aaatatatt tcaaggaac acagtgaaaa cctctctatg taggctgaca ggtgaaaatt       360
atgaattaat tgcattggcc aatgacaaat gaatagacaa aacagcaaat aaggttgcaa     420
aagtagccca acaaactag atttcggtta cgaattttcc atctttcaaa acaatgaatt     480
tgtttagagc tctgtgccat ttattgcaac taaaatgaat atgcaattaa acaatcagag    540
atgtattgga ttatccccgt ggtatacttt tgagttcacc attttgtttt ttttttgggt    600
taaattagtg ctcctactaa aaatcgcatt tatcttacac tcaccatttt gataagttat    660
ctctggtcaa tcgcaaatac tatgcttcta attaagagtt ctatgtaaat cccatttat     720 ttgatcaatc tattggtttg aagtaagagt tgattttctg taaagattta tttgacagtg  780
tagttcggtg tcaaaaatat attatgatgt acactaaaaa acactaaatt tcaagtcaat   840
ggggaacaca aaactgaatt aattactata tgttggtttg tgcactattt tgtgtcagaa    900
```

```
actgatcaat gaaaatgatg gttattatga gaatggaaaa ttttccatc acacatcagg      960 tgatgacaga actaaactat attgtgtagt ataaataagg gtatgaaata ccaacatccc     1020
agaatatcaa cgagatagaa gagaggagtt tcaatatata tcttgtgaat aataacttcg     1080
ttctaattca ctatacacaa ctagacgtgt acacgctcaa tctcaggtaa agaaagttta     1140
tattccatca ctatataaca acaatcaggc tttgcaaaaa acatttaaa actaatactg     1200 gtaatatgga aatataacgc ctcgtagttc tacgcacgtg gcatccttta tctatttatt     1260
caatttaccc ctaatttatg aattagctta ataagagcag tcaaattaac acggctcaat     1320
taatagtact taataatatg aagccgatca attaaccgat cctttgaata atttgaaaat     1380
aaaataaagt aatataaata ggtatgcatt ttccctacat ttatttcctc tttctatttt     1440
aatttgtttc ctaaacagca acaacaacaa ttgaaattca aaa                      1483

<210> SEQ ID NO 109
<211> LENGTH: 879
<212> TYPE: DNA
<213> ORGANISM: Unknown
<220> FEATURE:
<223> OTHER INFORMATION: sequence of retrotransposon from unknown
      organism

<400> SEQUENCE: 109
ggctcgtaga ttcggtatac ttgtctagaa taaaaatgaa atgaatgtt agttgaaatg      60 tcaggtggtg gtggtggttt tttttagat ttcaaaaact atacatactc ctatgagatc     120 aatttttcttg attgaatatc ttggtaaaat ggttatgagt tcattttctg ccaaaaaggt    180
aatttctgat ggcataagat tcccttgaag gttttttggg agtaccatga cgggttaagg    240
attatttgtt aatggttaaa actagatagt agtagtctat atttaattta ttttttttttt   300 tttgacacct tgtgcgaaag atctctgttg gttgtacac tattttgtgt cagaaactga     360
tcaatgaaaa tgatggttat tatgagaatg gaaaattttt ccatcacaca tcaggtgatg    420
acagaactaa actatattgt gtagtataaa taagggtatg aaataccaac atcccagaat    480
atcaactata tagaagggag gagttttcaat atatatcttg tgaataataa cttcgttcta    540
attcactata cacaactaga cgtgtacacg ctcaatctca ggtaaagaaa gtttatattc    600
catcaatctc tctcgatgtt gtaaagagac gcgtcaatta acaataaact ctaattttgt    660
ttttcttcta caaaactacc aaacataatc atgtcaaggt aaattacaat gatatttaat    720
tacgtaaata cttctatacc cttattgata ttcaatcatt ttcttcttat acgtggaagt    780
tcttccagat gtcatggcct tggcccttct agcaggtttt ggaccgtcac tatctctact    840
atacgggtca aatccacgtc tctgtctacc attagtcta                            879

<210> SEQ ID NO 110
<211> LENGTH: 974
<212> TYPE: DNA
<213> ORGANISM: Unknown
<220> FEATURE:
<223> OTHER INFORMATION: sequence of retrotransposon from unknown
      organism

<400> SEQUENCE: 110
acccgtctag tatcagctcg tcgttttcaa gtatgttgtt catgtccagg ttgttgtctg      60
tggtggcagg tactttgtcg tccaattta ggtcctcgta gtccatgttg gacaacatgt     120
cttcgtcggt attgccgttg atgtcaaagc caataaagtc gtcaaagttg tcaaactttt    180
gtggggcggt ctctgctttc tttctggcct ctgctttctg tttgttttac acttttcgtc    240
```

```
tttaattata gtttcgaaga atttcctagg aacttaagaa tttgtaggag aatgctaata      300
agaagttgta tttcttaatt gaaagttata attgtaagaa tatattgtat aaaagatgag      360
ttgataaaga aaagatataa aaagtcctat aaaaaagtat tgtaaaataa agtatataa      420 aaatcaagta aaatagaata tttgcacaca aattaaaagt agtgcaaatt tgacagaaaa      480
gttgttggtt tgtgcactat tttgtgtcag aaactgatct atgaaaatga tggttattat      540
gagaatgaaa aattttttctt tcacacatca ggtgatgaca gaactaaact atattgtgta    600
gtataaataa gggatgaaat accaacatcc cagaatatca actatataga aggcaggagt     660
ttcaatatat atcttgtgaa taataacttc gttctaattc actatacaca actaggcgtg    720
tacacgctca atctcaggta aagaaagttt atattccatc aaaagtaaaa taaaacactt    780
cttcgcttcc tctgctttct tggcttgctc tgccttcttg gcctcttctt ccttctttct    840
tgccgcttct tctttgactt tcaattcgtc aagtttcttt ttcttttcaa ccataacgcc    900
gagacaccac tctgcatcat tgagtttcga cactgtttgg tctagaatag catggaagtt    960
ttggatttcg ccgt                                                       974
```

<210> SEQ ID NO 111
<211> LENGTH: 3868
<212> TYPE: DNA
<213> ORGANISM: Unknown
<220> FEATURE:
<223> OTHER INFORMATION: sequence of retrotransposon from unknown
      organism
<221> NAME/KEY: misc_feature
<222> LOCATION: (1)..(3868)
<223> OTHER INFORMATION: 'n' can be any nucleotide 'a', 'c', 'g' or 't'

<400> SEQUENCE: 111

```
aatgaagtaa cttttttcaa ggcaacatct attcttttat taatctcgac gtctgtttga      60
ttaagttgct ctaacatttt atttagatcc ttctctatat tttctgcaat atcaaacacc     120
gattgctttt tgtctgaagt tgctggtata tcaccacttc cgccaattgt cgtatttcca    180
ctgtcctttg ttactgacag attggcactg acattacctg aattgttcat gtttgctgtt    240
gaaagagcag gaactgtact tggataagca gccgattcaa aagaagatgt ggacatgagt    300
gtcaagaaaa tgtgtagaat cagtacaaga ctggaaaaca gaaggaacaa agtgaactgg    360
atattgtagt tttgttgata gtactcgcga gctttaattt ttttttgtaa ctggcggaat    420
cagatcttat gcaatactca aatccaaaga aacagtcaat ccagatgaaa ggcatgtaat    480
cgctagtttt cataaacaga atcatgttac tagtcatatt ttctataaaa attcaatact    540
tcattctttt tgttcaatac taactataaa tgcttacaaa tagattcaaa tttcaaccag    600
atccaccact tcattaggct caaccaattc ttcataaata gaaacgtctt cctcagccaa    660
gcttaattga tgggaaaccc tagcttgcat tgaaggaaaa atacataatc caaataanca    720
actgtctttc caaatattct caaaattcaa cttcaccgtc tttcaccaag caggatctcg    780
tgattggacc aattctaatt cagaagttct tctcacacaa gtccgaacga ctcgatccat    840
cataatggat acatcgttca cgttgccacc aaatcgaatg actctgtttg cacctgtaca    900
aagtagaaca tatgcatgga aaagtaaaac tagtaaaacc gcataatgaa accataataat  960 catcatatgt tgattgagtc tgaaccccat caaatataaa acaaaagtga gtttaaccat   1020
agttataaga agcagtcttc cgttggtgta taatctatcc ataagatcgt caatttcagc   1080
atcttcaaca tcaatgttat tagcgtcacc tggaacggct tgttcattag attctgattc   1140
```

```
caggtcacta ccaatatcat acatcattac tagtactttt tgaatcaatg gctcaccaga   1200
agccagttta aacaccttgt gaacttttgc tgcacccata ggaccgagta gtagataagg   1260
atcgtgcaag ccgttatcca caacaatgca ttgtgctgta cccaagctta ctttcttcac   1320
aatattgtct actttcaaag taagttcata ctcaacatta gacaagtcat cctgtttcac   1380 tagaatttt ttccctgaat gctgttcaac catagtatcg tacgatgttc cctccatttc   1440
ccatgtggat ccaccacgta cctgaatact ggcaggttta tgggtctat gttaggagt   1500 tgaagactct gatggattat tgacaaatgg aatagagtct tgttgacttg gcaccagcgt   1560
ttcataattt gaaggtgaag gtactgggtt agccgaggtt ggtgatgttg aaatatcact   1620
atcaattcct tgttctgagg atgagctagt agcagttgga tttgttgtgc ttcttgcagc   1680
agacaaatct gatgttgatt ctaatggcac tgaattcgac agcgccaaat tgggttgctg   1740
taaagagtca ttggtggcag ggagaaatct aaatctatca tttgactgaa agtccttcca   1800
aaattctctg ctcaacaacc caccagtccc atttacatgt tcatgctttg taagttcaa   1860 ttttatgaca ctgttattct gttccaaaag ctcttgattc aatcccaaca attcataaac   1920
actagcttcc tcttcttgaa atgaggttgg tattatattc ccttcgtatg atagtttat   1980 ttgttctata aatgtacgtg tgacagaacc ttcgtcattc ttagctatta ttaattgctt   2040
gagttgctta accgtagttc ggtcatttat ttcaatcatt gacttttcat tctgtaaatt   2100
aggaagattt gactccaaca aaacccggaa tcttttgaaa ttactattca tttctaaagg   2160
tttgggttgt gtgattgaag ctaatggtgt gtgtactaag tggtttttca attataaata   2220
ttgatgaact acactatata tacactgaga aaaacacgac caaaattgac accgcactaa   2280
aaacacggaa ttaccgtatt cttttgtta acgattttgt ttcattacac gactgtcgtt   2340
atacacacat ttagagcaaa ttatttaga ttgatcagtg ttagcaactg gctatcgata   2400
atagagtacc ttcccgagtt agaatgtctt attagaacaa caattgtttc atataaattt   2460
gtcgcaaagc acacgtaata tactatatgg aagggctaa gtaaaaatgt cccgtttctt   2520
cttaatatga gaactcgtgt acgacacaat ttgctgtgtt gttaatcgag tatgctacaa   2580
cctgaaaatg gaccatagac ccaaactact tctctctttc tagcaccaca aaccccacaa   2640
ttagcacaac aatgaattgg acttcacttg tatatctatg gttcattttc aaaagcatat   2700 tgctgactt aacatcacac caactcaaga gcaaagtggt attcctagat actactatcc   2760
tggatgaagt ggcccgaagc tatttgggat cagaggacgg aaatgttaca catggtaatt   2820
atgaaatatt gtcaattgca aatgggcgcc aatgacggaa acatcacatc atatttatgc   2880
cagttgccaa gaaccaaaaa aatggcacca acaaaaccca agcccaccat gtcagttcat   2940
gaattgaaat cgcgagctat tgacttgata tcggaatcct ttgtcgaagg taccagttgc   3000
gtattttctt tcaacttgca tgcaaattat tggactatag gctattgcca tggaatcaac   3060
gttattcaat tccatgagaa tttggatgat tttataagcg gaattcataa accccattct   3120
ccaaatcatg tatatacatt aggcaatttc ctgaagcaaa cactgccatt agaattcgag   3180
tttgatacta agaacgcac aataagtcaa agattgttag gagaagtttg tgatttgaca   3240
ggagaaccac gtaccattga caccatttat agatgtgacc atatacttga aattgttgaa   3300
ttaacagaga taagaacatg tcaatatgag ttacacataa acgttcctaa gttgtgcctg   3360
ttgccggaat ttaaaaggac taaccttgaa gaaggtgtct cagaaatact ctgtacaaga   3420
attgaataag cattaaattt aataaaaaac atcaaaagt gtatgtcaaa gtattttac   3480 cttgtaatt agtagtttgt cagtttctat ataaacatag ggtagttcgt atatacgata   3540
```

```
tcggagcgat tctaaataag tcgtggaaat tggccgacaa tgggatttga attttacttg      3600
tgtgtgtgtg tgtgatctga ataatagtag tgctaaacaa cttaaattaa agaaaaaaag      3660
acaaaacaaa aaaaattaaa tctgcttatt gaaaattttt cgaaataggc taacccgtgt      3720
ttattagata ttagatagta cgatttgttc aagtgtcaaa gatagcaaat ttttattgtt      3780
tcttcttttt tatatacagc ttgttttaat ttcaggatca ttttacacta acctactcat      3840
cagcctattt taatttatcc ttttggct                                         3868
```

<210> SEQ ID NO 112
<211> LENGTH: 469
<212> TYPE: DNA
<213> ORGANISM: Unknown
<220> FEATURE:
<223> OTHER INFORMATION: sequence of retrotransposon from unknown
     organism

<400> SEQUENCE: 112

```
taacgaatga atataaaata cttgtattat gtagtgccaa taaaagttga acggtcgca        60 ctactttta gtcctgttgg tttgtgcact attttgtgtc agaaactgat ctatgaaaat       120
gatggttatt atgagaatgg aaaacttttc catcacacat caggtgatga cagaactaaa      180
ctatattgta tagtataaat aagggtatga aataccaaca tcccagaata ttaattatat      240
agaagggaag gagttttaat atatatcttg tgaataacaa cttcggtcta attcactata      300
cacaactagg cgtgtacacg ctcaatctca agtaaagaaa gtttatattc catcaagtcc      360
catctgttaa atattttgt atctttttat ttttatttt ttttctttta atttcattta         420
catacattaa cacatctact aaccatatat cacgagatac aaaggcaag                  469
```

<210> SEQ ID NO 113
<211> LENGTH: 4545
<212> TYPE: DNA
<213> ORGANISM: Unknown
<220> FEATURE:
<223> OTHER INFORMATION: sequence of retrotransposon from unknown
     organism

<400> SEQUENCE: 113

```
tgacgatcct gtatatttcg tcataattca cacattctta aaattatgca cacatccttg       60
aaatgtgtta atattcccaa cattatcaat tatatgtgtt cagaattggt tgcaaagtta      120
tcaactcaat tcacgctata taaaccttac aaattctcta cattttttata tttttttata     180 ttggcttttc ttttagaatc aatcaatact tttttttatca tttagataca tctttcatct    240
attaatagat tatctttcta tatatcaaaa cacgacacag tcacgtgcca aaaaggatat     300
aagaaggaac ttcagaaaat taattttctg attatactac ttactagatt gcataaagtc     360
aatatctgat tgatacaact tggttcatta ttcataaaac ttaacaacta attcaacaag    420
gaaacccaac aaaaaaatcc aaataaaata atcaggaaaa tattataatt aattaattac    480
aaaaaaaaac aaaaaaatac acacacacat acacacacac aaaatcttgt tgcaaaaaaa   540
aaaaaataat aataatataa taagaattaa ttaacaatgt cgtttccacg gacacattca    600
ccaagaccat ctggttcacg agaacaggaa gatctcacac tgatgattaa agcttttaga    660
gattcaatgg aagctaagct tgacttgcat tcgcagaagc ttactgcttt ggtagcaaac    720
attcccagaa cggacgaagg gtttgaagat ttatcacaaa ggatcactgt tcttaaaaat    780
catcaaaaag cattttttgcc caaacaagaa aaagaaatcg gaagtcttct ccacagacaa   840
```

```
agagaggaag aaggtgatat taaggatttc aaaacagtcg ttggtgaaga aaaagaagaa      900
ttgcaccagg ttgaagattt cgttttaaaa gatcaagaag aattacgaaa cgtcgaaaag      960
aaagttttga aagaagaaga agaattgcaa aaagtggaag agtcaatgga aaaggaaaaa     1020
caagagttat accaggttga agactttatt ttgcaaagag atgagacggt aaagaaactt     1080
ggagaaagca atcaatctca acaggaacca tatacacctg caacttctgg ttcggatcag     1140
agattcagat ctcaacaacc taacattgga aataccttag cgcaggatct agcattaatt     1200
ccaaaattag atctggaaat ttgcaaaatt gcagtcaaat atccaaaatt atttgaaaca     1260
aaattaagac caccaccacc cagagacttt caatataaaa ttcaactcac agaccacact     1320
caaatttatt caaaaccata taaatgcaat caagaagaac aagctctcat taaggatttc     1380
atcaatgaaa aattagaagc aggcgttttg gtaccagctc caattgatgc ttggttacac     1440
ccaatatttc caatcagaaa aaccaatgcc aaccaatcct ccaccaaaat agcagttgat     1500
ttaagacgtc tcaataaggt cacagtacga atgtacactt atccaacaga cacaaaagac     1560
ctcttatcct cactaacaga ttcccactat tttagcgctt tagacttaaa gaatgcgttc     1620
tatcaggtaa gcatacacaa ggatagtata aatatttttg ggatttcaac atccgagggg     1680
aattattgct ttacaacttt accgtttgga gcaatcaatt ccccaaccat ctttactaac     1740
tttgtgagac agattttaga ggggatccca tgtatattta tatacatgga tgatatcctc     1800
atccatacta aaaccttaca tgaccacatg tcattactca ggagaatcat ggagaaacta     1860
aatgagcatc agtttcaaat gaattataac aagatgcaat tattaacaac aaaaatcaat     1920
ttcttagggt acagcattca agcgaacaaa atatcaccag atatttccaa aattcaagca     1980
atacaaaatt gggaattgcc cacgaccact actcaaatca gagcatttgt caatttcagc     2040
aaccactttc gcatcttcat cccagaaata gcaaaattta ctaatccatt aaatgaatta     2100
ttgaagaaca acaatggtaa aaacataaag attgaacaca cccaagcatc cattgatggt     2160
tacaaggcat taaaagccgc catcattgga ttgccgacgc ttcaactttg caatccaaaa     2220
ctaccaacca tcatttttcac agatgctagc cacatggtag taggaggata tttatgtcaa     2280
ccaacattca gaaatgacaa agaagtcctt gtcccaattg cattttcatc acataaaatta    2340 acagaaacac aaagcagata tgctgctatg gaaaaggaac ttttggcaat tattgtgata     2400
ttggaaaaat ttagatatca ctgcagcaat acggtagaga tctatacaga ttatcaaagt     2460
ttggcatcat atttgataaa gaaaactact ccaccaccga gaattgctag gttttttagat    2520 ctaattggat cattttcccc aaaagtgtac tatttaagtg gaaagaaaaa tttcgttgct     2580
gatatcatta aagatatca aactcaaaat attaaggaat tggtagatga agacaagata     2640
ctaggacaga cttttacagt caagagaaat ttgaaacaac aactattacc aagattggaa     2700
gcaattgaat tggaaaatct taatgaatca caggttcaca aaatccaaac ttcattagaa     2760
caacaacaac aacatgattt ggaagacaat gatgaagagt tacctctcca actgttttaaa    2820 ttaatgaatg atgagttatt tgtaatcatt aacaaccaac ttttaaaata ccttccaaga     2880
ctggaataca atgatatttg tcaaacaatc catgacaaac accatccatc aactagagta     2940
acagactact tatgcacact cgcatattgg catcctgacc atctattaat tgctacaaac     3000
attacgagaa agtgtcacta ttgtcaacta aacacgtcaa ttcgtgaggc cattagacca     3060
taccgaccac ttgaaccact caaggcattt agcagatggg gaatggacta ctctggacca     3120
tactttaaca cagtccaaca caggtacata ttagtagccg tggaatatgt cactggttta     3180
actattgcag taccaacatt gcacaaagac gcagataacg caatcagtct tttacaatca     3240
```

```
atcattctga tcatgtcagc acctacagaa ttagttacag atcaaggtaa aaaaattttc    3300
atcacaagct ttggctaccc tatgtgacca gaataacata caacaccata ttacctccgc    3360
ccaccaccca cgtgggaatg gtcgggttga gaaggtgaac cacctattga agaaaatatt    3420
gaaagcatta actaacgata cgatgcaaga ctgggattta aaactatatg acgctttaag    3480
aatctacaat gctacaccta caattttttaa ctacactcca ctttatcttg cacttggaat    3540
tgaaccacac cataatttaa atcaattaca aaagattta attgaaaatt tgcaaaaaga    3600
attgccccca gaggtccaat ccacagaaga acacgaagaa acccaaatg atgaacaaca    3660 agaagagggc agagaacaac aaatttcaag agaagaacaa caggacggca gagatcttgt    3720
acacttaaga atttacgaat tggaagcaat taagaaagct cgcaagttac acacaaattt    3780
gaaaacacga agaaacgcag tccaaaatat gttaaaggaa ccatatggca ttccagcacc    3840
ttttacaaaa ggacaatggg tatacagaat tagagctaaa gcacgaaaat atgaaccaaa    3900
tttcgatggt ccatatcaag ttcaagaagt attaggtaaa ggtgcttata aattgagaga    3960
catcactgga agagaaaaag gaatctacaa tcaggatcaa ttgaagttag catattcagc    4020
agacaacgac ccaatacagg ttttttagttc tttcaataaa gaatatgatc gagtacaaca    4080
aaaattgtta gacaaaattc aatcggaaag agatcatcaa ttaaattgtt tgtcagtcca    4140
acatttacac agacaaagaa ggttactcga tatatccagc tgtcttgagc aaattctgca    4200
ataatttcgc taatcattgg aggaaagggt agatgacgat cctgcatatt tcgtcataat    4260
tcacacattc ttaaaattat gcacacatcc ttgaaatgtg ttaatattcc caacattatc    4320
aattatatgt gttcagaatt ggttgcaaag ttatcaactc aattcacgct atataaacct    4380
tacaatttct ctcatttta tatttttttta tattggcttt tcttttagaa tcaatcaata    4440 ctttttatc atttagatac atctttcatc tattaataga ttatctttct atatatcaaa    4500
acacgacaca gtcacgtgcc aaaaaggata taagaaggaa cttca                   4545
```

<210> SEQ ID NO 114
<211> LENGTH: 916
<212> TYPE: PRT
<213> ORGANISM: Unknown
<220> FEATURE:
<223> OTHER INFORMATION: sequence of retrotransposon from unknown
      organism

<400> SEQUENCE: 114

```
Met Ser Phe Pro Arg Thr His Ser Pro Arg Pro Ser Gly Ser Arg Glu
1               5                   10                  15

Gln Glu Asp Leu Thr Ser Met Ile Lys Ala Phe Arg Asp Ser Met Glu
            20                  25                  30

Ala Lys Leu Asp Leu His Ser Gln Lys Leu Thr Ala Leu Val Ala Asn
        35                  40                  45

Ile Pro Arg Thr Asp Glu Gly Phe Glu Asp Leu Ser Gln Arg Ile Thr
    50                  55                  60

Val Leu Lys Asn His Gln Lys Ala Phe Leu Pro Lys Gln Glu Lys Glu
65                  70                  75                  80

Ile Gly Ser Leu Leu His Arg Gln Arg Glu Glu Gly Asp Ile Lys
                85                  90                  95

Asp Phe Lys Thr Val Val Gly Glu Glu Lys Glu Glu Leu His Gln Val
            100                 105                 110

Glu Asp Phe Val Leu Lys Asp Gln Glu Glu Leu Arg Asn Val Glu Lys
        115                 120                 125
```

```
Lys Val Leu Lys Glu Glu Glu Leu Gln Lys Val Glu Ser Met
    130                 135                 140
Glu Lys Glu Lys Gln Glu Leu Tyr Gln Val Glu Asp Phe Ile Leu Gln
145                 150                 155                 160
Arg Asp Glu Thr Val Lys Lys Leu Gly Glu Ser Asn Gln Ser Gln Gln
                165                 170                 175
Glu Pro Tyr Thr Pro Ala Thr Ser Gly Ser Asp Gln Arg Phe Arg Ser
                180                 185                 190
Gln Gln Pro Asn Ile Gly Asn Thr Leu Ala Gln Asp Leu Ala Leu Ile
            195                 200                 205
Pro Lys Leu Asp Ser Glu Ile Cys Lys Ile Ala Val Lys Tyr Pro Lys
        210                 215                 220
Leu Phe Glu Thr Lys Leu Arg Pro Pro Pro Arg Asp Phe Gln Tyr
225                 230                 235                 240
Lys Ile Gln Leu Thr Asp His Thr Gln Ile Tyr Ser Lys Pro Tyr Lys
                245                 250                 255
Cys Asn Gln Glu Glu Gln Ala Leu Ile Lys Asp Phe Ile Asn Glu Lys
                260                 265                 270
Leu Glu Ala Gly Val Leu Val Pro Ala Pro Ile Asp Ala Trp Leu His
            275                 280                 285
Pro Ile Phe Pro Ile Arg Lys Thr Asn Ala Asn Gln Ser Ser Thr Lys
        290                 295                 300
Ile Ala Val Asp Leu Arg Arg Leu Asn Lys Val Thr Val Arg Met Tyr
305                 310                 315                 320
Thr Tyr Pro Thr Asp Thr Lys Asp Leu Leu Ser Ser Leu Thr Asp Ser
                325                 330                 335
His Tyr Phe Ser Ala Leu Asp Leu Lys Asn Ala Phe Tyr Gln Val Ser
                340                 345                 350
Ile His Lys Asp Ser Ile Lys Tyr Phe Gly Ile Ser Thr Ser Glu Gly
            355                 360                 365
Asn Tyr Cys Phe Thr Thr Leu Pro Phe Gly Ala Ile Asn Ser Pro Thr
370                 375                 380
Ile Phe Thr Asn Phe Val Arg Gln Ile Leu Glu Gly Ile Pro Cys Ile
385                 390                 395                 400
Phe Ile Tyr Met Asp Asp Ile Leu Ile His Thr Lys Thr Leu His Asp
                405                 410                 415
His Met Ser Leu Leu Arg Arg Ile Met Glu Lys Leu Asn Glu His Gln
                420                 425                 430
Phe Gln Met Asn Tyr Asn Lys Met Gln Leu Leu Thr Thr Lys Ile Asn
            435                 440                 445
Phe Leu Gly Tyr Ser Ile Gln Ala Asn Lys Ile Ser Pro Asp Ile Ser
        450                 455                 460
Lys Ile Gln Ala Ile Gln Asn Trp Glu Leu Pro Thr Thr Thr Gln
465                 470                 475                 480
Ile Arg Ala Phe Val Asn Phe Ser Asn His Phe Arg Ile Phe Ile Pro
                485                 490                 495
Glu Ile Ala Lys Phe Thr Asn Pro Leu Asn Glu Leu Leu Lys Asn Asn
                500                 505                 510
Asn Gly Lys Asn Ile Lys Ile Glu His Thr Gln Ala Ser Ile Asp Gly
            515                 520                 525
Tyr Lys Ala Leu Lys Ala Ala Ile Ile Gly Leu Pro Thr Leu Gln Leu
530                 535                 540
```

-continued

Tyr Asn Pro Lys Leu Pro Thr Ile Ile Phe Thr Asp Ala Ser His Met
545                 550                 555                 560

Val Val Gly Gly Tyr Leu Cys Gln Pro Thr Phe Arg Asn Asp Lys Glu
                565                 570                 575

Val Leu Val Pro Ile Ala Phe Ser Ser His Lys Leu Thr Glu Thr Gln
            580                 585                 590

Ser Arg Tyr Ala Ala Met Glu Lys Glu Leu Leu Ala Ile Ile Val Ile
        595                 600                 605

Leu Glu Lys Phe Arg Tyr His Cys Ser Asn Thr Val Glu Ile Tyr Thr
    610                 615                 620

Asp Tyr Gln Ser Leu Ala Ser Tyr Leu Asp Lys Lys Thr Thr Pro Pro
625                 630                 635                 640

Pro Arg Ile Ala Arg Phe Leu Asp Leu Ile Gly Ser Phe Ser Pro Lys
                645                 650                 655

Val Tyr Tyr Leu Ser Gly Lys Lys Asn Phe Val Ala Asp Ile Ile Thr
            660                 665                 670

Arg Tyr Gln Thr Gln Asn Ile Lys Glu Leu Val Asp Glu Asp Lys Ile
        675                 680                 685

Leu Gly Gln Thr Phe Thr Val Lys Arg Asn Leu Lys Gln Gln Leu Leu
    690                 695                 700

Pro Arg Leu Glu Ala Ile Glu Leu Glu Asn Leu Asn Glu Ser Gln Val
705                 710                 715                 720

His Lys Ile Gln Thr Ser Leu Glu Gln Gln Gln His Asp Leu Glu
                725                 730                 735

Asp Asn Asp Glu Glu Leu Pro Leu Gln Ser Phe Lys Leu Met Asn Asp
            740                 745                 750

Glu Leu Phe Val Ile Ile Asn Asn Gln Leu Leu Lys Tyr Leu Pro Arg
        755                 760                 765

Ser Glu Tyr Asn Asp Ile Cys Gln Thr Ile His Asp Lys His His Pro
770                 775                 780

Ser Thr Arg Val Thr Asp Tyr Leu Cys Thr Leu Ala Tyr Trp His Pro
785                 790                 795                 800

Asp His Leu Leu Ile Ala Thr Asn Ile Thr Arg Lys Cys His Tyr Cys
                805                 810                 815

Gln Leu Asn Thr Ser Ile Arg Glu Ala Ile Arg Pro Tyr Arg Pro Leu
            820                 825                 830

Glu Pro Leu Lys Ala Phe Ser Arg Trp Gly Met Asp Tyr Ser Gly Pro
        835                 840                 845

Tyr Phe Asn Thr Val Gln His Arg Tyr Ile Leu Val Ala Val Glu Tyr
    850                 855                 860

Val Thr Gly Leu Thr Ile Ala Val Pro Thr Leu His Lys Asp Ala Asp
865                 870                 875                 880

Asn Ala Ile Ser Leu Leu Gln Ser Ile Ile Ser Ile Met Ser Ala Pro
                885                 890                 895

Thr Glu Leu Val Thr Asp Gln Gly Lys Lys Ile Phe Ile Thr Ser Phe
            900                 905                 910

Gly Tyr Pro Met
        915

<210> SEQ ID NO 115
<211> LENGTH: 253
<212> TYPE: PRT
<213> ORGANISM: Unknown
<220> FEATURE:
<223> OTHER INFORMATION: sequence of retrotransposon from unknown -continued

```
<400> SEQUENCE: 115

Met Gln Asp Trp Asp Leu Lys Leu Tyr Asp Ala Leu Arg Ile Tyr Asn
1               5                   10                  15

Ala Thr Pro Thr Ile Phe Asn Tyr Thr Pro Leu Tyr Leu Ala Leu Gly
            20                  25                  30

Ile Glu Pro His His Asn Leu Asn Gln Leu Gln Lys Asp Leu Ile Glu
        35                  40                  45

Asn Leu Gln Lys Glu Leu Pro Pro Glu Val Gln Ser Thr Glu Glu His
    50                  55                  60

Glu Glu Asn Pro Asn Asp Glu Gln Gln Glu Glu Gly Arg Glu Gln Gln
65                  70                  75                  80

Ile Ser Arg Glu Glu Gln Gln Asp Gly Arg Asp Leu Val His Leu Arg
                85                  90                  95

Ile Tyr Glu Leu Glu Ala Ile Lys Lys Ala Arg Lys Leu His Thr Asn
            100                 105                 110

Leu Lys Thr Arg Arg Asn Ala Val Gln Asn Met Leu Lys Glu Pro Tyr
        115                 120                 125

Gly Ile Pro Ala Pro Phe Thr Lys Gly Gln Trp Val Tyr Arg Ile Arg
    130                 135                 140

Ala Lys Ala Arg Lys Tyr Glu Pro Asn Phe Asp Gly Pro Tyr Gln Val
145                 150                 155                 160

Gln Glu Val Leu Gly Lys Gly Ala Tyr Lys Leu Arg Asp Ile Thr Gly
                165                 170                 175

Arg Glu Lys Gly Ile Tyr Asn Gln Asp Gln Leu Lys Leu Ala Tyr Ser
            180                 185                 190

Ala Asp Asn Asp Pro Ile Gln Val Phe Ser Ser Phe Asn Lys Glu Tyr
        195                 200                 205

Asp Arg Val Gln Gln Lys Leu Leu Asp Lys Ile Gln Ser Glu Arg Asp
    210                 215                 220

His Gln Leu Asn Cys Leu Ser Val Gln His Leu His Arg Gln Arg Arg
225                 230                 235                 240

Leu Leu Asp Ile Ser Ser Cys Leu Glu Gln Ile Ser Gln
                245                 250

<210> SEQ ID NO 116
<211> LENGTH: 2093
<212> TYPE: DNA
<213> ORGANISM: Unknown
<220> FEATURE:
<223> OTHER INFORMATION: sequence of retrotransposon from unknown
      organism

<400> SEQUENCE: 116
ttttcccaca aataatatca acaatatttc atattttcca tcatgctaga gaagatcaag      60
ttataactac attaattggt tatgtttata aattgactca aatttgttta aaatttgaat     120
tacattctga aattagaaaa atcattgata aattaattaa atttactact ttaactcaca     180
cacctaaaaa ccttaatgaa attttaatta ctgaagtcaa attagataat aaaaccgaaa     240
tttatgttag tgattatgct tgttcatttg gtcgtgattt taaagctcaa ttatcaacgg     300
tggttttatt taaataatc aagaaaaata atcttaaatt gaaaaattgg gataaaattg     360
tggaaattat tgaaaatta tatcaatatt cattgattat tgatgagaag gatactacta     420
ctactactac taccaatgat aataaggaag gtgatgatga aaaggataat aaggaagcca     480
```

```
ctgttgagac tgacaactca atattgaaat tattgccttc aaaagatatt aaaaaattcc      540
ctattaaaag aataactaat gatctgtttc tttcaatatt gaaaaattta attgataatc      600
aacctactga agaagaaatt caatcaactt tagcagctat ggattgtatt aaatcattag      660
atatcttgaa tgtattaaga attgttgctg aatccaagaa acaagctaac taaatctaaa      720
caatctaaac atctaaacat ctaaatatat atatatatct attgtattat tatatttgta      780
aaattttgta gtttgcagtg gttggaataa atgataggag gatgttccat ttgtgataca      840
ctatttctac aaactgtcaa attcaataat caaacttgtt gccaagaaaa gataacaaag      900
aaggctattt ggtttacaag gtacaacaag aacatgggta tatcaccacg atagtttagt      960
aattttgtaa atcttctttc tctgttttac ttagcctcat ttagtccttt ctttcagttc     1020
caaagtagga tgtgcaacat ggccaattat caacaataag ctagcattgc ataatggtag     1080
tgattgtact gaagagaaca atacactaat ctattccatt gacgacggaa taagtggact     1140
gataattcac atggataatt cagtccactc tgagaggaat ttcctcttta tataatagaa     1200
aattcctcaa ggtattagat tgtatatttt ctatagataa ctaaccttga acacaagaat     1260
actatcgcct tcgttgcag attatcgctc aaaactttc aataactttt gggtcttttt      1320
ttaacaataa ccaataaatc attacaaaga attacaaaaa gggctataat gacaaatttc     1380
acatagataa gaaatatagg ttttattact ttttgcataa ttgctgactt ctattttggg     1440
tttggagata tttagaacgt ttgattgtgg gggtattact tccaaaaaaa acaaaaattt     1500
gtaaaccctg acgatcctgt atatttcgtc ataattcaca cattcttaaa attatgcaca     1560
catccttgaa atgtgttaat attcccaaca ttatcaatta tatgtgttca gaattggttg     1620
caaagttatc aactcaattc acgctatata aaccttacaa attctctaca ttttatatt      1680 tttttatatt ggcttttctt ttagaatcaa tcaatacttt ttttatcatt tagatacatc     1740
tttcatctat taatagatta tcttctata tatcaaaaca cgacacagtc acgtgccaaa      1800
aaggatataa gaaggaactt cacccccttg ctcttcttat tattgtgtgt ggtgtaagtt     1860
cagcgggtag tcctacctga tttgaggtca aagtttgaag atatacgtgg tggacgttac     1920
cgccgcaagc aatgtttttg gttagaccta agccattgtc aaagcgatcc cgccttacca     1980
ctaccgtctt tcaagcaaac ccaagtcgta ttgctcaaca ccaaacccag cggtttgagg     2040
gagaaacgac gctcaaacag gcatgccctc cggaatacca gagggcgcaa tgt            2093
```

<210> SEQ ID NO 117
<211> LENGTH: 2099
<212> TYPE: DNA
<213> ORGANISM: Unknown
<220> FEATURE:
<223> OTHER INFORMATION: sequence of retrotransposon from unknown
      organism

<400> SEQUENCE: 117

```
acatttttca atattgaaag ataaatatag cattccaaaa aaaaaagtga cttctgtgtt       60
cacatttaat caacaaattc ccacaacagc ttgcacaaac tgctatctac taggcttacg      120
agacacaagt gttaccaaat agtgatacac ttatactttta actcatagaa gagaattaga    180
tactcggaat attactcaac atattcccaa aataatcgta aagataaatc tttgagagtt     240
aatactagag agctcaattc taggcacaaa taccacactt tttacgagta gtgggtaaga    300
gttcgtacac atgatgcaac aactttctag tacctacttg cacaaagtgt agtttgcaaa     360
aaactttgct cctccatagc atgtatctca atactccaga aaatccgata aagcaactct     420
```

```
ccgatggtca tgcaagtatt cgcctttctc ttttgtagat ttatgtagtt tcaagatgac    480
actgaactcc tgagtattaa agtagattaa taatagaagg tattgcctaa tgccgagaaa    540
gtaaacacca gatcaaatat atgctttact atgaaacttg tttgtgttgt gtggattggc    600
caaacaaaga tcatgctgat atctgtaaat ctctggaacg ggggatagga ataaacttga    660
aacaatataa acgaggtgtt ttccttttct ggtgcttgat ttgaaacgtg tacattccct    720 cttttttctct tagttaacaa tattgcataa tagtgaggat gtgagcgtaa gacagaaagc    780
agcagcatgg gaatagttca gcctattatt gtcgcaaagc tgcatattgc ttcttctatt    840
aaacttttga atcttctctt ttaagtaaat taattaataa cttgattgtt ccatttacat    900
ccattttcta tttctgtgta atcttcgttt attttgcggt ttgaatactt ccaaatttaa    960
ttaaatttgt tcctaaaata gaagctgtta tacttgcgcc gccaaaccca ttttaatagt   1020
gatccttatt tcaatttaat ttgttcacgt tatatctctg aatttgatta atacttgcta   1080
cagatatttg gaaatcataa tttatgattt ctccggaatg taactgagtg gccagaagat   1140
atatagtaac acataaatac gtacacaaca ccagaacaac cgcaacattc aagtggaact   1200
agtatgtgtt gaaaaaacag acaaattaat cgggatagga agagatggga aaggggggtg   1260
agagaaaagc aaagaaaaaa aaaaagaaa aaaagaaca aaaatcaaat ggtacaaaaa   1320
aaaagacaca tcttctacac aattaacaaa aactgcctcc tgatggcaag aaatctacct   1380
cacatacata cttaaatgga ataagaaag taatctataa aaataattta acatgactaa   1440
cgtatttcaa gtaaaaaggt caaaattaga gaacccacca caatcaacta ttttctactc   1500
tcaattgttt tttctttta gttcttataa ttatcaacat tttccttact caaatctttc   1560
accttgacga tcctgcatat ttcgtcataa ttcacacatt cttaaaatta ttcacacatc   1620
cttgaaatgt gttaatattc ccaacattat caattatatg tgttcagaat tggttgcaaa   1680
gttatcaact caattcacgc tatataaacc ttacaatttc tctacatttt tatatttttt   1740
tatattggct tttcttttag aatcaatcaa tactttttt atcatttaga tacatctttc   1800
atctattaat agattatctt tctatatatc aaaacacgac acagtcacgt gccaaaaagg   1860
atataagaag gaacttcaac ctgttctttt ctttttatt tttaaatttg attattatta   1920
attttttttt cctttctttc cttaccaatt tttctttgct tgacttattc aaaaggtgaa   1980
acagggattt tccaattcac atagccaaaa gtatttttgg tttccacatt ccttcaaaac   2040
aatatttgtg ctacctcccc cttcccacca aaagtatccg attccaacca taaagcagc   2099
```

<210> SEQ ID NO 118
<211> LENGTH: 3284
<212> TYPE: DNA
<213> ORGANISM: Unknown
<220> FEATURE:
<223> OTHER INFORMATION: sequence of retrotransposon from unknown
organism

<400> SEQUENCE: 118

```
taataagtac caactaaatc aaacaagcg accaaattga ataataggaa gacaaaaaaa     60
aaagagagaa aacagtacca aaatagatat agtatgtagt tacatttact caacatagtt    120
attaggtaca aatccaattc tgtagctctc atcatcaatt cttgagactc caatcaacca    180
atttaactca tctgaatgat acaatgtatc aatattctga aaatctaata aaatttcaat    240
attatcgccc tgtttaaatg acaaatcacc tggttcataa ccactaaaat cgtattttgc    300
agttttcaaa actttattat cggtgttaat gttcaacttt tcaaaaaagc tttgtatcaa    360
```

```
attcaacttg taagtcaaac tcataggctt ttcaaacgta aaaggttcat actggattgg    420
cttggttgtg attgggcttt ccttaatctc attcttactg ccattgtata tccttcttaa    480
tttagcttcg gatgaatcat ggtttgagta cgaaacactt gacatggagc taattgatga    540
agcttctgac ataatagttg cgctctcgtc ttcaaaatct gatagcagta tagaatccat    600
agaatctgta gaaatagaat ataaccgtga ggcacctgca gaagacattg gcgagacaag    660
aacagaatgc tcataatag cagtgtttga cctaggtggc aattcaggac catctttctt    720
cggcactgct ggtaccttta tcttcctc atcgactaat ttccgtggat gatatgtttc    780
cgatgggttc atcgatggat cttggtactg tttgtatgcc accaagggat cgatttctaa    840
agtatcattg aatatgccat ttaccttgtc ttttgtattc acaacatgtt tcttttcaac    900
aaatttatta ctcatattac gccaaaatct gtaaagttc agcagcgaat cttcatcatt    960
gatctcctta tcaagcaaat ccgggtgttt ctcgtgcaca attgttagaa gagactctat   1020
ctgcaaacct tgtagctgtac tgttcagttc ccaatcgtct attatttcag tatacgattt   1080
tggtgaattt tctttaatca atccataaaa ctctgtaaaa tattgaaaag tatcagttag   1140
cttttttaaac gtctccaatt gttgacataa tatcatcttg gtaatatttt caacaaactc   1200
atcaagaaat gaaactatgt taggcaataa ttcaatacac ttttattca agctgttgaa   1260
cgcagcatca actgtctgat atgttgtttc taatttctca agtttgtcat tatctttctc   1320
gtccaatgga atcgctttct ggttcaattt ctcaattttg cgatgcaaat gatcctgttc   1380
tgttcgtttc atattacgct ttttaatcaa tttcaaagtt ttcttcaagt atttcttcat   1440
ttcgtcaatt ctatatttga gagattcgtc atatgcttcc caattatttt ccaaatcaaa   1500
ttttaagttc tccaccgtga tcaaataatt attcaactct tcatttatag attcattcaa   1560
aaattgcatc tcctttgggt gtacatgtgg gatttcttgt gttgcttgcc atgaatcaaa   1620
ttcttggtaa tactcgttga ttttatcaaa acgcaaagag tcttgaccaa tcaagttgat   1680
aaatcccttta ataattttaa tattcaggcc gagcacatgt ggcaagaaac tcttggacaa   1740
atggtgattc tgcgatgtga tgtacttcaa accagaaact gattgtttga tatcgtgata   1800
ataaatctca acaagttcat catccttatc gtaatctctg gtgtggaatg taactgtgtc   1860
ttcaatgttg taggatatat ttttgaattc tgattcagtg tacttgtacc cgtccttaat   1920
atgagttcca atattagacg atatcagaac aatattattt ttcaattgat ccacaaccat   1980
cgttgtcttt tatctatcag tagtaaattg aaaggtgggg ggatagaaaa tgaactagaa   2040
aaagaaagtg atgattctaa aaaaaaaatt tctcaaatac aaatactaag ataagtgttg   2100
attatatgac aacagggttg gaaagtcaat tattaattaa ggaccattgt agttaagctg   2160
cgcatagaag cagaaatgtg tgcaagaaca ggaacggacg ggaaaaataa taagctattt   2220
gaattaacac gaaataacgt gacctaaatt aaaataagaa taaggaaaaa aaaaaagat   2280
aggctttgaa ttaatggttt agtcactttt gaactgataa ttgttgatct tgaactagta   2340
atgattagtt taaaaccca acaggaacac ttagtttgga aaatatgagt ctccatagat   2400
cttctcttta acttatgcac ggagcttaaa agtacagtta gactcaaaaa cgaatatttt   2460
agtgcaatct ctacagtatt ggggtctgct cacaatcaag aagaataacc atttaaaggc   2520
gctctgttgt agaaattgtt tgtctctaca acgaccacg attagtaaga gaggggagga   2580
aagacaagaa aaaaggggt aatcatgata attgctaaaa agttgaattt tgtaaagtc   2640
cacccgagag ttggtagctt tttagattct agatctaaca gcagttctct gtaccgtgtc   2700
aaaatatcaa ttgtggatcc aatacagcta ttgtagtggt acttactgat gacgatcctg   2760
```

-continued

| | |
|---|---|
| catatttcgt cataattcac acattcttaa aattattcac acatccttga aatgtgttaa | 2820 |
| tattcccaac attatcaatt atatgtgttc agaattggtt gcaaagttat caactcaatt | 2880 |
| cacgctatat aaaccttaca atttctctac attttttatat tttttttatat tggcttttct | 2940 |
| tttagaatca atcaatactt tttttatcat ttagatacat ctttcatcta ttaatagatt | 3000 |
| atctttctat atatcaaaac acgacacagt cacgtgccaa aaaggatata agaaggaact | 3060 |
| tcaacctgtt cttttctttt ttatttttaa atttgattat tattaattt tttttccttt | 3120 |
| ctttccttac caatttttct ttgcttgact tattcaaaag gtgaaacagg gattttccaa | 3180 |
| ttcacatagc caaaagtatt tttggtttcc acattccttc aaaacaatat ttgtgctacc | 3240 |
| tcccccttcc caccaaaagt atccgattcc aaccataaag cagc | 3284 |

<210> SEQ ID NO 119
<211> LENGTH: 791
<212> TYPE: DNA
<213> ORGANISM: Unknown
<220> FEATURE:
<223> OTHER INFORMATION: sequence of retrotransposon from unknown
    organism

<400> SEQUENCE: 119

| | |
|---|---|
| aataatgtca atttattacc aagtttccaa agttgtcttg ttggtagatt atattgttta | 60 |
| cagattatgg tacgttataa aggtactaat aatgatcaaa atgaatttgc tgataatata | 120 |
| gttaaactag atgtaccaat attagtagga taaataaaga atcaataacc atggcacgtg | 180 |
| aatatgaaaa ggtaggggct aatataagtg taagtgtagt gtataaatta caaaacaaaa | 240 |
| aaggctgttg ttattaagat gagtcaactg tgtaagtgac gatcctgcat atttcgtcat | 300 |
| aattcacaca ttcttaaaat tattcacaca tccttgaaat gtgttaatat tcccaacatt | 360 |
| atcaattata tgtgttcaga attggttgca aagttatcaa ctcaattcac gctatataaa | 420 |
| ccttacaatt tctctacatt tttatatttt tttatattgg cttttctttt agaatcaatc | 480 |
| aatactttt ttatcattta gatacatctt tcatctatta atagattatc tttctatata | 540 |
| tcaaaacacg acacagtcac gtgccaaaaa ggatataaga aggaacttca tcttgattgc | 600 |
| gccgcaagca acaaacaata agccaaggaa agtatatact ccagatctac tatgagtatg | 660 |
| acacagctta ttaatgatca agtctacaac ttctactact aaacacgttc ttaacaaatc | 720 |
| aaacagtatt caattgtttt aaaaaacact atacaaaatt aatcaataaa aaacaactaa | 780 |
| agctaattct a | 791 |

<210> SEQ ID NO 120
<211> LENGTH: 4581
<212> TYPE: DNA
<213> ORGANISM: Unknown
<220> FEATURE:
<223> OTHER INFORMATION: sequence of retrotransposon from unknown
    organism

<400> SEQUENCE: 120

| | |
|---|---|
| tgggaattat tagaggattc tttttcagtg gatatataaa taacgaataa attccttgtt | 60 |
| taattatttt aagggaagaa aaaaaaaata atcaaacaac caaccctctt tataattaac | 120 |
| aagactacaa cttaataaaa atgggatatc caccaaattt caaaattgtt actaaatcat | 180 |
| taacagaaaa catttttatta gcatcaacgg ctttttcaag agttgataaa ttcaattttg | 240 |
| gtgctcgtat ggcggtattt aaatttcctc aatcaaataa aatcattta tggtcaccat | 300 |

-continued

| | |
|---|---|
| taccttatac accacaagta attgatgttt tgacaaaatt taccaataat accaatgaat | 360 |
| caaatttaaa tattgcttat gtgataattc ctgatcgtga acataattta gctgctaaat | 420 |
| catataaaga aaaatttccc gggtgtaaat taattggaat ggaaggatta gatgaaaatt | 480 |
| cattgaaatt ggattataaa tttataaaac tgatgggtaa taaagtttta aaaaatgatg | 540 |
| aattaaaaca aatctttaat gacagtgaca gtggcttgat tgttgataat tttgaatttg | 600 |
| tttatttacc aaatcatgca aatcaagaat tggttgtatt tgataaatca tcatcaacat | 660 |
| tatttgaagc cgatttatta ttcaatttag gtgtaccggg gtcaactctg ggtgaaacca | 720 |
| ttttagaaca atattcacca gagttggggt tccctaaagg gtttaatcct cattctggtt | 780 |
| ggtcatttat aactagatat ttacaaccat attctaaagt tggtcgtttc ttatttagaa | 840 |
| aaattgttga tataaatcat agtaaacctg gattagaagc tatttataat tcatgggatt | 900 |
| ttaaaactat tgttatgtgt catggaaata ttataactaa agatgctaaa gaagcattta | 960 |
| aacatgtttt tgtataaaag taaagaatt gaagaagata gtcaaatagt aataatcaga | 1020 |
| atatatgtat gttttttttt gaagaaaatt aaagaatata ttcacgaaat aataataata | 1080 |
| aaaataaaaa gactaactat tttgaataga aaaaaaaggt ggcactattt caatgagata | 1140 |
| aaccaattgt gaatatacgt agatgccttg cagcagacaa tataaccaaa tgttgaacaa | 1200 |
| tatgtgggat aaatagcatt tcatctgtg ccattgatat tgcatttata tcctattgtt | 1260 |
| gaacagtgac agcacctgtg gcggtggcta ttacataaca gaacaagtgg aacagcagtt | 1320 |
| accagtcaga acagatctaa cagcattgtt tttagcagca gcatctttat ctttggtttg | 1380 |
| accagatcca gttttttag attgttgttg agcagccatt ttttatttga atttgttgat | 1440 |
| tgagttaata tagtttataa gaattgagag ttacttgttt gagttgttga ttaagaatag | 1500 |
| attaaacaaa aatatacaag agaatctgta gacatattta tactcatgaa tttatatata | 1560 |
| tatctatgct tatattcatt tgatgtataa attgacatga ttatgaactg caagaggttt | 1620 |
| gattttgatt tgtctgcaaa aaaaatatgc tctattttc gcaattaccc cccaaccccc | 1680 |
| ccctcacaaa gttccgagtt tagttggaaa aatgtttcga tagagtaaaa tttcaggaac | 1740 |
| aaaattgact aattgggaga tgacaatgag aaacagtttt gagacttgat catacttccc | 1800 |
| catacgctca cctctttacg ttaaatatag ctctttacgt tctctacaat aattttttg | 1860 |
| acttattgat atttcttaaa atggttacat gaaataaaac aaagagattc ataggaatat | 1920 |
| tactttttca ggtagacaca atgcagctaa ggttggattt ctcaggaaat atcattcaag | 1980 |
| ctttatctgt tagttagtgc tgttatttat tactggtgaa ctacaccaaa gcatactgaa | 2040 |
| ggcattttac gaggttttg aaagctctta ctatgtagca actcatctag tacttagtag | 2100 |
| aggaagtgca tcaagtatgg atcaaccaag tgttacctta tatcattggt ttaaacattg | 2160 |
| taagactcag ttcgaaaaaa aaattaaggt ttctacttac cactttcatg tggcttaaag | 2220 |
| ttgtggatgt gatattgaat atgtttcaga tttgtcatga acaataaga acaataataa | 2280 |
| agaagaaatc aaatcaatct tcaatgtatg tatgtttctg tatggcgcat gtgggttctt | 2340 |
| tgttttaaaa aaaaaacttt aaattgagtt tgttttttct ttctttgtta gtcaatcaaa | 2400 |
| ctttaaaaaa gaagaacaag tagaaatagt atagtaaatt gatatagata cttttattac | 2460 |
| taataacaaa tctttaatgg aatttatctg aaattaattg tcaagtttta attcagtaat | 2520 |
| gattgatatt actctaaaac aaatgctgtg tggggttgtt ttgtttgacc tgaagtgtcc | 2580 |
| aagctttcct gcttcatgat ctaactcttt gtactgctac acctacattg ggaaatattg | 2640 |
| accttatagt aacacttact ttcttttatt aattgtctaa actatgcttt tgatcaattc | 2700 |

```
acacgtactt catttcttct ccccctgacga tcctgcatat ttcgtcataa ttcacacatt    2760
cttaaaatta tgcacacatc cttgaaatgt gttaatattc ccaacattat caattatatg    2820
tgttcagaat tggttgcaaa gttatcaact caattcacgc tatataaacc ttacaatttc    2880
tctacatttt tatatttttt tatattggct ttcttttaga atcaatcaat actttttta    2940 tcatttagat acatctttca tctattaata gattatcttt ctatatatca aaacacgaca    3000
cagtcacgtg ccaaaaagga tataagaagg aacttcaccc ccttgctctt cttattattg    3060
tgtgtggtgt aatagtttat ggtgtggtgt atgattgcgt gtgtgggtgc aaaaaaaagg    3120
tgaagaaaaa aatacctcaa aataaaaaca acttcaaaca ttcccctcat tttctttcac    3180
agtcatttgg tttcaatctc tattggtctt ctttaatcat cactatttat tccagtttat    3240
aagtcgaaaa aagttagttc attgttcaat tgggtttatt tatatttaat actatgcact    3300
tgttcttcct tgactaactc acatgagaaa gagagagtga ggagagggtg aatctattct    3360
ttctattgat tatgcataat tttcaatcag gtgataaata acattatcga ttgttctgtg    3420
tatacgtttg catatctttc ttatctatct tcatagtaag agagagatta gatatcatga    3480
tattgaatag agcgtgtaat tatcaattca ctatcattgt agaaccaccc tcagttgatc    3540
ttgtaattga agttacaga tgagttgatt atgcgtatag gaaagtattg aagtaaataa    3600
agtccgtgtg tattatctct ttttctccgc attttattgc tttatcattc atcatctctt    3660
ttcttttctt tttattcttc ctttaataca atagtggtca aggggggggag gaggaagaaa    3720 ttgcaatcta tagtaacatt gatgttcccc tctttctgat tagtaatccc cctttcacta    3780
ttagcaacaa taaactatat atatatgtat atcaaaccta ccttccttcc ggtcttcatt    3840
tttgttctct tttcgttgac tagaactttc ttaacaaact tcaaaactat catgcccgat    3900
ttatttgata atattttaa taaaattggt acaaaattca ctggtggcaa aaccactcat    3960
cattatggtg gtgcatctca agtaaatacc gggaaatggt atagttatac cagtagtgcc    4020
agtaataata attattggtt acctcgagaa agtcaaacaa agacaccagg tactcaagca    4080
gaagaaccag aaacagttca atttaaagtg gatcgatcaa tgagtgttgg atcaattact    4140
gaagattctg gtgctgctgg tgctggcggt gatcgatcaa gaatgaatag tattactgaa    4200
taattgtata tacaacgtat ataaataggc tggtcttatt attattgctt ttaatttagt    4260
atcttttgaa agataaattg gttagtgacg ttttttttt taataaattt gtttctatat    4320
taatataaaa ttcagttatt attattaata gtaatccaat tgtaattatt taaatgata    4380 tatataaata tatttaatat acagtttgtt attattattc tttagttttg ctttaaaatt    4440
tattttactt tactttactt tatatgatat tatatctgta ttaatgacga actgaaattg    4500
gtgaaatcgg cattagatta tggactgagg ataaaacagt tgaataaggg ggaggaggtt    4560
tgatgtggtg gtgtcatatc a                                              4581
```

<210> SEQ ID NO 121
<211> LENGTH: 5325
<212> TYPE: DNA
<213> ORGANISM: Unknown
<220> FEATURE:
<223> OTHER INFORMATION: sequence of retrotransposon from unknown
      organism

<400> SEQUENCE: 121

```
aatgggttta tacaatcaag gacaccggtc gctacaaggc tcgccttgtg gcacttggtt      60
atcgacaaca ggctggtgtg gactttctcg aaacgtatgc tcccgtgatt cgtggagaat     120
```

-continued

```
caatcaaact aatctttgca ctcgcgtcaa aatccaaact aaagattcat tccatagatg      180
ttaccacagc tttcctcaac ggggaaatac tggaactcat atttgtgaaa caacctccgg      240
gatatgaaga taagaagcgt cctaatcatg tttgtaagct caatcgcagc ttatatgggc      300
ttaagcagct gccactaatg tggaacatta aattaaatga tgtacttata aaggaaggtt      360
tccgtcgact tggtggtgac ttagggatat acattagtaa ggacaaaaga acaataatgg      420
gagtttatgt tgacgacatt ctcatttgtg gaccttctga cagtgaaatt gaacaagtaa      480
agaacaacgt gagaaaatac ttctcaataa ctgataatgg attatgccga aaattccttg      540
gaattaacgt ctatcaacaa gcaaatgaaa taagattaag tttgaatgat tatataagga      600
gaatgattga ggagttaaaa ttatctgtct cagaaacaaa cccagtatct ataccatctg      660
atgtcaatta tgaaatattt aaagttaacg aaaatgatga tgagaaacca tgtgatcaaa      720
ccaaataccg aagtttgata ggcaagctct tgtttgccag taatactata aggttttgaca     780
tcgcctattc tgtcaactcc ctatccaggt ttatcaacga tcccaaagaa aaacattgga     840
ttgcagctgt caaggtggta aaatatctca gtggtactca acggtatggt atttgttata     900
acggtaacgg tgacttgaat atttacgctg atagtgattg ggcttccact ccatctgatc     960
gaaagtctat tacggggtac attgttacct atgctggagc gccgataagt tggcgttcca     1020
agaagcagaa cgtgatagcc ttgagtacga cagaagcgga gtttatggct ctcacagagt     1080
ccataaagga agcccttggg ctaatataca ttttttcgaga tattaatgtg atattgaaat     1140
taccaattgt gatatatgaa gacaacctac tgtgtcagaa attacttgaa aatcctcgat     1200
tccataatag gacaaaacac attgacttga aatataaatt taccaaagac catatagaag     1260
ctggtacaat caaagtggaa tcaactaatt cagcagataa cttagccgac atgctaacta     1320
aacctttacc aaaaattaaa tttaaacatt taagatggct agcaggatta agacctttag     1380
attgattaga taatgataaa atgaaataaa gattaatttg gagatgcagg ttgatgggga     1440
ggatgttgga aaaatgaaat atgatcaatc ctgcatctag aacctgtggc agaatgaaac     1500
ctacgagatt atgaatgact tgtgaataca agttgaatgt tacagaatgt taccaagaag     1560
gttacacttg aatatatgaa tgactagaaa gtgaattgaa tgttacagaa cctgaataac     1620
aatgttacac gaatgtgtga atgatatgag tttatctata gtaatgtgac atatacacaa     1680
aggtgtgaat gaccgagaaa acagatgtta cattacgggc actggagagt gcaagtctaa     1740
agaatcttgg agtagaaata agtaaatataa aaaggaccaa agattcttta gagaaaagta     1800
aatgaaacta tattagattt tatataacta actaacaaat aaataaaaaa tataatatgt     1860
ctacaatgcc accaacttcc aaacgtacta gaaagagaac tagaaccgat gataatgctg     1920
aaccaactat tcaagatcct tcaccgccac ttgctaatgt tgaacccaca attcaagaga     1980
ctccaccgct ggttgaagtt agtgatgaga ctaattcaac tgaaatcaat gagacaaata     2040
gtaatactca tgaagaaaca aatgtattaa ctaatgtgca ctcctctcca atcgagacag     2100
ttactgagag gaacttcaat tttcaacagg ttattgcctc tatctccact gtggacaatc     2160
aaagtctctt gaaggataaa atttcttatg atcattggtt cagtaccttg aaagaaaatg     2220
caatcatgat tagtccagat tttcttgact ttattaacaa agacaccatg gatctccaac     2280
agtacccaac tgtctaccaa acattcttag atcgtcttat ttgtgccaca attgacccac     2340
atatcaaaca atctttaaaa tatcggaagt tatcaggaaa gaaatgcttt agtgaaatta     2400
tctctcaatt tggttctatg actattaaag acaaggttaa ctactccata attatggcta     2460
```

```
ccaaaattca ttctgatgtc accactcatt tagacaaaat gaatttactg gctcaatttt    2520
acgcatttct tatgcgtcaa cctcaggacc ttaaacctgc cctttactt attgcgggta     2580 tcaatgactc acgtttcaat gaaacatact ttcacgataa caaagaatta acgatctcta    2640
agttggaacg gtatatcatt aatcaaaact ccaaaattac tccgtcggta ccaacacctt    2700
ctccacgtga cgctgttacg ggtttactgg ttacccagcc tacgtccgct ctgggacaaa    2760
gtgaagtgtt taatacacaa tgttttaatt gctttgggtt gggccacact gcacgtcgct    2820
gtgcctctcc gaaacgtctt ggccaaataa acaaccttag atctaaatta cttgcgtttg    2880
aaactcgatc caaatccaga aagcgttttc cacctcaacc tcctcctacg aatcggtcgg    2940
caaactcaac aataataact aatccctcac ctactgacga taccatctcg tccaccactg    3000
aagattcttt tccacgggac gtctttggat gggcggcatc atctgaccaa atcaaatcaa    3060
aggacaacct ttctttattt tttgacacag gtgcctcggc acatcttatc aataatctca    3120
atctacttca tgattacaaa ccctctaaag aaaacaaaca tgtgatcact gcgaacggtg    3180
ataaaattcc tatcttagga actggaactg tgaaactcca acatggtcaa cacaagatat    3240
cacttcgcaa ttgccaatat tctccacatc tacacatcaa tcttatctca cccagactct    3300
tacttgatga ttccactagc atgactatca cccaatccgg gatttatcac tccaaaattg    3360
gacaaattgg gtattattcg actgaagatg gtaatctaat caagtgtatg ttccgtccca    3420
ttaccattcc tcatctttcg ttatattctc aatatgtcga aatgggtctt caatctaaca    3480
atgtactacg taacattcca gctttcacgg tccatattcc tcaactacat gactcccttg    3540
gacacacatc tactcaacaa gtttcaaatg tcatgaaacg tttcaatgtc actactgaca    3600
acattggtac ggactgcgaa acttgtcggc ttggaaaagc cattactcag attcccaaga    3660
tctcaaccca taccatctct agtcattgct tagaactact tcacgttgat gttcatggac    3720
caatatccgt tcctagtata tttcaagaac gttatttct tgtgatcctt gatgactact    3780
caaaatactt gacagttcaa ccactatgca acaaatctga tgctactgcc gaaattatcg    3840
aattcatcaa tcattgggaa aagttctttc tgggaaatgg caattaccat acgaaaattc    3900
tccggtcgga taatggaggg gaattcttaa acaaaacatt gactacctat cttgattcaa    3960
aatatattac tcaccaaacc tccaatgcct atgaacatca tgagaatggc gctgcagaac    4020
gagctattag atcggttaaa gacatggctc gagtaatatt gcttcaatcc aaattaccag    4080
tgccgttttg gtccctagca acccgatgtg ctgcgtttgt tatgaatcgt cttcctcata    4140
aaacaataaa tggtaagatt ccttatgaag tatggactaa acaacttgtc aatctcaaaa    4200
tgatgaaacc gtttggctct caagtatatg tgaaaattcc tattggagtc aaaagttttt    4260
ctgcacaagc actttctgga atcatggtgg gatatgccac taataagaaa ggctaccttg    4320
tatatgatcc cacacaaaat cgaatattca catcctcaca ataatatgt catccgagca    4380 tttatccagc agccaacctt acgtttaacg aacccttaat tatctcatcg aaagtcacgg    4440
ctgctcatct tcaccccctt accatttcca atttagttat tccacctacc aatgctgtat    4500
ctgagacacc tctgcaaatt gtgtgctctc ctcaaattcg tcagtatgtc ccaaagtttg    4560
ccaattacaa actgtcttgg aacatgggga ggataaaata tatgcactga ttataccaat    4620
atcgatcggc aatatgaaac gcacaagaac aaatgaaaac aaaatatgcc agctagatga    4680
atcgaacaat accaccatac cagatagtgt aattttatcg gctaacaatg tgttattaaa    4740
cttagaatcg agatcttcca ttcccaaaag ttataaggaa gctataacat ctaatgaaaa    4800
atccaaatgg gctgatgcta tggatagcga gtttaattca ttacaatcca acaacacgtg    4860
```

-continued

```
gtcacttgaa ccactaccgg agggacgcaa agctattggt gtcaaatggg tttatacaat   4920
caaggacacc ggtcgctaca aggctcgcct tgtggcactt ggttatcgac aacaggctgg   4980
tgtggacttt ctcgaaacgt atgctcccgt gattcgtgga gaatcaatca aactaatctt   5040
tgcactcgcg tcaaaatcca aactaaagat tcattccata gatgttacca cagctttcct   5100
caacggggaa atactggaac tcatatttgt gacacaaccc tccgggatat gaagataaga   5160
agcgtcctaa tcatgtttgt aagctcaatc gcagcttata tgggcttaag cagctgccac   5220
taatgtggaa cattaaatta aatgatgtac ttataaagga aggttccgtc gacttggtgg   5280
tgacttaggg atatacatta gtaaggacaa aagaacaata atggg            5325
```

<210> SEQ ID NO 122
<211> LENGTH: 2027
<212> TYPE: DNA
<213> ORGANISM: Unknown
<220> FEATURE:
<223> OTHER INFORMATION: sequence of retrotransposon from unknown
      organism

<400> SEQUENCE: 122

```
tttgtttgat aagaaaata aaaaaagaa acaagggtag taaatgagta cagtagccct      60
gttgaacaaa gtctgcgata acttaattat gggtgaactc aaggggacag tgtctttgtc    120
tatcatccga tccttaatca agtctattac tgaatatcaa ttatttggac acctgtttat    180
aaattactat ccaatctatg ttctttcaat tctttccttc aatattttgc cagccaataa    240
gaccaaacat aatccaaata tacataccag tgaattctaa attgtttggt gaaacatcca    300
tttttgatct atttcaaatt gtattttctt ttagtagtag tagtagtagc agtaattgat    360
taattattat caatatccga aatgatgata agaataataa ttatatatat aagaaagaga    420 aaagagaaa agaagaagaa gaagtataaa agaagttgtt atgggtttaa ttaaaaaga     480 aaaaattcaa tgaaatttgt gttgtgttgt gttgggtttg aatttctgta taactcaatt    540
tggagatttt ttttttttt ttttttttgaa atttttatta gtcgtgtaca ttgttacaat    600
tgtttctcgt tcccctttt tttttccttt ctttgttttg ttttgtttac cttgtgataa    660
ttttatacgt gttgagaggg ctctcgtcgt gcccgtgtcc gtttccgtgt cctgttgggt    720
cccctccgcc catgccgcac cgcaccgtac ggtaatgata tctgattgtt ggagcgttct    780
tcgctaacag gttctttatt tttgttcggg ggtttcgaaa gataatgtag aaacaccagg    840
gcttataact gagagttaga gtagtggaga ttagtagtag tagtacaatc ctatagccca    900
aacattattg gagagatctt accaaatagc aatcatcatg atgtatttac tactacataa    960
agaatttaag acgatattta ccagcaataa acaacatgac caactaatta acaaacattt   1020
gaaaaacata aagtaattag aaagtttaaa aagtgtacaa ccagtgtgga aaagaatgg   1080 aattggaatt gaacaaagtt attaattact gaaaaggaa atttaatttc ttgaaaggca    1140
aatctttgtt tgttttttt tttgggtctt ttctttcatt taataagcgt ggggtattaa    1200
tagataatga tattgttgtt gttattgtga tattgttgtg aaatttgaca tatgataaga    1260
taagtttctt tcttttcttt caactagtat aattgaacta agaccacca ccaccaccac    1320 cacatagtta gcaacctgat atgctgttca tgtaacagta aattatcttg gtactatacc   1380
acttgttgta atatagctaa tgctaattct tgattagtgt ggaaagccta ataaggttat    1440
attgtgcaca ggttaactac cttaatatag ttattgttaa tacagttatt gctgttgact   1500
actattgtta ttgttaaatt aaagtgttag gttgagttaa ttgattagtg aaaccaact    1560
```

-continued

```
aactaccgta ttaaattatt gtattaagat tgattcctat taaggataaa acagagagtg   1620
tgttagaaag agaaagggtg gattataaat atgtgtaaaa tcccctttag agactaacca   1680
ctagaaatct attgatggtt tcatatatag agattaacga ttatatttat aatataagtt   1740
ggtagttgct agtatatttg aaagcactac agtatagtat gtcagaatca gatcatttaa   1800
actctactaa taatacagga aacactttca ttagtctaga tcaagccagt acaataatgg   1860
cagatcaaac tcaaggagct aacccacaac aatgataatt catctttttt gtcaagacga   1920
taggttaatg ttacaagcac tttattgggc tcgaaatagt ggtaaataag tccatagata   1980
tgacctgtta caagttattt cgatgatcaa gccggctctg tgattac             2027
```

```
<210> SEQ ID NO 123
<211> LENGTH: 2118
<212> TYPE: DNA
<213> ORGANISM: Unknown
<220> FEATURE:
<223> OTHER INFORMATION: sequence of retrotransposon from unknown
      organism

<400> SEQUENCE: 123
```

```
ttttttaaa gaattaatta aatatgatgg atgatagaaa ttaaaggaaa aagaagaaga     60
acaaaacaaa agtttaattg aaaaaaaagg gagaaatgaa tattgaatta ttcagctttt   120
atattgctga tagatgttga aaaaaaaaac ggaagaatgg ggatagcaaa actgtgggtg   180
agattaactc atctatggcg ctaaaagtct ttttttttc tcttttatta gggggcacat   240
aaattattct tttcattgat aatctcgagt ccgttttag ttcattattc ggaatatatt     300
accgtattgg gaacgataat tattattagt tctccccgat ggttcgattt tgctggtgca   360
aaaatataaa tccgatatta ctttattggt gttttaataa atccgttta aaagttcgta    420 gacatataca ggatgataat aatttaaccg atttataagt tggaatcatt tggatgaatc   480
cgcttgggga gacgttttcc aatttagaa gtttaactat caattttatg tgacatccga    540
gtgtacacat tttgtgaatt tgatcttatc aactcacttg gtgtaccatg gcatttataa   600
caacactttt tagaatcggc tgagttacat gcatttcctc tatttgtaga ttaatggaaa   660
ttcataaaat cgttcacatt ttttctata atgagtacca ttctgtttcc ataagtaggg    720
gactaaaaaa taattgatat ctctaatcag tgacagctct agtcaacttg accgtaatgt   780
tttgacgacc attatatttc ttgtttgaac tattgattta tgagtgttgt cgtaacaaaa   840
gatcaattcc cgtcaaaacg catttggcac ttaatctttg attgaaccga ttttgatctc   900
aaaacatagt accaaggtca attatgttcg ctaatgaaag aaagctgtga cgaaaacctc   960
aaattcatga agaaagaatt actgttgtgg aaaataaaaa agtctttctt ctgatacttt  1020
acaagtccct caaccacaaa tacaaaaatg aaagttaccc atcgatcttt ttcattggtt   1080
aagaattaat acgagaatat caaattatct tagagagggt ctcacagagc aactttctga  1140
ggcacacggt caccaacatg atttgttata aaaaattcaa ccaaattttg gaaaaaatga   1200
aaacaaaaca aaacaaaatc tgaaacatcc cgaaagtcac aaatgcttga ttacttaaaa   1260
ttacttattt gcttcaagac gctattatta ttattatgac ataatactac ttgaataaca   1320
gtgaactgta attgtattaa gaacaaatca taacaaagga agatgatgac gatgatgatg  1380
accccttgaa atatccaggg cacatgcatt gtgatgattg ttgtaatata gctaatgcta   1440
attcttgatt agtgtggaaa gcctaataag gttatattgt gcacaggtta actaccttaa   1500
tatagttatt gttaatacag ttattgctgt tgactactat tgttattgtt aaattaaagt   1560
```

-continued

```
gttaggttga gttaattgat tagtgaaaac caactaacta ccgtattaaa ttattgtatt      1620
aagattgatt cctattaagg ataaaacaga gagtgtgtta gaaagagaaa gggtggatta      1680
taaatatgtg taaaaatccc ctttagagac taatcactag aaatctattg atggtttcat      1740
atatagagat taacgattat atttataata taagttggta gttgctagta tatttgaaag      1800
cactacagta tagtatgtca gaatcagatc atttaaactc tactaataat acaggaaaca      1860
ctttcattag tctagatcaa gccagtacaa taatggcaga tcaaactcaa ggagctaacc      1920
cacaacaatt accatattat atgaagaaga ctataacaaa actgtagata gtaggggatt      1980
ggttatttcc ggggagtaga agtattgggt tatctaagtc aatctttaac aaccaacaat      2040
caacaacaac caacaacgtt tttcctattc tcggagataa cttgattaac ttaaaaattt      2100
tcttgtcaaa aaatttct                                                   2118
```

<210> SEQ ID NO 124
<211> LENGTH: 4929
<212> TYPE: DNA
<213> ORGANISM: Unknown
<220> FEATURE:
<223> OTHER INFORMATION: sequence of retrotransposon from unknown organism

<400> SEQUENCE: 124

```
taattcgcgt atgaatgaga ttgatgccac tgttggtgct gaagttttaa aaagaaaaca        60
aatggaagat atgcaaaaca ataatagtaa taatggaggg aaaagattta atcagatcc        120 agtttctgat caagaaatat tagatgcttg ggaaaataat caattggata ggttttcagt       180
ggatcaattg aaggcatttta gaagaaaata tcctgatgtc aaatcagcta ataagaaagc      240
tgacttgatt gaaaatatca gtgagtttat aaggactcat agaaaatgag ttaatatgta       300
atagtgatat gtttatagct ctgtaaatac atgtaaattt tttggttgcc aatgaattga       360
ttgagactga aaatcgtttg tggtttgcca atgaacatta aacttattac ttgatctaga       420
aggcagttac ttgtttaaag aagtgatgag tcgtgattaa gtaaagtttg cagcactaaa       480
tattgtatgg tatttgactt aatttttttct gcaaaaaaaa ttacaaattt ttaatgaaaa      540
aacaaaacac aagataataa cattatagaa taaagattat aggatcctac caacatagtt       600
ccattgctga tcaggacgtt taataaaaga gcttcccaac agagacatat cttaataata       660
acaggctatt ttctgccttt aaaaagccat ctaggctcaa aaacctcaaa ataattcatc       720
tcccaccttg gcagcagagt agccataaca cagccaaatc aatttctata gtttacataa       780
tatataaaag gtttctaata gccagtaagc ttatagaaat tacccttttc aagtgatttg       840
atgaacaaat tatattcttg tacaaaatag tatatttaaa attaagaatt tggcttgcaa       900
aagaaactct cggtagctta gttggtaaag cattagactg taactgagtt attgtttgca       960
aacaaacaat tggaatgcga tctaaggatc gggtgttcga ctcactcccg ggagattttc      1020
ttttttacca ccaccatagt taacacgcta ccatatgaga cagaaatcta gcatgaatgg      1080
cttatataca agtggaccat ttagaagcat gagctgtgtc ctagtttttt atcatttaca      1140
attgaatttc cctctgaaat taaaattcta aggtattcat ttatctcaac tttcttagat      1200
gctgttagtg ggttaaaact tggtaatgaa ccactgacgg aagttatttt tgtgagaatt      1260
aactataaat atatcagctt ggttttttttt aacaacttag acagcaataa ccaacaccca      1320
actaattaat caacattgtt ataaagttgt tttcatctgt caaaccaggc acatggtagc      1380
acatcaaaat cactctcgat agcttagttg gtaaagcatt agactgtaac tgttcattct      1440
```

```
ggatattgat atctaaggat cgggtgttcg actcaccctc gggagaaata tttttttttt    1500
gcttataatt ccttcaaata tttacctcca gtatcggtat tgaattaaat acagagagca    1560
attggaaagg ttattttttt tgttatttat tccaaaaatt tcaggactca aagtttaata    1620
agccaaagcc tattttgtac tgcgcttccc tttaaagccc ctgctagccc ctgggcttgt    1680
tgttgttgtt gtgtatggaa caagtttatt aaatcccatg acgacgatga tgtaattgat    1740
tttgagaaaa aaaggatga acaatggaaa aagtacaat gggttatata ctttgccatg     1800
tggttgaaaa tatgtttaac ggctgtagaa cttttttta ttttgtgtta gtgagtgaat     1860
ttcgctacaa ttgttattat actccacaat tcagatttgt tgataacgtt taattactta   1920
aattttagta tgcatattga tatatttttt ctatgagatt gacgattaat tatcggtttg   1980
taaaattcta ttgaaacaca ttcaccagtg caacaattag acattttctc aaaaccatga   2040
atagcttgca actaaaacaa acaataaggc tgtacacttt gctggcaata atcagtgtc    2100 aagtcaatat aaacagtctt aagaacaatg agaaactcaa aagttagggt agttagttga   2160
ttacaaaaga aagagaccac ttagagacaa ataacaaga aatgacatca ccattgtaat    2220
agatacattt tccagttatt caagcaattg attgaatgta ttcatagcaa aatacattta   2280
agacatacaa gcttaaacat gggttattct ctagtggtgt tgttgttgcg attctaagac   2340
tccaatctat gattaataat cggatcacca tttgcacatg aactacatta agtactaaaa   2400
aatatgcaat tcgcctgttt tcttattgat taaatttaac aataaacttg tctttagctt   2460
tggcaaaagc ctccttgaaa atcctaacta agcacgttgg aagagcaatg gaattgtggt   2520
tagttataga aagcaaaaca atctgaaatt gtaaagtatt agatgatgtg caatgatatc   2580
agaataaaat agttgctgtt gaaaattttg ttcaagactc ttcacacagc atagcaaata   2640
gttatacata aagagaaaag ttcaacgtgc tttgttgccc gtgtctattt gttttttaa    2700 agccgaattc accactagag ggagtatata tgattcagag tatcaccatc atcatcatcg   2760
agcccccgta aaacttacc aactttcgtc gacatttccg atgagaaact tgattttttt    2820
ttccttccgt tgaaataatg tcagatagct cgcaaatatc ggaacgagca aattcttggt   2880
ccagcaccaa taattcggaa aatcacactc agttaatatt tacttacaaa ataaatttat   2940
ttgtaattta atggctataa aatgggaacg tagtaagaaa atcaacagct gttgtaatat   3000
agctaatgct aattcttgat tagtgtggaa agcctaataa ggttatattg tgcacaggtt   3060
aactacctta atatagttat tgttaataca gttattgctg ttgactacta ttgttattgt   3120
taaattaaag tgttaggttg agttaattga ttagtgaaaa ccaactaact accgtattaa   3180
attagtgtat taagattgat tcctattaag gataaaacag agagtgtgtt agaaagagaa   3240
agggtggatt ataaatatgt gtaaaatccc ctttagagac taatcactag aaatctattg   3300
atggtttcat atatagagat taacgattat atttataata taagttggta gttgctagta   3360
tatttgaaag cactacagta tagtatgtca gaatcagatc atttaaactc tactaataat   3420
acaggaaaca ctttcattag tctagatcaa gccagtacaa taatggcaga tcaaactcaa   3480
ggagctaacc cacaacaaca gcctagtctt cttgacacta aaaaaaaga gataaaaaac   3540 aatttcagcc aatcacatgt actacatttg taatagattt tattacttca gctgcttatt   3600
acacaaacaa ggttgaattg atattgtgta gagtaaattt tcggaaatag tttgaattgg   3660
gtgatcattt tctttatttt ttttatgtct tgtttctgtg aagatcggaa tgccagagtg   3720
gagctcgtga attgcaccac taattgcagc agcaccatat ttcaaataaa gtttctcatg   3780
```

-continued

| | |
|---|---|
| ttgtagtaag gattgcttgt ctccatgaaa ccaatcactt aactaagccc caggctaatt | 3840 |
| agtgtgtctt caaacagttt tgtactagag aaactcagac cttcccaggg caagtaacaa | 3900 |
| cctaaaaaaa tgccacaaaa ctaaatgcaa tttcagtttg atatgatagg caatgacatc | 3960 |
| aacacctgga aaaaaaaaa actttcaggt gatgaaacga ttaaggatta aagtttgcaa | 4020 |
| cgaaaaacaa gtggaactaa actttgcctt attgttttgt tccgcttacc taatgatgtt | 4080 |
| tactccttag aacaaacaac atcaactact tttaatcctg acgacgaaga agaagaccaa | 4140 |
| aaagaataat tagccgcagc tacggtggtg gcactagtag tagtgctagt gcttgttgtg | 4200 |
| tctcatccaa gagaaatgga aaaactgcaa aaatgccgca actttgaaca ttttggaaca | 4260 |
| caatacaact ttttttttcc ttttggattt acgattagcg cgatagacgt gaccataaaa | 4320 |
| ataccacacg atgtgtagat cctctaaaaa taatgtacac atttccaggc ttttgtttac | 4380 |
| tgcttaataa tttgtcatca tcggtaacaa tgatagtctc cccaccctaa ctacagtaga | 4440 |
| cggaattaga caccaaagat cttataaatc aaccccaaat tttcccattt tgattttga | 4500 |
| tttttttcgta ttccttgttg tttccataat tttttagtta ctcctcctca actaaactag | 4560 |
| ataactcgtc acagttaaca acagaaaggt atgttaaata tttatttcgt tctaaattca | 4620 |
| agtttggtat agaatattgc aaacaacaac aatctgaaaa atggacttta atttgctcta | 4680 |
| caaaatgcaa acacatctag aattaatatt tggtctggaa accgtatacg gaagttatgg | 4740 |
| ataatcacgt tatcctgata tctattatta acaccaccac aatatctatt atttcatgta | 4800 |
| tggattgcgg tgccaagatc aaagaatcat tttaacccga tatcttacat ttcacctcga | 4860 |
| tctaaatgtg attcagtatc accggctcat tgtttcacca ctcaacctcc ccatactggg | 4920 |
| agtacatat | 4929 |

<210> SEQ ID NO 125
<211> LENGTH: 4954
<212> TYPE: DNA
<213> ORGANISM: Unknown
<220> FEATURE:
<223> OTHER INFORMATION: sequence of retrotransposon from unknown organism

<400> SEQUENCE: 125

| | |
|---|---|
| tgttataaaa aattcaacca aattttggaa aaaatgagaa caaaacaaaa caaaatctga | 60 |
| aacatcccga aagtcacaaa tgcttgatta cttaaaatta cttatttgct tcaagacgct | 120 |
| attattatta ttatgacata atactacttg aataacagtg aactgtaatt gtattaagaa | 180 |
| caaatcataa caaaggaaga tgatgacgat gatgatgacc ccttgaaata tccagggcac | 240 |
| atgcattgtg atgattgttg taatatagct aatgctaatt cttgattagt gtggaaagcc | 300 |
| taataaggtt atattgtgca caggttaact accttaatat agttattgtt aatacagtta | 360 |
| ttgctgttga ctactattgt tattgttaaa ttaaagtgtt aggttgagtt aattgattag | 420 |
| tgaaaaccaa ctaactaccg tattaaatta ttgtattaag attgattcct attaaggata | 480 |
| aaacagagag tgtgttagaa agagaaaggg tggattataa atatgtgtaa atccccttt | 540 |
| agagactaac cactagaaat ctattgatgg tttcatatat agagattaac gattatattt | 600 |
| ataaataag ttggtagttg ctagtatatt tgaaagcact acagtatagt atgtcagaat | 660 |
| cagatcattt aaactctact aataatacag gaaacacttt cattagtcta gatcaagcca | 720 |
| gtacaataat ggcagatcaa actcaaggag ctaacccaca acaatgataa ttcatctttt | 780 |
| ttgtcaagac gatagttaat gttacaagca ctttattggg ctcgaaatag tggtaaatag | 840 |

-continued

| | |
|---|---|
| gtccatagat atgacctgtt acaagtttat ttcgatgatc aagccgcctc tgtgattacg | 900 |
| gcaattattt tactattgat aatgagtaaa agttcacaac aatagaaga tatccaccca | 960 |
| agcaatttct ctcgacgaac atctttagaa tagttggtat aataaccta cgaaacatta | 1020 |
| ataaagaaat tgtacccgat cttgttttcg agtcaaaaac aaagaaatca aacctagaat | 1080 |
| caacaatgtt ctagccatca tctcccgcca cccaagtgat gtaccccat ttcttgattc | 1140 |
| tattattttc tgaccctgtg agggaacaaa gatactatct ttaataaaga aacaaaacct | 1200 |
| caacaacaac aacaacacac taacacacta agaaactaaa acttgacgac aatatgatat | 1260 |
| tgtgatatat taatactgcc caacattcat cgtcgtcaaa tcagaattca gagcaaaaaa | 1320 |
| gagacgttta cgttacattc cccgatgttt ttgtgacgta acaagccgaa gagagggaaa | 1380 |
| aaaaagtat ggttattgaa aatctagtta ggatctactt tccttttgt ctcatctatt | 1440 |
| tatcaaacac tatcaacgcg ttttgaattg acgaccagat ctatatcatc tagtttataa | 1500 |
| tattctttgt cagatctgaa ttgatcaatg tgtggttgtt gtttgtagtt ttttgttgga | 1560 |
| tttaaactac tcacaaacat caagcttttg agtaagaatt gaatcaaatt caatattgtc | 1620 |
| ttgtcacttt ttttctgcgt ggtacactac tacgaaacaa aatttaaatt gtcgtgttct | 1680 |
| ttttgataat ttgtttgtta aattttttt gcttgtgtga aaaaaaaga gaaatgataa | 1740 |
| ttcgttttt ttatagggt ttttctaatt caactcttat aataaattaa cttatcaaca | 1800 |
| ccgtaaatat aattaaacca actgtgttgc gccataaata aataagttgt tcgggatca | 1860 |
| acacatctcc aacaaattga atcgtaggtg aaaatttttt ttttactagt aattggtagt | 1920 |
| aatggtgttc acgagtattt ttttttgggg agtatttgtg tcccttacaa gaaataaagc | 1980 |
| cagggccatg aaaaaaaaat taatacaaaa caaatatttc gtatcagcac agcagcactt | 2040 |
| ccccccttt cccctttcggc acgccctaaa aagaatttac tcatgtagtc gttatcactt | 2100 |
| caacaccaca caagaatacc tcgagtgaaa gaaaattgct tggggaatgt gtgtaattgg | 2160 |
| ctatgtagaa tttggtatta ataacatttc tactgttttt cttgtgccat aacatacttt | 2220 |
| tatcgcgata tattgcaaag cccccccttc tagctcctaa taaaaaaaac ccacattact | 2280 |
| attatattta aagtgtgaat tggaggggac aaaaacagaa caatgagcaa tttataatag | 2340 |
| tgaataacct ttagcaaaaa aaaaacattg taaattcaat atttgacgat ggatttaaca | 2400 |
| aacaatcaat caaattctta gtgttgaact gaactgaagt gatatttttt gccatatgca | 2460 |
| caaaatctta aatattcaag tctacacgag aaaacccaaa aaaaatgtta ttgtttcaaa | 2520 |
| aattaatgct tatgtaacac aacgccaaat ttaaaccatt ttttttgtgg ttactaaaaa | 2580 |
| aaaaaacaaa caaacaaat aaaaaaaaag gattacaaat ttcaggcaca ttgtttaaat | 2640 |
| ttactgacgc caattattgt ttgattcaag tataagttga gaatgatttt cccaatttat | 2700 |
| taaaactaca tacaaaagaa tattaacctt tctattttct ttattttttc aatttaaaag | 2760 |
| atataaaatc gtttcacctt ttcttaaaa ttataatttt caagacttac cttatttgcg | 2820 |
| ttttctaatc gcgtccactc ctttattact actattagct taagtctttc gttcaaaaaa | 2880 |
| caactacaat gcgtgccaac tatttgttat tattagctgc cacagctgtt caagctgctc | 2940 |
| cattcattaa gagatatgaa aacactactg ctccagccag tcaattgtcc acttcattgg | 3000 |
| ctgatggttc cactaccatt cttggttctt catcatccag tgttgaagaa gatgaaacca | 3060 |
| tcacttccac tatcgttcaa tatgttactg tcacttcttc tgacaccact tacgtttctg | 3120 |
| ccaccaacac tttgactact actttaacta ctaaaccaac cccagttatc accactgaag | 3180 |
| ctgaagatga cgaagaagac aatgaaacca ttacttccac catcctccaa tacgttactg | 3240 |

-continued

| | |
|---|---|
| ttacttcttc tgacaccact tacgtttctg ctactaacac tttgactact actttaacta | 3300 |
| ccaaagcagc cgaagctact gaatccgaag aagaagaaaa cgaaactatc acttccacca | 3360 |
| ttcttcaata cgtcaccgtc acttcttctg acaccaccta cgtttctgcc accaacacta | 3420 |
| taaccagtgt tttgactacc aaagcagcag tatctaccaa cgacgtcagt gaaaatgcca | 3480 |
| aggctgctac tactgaagat gatggtgaaa ccactacttc aaccattact agtatcgtta | 3540 |
| ctattactga tgccaatggt aacaccgaag tgttgaccga agttgcagct gagaccagtg | 3600 |
| gtgcagaaga tgcttcctac tgtgttcctt ctactgtcac tgttactgtc actgctgaac | 3660 |
| aaacttccga agttgtttca actattgttc acactaccca agttccactt actgctgaat | 3720 |
| ttacccttga tgataccact actacccta catcttgggt cgacttgact tctacagatc | 3780 |
| tcgttactat aacttctact tcaagtgtct atgattcata ctcaactggc gtttctcaat | 3840 |
| cccatccaat tcctcatact ccaactacac aatttcggac tatgccccac caatcagttc | 3900 |
| ttactactct ttgtaaagag cttgatatga agtttgtga tagtgatact actaccgccg | 3960 |
| ccaccaccac acctttagag taaagatttg tttttaaaaa aatcattctc atcattttt | 4020 |
| ttttattggt tttccatttt atgtcgtttt tgacgttact catttgtttt tattgtattt | 4080 |
| tgataactgg gtttatttga attttgctt tttttatt ttatttttaa cattgttatt | 4140 |
| cctttttcct ttgattattc ctttagtggt tggtgttatt ttgattttg cttacatttt | 4200 |
| tgcttacatt gttatatttg ttattccttt gttagagttt ttttttattt ttgcccttt | 4260 |
| cccttttgga ttttttatc attgtctgtc ttattcaatg gttttctagt ctaaaaattt | 4320 |
| tggtctagtt gctatttcat atctctgttc attatctcta tccttttctt agaaacatca | 4380 |
| ttctctctct ttctctctaa cattcctctc tctcatattc tctacaattg tctagataga | 4440 |
| ttttttatag tccttattgt tttttatttc tctaactata tgtatcattt tttattcttt | 4500 |
| tacatatatc tttactcttc tttctctttt tattttttt ggataataata ataaatata | 4560 |
| catttgccgt gttatattca aagatggatt gatattggaa ttggaattga aattggtgtt | 4620 |
| gcaaaaaaaa tagcaaccaa aaaaaatgac aacatcaaca acaaccacga ataggagaaa | 4680 |
| aaataaaaaa agaaagggaa agaaagaaag gaaaacaata gaggtggttt gattacataa | 4740 |
| gcaaccaaaa tttctcgcgt cttcgctct gtttgttttt ctgcctttga aagggatgac | 4800 |
| agcagcagaa aagcaagaag aaaaaaaaca acacctacaa ttcttcatt gttttgagtt | 4860 |
| ggccctacat tcaaagatcc aatttagcag tcatcaagaa taatttacaa tcgatcgacc | 4920 |
| tcagtcatca ccaaatagtc aaaccaatta ttaa | 4954 |

<210> SEQ ID NO 126
<211> LENGTH: 1047
<212> TYPE: DNA
<213> ORGANISM: Unknown
<220> FEATURE:
<223> OTHER INFORMATION: sequence of retrotransposon from unknown
      organism

<400> SEQUENCE: 126

| | |
|---|---|
| taataattga ttgggttttt gggaaatcac caattgtcta caaatctatc catatataac | 60 |
| ttaacactaa ggttaacctt gatcaagaag aagggagtgg ggggggggt gcatttatcc | 120 |
| tttatcttgg ctattgtggc gatgcataat tcgtaatata acgtaattaa tgagcaatta | 180 |
| aataaataaa ttgatctgat acaacaaaat aaaaagaaga aatttaatta atactgtggc | 240 |
| acgtgacagt tgattctaga tcaattcata gtccgcgtcc ccgaaccgaa caaaaacagg | 300 |

```
gcaaaatgat tactgttgta atatagctaa tgctaattct tgattagtgt ggaaagccta    360
ataaggttat attgtgcaca ggttaactac cttaatatag ttattgttaa tacagttatt    420
gctgttgact actattgtta ttgttaaatt aaagtgttag gttgagttaa ttgattagtg    480
aaaaccaact aactaccgta ttaaattatt gtattaagat tgattcctat taaggataaa    540
acagagagtg tgttagaaag agaaagggtg gattataaat atgtgtaaaa atccccttta    600
gagactaatc actagaaatc tattgatggt ttcatatata gagattaacg attatattta    660
taatataagt tggtagttgc tagtatattt gaaagcacta cagtatagta tgtcagaatc    720
agatcattta aactctacta ataatacagg aaacactttc attagtctag atcaagccag    780
tacaataatg gcagatcaaa ctcaaggagc taacccacaa caccactcag atttagcccc    840
tctaaaatgc atatggcaca atgatctcac ctcggttggt taaaccttt tcttcttatt    900 aaatctatct tagttgtagg ttggtctccc ccccctaact agttttacaa ttcaattatt    960
aaaccaattg tcaattcttg gtattttgta aacaagactc attaataatc aatcgtcaat   1020
gcatatgatc aaaacaaata gaaactt                                       1047
```

<210> SEQ ID NO 127
<211> LENGTH: 7929
<212> TYPE: DNA
<213> ORGANISM: Unknown
<220> FEATURE:
<223> OTHER INFORMATION: sequence of retrotransposon from unknown
      organism

<400> SEQUENCE: 127

```
aagagattgt agtgaagaat tcagctcatt attactgttt tgtcgttgct ggaaggagga     60
gggataattc aatgcgccac aacagtgtta ctatgcatgt ggttctgact gactgatatt    120
gtttaaaaat taaccagctc tcaaataaca aaagtttaaa ttttcaaggt ttgtaaacat    180
ggcagctagt agtaggatgg ttcataatat taattaatta ttagtaataa tggctaagtt    240
tttgaagcat tgttttaaat tttcaaattg aaattcaatt tcattacaaa tggattacta    300
acggaattcc taagctcaac tgaataccgt gattgaaaca tttgaatttg tatcttttag    360
attagctatt tttactttttt ttgtcattgt agttggttat gataattaca agaaactaaa    420
gtttaatatt ttcatattca ttttcttttt tggccaactt gcaataaca cacaaaccca     480 aaattaaata attagattta atgcatgcat aattacacag aatgtttagc cttaacaagt    540
attctagaaa caagaaagaa aaaatgtcgt cttggcgttt atcttaattg tattctgtaa    600
actgggttaa ttcttatttc caacttttca ttttttttgga tcttgtatgg attaaaaatt    660
aaatatggta tgttttaggg ttgtattaac aatacttaca attatcaatc atacagcttt    720 actatttttta tttatcagca ataggggaa ttcaagttgc atgtgttatt cagtggcagt    780
gaatcataaa acagccaact tgcagcttat ttcactccag gagcaatcat cacggaattc    840
cgtttcccat ctcattttca tactctgtgg attatgtata gaggctattt acaatatcac    900
caagcagtaa aacattctct cctcaaaata acaataagat tagtcaagat gaacgacttg    960
aatctattca tatgcattac acatttagtt tctattacaa atagtgatgc aatggtgcaa   1020
gattacgtct tgtctgcact aactatttgt aacgatgatt atgtgatcaa gaattggaat   1080
tcttattata ttcagtcgtg agtgtaagct atttcgttag ggttatctta actcgaagtt   1140
aaagttccaa aactattcca tttggagttt ctgttgttga gaaatacaaa atactcttct   1200
tggtggggag gaaatccatt aatgattata aaatgaaact cttggtaacc taattgaaac   1260
```

```
accacattca gtacatttc  aaccgtcact attattattg tggcaaatgg attaaacaat    1320
agacctaact taatctaatg gaaattttaa atccatgaaa ggggtgaaaa tttgaaatca    1380
aaataaacta ctgaactgaa atacccatg  gatctgatat cttatacaat ctatcaacta   1440
aacagggaag agtacctgga attccaaatg acaattccta ttataattat ttaaacagac   1500
tatgccgtat tgtttgtgac attcattgtt ttccacaact ctaatgtcaa attttttgtta 1560
ttgtcatgta atcccggtgt ttcttttttc ttttcggtgt tgcgttccat gatattttgt  1620
tatctcttgt ttagattgag ataaagaatt ggttagcagt gtagccattt atgagtggtt  1680
tgtaaaaaca agaattacaa ggtttgaatg aattccaggc aggcagtatt ataaaacctc  1740
gaaataacta atcaaaccat cagaaaagaa agcttactat gatgtactgc ttaatctcat  1800
atctatctta caaacttaat tcactgattg tggcttgtcc gtgaataatt cggaaacctt  1860
gtcttttcg  gtccagtagg gggtgccata gtcttgggtg gtgacaaaaa aaaaaaaaat  1920
tatagttggg gtggtgggt  gtacgtctga gtaagtcagg ggaatgaact caagacaaaa  1980
atagaagttc taaacatggt acgttctgct aagtaatatc atcgatctat ctattttgct  2040
ctaaattttc ataagcaaat ccagaacttc ctcgtcagtt tcaatttcaa gcatacgaag  2100
ggatagtgat taaattatat tttgaacctt ctattactga ttaagtgttc ctattagtct  2160
acggattaga cggttagaat gggattttca aaagcacaaa ggtcaagact tataggaaat  2220
tcatagaaaa aacactctga agtactcgat ggttggatat ataatagttt tgctaattta  2280
aactcttgct gttcggctaa gctattgtac ccaaatgcgg tactccgata gtcttataaa  2340
taatacttgg caaagttca  ataaatatat gtcaatggta ttgctttcca attaccattg   2400
acgaggttgt aaattaattc atacttaggt gacatcgatt aatttaacaa atatgtctgt  2460
ttcaacgctt acatcatcag tcttgcagga aaaatgttat tgccacgaca cctcaaatta  2520
gcccaacccc ttcgtctacc aaaacaatgt caaaaaccca cttaaaagaa gtcggacaaa  2580
cctgaacccg gtatttata  aagtagtttt gtgaataata tcagtacatc gattacactt  2640
tccgtctcaa gactggaagt tgcaaagcca tgacaattgc tcaaccaaat gtgaattttt  2700
aggttccata gtcttgatcg ggtaatgtaa acactttaac ttttagtaaa tgataccacc  2760
aagaagaaag cactatttta agctttattt aacactatac attggaaaat aaaaaagtgg  2820
ctatgagaat taaacaagat gaccgagtaa ttaaaatagt gctgtcggtg ttaagcaata  2880
ccgctagggt tcaatcaatt aagtgctgct ttttttttgtc gttgtatttc cattcctcca  2940
ctccttcctt tactcttgca atctaacata ttttttttaa aaagaaaaca tattgatact  3000
tacatgtggt aactattgtc tgattcatca attccgctct tcaatctcgg tgttcggata  3060
atttcgatga aattataatt acctgccgca attctagaaa ttccttttt  ttctttttctt 3120
tttctcggag ttggttccaa tacaaagatt gaattgaatt aggtgagaag aagaagagtc  3180
ttaacaccag atgtattaca gctttaaact ttgtttctaa tttgaccaca aaaagttgtc  3240
tggacgcctc agtttgaaat tagttttggg agatttctgt tttctcattg gccttactct  3300
atggaagttt ttatacaaga gcttccttct aaaattaact ctttgtgttg taatatagct  3360
aatgctaatt cttgattagt gtggaaagcc taataaggtt atattgtgca caggttaact  3420
accttaatat agtgtattgtt aatacagtta ttgctgttga ctactattgt tattgttaaa  3480
ttaaagtgtt aggttgagtt aattgaatag tgaaaaccaa ctaactaccg tattaaatta  3540
ttgtattaag attgattcct attaaggata aaacagagag tgtgttagaa agagaaaggg  3600
```

```
tggattataa atatgtgtaa aatcccnttt agagactaac cactagaaat ctattgatgg   3660
tttcatatat agagattaac gattatattt ataatataag ttggtagttg ctagtatatt   3720
tgaaagcact acagtatagt atgtcagaat cagatcattt aaactctact aataatacag   3780
gaaacacttt cattagtcta gatcaagcca gtacaataat ggcagatcaa actcaaggag   3840
ctaacccaca caacagcct agtcttcttg cactaaaaa aaaagagat aaaaaacaat      3900 ttcagccaat cacatgtact acatttgtaa tagattttat tacttcagct gcttattaca   3960
caaacaaggt tgaattgata ttgtgtagag taaattttcg gaaatagttt gaattgggtg   4020
atcattttct ttatttttt ttatgtcttg tttctgtgaa gatcggaatg ccagggtgga    4080
gctcgtgaat tgcaccacta attgcagcag caccatattt caaataaagt ttctcatgtt   4140
gtaataggat tgcttgtctc catgaaacca atcacttaac taagcccag gctgattagt    4200 gtgttttcaa acagttttgt actagagaaa ctcagacctt ctcagggcaa gtaataacct   4260 aaaaaatgc cacaaaacta aatgcaattt cagtttgata tgataggcaa tgacatcaac    4320
acctggaaaa aaaaaaaact ttcaggtgat gaaacgatta aggattaaag tttgcaacga   4380
aaaacaagtg gaactaaact ttgccttatt gttttgttcc gcttacctaa tgatgtttac   4440
tccttagaac aaacaacatc aactactttt aatcctgacg acgaagaaga agaccaaaaa  4500
gaataattag ccgcagctac ggtggtggca ctagtagtag tgctagtgct tgttgtgtct   4560
catccaagag aaatggaaaa actgcaaaaa tgccgcaact ttgaacattt tggaacacaa   4620
tacaactttt tttttccttt tggatttacg attagcgcga tagacgtgac cataaaaata   4680
ccacacgatg tgtagatcct ctaaaaataa tgtacacatt tccaggcttt tgtttactgc   4740
ttaataattt gtcatcatcg gtaacaatga tagtctcccc accctaacta cagtagacgg   4800
aattagacac caaagatctt ataaatcaac cccaaatttt cccattttga tttttgattt   4860
tttcgtattc cttgttgttt ccataatttt ttagttactc ctcctcaact aaactagata   4920
actcgtcaca gttaacaaca gaaaggtatg ttaaatattt atttcgttct aaattcaagt   4980
ttggtataga atattgcaaa caacaacaat ttgaaaaatg gactttaatt tgttctacaa   5040
aatgcaaaca catctagaat taatatttgc tctggaaacc gtatacggaa gttatggata   5100
atcacgttat cctgatatct attattaaca ccaccacaat atctattatt tcttgtatgg   5160
attgcggtgc caagatcaaa gaatcatttt aacccgatat cttacatttc acctcgatct   5220
aaatgtgatt cagtatcacc gcctcattgt ttcaccactc aacctcccca tactggcagt   5280
acatattttt ttttcatttt tagagagttt taacataact tatcggcatt ttcaataatg   5340
tttatttgga aatttagtat ataccgataa atcctgaatt ctcgtattgg cgatggattt   5400
accaaaaaaa tggggaatga gtgtacacca agaaaaaaaa gaaaaattca agaaaaagcg   5460
agtgactaaa aatgtcgtgg gaatttaatt tatcctggaa agatgccccg attcagaagt   5520
aatgtcgagt acttcacccc acatacaatg aacgactttt atttattcct tcaccccaca   5580
cagcaacaac tacatttaaa tttcagtatt taagcgacca tgaatttaaa ttacaatact   5640
ccacagatta aagcatttg tttataactt ttctattctt atcaattttt tttggtatag    5700
ttgtggtttg cgtcacggtt gttttctttt tttcatttc cttagtttac tccacataca    5760
catacacgta catttctata tacccccat gattccccc ccatttgatt tttgttgttg     5820
ttgttcagca atatctactt tatttattgg tttttatgtt tatatgatac taacttgtct   5880
ttgtttgctt tagtcatgaa ctccgatata ccacctccac caccacctcc agaatatacc   5940
cagtcccatg aagatttacc agcatacact tcgtcgttga actattatgg attatcattg   6000
```

```
attaaaacag aattcataac cccatatcaa tacaatagcg gtaaccgttc ctggaaacca    6060
gtattgcttg aattgaactc tactcaattg aaaatataca acttgaacat tgataagaaa    6120
ctacaagatt tgctaatatg tttatatttt gaattaaatt gtttagatca attaactaaa    6180
gacatcaatt ctcattataa aaagagtaaa ggttttgact ttagtgaatt atcgtctaat    6240
gatgccgacg atgtcggcga tttgttttcc ggtgatgcat atggtggtac tgatagctcc    6300
aagttatctt taaatgattc caagtttggc aaattgaaaa acaaattgag aaatcaaaaa    6360
tctaataaaa ccttgcaatc aataaaagct cattacgatg aattaaaaga taacaaattt    6420
ttctttgaac caacatcctc aacaaaggaa tataaccaat tcgctaaaaa gtatagagga    6480
aatttgttgc actgttattc tttggcaaac ttgcagattg gggaagcacc atctttgaac    6540
caaataattt cagcaatcta caaggaagag cataatggca acaccaacaa ttcatcactc    6600
gtcaaataca aaaacacatt gcgtcttcga attgaatata aacaaatctt acttcaattt    6660
tggtcttttct acggtatgat cagttggttt aggaatttca ccattggaag agatttgagt    6720
gtacccgtcg aagcaagaca tgtatcgaaa ctcaaatcta taccctcaag aaacactagt    6780
caaaacaatg cattattggc cgctactgcc gcagctgcaa actatggaag aaacagagcc    6840
aatactccag tggacggtgt cgaagaagac atatccatgt ttcgctccaa ctatttgact    6900
attaaagatg aagataatac tcattctgac accagtagtg agaattcatc tgtgttcgac    6960
aatgagagaa gagggtccat agtttcaaca actacgtcaa tcgaaccagt cgactatgtt    7020
actattaaca attacaagtt ttattcccaa gagtacacct ttaccactgt tgagaaacaa    7080
tacatttcca attgcatacc agatttgaac tcttttgata aatggaatgg caagttaatc    7140
accgtcagta acgtggatca ttttattaga gataagagat cttttgaaga caaagatgac    7200
gttttcatta gttatgctgc attggggaac ttggtacaat catatgataa aaaatcacat    7260
aacgactcat ccatgcttac cacccaaact tttatcattc atcaaaaagg gttagttggt    7320
ttaggaacac aagtttgatt cttaaaacat atatagattg atagatacca tttaatatttt   7380
ctaaacatat ctttacgaat taataaatac gacttttaat gatataaggt attttggttg    7440
taattgtaga tttggcaaaa aaaaaaaaa taaacaacca tcgtagtagt tgttgttaca    7500
gtggttcaag ttcacgccct aaattcttgt ggctgtctcg cctttaactt tcttttcttcc   7560
tcccttaact taacatgtac gtgtacttaa tattattttg aaaaattttt tttttctgtc    7620
tgtttctctc tctcctttgt tcccaacacc agttggtact tttaattcta ttttattttt    7680
acgttgatct gatattatt tatatattta tatatttcca tcaattctaa aacttaatta     7740
cttcaaagac caagttcttg aatcttcttt tgttttgct tgtttgtata ccaaaacact     7800
cttttttcaat tatttccctg ctgttttctt ttagaaaagc attgtccatt tgtctattag   7860
tctgtaactg gaaatttgtc ccgtccttaa attattttt ttttgaagaa tcttttcatt    7920
tgaatcatt                                                             7929

<210> SEQ ID NO 128
<211> LENGTH: 2292
<212> TYPE: DNA
<213> ORGANISM: Unknown
<220> FEATURE:
<223> OTHER INFORMATION: sequence of retrotransposon from unknown
      organism

<400> SEQUENCE: 128
gatattaagt cgtctaatgc tattttttat ttgaaaaaaa aaaaacaaga aacaaatgt       60
```

```
ataaaggtgg aagaaaaata aaaattaaaa aaaaaaaaaa ctcgaatatt aaaatgaaag      120
tggacaatta attgattgat taataaattg gttttattag tattatgtaa gggatttcaa      180
agaagtcatc taaaaattgt taatgtagat gtagatgtag atgtggttgt tgttctatgt      240
gtttacagaa attgatcatc aaagtccaag attttacatt gcctcgccag ttctattttt      300
ataaatattg gctgtgtgtt ttgggtgtgc ttgggccggg cagagggtgg gagagaggca      360
tgaatgcgga agaggaagga ggtcattcca ttccattcca tcgcctcatt cttctccatc      420
gttcattcat ttaattacga cagcagcaga agaaaaaaaa aaagaattca gatgtagatc      480
acgtgccaat attatgaaat attccatttt gggaaagtca gcttcaatgg cttacatggt      540
agcgcatact catagatttt aaaaaatctg aataatttgt tagttctcta tgaatgaata      600
aacagattac tgataagaac cagattaatt acttagaggt tttcttattt tttcttttt       660
gatagcaaaa gtattcatga attattcgta ttcgtaaaaa atttaagaag gagggagaac      720
aacaactgtt aacccaaatg gtgttttgt taaaactcta tctactaaat tcaacatttg       780
tgaagataaa agtggttcaa attttttgta tgaaaaaaca acatagattt atatagcaac      840
atcactacag taatatatcg aatacaataa atatatatat ataataaatt aaaataaaaa      900
taaaaatata catctacaat atgaaaaaaa tcatttaact atatagtatg tctaaattat      960
cgaatgaaag ttagtaatac aaactcccat gtttagtggg gagcttggta gagccttcaa     1020
ggcaattcat agtaggttgg aggaggccct aatcagaggg tctgagttga acaaaagcgc     1080
ccaaagcttt gtttgattca ttggaatata ctctcggtta tgtcgaaagt attggagctg     1140
aaaatagaaa agaaaaagt gaataattat gataattatt ggtgtgattt tgtcacccttt     1200
ttatacccaa ttttttttta tcaagagaga ttcttagatt tgccattttg agtgtttcaa     1260
atttcccatg tggattgaat tttcaaaatt ggttacatat atccttgaaa gtgttcataa     1320
tttttgtgtt gtaatatagc taatgctaat tcttgattag tgtggaaagc ctaataaggt     1380
tatattgtgc acaggttaac taccttaata tagttattgt taatacagtt attgctgttg     1440
actactattg ttattgttaa attaaagtgt taggttgagt taattgatta gtgaaaacca     1500
actaactacc gtattaaatt attgtattaa gattgattcc tattaaggat aaaacagaga     1560
gtgtgttaga aagagaaagg gtggattata aatatgtgta aaatcccctt tagagactaa     1620
tcactagaaa tctattgatg gtttcatata tagagtttaa cgattatatt tataatataa     1680
gttggtagtt gctagtatat ttgaaagcac tacagtatag tatgtcagaa tcagatcatt     1740
taaactctac taataataca ggaaacactt tcattagtct agatcaagcc agtacaataa     1800
tggcagatca aactcaagga gttaacccac aacattttgt agtcgtaaac ttgaaattca     1860
aagagaaggg ggggaattaa attgggtgca acgtgttgt caaaaatttg gtgtgaaaaa      1920
aattaattta acactctgca ttgtaccata gggaatataa tacccagaaa taagagaaat     1980
tatcacgtga gactaaaact aaatataata aattaatatc acaattgaga aagacactga     2040
aactaacttc ttggtgtatt aattttcaac acttgatcac aagtgcgggg attaatcata     2100
attgcaaaga gtgtgttaga aagagcgaag gtggattatg aatattggag aatcctcttt     2160
agagactatc cgctaacaaa atagatgaac ttgctcaaca gaaacaacta atcgactaac     2220
tgactaaaat taatatacta agtatagatt aagttatcac gttaatattc tatactatcc     2280
atctccatca ct                                                         2292
```

<210> SEQ ID NO 129

<211> LENGTH: 2025
<212> TYPE: DNA
<213> ORGANISM: Unknown
<220> FEATURE:
<223> OTHER INFORMATION: sequence of retrotransposon from unknown organism

<400> SEQUENCE: 129

| | | | | | |
|---|---|---|---|---|---|
| tggggagcaa | atgtgaaatt | aaagagtgtg | gtgatatgta | atttttttc | aaaaaagatt | 60 |
| ggattgacga | agcattatat | attcgtctaa | aaaccatttt | tgctggttcc | gcaataaatc | 120 |
| tcggagatta | tttctcgatt | accaatttat | gttgttttgt | gacatttctt | atattttgtt | 180 |
| ctattttaca | cgactatta | ttgttaataa | atatgtcacc | taaagaatat | ttctatttag | 240 |
| ttttacatat | gttttttgac | gacaatcaac | tattacaaat | taacctacat | ttttttaattt | 300 |
| gaatatatac | aatttatatt | gaattaacat | taccatttag | tttttgataa | gaatagattg | 360 |
| cgctatttca | acatttgtt | aaattattta | ttgtgaaaca | actatgtaga | ataaaagtat | 420 |
| gaacaaattc | tacgttcatc | atgtggggtg | tgccttcata | tatatctttg | gatgagaatg | 480 |
| ccaagaaaaa | tgatggcgtg | acaattcaat | acggcaaaac | aaactaatcc | cctctaagat | 540 |
| tttactagtg | tgtttcccta | tcgtctgagg | aaaaggtaac | aaaacatcgt | ttaaccaatt | 600 |
| ggtgtttgtt | acgatggtga | cgttgagtac | tgcatatagt | tgcaacggca | aattgcatcc | 660 |
| agcgagttaa | cagcgaatgg | caaagtgaag | cctccgactt | gtgttcattg | actactggga | 720 |
| ttggactggg | aataacgact | taactaatta | atgttctcgt | ggactcgttt | agctagaact | 780 |
| aacatttgtt | ataatatagc | taatgctaat | tcttgattag | tgtggaaagc | ctaataaggt | 840 |
| tatattgcgc | acaggttaac | taccttaata | tagttattgt | taatacagtt | attgctgttg | 900 |
| actactattg | ttattgttaa | attaaagtgt | taggttgagt | taattgatta | gtgaaaacca | 960 |
| actaactacc | gtattaaatt | attgtattaa | gattgattcc | tattaaggat | aaaacagaga | 1020 |
| gtgtgttaga | aagagaaagg | gtggattata | aatatgtgta | aaatcccctt | tagagactaa | 1080 |
| ccactagaaa | tctattgatg | gtttcatata | tagagattaa | cgattatatt | tataatataa | 1140 |
| gttggtagtt | gctagtatat | ttgaaagcac | tacagtatag | tatgtcagaa | tcagattatt | 1200 |
| taaactctac | taataataca | ggaaacactt | tcattagtct | agatcaagcc | agtacaataa | 1260 |
| tggcagatca | aactcaagga | gctaacccac | acagcattg | attatataat | catctatgta | 1320 |
| gccaatatac | actaccgtcc | aaactcccac | tacacacttg | taacagtgtt | ttacaaatct | 1380 |
| atgaacgaat | aaccgattca | aatgacacaa | taaagaacat | ttcaccgatt | tgaattgcta | 1440 |
| atcggtacta | taatattgat | ggaaggttaa | gagtttaatg | ctaccctagg | tttaccggag | 1500 |
| atcaacagtt | gcatatacaa | aacgtgttat | ctgtctacga | atggctttct | atgtgtataa | 1560 |
| aatgtttcat | caattgataa | ttaattatta | atctgcttac | tgaggtaaac | ccctttaat | 1620 |
| gcaatagcaa | atatgaggta | ttttttttgct | attgacatgc | gtatatgaat | ccatttgtat | 1680 |
| caaattgccg | atataatgaa | atggaaatta | agggaaaaaa | aaagtttat | atccaaattc | 1740 |
| atgcgattaa | caggttcttg | tgattataat | tggtaacccc | ctcccccta | aaactctat | 1800 |
| ctgccaaaag | aggaggatat | ttgaatatgc | tattatgaac | cccattgatt | ttgactacaa | 1860 |
| ttggatttgt | cgggtattga | aacccaaaca | tattataatt | tgctatgcgt | ttaaatcaac | 1920 |
| cgtttactgg | tagatcctat | actataaata | cagccaacaa | tccccaattg | ttcagataaa | 1980 |
| gtaacactca | atatcatttg | atcaatcaat | caagaggatt | acaaa | | 2025 |

<210> SEQ ID NO 130

<211> LENGTH: 2731
<212> TYPE: DNA
<213> ORGANISM: Unknown
<220> FEATURE:
<223> OTHER INFORMATION: sequence of retrotransposon from unknown organism

<400> SEQUENCE: 130

| | |
|---|---|
| acatattttt ttttaaaaag aaaacatatt gatacttaca tgtggtacta ttgtctgatt | 60 |
| catcaattcc gctcttcaat ctcggtgttc ggataatttc gatgaaatta taattacctg | 120 |
| ccgcaattct agaaattcct ttttttcttt tcttttctc ggagttggtt acaatacaaa | 180 |
| gattgaattg aattaggtga gaagaagaag agtcttaaca ccagatgtat tacagcttta | 240 |
| aactttgttt ctaatttgac cacaaaaagt tgtctgcacg cctcagtttg aaattagttt | 300 |
| tgggagattt ctgttttctc attggcctta ctctatggaa gtttttatac aagagcttcc | 360 |
| ttctaaaatt aactctttgt gttgtaatat agctaatgct aattcttgat tagtgtggaa | 420 |
| agcctaataa ggttatattg tgcacaggtt aactacctta atatagttat tgttaataca | 480 |
| gttattgctg ttgactacta ttgttattgt taaattaaag tgttaggttg agttaattga | 540 |
| atagtgaaaa ccaactaact accgtattaa attattgtat taagattgat tcctattaag | 600 |
| gataaaacag agagtgtgtt agaaagagaa agggtggatt ataaatatgt gtaaaatccc | 660 |
| ctttagagac taaccactag aaatctattg atggtttcat atatagagat taacgattat | 720 |
| atttataata taagttggta gttgctagta tatttgaaag cactacagta tagtatgtca | 780 |
| gaatcagatc aattaaactc tactaataat acaggaaaca ctttcattag tctagatcaa | 840 |
| gccagtacaa taatggcaga tcaaactcaa ggaggtaacc cacaacaggt tatgagcctc | 900 |
| gcccgcttat tgaatttaga taatataggg gcaatgaaag cttttgaaag tgttgatttt | 960 |
| cctgaatcat taaaactaga atccaagatt aattttcaag tgtggagaaa tgaaatcctt | 1020 |
| agatatgcac gtggtattgg tgctgagttt gaaaactttg tattgaatga aactccagct | 1080 |
| cacctgtatg atcttagatt gggaaatatg cttcatcaat tattgattcg cactgtgaaa | 1140 |
| gaaaaagtta gaatgcctag gcaagaactt ggaaaatcag gaaaagaact ttatcttgat | 1200 |
| cttattaaat cattcggtac tcaataccca tacgataaat ttgagatagt taaatactat | 1260 |
| tgggatcagt taacaaaccc tttaattaat gtgaagagac gttttgaaat tgaagaagta | 1320 |
| tgggttcaat acattaatgc tcaaactgca acagagagag aagttcttaa ttcatttgtt | 1380 |
| tggttacatt tgtcaaaatc tatattacca caagagtacc ttagaagtgc ccatccagtt | 1440 |
| cttgataaaa atgtgattaa aatatttctt gatacccatc caaaatgtga tattgatcaa | 1500 |
| attatgtcat ttgtaaataa tgaactgatt aattatgtag ggaaaaatga tacaagggaa | 1560 |
| aatgatatgg gacagaattt aagagagagt gatttaagag agagtgactt aagtgaaaat | 1620 |
| gatatacaac aaaatgagtt aagcgaaagc gattcaagtg aaaatgattt aagagaaata | 1680 |
| gcaacaaaag aaactgttag tgaacttttt gaaaatcaat gtcagaattg ttttggactt | 1740 |
| ggtcatgatt catatgaatg ttcactggca tttagaaaca atcagtatat tccagattta | 1800 |
| ttttctagac ttcagagttt tcgtggaaat agaattcaaa ataataatag aaatgtctgg | 1860 |
| tctagattct cagaacaaga tgagtcaatt gcaaatacag aaaaaggtaa ctagatctaa | 1920 |
| tgataaaaat gaaaatcagt ggcagtcaaa acaatttaca tattaaacaa gtttgaatgt | 1980 |
| aagttgttgt tgtttagata aactatgtca tggtatccaa agttttattt tatatttatt | 2040 |
| atttaagtgg tcatgtttat ttacttataa ttgttattta gttttttcaag tgtgaatttt | 2100 |

-continued

```
acttacttat aattgtattt agttttcaag tgtgaatttt acttacttat aattgtcatt   2160
tattgttcaa gtgttatttt tacttactta taattgttat ttagttttca agtgtgaatt   2220
ttacttactt ataattgtta tttagttttc aagtgttatc tttacttact tataattgtc   2280
atttattgtt caagtgttat ttttactta cttataattg ttatttatgt gtccaagttt    2340
taatattatt tacttataat tgttatttat tgtatatgtg ttaatttaat tcaattgtta   2400
attgttattt attgttcaag ttttaatttt atttacttat aattgttatt tattgtttat   2460
gtgttaattt aatttaattt aattgttatt tttactattt aaatgttgat tttatttatt   2520
taatgttaac ttgtcatttt taattttact tattatattt tacgtgtgac tattatctat   2580
gataaaacac taatagtgga tattgagtgt ttatttgttt catcgcagag gatatttatt   2640
ggaggaggga gaaaatgtct atttggtata aggaagacca taaaagttgg ttccaaatag   2700
tcaaccaacc aataaacatt ccctcatgct t                                  2731
```

<210> SEQ ID NO 131
<211> LENGTH: 2858
<212> TYPE: DNA
<213> ORGANISM: Unknown
<220> FEATURE:
<223> OTHER INFORMATION: sequence of retrotransposon from unknown
      organism

<400> SEQUENCE: 131

```
cctccgggcg tctatttaca agctgcttta ttatttgtta ttacctgggt gtaaaagccc     60
tcttgcattt gagctatttc tattcccact tcggtatttt ttttacagcc tcgttagacg    120
agttcttgat attactaaat tagttgttta ctgagtggcc tgatggttcc tcgtcactct    180 agttttggt ctatataagg gtcagaaatt tcccttctcc ttaggtccat caagtcaaga     240
tatacattag ttggtagcat cgtatggaat tttcgtatga acggcatacc aagtattaat    300
ttccgatcga aattttttag gacgtcttga taatcaggac aaacatcatg aaaggtctat    360
acgacgaaag tttactttac acaaggggag accatatgtc ttctttatta caactagtt    420 atatagcgaa caaataagtt tatacagaaa tatatgtaca caaacaaagt tattgtttat   480
taattattta attagctcgg aagaataact ctgtgatact gcatacattc aaacaaaatc   540
aatctagttt ccaacatctt tttcacttgg taatgtaatt attcttgttc tggcaccgac   600
aatgggtatt gttttgtagc tggaggacta atatgggta ccacctcaat ttttggatcc    660
cagctcccac gcagggtgg cttctgatct aactcacttt cgaaaatatc ctgatagttt    720
ccaattaatt cagcaaaata gctcttgttt gtacccttaa ccaatgacat gatatccttt    780
ttattatcac cgataccacc tgtgtcttcg tcttgttgta atatagctaa tgctaattct    840
tgattagtgt ggaaagccta ataaggttat attgtgcaca ggttaactac cttaatatag    900
ttattgttaa tacagttatt gctgttgact actattgtta ttgttaaatt aaagtgttag    960
gttgagttaa ttgattagtg aaaaccaact aactaccgta ttaaattatt gtattaagat   1020
tgattcctat taaggataaa acagagagtg tgttagaaag agaaagggtg gattataaat   1080
acgtgtaaaa tccccttag agactaacca ctagaaatct attgatggtt tcatagatag    1140
agattaacga ttatatttat aatataagtt ggtagttgct agtatatttg aaagcactac   1200
agtatagtat gtcagaatca gatcatttaa attctactaa taatacagga aacactttca   1260
ttagtctaga tcaagccagt acaataatgg cagatcaaac tcaaggagct aacccacaac   1320
acgtcttctt cagtattagg gaacaacata ctaacttgac cttttctagc ttcaaccaaa   1380
```

```
aattcctcta tatccattaa tggaatttca tcaaactgag cagccccaaa aaacgttttg      1440
cttccaaagt ctaaatgagc atggaatttc cttatgaaag gtataccaag tattaatttc      1500
ttatggaagc tgtccactac agcaaaattc tcttggaatg taataccatt aaactggaac      1560
ttgaggttaa ttatttggtt aaagtttctg ttgattttg gtccaataaa gtacccaaac       1620
tactagagct ccaacaacat tttcagaaaa tggccaataa tacaataagt gggtatattt      1680
tatcaaaaga gtttatatta tggttactcg acggtattat tctctgttga tttaaggcat      1740
tctggtcgac cagtggacaa aattcaagag tagtgtttgt ttagacttta caggacatga      1800
tagtatatat aacaaaaatg aaatacatta atcaaaacta actaaatcct aaattaatgc      1860
caatttctat tgaattggtt tgctactttg taaaatttgt gagtaatctt aagtacttat      1920
atggaaatca acaatggcaa aaatacaaga gaatgacccc atgacacatt cagtgcacaa      1980
ttcatagtaa ctgcttggtc acttgcacat gactctgcta gtatactcaa ccactcttgt      2040
gacttccata tagatactct cgatgaaatg tctcaaatta gaggacaaac aatctgctat      2100
aatcttggct aatcacccat gtaacatgga ggaaccaaac acatagatat acggtaccat      2160
ttcatacaga atttatcact aaagaaatta agaaaaactt gtgttatcaa agtggtttgc      2220
gaactttgta gtaagggaga gtgttgagaa ttagagattc taagttccag aaaaatatct      2280
atatttatat atataaggt agtgcaacac tacataaaag ggactgattt gaatgtatgt       2340
atgtcaaatg acacccttat aatgttgagt gacatcatat caaaatggaa atctactgta      2400
tcaattaaga gattactaaa agcaatatac ttaatatgag gtcgtacttt aagattgtga      2460
atagtatcag tagcgagtgg ctatgtgttg tgatggagca tcactggtag tttcttagat      2520
gtaaatctca gtgactataa gcatactaaa ttagttatga agatatgttc cattaaagta      2580
tttaaaaaat aatagacagg ctatcaattt ctaatagatt taccgtccag attataaaaa      2640
aattatcgag atacatatta caccgattga attaataata tgtctactac aaacccatca      2700
cggaacttga tgcaattgat tgaataagtg tctctctaac gatgacatgt ccaattctaa      2760
tcaaaataat tattattcta attgtaatat ctggtattta attatttata attcacgaaa      2820
cagtttgatt ggtttctgat tcttctgaca aaaataag                              2858
```

<210> SEQ ID NO 132
<211> LENGTH: 1636
<212> TYPE: DNA
<213> ORGANISM: Unknown
<220> FEATURE:
<223> OTHER INFORMATION: sequence of retrotransposon from unknown
      organism

<400> SEQUENCE: 132

```
atgtttattt aataattaaa ccccagttga ccaactatga aatagtataa tgataaatgc       60
aaaataaata tagtatgaac aatatgatag tttttagtgtg aattttgaat aagaaaaaga     120
agggataagg atattttttac taggaaactc aattataatt actaatgata aaaactccat    180
cagctactat tattactcaa attttaaatc atttgtttat cacctacaca aacagggatt     240
gtccaatatt gattactaaa attagaacaa ataagagaat ataattgaag ttaaataatt     300
cttttactaa atctattgac caagaactac atcaagggaa agtgttgcat atacatctaa    360
tgtttattct tggttagagt attgatacaa aattatatca tcaccaacga atcacattaa     420
gggaaagtgt tgtgcatata cctgatgctt agtcttggtt aaagtatttg tgtgaaaggt     480
tatcgtgacc aaagattata gtaagggaaa gtattatgaa taaatccaat gtctacttt      540
```

```
acagaagtat tgacatgaga gattataact atcaagaatt gcattaaggg aaagtgttgt     600
aatatagcta atgctaattc ttgattagtg tggaaagcct aataaggtta tattgtgcac     660
aggttaacta ccttaatata gttattgtta atacagttat tgctgttgac tactattgtt     720
attgttaaat taaagtgtta ggttgagtta attgattagt gaaaaccaac taactaccgt     780
attaaattat tgtattaaga ttgattccta ttaaggataa aacagagagt gtgttagaaa     840
gagaaagggt ggattataaa tatgtgtaaa atccccttta gagactaacc actagaaatc     900
tattgatggt ttcatatata gagattaacg attatattta taatataagt tggtagttgc     960
tagtatattt gaaagcacta cagtatagta tgtcagaatc agatcaatta aactctacta    1020
ataatacagg aaacactttc attagtctag atcaagccag tacaataatg gcagatcaaa    1080
ctcaaggagg taacccacta caggttatga gcctcgcccg cttattgaat ttagataata    1140
taggggcaat gaaagctttt gaaagtgttg attttcctga atcattaaaa ctagaatcca    1200
agattaattt tcaagtgtgg agaaatgaaa tccttagata tgcacgtggt attggtgctg    1260
agtttgaaaa ctttgtattg aatgaaactc cagctcacct gtatgatctt agattgggaa    1320
atatgcttca tcaattattg attcgcactg tgaaagaaaa agttagaatg cctaggcaag    1380
aacttggaaa atcaggaaaa gaactttatc ttgatcttat taaatcattc ggtactcaat    1440
acccatacga taaatttgag atagttaaat actattggga tcagttaaca aaccctttaa    1500
ttaatgtgaa gagacgtttt gaaattgaag aagtatgggt tcaatacatt aatgctcaaa    1560
ctgcaacaga gagagaagtt cttaattcat ttgtttggtt acatttgtca aaatctatat    1620
taccacaaga gtacct                                                    1636
```

<210> SEQ ID NO 133
<211> LENGTH: 2125
<212> TYPE: DNA
<213> ORGANISM: Unknown
<220> FEATURE:
<223> OTHER INFORMATION: sequence of retrotransposon from unknown
      organism

<400> SEQUENCE: 133

```
tgagtagcct tttcttgggc gactttatta gcttcatcaa caagacgttt atcttcagct      60
tcctttccca taataattct cttccattct ggaattggtt ttggtttctt tttatttatc     120
tcctcttctt tcatagccaa caaaagagta cccaataata atataatggt gataccttgt     180
gcgtacattc ttgcttgaac agcttttttgt gcggtatcca taattttgtc tctgttaacc     240 aataccaag aaccatataa ggaaccagcc caagcactta tgataatttt atatttattg     300
tcattcaata cggtgaaaca tttgtcacta agcgataatc tgttccattc acggtattct     360
tccaaatatt tagcttcctg atactccgat tgatgcatct ttctatcgaa ttcaacagaa     420
ccttgatcag cgaaaaaggc agccacagaa attgttggca tagcaattat ggctgctttg     480
atacttggat tgaatgttgc aaatcttgct ggatgtctat gctttaaata ttggtacaaa     540
ccgactgaaa gtgcaccacc ataaaacaac ccttttggcac cttctgaaat aatatgtgaa     600
atgtgagcgt cttttttcttc tttggataag atcttcattg tggaattaag atgactttgt     660 gattaaaattg ttgacttctt taagcctttt aatgtggagg aaaaagaaaa atctataatt     720
aaaaaaaaaa aagataaagc agataattct ttgatctttta tacttggt ctatatgtag     780 taggggaaag tcggagtcgg aatttgaaaa aaaaagagaa aaaagaacga atatttagac     840 tgtaaaaattc aaaccccctgc tgattagtat ataaaaaaaa tgagttcatt tttcctttct     900
```

```
tttttttttt ttcgcgcgga tagcaacggt cattaagtta acgagataaa aaagaaacaa    960
ccagataatt atgaaaagtt gtgatggtgt cacgtgcgaa catgagagtc atgaattttg   1020
acgaaaacgt caagcttcag tttacaaaag acctctttat taaaatcgaa ttgcttatag   1080
ggtcgtcgat gatgagaagg tgtatgttgt aatatagcta atgctaattc ttgattagtg   1140
tggaaagcct aataaggtta tattgtgcac aggttaacta ccttaatata gttattgtta   1200
atacagttat tgctgttgac tactattgtt attgttaaat taaagtgtta ggttgagtta   1260
attgattagt gaaaaccaac taactaccgt attaaattat tgtattaaga ttgattccta   1320
ttaaggataa aacagagagt gtgttagaaa gagaaagggt ggattataaa tatgtgtaaa   1380
atcccctta gagactaacc actagaaatc tattgatggt ttcatatata gagattaaag    1440
attatattca taatataagt tggtagttgc tagtatattt gaaagcacta cagtatagta   1500
tgtcagaatc agatcaatta aactctacta ataatacagg aaacactttc attagtctag   1560
atcaagccag tacaataata gcagatcaaa ctcaaggagg taacccacaa catagaatac   1620
gttttcaact acttaagtat ccactaacct aaattttttt tttaataaaa tttcattgta   1680
ttagtctttc ttactgcttt taatcaacta taagtatagg tttccgtttt ttttgcagta   1740
aaatttatcg ttcaggagaa ataacaaaat gtacacgact tattcgcagc attttttttt   1800
ttgtttgggg tttttgtatc aaattgttac aacaacaaca acaacctcaa ttcttaacca   1860
aatctacccc tcctattttt ttttctcata cacacaatac atcttacact atcttttgat   1920
aggctttatt gaagaagtat ttaaggagtg taatgacaat ctgcttaact catatatata   1980
tatatagata gtagtcaaca atagctttat ctactttttt tttttggcga cccctgcaac   2040
ttcaggccca ccagtttgcc cattttggtg cccccattga gtaaacatgg ggatttggag   2100
cacactttt tttaggtaaa aatgg                                           2125

<210> SEQ ID NO 134
<211> LENGTH: 1292
<212> TYPE: DNA
<213> ORGANISM: Unknown
<220> FEATURE:
<223> OTHER INFORMATION: sequence of retrotransposon from unknown
      organism

<400> SEQUENCE: 134
ctaatccaaa aatccataac ccaactgctc aacggcgaaa tccaaaactt ccatgctatt     60
ctagaccaaa cagtgtcgaa actcaatgat gcagagtggt gtctcggcgt tatggttgaa   120
aagaaaaaga aacttgacga attgaaagtc aaagaagaag cggcaagaaa gaaggaagaa   180
ggggcaaaga aaaaggaaga agaggcaaag aaaaaggcag aggaagcgaa gaagtgtttt   240
attttacttt tctgtcaaat ttgcactact tttaatttgt gtgcaaatat tctattttac   300
ttgattttta tactttta ttttacaata cttttttata ggactttta tatcttttct     360
ttatcaactg ttcgctatag ggtaggtctt ccaagctaat tttacccgac acaagatgaa   420
atattttctg ttgagcactc gttgtcgaca gtgaaaaatt ttcactcaag aaaatatttt   480
atcatcactt tttctagaag ggaggttcaa gtgttggaga atagacagcg aacacctgat   540
attcccaagg tcgaattaga ttgaaagata ataatagtc atatttattt tgtatttagt    600
caataaatta tctttttata tttaaattct tagtattgtc ataccacgta gattgatacg   660
gacatactta gcacatttaa catatattaa gcaccgatta cctgtgacat tccggagttt   720
actgtttcgc gcacgctggc agacgaacat caactcatct tttatacaat atattcttac   780
```

| | |
|---|---:|
| gattataact ttcaattaag aaatacaact tcttattagc attctcctac aagttcttaa | 840 |
| gttcctagga atttcttcga aactataatt aaagacgaaa agtgtaaaac aaacagaaag | 900 |
| cagaggaggc ccagaagaag gcagaggagg ccgtcccaca aaagtttgac aactttgacg | 960 |
| actttattgg ctttgacatc aacgacatgc agaacgacga taccatcgac gataccatcg | 1020 |
| acgataccat cgacgaaacc atcgatgaaa ccatcgacga taccaacgac gaagacatgt | 1080 |
| tgtccaacat ggactacgaa aatctagatc cggacgagac catcgacgaa gtacctgcca | 1140 |
| ccacagacag cgacttggac atgaacaaca tacttgaaaa caacgagctg atattagacg | 1200 |
| ggttgaacat gacattcctc gacaatggca acaacaccaa ccacgtaaac gaagagtttg | 1260 |
| atgtagacgg cttttttaaac cagtttggta at | 1292 |

<210> SEQ ID NO 135
<211> LENGTH: 568
<212> TYPE: DNA
<213> ORGANISM: Unknown
<220> FEATURE:
<223> OTHER INFORMATION: sequence of retrotransposon from unknown
    organism

<400> SEQUENCE: 135

| | |
|---|---:|
| gattgtatag tggtgtggtt gatcgacttc aatataacaa gagagagatg agatgagatg | 60 |
| cttttatcgc gtatatattt ttttttccat tgacaattct gatttcacaa attgttcgct | 120 |
| ataggggtagg tcttccaagc taattttacc cgacacaaga tgaaatattt tctgttgagc | 180 |
| actcgttgtc gacagtgaaa aattttcact caagaaaata ttttatcatc acttttctta | 240 |
| gaatggaggt tcaagtgttg gagaatagac agcgaacacc tgatattccc aaggtcgaat | 300 |
| tagattgaaa gataaataat agtcatattt attttgtatt tagtcaataa attatctttt | 360 |
| tatatttaaa ttcttagtat tgtcatacca cgtagattga tacggacata cttagcacat | 420 |
| ttaacatata ttaagcaccg attacctgtg acattccgga gtttactgtt tcgcgcacgc | 480 |
| tggcagacga acagattaga agcttggtaa atctttggtt attcatcacg tcttgagaat | 540 |
| aatacaaagt ttaatatagt attttcaa | 568 |

<210> SEQ ID NO 136
<211> LENGTH: 946
<212> TYPE: DNA
<213> ORGANISM: Unknown
<220> FEATURE:
<223> OTHER INFORMATION: sequence of retrotransposon from unknown
    organism

<400> SEQUENCE: 136

| | |
|---|---:|
| gattgtatag tggtgtggtt gatcgacttc aatataacaa gagagagatg agatgagatg | 60 |
| cttttatcgc gtatatattt ttttttccat tgacaattct gatttcacaa attgttcgct | 120 |
| ataggggtagg tcttccaagc taattttacc cgacacaaga tgaaatattt tctgttgagc | 180 |
| actcgttgtc gacagtgaaa aattttcact caagaaaata ttttatcatc acttttctta | 240 |
| gaatggaggt tcaagtgttg gagaatagac agcgaacacc tgatattccc aaggtcgaat | 300 |
| tagattgaaa gataaataat agtcatattt attttgtatt tagtcaataa attatctttt | 360 |
| tatatttaaa ttcttagtat tgtcatacca cgtagattga tacggacata cttagcacat | 420 |
| ttaacatata ttaagcaccg attacctgtg acattccgga gtttactgtt tcgcgcacgc | 480 |
| tggcagacga acatcaactc atctttttata caatatattc ttacgattat aactttcaat | 540 |
| taagaaatac aacttcttat tagcattctc ctacaagttc ttaagttcct aggaaattct | 600 |

| | |
|---|---|
| tcgaaactat aattaaagac gaaaagtgta aaacaaacag aaagcagagg aggccaagaa | 660 |
| gaaagcagag gaggccgccc cacaaaagtt tgacaacttt gacgacttta ttggctttga | 720 |
| catcaacgac aataccaacg acgaagacat gttgtccaac atggactacg aggacctaaa | 780 |
| attggacgac aaagtacatg ccaccacaga caacaacttg gacatgaaca acatacttga | 840 |
| aaacgacgag ctgatactag acgggttgaa catgacattg ctcgacaatg gcgaccacgc | 900 |
| aaacgaagag tttgatgtag acagcttttt aaaccagttt ggcaat | 946 |

<210> SEQ ID NO 137
<211> LENGTH: 951
<212> TYPE: DNA
<213> ORGANISM: Unknown
<220> FEATURE:
<223> OTHER INFORMATION: sequence of retrotransposon from unknown organism

<400> SEQUENCE: 137

| | |
|---|---|
| gatttgagaa ataccattga agatctagag ttaaaaataa ggaatttgca tgtacatgag | 60 |
| gataatcaag cggtcattac aatcttaaag aatgataatt tccacccaca tagaccgatt | 120 |
| gatatatgtt acaaatttct cagacaaaaa ttgaaagatg gattttttc aatatcatat | 180 |
| gttgaatctg gagataattt agctgactca ttcacgaaag ctttaggaag aaataaattg | 240 |
| attgaacata ccaaaaggat tagagaaaga aaggattatg ataataatgc tacactgata | 300 |
| gtggacgtta ggacgctcga agagattaag ataaacaaga aattggtaca tcattaatta | 360 |
| atttagctgt ttacctgaat caggggagtg ttcgctatag ggtaggtctt ccaagctaat | 420 |
| tttacccgac acaagatgaa atattttctg ttgagcactc gttgtcgaca gtgaaaaatt | 480 |
| ttcactcaag aaaatatttt atcatcactt tttctagaat ggaggttcaa gtgttggaga | 540 |
| atagacagcg aacacctgat attcccaagg tcgaattaga ttgaaagata ataatagtc | 600 |
| atatttattt tgtatttagt caataaatta tcttttttata tttaaattct tagtattgtc | 660 |
| ataccacgta gattgatacg gacatactta gcacatttaa catatattaa gcaccgatta | 720 |
| cctgtgacat tccggagttt actgtttcgc gcacgctggc agacgaacac aaatgcttga | 780 |
| actatctgcc gacttttttt tatttatggc gtgagacatt gttctcgcac acggttgtga | 840 |
| tttatctacc aggctctcat atttagagcg acaactactt tgagcaagca aaacgcatat | 900 |
| ctcaccacac accaattgta ggctattctc aaccggaaag tacaactagc a | 951 |

<210> SEQ ID NO 138
<211> LENGTH: 107
<212> TYPE: PRT
<213> ORGANISM: Unknown
<220> FEATURE:
<223> OTHER INFORMATION: sequence of retrotransposon from unknown organism

<400> SEQUENCE: 138

Asp Leu Arg Asn Thr Ile Glu Asp Leu Glu Leu Lys Ile Arg Asn Leu
1               5                   10                  15

His Val His Glu Asp Asn Gln Ala Val Ile Thr Ile Leu Lys Asn Asp
            20                  25                  30

Asn Phe His Pro His Arg Pro Ile Asp Ile Cys Tyr Lys Phe Leu Arg
        35                  40                  45

Gln Lys Leu Lys Asp Gly Phe Phe Ser Ile Ser Tyr Val Glu Ser Gly
    50                  55                  60

-continued

```
Asp Asn Leu Ala Asp Ser Phe Thr Lys Ala Leu Gly Arg Asn Lys Leu
 65                  70                  75                  80

Ile Glu His Thr Lys Arg Ile Arg Glu Arg Lys Asp Tyr Asp Asn Asn
                 85                  90                  95

Ala Thr Ser Ile Val Asp Val Arg Thr Leu Glu
            100                 105
```

<210> SEQ ID NO 139
<211> LENGTH: 9850
<212> TYPE: DNA
<213> ORGANISM: Candida albicans
<220> FEATURE:
<221> NAME/KEY: misc_feature
<222> LOCATION: (1)..(9850)
<223> OTHER INFORMATION: 'n' can be any nucleotide 'a', 'c', 'g' or 't'

<400> SEQUENCE: 139

| | | | | | |
|---|---|---|---|---|---|
| ctaatccaaa | aatccataac | ccaactgctc | aacggcgaaa | tccaaaactt | ccatgctatt | 60 |
| ctagaccaaa | cagtgtcgaa | actcaatgat | gcagagtggt | gtctcggcgt | tatggttgaa | 120 |
| aagaaaaaga | aacttgacga | attgaaagtc | aagaagaag | cggcaagaaa | gaaggaagaa | 180 |
| ggggcaaaga | aaaggaaga | agaggcaaag | aaaaaggcag | aggaagcgaa | gaagtgtttt | 240 |
| attttacttt | tctgtcaaat | ttgcactact | tttaatttgt | gtgcaaatat | tctattttac | 300 |
| ttgattttta | tactttta | ttttacaata | cttttttata | ggactttta | tatcttttct | 360 |
| ttatcaactg | ttcgctatag | ggtaggtctt | ccaagctaat | tttacccgac | acaagatgaa | 420 |
| atattttctg | ttgagcactc | gttgtcgaca | gtgaaaaatt | ttcactcaag | aaaatatttt | 480 |
| atcatcactt | tttctagaag | ggaggttcaa | gtgttggaga | atagacagcg | aacacctgat | 540 |
| attcccaagg | tcgaattaga | ttgaaagata | aataatagtc | atatttattt | tgtatttagt | 600 |
| caataaatta | tcttttata | tttaaattct | tagtattgtc | ataccacgta | gattgatacg | 660 |
| gacatactta | gcacatttaa | catatattaa | gccccgatta | cctgtgacat | tccggagttt | 720 |
| cttgtttcgc | gcacgctggc | agacgaacag | attagaagct | tggtaaatct | ttggttattc | 780 |
| atcacgtctt | gagaataata | caaagtttaa | tatagtattt | tcaaatttg | gaatacaaaa | 840 |
| gttgctaatt | ggtaaataag | ttattgattt | atttcataaa | tcttttttgg | tatcatattt | 900 |
| caaagagttg | caattgaaag | ctaaagacat | cctataaat | ggctgaattt | agcgatgctg | 960 |
| agctcagaaa | gatgatgggt | acactttcac | tcttggtaca | agattccagg | agagaaatta | 1020 |
| accacttgca | tgataagttg | gagaacaata | gtgactcaaa | atatcaatct | ttagaaacgt | 1080 |
| acatcaactc | aaagtatgca | gatactataa | aatcatttga | aaaattaaaa | tatttggaca | 1140 |
| ttgataattc | agagttggtt | aataccctgga | tcatgtgttt | taatcaggtt | aaaaggtttc | 1200 |
| accctcaggt | ttttgatgct | ttcatggagg | cagagaacga | ggacgaaatt | ggaatcgaaa | 1260 |
| agatccaata | tacgccatac | acaggtaaac | acttgaatga | tatgatcaga | atcttctaca | 1320 |
| tgaagatatc | cgaattaata | gaaagaaaag | ttagtccaaa | tgtttctaga | gagatgaatg | 1380 |
| atggacagcc | acaatttgtt | ccgaatttgt | ttaaaaagt | ttacgagatg | attatttcaa | 1440 |
| aaccagatgt | ttctgctgct | gaaagaattg | gaaaagctct | tttcaagtta | caatctaaac | 1500 |
| tgagagaact | tgaaagagaa | tcagcatttt | tgttatgtca | acatttaatg | accaatgacc | 1560 |
| accagcacga | tgatattatt | cttaaatttc | tcgttagcgg | tgtctcacca | tggtacttac | 1620 |
| atctgcaaat | ttcatgctg | tcatataaac | ttggattctc | aaatttgttt | ttagagattt | 1680 |
| atgctcaaca | ttatgaattg | tataaagcag | atcccatta | caaattgcca | gatagtatga | 1740 |

-continued

```
cattgttgaa tgaaataaga tcaaatagag attatcctaa agtggtaaat gctgcaaaaa    1800
atacagtaca agtcaataat gtttcatcca agaacaataa aaagaaggat gaatgacaac    1860
aattagccaa taaaattgag gaagtaggac gttatagcga aataaacgca acatctacat    1920
atcatgaaat tggcgatacc aacaaaaaca aagaacaatt aatattgaat ttgaaaaatc    1980
atacaaaatt aagtgaacaa aagaagaaaa caaacctatt ggtatatgat ctggagccaa    2040
cagtatccgt ggtgaatgat aagactttac ttaacgacat taaagaatca aatatcgaaa    2100
ttgcaactgc tgaaggggag acatctacgg cttatgcttt aggtactcta accatatctg    2160
tgaatggatt gaatgcgaaa ttagatggtg ttctatactt gccatctatt caattaaact    2220
taatatctat aaaacaattt gaagatttat gctacgcaat tttgatttcc gaaaatctaa    2280
tgtgtctagt tcacagtgac cacgaccta cggtcattgc gaaatattca cctaaagatg    2340
acttatactc aggcccaaga tcgggaacct tttttaaaa gaattcataa tgaccaaacc    2400 catttttttgc ttgccnctgc taaaaaactt ttagaatcag agaccatatt tctggagaat    2460
ccctgaaaaa tccaatggat tgatcaagaa aaattagatc cgttgaaaat gaccaataaa    2520
gtagaaaagg ttacctatgt cagcatacgc aacatcaaac aagaagtggc agacaaatat    2580
atgataaaag atctttacta ctatcattta ttaattaatc acctttcaca tgaaaaacta    2640
caattattag taaaagggg agtgattaaa ccagtcaaat ctactccggc tgagtcggcc    2700 atttttaaatt gtcagatatg tgttgcagcc catgcaaaat tagctagcca taatcacact    2760
caacaacggg aattggagcg accattacaa cgcctccatt tggataccgc cggaccattt    2820
acctcaaata aaactaagag ctatcttaca accgtgattg atcaattttc cagatatact    2880
gaagttattg tatctgacac caaagcagtc aaacaaagca tattgcatag acttagggtc    2940
tggaacaata gatttcagtt taagatcgcg gagataagat atgataatgc attggagtat    3000
ccatcggctg aggagttaga ggagttagga atttataaac accttctccc aaactactct    3060
cctatgctta acggtacagc tgaagcaacc aaccgcccca ttgtccaagg tatttataag    3120
gtagtgttaa attttagttg tcaagtatta atacttttcc catttatagt ggagtatgcg    3180
gttcatatcc ggaatcatac acctataaaa gaatttgatg gtgctactcc ttatgaacgt    3240
tactatggtt tatctaaata cgtcatacca ttttttcagt ttggaaccga cgttttgata    3300
aaatgtgcta gtgtacaaga agctatttca ttaaaactac catcttcaag agataaagct    3360
tttcctacag tgatgtttgg tgcttttctc ggttacggct cagattcctt taccttcaga    3420
gttttagttt ccacgaaagg atatccagtt attacaacat caaacatccg tccaatagcg    3480
acgatgcaag tactcaatga ctatttggca tacatatcgg agaatagctc aataagctat    3540
gacgatacat tcttatcacc tttgaatcac ccaatgattc gcacaaacca acatgataga    3600
cgtggagaca atataaatgt cgaatatgaa aaccgtccaa atgtaccatt tgaatatcat    3660
gctgaacctc ctcgtacaaa ttcatcgacg ggaattatcg atcgaccaga tattagacct    3720
agagctgatc ccacctggca acgtatgcct gatgccaaca tacatcagga acaacaact    3780 gtacagactc ctgatcatgg ggagttagat accatgatca caacgaaaca ccaactacca    3840
cgatctgggg agggtaatta ccccgggcaa caggtgcgca ccgatattat tgggcaattt    3900
cgagatcgcg ggcctaccac tctaaacact ccgatcgatc taggtgtacc cgatgaaaca    3960
gacgatatta gtatgacatc agagaatcca attgattccc caaattccga gatgatcata    4020
tccccatctt tacccacaaa tgaattggaa catcaaatcg atatcagttc agggggagatg    4080 tcgttattgc aaacgaatat ggaagcagat aacgaattga aaacaaatga aatggtatta    4140
```

-continued

```
tacaaatcaa aaaatgatgg tattatcatt caacaacaac aattcactga aaatttgtca    4200
gatgaaaatg aagaagattc atcaacagat gaggaaacat tggaagacaa aaacaacag    4260 cgattggaat ataatatttc accaaacgat gagtggataa ataatgacgt tcagaacgaa    4320
gatgacacac aagtgccaca tgttaaggaa ccaatcaatt atgaaactca agtagaaat    4380 gaaacaaaca tgccacgaat tgaaatgggc ataatagaaa acttaagtga tgatggaaag    4440
aatacaccac gtgaattacg tatcgtcacc tacgataata ataaagaaat tgaaaagtac    4500
caagacagta atatcgagat cctggaaccc agaaacgaaa atgaaaacca gacattcatt    4560
gaaagcaact tagaattact tgacaatcaa gaaatgtttc aagaagatcc tcaagttgaa    4620
gatattcgat tgacaactcc aaaaaaggac aaatcgttat cacctgattt caatcaaacc    4680
cataatgaaa tacaactatt catggcagat atcaatgaag atatgctaga agaatatgat    4740
gaaaatataa atatgaatga agtgttagct gactccacgg agacgttgga caagaattaa    4800
gatttagatg aagaaagtgg aaggatcgaa tatattgctg atagagttag aaaaaagaca    4860
gaggtactga tggtgcgcca cacgggaaat atttaaagaa aaatgataaa gattttggtt    4920
caataaaaag tcagaaaaaa tctgacgcac aaatggatga tgaagttgga attgctatt    4980 cgaagatcag aaactttcca tttagattga aggatggacg agcaagtttc ttccctccat    5040
ataaaacaaa atttggaaga tcagtgcatc cacctaaaag atatttaaat gccattgtta    5100 agaaataga ttacaatcaa aaagaatggc gtcaaagtat ggaagaagaa atcgaaaaat    5160
ttaaggctaa ccaagtttac accgttgaaa aaacaccaaa gaacgttgtc ccattgaaaa    5220
ccatgtgggt acatacttac aaaaccaatg acctcaaaaa tcataattac aaaagccgtt    5280
gcgtggtaat gggaaactat atggtcgaaa atcgtgattt tgatccccat gccatctcct    5340
ccccggtagt agatctcaca agtatacgac tattatctgc catagctgtt gaaaataact    5400
tggttatgca ccaattggac atcgcctcag cttatttgaa cgccagtttg gaggatggaa    5460
gagtaatctt tgtgagacca ccgcgtggtt ttgaggttaa acctggctat agttggcgtt    5520
tacacaagtc tgtgtacggt cttaggcaga gtgcccataa ttggtactca cattttaaga    5580
atgtgttgga ggcaaatggt ttaaaacaaa cactacacaa tgatggcatt ttttggaaaa    5640
attatgaaaa tggagatgta ttatatgtga gtgtatatgt ggatgatgtt tttatcaaag    5700
cgaattcaat gagtttgtgc aactaaattt agagttgctt ttagtttact aaacaaattt    5760
tatccttgct aatcaatact atctattatg cacgatctag caaccttaaa acaaccaatg    5820
gaaaaattaa aaaaattccc tcatcaatct ggcatgttcg aattgaaaaa aaaaaagaa    5880 aacaatagaa attcaataca atagagcata gaactggcca gaatgtgaga caataagtca    5940
gaacaagtga ttgccagtat aggtagggag aagcaacaaa gagagtttac acagctgaaa    6000
acaatcatat cgacggttat tgcaacttgg ttgctatttc aactattcgt aatggtccca    6060
tttttagcca acacaatttc agagaagacg cgaaaaagga cttggaaact tcatagttta    6120
gagccacaaa ctataagaaa taatagtacg atctaaattg gttccctagg ataatgccca    6180
acaaagaaat cccccaaata attgtaaatt gttcaacctt agtaactcta tctagcattg    6240
cggagttcct tgaaaatgaa ttggtttggt gttcctacct gttcagtact taatcactaa    6300
ctagacaaat tctttggcga aagctcaact tttgtgaagg tctttctcta ctatgaacat    6360
gactcccagc aagtctaggt ttggctgcac tatgagttta atttagtttt atcgggctaa    6420
tactacttat ttccgttatc ggtgtgaccc ccgaagaaag ggtattacgg ggctcataat    6480
```

```
tttttttttt ttggcaagta gagtgagatt caaaaaagaa aagtgaacca gagcaataat    6540
tgctattaat tttagttttt tactcactag ctatacttgg ctcccaaact gattttgtaa    6600 cccttttgagc aaggttgttg gtcaactgca agatcaacta agcaagatca cgccttatac   6660
gcaagccctg ccaaaaaata attcactctt gaaacaagga attagcagct attaggtaga    6720
cttttttttg tacctgtatt tcgttaccaa cactaaccga ggcactaccc aaactcatat    6780
aaacatgact aagagaaaac aatagagaag gggtttagtt gattttccaa tacatttag    6840 tgctgaatta catttatcta tttagtttag ttccataatc tttctaatat tgttgaacca    6900 ttagcaaaact ttttagatta aaagctcttt tgtaactgtt tttttttctgt agttatcgcg    6960 taacctttcc ccctcagaat ttctaaaccc tccccccct ttcttcaaaa cattaaagac    7020 tttgaactt atcatcacca caaaaactta ttaagctcca gcaaatttca ggtgacacca    7080
aggaaaacaa caattaacat tcttggagtt aagagtatat gctggtgcat ggattaaata    7140
tgcctgttct taacccccagc gaaaagaata tgttattttt gaacaaaaaa atagaatatc    7200
tcaaataaat ttgttctccc cttttgtcta tctatcccctt tagcttttg ccaaattcca    7260 acacaaaatg cttagtctg cagaaatgat gactaaaata ttcctttct tcaaaattca    7320 tattttcaaa atttagcaaa tggttgtact agatatcaga atttttatctg gtgagtttac    7380 tcaaccatag tagtcttttt ttagatcaaa aattagactt atgaacccta tattgaataa    7440
agttagtgtt ccccacagct attcataata aaaagctta acaaaaagtt gagattatca    7500
gcgacgatcg atcatgtcgt tccagagatt gtgttatagc gcctccttat gaacaggtaa    7560
actattagtt gcatgtagat ctattgtgtt caaatttaaa ttttaagaat tgttagctca    7620
aaacaaagac gacctgaaat tccaaaatc ataaagttta ccccaaaaa agtaacgaca    7680 ataaggtgc accaagaat aatggttgta gttttttcctt tatctgttttt agattgcttt    7740 attaggggt atcactaatt agcaattgta gcccttgctc gttattgttg cttgattttt    7800 tctaaaaca tttgcttagc attattgttg taagacatat ttatctattg tttctcaccc    7860
ttttagacaa atgattagcg ccccttgaca cgatcacagc ctattgttg gtgcactatt    7920 tgagcttta agtactaact tgttttcaga ctatcaatct atgtgtttgt tcaaagccag    7980
gcactcgagt cattagtcaa caataggctg tatgttgcta tccatgtagt gcctgtctta    8040
cagaaatttg cttttttaat tcacaagcat gagattttt gttgtgtgg tatttgacgt    8100 aaatgtaaca tgattacttg aaattcgata cgatctttt cgtcgtctat acaaaattta    8160
tcaagtgcta ctctgtgata ttttgcaaaa ccaatctcat tgttccttgc atgagaatga    8220
tttcgttgtc atcaaagaaa tataagcttt cattaccaca acaaatagca catggtacta    8280
ccttcccaat taaagtatga tgtaaccgtc gttgtcccct tatgtcaaat gcaaagtgaa    8340
cattcaaact taaatgcgag caagagcaat tataatatta cttcttctag ctttacaaaa    8400
taatattttc atcatttctg agtttattag tagaaacgtt aatattattt cagaaaagac    8460
tacaataaat tattggggta attcttagcg gtaggttctc ctgcccacga gtgctttgca    8520
ctgtaggtta aatttatttc ttcaggatat tcctacccct ctaggttgta ctaaccattg    8580
ataattactt gcaaatattt ttttcaaaaa aagaaaaccc tttacataaa taagctttat    8640
ataattatac gttgaaaaat gaccctaatt agtgtgcagt tttcaaatct taaatgtttc    8700
tctacccaat gattacagag atcatcaaca cttgtgaatg gacatcatat ctgtacgctt    8760
ttctaggctg cgaaattatg taacttcttg gtgtacaaaa aattgcaacc cctaagaaaa    8820
tcataagttt atatccaaga aaaaaatggt ttataagcgt ataatgaaaa taataatatt    8880
```

```
attaaccacg atggccaaaa gaaatctaaa gttggcaata attcgctagt tgggggGaag    8940
ttgccaataa taaatgagca ggcgttttga tatttataat aataggtcac ctgttttgag    9000
tatttcctac agggactttt attttcataa ggtggatatg ctatcacttg gtgaaacaac    9060
ttcaaattcg tgtactttgc ttatgccaga tacttagcac tgggaaattg ttacaacccc    9120
atttctggaa atgtaacgtc acctgaaacc atcttatggt cctgccattg gtgtttcatc    9180
gtgttacaat gctaggtttt ttaaatgtct acaagtcaat attatattca agataaactt    9240
ttcaaaacat ctgatttatt atgacattat tcttgttgac atttttttgg ggtagacaag    9300
aaataattgc agataatata gaacacttat gccacgtggg tggatttaat agaatccttg    9360
taaaatatta tctctagaga attataaggg gaggagagaa gatctatggc aatgcaagaa    9420
aatgcaagat catcgtaaaa aaagtataag aatgactcca taagatatat aaacccactt    9480
gtttgaagag cgcttactac acggggttgt cttaatacaa aggcggcagg gttgcagtac    9540
ttctgtagtt tctaaccttt gtattcctta ggccctggaa tataatactt cctgtagtaa    9600
atgtcggagt ttaaattgct gacattgcaa gaaaataaaa ccaatataat attttttatg    9660
tcacgaaaga aatggaacaa caatgtagca ccaaaagggg tagagactag gcagtactat    9720
atttggaggt aaaagtatat tagaaaaaga acctatacat gaaccagtaa ccataacaaa    9780
aaaaaactaa acccaagcaa ttaaccatcc aaatttaacc cgttttataa tacaattttg    9840
accacatcta                                                          9850
```

```
<210> SEQ ID NO 140
<211> LENGTH: 305
<212> TYPE: PRT
<213> ORGANISM: Unknown
<220> FEATURE:
<223> OTHER INFORMATION: sequence of retrotransposon from unknown
      organism

<400> SEQUENCE: 140
```

```
Met Ala Glu Phe Ser Asp Ala Glu Leu Arg Lys Met Met Gly Thr Leu
1               5                   10                  15

Ser Leu Leu Val Gln Asp Ser Arg Arg Glu Ile Asn His Leu His Asp
            20                  25                  30

Lys Leu Glu Asn Asn Ser Asp Ser Lys Tyr Gln Ser Leu Glu Thr Tyr
        35                  40                  45

Ile Asn Ser Lys Tyr Ala Asp Thr Ile Lys Ser Phe Glu Lys Leu Lys
    50                  55                  60

Tyr Leu Asp Ile Asp Asn Ser Glu Leu Val Asn Thr Trp Ile Met Cys
65                  70                  75                  80

Phe Asn Gln Val Lys Arg Phe His Pro Gln Val Phe Asp Ala Phe Met
                85                  90                  95

Glu Ala Glu Asn Glu Asp Glu Ile Gly Ile Glu Lys Ile Gln Tyr Thr
            100                 105                 110

Pro Tyr Thr Gly Lys His Leu Asn Asp Met Ile Arg Ile Phe Tyr Met
        115                 120                 125

Lys Ile Ser Glu Leu Ile Glu Arg Lys Val Ser Pro Asn Val Ser Arg
    130                 135                 140

Glu Met Asn Asp Gly Gln Pro Gln Phe Val Pro Asn Leu Phe Lys Lys
145                 150                 155                 160

Val Tyr Glu Met Ile Ile Ser Lys Pro Asp Val Ser Ala Ala Glu Arg
                165                 170                 175
```

Ile Gly Lys Ala Leu Phe Lys Leu Gln Ser Lys Ser Arg Glu Leu Glu
              180                 185                 190

Arg Glu Ser Ala Phe Leu Leu Cys Gln His Leu Met Thr Asn Asp His
          195                 200                 205

Gln His Asp Asp Ile Ile Leu Lys Phe Leu Val Ser Gly Val Ser Pro
      210                 215                 220

Trp Tyr Leu His Ser Gln Ile Tyr Met Ser Ser Tyr Lys Leu Gly Phe
225                 230                 235                 240

Ser Asn Leu Phe Leu Glu Ile Tyr Ala Gln His Tyr Glu Leu Tyr Lys
                  245                 250                 255

Ala Asp Pro Ile Tyr Lys Leu Pro Asp Ser Met Thr Leu Leu Asn Glu
              260                 265                 270

Ile Arg Ser Asn Arg Asp Tyr Pro Lys Val Val Asn Ala Ala Lys Asn
          275                 280                 285

Thr Val Gln Val Asn Asn Val Ser Ser Lys Asn Asn Lys Lys Lys Asp
      290                 295                 300

Glu
305

<210> SEQ ID NO 141
<211> LENGTH: 155
<212> TYPE: PRT
<213> ORGANISM: Unknown
<220> FEATURE:
<223> OTHER INFORMATION: sequence of retrotransposon from unknown
      organism

<400> SEQUENCE: 141

Ser Glu Ile Asn Ala Thr Ser Thr Tyr His Glu Ile Gly Asp Thr Asn
1               5                   10                  15

Lys Asn Lys Glu Gln Leu Ile Leu Asn Leu Lys Asn His Thr Lys Leu
              20                  25                  30

Ser Glu Gln Lys Lys Thr Asn Leu Leu Val Tyr Asp Ser Gly Ala
          35                  40                  45

Thr Val Ser Val Val Asn Asp Lys Thr Leu Leu Asn Asp Ile Lys Glu
      50                  55                  60

Ser Asn Ile Glu Ile Ala Thr Ala Glu Gly Glu Thr Ser Thr Ala Tyr
65                  70                  75                  80

Ala Leu Gly Thr Leu Thr Ile Ser Val Asn Gly Leu Asn Ala Lys Leu
              85                  90                  95

Asp Gly Val Leu Tyr Leu Pro Ser Ile Gln Leu Asn Leu Ile Ser Ile
          100                 105                 110

Lys Gln Phe Glu Asp Leu Cys Tyr Ala Ile Leu Ile Ser Glu Asn Leu
      115                 120                 125

Met Cys Leu Val His Ser Asp His Gly Pro Thr Val Ile Ala Lys Tyr
130                 135                 140

Ser Pro Lys Asp Asp Leu Tyr Ser Gly Pro Arg
              145                 150                 155

<210> SEQ ID NO 142
<211> LENGTH: 795
<212> TYPE: PRT
<213> ORGANISM: Unknown
<220> FEATURE:
<223> OTHER INFORMATION: sequence of retrotransposon from unknown
      organism

<400> SEQUENCE: 142

-continued

```
Met Thr Asn Lys Val Glu Arg Val Thr Tyr Val Ser Ile Arg Asn Ile
1               5                   10                  15

Lys Gln Glu Val Ala Asp Lys Tyr Met Ile Lys Asp Leu Tyr Tyr Tyr
            20                  25                  30

His Leu Leu Ile Asn His Leu Ser His Glu Lys Leu Gln Leu Leu Val
        35                  40                  45

Lys Arg Gly Val Ile Lys Pro Val Lys Ser Thr Ser Ala Glu Ser Ala
50                  55                  60

Ile Leu Asn Cys Gln Ile Cys Val Ala Ala His Ala Lys Leu Ala Ser
65                  70                  75                  80

His Asn His Thr Gln Gln Arg Glu Leu Glu Arg Pro Leu Gln Arg Leu
                85                  90                  95

His Leu Asp Thr Ala Gly Pro Phe Thr Ser Asn Lys Thr Lys Ser Tyr
            100                 105                 110

Leu Thr Thr Val Ile Asp Gln Phe Ser Arg Tyr Thr Glu Val Ile Val
            115                 120                 125

Ser Asp Thr Lys Ala Val Lys Gln Ser Ile Leu His Arg Leu Arg Val
        130                 135                 140

Trp Asn Asn Arg Phe Gln Phe Lys Ile Ala Glu Ile Arg Tyr Asp Asn
145                 150                 155                 160

Ala Leu Glu Tyr Pro Ser Ala Glu Glu Leu Glu Glu Leu Gly Ile Tyr
                165                 170                 175

Lys His Leu Leu Pro Asn Tyr Ser Pro Met Leu Asn Gly Thr Ala Glu
            180                 185                 190

Ala Thr Asn Arg Pro Ile Val Gln Gly Ile Tyr Lys Val Val Leu Asn
        195                 200                 205

Phe Ser Cys Gln Val Leu Ile Leu Phe Pro Phe Ile Val Glu Tyr Ala
210                 215                 220

Val His Ile Arg Asn His Thr Pro Ile Lys Glu Phe Asp Gly Ala Thr
225                 230                 235                 240

Pro Tyr Glu Arg Tyr Tyr Gly Leu Ser Lys Tyr Val Ile Pro Phe Phe
                245                 250                 255

Gln Phe Gly Thr Asp Val Leu Ile Lys Cys Ala Ser Val Gln Glu Ala
            260                 265                 270

Ile Ser Leu Lys Leu Pro Ser Ser Arg Asp Lys Ala Phe Pro Thr Val
        275                 280                 285

Met Phe Gly Ala Phe Leu Gly Tyr Gly Ser Asp Ser Phe Thr Phe Arg
290                 295                 300

Val Leu Val Ser Thr Lys Gly Tyr Pro Val Ile Thr Thr Ser Asn Ile
305                 310                 315                 320

Arg Pro Ile Ala Thr Met Gln Val Leu Asn Asp Tyr Leu Ala Tyr Ile
                325                 330                 335

Ser Glu Asn Ser Ser Ile Ser Tyr Asp Asp Thr Phe Leu Ser Pro Leu
            340                 345                 350

Asn His Pro Met Ile Arg Thr Asn Gln His Asp Arg Arg Gly Asp Asn
        355                 360                 365

Ile Asn Val Glu Tyr Glu Asn Arg Pro Asn Val Pro Phe Glu Tyr His
370                 375                 380

Ala Glu Pro Pro Arg Thr Asn Ser Ser Thr Gly Ile Ile Asp Arg Pro
385                 390                 395                 400

Asp Ile Arg Pro Arg Ala Asp Pro Thr Trp Gln Arg Met Pro Asp Ala
                405                 410                 415

Asn Ile His Gln Glu Thr Thr Thr Val Gln Thr Pro Asp His Gly Glu
```

```
                        420             425             430
Leu Asp Thr Met Ile Asn Asn Glu His Gln Leu Pro Arg Ser Gly Glu
            435                 440                 445
Gly Asn Tyr Pro Gly Gln Gln Val Arg Thr Asp Ile Ile Gly Gln Phe
        450                 455                 460
Arg Asp Arg Gly Pro Thr Thr Leu Asn Thr Pro Ile Asp Leu Gly Val
465                 470                 475                 480
Pro Asp Glu Thr Asp Asp Ile Ser Met Thr Ser Glu Asn Pro Ile Asp
                485                 490                 495
Ser Pro Asn Ser Glu Met Ile Ile Ser Pro Ser Leu Pro Thr Asn Glu
            500                 505                 510
Leu Glu His Gln Ile Asp Ile Ser Ser Gly Glu Met Ser Leu Leu Gln
            515                 520                 525
Thr Asn Met Glu Ala Asp Asn Glu Leu Lys Thr Asn Glu Met Val Leu
        530                 535                 540
Tyr Lys Ser Lys Asn Asp Gly Ile Ile Ile Gln Gln Gln Phe Thr
545                 550                 555                 560
Glu Asn Leu Ser Asp Glu Asn Glu Glu Asp Ser Ser Thr Asp Glu Glu
                565                 570                 575
Thr Leu Glu Asp Lys Lys Gln Gln Arg Leu Glu Tyr Asn Ile Ser Pro
            580                 585                 590
Asn Asp Glu Trp Ile Asn Asn Asp Val Gln Asn Glu Asp Asp Thr Gln
            595                 600                 605
Val Pro His Val Lys Glu Pro Ile Asn Tyr Glu Thr Gln Ser Arg Asn
        610                 615                 620
Glu Thr Asn Met Pro Arg Ile Glu Met Gly Ile Ile Glu Asn Leu Ser
625                 630                 635                 640
Asp Asp Gly Lys Asn Thr Pro Arg Glu Leu Arg Ile Val Thr Tyr Asp
                645                 650                 655
Asn Asn Lys Glu Ile Glu Lys Tyr Gln Asp Ser Asn Ile Glu Ile Ser
            660                 665                 670
Glu Pro Arg Asn Glu Asn Glu Asn Gln Thr Phe Ile Glu Ser Asn Leu
            675                 680                 685
Glu Leu Leu Asp Asn Gln Glu Met Phe Gln Glu Asp Pro Gln Val Glu
        690                 695                 700
Asp Ile Arg Leu Thr Thr Pro Lys Lys Asp Lys Ser Leu Ser Pro Asp
705                 710                 715                 720
Phe Asn Gln Thr His Asn Glu Ile Gln Leu Phe Met Ala Asp Ile Asn
                725                 730                 735
Glu Asp Met Leu Glu Glu Tyr Asp Glu Asn Ile Asn Met Asn Glu Val
            740                 745                 750
Leu Ala Asp Ser Thr Glu Thr Leu Asp Lys Glu Leu Asp Leu Asp Glu
            755                 760                 765
Glu Ser Gly Arg Ile Glu Tyr Ile Ala Asp Arg Val Arg Lys Lys Thr
        770                 775                 780
Glu Val Ser Met Val Arg His Thr Gly Asn Ile
785                 790                 795

<210> SEQ ID NO 143
<211> LENGTH: 257
<212> TYPE: PRT
<213> ORGANISM: Unknown
<220> FEATURE:
<223> OTHER INFORMATION: sequence of retrotransposon from unknown
      organism
```

<400> SEQUENCE: 143

```
Met Asp Asp Glu Val Gly Ile Ala Ile Ser Lys Ile Arg Asn Phe Pro
1               5                   10                  15
Phe Arg Leu Lys Asp Gly Arg Ala Ser Phe Phe Pro Tyr Lys Thr
            20                  25                  30
Lys Phe Gly Arg Ser Val His Pro Pro Lys Arg Tyr Leu Asn Ala Ile
            35                  40                  45
Val Lys Lys Ile Asp Tyr Asn Gln Lys Glu Trp Arg Gln Ser Met Glu
    50                  55                  60
Glu Glu Ile Glu Lys Phe Lys Ala Asn Gln Val Tyr Thr Val Glu Lys
65                  70                  75                  80
Thr Pro Lys Asn Val Val Pro Leu Lys Thr Met Trp Val His Thr Tyr
                85                  90                  95
Lys Thr Asn Asp Leu Lys Asn His Asn Tyr Lys Ser Arg Cys Val Val
            100                 105                 110
Met Gly Asn Tyr Met Val Glu Asn Arg Asp Phe Asp Pro His Ala Ile
            115                 120                 125
Ser Ser Pro Val Val Asp Leu Thr Ser Ile Arg Leu Leu Ser Ala Ile
    130                 135                 140
Ala Val Glu Asn Asn Leu Val Met His Gln Leu Asp Ile Ala Ser Ala
145                 150                 155                 160
Tyr Leu Asn Ala Ser Leu Glu Asp Gly Arg Val Ile Phe Val Arg Pro
                165                 170                 175
Pro Arg Gly Phe Glu Val Lys Pro Gly Tyr Ser Trp Arg Leu His Lys
            180                 185                 190
Ser Val Tyr Gly Leu Arg Gln Ser Ala His Asn Trp Tyr Ser His Phe
            195                 200                 205
Lys Asn Val Leu Glu Ala Asn Gly Leu Lys Gln Thr Leu His Asn Asp
    210                 215                 220
Gly Ile Phe Trp Lys Asn Tyr Glu Asn Gly Asp Val Leu Tyr Val Ser
225                 230                 235                 240
Val Tyr Val Asp Asp Val Phe Ile Lys Ala Asn Ser Met Ser Leu Cys
                245                 250                 255
Asn
```

<210> SEQ ID NO 144
<211> LENGTH: 3159
<212> TYPE: DNA
<213> ORGANISM: Unknown
<220> FEATURE:
<223> OTHER INFORMATION: sequence of retrotransposon from unknown organism

<400> SEQUENCE: 144

```
aatctgtcca cctcgttttg agaggttctc aaaattcttt gtaattttca aacttcacct    60
ttggctttgt aaagttggtt ttttaaggaa tagctttgat tatttgacat tgcaaacagt   120
atagtcaaga tgcacacaga ttggacctga aattattcct tcgcaaaaac ttaaataac    180
ccaaatatta aacatccact cggattcaaa tacctcagca ctctttttata ggcacttgta   240
taatttgtta tatgaatcat ttccagcttc cttgtagaac cgccaaatat ttgaatcaca   300
tgggaaacag atttgaccat ctaactttca tggttcttat gaaaaagatc tggaaatggt   360
gatatagctt gattgtctag catattcagc gattacccta ttttgtggtt gcctgggata   420
acccctggct gttgttggaa aagactcgtg acaagtattt ttgcccacga gtttctaatt   480
```

```
actgcgatat tatccagtta cattttcgca actcgttcta cttgagctcc ttctatgaat    540
caactagctg gctatttccc tggatagaaa accttcattc ttcttctcct ggttgagtat    600
caccgacttg tggccgtacc gttcaacccc ctacaataca ccatcaactt tatacttgta    660
atactcggct ttgccactcc ccaaactaac cactataagt tcatactcct tggcttgctt    720
gactttccta tttcttaacc cactactctt ctgtaccact ccgatcatca gattgacaga    780
ggttacttca tacccaacaa cattttcata ccagtcgacc ttctcctctg caccaccaaa    840
cccaacacat cggatttccc tgggatctct ctcaactctc aaacatattg ctttcttatc    900
taccctgaac gtgtgcacca ctaccacccc ttctatctca tataccacac tgaacgatga    960
gatcgcagca ctcccacaaa accgacaatg cagcggctca ggatacgaca ccctcaacga   1020
gttcaccttc atattcccga ccccaaacag tttgatgacc accccgtgt tcacatctat   1080 aagctgacac tctaacccgt caacacgtat aaagaacccc acaaactcaa ccggaaatat   1140
cccacacagt ttcaggggcg ccacctctag ctttctgctc ttcatgctgt tgttgacgat   1200
gttcaccaca ataatatcca actccttcgt ctgcacaaca attctatcca tcacccttgg   1260
tgttcttatc tttattgcac agaccaactg ctgcttcaca tcataactct gtactttccc   1320
atcattacac gacacaacaa gtatctcccc actatccatg accatcacaa actcttccct   1380
actagtcctc tcacgctgtt tctgtccaaa cgatttcatc tgtattggtg gcggaaagtt   1440
cgcattgatc agcgaattta ccgacgacat tgacgcatca ctgcccctcc tctttctaat   1500
cattttacgt gctaaaaacc ccggcacagt tctccgcctg aaaaacgact ccaacacttt   1560
acctcgaaag tgcaccgaca gtgtccactt caactcccgc ttgtcataac cctgtatgac   1620
accctgtcta gtactcacca acacaaccat actcccatca tcattgagcc ccacatggct   1680
gaccggccac atctgacagg gtatggctag tggttcaggg tcgtaacagt actcgacatc   1740
ttggggttgg tagtgatata tctgaactcg tatccatcat ataactcttc tcctcagcaa   1800
actcaatggc ctgggttttt gccggaacca ctagtgcaac caccaacaag aggtactcca   1860
catagtaaat gtacgtgtta gactgggaaa caaccacact ggtttggtcg actcagcacg   1920
ctattcatca acaatacccc caacagaatc accaagttat tgtcagcct cagtttgtac    1980 ttccaccact gaccccacca ccgcatagtt caccaaaagg gtcttgcata atccacgtcc   2040
caccatatca cttcaactcc catattcctc gatgcaagaa taaccacaat aatcggcttt   2100
cgtaaacgtc gtcagtggct caaacacatt gctgcacctt gagctctaga acaaccccac   2160
actcactagc catcgccaca ccaacaacca aattgctgat ccagaaaaaa taccaccccc   2220
gtagtccggc ttgtatggaa taattgcttg gccaggtacg tccccacctc atcgtgtctt   2280
ttctggttga aatatgtcat ctcccgggct aacagtaccg tatctctgtg gctggggcat   2340
ctatactctt tcattctcgg cttacaaatc tatcttgttc acacatttca tatatctggg   2400
acttgtcgaa ctctctgcac tctatcataa actggaactc gcttgcattc tgggacacac   2460
actggagctg gaatccatgg tcaggaaatg tgaaaatttt cttctcggga atatttgtg    2520 acaattagtc ctagtacacg atagtttcat tacgcccact aaaagtgtct actgaaactc   2580
ggtctctata tcgtcaatat cttcattttc tcttcctggc ttttcactgc gacttattgt   2640
tcgctatagg gtaggtcttc caagctaatt ttacccgaca caagatgaaa tattttctgt   2700
tgagcactcg ttgtcgacag tgaaaaattt tcactcaaga aaatattttc atcatcactt   2760
tttctagaaa ggaggttcaa gtgttggaga atagacagcg aacacctgat attcccaagg   2820
```

-continued

```
tcgaattaga ttgaaagata aataatagtc atatttattt tgtatttagt caataaatta     2880 tcttttata  tttaaattct tagtattgtc ataccacgta gattgatacg gacatactta     2940
gcacatttaa catatattaa gcaccgatta cctgtgacat tccgaagttt actgtttcgc     3000
gcacgctggc agacgaacac ttatcaaggt gctactcccg cgcatcagtt tcctctgggt     3060 tctcttttg  atcttggtga actacctttt tttcccactc gcgtgagaag ttcaacactt     3120 tttttaccc  atccaccaaa ctttattctt tccccacc                             3159
```

<210> SEQ ID NO 145
<211> LENGTH: 280
<212> TYPE: DNA
<213> ORGANISM: Candida albicans
<300> PUBLICATION INFORMATION:
<308> DATABASE ACCESSION NUMBER: AF007776
<309> DATABASE ENTRY DATE: 1997-11-21
<313> RELEVANT RESIDUES: (1)..(280)

<400> SEQUENCE: 145

```
tgttggtttg tgcactattt tgtgtcagaa actgatcaat gaaaatgatg gttattatga       60
gaatggaaaa ttttccatc  acacatcagg tgatgacaga actaaactat attgtgtagt      120
ataaataagg gtatgaaata ccaacatccc agaatatcaa cgagatagaa gggaggagtt      180
tcaatatata tcttgtgaat aataacttcg ttctaattca ctatacacaa ctagacgtgt      240
acacgctcaa tctcaggtaa agaaagttta tattccatca                            280
```

<210> SEQ ID NO 146
<211> LENGTH: 11
<212> TYPE: DNA
<213> ORGANISM: Candida albicans

<400> SEQUENCE: 146

```
gattagaagt c                                                           11
```

<210> SEQ ID NO 147
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 147

```
gatacaaaat gcattaacgg cag                                              23
```

<210> SEQ ID NO 148
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 148

```
ctgccgttaa tgcattttgt atc                                              23
```

<210> SEQ ID NO 149
<211> LENGTH: 33
<212> TYPE: DNA
<213> ORGANISM: Artificial Sequence
<220> FEATURE:
<221> NAME/KEY: misc_feature

```
<222> LOCATION: (1)..(33)
<223> OTHER INFORMATION: primer

<400> SEQUENCE: 149
cgacggctgc agttcttcaa tgatgatttc aac                               33

<210> SEQ ID NO 150
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: primer

<400> SEQUENCE: 150
cgacggctgc agccttcaca tttataattg gc                                32

<210> SEQ ID NO 151
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: primer

<400> SEQUENCE: 151
gcgagatcta gatatgacag tcaacactaa g                                 31

<210> SEQ ID NO 152
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: primer

<400> SEQUENCE: 152
cgacgcctgc aggtgatgga atataaactt tc                                32

<210> SEQ ID NO 153
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: primer

<400> SEQUENCE: 153
agtgagctct gttggtttgt gcact                                        25

<210> SEQ ID NO 154
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 154
gcgtctagaa attctgtacc ttc                                          23

<210> SEQ ID NO 155
```

-continued

```
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer

<400> SEQUENCE: 155
gcgtctagaa cattccagtg aagt                                              24

<210> SEQ ID NO 156
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: primer

<400> SEQUENCE: 156
tctaagctac caaagcac                                                     18
```